US009642831B2

(12) United States Patent
Altenbach et al.

(10) Patent No.: US 9,642,831 B2
(45) Date of Patent: May 9, 2017

(54) SUBSTITUTED CHROMANES AND METHOD OF USE

(71) Applicants: AbbVie S.á.r.l., Luxembourg (LU); Galapagos NV, Mechelen (BE)

(72) Inventors: Robert J. Altenbach, Chicago, IL (US); Andrew Bogdan, Evanston, IL (US); Stephen N. Greszler, Vernon Hills, IL (US); John R. Koenig, Chicago, IL (US); Philip R. Kym, Libertyville, IL (US); Bo Liu, Waukegan, IL (US); Xenia B. Searle, Grayslake, IL (US); Eric Voight, Pleasant Prairie, WI (US); Xueqing Wang, Northbrook, IL (US); Ming C. Yeung, Grayslake, IL (US)

(73) Assignees: AbbVie S.á.r.l., Luxembourg (LU); Galapagos NV, Mechelen (BE)

( * ) Notice: Subject to any disclaimer, the term of this patent is extended or adjusted under 35 U.S.C. 154(b) by 0 days.

(21) Appl. No.: 14/925,649

(22) Filed: Oct. 28, 2015

(65) Prior Publication Data
US 2016/0120841 A1 May 5, 2016

Related U.S. Application Data

(60) Provisional application No. 62/073,573, filed on Oct. 31, 2014.

(51) Int. Cl.
| C07D 407/12 | (2006.01) |
| A61K 31/353 | (2006.01) |
| A61K 45/06 | (2006.01) |
| C07D 405/14 | (2006.01) |
| A61K 31/4433 | (2006.01) |
| C07D 491/052 | (2006.01) |
| A61K 31/436 | (2006.01) |
| A61K 31/4025 | (2006.01) |
| A61K 31/453 | (2006.01) |
| C07D 413/14 | (2006.01) |
| A61K 31/5377 | (2006.01) |
| A61K 31/397 | (2006.01) |
| C07D 491/107 | (2006.01) |
| A61K 31/435 | (2006.01) |
| A61K 31/00 | (2006.01) |

(52) U.S. Cl.
CPC ............ *A61K 31/353* (2013.01); *A61K 31/00* (2013.01); *A61K 31/397* (2013.01); *A61K 31/4025* (2013.01); *A61K 31/435* (2013.01); *A61K 31/436* (2013.01); *A61K 31/4433* (2013.01); *A61K 31/453* (2013.01); *A61K 31/5377* (2013.01); *A61K 45/06* (2013.01); *C07D 405/14* (2013.01); *C07D 407/12* (2013.01); *C07D 413/14* (2013.01); *C07D 491/052* (2013.01); *C07D 491/107* (2013.01)

(58) Field of Classification Search
None
See application file for complete search history.

(56) References Cited

U.S. PATENT DOCUMENTS

| 7,645,789 B2 | 1/2010 | Hadida Ruah et al. |
| 7,659,268 B2 | 2/2010 | Hadida Ruah et al. |
| 7,671,221 B2 | 3/2010 | Hadida Ruah et al. |

(Continued)

FOREIGN PATENT DOCUMENTS

| WO | 2005075435 A1 | 8/2005 |
| WO | 2007021982 A2 | 2/2007 |

(Continued)

OTHER PUBLICATIONS

Pitt "Heteroaromatic Rings of the Future" J. Med. Chem. 2009, 52, 2952-2963.*
Pozharskii et. al. Heterocycles in Life and Society Wiley, 1997, pp. 1-6.*
PCT International Search Report and Written Opinion, PCT/US2015/057837, Jan. 27, 2016, 13 pages.
U.S. National Library of Medicine, National Center for Biotechnology Information, Compound Summary for PubChem CID 45835805, Create Date: Jun. 21, 2010, 10 pages.
U.S. National Library of Medicine, National Center for Biotechnology Information, Compound Summary for PubChem CID 71495726, Create Date: Jun. 10, 2013, 8 pages.
U.S. National Library of Medicine, National Center for Biotechnology Information, Compound Summary for PubChem CID 8321594, Create Date: Jul. 30, 2006, 10 pages.

(Continued)

Primary Examiner — David K O'Dell
(74) Attorney, Agent, or Firm — Quarles & Brady LLP

(57) ABSTRACT

The invention provides for compounds of formula (I)

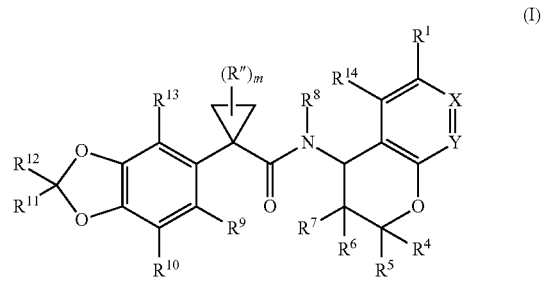

wherein $R^1$, X, Y, $R^4$, $R^5$, $R^6$, $R^7$, $R^8$, $R^9$, $R^{10}$, $R^{11}$, $R^{12}$, $R^{13}$, $R^{14}$, m, and R" have any of the values defined in the specification, and pharmaceutically acceptable salts thereof, that are useful as agents in the treatment of diseases and conditions mediated and modulated by CFTR, including cystic fibrosis, Sjögren's syndrome, pancreatic insufficiency, chronic obstructive lung disease, and chronic obstructive airway disease. Also provided are pharmaceutical compositions comprised of one or more compounds of formula (I).

69 Claims, No Drawings

(56) References Cited

U.S. PATENT DOCUMENTS

| | | | |
|---|---|---|---|
| 7,691,902 B2 | 4/2010 | Hadida Ruah et al. | |
| 7,741,321 B2 | 6/2010 | Hadida Ruah et al. | |
| 7,754,739 B2 | 7/2010 | Hadida Ruah et al. | |
| 7,776,905 B2 * | 8/2010 | Hadida Ruah | C07D 405/12 514/414 |
| 7,956,052 B2 | 6/2011 | Hadida Ruah et al. | |
| 7,973,038 B2 | 7/2011 | Hadida Ruah et al. | |
| 7,977,322 B2 * | 7/2011 | Ruah | C07D 231/40 514/92 |
| 7,999,113 B2 * | 8/2011 | Hadida-Ruah | A61K 31/427 548/195 |
| 8,227,615 B2 | 7/2012 | Hadida-Ruah et al. | |
| 8,299,099 B2 | 10/2012 | Hadida Ruah et al. | |
| 8,318,733 B2 | 11/2012 | Hadida Ruah et al. | |
| 8,324,207 B2 | 12/2012 | Hadida Ruah et al. | |
| 8,415,387 B2 | 4/2013 | Hadida Ruah et al. | |
| 8,461,156 B2 | 6/2013 | Hadida Ruah et al. | |
| 8,507,524 B2 | 8/2013 | Hadida Ruah et al. | |
| 8,524,767 B2 | 9/2013 | Miller et al. | |
| 8,524,910 B2 | 9/2013 | Hadida Ruah et al. | |
| 8,563,573 B2 * | 10/2013 | Ruah | C07D 471/04 514/300 |
| 8,575,209 B2 | 11/2013 | Hadida Ruah et al. | |
| 8,586,615 B2 | 11/2013 | Hadida-Ruah et al. | |
| 8,598,181 B2 | 12/2013 | Hadida Ruah et al. | |
| 8,623,905 B2 | 1/2014 | Hadida Ruah et al. | |
| 8,722,704 B2 | 5/2014 | Hadida Ruah et al. | |
| 8,741,933 B2 | 6/2014 | Hadida Ruah et al. | |
| 8,759,335 B2 | 6/2014 | Hadida Ruah et al. | |
| 8,796,312 B2 | 8/2014 | Hadida Ruah et al. | |
| 8,846,753 B2 | 9/2014 | Hadida Ruah et al. | |
| 8,889,875 B2 | 11/2014 | Hadida Ruah et al. | |
| 8,912,199 B2 * | 12/2014 | Hadida Ruah | C07D 405/12 514/255.05 |
| 8,952,049 B2 | 2/2015 | Hadida Ruah et al. | |
| 8,952,050 B2 | 2/2015 | Hadida Ruah et al. | |
| 8,962,856 B2 | 2/2015 | Hadida-Ruah et al. | |
| 8,969,386 B2 | 3/2015 | Hadida-Ruah et al. | |
| 8,993,600 B2 | 3/2015 | Hadida Ruah et al. | |
| 9,012,473 B2 | 4/2015 | Hadida Ruah et al. | |
| 9,079,916 B2 | 7/2015 | Hadida Ruah et al. | |
| 9,221,832 B2 * | 12/2015 | Hilpert | C07D 491/052 |
| 2006/0052358 A1 | 3/2006 | Ruah et al. | |
| 2007/0244159 A1 | 10/2007 | Hadida Ruah et al. | |
| 2008/0009524 A1 | 1/2008 | Hadida Ruah et al. | |
| 2008/0019915 A1 | 1/2008 | Hadida Ruah et al. | |
| 2008/0044355 A1 | 2/2008 | Hadida Ruah et al. | |
| 2008/0113985 A1 | 5/2008 | Hadida Ruah et al. | |
| 2008/0161371 A1 | 7/2008 | Hadida-Ruah et al. | |
| 2008/0176899 A1 | 7/2008 | Hadida Ruah et al. | |
| 2008/0286204 A1 | 11/2008 | Hadida-Ruah et al. | |
| 2008/0306062 A1 | 12/2008 | Hadida Ruah et al. | |
| 2009/0131492 A1 | 5/2009 | Hadida Ruah et al. | |
| 2009/0143381 A1 | 6/2009 | Hadida Ruah et al. | |
| 2009/0221597 A1 | 9/2009 | Hadida Ruah et al. | |
| 2009/0246137 A1 | 10/2009 | Hadida Ruah et al. | |
| 2009/0253736 A1 | 10/2009 | Hadida-Ruah et al. | |
| 2010/0087435 A1 | 4/2010 | Hadida Ruah et al. | |
| 2010/0105739 A1 | 4/2010 | Hadida Ruah et al. | |
| 2010/0113555 A1 | 5/2010 | Ruah et al. | |
| 2010/0210638 A1 | 8/2010 | Hadida Ruah et al. | |
| 2010/0249113 A1 | 9/2010 | Hadida Ruah et al. | |
| 2010/0331344 A1 | 12/2010 | Hadida Ruah et al. | |
| 2011/0060024 A1 | 3/2011 | Hadida Ruah et al. | |
| 2011/0071206 A1 | 3/2011 | Hadida Ruah et al. | |
| 2011/0172229 A1 | 7/2011 | Hadida-Ruah et al. | |
| 2011/0312958 A1 | 12/2011 | Hadida Ruah et al. | |
| 2012/0010257 A1 | 1/2012 | Hadida-Ruah et al. | |
| 2012/0232059 A1 | 9/2012 | Hadida-Ruah et al. | |
| 2012/0270869 A1 | 10/2012 | Hadida Ruah et al. | |
| 2012/0322798 A1 | 12/2012 | Hadida Ruah et al. | |
| 2013/0023538 A1 | 1/2013 | Hadida Ruah et al. | |
| 2013/0178471 A1 | 7/2013 | Hadida Ruah et al. | |
| 2013/0237568 A1 | 9/2013 | Hadida Ruah et al. | |
| 2013/0237569 A1 | 9/2013 | Hadida Ruah et al. | |
| 2013/0245010 A1 | 9/2013 | Hadida Ruah et al. | |
| 2013/0245011 A1 | 9/2013 | Hadida Ruah et al. | |
| 2013/0296306 A1 | 11/2013 | Hadida Ruah et al. | |
| 2013/0296364 A1 | 11/2013 | Hadida Ruah et al. | |
| 2013/0317020 A1 | 11/2013 | Hadida Ruah et al. | |
| 2014/0057906 A1 | 2/2014 | Hadida Ruah et al. | |
| 2014/0080825 A1 | 3/2014 | Hadida-Ruah et al. | |
| 2014/0080826 A1 | 3/2014 | Hadida Ruah et al. | |
| 2014/0121381 A1 | 5/2014 | Hadida-Ruah et al. | |
| 2014/0206689 A1 | 7/2014 | Hadida Ruah et al. | |
| 2014/0371230 A1 | 12/2014 | Hadida Ruah et al. | |
| 2015/0031708 A1 | 1/2015 | Hadida-Ruah et al. | |
| 2015/0065497 A1 | 3/2015 | Hadida Ruah et al. | |
| 2015/0065500 A1 | 3/2015 | Hadida-Ruah et al. | |
| 2015/0094304 A1 | 4/2015 | Hadida Ruah et al. | |
| 2015/0119441 A1 | 4/2015 | Hadida Ruah et al. | |
| 2015/0126566 A1 | 5/2015 | Hadida-Ruah et al. | |
| 2015/0166516 A1 | 6/2015 | Hadida-Ruah et al. | |
| 2015/0174098 A1 | 6/2015 | Hadida Ruah et al. | |
| 2015/0190390 A1 | 7/2015 | Hadida Ruah et al. | |

FOREIGN PATENT DOCUMENTS

| | | | |
|---|---|---|---|
| WO | 2007021982 A3 | 5/2007 | |
| WO | 2007056341 A1 | 5/2007 | |
| WO | 2007087066 A2 | 8/2007 | |
| WO | 2007087066 A3 | 10/2007 | |
| WO | 2007117715 A2 | 10/2007 | |
| WO | 2008127399 A2 | 10/2008 | |
| WO | 2008141119 A2 | 11/2008 | |
| WO | 2008127399 A3 | 12/2008 | |
| WO | 2008141119 A3 | 4/2009 | |
| WO | 2009064959 A1 | 5/2009 | |
| WO | 2009108657 A2 | 9/2009 | |
| WO | 2009123896 A1 | 10/2009 | |
| WO | WO 2009108657 A3 * | 12/2009 | C07D 213/75 |
| WO | 2011008931 A2 | 1/2011 | |
| WO | 2011008931 A3 | 4/2012 | |

* cited by examiner

SUBSTITUTED CHROMANES AND METHOD OF USE

CROSS REFERENCE TO RELATED APPLICATIONS

This application claims priority to U.S. Provisional Patent Application No. 60/073,573, filed Oct. 31, 2014, which is incorporated herein by reference for all purposes.

BACKGROUND

The invention relates to substituted chromane compounds that are modulators of the Cystic Fibrosis Transmembrane Conductance Regulator (CFTR) protein, useful in treating diseases and conditions mediated and modulated by CFTR. Additionally, the invention relates to compositions containing compounds of the invention and processes for their preparation.

Cystic fibrosis (CF), one of the most common autosomal recessive genetic diseases in the Caucasian population, is caused by loss of function mutations in the Cystic Fibrosis Transmembrane Conductance Regulator (CFTR) gene, which is located on chromosome 7 (http://www.cff.org/AboutCF/; Rowe S. M et al. (2005); N Eng J Med. (352), 1992-2001). Approximately 1:3500 and 1:3000 infants born in the United States and in Europe, respectively, are affected by CF, resulting in ~75,000 cases worldwide, ~30,000 of which are in the United State. Approximately 1,000 new cases of CF are diagnosed each year, with more than 75% of patients being diagnosed by 2 years of age. Nearly half the CF population is currently 18 years of age and older. The CFTR protein (Gregory, R. J. et al. (1990) Nature 347:382-386; Rich, D. P. et al. (1990) Nature 347:358-362; Riordan, J. R. et al. (1989) Science 245:1066-1073) is a cAMP/ATP-mediated ion channel expressed in a variety of cell types, including secretory and absorptive epithelial cells. CFTR regulates chloride and bicarbonate anion flux across the cell membrane, maintaining electro neutrality and osmolarity across the epithelial membrane (Quinton, P. M. (1990), FASEB J. 4: 2709-2727). CFTR is also responsible for regulating the activity of other ion channels and proteins (Guggino, W. B. et al. (2006), Nat Revs Molecular Cell Biology 7, 426-436).

Aberrations in CFTR function result in imbalance of the airway surface liquid, leading to mucus dehydration, inflammation, recurrent bacterial infection and irreversible lung damage, which lead to premature death in affected patients. Besides respiratory disease, CF patients suffer from gastrointestinal problems and pancreatic insufficiency. The majority of males (95%) with cystic fibrosis are infertile as a result of azoospermia caused by altered vas deferens; which may be absent, atrophic, or fibrotic. Fertility is also decreased among females with cystic fibrosis due to abnormal cervical mucus.

The F508del mutation, the most common of the approximately 1900 identified polymorphisms in CFTR, results in defective processing of CFTR in the endoplasmic reticulum (ER) (http://www.cftr2.org/index.php). Approximately 90% of the CF patients carry at least one copy of the F508del mutation (deletion of a phenylalanine on position 508), and 50%-60% of the patients are homozygous for this mutation. The defective processing of CFTR results in early CFTR degradation, which leads to reduced trafficking or absence of the protein on the membrane. As there have been over 100 CF disease-causing mutations identified, they have been classified according to their phenotypic consequences and belong to synthesis, maturation, regulation, conductance, reduced number due to quantity and reduced number due to stability classifications.

Current CF drug discovery efforts focus upon developing two classes of compounds to modulate CFTR. One class, called Correctors, helps to overcome the folding defects of the mutated CFTR protein to promote its maturation resulting in higher cell surface expression. The other classes of compounds, called Potentiators, help overcome the defective regulation and/or conductance of the protein by increasing the probability of channel opening on the membrane surface.

In addition, as the modulation of CFTR protein mutations to promote proper protein folding is beneficial for CF, there are other diseases mediated by CFTR. For example, Sjögren's Syndrome (SS), an autoimmune disorder that results in symptoms of xerostomia (dry mouth) and keratoconjunctivitis sicca (KCS, dry eyes) may result from dysregulation of moisture producing glands throughout the body. Chronic obstructive lung disease (COLD), or chronic obstructive airway disease (COAD), which is a progressive and irreversible airflow limitation in the airways is result of several physiologic abnormalities, including mucus hyper secretion and impaired mucociliary secretion. Increasing the anion secretion by CFTR potentiators have been suggested to overcome these phenotypic complexities with Sjögren's Syndrome by increasing the corneal hydration and by overcoming the impaired mucociliary secretion in COAD (Bhowmik A, et al. (2009) Vol. 103(4), 496-502; Sloane P, et al. PLOS One (2012) Vol 7(6), 239809 (1-13)).

Accordingly, there is a need for novel compounds able to modulate CFTR. In particular, the present invention discloses compounds that may act as CFTR modulators for the treatment of cystic fibrosis. The present invention also provides methods for the preparation of these compounds, pharmaceutical compositions comprising these compounds and methods for the treatment of cystic fibrosis by administering the compounds of the invention.

SUMMARY

In one aspect the invention provides for compounds of formula (I)

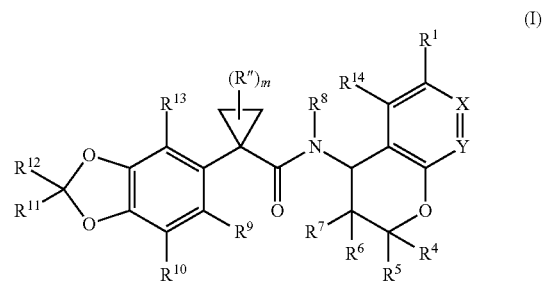

or a pharmaceutically acceptable salt thereof, wherein:
X is $CR^2$ and Y is $CR^3$; or
X is N and Y is $CR^3$; or
X is $CR^2$ and Y is N;
m is 0, 1, 2, or 3;
R" are optional substituents on the cyclopropyl ring, and at each occurrence, are each independently halogen, $C_1$-$C_6$ haloalkyl, or $C_1$-$C_6$ alkyl;

$R^1$ and $R^2$, are each independently hydrogen, halogen, $C_1$-$C_6$ haloalkyl, $C_1$-$C_6$ alkyl, $-OR^{1A}$, $-C(O)OR^{1B}$, $-NR^{1A}R^{2A}$, or $-C(O)NR^{1A}R^{2A}$;

$R^{1A}$ and $R^{2A}$, at each occurrence, are each independently hydrogen, $C_1$-$C_6$ haloalkyl, $G^{1A}$, or $C_1$-$C_6$ alkyl; wherein the $C_1$-$C_6$ haloalkyl and the $C_1$-$C_6$ alkyl are each optionally substituted with one or two substituents independently selected from the group consisting of $-OR^{ZA}$, $-SR^{ZA}$, $-S(O)_2R^{ZA}$, $-C(O)R^{ZA}$, $-C(O)OR^{ZA}$, $-C(O)N(R^{ZA})_2$, $-N(R^{ZA})_2$, $-N(R^{ZA})C(O)R^{ZB}$, $-N(R^{ZA})S(O)_2R^{ZB}$, $-N(R^{ZA})C(O)OR^{ZB}$, $-N(R^{ZA})C(O)N(R^{ZA})_2$, $-CN$, and $G^{1A}$; or $R^{1A}$ and $R^{2A}$ together with the nitrogen atom to which they are attached form a 4-6 membered heterocycle wherein the 4-6 membered heterocycle is optionally substituted with 1, 2, or 3 substituents independently selected from the group consisting of halogen, $C_1$-$C_6$ alkyl, $C_1$-$C_6$ haloalkyl, $-OR^j$, and $N(R^j)_2$; wherein $R^{ZA}$, at each occurrence, is independently hydrogen, $C_1$-$C_6$ haloalkyl, $C_1$-$C_6$ alkyl, $G^{1A}$, or $-(C_1$-$C_6$ alkylenyl)-$G^{1A}$; and $R^{ZB}$, at each occurrence, is independently $C_1$-$C_6$ haloalkyl, $C_1$-$C_6$ alkyl, $G^{1A}$, or $-(C_1$-$C_6$ alkylenyl)-$G^{1A}$;

$R^{1B}$ is hydrogen, $C_1$-$C_6$ haloalkyl, or $C_1$-$C_6$ alkyl;

$R^3$ and $R^{14}$, are each independently hydrogen, halogen, $C_1$-$C_6$ haloalkyl, $C_1$-$C_6$ alkyl, $-OH$, or $-O-(C_1$-$C_6$ alkyl);

$R^4$ is hydrogen, $C_1$-$C_6$ haloalkyl, or $C_1$-$C_6$ alkyl;

$R^5$ is hydrogen, $-C(O)R^i$, $-C(O)OH$, $-C(O)O(C_1$-$C_6$ alkyl), $-C(O)N(R^h)_2$, $C_1$-$C_6$ haloalkyl, $C_1$-$C_6$ alkyl, or $G^{2A}$; wherein the $C_1$-$C_6$ haloalkyl and the $C_1$-$C_6$ alkyl are each optionally substituted with one or two substituents independently selected from the group consisting of $-OR^h$, $-OC(O)N(R^h)_2$, $-C(O)R^h$, $-C(O)OR^h$, $-C(O)N(R^h)_2$, $-N(R^h)_2$, $-N(R^h)C(O)R^i$, $-N(R^h)S(O)_2R^i$, $-N(R^h)C(O)O(R^i)$, $-N(R^h)C(O)N(R^h)_2$, and $G^{2A}$; or $R^4$ and $R^5$, together with the carbon atom to which they are attached, form a $C_3$-$C_6$ cycloalkyl or a 4-6 membered heterocycle; wherein the $C_3$-$C_6$ cycloalkyl and the 4-6 membered heterocycle are each optionally substituted with 1, 2, or 3 independently selected $R^p$ groups;

$G^{2A}$, at each occurrence, is independently cycloalkyl, cycloalkenyl, heterocycle, aryl, or heteroaryl, each of which is independently unsubstituted or substituted with 1, 2, or 3 independently selected $R^q$ groups;

$R^p$ and $R^q$, at each occurrence, are each independently $C_1$-$C_6$ alkyl, halogen, $C_1$-$C_6$ haloalkyl, $-CN$, oxo, $NO_2$, $-OR^h$, $-OC(O)R^i$, $-OC(O)N(R^h)_2$, $-SR^h$, $-S(O)_2R^h$, $-S(O)_2N(R^h)_2$, $-C(O)R^h$, $-C(O)OR^h$, $-C(O)N(R^h)_2$, $-C(O)N(R^h)S(O)_2R^h$, $-N(R^h)_2$, $-N(R^h)C(O)R^i$, $-N(R^h)S(O)_2R^i$, $-N(R^h)C(O)O(R^i)$, $-N(R^h)C(O)N(R^h)_2$, or $G^A$, wherein the $C_1$-$C_6$ haloalkyl and the $C_1$-$C_6$ alkyl are each optionally substituted with one or two substituents independently selected from the group consisting of $-OR^h$, $-OC(O)R^i$, $-OC(O)N(R^h)_2$, $-SR^h$, $-S(O)_2R^h$, $-S(O)_2N(R^h)_2$, $-C(O)R^h$, $-C(O)OR^h$, $-C(O)N(R^h)_2$, $-C(O)N(R^h)S(O)_2R^h$, $-N(R^h)_2$, $-N(R^h)C(O)R^i$, $-N(R^h)S(O)_2R^i$, $-N(R^h)C(O)O(R^i)$, $-N(R^h)C(O)N(R^h)_2$, $-CN$, and $G^A$;

$R^h$, at each occurrence, is independently hydrogen, $C_1$-$C_6$ haloalkyl, $C_1$-$C_6$ alkyl, or $G^A$, wherein the $C_1$-$C_6$ haloalkyl and the $C_1$-$C_6$ alkyl are each optionally substituted with one or two substituents independently selected from the group consisting of $-OR^j$, $-OC(O)N(R^j)_2$, $-SR^j$, $-C(O)OR^j$, $-C(O)N(R^j)_2$, $-N(R^j)_2$, $-CN$, and $G^A$;

$R^i$, at each occurrence, is independently $C_1$-$C_6$ haloalkyl, $C_1$-$C_6$ alkyl, or $G^A$, wherein the $C_1$-$C_6$ haloalkyl and the $C_1$-$C_6$ alkyl are each optionally substituted with one or two substituents independently selected from the group consisting of $-OR^j$, $-OC(O)N(R^j)_2$, $-SR^j$, $-C(O)OR^j$, $-C(O)N(R^j)_2$, $-N(R^j)_2$, $-CN$, and $G^A$;

$R^6$ is hydrogen, halogen, $C_1$-$C_6$ haloalkyl, or $C_1$-$C_6$ alkyl;

$R^7$ is hydrogen, halogen, $-OR^j$, $-N(R^j)_2$, $-N(R^j)C(O)R^k$, $C_1$-$C_6$ haloalkyl, $C_1$-$C_6$ alkyl, $C_2$-$C_6$ alkenyl, or $-(C_1$-$C_6$ alkylenyl)-$G^{3A}$;

$R^8$ is hydrogen, $C_1$-$C_6$ haloalkyl, or $C_1$-$C_6$ alkyl;

$R^9$, $R^{10}$, and $R^{13}$, are each independently hydrogen, halogen, $-OR^j$, $C_1$-$C_6$ haloalkyl, or $C_1$-$C_6$ alkyl;

$R^{11}$ and $R^{12}$ are each independently hydrogen, $C_1$-$C_3$ alkyl, or halogen;

$G^{1A}$, $G^{3A}$, and $G^A$, at each occurrence, are each independently cycloalkyl, cycloalkenyl, heterocycle, aryl, or heteroaryl, each of which is independently unsubstituted or substituted with 1, 2, or 3 independently selected $R^s$ groups; wherein $R^s$, at each occurrence, is independently $C_1$-$C_6$ alkyl, $C_2$-$C_6$ alkenyl, $C_2$-$C_6$ alkynyl, halogen, $C_1$-$C_6$ haloalkyl, $-CN$, oxo, $NO_2$, $-OR^j$, $-OC(O)R^k$, $-OC(O)N(R^j)_2$, $-SR^j$, $-S(O)_2R^j$, $-S(O)_2N(R^j)_2$, $-C(O)R^j$, $-C(O)OR^j$, $-C(O)N(R^j)_2$, $-N(R^j)_2$, $-N(R^j)C(O)R^k$, $-N(R^j)S(O)_2R^k$, $-N(R^j)C(O)O(R^k)$, $-N(R^j)C(O)N(R^j)_2$, $-(C_1$-$C_6$ alkylenyl)-$OR^j$, $-(C_1$-$C_6$ alkylenyl)-$OC(O)R^k$, $-(C_1$-$C_6$ alkylenyl)-$OC(O)N(R^j)_2$, $-(C_1$-$C_6$ alkylenyl)-$SR^j$, $-(C_1$-$C_6$ alkylenyl)-$S(O)_2R^j$, $-(C_1$-$C_6$ alkylenyl)-$S(O)_2N(R^j)_2$, $-(C_1$-$C_6$ alkylenyl)-$C(O)R^j$, $-(C_1$-$C_6$ alkylenyl)-$C(O)OR^j$, $-(C_1$-$C_6$ alkylenyl)-$C(O)N(R^j)_2$, $-(C_1$-$C_6$ alkylenyl)-$N(R^j)_2$, $-(C_1$-$C_6$ alkylenyl)-$N(R^j)C(O)R^k$, $-(C_1$-$C_6$ alkylenyl)-$N(R^j)S(O)_2R^k$, $-(C_1$-$C_6$ alkylenyl)-$N(R^j)C(O)O(R^k)$, $-(C_1$-$C_6$ alkylenyl)-$N(R^j)C(O)N(R^j)_2$, or $-(C_1$-$C_6$ alkylenyl)-$CN$;

$R^j$, at each occurrence, is independently hydrogen, $C_1$-$C_6$ alkyl, or $C_1$-$C_6$ haloalkyl; and $R^k$, at each occurrence, is independently $C_1$-$C_6$ alkyl or $C_1$-$C_6$ haloalkyl.

Another aspect of the invention relates to pharmaceutical compositions comprising compounds of the invention or pharmaceutically acceptable salts thereof, and a pharmaceutical carrier. Such compositions can be administered in accordance with a method of the invention, typically as part of a therapeutic regimen for treatment or prevention of conditions and disorders related to Cystic Fibrosis Transmembrane Conductance Regulator activity. In a particular aspect, the pharmaceutical compositions may additionally comprise further one or more therapeutically active ingredients suitable for use in combination with the compounds of the invention. In a more particular aspect, the further therapeutically active ingredient is an agent for the treatment of cystic fibrosis.

Moreover, the compounds of the invention or pharmaceutically acceptable salts thereof, useful in the pharmaceutical compositions and treatment methods disclosed herein, are pharmaceutically acceptable as prepared and used.

Yet another aspect of the invention relates to a method of correcting the folding defects of the mutated CFTR protein(s) to promote its maturation resulting in higher cell surface expression. The method is useful for treating, or preventing conditions and disorders related to Cystic Fibrosis Transmembrane Conductance Regulator activity in mammals. More particularly, the method is useful for treating or preventing conditions and disorders related to cystic fibrosis, Sjögren's syndrome, pancreatic insufficiency, chronic obstructive lung disease, or chronic obstructive airway disease. Accordingly, the compounds and compositions of the invention are useful as a medicament for treating or preventing Cystic Fibrosis Transmembrane Conductance Regulator modulated disease.

The compounds, compositions comprising the compounds or pharmaceutically acceptable salts thereof, methods for making the compounds, and methods for treating or preventing conditions and disorders by administering the compounds are further described herein.

In a particular aspect, the compounds of the invention or pharmaceutically acceptable salts thereof are provided for use in the treatment of cystic fibrosis. In a particular aspect, the compounds of the invention or pharmaceutically acceptable salts thereof are provided for use in the treatment of cystic fibrosis caused by class I, II, III, IV, V, and/or VI mutations.

The present invention also provides pharmaceutical compositions comprising a compound of the invention or pharmaceutically acceptable salts thereof, and a suitable pharmaceutical carrier for use in medicine. In a particular aspect, the pharmaceutical composition is for use in the treatment of cystic fibrosis.

In an alternative embodiment, certain compounds of the invention have a corrector activity.

In another particular aspect, certain compounds of the invention have improved potency, in addition to exhibiting low effects on CYP3A4 expression, which suggest low drug-drug interaction potential, and accordingly may be advantageous for patients under multiple therapies.

These and other objects of the invention are described in the following paragraphs. These objects should not be deemed to narrow the scope of the invention.

DETAILED DESCRIPTION OF THE INVENTION

Described herein are compounds of formula (I)

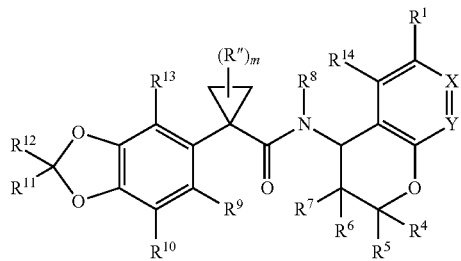

(I)

wherein $R^1$, X, Y, $R^4$, $R^5$, $R^6$, $R^7$, $R^8$, $R^9$, $R^{10}$, $R^{11}$, $R^{12}$, $R^{13}$, $R^{14}$, m, and R'' are defined above in the Summary of the Invention and below in the Detailed Description. Further, compositions comprising such compounds and methods for treating conditions and disorders using such compounds and compositions are also included.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_6$ alkenyl" means an alkenyl group containing 2-6 carbon atoms. Non-limiting examples of $C_2$-$C_6$ alkenyl include buta-1,3-dienyl, ethenyl, 2-propenyl, 2-methyl-2-propenyl, 3-butenyl, 4-pentenyl, and 5-hexenyl.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" refers to an alkyl substituent containing from 1 to 3 carbon atoms. Representative examples of $C_1$-$C_6$ alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms or of 1 to 3 carbon atoms ($C_1$-$C_3$ alkylenyl) or of 2 to 6 carbon atoms ($C_2$-$C_6$ alkylenyl). Examples of $C_1$-$C_6$ alkylenyl include, but are not limited to, —CH$_2$—, —CH$_2$CH$_2$—, —C((CH$_3$)$_2$)—CH$_2$CH$_2$CH$_2$—, —C((CH$_3$)$_2$)—CH$_2$CH$_2$, —CH$_2$CH$_2$CH$_2$CH$_2$—, and —CH$_2$CH(CH$_3$)CH$_2$—.

The term "$C_2$-$C_6$ alkynyl" as used herein, means a straight or branched chain hydrocarbon radical containing from 2 to 6 carbon atoms and containing at least one carbon-carbon triple bond. Representative examples of $C_2$-$C_6$ alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The phenyl and the bicyclic aryls (including exemplary rings) are optionally substituted unless otherwise indicated. The phenyl and the bicyclic aryls are attached to the parent molecular moiety through any carbon atom contained within the bicyclic ring systems.

The term "cycloalkyl" as used herein, refers to a radical that is a monocyclic cycloalkyl or a bicyclic cycloalkyl. The monocyclic cycloalkyl is a carbocyclic ring system containing three to eight carbon atoms, zero heteroatoms and zero double bonds. Examples of monocyclic cycloalkyl include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic and the bicyclic cycloalkyl groups may further contain one or two alkylene bridges, each consisting of one, two, three, or four carbon atoms in length, and each bridge links two non-adjacent carbon atoms of the ring system. Non-limiting examples of bridged ring systems include bicyclo[3.1.1]heptyl, bicyclo[2.2.1]heptyl, bicyclo[2.2.2]octyl, bicyclo[1.1.1]pentyl, bicyclo[3.2.2]nonyl, bicyclo [3.3.1]nonyl, bicyclo[4.2.1]nonyl, tricyclo[3.3.1.0$^{3,7}$]nonyl (octahydro-2,5-methanopentalene or noradamantyl), and tricyclo[3.3.1.1$^{3,7}$]decane (adamantyl).

The monocyclic and the bicyclic cycloalkyls, including exemplary rings, are optionally substituted unless otherwise indicated. The monocyclic cycloalkyl and the bicyclic cycloalkyl are attached to the parent molecular moiety through any substitutable carbon atom contained within the ring systems.

The term "$C_3$-$C_6$ cycloalkyl" as used herein, means cyclopropyl, cyclobutyl, cyclopentyl, and cyclohexyl, each of which is optionally substituted unless otherwise indicated.

The term "cycloalkenyl" as used herein, refers to a monocyclic or a bicyclic hydrocarbon ring radical. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic and bicyclic cycloalkenyl ring may contain one or two alkylene bridges, each consisting of one, two, or three carbon atoms, and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and the bicyclic cycloalkenyls, including exemplary rings, are optionally substituted unless otherwise indicated. The monocyclic cycloalkenyl and bicyclic cycloalkenyl are attached to the parent molecular moiety through any substitutable atom contained within the ring systems.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Representative examples of $C_1$-$C_6$ haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl.

The term "heterocycle" or "heterocyclic" as used herein, means a radical of a monocyclic heterocycle and a bicyclic heterocycle. A monocyclic heterocycle is a three-, four-, five-, six-, seven-, or eight-membered carbocyclic ring wherein at least one carbon atom is replaced by heteroatom independently selected from the group consisting of O, N, and S. A three- or four-membered ring contains zero or one double bond, and one heteroatom selected from the group consisting of O, N, and S. A five-membered ring contains zero or one double bond and one, two, or three heteroatoms selected from the group consisting of O, N, and S. Examples of five-membered heterocyclic rings include those containing in the ring: 1 O; 1 S; 1 N; 2 N; 3 N; 1 S and 1 N; 1 S, and 2 N; 1 O and 1 N; or 1 O and 2 N. Non limiting examples of 5-membered heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered ring contains zero, one, or two double bonds and one, two, or three heteroatoms selected from the group consisting of O, N, and S. Examples of six-membered heterocyclic rings include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of 6-membered heterocyclic groups include tetrahydropyranyl, dihydropyranyl, dioxanyl, 1,4-dithianyl, hexahydropyrimidine, morpholinyl, piperazinyl, piperidinyl, 1,2,3,6-tetrahydropyridinyl, tetrahydrothiopyranyl, thiomorpholinyl, thioxanyl, and trithianyl. Seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, benzopyranyl, benzothiopyranyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl. The monocyclic heterocycle and the bicyclic heterocycle may further contain one or two alkylene bridges, each consisting of no more than four carbon atoms and each linking two non-adjacent atoms of the ring system. Examples of such bridged heterocycle include, but are not limited to, azabicyclo[2.2.1]heptyl (including 2-azabicyclo[2.2.1]hept-2-yl), 8-azabicyclo[3.2.1] oct-8-yl, octahydro-2,5-epoxypentalene, hexahydro-2H-2,5-methanocyclopenta[b]furan, hexahydro-1H-1,4-methanocyclopenta[c]furan, aza-admantane (1-azatricyclo [3.3.1.1$^{3,7}$]decane), and oxa-adamantane (2-oxatricyclo [3.3.1.1$^{3,7}$]decane). The monocyclic and the bicyclic heterocycles, including exemplary rings, are optionally substituted unless otherwise indicated. The monocyclic and the bicyclic heterocycles are connected to the parent molecular moiety through any carbon atom or any nitrogen atom contained within the ring systems. The nitrogen and sulfur heteroatoms in the heterocycle rings may optionally be oxidized (e.g. 1,1-dioxidotetrahydrothienyl, 1,1-dioxido-1,2-thiazolidinyl, 1,1-dioxidothiomorpholinyl)) and the nitrogen atoms may optionally be quarternized.

The term "4-6 membered heterocycle" or "4-6 membered heterocyclic" as used herein, means a 4, 5, or 6 membered monocyclic heterocycle as defined herein above. Examples of 4-6 membered heterocycle include azetidinyl, pyrrolidinyl, tetrahydrofuranyl, tetrahydropyranyl, piperazinyl, piperidinyl, thiomorpholinyl, and morpholinyl. The 4-6 membered heterocycles, including exemplary rings, are optionally substituted unless indicated otherwise.

The term "5-6 membered heterocycle" or "5-6 membered heterocyclic" as used herein, means a 5 or 6 membered monocyclic heterocycle as defined herein above. Examples of 5-6 membered heterocycle include 1,3-dioxolanyl, pyrrolidinyl, 1,2-thiazolidinyl, tetrahydrofuranyl, tetrahydropyranyl, piperazinyl, piperidinyl, thiomorpholinyl, and morpholinyl. The 5-6 membered heterocycles, including exemplary rings, are optionally substituted unless indicated otherwise.

The term "heteroaryl" as used herein, means a monocyclic heteroaryl and a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryls include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryls, including exemplary rings, are optionally substituted unless otherwise indicated. The monocyclic and bicyclic heteroaryls are connected to the parent molecular moiety through any substitutable carbon atom or any substitutable nitrogen atom contained within the ring systems. The nitrogen atom in the heteroaryl rings may optionally be oxidized and may optionally be quarternized.

The term "5-6 membered heteroaryl" as used herein, means a 5- or 6-membered monocyclic heteroaryl as described above. Examples of 5-6 membered heteroaryl include furanyl, thienyl, pyrazolyl, imidazolyl, 1,2,4-oxadiazolyl, 1,2,4-triazolyl, 1,3-thiazolyl, pyridinyl, pyrimidinyl, and pyrazinyl. The 5-6 membered heteroaryls, including exemplary rings, are optionally substituted unless indicated otherwise.

The term "heteroatom" as used herein, means a nitrogen, oxygen, and sulfur.

The term "oxo" as used herein, means a =O group.

The term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

Unless otherwise indicated, the terms $C_1$-$C_6$ alkyl, $C_1$-$C_3$ alkyl, $C_1$-$C_6$ haloalkyl, and $C_1$-$C_3$ haloalkyl are not further substituted.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with one or more additional therapeutic agents for treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In preferred embodiments, the subject is a human.

The term 'one or more' refers to one to four. In one embodiment it refers to one or three. In another embodiment it refers to one to three. In a further embodiment it refers to one to two. In yet other embodiment it refers to two. In yet other further embodiment it refers to one.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G; G1349D; S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5](5T allele), c.S3140-26A>G (3272-26A>G), c.3850-2477C>T (3849+10kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326delITC, or 4279insA mutations. More particularly, Class VI mutation(s) refers to Rescued F508del mutations.

Compounds

Compounds of the invention have the general formula (I) as described above.

Particular values of variable groups are as follows. Such values may be used where appropriate with any of the other values, definitions, claims or embodiments defined hereinbefore or hereinafter.

In certain embodiments of formula (I), X is $CR^2$ and Y is $CR^3$. Thus, included herein are compounds of formula (I-a) or pharmaceutically acceptable salts thereof

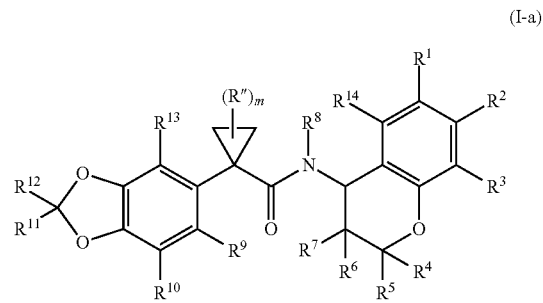

(I-a)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, m, and R", are as defined in the Summary and embodiments herein below.

In certain embodiments of formula (I), X is N and Y is $CR^3$. Thus, included herein are compounds of formula (I-b) or pharmaceutically acceptable salts thereof

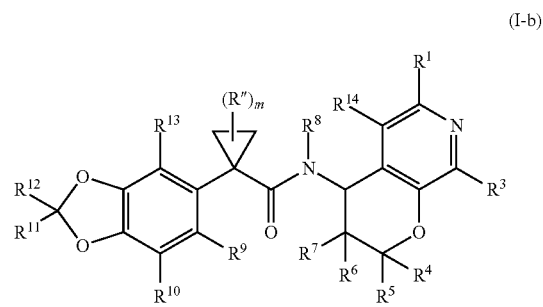

(I-b)

wherein $R^1$, $R^3$, $R^4$, $R^5$, $R^6$, $R^7$, $R^8$, $R^9$, $R^{10}$, $R^{11}$, $R^{12}$, $R^{13}$, $R^{14}$, m, and R", are as defined in the Summary and embodiments herein below.

In certain embodiments of formula (I), X is $CR^2$ and Y is N. Thus, included herein are compounds of formula (I-c) or pharmaceutically acceptable salts thereof

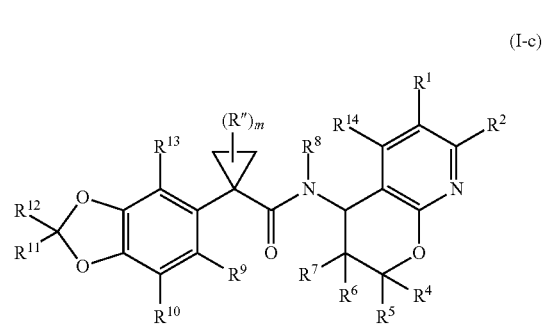

(I-c)

wherein $R^1$, $R^2$, $R^4$, $R^5$, $R^6$, $R^7$, $R^8$, $R^9$, $R^{10}$, $R^{11}$, $R^{12}$, $R^{13}$, $R^{14}$, m, and R", are as defined in the Summary and embodiments herein below.

In certain embodiments, m is 0, 1, 2, or 3.

In certain embodiments, m is 0.

In certain embodiments, m is 2.

In certain embodiments, R", if present, is halogen. In some such embodiments, R" is F.

In certain embodiments, $R^1$ is hydrogen, halogen, $C_1$-$C_6$ haloalkyl, $C_1$-$C_6$ alkyl, —$OR^{1A}$, —$C(O)OR^{1B}$, —$NR^{1A}R^{2A}$, or —$C(O)NR^{1A}R^{2A}$.

In certain embodiments, $R^1$ is hydrogen, halogen, $C_1$-$C_6$ haloalkyl, $C_1$-$C_6$ alkyl, —$OR^{1A}$, or —$C(O)OR^{1B}$. In some such embodiments, $R^{1A}$ is $C_1$-$C_3$ haloalkyl or $C_1$-$C_3$ alkyl; and $R^{1B}$ is hydrogen or $C_1$-$C_3$ alkyl.

In certain embodiments, $R^1$ is hydrogen, halogen, $C_1$-$C_3$ haloalkyl, $C_1$-$C_3$ alkyl, or —$OR^{1A}$. In some such embodiments, $R^{1A}$ is $C_1$-$C_3$ alkyl.

In certain embodiments, $R^1$ is hydrogen, $C_1$-$C_3$ alkyl, or —$OR^{1A}$. In some such embodiments, $R^{1A}$ is $C_1$-$C_3$ alkyl.

In certain embodiments, $R^1$ is hydrogen, $CH_3$, or —$OCH_3$.

In certain embodiments, $R^1$ is hydrogen.

In certain embodiments, $R^1$ is halogen. In some such embodiments, $R^1$ is F or Cl. In some such embodiments, $R^1$ is F.

In certain embodiments, $R^1$ is —$OR^{1A}$. In some such embodiments, $R^{1A}$ is $C_1$-$C_3$ haloalkyl or $C_1$-$C_3$ alkyl. In some such embodiments, $R^{1A}$ is $C_1$-$C_3$ alkyl. In some such embodiments, $R^{1A}$ is $CH_3$.

In certain embodiments, $R^1$ is $C_1$-$C_6$ alkyl. In some such embodiments, $R^1$ is $C_1$-$C_3$ alkyl.

In some such embodiments, $R^1$ is $CH_3$.

In certain embodiments, $R^1$ is —$C(O)OR^{1B}$. In some such embodiments, $R^{1B}$ is hydrogen or $C_1$-$C_3$ alkyl. In some such embodiments, $R^{1B}$ is hydrogen or $CH_3$. In some such embodiments, $R^{1B}$ is hydrogen. In some such embodiments, $R^{1B}$ is $CH_3$ In certain embodiments, $R^2$ is hydrogen, halogen, $C_1$-$C_6$ haloalkyl, $C_1$-$C_6$ alkyl, —$OR^{1A}$, or —$C(O)OR^{1B}$. In some such embodiments, $R^{1A}$ is hydrogen, $C_1$-$C_3$ haloalkyl, or $C_1$-$C_3$ alkyl wherein the $C_1$-$C_3$ alkyl is optionally substituted with one substituent selected from the group consisting of —$OR^{ZA}$, —$C(O)OH$, and $G^{1A}$; and $R^{1B}$ is hydrogen or $C_1$-$C_3$ alkyl. In some such embodiments, $G^{1A}$ is phenyl optionally substituted with 1, 2, or 3 $R^s$ groups wherein each $R^s$ is independently $C_1$-$C_3$ alkyl, $C_1$-$C_3$ haloalkyl, halogen, or —$OCH_3$. In some such embodiments, $G^{1A}$ is unsubstituted phenyl. In some such embodiments, $R^{ZA}$ is $C_1$-$C_3$ haloalkyl or $C_1$-$C_3$ alkyl.

In certain embodiments, $R^2$ is hydrogen, halogen, $C_1$-$C_3$ haloalkyl, $C_1$-$C_3$ alkyl, or —$OR^{1A}$ In some such embodiments, the halogen is Br, F or Cl. In some such embodiments, $R^{1A}$ is $C_1$-$C_3$ haloalkyl or $C_1$-$C_3$ alkyl wherein the $C_1$-$C_3$ alkyl is optionally substituted with one —$OR^{ZA}$ wherein $R^{ZA}$ is $C_1$-$C_3$ alkyl.

In certain embodiments, $R^2$ is hydrogen, halogen, or —$OR^{1A}$ wherein $R^{1A}$ is $C_1$-$C_3$ alkyl or $C_1$-$C_3$ haloalkyl. In some such embodiments, the halogen is F or Cl.

In certain embodiments, $R^2$ is hydrogen, F, $CF_3$, $CH_3$, —$OCH_3$, —$OCHF_2$, —$OCH_2CH_2F$, or —$OCH_2CH_2OCH_3$.

In certain embodiments, $R^2$ is hydrogen.

In certain embodiments, $R^2$ is halogen. In some such embodiments, the halogen is F, Cl, or Br. In some such embodiments, the halogen is F or Cl.

In certain embodiments, $R^2$ is $C_1$-$C_6$ haloalkyl. In certain embodiments, $R^2$ is $C_1$-$C_3$ haloalkyl. In some such embodiments, $R^2$ is $CF_3$.

In certain embodiments, $R^2$ is $C_1$-$C_6$ alkyl. In some such embodiments, $R^2$ is $C_1$-$C_3$ alkyl.

In some such embodiments, $R^2$ is $CH_3$.

In certain embodiments, $R^2$ is —$OR^{1A}$.

In certain embodiments, $R^2$ is —$OR^{1A}$ wherein $R^{1A}$ is $C_1$-$C_3$ haloalkyl or $C_1$-$C_3$ alkyl wherein the $C_1$-$C_3$ alkyl is optionally substituted with one substituent selected from the group consisting of —$OR^{ZA}$, —$C(O)OH$, and $G^{1A}$. In some such embodiments, $G^{1A}$ is phenyl optionally substituted with 1, 2, or 3 $R^s$ groups wherein each $R^s$ is independently $C_1$-$C_3$ alkyl, $C_1$-$C_3$ haloalkyl, halogen, or —$OCH_3$. In some such embodiments, $G^{1A}$ is unsubstituted phenyl. In some such embodiments, $R^{ZA}$ is $C_1$-$C_3$ haloalkyl or $C_1$-$C_3$ alkyl. In some such embodiments, $R^{ZA}$ is $C_1$-$C_3$ alkyl.

In certain embodiments $R^2$ is —$OR^{1A}$ wherein $R^{1A}$ is —$CHF_2$, —$CH_2CH_2F$, or $C_1$-$C_3$ alkyl wherein the $C_1$-$C_3$ alkyl is optionally substituted with one —$OCH_3$.

In certain embodiments, $R^3$ is hydrogen, halogen, $C_1$-$C_6$ haloalkyl, $C_1$-$C_6$ alkyl, —$OH$, or —$O$—($C_1$-$C_6$ alkyl).

In certain embodiments, $R^3$ is hydrogen or halogen. In some such embodiments, the halogen is F or Cl. In some such embodiments, the halogen is F.

In certain embodiments, $R^3$ is hydrogen.

In certain embodiments, $R^3$ is halogen. In some such embodiments, the halogen is F or Cl. In some such embodiments, the halogen is F.

In certain embodiments, $R^4$ is hydrogen, $C_1$-$C_6$ haloalkyl, or $C_1$-$C_6$ alkyl; and $R^5$ is hydrogen, —$C(O)R^i$, —$C(O)OH$, —$C(O)O(C_1$-$C_6$ alkyl), —$C(O)N(R^h)_2$, $C_1$-$C_6$ haloalkyl, $C_1$-$C_6$ alkyl, or $G^{2A}$.

In certain embodiments, $R^4$ is hydrogen, $C_1$-$C_6$ haloalkyl, or $C_1$-$C_6$ alkyl; and $R^5$ is hydrogen, $C_1$-$C_6$ haloalkyl, $C_1$-$C_6$ alkyl, or $G^{2A}$. In some such embodiments, $G^{2A}$ is phenyl, $C_3$-$C_6$ cycloalkyl, 4-6 membered heterocycle, or 5-6 membered heteroaryl. In some such embodiments, $G^{2A}$ is phenyl, cyclopropyl, cyclohexyl, azetidinyl, tetrahydrofuranyl or pyridinyl. In some such embodiments, $G^{2A}$ is phenyl or cyclohexyl. In some such embodiments, $G^{2A}$ is phenyl. In some such embodiments, $G^{2A}$ is monocyclic cycloalkyl. In some such embodiments, $G^{2A}$ is cyclopropyl, cyclobutyl, bicyclo[1.1.1]pentyl, or cyclohexyl. In some such embodiments, $G^{2A}$ is $C_3$-$C_6$ cycloalkyl. In some such embodiments, $G^{2A}$ is cyclopropyl or cyclohexyl. In some such embodiments, $G^{2A}$ is cyclohexyl. In some such embodiments, $G^{2A}$ is 5-6 membered heteroaryl. In some such embodiments, $G^{2A}$ is thiazolyl or pyridinyl. In some such embodiments, $G^{2A}$ is pyridinyl. In some such embodiments, $G^{2A}$ is 4-6 membered heterocycle. In some such embodiments, $G^{2A}$ is azetidinyl or tetrahydrofuranyl.

In certain embodiments, $R^4$ is hydrogen, $C_1$-$C_6$ haloalkyl, or $C_1$-$C_6$ alkyl; and $R^5$ is hydrogen, $C_1$-$C_6$ haloalkyl, or $C_1$-$C_6$ alkyl.

In certain embodiments, $R^4$ is hydrogen, $CH_2F$, $CHF_2$, $CF_3$, $CH_3$, or $CH_2CH_3$; and $R^5$ is hydrogen, $CH_2F$, $CHF_2$, $CH_3$, or $CH_2CH_3$.

In certain embodiments, $R^4$ is hydrogen or $C_1$-$C_3$ alkyl; and $R^5$ is hydrogen or $C_1$-$C_3$ alkyl.

In certain embodiments, $R^4$ is hydrogen; and $R^5$ is hydrogen.

In certain embodiments, $R^4$ is hydrogen, $C_1$-$C_3$ haloalkyl, or $C_1$-$C_3$ alkyl; and $R^5$ is $G^{2A}$.

In certain embodiments, $R^4$ is hydrogen or $C_1$-$C_3$ alkyl; and $R^5$ is $G^{2A}$.

In certain embodiments, $R^4$ is hydrogen and $R^5$ is $G^{2A}$.

In certain embodiments, examples of $G^{2A}$ include phenyl, monocyclic cycloalkyl (for example, cyclopropyl, cyclobutyl, bicyclo[1.1.1]pentyl, or cyclohexyl), 4-6 membered heterocycle (for example, azetidinyl or tetrahyrofuranyl), or 5-6 membered heteroaryl (for example, thiazolyl or pyridinyl).

In certain embodiments, examples of $G^{2A}$ include phenyl, $C_3$-$C_6$ cycloalkyl (for example, cyclopropyl, cyclohexyl), 4-6 membered heterocycle (for example, azetidinyl, tetrahydrofuranyl), or 5-6 membered heteroaryl (for example, pyridinyl).

In certain embodiments, $G^{2A}$ is phenyl, cyclopropyl, cyclobutyl, cyclohexyl, bicyclo[1.1.1]pentyl, azetidinyl, tetrahydrofuranyl, thiazolyl, or pyridinyl.

In certain embodiments, $G^{2A}$ is phenyl, cyclopropyl, cyclohexyl, azetidinyl, tetrahydrofuranyl, or pyridinyl.

In certain embodiments, $G^{2A}$ is phenyl.

In certain embodiments, $G^{2A}$ is monocyclic cycloalkyl.

In certain embodiments, $G^{2A}$ is $C_3$-$C_6$ cycloalkyl.

In certain embodiments, $G^{2A}$ is 4-6 membered heterocycle.

In certain embodiments, $G^{2A}$ is 5-6 membered heteroaryl.

In certain embodiments, $G^{2A}$ is phenyl or cyclohexyl.

In certain embodiments, $G^{2A}$ is cyclopropyl or cyclohexyl.

In certain embodiments, $G^{2A}$ is cyclohexyl.

Each $G^{2A}$, including specific examples, is optionally substituted with 1, 2, or 3 independently selected $R^q$ groups.

In certain embodiments, $G^{2A}$, including specific examples, is unsubstituted.

In certain embodiments, $G^{2A}$, including specific examples, is substituted with 1, 2, or 3 independently selected $R^q$ groups.

In certain embodiments, $G^{2A}$, including specific examples, is substituted with one $R^q$ group.

In certain embodiments, $R^q$, when present, is $C_1$-$C_6$ alkyl wherein the $C_1$-$C_6$ alkyl is optionally substituted with one —OH group;

halogen, $C_1$-$C_6$ haloalkyl;

—OR$^h$ wherein R$^h$ is hydrogen or $C_1$-$C_3$ alkyl,

—C(O)R$^h$ wherein R$^h$ is G$^A$; and G$^A$ is optionally substituted 4-6 membered heterocycle;

—C(O)OR$^h$ wherein R$^h$ is hydrogen or $C_1$-$C_6$ alkyl;

—C(O)N(R$^h$)$_2$; wherein R$^h$, at each occurrence, is independently hydrogen, optionally substituted cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 substituents independently selected from the group consisting of —OH and optionally substituted cycloalkyl;

—C(O)N(R$^h$)S(O)$_2$R$^h$ wherein R$^h$ is hydrogen or $C_1$-$C_6$ alkyl; or

—SO$_2$R$^h$ wherein R$^h$ is $C_1$-$C_6$ haloalkyl or $C_1$-$C_6$ alkyl.

In certain embodiments, $R^q$, when present, is $C_1$-$C_6$ alkyl wherein the $C_1$-$C_6$ alkyl is optionally substituted with one —OH group;

halogen, $C_1$-$C_6$ haloalkyl;

—OR$^h$ wherein R$^h$ is hydrogen or $C_1$-$C_3$ alkyl,

—C(O)R$^h$ wherein R$^h$ is G$^A$; and G$^A$ is optionally substituted 4-6 membered heterocycle;

—C(O)OR$^h$ wherein R$^h$ is hydrogen or $C_1$-$C_6$ alkyl;

—C(O)N(R$^h$)$_2$; wherein R$^h$, at each occurrence, is independently hydrogen, optionally substituted cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or —SO$_2$R$^h$ wherein R$^h$ is $C_1$-$C_6$ haloalkyl or $C_1$-$C_6$ alkyl.

In certain embodiments, $R^q$, when present, is —OR$^h$ wherein R$^h$ is $C_1$-$C_3$ alkyl, or $R^q$ is —C(O)OR$^h$ wherein R$^h$ is hydrogen or $C_1$-$C_6$ alkyl.

In certain embodiments, one of $R^q$ is —C(O)OR$^h$ wherein R$^h$ is hydrogen or $C_1$-$C_6$ alkyl, or one of $R^q$ is —C(O)N(H)(R$^h$) wherein R$^h$ is cyclopentyl, or R$^h$ is $C_1$-$C_6$ alkyl which is substituted with 1 or 2 —OH groups; and the other optional $R^q$ groups are independently selected from the group consisting of $C_1$-$C_3$ alkyl, halogen, and $C_1$-$C_3$ haloalkyl.

In certain embodiments, $R^q$ is —C(O)OR$^h$ wherein R$^h$ is hydrogen or $C_1$-$C_3$ alkyl. In some such embodiments, R$^h$ is hydrogen. In some such embodiments, R$^h$ is $C_1$-$C_3$ alkyl.

In certain embodiments, $G^{2A}$ is

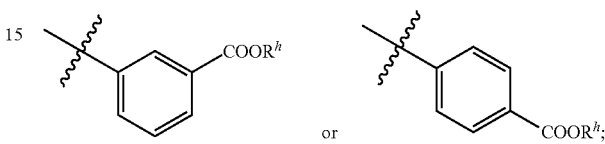

or wherein R$^h$ is hydrogen or $C_1$-$C_3$ alkyl. In some such embodiments, R$^h$ is hydrogen. In some such embodiments, R$^h$ is $C_1$-$C_3$ alkyl.

In certain embodiments, $G^{2A}$ is

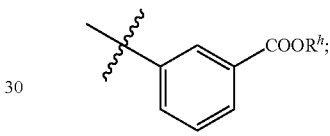

wherein R$^h$ is hydrogen or $C_1$-$C_3$ alkyl. In some such embodiments, R$^h$ is hydrogen. In some such embodiments, R$^h$ is $C_1$-$C_3$ alkyl.

In certain embodiments, $G^{2A}$ is

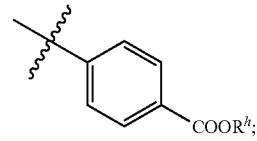

wherein R$^h$ is hydrogen or $C_1$-$C_3$ alkyl. In some such embodiments, R$^h$ is hydrogen. In some such embodiments, R$^h$ is $C_1$-$C_3$ alkyl.

In certain embodiments, $G^{2A}$ is

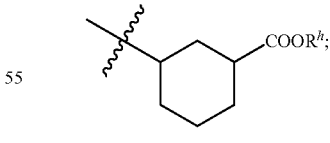

wherein R$^h$ is hydrogen or $C_1$-$C_3$ alkyl. In some such embodiments, R$^h$ is hydrogen. In some such embodiments, R$^h$ is $C_1$-$C_3$ alkyl.

In certain embodiments, R$^4$ is hydrogen, $C_1$-$C_6$ haloalkyl, or $C_1$-$C_6$ alkyl; and R$^5$ is —C(O)OH, —C(O)O($C_1$-$C_6$ alkyl), —C(O)R$^i$, or —C(O)N(R$^h$)$_2$. In some such embodiments, R$^i$ is optionally substituted monocyclic heterocycle. In some such embodiments, one of R$^h$ is hydrogen or $C_1$-$C_6$ alkyl which is optionally substituted with one or two —OH, and the other $R^h$ is optionally substituted monocyclic heterocycle, optionally substituted aryl, or $C_1$-$C_6$ alkyl which is optionally substituted with one or two substituents independently selected from the group consisting of —OH and optionally substituted phenyl.

In certain embodiments, $R^4$ and $R^5$, together with the carbon atom to which they are attached, form a $C_3$-$C_6$ cycloalkyl or a 4-6 membered heterocycle.

In certain embodiments $R^4$ and $R^5$, together with the carbon atom to which they are attached, form a 4-6 membered heterocycle. In some such embodiments, the 4-6 membered heterocycle is azetidinyl or piperidinyl.

In certain embodiments $R^4$ and $R^5$, together with the carbon atom to which they are attached, form a $C_3$-$C_6$ cycloalkyl, optionally substituted with 1 or 2 $R^p$ groups.

In certain embodiments, the $C_3$-$C_6$ cycloalkyl is unsubstituted cyclobutyl or unsubstituted cyclopentyl.

In certain embodiments, the 4-6 membered heterocycle formed by $R^4$ and $R^5$, and the carbon atom to which they are attached, is optionally substituted with 1 or 2 $R^p$ groups.

In certain embodiments, $R^p$, when present, are each independently $C_1$-$C_6$ alkyl wherein the $C_1$-$C_6$ alkyl is optionally substituted with 1 or 2 —OH groups;

—C(O)$R^h$ wherein $R^h$ is $C_1$-$C_6$ alkyl;

C(O)O$R^h$ wherein $R^h$ is hydrogen, $C_1$-$C_6$ alkyl or —CH$_2$-phenyl; or

—SO$_2R^h$ wherein $R^h$ is $C_1$-$C_6$ haloalkyl or $C_1$-$C_6$ alkyl.

In certain embodiments, $R^6$ is hydrogen or $C_1$-$C_3$ alkyl; and $R^7$ is hydrogen or $C_1$-$C_3$ alkyl.

In certain embodiments, $R^6$ is hydrogen and $R^7$ is hydrogen.

In certain embodiments, $R^6$ is hydrogen or $C_1$-$C_3$ alkyl; and $R^7$ is —($C_1$-$C_6$ alkylenyl)-$G^{3A}$. In some such embodiments, $R^7$ is —(CH$_2$)-$G^{3A}$.

In certain embodiments, $G^{3A}$ is phenyl which is optionally substituted with 1, 2, or 3 independently selected $R^s$ groups. In some such embodiments, each $R^s$ is independently $C_1$-$C_3$ alkyl, halogen, $C_1$-$C_3$ haloalkyl, or —O$R^j$ wherein $R^j$ is hydrogen or $C_1$-$C_3$ alkyl. In some such embodiments, each $R^s$ is independently —O$R^j$ wherein $R^j$ is $C_1$-$C_3$ alkyl.

In certain embodiments of, $R^8$ is hydrogen, $C_1$-$C_6$ haloalkyl, or $C_1$-$C_6$ alkyl.

In certain embodiments, $R^8$ is hydrogen.

In certain embodiments, $R^9$, $R^{10}$, and $R^{13}$, are each independently hydrogen, halogen, —O$R^j$, $C_1$-$C_6$ haloalkyl, or $C_1$-$C_6$ alkyl.

In certain embodiments, $R^9$, $R^{10}$, and $R^{13}$, are each independently hydrogen or halogen.

In certain embodiments, $R^9$, $R^{10}$, and $R^{13}$ are hydrogen.

In certain embodiments, $R^{11}$ and $R^{12}$, are each independently hydrogen, $C_1$-$C_3$ alkyl, or halogen.

In certain embodiments, $R^{11}$ and $R^{12}$ are each independently hydrogen or halogen. In some such embodiments, the halogen is F.

In certain embodiments, $R^{11}$ and $R^{12}$ are hydrogen, or $R^{11}$ and $R^{12}$ are halogen. In some such embodiments, the halogen is F.

In certain embodiments, $R^{11}$ and $R^{12}$ are hydrogen.

In certain embodiments, $R^{11}$ and $R^{12}$ are halogen.

In certain embodiments, $R^{11}$ and $R^{12}$ are F.

In certain embodiments, $R^{14}$ is hydrogen or halogen.

In certain embodiments, $R^{14}$ is hydrogen.

Various embodiments of substituents $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, m, and R" have been discussed above. These substituents embodiments can be combined to form various embodiments of the invention. All embodiments of present compounds, formed by combining the substituent embodiments discussed above are within the scope of Applicant's invention, and some illustrative embodiments of present compounds are provided below.

In one embodiment, the invention is directed to compounds of formula (I), (Ia), (I-b), or (I-c) wherein $R^8$ is hydrogen; and m is 0.

In one embodiment, the invention is directed to compounds of formula (I), (Ia), (I-b), or (I-c) wherein $R^8$ is hydrogen; m is 0, and $R^9$, $R^{10}$, and $R^{13}$ are each independently hydrogen or halogen.

In one embodiment, the invention is directed to compounds of formula (I), (Ia), (I-b), or (I-c) wherein $R^8$ is hydrogen; m is 0, and $R^9$, $R^{10}$, and $R^{13}$ are hydrogen.

In one embodiment, the invention is directed to compounds of formula (I), (Ia), (I-b), or (I-c) wherein $R^8$ is hydrogen; m is 0, $R^9$, $R^{10}$, and $R^{13}$ are each independently hydrogen or halogen; and $R^{11}$ and $R^{12}$ are hydrogen, or $R^{11}$ and $R^{12}$ are halogen. In some such embodiment, the halogen is F.

In one embodiment, the invention is directed to compounds of formula (I), (Ia), (I-b), or (I-c) wherein $R^8$ is hydrogen; m is 0, $R^9$, $R^{10}$, and $R^{13}$ are hydrogen, and $R^{11}$ and $R^{12}$ are halogen. In some such embodiment, $R^{11}$ and $R^{12}$ are F.

In one embodiment, the invention is directed to compounds of formula (I), (Ia), (I-b), or (I-c) wherein $R^8$ is hydrogen; m is 0, $R^9$, $R^{10}$, and $R^{13}$ are hydrogen, $R^{11}$ and $R^{12}$ are halogen, and $R^1$ is hydrogen, halogen, $C_1$-$C_6$ haloalkyl, $C_1$-$C_6$ alkyl, —O$R^{14}$, or —C(O)O$R^{1B}$; wherein $R^{14}$ is $C_1$-$C_3$ haloalkyl or $C_1$-$C_3$ alkyl; and $R^{1B}$ is hydrogen or $C_1$-$C_3$ alkyl. In some such embodiment, $R^{11}$ and $R^{12}$ are F.

In one embodiment, the invention is directed to compounds of formula (I), (Ia), or (I-c), wherein
$R^8$ is hydrogen;
m is 0,
$R^9$, $R^{10}$, and $R^{13}$ are hydrogen,
$R^{11}$ and $R^{12}$ are halogen,
$R^1$ is hydrogen, halogen, $C_1$-$C_6$ haloalkyl, $C_1$-$C_6$ alkyl, —O$R^{14}$, or —C(O)O$R^{1B}$; wherein $R^{14}$ is $C_1$-$C_3$ haloalkyl or $C_1$-$C_3$ alkyl; and $R^{1B}$ is hydrogen or $C_1$-$C_3$ alkyl; and
$R^2$ is hydrogen, halogen, $C_1$-$C_6$ haloalkyl, $C_1$-$C_6$ alkyl, —O$R^{14}$, or —C(O)O$R^{1B}$; wherein $R^{14}$ is hydrogen, $C_1$-$C_3$ haloalkyl, or $C_1$-$C_3$ alkyl wherein the $C_1$-$C_3$ alkyl is optionally substituted with one substituent selected from the group consisting of —O$R^{ZA}$, —C(O)OH, and $G^{1A}$; and $R^{1B}$ is hydrogen or $C_1$-$C_3$ alkyl.

In some such embodiment, $G^{1A}$ is phenyl optionally substituted with 1, 2, or 3 $R^s$ groups wherein each $R^s$ is independently $C_1$-$C_3$ alkyl, $C_1$-$C_3$ haloalkyl, halogen, or —OCH$_3$. In some such embodiment, $G^{1A}$ is unsubstituted phenyl. In some such embodiment, $R^{ZA}$ is $C_1$-$C_3$ haloalkyl or $C_1$-$C_3$ alkyl.

In one embodiment, the invention is directed to compounds of formula (I), (Ia), or (I-b), wherein
$R^8$ is hydrogen;
m is 0,
$R^9$, $R^{10}$, and $R^{13}$ are hydrogen,
$R^{11}$ and $R^{12}$ are halogen,
$R^1$ is hydrogen, halogen, $C_1$-$C_6$ haloalkyl, $C_1$-$C_6$ alkyl, —O$R^{14}$, or —C(O)O$R^{1B}$; wherein $R^{14}$ is $C_1$-$C_3$ haloalkyl or $C_1$-$C_3$ alkyl; and $R^{1B}$ is hydrogen or $C_1$-$C_3$ alkyl; and
$R^3$ is hydrogen or halogen.

In one embodiment, the invention is directed to compounds of formula (I), (Ia), (I-b), or (I-c) wherein
$R^8$ is hydrogen;
m is 0, $R^9$, $R^{10}$, and $R^{13}$ are hydrogen,
$R^{11}$ and $R^{12}$ are halogen, and
$R^{14}$ is hydrogen or halogen.

In one embodiment, the invention is directed to compounds of formula (I), (Ia), (I-b), or (I-c) wherein
$R^4$ is hydrogen, $C_1$-$C_6$ haloalkyl, or $C_1$-$C_6$ alkyl;
$R^5$ is hydrogen, $C_1$-$C_6$ haloalkyl, $C_1$-$C_6$ alkyl, or $G^{2A}$;
$R^6$ is hydrogen or $C_1$-$C_3$ alkyl; and
$R^7$ is hydrogen or $C_1$-$C_3$ alkyl.

In some such embodiment, $G^{2A}$ is phenyl, $C_3$-$C_6$ cycloalkyl, 5-6 membered heteroaryl, or 4-6 membered heterocycle. In some such embodiment, $G^{2A}$ is phenyl, cyclopropyl, cyclohexyl, pyridinyl, tetrahydropyranyl, or azetidinyl. In some such embodiment, $G^{2A}$ is phenyl or cyclohexyl. In some such embodiment, $G^{2A}$ is phenyl. In some such embodiment, $G^{2A}$ is cyclohexyl. Each $G^{2A}$ is optionally substituted with 1, 2, or 3 independently selected $R^q$ groups.

In one embodiment, the invention is directed to compounds of formula (I) or (Ia) wherein
$R^4$ and $R^5$, together with the carbon atom to which they are attached, form a $C_3$-$C_6$ cycloalkyl or a 4-6 membered heterocycle; wherein the $C_3$-$C_6$ cycloalkyl and the 4-6 membered heterocycle are each optionally substituted with 1, 2, or 3 independently selected $R^p$ groups;
$R^6$ is hydrogen or $C_1$-$C_3$ alkyl; and
$R^7$ is hydrogen or $C_1$-$C_3$ alkyl.

In some such embodiment, $R^p$, when present, are each independently
$C_1$-$C_6$ alkyl wherein the $C_1$-$C_6$ alkyl is optionally substituted with 1 or 2 —OH groups;
—C(O)$R^h$ wherein $R^h$ is $C_1$-$C_6$ alkyl;
—C(O)O$R^h$ wherein $R^h$ is hydrogen, $C_1$-$C_6$ alkyl, or —CH$_2$-phenyl; or
—SO$_2R^h$ wherein $R^h$ is $C_1$-$C_6$ haloalkyl or $C_1$-$C_6$ alkyl.

In one embodiment, the invention is directed to compounds of formula (I) or (I-a) wherein
$R^4$ is hydrogen or $C_1$-$C_3$ alkyl;
$R^5$ is hydrogen or $C_1$-$C_3$ alkyl;
$R^6$ is hydrogen or $C_1$-$C_3$ alkyl; and
$R^7$ is —($C_1$-$C_6$ alkylenyl)-$G^{3A}$.

In some such embodiment, $R^7$ is —(CH$_2$)-$G^{3A}$. In some such embodiment, $G^{3A}$ is phenyl optionally substituted with 1, 2, or 3 independently selected $R^s$ groups. In some such embodiment, $G^{3A}$ is phenyl optionally substituted with 1, 2, or 3 $R^s$ groups wherein each $R^s$ is independently $C_1$-$C_3$ alkyl, $C_1$-$C_3$ haloalkyl, halogen, or —O$R^j$ wherein $R^j$ is $C_1$-$C_3$ alkyl.

In one embodiment, the invention is directed to compounds of formula (I) wherein
$R^8$ is hydrogen;
m is 0,
$R^9$, $R^{10}$, and $R^{13}$ are hydrogen,
$R^{11}$ and $R^{12}$ are halogen,
$R^4$ is hydrogen, $C_1$-$C_6$ haloalkyl, or $C_1$-$C_6$ alkyl;
$R^5$ is hydrogen, $C_1$-$C_6$ haloalkyl, $C_1$-$C_6$ alkyl, or $G^{2A}$;
$R^6$ is hydrogen or $C_1$-$C_3$ alkyl;
$R^7$ is hydrogen or $C_1$-$C_3$ alkyl; and
$R^{14}$ and $R^3$ are each independently hydrogen or halogen.

In some such embodiment, $G^{2A}$ is phenyl, $C_3$-$C_6$ cycloalkyl, 5-6 membered heteroaryl, or 4-6 membered heterocycle. In some such embodiment, $G^{2A}$ is phenyl, cyclopropyl, cyclohexyl, pyridinyl, tetrahydropyranyl, or azetidinyl. In some such embodiment, $G^{2A}$ is phenyl or cyclohexyl. In some such embodiment, $G^{2A}$ is phenyl. In some such embodiment, $G^{2A}$ is cyclohexyl. Each $G^{2A}$ is optionally substituted with 1, 2, or 3 independently selected $R^q$ groups.

In one embodiment, the invention is directed to compounds of formula (I) wherein
$R^8$ is hydrogen;
m is 0,
$R^9$, $R^{10}$, and $R^{13}$ are hydrogen,
$R^{11}$ and $R^{12}$ are halogen,
$R^4$ and $R^5$, together with the carbon atom to which they are attached, form a $C_3$-$C_6$ cycloalkyl or a 4-6 membered heterocycle; wherein the $C_3$-$C_6$ cycloalkyl and the 4-6 membered heterocycle are each optionally substituted with 1, 2, or 3 independently selected $R^p$ groups;
$R^6$ is hydrogen or $C_1$-$C_3$ alkyl;
$R^7$ is hydrogen or $C_1$-$C_3$ alkyl; and
$R^{14}$ and $R^3$ are each independently hydrogen or halogen.

In some such embodiment, $R^p$, when present, are each independently
$C_1$-$C_6$ alkyl wherein the $C_1$-$C_6$ alkyl is optionally substituted with 1 or 2 —OH groups;
—C(O)$R^h$ wherein $R^h$ is $C_1$-$C_6$ alkyl;
—C(O)O$R^h$ wherein $R^h$ is hydrogen, $C_1$-$C_6$ alkyl, or —CH$_2$-phenyl; or
—SO$_2R^h$ wherein $R^h$ is $C_1$-$C_6$ haloalkyl or $C_1$-$C_6$ alkyl.

In one embodiment, the invention is directed to compounds of formula (I) wherein
$R^8$ is hydrogen;
m is 0,
$R^9$, $R^{10}$, and $R^{13}$ are hydrogen,
$R^{11}$ and $R^{12}$ are halogen,
$R^4$ is hydrogen or $C_1$-$C_3$ alkyl;
$R^5$ is hydrogen or $C_1$-$C_3$ alkyl;
$R^6$ is hydrogen or $C_1$-$C_3$ alkyl;
$R^7$ is —($C_1$-$C_6$ alkylenyl)-$G^{3A}$; and
$R^{14}$ and $R^3$ are each independently hydrogen or halogen.

In some such embodiment, $R^7$ is —(CH$_2$)-$G^{3A}$. In some such embodiment, $G^{3A}$ is phenyl optionally substituted with 1, 2, or 3 independently selected $R^s$ groups. In some such embodiment, $G^{3A}$ is phenyl optionally substituted with 1, 2, or 3 $R^s$ groups wherein each $R^s$ is independently $C_1$-$C_3$ alkyl, $C_1$-$C_3$ haloalkyl, halogen, or —O$R^j$ wherein $R^j$ is $C_1$-$C_3$ alkyl.

In one embodiment, the invention is directed to compounds of formula (I-a) wherein $R^8$ is hydrogen; and m is 0.

In one embodiment, the invention is directed to compounds of formula (I-a) wherein $R^8$ is hydrogen; m is 0, and $R^9$, $R^{10}$, and $R^{13}$ are each independently hydrogen or halogen.

In one embodiment, the invention is directed to compounds of formula (I-a) wherein $R^8$ is hydrogen; m is 0, and $R^9$, $R^{10}$, and $R^{13}$ are hydrogen.

In one embodiment, the invention is directed to compounds of formula (I-a) wherein $R^8$ is hydrogen; m is 0, $R^9$, $R^{10}$, and $R^{13}$ are each independently hydrogen or halogen; and $R^{11}$ and $R^{12}$ are hydrogen, or $R^{11}$ and $R^{12}$ are halogen. In some such embodiment, the halogen is F.

In one embodiment, the invention is directed to compounds of formula (I-a) wherein $R^8$ is hydrogen; m is 0, $R^9$, $R^{10}$, and $R^{13}$ are hydrogen, and $R^{11}$ and $R^{12}$ are halogen. In some such embodiment, $R^{11}$ and $R^{12}$ are F.

In one embodiment, the invention is directed to compounds of formula (I-a) wherein $R^8$ is hydrogen; m is 0, $R^9$, $R^{10}$, and $R^{13}$ are hydrogen, $R^{11}$ and $R^{12}$ are halogen, and $R^1$ is hydrogen, halogen, $C_1$-$C_6$ haloalkyl, $C_1$-$C_6$ alkyl, —O$R^{14}$, or —C(O)O$R^{1B}$; wherein $R^{14}$ is $C_1$-$C_3$ haloalkyl or $C_1$-$C_3$ alkyl; and $R^{1B}$ is hydrogen or $C_1$-$C_3$ alkyl. In some such embodiment, $R^{11}$ and $R^{12}$ are F.

In one embodiment, the invention is directed to compounds of formula (I-a) wherein
$R^8$ is hydrogen;
m is 0,
$R^9$, $R^{10}$, and $R^{13}$ are hydrogen,
$R^{11}$ and $R^{12}$ are halogen,
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl; and
$R^2$ is hydrogen, halogen, $C_1$-$C_6$ haloalkyl, $C_1$-$C_6$ alkyl, —$OR^{1A}$, or —$C(O)OR^{1B}$; wherein $R^{1A}$ is hydrogen, $C_1$-$C_3$ haloalkyl, or $C_1$-$C_3$ alkyl wherein the $C_1$-$C_3$ alkyl is optionally substituted with one substituent selected from the group consisting of —$OR^{ZA}$, —$C(O)OH$, and $G^{1A}$; and $R^{1B}$ is hydrogen or $C_1$-$C_3$ alkyl.

In some such embodiment, $G^{1A}$ is phenyl optionally substituted with 1, 2, or 3 $R^s$ groups wherein each $R^s$ is independently $C_1$-$C_3$ alkyl, $C_1$-$C_3$ haloalkyl, halogen, or —$OCH_3$. In some such embodiments, $G^{1A}$ is unsubstituted phenyl. In some such embodiments, $R^{ZA}$ is $C_1$-$C_3$ haloalkyl or $C_1$-$C_3$ alkyl.

In one embodiment, the invention is directed to compounds of formula (I-a) wherein
$R^8$ is hydrogen;
m is 0,
$R^9$, $R^{10}$, and $R^{13}$ are hydrogen,
$R^{11}$ and $R^{12}$ are halogen,
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl; and
$R^3$ is hydrogen or halogen.

In one embodiment, the invention is directed to compounds of formula (I-a) wherein
$R^8$ is hydrogen;
m is 0,
$R^9$, $R^{10}$, and $R^{13}$ are hydrogen,
$R^{11}$ and $R^{12}$ are halogen, and
$R^{14}$ is hydrogen or halogen.

In one embodiment, the invention is directed to compounds of formula (I-a) wherein
$R^4$ is hydrogen, $C_1$-$C_6$ haloalkyl, or $C_1$-$C_6$ alkyl;
$R^5$ is hydrogen, $C_1$-$C_6$ haloalkyl, $C_1$-$C_6$ alkyl, or $G^{2A}$;
$R^6$ is hydrogen or $C_1$-$C_3$ alkyl; and
$R^7$ is hydrogen or $C_1$-$C_3$ alkyl.

In some such embodiment, $G^{2A}$ is phenyl, $C_3$-$C_6$ cycloalkyl, 5-6 membered heteroaryl, or 4-6 membered heterocycle. In some such embodiment, $G^{2A}$ is phenyl, cyclopropyl, cyclohexyl, pyridinyl, tetrahydropyranyl, or azetidinyl. In some such embodiment, $G^{2A}$ is phenyl or cyclohexyl. In some such embodiment, $G^{2A}$ is phenyl. In some such embodiment, $G^{2A}$ is cyclohexyl. Each $G^{2A}$ is optionally substituted with 1, 2, or 3 independently selected $R^q$ groups.

In one embodiment, the invention is directed to compounds of formula (I-a) wherein
$R^4$ and $R^5$, together with the carbon atom to which they are attached, form a $C_3$-$C_6$ cycloalkyl or a 4-6 membered heterocycle; wherein the $C_3$-$C_6$ cycloalkyl and the 4-6 membered heterocycle are each optionally substituted with 1, 2, or 3 independently selected $R^p$ groups;
$R^6$ is hydrogen or $C_1$-$C_3$ alkyl; and
$R^7$ is hydrogen or $C_1$-$C_3$ alkyl.

In some such embodiment, $R^p$, when present, are each independently $C_1$-$C_6$ alkyl wherein the $C_1$-$C_6$ alkyl is optionally substituted with 1 or 2 —OH groups;
—$C(O)R^h$ wherein $R^h$ is $C_1$-$C_6$ alkyl;
—$C(O)OR^h$ wherein $R^h$ is hydrogen, $C_1$-$C_6$ alkyl, or —$CH_2$-phenyl; or
—$SO_2R^h$ wherein $R^h$ is $C_1$-$C_6$ haloalkyl or $C_1$-$C_6$ alkyl.

In one embodiment, the invention is directed to compounds of formula (I-a) wherein
$R^4$ is hydrogen or $C_1$-$C_3$ alkyl;
$R^5$ is hydrogen or $C_1$-$C_3$ alkyl;
$R^6$ is hydrogen or $C_1$-$C_3$ alkyl; and
$R^7$ is —($C_1$-$C_6$ alkylenyl)-$G^{3A}$.

In some such embodiment, $R^7$ is —$(CH_2)$-$G^{3A}$. In some such embodiment, $G^{3A}$ is phenyl optionally substituted with 1, 2, or 3 independently selected $R^s$ groups. In some such embodiment, $G^{3A}$ is phenyl optionally substituted with 1, 2, or 3 $R^s$ groups wherein each $R^s$ is independently $C_1$-$C_3$ alkyl, $C_1$-$C_3$ haloalkyl, halogen, or —OR wherein $R^j$ is $C_1$-$C_3$ alkyl.

In one embodiment, the invention is directed to compounds of formula (I-a) wherein
$R^8$ is hydrogen;
m is 0,
$R^9$, $R^{10}$, and $R^{13}$ are hydrogen,
$R^{11}$ and $R^{12}$ are halogen,
$R^4$ is hydrogen, $C_1$-$C_6$ haloalkyl, or $C_1$-$C_6$ alkyl;
$R^5$ is hydrogen, $C_1$-$C_6$ haloalkyl, $C_1$-$C_6$ alkyl, or $G^{2A}$;
$R^6$ is hydrogen or $C_1$-$C_3$ alkyl;
$R^7$ is hydrogen or $C_1$-$C_3$ alkyl; and
$R^{14}$ and $R^3$ are each independently hydrogen or halogen.

In some such embodiment, $G^{2A}$ is phenyl, $C_3$-$C_6$ cycloalkyl, 5-6 membered heteroaryl, or 4-6 membered heterocycle. In some such embodiment, $G^{2A}$ is phenyl, cyclopropyl, cyclohexyl, pyridinyl, tetrahydropyranyl, or azetidinyl. In some such embodiment, $G^{2A}$ is phenyl or cyclohexyl. In some such embodiment, $G^{2A}$ is phenyl. In some such embodiment, $G^{2A}$ is cyclohexyl. Each $G^{2A}$ is optionally substituted with 1, 2, or 3 independently selected $R^q$ groups.

In one embodiment, the invention is directed to compounds of formula (I-a) wherein
$R^8$ is hydrogen;
m is 0,
$R^9$, $R^{10}$, and $R^{13}$ are hydrogen,
$R^{11}$ and $R^{12}$ are halogen,
$R^4$ and $R^5$, together with the carbon atom to which they are attached, form a $C_3$-$C_6$ cycloalkyl or a 4-6 membered heterocycle; wherein the $C_3$-$C_6$ cycloalkyl and the 4-6 membered heterocycle are each optionally substituted with 1, 2, or 3 independently selected $R^p$ groups;
$R^6$ is hydrogen or $C_1$-$C_3$ alkyl;
$R^7$ is hydrogen or $C_1$-$C_3$ alkyl; and
$R^{14}$ and $R^3$ are each independently hydrogen or halogen.

In some such embodiment, $R^p$, when present, are each independently
$C_1$-$C_6$ alkyl wherein the $C_1$-$C_6$ alkyl is optionally substituted with 1 or 2 —OH groups;
—$C(O)R^h$ wherein $R^h$ is $C_1$-$C_6$ alkyl;
—$C(O)OR^h$ wherein $R^h$ is hydrogen, $C_1$-$C_6$ alkyl, or —$CH_2$-phenyl; or
—$SO_2R^h$ wherein $R^h$ is $C_1$-$C_6$ haloalkyl or $C_1$-$C_6$ alkyl.

In one embodiment, the invention is directed to compounds of formula (I-a) wherein
$R^8$ is hydrogen;
m is 0,
$R^9$, $R^{10}$, and $R^{13}$ are hydrogen,
$R^{11}$ and $R^{12}$ are halogen, $R^4$ is hydrogen or $C_1$-$C_3$ alkyl;
$R^5$ is hydrogen or $C_1$-$C_3$ alkyl;
$R^6$ is hydrogen or $C_1$-$C_3$ alkyl;
$R^7$ is —($C_1$-$C_6$ alkylenyl)-$G^{3A}$; and
$R^{14}$ and $R^3$ are each independently hydrogen or halogen.

In some such embodiment, $R^7$ is —$(CH_2)$-$G^{3A}$. In some such embodiment, $G^{3A}$ is phenyl optionally substituted with 1, 2, or 3 independently selected $R^s$ groups. In some such embodiment, $G^{3A}$ is phenyl optionally substituted with 1, 2, or 3 $R^s$ groups wherein each $R^s$ is independently $C_1$-$C_3$ alkyl, $C_1$-$C_3$ haloalkyl, halogen, or —$OR^j$ wherein $R^j$ is $C_1$-$C_3$ alkyl.

In one embodiment, the invention is directed to compounds of formula (I-b) wherein $R^8$ is hydrogen; and m is 0.

In one embodiment, the invention is directed to compounds of formula (I-b) wherein $R^8$ is hydrogen; m is 0, and $R^9$, $R^{10}$, and $R^{13}$ are each independently hydrogen or halogen.

In one embodiment, the invention is directed to compounds of formula (I-b) wherein $R^8$ is hydrogen; m is 0, and $R^9$, $R^{10}$, and $R^{13}$ are hydrogen.

In one embodiment, the invention is directed to compounds of formula (I-b) wherein $R^8$ is hydrogen; m is 0, $R^9$, $R^{10}$, and $R^{13}$ are each independently hydrogen or halogen; and $R^{11}$ and $R^{12}$ are hydrogen, or $R^{11}$ and $R^{12}$ are halogen. In some such embodiment, the halogen is F.

In one embodiment, the invention is directed to compounds of formula (I-b) wherein $R^8$ is hydrogen; m is 0, $R^9$, $R^{10}$, and $R^{13}$ are hydrogen, and $R^{11}$ and $R^{12}$ are halogen. In some such embodiment, $R^{11}$ and $R^{12}$ are F.

In one embodiment, the invention is directed to compounds of formula (I-b) wherein $R^8$ is hydrogen; m is 0, $R^9$, $R^{10}$, and $R^{13}$ are hydrogen, $R^{11}$ and $R^{12}$ are halogen, and $R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl. In some such embodiment, $R^{11}$ and $R^{12}$ are F.

In one embodiment, the invention is directed to compounds of formula (I-b) wherein
$R^8$ is hydrogen;
m is 0,
$R^9$, $R^{10}$, and $R^{13}$ are hydrogen,
$R^{11}$ and $R^{12}$ are halogen,
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl; and
$R^3$ is hydrogen or halogen.

In one embodiment, the invention is directed to compounds of formula (I-b) wherein
$R^8$ is hydrogen;
m is 0,
$R^9$, $R^{10}$, and $R^{13}$ are hydrogen,
$R^{11}$ and $R^{12}$ are halogen, and
$R^{14}$ is hydrogen or halogen.

In one embodiment, the invention is directed to compounds of formula (I-b) wherein
$R^4$ is hydrogen, $C_1$-$C_6$ haloalkyl, or $C_1$-$C_6$ alkyl;
$R^5$ is hydrogen, $C_1$-$C_6$ haloalkyl, $C_1$-$C_6$ alkyl, or $G^{2A}$;
$R^6$ is hydrogen or $C_1$-$C_3$ alkyl; and
$R^7$ is hydrogen or $C_1$-$C_3$ alkyl.

In some such embodiment, $G^{2A}$ is phenyl, $C_3$-$C_6$ cycloalkyl, 5-6 membered heteroaryl, or 4-6 membered heterocycle. In some such embodiment, $G^{2A}$ is phenyl, cyclopropyl, cyclohexyl, pyridinyl, tetrahydropyranyl, or azetidinyl. In some such embodiment, $G^{2A}$ is phenyl or cyclohexyl. In some such embodiment, $G^{2A}$ is phenyl. In some such embodiment, $G^{2A}$ is cyclohexyl. Each $G^{2A}$ is optionally substituted with 1, 2, or 3 independently selected $R^q$ groups.

In one embodiment, the invention is directed to compounds of formula (I-b) wherein
$R^8$ is hydrogen;
m is 0,
$R^9$, $R^{10}$, and $R^{13}$ are hydrogen,
$R^{11}$ and $R^{12}$ are halogen,
$R^4$ is hydrogen, $C_1$-$C_6$ haloalkyl, or $C_1$-$C_6$ alkyl;
$R^5$ is hydrogen, $C_1$-$C_6$ haloalkyl, $C_1$-$C_6$ alkyl, or $G^{2A}$;
$R^6$ is hydrogen or $C_1$-$C_3$ alkyl;
$R^7$ is hydrogen or $C_1$-$C_3$ alkyl; and
$R^{14}$ and $R^3$ are each independently hydrogen or halogen.

In some such embodiment, $G^{2A}$ is phenyl, $C_3$-$C_6$ cycloalkyl, 5-6 membered heteroaryl, or 4-6 membered heterocycle. In some such embodiment, $G^{2A}$ is phenyl, cyclopropyl, cyclohexyl, pyridinyl, tetrahydropyranyl, or azetidinyl. In some such embodiment, $G^{2A}$ is phenyl or cyclohexyl. In some such embodiment, $G^{2A}$ is phenyl. In some such embodiment, $G^{2A}$ is cyclohexyl. Each $G^{2A}$ is optionally substituted with 1, 2, or 3 independently selected $R^q$ groups.

In one embodiment, the invention is directed to compounds of formula (I-b) wherein
$R^8$ is hydrogen;
m is 0,
$R^9$, $R^{10}$, and $R^{13}$ are hydrogen,
$R^{11}$ and $R^{12}$ are halogen,
$R^4$ is hydrogen or $C_1$-$C_3$ alkyl;
$R^5$ is $G^{2A}$ wherein $G^{2A}$ is phenyl which is substituted with one $R^q$; wherein $R^q$ is —$C(O)OR^h$ wherein $R^h$ is hydrogen or $C_1$-$C_3$ alkyl;
$R^6$ is hydrogen or $C_1$-$C_3$ alkyl;
$R^7$ is hydrogen or $C_1$-$C_3$ alkyl;
$R^{14}$ and $R^3$ are each independently hydrogen or halogen; and
$R^1$ is hydrogen.

In some such embodiment, $R^q$ is —$C(O)OR^h$ wherein $R^h$ is hydrogen. In some such embodiment, $R^q$ is —$C(O)OR^h$ wherein $R^h$ is $C_1$-$C_3$ alkyl.

In one embodiment, the invention is directed to compounds of formula (I-c) wherein $R^8$ is hydrogen; and m is 0.

In one embodiment, the invention is directed to compounds of formula (I-c) wherein $R^8$ is hydrogen; m is 0, and $R^9$, $R^{10}$, and $R^{13}$ are each independently hydrogen or halogen.

In one embodiment, the invention is directed to compounds of formula (I-c) wherein $R^8$ is hydrogen; m is 0, and $R^9$, $R^{10}$, and $R^{13}$ are hydrogen.

In one embodiment, the invention is directed to compounds of formula (I-c) wherein $R^8$ is hydrogen; m is 0, $R^9$, $R^{10}$, and $R^{13}$ are each independently hydrogen or halogen; and $R^{11}$ and $R^{12}$ are hydrogen, or $R^{11}$ and $R^{12}$ are halogen. In some such embodiment, the halogen is F.

In one embodiment, the invention is directed to compounds of formula (I-c) wherein $R^8$ is hydrogen; m is 0, $R^9$, $R^{10}$, and $R^{13}$ are hydrogen, and $R^{11}$ and $R^{12}$ are halogen. In some such embodiment, $R^{11}$ and $R^{12}$ are F.

In one embodiment, the invention is directed to compounds of formula (I-c) wherein $R^8$ is hydrogen; m is 0, $R^9$, $R^{10}$, and $R^{13}$ are hydrogen, $R^{11}$ and $R^{12}$ are halogen, and $R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl. In some such embodiment, $R^{11}$ and $R^{12}$ are F.

In one embodiment, the invention is directed to compounds of formula (I-c) wherein R⁸ is hydrogen;
m is 0,
R⁹, R¹⁰, and R¹³ are hydrogen,
R¹¹ and R¹² are halogen,
R¹ is hydrogen, halogen, $C_1$-$C_6$ haloalkyl, $C_1$-$C_6$ alkyl, —OR$^{1A}$, or —C(O)OR$^{1B}$; wherein R$^{1A}$ is $C_1$-$C_3$ haloalkyl or $C_1$-$C_3$ alkyl; and R$^{1B}$ is hydrogen or $C_1$-$C_3$ alkyl; and
R² is hydrogen, halogen, $C_1$-$C_6$ haloalkyl, $C_1$-$C_6$ alkyl, —OR$^{1A}$, or —C(O)OR$^{1B}$; wherein R$^{1A}$ is hydrogen, $C_1$-$C_3$ haloalkyl, or $C_1$-$C_3$ alkyl wherein the $C_1$-$C_3$ alkyl is optionally substituted with one substituent selected from the group consisting of —OR$^{ZA}$, —C(O)OH, and G$^{1A}$; and R$^{1B}$ is hydrogen or $C_1$-$C_3$ alkyl.

In some such embodiment, G$^{1A}$ is phenyl optionally substituted with 1, 2, or 3 R$^s$ groups wherein each R$^s$ is independently $C_1$-$C_3$ alkyl, $C_1$-$C_3$ haloalkyl, halogen, or —OCH₃. In some such embodiments, G$^{1A}$ is unsubstituted phenyl. In some such embodiments, R$^{ZA}$ is $C_1$-$C_3$ haloalkyl or $C_1$-$C_3$ alkyl.

In one embodiment, the invention is directed to compounds of formula (I-c) wherein
R⁸ is hydrogen;
m is 0,
R⁹, R¹⁰, and R¹³ are hydrogen,
R¹¹ and R¹² are halogen, and
R¹⁴ is hydrogen or halogen.

In one embodiment, the invention is directed to compounds of formula (I-c) wherein
R⁴ is hydrogen, $C_1$-$C_6$ haloalkyl, or $C_1$-$C_6$ alkyl;
R⁵ is hydrogen, $C_1$-$C_6$ haloalkyl, $C_1$-$C_6$ alkyl, or G$^{2A}$;
R⁶ is hydrogen or $C_1$-$C_3$ alkyl; and
R⁷ is hydrogen or $C_1$-$C_3$ alkyl.

In some such embodiment, G$^{2A}$ is phenyl, $C_3$-$C_6$ cycloalkyl, 5-6 membered heteroaryl, or 4-6 membered heterocycle. In some such embodiment, G$^{2A}$ is phenyl, cyclopropyl, cyclohexyl, pyridinyl, tetrahydropyranyl, or azetidinyl. In some such embodiment, G$^{2A}$ is phenyl or cyclohexyl. In some such embodiment, G$^{2A}$ is phenyl. In some such embodiment, G$^{2A}$ is cyclohexyl. Each G$^{2A}$ is optionally substituted with 1, 2, or 3 independently selected R$^q$ groups.

In one embodiment, the invention is directed to compounds of formula (I-c) wherein
R⁸ is hydrogen;
m is 0,
R⁹, R¹⁰, and R¹³ are hydrogen,
R¹¹ and R¹² are halogen,
R⁴ is hydrogen, $C_1$-$C_6$ haloalkyl, or $C_1$-$C_6$ alkyl;
R⁵ is hydrogen, $C_1$-$C_6$ haloalkyl, $C_1$-$C_6$ alkyl, or G$^{2A}$;
R⁶ is hydrogen or $C_1$-$C_3$ alkyl;
R⁷ is hydrogen or $C_1$-$C_3$ alkyl; and
R¹⁴ is hydrogen or halogen.

In some such embodiment, G$^{2A}$ is phenyl, $C_3$-$C_6$ cycloalkyl, 5-6 membered heteroaryl, or 4-6 membered heterocycle. In some such embodiment, G$^{2A}$ is phenyl, cyclopropyl, cyclohexyl, pyridinyl, tetrahydropyranyl, or azetidinyl. In some such embodiment, G$^{2A}$ is phenyl or cyclohexyl. In some such embodiment, G$^{2A}$ is phenyl. In some such embodiment, G$^{2A}$ is cyclohexyl. Each G$^{2A}$ is optionally substituted with 1, 2, or 3 independently selected R$^q$ groups.

In one embodiment, the invention is directed to compounds of formula (I-c) wherein
R⁸ is hydrogen;
m is 0,
R⁹, R¹⁰, and R¹³ are hydrogen,
R¹¹ and R¹² are halogen,
R⁴ is hydrogen or $C_1$-$C_3$ alkyl;
R⁵ is G$^{2A}$ wherein G$^{2A}$ is phenyl which is substituted with one R$^q$; wherein R$^q$ is —C(O)OR$^h$ wherein R$^h$ is hydrogen or $C_1$-$C_3$ alkyl;
R⁶ is hydrogen or $C_1$-$C_3$ alkyl;
R⁷ is hydrogen or $C_1$-$C_3$ alkyl;
R¹⁴ is hydrogen or halogen;
R¹ is hydrogen; and
R² is hydrogen, halogen, or —OR$^{1A}$ wherein R$^{1A}$ is $C_1$-$C_3$ alkyl or $C_1$-$C_3$ haloalkyl.

In some such embodiment, R$^q$ is —C(O)OR$^h$ wherein R$^h$ is hydrogen. In some such embodiment, R$^q$ is —C(O)OR$^h$ wherein R$^h$ is $C_1$-$C_3$ alkyl.

One embodiment is directed to compounds of formula (I-d)

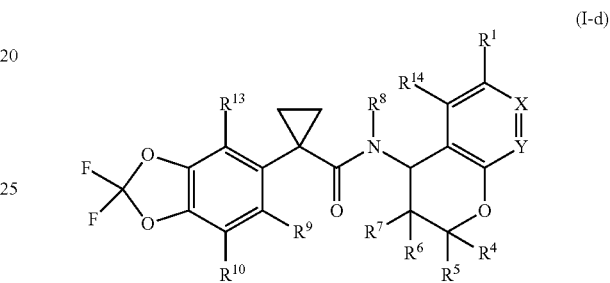

wherein
X is CR² and Y is CR³; or
X is N and Y is CR³; or
X is CR² and Y is N;
R¹ and R², at each occurrence, are each independently hydrogen, halogen, $C_1$-$C_6$ haloalkyl, $C_1$-$C_6$ alkyl, —OR$^{1A}$, —C(O)OR¹, —NR$^{1A}$R$^{2A}$, or —C(O)NR$^{1A}$R$^{2A}$;
R$^{1A}$ and R$^{2A}$, at each occurrence, are each independently hydrogen, $C_1$-$C_6$ haloalkyl, G$^{1A}$, or $C_1$-$C_6$ alkyl; wherein the $C_1$-$C_6$ haloalkyl and the $C_1$-$C_6$ alkyl are each optionally substituted with one or two substituents independently selected from the group consisting of —OR$^{ZA}$, —SR$^{ZA}$, —S(O)₂R$^{ZA}$, —C(O)R$^{ZA}$, —C(O)OR$^{ZA}$, —C(O)N(R$^{ZA}$)₂, —N(R$^{ZA}$)₂, —N(R$^{ZA}$)C(O)R$^{ZB}$, —N(R$^{ZA}$)S(O)₂R$^{ZB}$, —N(R$^{ZA}$)C(O)OR$^{ZB}$, —N(R$^{ZA}$)C(O)N(R$^{ZA}$)₂, —CN, and G$^{1A}$; or R$^{1A}$ and R$^{2A}$ together with the nitrogen atom to which they are attached form a 4-6 membered heterocycle wherein the 4-6 membered heterocycle is optionally substituted with 1, 2, or 3 substituents independently selected from the group consisting of halogen, $C_1$-$C_6$ alkyl, $C_1$-$C_6$ haloalkyl, —OR$^j$, and N(R$^j$)₂; wherein
R$^{ZA}$, at each occurrence, is independently hydrogen, $C_1$-$C_6$ haloalkyl, $C_1$-$C_6$ alkyl, G$^{1A}$, or —($C_1$-$C_6$ alkylenyl)-G$^{1A}$; and
R$^{ZB}$, at each occurrence, is independently $C_1$-$C_6$ haloalkyl, $C_1$-$C_6$ alkyl, G$^{1A}$, or —($C_1$-$C_6$ alkylenyl)-G$^{1A}$;
R$^{1B}$ is hydrogen, $C_1$-$C_6$ haloalkyl, or $C_1$-$C_6$ alkyl;
R³ and R¹⁴ are each independently hydrogen or halogen;
R⁴ is hydrogen, $C_1$-$C_6$ haloalkyl, or $C_1$-$C_6$ alkyl;
R⁵ is hydrogen, —C(O)R$^i$, —C(O)OH, —C(O)N(R$^h$)₂, $C_1$-$C_6$ haloalkyl, $C_1$-$C_6$ alkyl, or G$^{2A}$; wherein the $C_1$-$C_6$ haloalkyl and the $C_1$-$C_6$ alkyl are each optionally substituted with one or two substituents independently selected from the group consisting of —OR$^h$, —OC(O)N(R$^h$)₂, —C(O)R$^h$, —C(O)OR$^h$, —C(O)N(R$^h$)₂, —N(R$^h$)₂, —N(R$^h$)C(O)R$^i$, —N(R$^h$)S(O)₂R$^i$, —N(R$^h$)C(O)O(R$^i$), —N(R$^h$)C(O)N(R$^h$)₂, and G$^{2A}$; or $R^4$ and $R^5$, together with the carbon atom to which they are attached, form a $C_3$-$C_6$ cycloalkyl or a 4-6 membered heterocycle; wherein the $C_3$-$C_6$ cycloalkyl and the 4-6 membered heterocycle are each optionally substituted with 1, 2, or 3 independently selected $R^p$ groups;

$G^{2A}$, at each occurrence, is independently cycloalkyl, cycloalkenyl, heterocycle, aryl, or heteroaryl, each of which is independently unsubstituted or substituted with 1, 2, or 3 independently selected $R^q$ groups;

$R^p$ and $R^q$, at each occurrence, are each independently $C_1$-$C_6$ alkyl, halogen, $C_1$-$C_6$ haloalkyl, —CN, oxo, $NO_2$, —$OR^h$, —OC(O)$R^i$, —OC(O)N($R^h$)$_2$, —$SR^h$, —S(O)$_2R^h$, —S(O)$_2$N($R^h$)$_2$, —C(O)$R^h$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, or $G^A$, wherein the $C_1$-$C_6$ haloalkyl and the $C_1$-$C_6$ alkyl are each optionally substituted with one or two substituents independently selected from the group consisting of —$OR^h$, —OC(O)$R^i$, —OC(O)N($R^h$)$_2$, —$SR^h$, —S(O)$_2R^h$, —S(O)$_2$N($R^h$)$_2$, —C(O)$R^h$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, —CN, and $G^A$;

$R^h$, at each occurrence, is independently hydrogen, $C_1$-$C_6$ haloalkyl, $C_1$-$C_6$ alkyl, or $G^A$, wherein the $C_1$-$C_6$ haloalkyl and the $C_1$-$C_6$ alkyl are each optionally substituted with one or two substituents independently selected from the group consisting of —$OR^j$, —OC(O)N($R^j$)$_2$, —$SR^j$, —C(O)O$R^j$, —C(O)N($R^j$)$_2$, —N($R^j$)$_2$, —CN, and $G^A$;

$R^i$, at each occurrence, is independently $C_1$-$C_6$ haloalkyl, $C_1$-$C_6$ alkyl, or $G^A$, wherein the $C_1$-$C_6$ haloalkyl and the $C_1$-$C_6$ alkyl are each optionally substituted with one or two substituents independently selected from the group consisting of —$OR^j$, —OC(O)N($R^j$)$_2$, —$SR^j$, —C(O)O$R^j$, —C(O)N($R^j$)$_2$, —N($R^j$)$_2$, —CN, and $G^A$;

$R^6$ is hydrogen, halogen, $C_1$-$C_6$ haloalkyl, or $C_1$-$C_6$ alkyl;

$R^7$ is hydrogen, halogen, —$OR^j$, —N($R^j$)$_2$, —N($R^j$)C(O)$R^k$, $C_1$-$C_6$ haloalkyl, $C_1$-$C_6$ alkyl, $C_2$-$C_6$ alkenyl, or —($C_1$-$C_6$ alkylenyl)-$G^{3A}$;

$R^9$, $R^{10}$, and $R^{13}$, are each independently hydrogen or halogen;

$G^{1A}$, $G^{3A}$, and $G^A$, at each occurrence, are each independently cycloalkyl, cycloalkenyl, heterocycle, aryl, or heteroaryl, each of which is independently unsubstituted or substituted with 1, 2, or 3 independently selected $R^s$ groups; wherein $R^s$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, $NO_2$, —$OR^j$, —OC(O)$R^k$, —OC(O)N($R^j$)$_2$, —$SR^j$, —S(O)$_2R^j$, —S(O)$_2$N($R^j$)$_2$, —C(O)$R^j$, —C(O)O$R^j$, —C(O)N($R^j$)$_2$, —N($R^j$)$_2$, —N($R^j$)C(O)$R^k$, —N($R^j$)S(O)$_2R^k$, —N($R^j$)C(O)O($R^k$), —N($R^j$)C(O)N($R^j$)$_2$, —($C_1$-$C_6$ alkylenyl)-$OR^j$, —($C_1$-$C_6$ alkylenyl)-OC(O)$R^k$, —($C_1$-$C_6$ alkylenyl)-OC(O)N($R^j$)$_2$, —($C_1$-$C_6$ alkylenyl)-$SR^j$, —($C_1$-$C_6$ alkylenyl)-S(O)$_2R^j$, —($C_1$-$C_6$ alkylenyl)-S(O)$_2$N($R^j$)$_2$, —($C_1$-$C_6$ alkylenyl)-C(O)$R^j$, —($C_1$-$C_6$ alkylenyl)-C(O)O$R^j$, —($C_1$-$C_6$ alkylenyl)-C(O)N($R^j$)$_2$, —($C_1$-$C_6$ alkylenyl)-N($R^j$)$_2$, —($C_1$-$C_6$ alkylenyl)-N($R^j$)C(O)$R^k$, —($C_1$-$C_6$ alkylenyl)-N($R^j$)S(O)$_2R^k$, —($C_1$-$C_6$ alkylenyl)-N($R^j$)C(O)O($R^k$), —($C_1$-$C_6$ alkylenyl)-N($R^j$)C(O)N($R^j$)$_2$, or —($C_1$-$C_6$ alkylenyl)-CN;

$R^j$, at each occurrence, is independently hydrogen, $C_1$-$C_6$ alkyl, or $C_1$-$C_6$ haloalkyl; and $R^k$, at each occurrence, is independently $C_1$-$C_6$ alkyl or $C_1$-$C_6$ haloalkyl.

In one embodiment, the invention is directed to compounds of formula (I-d), wherein $R^9$, $R^{10}$, and $R^{13}$ are hydrogen.

In one embodiment, the invention is directed to compounds of formula (I-d), wherein $R^1$ is hydrogen, halogen, $C_1$-$C_6$ haloalkyl, $C_1$-$C_6$ alkyl, —$OR^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl.

In one embodiment, the invention is directed to compounds of formula (I-d), wherein
$R^9$, $R^{10}$, and $R^{13}$ are hydrogen; and
$R^1$ is hydrogen, halogen, $C_1$-$C_6$ haloalkyl, $C_1$-$C_6$ alkyl, —$OR^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen, $C_1$-$C_6$ haloalkyl, or $C_1$-$C_6$ alkyl;
$R^5$ is hydrogen, $C_1$-$C_6$ haloalkyl, or $C_1$-$C_6$ alkyl;
$R^6$ is hydrogen or $C_1$-$C_3$ alkyl; and
$R^7$ is hydrogen or $C_1$-$C_3$ alkyl.

In some such embodiment, $R^4$ is hydrogen, $CH_2F$, $CHF_2$, $CH_3$, or $CH_2CH_3$; and $R^5$ is hydrogen, $CH_2F$, $CHF_2$, $CH_3$, or $CH_2CH_3$.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl, $C_3$-$C_6$ cycloalkyl, 4-6 membered heterocycle, or 5-6 membered heteroaryl; each of which is optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl which is optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl which is optionally substituted with 1, 2, or 3 $R^q$ groups; wherein each $R^q$ is independently
$C_1$-$C_6$ alkyl wherein the $C_1$-$C_6$ alkyl is optionally substituted with one —OH;
halogen;
$C_1$-$C_6$ haloalkyl;
—$OR^h$ wherein $R^h$ is hydrogen or $C_1$-$C_3$ alkyl, —C(O)R$^h$ wherein R$^h$ is G$^A$; wherein G$^A$ is 4-6 membered heterocycle;

—C(O)OR$^h$ wherein R$^h$ is hydrogen or C$_1$-C$_6$ alkyl,

—C(O)N(R$^h$)$_2$, wherein R$^h$ at each occurrence, is independently hydrogen, C$_3$-C$_6$ cycloalkyl, C$_1$-C$_6$ haloalkyl, or C$_1$-C$_6$ alkyl; wherein the C$_1$-C$_6$ haloalkyl and C$_1$-C$_6$ alkyl are each optionally substituted with 1 or 2 —OH groups; or —SO$_2$R$^h$ wherein R$^h$ is C$_1$-C$_6$ haloalkyl or C$_1$-C$_6$ alkyl;

R$^6$ is hydrogen or C$_1$-C$_3$ alkyl; and

R$^7$ is hydrogen or C$_1$-C$_3$ alkyl.

In one embodiment, the invention is directed to compounds of formula (I-d), wherein R$^9$, R$^{10}$, and R$^{13}$ are hydrogen;

R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;

R$^4$ is hydrogen or C$_1$-C$_3$ alkyl;

R$^5$ is G$^{2A}$ wherein G$^{2A}$ is phenyl which is optionally substituted with 1, 2, or 3 R$^q$ groups; wherein one of R$^q$ is —C(O)OR$^h$ wherein R$^h$ is hydrogen or C$_1$-C$_6$ alkyl, or one of R$^q$ is —C(O)N(H)(R$^h$) wherein R$^h$ is cyclopentyl, or R$^h$ is C$_1$-C$_6$ alkyl which is substituted with 1 or 2 —OH groups; and the other optional R$^q$ groups are independently selected from the group consisting of C$_1$-C$_3$ alkyl, halogen, and C$_1$-C$_3$ haloalkyl;

R$^6$ is hydrogen or C$_1$-C$_3$ alkyl; and

R$^7$ is hydrogen or C$_1$-C$_3$ alkyl.

In one embodiment, the invention is directed to compounds of formula (I-d), wherein R$^9$, R$^{10}$, and R$^{13}$ are hydrogen;

R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;

R$^4$ is hydrogen or C$_1$-C$_3$ alkyl;

R$^5$ is G$^{2A}$ wherein G$^{2A}$ is phenyl which is substituted with one R$^q$; wherein R$^q$ is —C(O)OR$^h$ wherein R$^h$ is hydrogen or C$_1$-C$_3$ alkyl;

R$^6$ is hydrogen or C$_1$-C$_3$ alkyl; and

R$^7$ is hydrogen or C$_1$-C$_3$ alkyl.

In some such embodiments, R$^h$ is hydrogen. In some such embodiments, R$^h$ is C$_1$-C$_3$ alkyl.

In one embodiment, the invention is directed to compounds of formula (I-d), wherein R$^9$, R$^{10}$, and R$^{13}$ are hydrogen;

R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;

R$^4$ is hydrogen or C$_1$-C$_3$ alkyl;

R$^5$ is G$^{2A}$ wherein G$^{2A}$ is

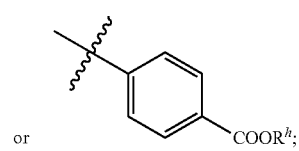

or wherein R$^h$ is hydrogen or C$_1$-C$_3$ alkyl;

R$^6$ is hydrogen or C$_1$-C$_3$ alkyl; and

R$^7$ is hydrogen or C$_1$-C$_3$ alkyl.

In some such embodiments, R$^h$ is hydrogen. In some such embodiments, R$^h$ is C$_1$-C$_3$ alkyl.

In one embodiment, the invention is directed to compounds of formula (I-d), wherein R$^9$, R$^{10}$, and R$^{13}$ are hydrogen;

R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;

R$^4$ is hydrogen or C$_1$-C$_3$ alkyl;

R$^5$ is G$^{2A}$ wherein G$^{2A}$ is

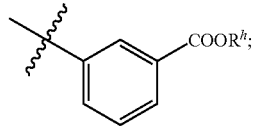

wherein R$^h$ is hydrogen or C$_1$-C$_3$ alkyl;

R$^6$ is hydrogen or C$_1$-C$_3$ alkyl; and

R$^7$ is hydrogen or C$_1$-C$_3$ alkyl.

In some such embodiments, R$^h$ is hydrogen. In some such embodiments, R$^h$ is C$_1$-C$_3$ alkyl.

In one embodiment, the invention is directed to compounds of formula (I-d), wherein R$^9$, R$^{10}$, and R$^{13}$ are hydrogen;

R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;

R$^4$ is hydrogen or C$_1$-C$_3$ alkyl;

R$^5$ is G$^{2A}$ wherein G$^{2A}$ is

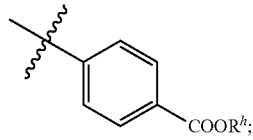

wherein R$^h$ is hydrogen or C$_1$-C$_3$ alkyl;

R$^6$ is hydrogen or C$_1$-C$_3$ alkyl; and

R$^7$ is hydrogen or C$_1$-C$_3$ alkyl.

In some such embodiments, R$^h$ is hydrogen. In some such embodiments, R$^h$ is C$_1$-C$_3$ alkyl.

In one embodiment, the invention is directed to compounds of formula (I-d), wherein R$^9$, R$^{10}$, and R$^{13}$ are hydrogen;

R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;

R$^4$ is hydrogen or C$_1$-C$_3$ alkyl;

R$^5$ is G$^{2A}$ wherein G$^{2A}$ is C$_3$-C$_6$ cycloalkyl which is optionally substituted with 1, 2, or 3 R$^q$ groups; wherein each R$^q$ is independently C$_1$-C$_6$ alkyl wherein the C$_1$-C$_6$ alkyl is optionally substituted with one —OH;

halogen;

C$_1$-C$_6$ haloalkyl;

—OR$^h$ wherein R$^h$ is hydrogen or C$_1$-C$_3$ alkyl,

—C(O)R$^h$ wherein R$^h$ is G$^A$; wherein G$^A$ is 4-6 membered heterocycle;

—C(O)OR$^h$ wherein R$^h$ is hydrogen or C$_1$-C$_6$ alkyl,

—C(O)N(R$^h$)$_2$, wherein R$^h$ at each occurrence, is independently hydrogen, C$_3$-C$_6$ cycloalkyl, C$_1$-C$_6$ haloalkyl, or C$_1$-C$_6$ alkyl; wherein the C$_1$-C$_6$ haloalkyl and C$_1$-C$_6$ alkyl are each optionally substituted with 1 or 2 —OH groups; or —SO$_2$R$^h$ wherein R$^h$ is C$_1$-C$_6$ haloalkyl or C$_1$-C$_6$ alkyl;

R$^6$ is hydrogen or C$_1$-C$_3$ alkyl; and

R$^7$ is hydrogen or C$_1$-C$_3$ alkyl.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is cyclopropyl or cyclohexyl, each of which is optionally substituted with one $R^q$; wherein $R^q$ is —$OR^h$ wherein $R^h$ is $C_1$-$C_3$ alkyl, or —$C(O)OR^h$ wherein $R^h$ is hydrogen or $C_1$-$C_6$ alkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is cyclohexyl which is substituted with one $R^q$; wherein $R^q$ is —$C(O)OR^h$ wherein $R^h$ is hydrogen or $C_1$-$C_3$ alkyl,
$R^6$ is hydrogen or $C_1$-$C_3$ alkyl; and
$R^7$ is hydrogen or $C_1$-$C_3$ alkyl.

In some such embodiment, $R^q$ is —$C(O)OR^h$ wherein $R^h$ is hydrogen. In some such embodiment, $R^q$ is —$C(O)OR^h$ wherein $R^h$ is $C_1$-$C_3$ alkyl.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

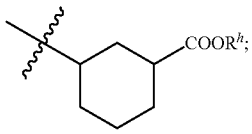

wherein $R^h$ is hydrogen or $C_1$-$C_3$ alkyl.
$R^6$ is hydrogen or $C_1$-$C_3$ alkyl; and
$R^7$ is hydrogen or $C_1$-$C_3$ alkyl.

In some such embodiment, $R^h$ is hydrogen. In some such embodiments, $R^h$ is $C_1$-$C_3$ alkyl.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is 4-6 membered heterocycle which is optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In some such embodiment, $G^{2A}$ is tetrahydrofuranyl or azetidinyl, each of which is optionally substituted with 1, 2, or 3 independently selected $R^q$ groups.

In some such embodiments, $G^{2A}$ tetrahydrofuranyl or azetidinyl, each of which is optionally substituted with 1, 2, or 3 $R^q$ groups; wherein each $R^q$ is independently
$C_1$-$C_6$ alkyl wherein the $C_1$-$C_6$ alkyl is optionally substituted with one —OH;
halogen;
$C_1$-$C_6$ haloalkyl;
—$OR^h$ wherein $R^h$ is hydrogen or $C_1$-$C_3$ alkyl,
—$C(O)R^h$ wherein $R^h$ is $G^A$; wherein $G^A$ is 4-6 membered heterocycle;
—$C(O)OR^h$ wherein $R^h$ is hydrogen or $C_1$-$C_6$ alkyl,
—$C(O)N(R^h)_2$, wherein $R^h$ at each occurrence, is independently hydrogen, $C_3$-$C_6$ cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or
—$SO_2R^h$ wherein $R^h$ is $C_1$-$C_6$ haloalkyl or $C_1$-$C_6$ alkyl.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is 5-6 membered heteroaryl which is optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In some such embodiment, $G^{2A}$ is pyridinyl which is optionally substituted with 1, 2, or 3 independently selected $R^q$ groups.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a $C_3$-$C_6$ cycloalkyl or a 4-6 membered heterocycle; wherein the $C_3$-$C_6$ cycloalkyl and the 4-6 membered heterocycle are each optionally substituted with 1, 2, or 3 independently selected $R^p$ groups; and
$R^6$ and $R^7$ are each independently hydrogen or $C_1$-$C_3$ alkyl.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a $C_3$-$C_6$ cycloalkyl which is optionally substituted with 1 or 2 $R^p$ groups; and
$R^6$ and $R^7$ are each independently hydrogen or $C_1$-$C_3$ alkyl.

In some such embodiment, the $C_3$-$C_6$ cycloalkyl formed is cyclobutyl or cyclopentyl, each of which is optionally substituted with 1 or 2 $R^p$ groups. In some such embodiment, the $C_3$-$C_6$ cycloalkyl formed is unsubstituted cyclobutyl or unsubstituted cyclopentyl.

In some such embodiments, each $R^p$ is independently
$C_1$-$C_6$ alkyl wherein the $C_1$-$C_6$ alkyl is optionally substituted with 1 or 2 —OH groups;
—$C(O)R^h$ wherein $R^h$ is $C_1$-$C_6$ alkyl;
—$C(O)OR^h$ wherein $R^h$ is hydrogen, $C_1$-$C_6$ alkyl, or —$CH_2$-phenyl; or
—$SO_2R^h$ wherein $R^h$ is $C_1$-$C_6$ haloalkyl or $C_1$-$C_6$ alkyl.

In one embodiment, the invention is directed to compounds of formula (I-d), wherein $R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a 4-6 membered heterocycle which is optionally substituted with 1 or 2 $R^p$ groups; and
$R^6$ and $R^7$ are each independently hydrogen or $C_1$-$C_3$ alkyl.

In some such embodiment, the 4-6 membered heterocycle formed is azetidinyl, piperidinyl, each of which is optionally substituted with 1 or 2 independently selected $R^p$ groups.

In some such embodiments, each $R^p$ is independently
$C_1$-$C_6$ alkyl wherein the $C_1$-$C_6$ alkyl is optionally substituted with 1 or 2 —OH groups;
—$C(O)R^h$ wherein $R^h$ is $C_1$-$C_6$ alkyl;
—$C(O)OR^h$ wherein $R^h$ is hydrogen, $C_1$-$C_6$ alkyl, or —$CH_2$-phenyl; or
—$SO_2R^h$ wherein $R^h$ is $C_1$-$C_6$ haloalkyl or $C_1$-$C_6$ alkyl.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ hydrogen or $C_1$-$C_3$ alkyl; and
$R^5$ is hydrogen or $C_1$-$C_3$ alkyl;
$R^6$ is hydrogen or $C_1$-$C_3$ alkyl; and
$R^7$ is —($C_1$-$C_6$ alkylenyl)-$G^{3A}$.

In one embodiment, the invention is directed to compounds of formula (I-d), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ hydrogen or $C_1$-$C_3$ alkyl; and
$R^5$ is hydrogen or $C_1$-$C_3$ alkyl;
$R^6$ is hydrogen or $C_1$-$C_3$ alkyl;
$R^7$ is —($CH_2$)-$G^{3A}$ wherein $G^{3A}$ is phenyl which is optionally substituted with 1, 2, or 3 $R^s$ group; and each $R^s$ is independently $C_1$-$C_3$ alkyl, halogen, $C_1$-$C_3$ haloalkyl, or —$OR^j$ wherein $R^j$ is hydrogen or $C_1$-$C_3$ alkyl.

In some such embodiments, each $R^s$ is independently —$OR^j$ wherein $R^j$ is $C_1$-$C_3$ alkyl.

In one embodiment, the invention is directed to compounds of formula (I-e)

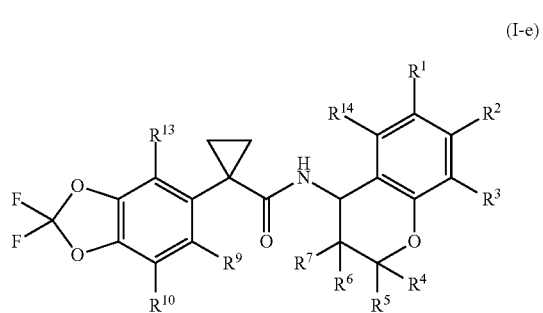

(I-e)

wherein $R^1$, $R^2$, $R^3$, $R^4$, $R^5$, $R^6$, $R^7$, $R^9$, $R^{10}$, $R^{13}$, and $R^{14}$ are as described in formula (I-d).

In one embodiment, the invention is directed to compounds of formula (I-e), wherein $R^9$, $R^{10}$, and $R^{13}$ are hydrogen.

In one embodiment, the invention is directed to compounds of formula (I-e), wherein $R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl.

In one embodiment, the invention is directed to compounds of formula (I-e), wherein
$R^9$, $R^{10}$, and $R^{13}$ are hydrogen; and
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen, $C_1$-$C_6$ haloalkyl, or $C_1$-$C_6$ alkyl;
$R^5$ is hydrogen, $C_1$-$C_6$ haloalkyl, or $C_1$-$C_6$ alkyl;
$R^6$ is hydrogen or $C_1$-$C_3$ alkyl; and
$R^7$ is hydrogen or $C_1$-$C_3$ alkyl.

In some such embodiment, $R^4$ is hydrogen, $CH_2F$, $CHF_2$, $CH_3$, or $CH_2CH_3$; and $R^5$ is hydrogen, $CH_2F$, $CHF_2$, $CH_3$, or $CH_2CH_3$.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl, $C_3$-$C_6$ cycloalkyl, 4-6 membered heterocycle, or 5-6 membered heteroaryl; each $G^{2A}$ is optionally substituted with 1, 2, or 3 independently selected $R^q$ groups.
$R^6$ is hydrogen or $C_1$-$C_3$ alkyl; and
$R^7$ is hydrogen or $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl which is optionally substituted with 1, 2, or 3 $R^q$ groups; wherein each $R^q$ is independently
$C_1$-$C_6$ alkyl wherein the $C_1$-$C_6$ alkyl is optionally substituted with one —OH;
halogen;
$C_1$-$C_6$ haloalkyl;
—$OR^h$ wherein $R^h$ is hydrogen or $C_1$-$C_3$ alkyl,
—$C(O)R^h$ wherein $R^h$ is $G^A$; wherein $G^A$ is 4-6 membered heterocycle;
—$C(O)OR^h$ wherein $R^h$ is hydrogen or $C_1$-$C_6$ alkyl,
—$C(O)N(R^h)_2$, wherein $R^h$ at each occurrence, is independently hydrogen, $C_3$-$C_6$ cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or
—$SO_2R^h$ wherein $R^h$ is $C_1$-$C_6$ haloalkyl or $C_1$-$C_6$ alkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl which is optionally substituted with 1, 2, or 3 $R^q$ groups; wherein one of $R^q$ is —$C(O)OR^h$ wherein $R^h$ is hydrogen or $C_1$-$C_6$ alkyl, or one of $R^q$ is —$C(O)N(H)(R^h)$ wherein $R^h$ is cyclopentyl, or $R^h$ is $C_1$-$C_6$ alkyl which is substituted with 1 or 2 —OH groups; and the other optional $R^q$ groups are independently selected from the group consisting of $C_1$-$C_3$ alkyl, halogen, and $C_1$-$C_3$ haloalkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl which is substituted with one $R^q$; wherein $R^q$ is —$C(O)OR^h$ wherein $R^h$ is hydrogen or $C_1$-$C_3$ alkyl;
$R^6$ is hydrogen or $C_1$-$C_3$ alkyl; and
$R^7$ is hydrogen or $C_1$-$C_3$ alkyl.

In some such embodiments, $R^h$ is hydrogen. In some such embodiments, $R^h$ is $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

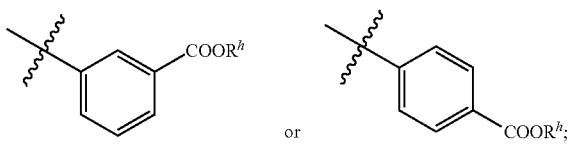

wherein $R^h$ is hydrogen or $C_1$-$C_3$ alkyl;
$R^6$ is hydrogen or $C_1$-$C_3$ alkyl; and
$R^7$ is hydrogen or $C_1$-$C_3$ alkyl.

In some such embodiments, $R^h$ is hydrogen. In some such embodiments, $R^h$ is $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

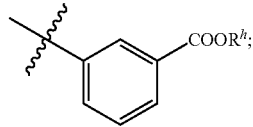

wherein $R^h$ is hydrogen or $C_1$-$C_3$ alkyl;
$R^6$ is hydrogen or $C_1$-$C_3$ alkyl; and
$R^7$ is hydrogen or $C_1$-$C_3$ alkyl.

In some such embodiments, $R^h$ is hydrogen. In some such embodiments, $R^h$ is $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

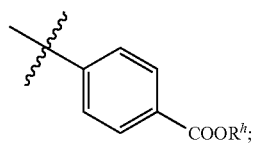

wherein $R^h$ is hydrogen or $C_1$-$C_3$ alkyl;
$R^6$ is hydrogen or $C_1$-$C_3$ alkyl; and
$R^7$ is hydrogen or $C_1$-$C_3$ alkyl.

In some such embodiments, $R^h$ is hydrogen. In some such embodiments, $R^h$ is $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is $C_3$-$C_6$ cycloalkyl which is optionally substituted with 1, 2, or 3 $R^q$ groups; wherein each $R^q$ is independently
$C_1$-$C_6$ alkyl wherein the $C_1$-$C_6$ alkyl is optionally substituted with one —OH;
halogen;
$C_1$-$C_6$ haloalkyl;
—$OR^h$ wherein $R^h$ is hydrogen or $C_1$-$C_3$ alkyl,
—$C(O)R^h$ wherein $R^h$ is $G^A$; wherein $G^A$ is 4-6 membered heterocycle;
—$C(O)OR^h$ wherein $R^h$ is hydrogen or $C_1$-$C_6$ alkyl,
—$C(O)N(R^h)_2$, wherein $R^h$ at each occurrence, is independently hydrogen, $C_3$-$C_6$ cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or
—$SO_2R^h$ wherein $R^h$ is $C_1$-$C_6$ haloalkyl or $C_1$-$C_6$ alkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;

$R^4$ is hydrogen or $C_1$-$C_3$ alkyl;
$R^5$ is $G^{2A}$ wherein $G^{2A}$ is cyclopropyl or cyclohexyl, each of which is optionally substituted with one $R^q$; wherein $R^q$ is —$OR^h$ wherein $R^h$ is $C_1$-$C_3$ alkyl, or $R^q$ is —$C(O)OR^h$ wherein $R^h$ is hydrogen or $C_1$-$C_6$ alkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is cyclohexyl which is substituted with one $R^q$; wherein $R^q$ is —$C(O)OR^h$ wherein $R^h$ is hydrogen or $C_1$-$C_3$ alkyl,
$R^6$ is hydrogen or $C_1$-$C_3$ alkyl; and
$R^7$ is hydrogen or $C_1$-$C_3$ alkyl.

In some such embodiment, $R^h$ is hydrogen. In some such embodiment, $R^h$ is $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

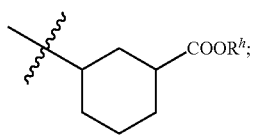

wherein $R^h$ is hydrogen or $C_1$-$C_3$ alkyl.
$R^6$ is hydrogen or $C_1$-$C_3$ alkyl; and
$R^7$ is hydrogen or $C_1$-$C_3$ alkyl.

In some such embodiment, $R^h$ is hydrogen. In some such embodiments, $R^h$ is $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is 4-6 membered heterocycle optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In some such embodiment, $G^{2A}$ is tetrahydrofuranyl or azetidinyl, each of which is optionally substituted with 1, 2, or 3 independently selected $R^q$ groups.

In some such embodiments, $G^{2A}$ tetrahydrofuranyl or azetidinyl, each of which is optionally substituted with 1, 2, or 3 $R^q$ groups; wherein each $R^q$ is independently
  $C_1$-$C_6$ alkyl wherein the $C_1$-$C_6$ alkyl is optionally substituted with one —OH;
  halogen;
  $C_1$-$C_6$ haloalkyl;
  —$OR^h$ wherein $R^h$ is hydrogen or $C_1$-$C_3$ alkyl,
  —$C(O)R^h$ wherein $R^h$ is $G^A$; wherein $G^A$ is 4-6 membered heterocycle;
  —$C(O)OR^h$ wherein $R^h$ is hydrogen or $C_1$-$C_6$ alkyl,
  —$C(O)N(R^h)_2$, wherein $R^h$ at each occurrence, is independently hydrogen, $C_3$-$C_6$ cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or
  —$SO_2R^h$ wherein $R^h$ is $C_1$-$C_6$ haloalkyl or $C_1$-$C_6$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is 5-6 membered heteroaryl optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In some such embodiment, $G^{2A}$ is pyridinyl optionally substituted with 1, 2, or 3 independently selected $R^q$ groups.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a $C_3$-$C_6$ cycloalkyl or a 4-6 membered heterocycle; wherein the $C_3$-$C_6$ cycloalkyl and the 4-6 membered heterocycle are each optionally substituted with 1, 2, or 3 independently selected $R^p$ groups; and
$R^6$ and $R^7$ are each independently hydrogen or $C_1$-$C_3$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a $C_3$-$C_6$ cycloalkyl which is optionally substituted with 1 or 2 $R^p$ groups; and
$R^6$ and $R^7$ are each independently hydrogen or $C_1$-$C_3$ alkyl.

In some such embodiment, the $C_3$-$C_6$ cycloalkyl formed is cyclobutyl or cyclopentyl, each of which is optionally substituted with 1 or 2 $R^p$ groups. In some such embodiment, the $C_3$-$C_6$ cycloalkyl formed is unsubstituted cyclobutyl or unsubstituted cyclopentyl.

In some such embodiment, each $R^p$ is independently
  $C_1$-$C_6$ alkyl wherein the $C_1$-$C_6$ alkyl is optionally substituted with 1 or 2 —OH groups;
  —$C(O)R^h$ wherein $R^h$ is $C_1$-$C_6$ alkyl;
  —$C(O)OR^h$ wherein $R^h$ is hydrogen, $C_1$-$C_6$ alkyl, or —$CH_2$-phenyl; or
  —$SO_2R^h$ wherein $R^h$ is $C_1$-$C_6$ haloalkyl or $C_1$-$C_6$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a 4-6 membered heterocycle which is optionally substituted with 1 or 2 $R^p$ groups; and
$R^6$ and $R^7$ are each independently hydrogen or $C_1$-$C_3$ alkyl.

In some such embodiment, the 4-6 membered heterocycle formed is azetidinyl or piperidinyl, each of which is optionally substituted with 1 or 2 $R^p$ groups.

In some such embodiments, each $R^p$ is independently
$C_1$-$C_6$ alkyl wherein the $C_1$-$C_6$ alkyl is optionally substituted with 1 or 2 —OH groups;
—C(O)$R^h$ wherein $R^h$ is $C_1$-$C_6$ alkyl;
—C(O)O$R^h$ wherein $R^h$ is hydrogen, $C_1$-$C_6$ alkyl, or —CH$_2$-phenyl; or
—SO$_2$$R^h$ wherein $R^h$ is $C_1$-$C_6$ haloalkyl or $C_1$-$C_6$ alkyl.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —O$R^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ hydrogen or $C_1$-$C_3$ alkyl; and
$R^5$ is hydrogen or $C_1$-$C_3$ alkyl;
$R^6$ is hydrogen or $C_1$-$C_3$ alkyl; and
$R^7$ is —($C_1$-$C_6$ alkylenyl)-$G^{3A}$.

In one embodiment, the invention is directed to compounds of formula (I-e), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —O$R^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ hydrogen or $C_1$-$C_3$ alkyl; and
$R^5$ is hydrogen or $C_1$-$C_3$ alkyl;
$R^6$ is hydrogen or $C_1$-$C_3$ alkyl; and
$R^7$ is —(CH$_2$)-$G^{3A}$ wherein $G^{3A}$ is phenyl which is optionally substituted with 1, 2, or 3 $R^s$ group; and each $R^s$ is independently $C_1$-$C_3$ alkyl, halogen, $C_1$-$C_3$ haloalkyl, or —OR wherein $R^j$ is hydrogen or $C_1$-$C_3$ alkyl.

In some such embodiments, each $R^s$ is independently —O$R^j$ wherein $R^j$ is $C_1$-$C_3$ alkyl.

One embodiment is directed to compounds of formula (I-f)

(I-f)

wherein $R^1$, $R^3$, $R^4$, $R^5$, $R^6$, $R^7$, $R^9$, $R^{10}$, $R^{13}$, and $R^{14}$ are as described in formula (I-d).

In one embodiment, the invention is directed to compounds of formula (I-f), wherein $R^9$, $R^{10}$, and $R^{13}$ are hydrogen.

In one embodiment, the invention is directed to compounds of formula (I-f), wherein $R^1$ is hydrogen, halogen, $C_1$-$C_6$ haloalkyl, $C_1$-$C_6$ alkyl, —O$R^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl.

In one embodiment, the invention is directed to compounds of formula (I-f), wherein
$R^9$, $R^{10}$, and $R^{13}$ are hydrogen; and
$R^1$ is hydrogen, halogen, $C_1$-$C_6$ haloalkyl, $C_1$-$C_6$ alkyl, —O$R^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —O$R^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen, $C_1$-$C_6$ haloalkyl, or $C_1$-$C_6$ alkyl;
$R^5$ is hydrogen, $C_1$-$C_6$ haloalkyl, or $C_1$-$C_6$ alkyl;
$R^6$ is hydrogen or $C_1$-$C_3$ alkyl; and
$R^7$ is hydrogen or $C_1$-$C_3$ alkyl.

In some such embodiment, $R^4$ is hydrogen, CH$_2$F, CHF$_2$, CH$_3$, or CH$_2$CH$_3$; and $R^5$ is hydrogen, CH$_2$F, CHF$_2$, CH$_3$, or CH$_2$CH$_3$.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —O$R^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl, $C_3$-$C_6$ cycloalkyl, 4-6 membered heterocycle, or 5-6 membered heteroaryl; each of which is optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —O$R^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl which is optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —O$R^{1A}$, or —C(O)O$R^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl which is optionally substituted with 1, 2, or 3 $R^q$ groups; wherein each $R^q$ is independently
$C_1$-$C_6$ alkyl wherein the $C_1$-$C_6$ alkyl is optionally substituted with one —OH;
halogen;
$C_1$-$C_6$ haloalkyl;
—O$R^h$ wherein $R^h$ is hydrogen or $C_1$-$C_3$ alkyl,
—C(O)$R^h$ wherein $R^h$ is $G^A$; wherein $G^A$ is 4-6 membered heterocycle;
—C(O)O$R^h$ wherein $R^h$ is hydrogen or $C_1$-$C_6$ alkyl,
—C(O)N($R^h$)$_2$, wherein $R^h$ at each occurrence, is independently hydrogen, $C_3$-$C_6$ cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or
—SO$_2$$R^h$ wherein $R^h$ is $C_1$-$C_6$ haloalkyl or $C_1$-$C_6$ alkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl which is optionally substituted with 1, 2, or 3 $R^q$ groups; wherein one of $R^q$ is —$C(O)OR^h$ wherein $R^h$ is hydrogen or $C_1$-$C_6$ alkyl, or one of $R^q$ is —$C(O)N(H)(R^h)$ wherein $R^h$ is cyclopentyl, or $R^h$ is $C_1$-$C_6$ alkyl which is substituted with 1 or 2 —OH groups; and the other optional $R^q$ groups are independently selected from the group consisting of $C_1$-$C_3$ alkyl, halogen, and $C_1$-$C_3$ haloalkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl which is substituted with one $R^q$; wherein $R^q$ is —$C(O)OR^h$ wherein $R^h$ is hydrogen or $C_1$-$C_3$ alkyl;
$R^6$ is hydrogen or $C_1$-$C_3$ alkyl; and
$R^7$ is hydrogen or $C_1$-$C_3$ alkyl.

In some such embodiments, $R^h$ is hydrogen. In some such embodiments, $R^h$ is $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

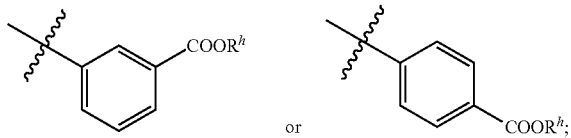

wherein $R^h$ is hydrogen or $C_1$-$C_3$ alkyl;
$R^6$ is hydrogen or $C_1$-$C_3$ alkyl; and
$R^7$ is hydrogen or $C_1$-$C_3$ alkyl.

In some such embodiments, $R^h$ is hydrogen. In some such embodiments, $R^h$ is $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

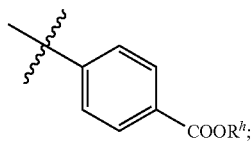

wherein $R^h$ is hydrogen or $C_1$-$C_3$ alkyl;
$R^6$ is hydrogen or $C_1$-$C_3$ alkyl; and
$R^7$ is hydrogen or $C_1$-$C_3$ alkyl.

In some such embodiments, $R^h$ is hydrogen. In some such embodiments, $R^h$ is $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is $C_3$-$C_6$ cycloalkyl which is optionally substituted with 1, 2, or 3 $R^q$ groups; wherein each $R^q$ is independently
 $C_1$-$C_6$ alkyl wherein the $C_1$-$C_6$ alkyl is optionally substituted with one —OH;
 halogen;
 $C_1$-$C_6$ haloalkyl;
 —$OR^h$ wherein $R^h$ is hydrogen or $C_1$-$C_3$ alkyl,
 —$C(O)R^h$ wherein $R^h$ is $G^A$; wherein $G^A$ is 4-6 membered heterocycle;
 —$C(O)OR^h$ wherein $R^h$ is hydrogen or $C_1$-$C_6$ alkyl,
 —$C(O)N(R^h)_2$, wherein $R^h$ at each occurrence, is independently hydrogen, $C_3$-$C_6$ cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or
 —$SO_2R^h$ wherein $R^h$ is $C_1$-$C_6$ haloalkyl or $C_1$-$C_6$ alkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is cyclopropyl or cyclohexyl, each of which is optionally substituted with one $R^q$; wherein $R^q$ is $OR^h$ wherein $R^h$ is $C_1$-$C_3$ alkyl, or $R^q$ is —$C(O)OR^h$ wherein $R^h$ is hydrogen or $C_1$-$C_6$ alkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is cyclohexyl which is substituted with one $R^q$; wherein $R^q$ is —$C(O)OR^h$ wherein $R^h$ is hydrogen or $C_1$-$C_3$ alkyl,
$R^6$ is hydrogen or $C_1$-$C_3$ alkyl; and
$R^7$ is hydrogen or $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

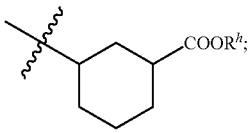

wherein $R^h$ is hydrogen or $C_1$-$C_3$ alkyl.
$R^6$ is hydrogen or $C_1$-$C_3$ alkyl; and
$R^7$ is hydrogen or $C_1$-$C_3$ alkyl.

In some such embodiment, $R^h$ is hydrogen. In some such embodiments, $R^h$ is $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is 4-6 membered heterocycle which is optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In some such embodiment, $G^{2A}$ is tetrahydrofuranyl or azetidinyl; each of which is optionally substituted with 1, 2, or 3 independently selected $R^q$ groups.

In some such embodiments, $G^{2A}$ tetrahydrofuranyl or azetidinyl, each of which is
optionally substituted with 1, 2, or 3 $R^q$ groups; wherein each $R^q$ is independently
$C_1$-$C_6$ alkyl wherein the $C_1$-$C_6$ alkyl is optionally substituted with one —OH;
halogen;
$C_1$-$C_6$ haloalkyl;
—$OR^h$ wherein $R^h$ is hydrogen or $C_1$-$C_3$ alkyl,
—$C(O)R^h$ wherein $R^h$ is $G^A$; wherein $G^A$ is 4-6 membered heterocycle;
—$C(O)OR^h$ wherein $R^h$ is hydrogen or $C_1$-$C_6$ alkyl,
—$C(O)N(R^h)_2$, wherein $R^h$ at each occurrence, is independently hydrogen, $C_3$-$C_6$ cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or
—$SO_2R^h$ wherein $R^h$ is $C_1$-$C_6$ haloalkyl or $C_1$-$C_6$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is 5-6 membered heteroaryl which is optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In some such embodiment, $G^{2A}$ is pyridinyl which is optionally substituted with 1, 2, or 3 independently selected $R^q$ groups.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a $C_3$-$C_6$ cycloalkyl or a 4-6 membered heterocycle; wherein the $C_3$-$C_6$ cycloalkyl and the 4-6 membered heterocycle are each optionally substituted with 1, 2, or 3 independently selected $R^p$ groups; and
$R^6$ and $R^7$ are each independently hydrogen or $C_1$-$C_3$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a $C_3$-$C_6$ cycloalkyl which is optionally substituted with 1 or 2 $R^p$ groups; and
$R^6$ and $R^7$ are each independently hydrogen or $C_1$-$C_3$ alkyl.

In some such embodiment, the $C_3$-$C_6$ cycloalkyl formed is cyclobutyl or cyclopentyl, each of which is optionally substituted with 1 or 2 $R^p$ groups. In some such embodiment, the $C_3$-$C_6$ cycloalkyl formed is unsubstituted cyclobutyl or unsubstituted cyclopentyl.

In some such embodiment, each $R^p$ is independently
$C_1$-$C_6$ alkyl wherein the $C_1$-$C_6$ alkyl is optionally substituted with 1 or 2 —OH groups;
—$C(O)R^h$ wherein $R^h$ is $C_1$-$C_6$ alkyl;
—$C(O)OR^h$ wherein $R^h$ is hydrogen, $C_1$-$C_6$ alkyl, or —$CH_2$-phenyl; or
—$SO_2R^h$ wherein $R^h$ is $C_1$-$C_6$ haloalkyl or $C_1$-$C_6$ alkyl.

In one embodiment, the invention is directed to compounds of formula (I-f), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a 4-6 membered heterocycle which is optionally substituted with 1 or 2 independently selected $R^p$ groups; and
$R^6$ and $R^7$ are each independently hydrogen or $C_1$-$C_3$ alkyl.

In some such embodiment, the 4-6 membered heterocycle formed is azetidinyl or piperidinyl, each of which is optionally substituted with 1 or 2 $R^p$ groups.

In some such embodiments, each $R^p$ is independently
$C_1$-$C_6$ alkyl wherein the $C_1$-$C_6$ alkyl is optionally substituted with 1 or 2 —OH groups;
—$C(O)R^h$ wherein $R^h$ is $C_1$-$C_6$ alkyl;

—C(O)OR$^h$ wherein R$^h$ is hydrogen, C$_1$-C$_6$ alkyl, or —CH$_2$-phenyl; or

—SO$_2$R$^h$ wherein R$^h$ is C$_1$-C$_6$ haloalkyl or C$_1$-C$_6$ alkyl.

In one embodiment, the invention is directed to compounds of formula (I-f), wherein
R$^9$, R$^{10}$, and R$^{13}$ are hydrogen;
R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;
R$^4$ hydrogen or C$_1$-C$_3$ alkyl; and
R$^5$ is hydrogen or C$_1$-C$_3$ alkyl;
R$^6$ is hydrogen or C$_1$-C$_3$ alkyl; and
R$^7$ is —(C$_1$-C$_6$ alkylenyl)-G$^{3A}$.

In one embodiment, the invention is directed to compounds of formula (I-f), wherein
R$^9$, R$^{10}$, and R$^{13}$ are hydrogen;
R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;
R$^4$ hydrogen or C$_1$-C$_3$ alkyl; and
R$^5$ is hydrogen or C$_1$-C$_3$ alkyl;
R$^6$ is hydrogen or C$_1$-C$_3$ alkyl;
R$^7$ is —(CH$_2$)-G$^{3A}$ wherein G$^{3A}$ is phenyl which is optionally substituted with 1, 2, or 3 R$^s$ group; and each R$^s$ is independently C$_1$-C$_3$ alkyl, halogen, C$_1$-C$_3$ haloalkyl, or —OR wherein R$^j$ is hydrogen or C$_1$-C$_3$ alkyl.

In some such embodiments, each R$^s$ is independently —OR$^j$ wherein R$^j$ is C$_1$-C$_3$ alkyl.

One embodiment is directed to compounds of formula (I-g)

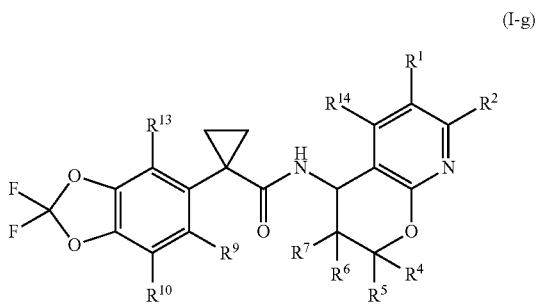

(I-g)

wherein R$^1$, R$^2$, R$^4$, R$^5$, R$^6$, R$^7$, R$^9$, R$^{10}$, R$^{13}$, and R$^{14}$ are as described in formula (I-d).

In one embodiment, the invention is directed to compounds of formula (I-g), wherein R$^9$, R$^{10}$, and R$^{13}$ are hydrogen.

In one embodiment, the invention is directed to compounds of formula (I-g), wherein R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl.

In one embodiment, the invention is directed to compounds of formula (I-g), wherein
R$^9$, R$^{10}$, and R$^{13}$ are hydrogen; and
R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl.

In one embodiment, the invention is directed to compounds of formula (I-g), wherein
R$^9$, R$^{10}$, and R$^{13}$ are hydrogen;
R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;
R$^4$ is hydrogen, C$_1$-C$_6$ haloalkyl, or C$_1$-C$_6$ alkyl;
R$^5$ is hydrogen, C$_1$-C$_6$ haloalkyl, or C$_1$-C$_6$ alkyl;
R$^6$ is hydrogen or C$_1$-C$_3$ alkyl; and
R$^7$ is hydrogen or C$_1$-C$_3$ alkyl.

In some such embodiment, R$^4$ is hydrogen, CH$_2$F, CHF$_2$, CH$_3$, or CH$_2$CH$_3$; and R$^5$ is hydrogen, CH$_2$F, CHF$_2$, CH$_3$, or CH$_2$CH$_3$.

In one embodiment, the invention is directed to compounds of formula (I-g), wherein
R$^9$, R$^{10}$, and R$^{13}$ are hydrogen;
R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;
R$^4$ is hydrogen or C$_1$-C$_3$ alkyl;
R$^5$ is G$^{2A}$ wherein G$^{2A}$ is phenyl, C$_3$-C$_6$ cycloalkyl, 4-6 membered heterocycle, or 5-6 membered heteroaryl; each of which is optionally substituted with 1, 2, or 3 independently selected R$^q$ groups
R$^6$ is hydrogen or C$_1$-C$_3$ alkyl; and
R$^7$ is hydrogen or C$_1$-C$_3$ alkyl.

In one embodiment, the invention is directed to compounds of formula (I-g), wherein
R$^9$, R$^{10}$, and R$^{13}$ are hydrogen;
R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;
R$^4$ is hydrogen or C$_1$-C$_3$ alkyl;
R$^5$ is G$^{2A}$ wherein G$^{2A}$ is phenyl which is optionally substituted with 1, 2, or 3 independently selected R$^q$ groups;
R$^6$ is hydrogen or C$_1$-C$_3$ alkyl; and
R$^7$ is hydrogen or C$_1$-C$_3$ alkyl.

In one embodiment, the invention is directed to compounds of formula (I-g), wherein
R$^9$, R$^{10}$, and R$^{13}$ are hydrogen;
R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;
R$^4$ is hydrogen or C$_1$-C$_3$ alkyl;
R$^5$ is G$^{2A}$ wherein G$^{2A}$ is phenyl which is optionally substituted with 1, 2, or 3 R$^q$ groups; wherein each R$^q$ is independently
C$_1$-C$_6$ alkyl wherein the C$_1$-C$_6$ alkyl is optionally substituted with one —OH;
halogen;
C$_1$-C$_6$ haloalkyl;
—OR$^h$ wherein R$^h$ is hydrogen or C$_1$-C$_3$ alkyl,
—C(O)R$^h$ wherein R$^h$ is G$^A$; wherein G$^A$ is 4-6 membered heterocycle;
—C(O)OR$^h$ wherein R$^h$ is hydrogen or C$_1$-C$_6$ alkyl,
—C(O)N(R$^h$)$_2$, wherein R$^h$ at each occurrence, is independently hydrogen, C$_3$-C$_6$ cycloalkyl, C$_1$-C$_6$ haloalkyl, or C$_1$-C$_6$ alkyl; wherein the C$_1$-C$_6$ haloalkyl and C$_1$-C$_6$ alkyl are each optionally substituted with 1 or 2 —OH groups; or
—SO$_2$R$^h$ wherein R$^h$ is C$_1$-C$_6$ haloalkyl or C$_1$-C$_6$ alkyl;
R$^6$ is hydrogen or C$_1$-C$_3$ alkyl; and
R$^7$ is hydrogen or C$_1$-C$_3$ alkyl.

In one embodiment, the invention is directed to compounds of formula (I-g), wherein
R$^9$, R$^{10}$, and R$^{13}$ are hydrogen;
R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl;
R$^4$ is hydrogen or C$_1$-C$_3$ alkyl;
R$^5$ is G$^{2A}$ wherein G$^{2A}$ is phenyl which is optionally substituted with 1, 2, or 3 R$^q$ groups wherein one of R$^q$ is —C(O)OR$^h$ wherein R$^h$ is hydrogen or C$_1$-C$_6$ alkyl, or one of $R^q$ is —C(O)N(H)($R^h$) wherein $R^h$ is cyclopentyl, or $R^h$ is $C_1$-$C_6$ alkyl which is substituted with 1 or 2 —OH groups; and the other optional $R^q$ groups are independently selected from the group consisting of $C_1$-$C_3$ alkyl, halogen, and $C_1$-$C_3$ haloalkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —C(O)$OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is phenyl which is substituted with one $R^q$; wherein $R^q$ is —C(O)$OR^h$ wherein $R^h$ is hydrogen or $C_1$-$C_3$ alkyl;
$R^6$ is hydrogen or $C_1$-$C_3$ alkyl; and
$R^7$ is hydrogen or $C_1$-$C_3$ alkyl.

In some such embodiments, $R^h$ is hydrogen. In some such embodiments, $R^h$ is $C_1$-$C_3$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —C(O)$OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

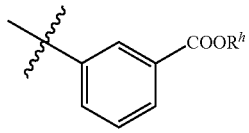 or 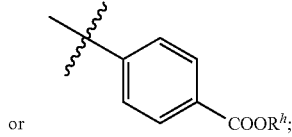

wherein $R^h$ is hydrogen or $C_1$-$C_3$ alkyl;
$R^6$ is hydrogen or $C_1$-$C_3$ alkyl; and
$R^7$ is hydrogen or $C_1$-$C_3$ alkyl.

In some such embodiments, $R^h$ is hydrogen. In some such embodiments, $R^h$ is $C_1$-$C_3$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —C(O)$OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

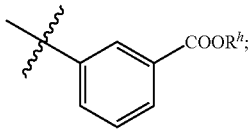

wherein $R^h$ is hydrogen or $C_1$-$C_3$ alkyl;
$R^6$ is hydrogen or $C_1$-$C_3$ alkyl; and
$R^7$ is hydrogen or $C_1$-$C_3$ alkyl.

In some such embodiments, $R^h$ is hydrogen. In some such embodiments, $R^h$ is $C_1$-$C_3$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —C(O)$OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

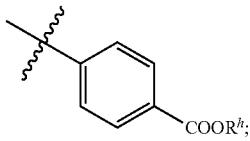

wherein $R^h$ is hydrogen or $C_1$-$C_3$ alkyl;
$R^6$ is hydrogen or $C_1$-$C_3$ alkyl; and
$R^7$ is hydrogen or $C_1$-$C_3$ alkyl.

In some such embodiments, $R^h$ is hydrogen. In some such embodiments, $R^h$ is $C_1$-$C_3$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —C(O)$OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is $C_3$-$C_6$ cycloalkyl which is optionally substituted with 1, 2, or 3 $R^q$ groups; wherein each $R^q$ is independently
$C_1$-$C_6$ alkyl wherein the $C_1$-$C_6$ alkyl is optionally substituted with one —OH;
halogen;
$C_1$-$C_6$ haloalkyl;
—$OR^h$ wherein $R^h$ is hydrogen or $C_1$-$C_3$ alkyl,
—C(O)$R^h$ wherein $R^h$ is $G^A$; wherein $G^A$ is 4-6 membered heterocycle;
—C(O)$OR^h$ wherein $R^h$ is hydrogen or $C_1$-$C_6$ alkyl,
—C(O)N($R^h$)$_2$, wherein $R^h$ at each occurrence, is independently hydrogen, $C_3$-$C_6$ cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or
—$SO_2R^h$ wherein $R^h$ is $C_1$-$C_6$ haloalkyl or $C_1$-$C_6$ alkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —C(O)$OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is cyclopropyl or cyclohexyl, each of which is optionally substituted with one $R^q$; wherein $R^q$ is —$OR^h$ wherein $R^h$ is $C_1$-$C_3$ alkyl, or $R^q$ is —C(O)$OR^h$ wherein $R^h$ is hydrogen or $C_1$-$C_6$ alkyl;
$R^6$ is hydrogen or $C_1$-$C_3$ alkyl; and
$R^7$ is hydrogen or $C_1$-$C_3$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{1A}$, or —C(O)$OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;

$R^5$ is $G^{2A}$ wherein $G^{2A}$ is cyclohexyl which is substituted with one $R^q$; wherein $R^q$ is —C(O)OR$^h$ wherein $R^h$ is hydrogen or $C_1$-$C_3$ alkyl,
$R^6$ is hydrogen or $C_1$-$C_3$ alkyl; and
$R^7$ is hydrogen or $C_1$-$C_3$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —OR$^{1A}$, or —C(O)OR$^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is

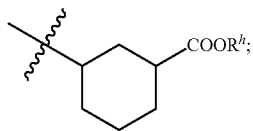

wherein $R^h$ is hydrogen or $C_1$-$C_3$ alkyl.
$R^6$ is hydrogen or $C_1$-$C_3$ alkyl; and
$R^7$ is hydrogen or $C_1$-$C_3$ alkyl.

In some such embodiment, $R^h$ is hydrogen. In some such embodiments, $R^h$ is $C_1$-$C_3$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —OR$^{1A}$, or —C(O)OR$^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is 4-6 membered heterocycle optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In some such embodiment, $G^{2A}$ is tetrahydrofuranyl or azetidinyl, each of which is optionally substituted with 1, 2, or 3 independently selected $R^q$ groups.

In some such embodiments, $G^{2A}$ tetrahydrofuranyl or azetidinyl, each of which is
optionally substituted with 1, 2, or 3 $R^q$ groups; wherein each $R^q$ is independently
$C_1$-$C_6$ alkyl wherein the $C_1$-$C_6$ alkyl is optionally substituted with one —OH;
halogen;
$C_1$-$C_6$ haloalkyl;
—OR$^h$ wherein $R^h$ is hydrogen or $C_1$-$C_3$ alkyl,
—C(O)R$^h$ wherein $R^h$ is $G^A$; wherein $G^A$ is 4-6 membered heterocycle;
—C(O)OR$^h$ wherein $R^h$ is hydrogen or $C_1$-$C_6$ alkyl,
—C(O)N(R$^h$)$_2$, wherein $R^h$ at each occurrence, is independently hydrogen, $C_3$-$C_6$ cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or
—SO$_2$R$^h$ wherein $R^h$ is $C_1$-$C_6$ haloalkyl or $C_1$-$C_6$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —OR$^{1A}$, or —C(O)OR$^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ is hydrogen or $C_1$-$C_3$ alkyl;
$R^5$ is $G^{2A}$ wherein $G^{2A}$ is 5-6 membered heteroaryl optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

In some such embodiment, $G^{2A}$ is pyridinyl optionally substituted with 1, 2, or 3 independently selected $R^q$ groups.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —OR$^{1A}$, or —C(O)OR$^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a $C_3$-$C_6$ cycloalkyl or a 4-6 membered heterocycle; wherein the $C_3$-$C_6$ cycloalkyl and the 4-6 membered heterocycle are each optionally substituted with 1, 2, or 3 independently selected $R^p$ groups; and
$R^6$ and $R^7$ are each independently hydrogen or $C_1$-$C_3$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —OR$^{1A}$, or —C(O)OR$^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a $C_3$-$C_6$ cycloalkyl which is optionally substituted with 1 or 2 $R^p$ groups; and
$R^6$ and $R^7$ are each independently hydrogen or $C_1$-$C_3$ alkyl.

In some such embodiment, the $C_3$-$C_6$ cycloalkyl formed is cyclobutyl or cyclopentyl, each of which is optionally substituted with 1 or 2 $R^p$ groups. In some such embodiment, the $C_3$-$C_6$ cycloalkyl formed is unsubstituted cyclobutyl or unsubstituted cyclopentyl.

In some such embodiment, each $R^p$ is independently
$C_1$-$C_6$ alkyl wherein the $C_1$-$C_6$ alkyl is optionally substituted with 1 or 2 —OH groups;
—C(O)R$^h$ wherein $R^h$ is $C_1$-$C_6$ alkyl;
—C(O)OR$^h$ wherein $R^h$ is hydrogen, $C_1$-$C_6$ alkyl, or —CH$_2$-phenyl; or
—SO$_2$R$^h$ wherein $R^h$ is $C_1$-$C_6$ haloalkyl or $C_1$-$C_6$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —OR$^{1A}$, or —C(O)OR$^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;
$R^4$ and $R^5$, together with the carbon atom to which they are attached, form a 4-6 membered heterocycle which is optionally substituted with 1 or 2 $R^p$ groups; and
$R^6$ and $R^7$ are each independently hydrogen or $C_1$-$C_3$ alkyl.

In some such embodiment, the 4-6 membered heterocycle formed is azetidinyl or piperidinyl, each of which is optionally substituted with 1 or 2 $R^p$ groups.

In some such embodiments, each $R^p$ is independently
$C_1$-$C_6$ alkyl wherein the $C_1$-$C_6$ alkyl is optionally substituted with 1 or 2 —OH groups;
—C(O)R$^h$ wherein $R^h$ is $C_1$-$C_6$ alkyl;
—C(O)OR$^h$ wherein $R^h$ is hydrogen, $C_1$-$C_6$ alkyl, or —CH$_2$-phenyl; or
—SO$_2$R$^h$ wherein $R^h$ is $C_1$-$C_6$ haloalkyl or $C_1$-$C_6$ alkyl.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —OR$^{1A}$, or —C(O)OR$^{1B}$; wherein $R^{1A}$ is $C_1$-$C_3$ haloalkyl or $C_1$-$C_3$ alkyl; and $R^{1B}$ is hydrogen or $C_1$-$C_3$ alkyl;

$R^4$ hydrogen or $C_1$-$C_3$ alkyl; and
$R^5$ is hydrogen or $C_1$-$C_3$ alkyl;
$R^6$ is hydrogen or $C_1$-$C_3$ alkyl; and
$R^7$ is —($C_1$-$C_6$ alkylenyl)-$G^{3A}$.

In one embodiment, the invention is directed to compounds of formula (I-g), wherein
$R^9$, $R^{10}$, and $R^{13}$ are hydrogen;
$R^1$ is hydrogen, halogen, $C_1$-$C_6$ haloalkyl, $C_1$-$C_6$ alkyl, —$OR^{14}$, or —$C(O)OR^{1B}$; wherein $R^{14}$ is $C_1$-$C_3$ haloalkyl or $C_1$-$C_3$ alkyl; and $R^{1B}$ is hydrogen or $C_1$-$C_3$ alkyl;
$R^4$ hydrogen or $C_1$-$C_3$ alkyl; and
$R^5$ is hydrogen or $C_1$-$C_3$ alkyl;
$R^6$ is hydrogen or $C_1$-$C_3$ alkyl; and
$R^7$ is —($CH_2$)-$G^{3A}$ wherein $G^{3A}$ is phenyl which is optionally substituted with 1, 2, or 3 $R^s$ group; wherein each $R^s$ is independently $C_1$-$C_3$ alkyl, halogen, $C_1$-$C_3$ haloalkyl, or —$OR^j$ wherein $R^j$ is hydrogen or $C_1$-$C_3$ alkyl.

In some such embodiments, each $R^s$ is independently —$OR^j$ wherein $R^j$ is $C_1$-$C_3$ alkyl.

Compounds described herein may contain one or more asymmetrically substituted atoms, and thus may exist as individual stereoisomers (including enantiomers and diastereomers) or mixtures thereof. For example, certain embodiments are directed to compounds of formula (I-h)

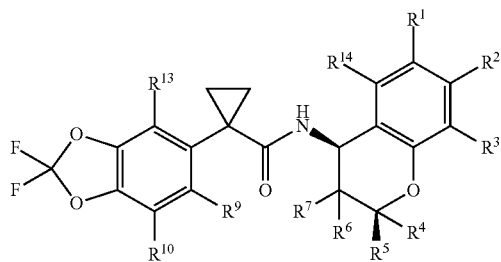

(I-h)

wherein
$R^1$ is hydrogen, halogen, $C_1$-$C_6$ haloalkyl, $C_1$-$C_6$ alkyl, —$OR^{14}$, or —$C(O)OR^{1B}$; wherein $R^{14}$ is $C_1$-$C_3$ haloalkyl or $C_1$-$C_3$ alkyl;
$R^2$ is hydrogen, halogen, $C_1$-$C_6$ haloalkyl, $C_1$-$C_6$ alkyl, —$OR^{14}$, or —$C(O)OR^{1B}$; wherein $R^{14}$ is hydrogen, $C_1$-$C_3$ haloalkyl, or $C_1$-$C_3$ alkyl; wherein the $C_1$-$C_3$ alkyl is optionally substituted with one substituent selected from the group consisting of —$OR^{ZA}$, —$C(O)OH$, and $G^{1A}$; wherein $G^{1A}$ is phenyl which is optionally substituted with 1, 2, or 3 $R^s$ groups wherein each $R^s$ is independently $C_1$-$C_3$ alkyl, $C_1$-$C_3$ haloalkyl, halogen, or —$OCH_3$; and $R^{ZA}$ is $C_1$-$C_3$ haloalkyl or $C_1$-$C_3$ alkyl;
$R^{1B}$ is hydrogen or $C_1$-$C_3$ alkyl;
$R^3$ and $R^{14}$ are each independently hydrogen or halogen;
$R^4$ is hydrogen, $C_1$-$C_3$ haloalkyl, or $C_1$-$C_3$ alkyl;
$R^5$ is $G^{2A}$;
$G^{2A}$ is $C_3$-$C_6$ cycloalkyl, 4-6 membered heterocycle, phenyl, or 5-6 membered heteroaryl, each of which is independently unsubstituted or substituted with 1, 2, or 3 independently selected $R^q$ groups;
$R^q$, at each occurrence, is independently $C_1$-$C_6$ alkyl, halogen, $C_1$-$C_6$ haloalkyl, —CN, oxo, $NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^h$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, or $G^A$, wherein the $C_1$-$C_6$ haloalkyl and the $C_1$-$C_6$ alkyl are each optionally substituted with one or two substituents independently selected from the group consisting of —$OR^h$, —$OC(O)R^i$, —$OC(O)N(R^h)_2$, —$SR^h$, —$S(O)_2R^h$, —$S(O)_2N(R^h)_2$, —$C(O)R^h$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, —CN, and $G^A$;
$R^h$, at each occurrence, is independently hydrogen, $C_1$-$C_6$ haloalkyl, $C_1$-$C_6$ alkyl, or $G^A$, wherein the $C_1$-$C_6$ haloalkyl and the $C_1$-$C_6$ alkyl are each optionally substituted with one or two substituents independently selected from the group consisting of —$OR^j$, —$OC(O)N(R^j)_2$, —$SR^j$, —$C(O)OR^j$, —$C(O)N(R^j)_2$, —$N(R^j)_2$, —CN, and $G^A$;
$R^i$, at each occurrence, is independently $C_1$-$C_6$ haloalkyl, $C_1$-$C_6$ alkyl, or $G^A$, wherein the $C_1$-$C_6$ haloalkyl and the $C_1$-$C_6$ alkyl are each optionally substituted with one or two substituents independently selected from the group consisting of —$OR^j$, —$OC(O)N(R^j)_2$, —$SR^j$, —$C(O)OR^j$, —$C(O)N(R^j)_2$, —$N(R^j)_2$, —CN, and $G^A$;
$R^6$ is hydrogen or $C_1$-$C_3$ alkyl;
$R^7$ is hydrogen or $C_1$-$C_3$ alkyl;
$R^9$, $R^{10}$, and $R^{13}$, are each independently hydrogen or halogen;
$G^A$, at each occurrence, is independently cycloalkyl, cycloalkenyl, heterocycle, aryl, or heteroaryl, each of which is independently unsubstituted or substituted with 1, 2, or 3 independently selected $R^s$ groups;
$R^s$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, $NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^j$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$ alkylenyl)-$OR^j$, —($C_1$-$C_6$ alkylenyl)-$OC(O)R^k$, —($C_1$-$C_6$ alkylenyl)-$OC(O)N(R^j)_2$, —($C_1$-$C_6$ alkylenyl)-$SR^j$, —($C_1$-$C_6$ alkylenyl)-$S(O)_2R^j$, —($C_1$-$C_6$ alkylenyl)-$S(O)_2N(R^j)_2$, —($C_1$-$C_6$ alkylenyl)-$C(O)R^j$, —($C_1$-$C_6$ alkylenyl)-$C(O)OR^j$, —($C_1$-$C_6$ alkylenyl)-$C(O)N(R^j)_2$, —($C_1$-$C_6$ alkylenyl)-$N(R^j)_2$, —($C_1$-$C_6$ alkylenyl)-$N(R^j)C(O)R^k$, —($C_1$-$C_6$ alkylenyl)-$N(R^j)S(O)_2R^k$, —($C_1$-$C_6$ alkylenyl)-$N(R^j)C(O)O(R^k)$, —($C_1$-$C_6$ alkylenyl)-$N(R^j)C(O)N(R^j)_2$, or —($C_1$-$C_6$ alkylenyl)-CN;
$R^j$, at each occurrence, is independently hydrogen, $C_1$-$C_6$ alkyl, or $C_1$-$C_6$ haloalkyl; and
$R^k$, at each occurrence, is independently $C_1$-$C_6$ alkyl or $C_1$-$C_6$ haloalkyl.

In one embodiment, the invention is directed to compounds of formula (I-h) wherein $R^3$, $R^{14}$, $R^9$, $R^{10}$, and $R^{13}$ are hydrogen.

In one embodiment, the invention is directed to compounds of formula (I-h) wherein $G^{2A}$ is phenyl, cyclopropyl, cyclohexyl, pyridinyl, azetidinyl, or tetrahydrofuranyl; each of which is optionally substituted with 1, 2, or 3 independently selected $R^q$ groups.

In one embodiment, the invention is directed to compounds of formula (I-h) wherein $G^{2A}$ is phenyl, pyridinyl, cyclopropyl, cyclohexyl, pyridinyl, azetidinyl, or tetrahydrofuranyl; each of which is optionally substituted with 1, 2, or 3 independently selected $R^q$ groups; and $R^3$, $R^{14}$, $R^9$, $R^{10}$, and $R^{13}$ are hydrogen.

In one embodiment, the invention is directed to compounds of formula (I-h) wherein
$R^1$ is hydrogen, halogen, $C_1$-$C_3$ haloalkyl, $C_1$-$C_3$ alkyl, or —$OR^{14}$; wherein $R^{14}$ is $C_1$-$C_3$ alkyl; and
$R^2$ is hydrogen, halogen, $C_1$-$C_3$ haloalkyl, $C_1$-$C_3$ alkyl, or —$OR^{14}$; wherein $R^{14}$ is $C_1$-$C_3$ haloalkyl, or $C_1$-$C_3$ alkyl wherein the $C_1$-$C_3$ alkyl is optionally substituted with one —$OR^{ZA}$ wherein $R^{ZA}$ is $C_1$-$C_3$ alkyl.

In one embodiment, the invention is directed to compounds of formula (I-h) wherein
$R^1$ is hydrogen, halogen, $C_1$-$C_3$ haloalkyl, $C_1$-$C_3$ alkyl, or —$OR^{1A}$; wherein $R^{1A}$ is $C_1$-$C_3$ alkyl;
$R^2$ is hydrogen, halogen, $C_1$-$C_3$ haloalkyl, $C_1$-$C_3$ alkyl, or —$OR^{1A}$; wherein $R^{1A}$ is $C_1$-$C_3$ haloalkyl, or $C_1$-$C_3$ alkyl wherein the $C_1$-$C_3$ alkyl is optionally substituted with one —$OR^{ZA}$ wherein $R^{ZA}$ is $C_1$-$C_3$ alkyl; and
$R^3$, $R^{14}$, $R^9$, $R^{10}$, and $R^{13}$ are hydrogen.

In one embodiment, the invention is directed to compounds of formula (I-h) wherein
$R^1$ is hydrogen, halogen, $C_1$-$C_3$ haloalkyl, $C_1$-$C_3$ alkyl, or —$OR^{1A}$; wherein $R^{1A}$ is $C_1$-$C_3$ alkyl;
$R^2$ is hydrogen, halogen, $C_1$-$C_3$ haloalkyl, $C_1$-$C_3$ alkyl, or —$OR^{1A}$; wherein $R^{1A}$ is $C_1$-$C_3$ haloalkyl, or $C_1$-$C_3$ alkyl wherein the $C_1$-$C_3$ alkyl is optionally substituted with one —$OR^{ZA}$ wherein $R^{ZA}$ is $C_1$-$C_3$ alkyl;
$R^4$ is hydrogen;
$R^6$ is hydrogen; and
$R^7$ is hydrogen.

In one embodiment, the invention is directed to compounds of formula (I-h) wherein
$R^1$ is hydrogen, halogen, $C_1$-$C_3$ haloalkyl, $C_1$-$C_3$ alkyl, or —$OR^{1A}$; wherein $R^{1A}$ is $C_1$-$C_3$ alkyl;
$R^2$ is hydrogen, halogen, $C_1$-$C_3$ haloalkyl, $C_1$-$C_3$ alkyl, or —$OR^{1A}$; wherein $R^{1A}$ is $C_1$-$C_3$ haloalkyl, or $C_1$-$C_3$ alkyl wherein the $C_1$-$C_3$ alkyl is optionally substituted with one —$OR^{ZA}$ wherein $R^{ZA}$ is $C_1$-$C_3$ alkyl;
$R^4$ is hydrogen;
$R^6$ is hydrogen;
$R^7$ is hydrogen; and
$R^3$, $R^{14}$, $R^9$, $R^{10}$, and $R^{13}$ are hydrogen.

In one embodiment, the invention is directed to compounds of formula (I-h) wherein
$R^1$ is hydrogen, $CH_3$, or —$OCH_3$;
$R^2$ is hydrogen, F, $CF_3$, $CH_3$, —$OCHF_2$, —$OCH_2CH_2F$, or —$OCH_2CH_2OCH_3$;
$R^4$ is hydrogen;
$R^6$ is hydrogen;
$R^7$ is hydrogen; and
$R^3$, $R^{14}$, $R^9$, $R^{10}$, and $R^{13}$ are hydrogen.

In one embodiment, the invention is directed to compounds of formula (I-h) wherein
$R^1$ is hydrogen, halogen, $C_1$-$C_3$ haloalkyl, $C_1$-$C_3$ alkyl, or —$OR^{1A}$; wherein $R^{1A}$ is $C_1$-$C_3$ alkyl;
$R^2$ is hydrogen, halogen, $C_1$-$C_3$ haloalkyl, $C_1$-$C_3$ alkyl, or —$OR^{1A}$; wherein $R^{1A}$ is $C_1$-$C_3$ haloalkyl, or $C_1$-$C_3$ alkyl wherein the $C_1$-$C_3$ alkyl is optionally substituted with one —$OR^{ZA}$ wherein $R^{ZA}$ is $C_1$-$C_3$ alkyl;
$R^4$ is hydrogen;
$R^6$ is hydrogen;
$R^7$ is hydrogen; and
$G^{2A}$ is phenyl substituted with 1, 2, or 3 $R^q$ groups; wherein one of $R^q$ groups is $C(O)OR^h$ wherein $R^h$ is hydrogen or $C_1$-$C_6$ alkyl; or one of $R^q$ groups is —$C(O)N(H)(R^h)$, wherein $R^h$ is cyclopentyl, or $R^h$ is $C_1$-$C_6$ alkyl substituted with 1 or 2 —OH groups; and the other optional $R^q$ groups are independently selected from the group consisting of $C_1$-$C_3$ alkyl, halogen, and $C_1$-$C_3$ haloalkyl.

In one embodiment, the invention is directed to compounds of formula (I-h) wherein
$R^1$ is hydrogen, halogen, $C_1$-$C_3$ haloalkyl, $C_1$-$C_3$ alkyl, or —$OR^{1A}$; wherein $R^{1A}$ is $C_1$-$C_3$ alkyl;
$R^2$ is hydrogen, halogen, $C_1$-$C_3$ haloalkyl, $C_1$-$C_3$ alkyl, or —$OR^{1A}$; wherein $R^{1A}$ is $C_1$-$C_3$ haloalkyl, or $C_1$-$C_3$ alkyl wherein the $C_1$-$C_3$ alkyl is optionally substituted with one —$OR^{ZA}$ wherein $R^{ZA}$ is $C_1$-$C_3$ alkyl;
$R^4$ is hydrogen;
$R^6$ is hydrogen;
$R^7$ is hydrogen;
$R^3$, $R^{14}$, $R^9$, $R^{10}$, and $R^{13}$ are hydrogen; and
$G^{2A}$ is phenyl substituted with 1, 2, or 3 $R^q$ groups; wherein one of $R^q$ groups is $C(O)OR^h$ wherein $R^h$ is hydrogen or $C_1$-$C_6$ alkyl; or one of $R^q$ groups is —$C(O)N(H)(R^h)$, wherein $R^h$ is cyclopentyl, or $R^h$ is $C_1$-$C_6$ alkyl substituted with 1 or 2 —OH groups; and the other optional $R^q$ groups are independently selected from the group consisting of $C_1$-$C_3$ alkyl, halogen, and $C_1$-$C_3$ haloalkyl.

In one embodiment, the invention is directed to compounds of formula (I-h) wherein
$R^1$ is hydrogen, halogen, $C_1$-$C_3$ haloalkyl, $C_1$-$C_3$ alkyl, or —$OR^{1A}$; wherein $R^{1A}$ is $C_1$-$C_3$ alkyl;
$R^2$ is hydrogen, halogen, $C_1$-$C_3$ haloalkyl, $C_1$-$C_3$ alkyl, or —$OR^{1A}$; wherein $R^{1A}$ is $C_1$-$C_3$ haloalkyl, or $C_1$-$C_3$ alkyl wherein the $C_1$-$C_3$ alkyl is optionally substituted with one —$OR^{ZA}$ wherein $R^{ZA}$ is $C_1$-$C_3$ alkyl;
$R^4$ is hydrogen;
$R^6$ is hydrogen;
$R^7$ is hydrogen; and
$G^{2A}$ is phenyl or cyclohexyl; each of which is substituted with one $C(O)OR^h$ wherein $R^h$ is hydrogen or $C_1$-$C_3$ alkyl.

In one embodiment, the invention is directed to compounds of formula (I-h) wherein
$R^1$ is hydrogen, halogen, $C_1$-$C_3$ haloalkyl, $C_1$-$C_3$ alkyl, or —$OR^{1A}$; wherein $R^{1A}$ is $C_1$-$C_3$ alkyl;
$R^2$ is hydrogen, halogen, $C_1$-$C_3$ haloalkyl, $C_1$-$C_3$ alkyl, or —$OR^{1A}$; wherein $R^{1A}$ is $C_1$-$C_3$ haloalkyl, or $C_1$-$C_3$ alkyl wherein the $C_1$-$C_3$ alkyl is optionally substituted with one —$OR^{ZA}$ wherein $R^{ZA}$ is $C_1$-$C_3$ alkyl;
$R^4$ is hydrogen;
$R^6$ is hydrogen;
$R^7$ is hydrogen;
$R^3$, $R^{14}$, $R^9$, $R^{10}$, and $R^{13}$ are hydrogen; and
$G^{2A}$ is phenyl or cyclohexyl; each of which is substituted with one $C(O)OR^h$ wherein $R^h$ is hydrogen or $C_1$-$C_3$ alkyl.

In one embodiment, the invention is directed to compounds of formula (I-h) wherein
$R^1$ is hydrogen, halogen, $C_1$-$C_3$ haloalkyl, $C_1$-$C_3$ alkyl, or —$OR^{1A}$; wherein $R^{1A}$ is $C_1$-$C_3$ alkyl;
$R^2$ is hydrogen, halogen, $C_1$-$C_3$ haloalkyl, $C_1$-$C_3$ alkyl, or —$OR^{1A}$; wherein $R^{1A}$ is $C_1$-$C_3$ haloalkyl, or $C_1$-$C_3$ alkyl wherein the $C_1$-$C_3$ alkyl is optionally substituted with one —$OR^{ZA}$ wherein $R^{ZA}$ is $C_1$-$C_3$ alkyl;
$R^4$ is hydrogen;
$R^6$ is hydrogen;
$R^7$ is hydrogen; and
$G^{2A}$ is phenyl substituted with one $C(O)OR^h$ wherein $R^h$ is hydrogen or $C_1$-$C_3$ alkyl.

In some such embodiment, $R^h$ is hydrogen. In some such embodiment, $R^h$ is $C_1$-$C_3$ alkyl.

In one embodiment, the invention is directed to compounds of formula (I-h) wherein
$R^1$ is hydrogen, halogen, $C_1$-$C_3$ haloalkyl, $C_1$-$C_3$ alkyl, or —$OR^{1A}$; wherein $R^{1A}$ is $C_1$-$C_3$ alkyl;
$R^2$ is hydrogen, halogen, $C_1$-$C_3$ haloalkyl, $C_1$-$C_3$ alkyl, or —$OR^{1A}$; wherein $R^{1A}$ is $C_1$-$C_3$ haloalkyl, or $C_1$-$C_3$ alkyl wherein the $C_1$-$C_3$ alkyl is optionally substituted with one —$OR^{ZA}$ wherein $R^{ZA}$ is $C_1$-$C_3$ alkyl;
$R^4$ is hydrogen;
$R^6$ is hydrogen;
$R^7$ is hydrogen;
$R^3$, $R^{14}$, $R^9$, $R^{10}$, and $R^{13}$ are hydrogen; and $G^{2A}$ is phenyl substituted with one C(O)OR$^h$ wherein R$^h$ is hydrogen or $C_1$-$C_3$ alkyl.

In some such embodiment, R$^h$ is hydrogen. In some such embodiment, R$^h$ is $C_1$-$C_3$ alkyl.

In one embodiment, the invention is directed to compounds of formula (I-h) wherein
$R^1$ is hydrogen, halogen, $C_1$-$C_3$ haloalkyl, $C_1$-$C_3$ alkyl, or —OR$^{1A}$; wherein R$^{1A}$ is $C_1$-$C_3$ alkyl;
$R^2$ is hydrogen, halogen, $C_1$-$C_3$ haloalkyl, $C_1$-$C_3$ alkyl, or —OR$^{1A}$; wherein R$^{1A}$ is $C_1$-$C_3$ haloalkyl, or $C_1$-$C_3$ alkyl wherein the $C_1$-$C_3$ alkyl is optionally substituted with one —OR$^{ZA}$ wherein R$^{ZA}$ is $C_1$-$C_3$ alkyl;
$R^4$ is hydrogen;
$R^6$ is hydrogen;
$R^7$ is hydrogen; and
$G^{2A}$ is cyclohexyl substituted with one C(O)OR$^h$ wherein R$^h$ is hydrogen or $C_1$-$C_3$ alkyl.

In some such embodiment, R$^h$ is hydrogen. In some such embodiment, R$^h$ is $C_1$-$C_3$ alkyl.

In one embodiment, the invention is directed to compounds of formula (I-h) wherein
$R^1$ is hydrogen, halogen, $C_1$-$C_3$ haloalkyl, $C_1$-$C_3$ alkyl, or —OR$^{1A}$; wherein R$^{1A}$ is $C_1$-$C_3$ alkyl;
$R^2$ is hydrogen, halogen, $C_1$-$C_3$ haloalkyl, $C_1$-$C_3$ alkyl, or —OR$^{1A}$; wherein R$^{1A}$ is $C_1$-$C_3$ haloalkyl, or $C_1$-$C_3$ alkyl wherein the $C_1$-$C_3$ alkyl is optionally substituted with one —OR$^{ZA}$ wherein R$^{ZA}$ is $C_1$-$C_3$ alkyl;
$R^4$ is hydrogen;
$R^6$ is hydrogen;
$R^7$ is hydrogen;
$R^3$, $R^{14}$, $R^9$, $R^{10}$, and $R^{13}$ are hydrogen; and
$G^{2A}$ is cyclohexyl substituted with one C(O)OR$^h$ wherein R$^h$ is hydrogen or $C_1$-$C_3$ alkyl.

In some such embodiment, R$^h$ is hydrogen. In some such embodiment, R$^h$ is $C_1$-$C_3$ alkyl.

One embodiment is directed to compounds of formula (I-i)

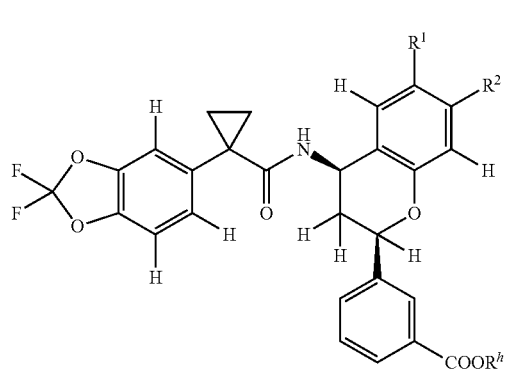

(I-i)

wherein
$R^1$ is hydrogen, halogen, $C_1$-$C_3$ haloalkyl, $C_1$-$C_3$ alkyl, or —OR$^{1A}$; wherein R$^{1A}$ is $C_1$-$C_3$ alkyl; and
$R^2$ is hydrogen, halogen, $C_1$-$C_3$ haloalkyl, $C_1$-$C_3$ alkyl, or —OR$^{1A}$; wherein R$^{1A}$ is $C_1$-$C_3$ haloalkyl, or $C_1$-$C_3$ alkyl wherein the $C_1$-$C_3$ alkyl is optionally substituted with one —OR$^{ZA}$, and R$^{ZA}$ is $C_1$-$C_3$ alkyl; and
$R^h$ is hydrogen or $C_1$-$C_3$ alkyl.

In one embodiment, the invention is directed to compounds of formula (I-i) wherein
$R^1$ is hydrogen, $C_1$-$C_3$ alkyl, or —OR$^{1A}$; wherein R$^{1A}$ is $C_1$-$C_3$ alkyl; and
$R^h$ is hydrogen.

One embodiment is directed to compounds of formula (I-j)

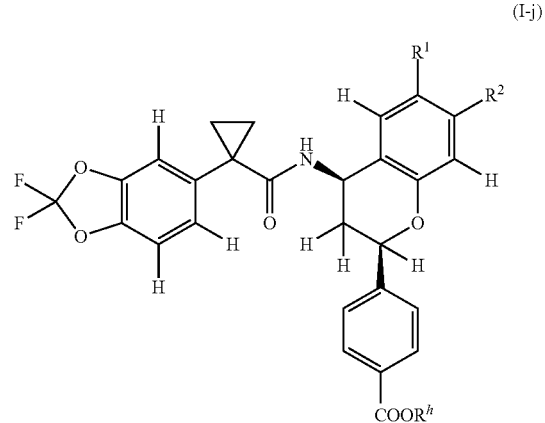

(I-j)

wherein
$R^1$ is hydrogen, halogen, $C_1$-$C_3$ haloalkyl, $C_1$-$C_3$ alkyl, or —OR$^{1A}$; wherein R$^{1A}$ is $C_1$-$C_3$ alkyl; and
$R^2$ is hydrogen, halogen, $C_1$-$C_3$ haloalkyl, $C_1$-$C_3$ alkyl, or —OR$^{1A}$; wherein R$^{1A}$ is $C_1$-$C_3$ haloalkyl, or $C_1$-$C_3$ alkyl wherein the $C_1$-$C_3$ alkyl is optionally substituted with one —OR$^{ZA}$, and R$^{ZA}$ is $C_1$-$C_3$ alkyl; and
$R^h$ is hydrogen or $C_1$-$C_3$ alkyl.

In one embodiment, the invention is directed to compounds of formula (I-j) wherein
$R^1$ is hydrogen, $C_1$-$C_3$ alkyl, or —OR$^{1A}$; wherein R$^{1A}$ is $C_1$-$C_3$ alkyl; and
$R^h$ is hydrogen.

One embodiment is directed to compounds of formula (I) wherein
X is CR$^2$ and Y is CR$^3$; or
X is N and Y is CR$^3$; or
X is CR$^2$ and Y is N;
m is 0, 1, 2, or 3;
R" are optional substituents on the cyclopropyl ring, and at each occurrence, are each independently halogen, $C_1$-$C_6$ haloalkyl, or $C_1$-$C_6$ alkyl;
$R^1$ and $R^2$, are each independently hydrogen, halogen, $C_1$-$C_6$ haloalkyl, $C_1$-$C_6$ alkyl, —OR$^{1A}$, —C(O)OR$^{1B}$, —NR$^{1A}$R$^{2A}$, or —C(O)NR$^{1A}$R$^{2A}$;
$R^{1A}$ and $R^{2A}$, at each occurrence, are each independently hydrogen, $C_1$-$C_6$ haloalkyl, $G^{1A}$, or $C_1$-$C_6$ alkyl; wherein the $C_1$-$C_6$ haloalkyl and the $C_1$-$C_6$ alkyl are each optionally substituted with one or two substituents independently selected from the group consisting of —OR$^{ZA}$, —SR$^A$, —S(O)$_2$R$^{ZA}$, —C(O)R$^{ZA}$, —C(O)OR$^{ZA}$, —C(O)N(R$^{ZA}$)$_2$, —N(R$^{ZA}$)$_2$, —N(R$^{ZA}$)C(O)R$^{ZB}$, —N(R$^{ZA}$)S(O)$_2$R$^{ZB}$, —N(R$^{ZA}$)C(O)OR$^{ZB}$, —N(R$^{ZA}$)C(O)N(R$^{ZA}$)$_2$, —CN, and $G^{1A}$; or R$^{1A}$ and R$^{2A}$ together with the nitrogen atom to which they are attached form a 4-6 membered heterocycle wherein the 4-6 membered heterocycle is optionally substituted with 1, 2, or 3 substituents independently selected from the group consisting of halogen, $C_1$-$C_6$ alkyl, $C_1$-$C_6$ haloalkyl, —OR$^j$, and N(R$^j$)$_2$; wherein R$^{ZA}$, at each occurrence, is independently hydrogen, $C_1$-$C_6$ haloalkyl, $C_1$-$C_6$ alkyl, $G^{1A}$, or —($C_1$-$C_6$ alkylenyl)-$G^{1A}$; and
R$^{ZB}$, at each occurrence, is independently $C_1$-$C_6$ haloalkyl, $C_1$-$C_6$ alkyl, $G^{1A}$, or —($C_1$-$C_6$ alkylenyl)-$G^{1A}$;

R$^{1B}$ is hydrogen, C$_1$-C$_6$ haloalkyl, or C$_1$-C$_6$ alkyl;

R$^3$ and R$^{14}$, are each independently hydrogen, halogen, C$_1$-C$_6$ haloalkyl, C$_1$-C$_6$ alkyl, —OH, or —O—(C$_1$-C$_6$ alkyl);

R$^4$ is hydrogen, C$_1$-C$_6$ haloalkyl, or C$_1$-C$_6$ alkyl;

R$^5$ is hydrogen, —C(O)R$^i$, —C(O)OH, —C(O)N(R$^h$)$_2$, C$_1$-C$_6$ haloalkyl, C$_1$-C$_6$ alkyl, or G$^{2A}$; wherein the C$_1$-C$_6$ haloalkyl and the C$_1$-C$_6$ alkyl are each optionally substituted with one or two substituents independently selected from the group consisting of —OR$^h$, —OC(O)N(R$^h$)$_2$, —C(O)R$^h$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^{2A}$; or R$^4$ and R$^5$, together with the carbon atom to which they are attached, form a C$_3$-C$_6$ cycloalkyl or a 4-6 membered heterocycle; wherein the C$_3$-C$_6$ cycloalkyl and the 4-6 membered heterocycle are each optionally substituted with 1, 2, or 3 independently selected R$^p$ groups;

G$^{2A}$, at each occurrence, is independently cycloalkyl, cycloalkenyl, heterocycle, aryl, or heteroaryl, each of which is independently unsubstituted or substituted with 1, 2, or 3 independently selected R$^q$ groups;

R$^p$ and R$^q$, at each occurrence, are each independently C$_1$-C$_6$ alkyl, halogen, C$_1$-C$_6$ haloalkyl, —CN, oxo, NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^h$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, or G$^A$, wherein the C$_1$-C$_6$ haloalkyl and the C$_1$-C$_6$ alkyl are each optionally substituted with one or two substituents independently selected from the group consisting of —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^h$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, —CN, and G$^A$;

R$^h$, at each occurrence, is independently hydrogen, C$_1$-C$_6$ haloalkyl, C$_1$-C$_6$ alkyl, or G$^A$, wherein the C$_1$-C$_6$ haloalkyl and the C$_1$-C$_6$ alkyl are each optionally substituted with one or two substituents independently selected from the group consisting of —OR, —OC(O)N(R$^j$)$_2$, —SR$^j$, —C(O)OR$^j$, —C(O)N(R$^j$)$_2$, —N(R$^j$)$_2$, —CN, and G$^A$;

R$^i$, at each occurrence, is independently C$_1$-C$_6$ haloalkyl, C$_1$-C$_6$ alkyl, or G$^A$, wherein the C$_1$-C$_6$ haloalkyl and the C$_1$-C$_6$ alkyl are each optionally substituted with one or two substituents independently selected from the group consisting of —OR$^j$, —OC(O)N(R$^j$)$_2$, —SR$^j$, —C(O)OR$^j$, —C(O)N(R$^j$)$_2$, —N(R$^j$)$_2$, —CN, and G$^A$;

R$^6$ is hydrogen, halogen, C$_1$-C$_6$ haloalkyl, or C$_1$-C$_6$ alkyl;

R$^7$ is hydrogen, halogen, —OR$^j$, —N(R$^j$)$_2$, —N(R$^j$)C(O)R$^k$, C$_1$-C$_6$ haloalkyl, C$_1$-C$_6$ alkyl, C$_2$-C$_6$ alkenyl, or —(C$_1$-C$_6$ alkylenyl)-G$^{3A}$;

R$^8$ is hydrogen, C$_1$-C$_6$ haloalkyl, or C$_1$-C$_6$ alkyl;

R$^9$, R$^{10}$, and R$^{13}$, are each independently hydrogen, halogen, —OR$^j$, C$_1$-C$_6$ haloalkyl, or C$_1$-C$_6$ alkyl;

R$^{11}$ and R$^{12}$ are each independently hydrogen, C$_1$-C$_3$ alkyl, or halogen;

G$^{1A}$, G$^{3A}$, and G$^A$, at each occurrence, are each independently cycloalkyl, cycloalkenyl, heterocycle, aryl, or heteroaryl, each of which is independently unsubstituted or substituted with 1, 2, or 3 independently selected R$^s$ groups; wherein R$^s$, at each occurrence, is independently C$_1$-C$_6$ alkyl, C$_2$-C$_6$ alkenyl, C$_2$-C$_6$ alkynyl, halogen, C$_1$-C$_6$ haloalkyl, —CN, oxo, NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^j$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$ alkylenyl)-OR$^j$, —(C$_1$-C$_6$ alkylenyl)-OC(O)R$^k$, —(C$_1$-C$_6$ alkylenyl)-OC(O)N(R$^j$)$_2$, —(C$_1$-C$_6$ alkylenyl)-SR$^j$, —(C$_1$-C$_6$ alkylenyl)-S(O)$_2$R$^j$, —(C$_1$-C$_6$ alkylenyl)-S(O)$_2$N(R$^j$)$_2$, —(C$_1$-C$_6$ alkylenyl)-C(O)R$^j$, —(C$_1$-C$_6$ alkylenyl)-C(O)OR$^j$, —(C$_1$-C$_6$ alkylenyl)-C(O)N(R$^j$)$_2$, —(C$_1$-C$_6$ alkylenyl)-N(R$^j$)$_2$, —(C$_1$-C$_6$ alkylenyl)-N(R$^j$)C(O)R$^k$, —(C$_1$-C$_6$ alkylenyl)-N(R$^j$)S(O)$_2$R$^k$, —(C$_1$-C$_6$ alkylenyl)-N(R$^j$)C(O)O(R$^k$), —(C$_1$-C$_6$ alkylenyl)-N(R$^j$)C(O)N(R$^j$)$_2$, or —(C$_1$-C$_6$ alkylenyl)-CN;

R$^j$, at each occurrence, is independently hydrogen, C$_1$-C$_6$ alkyl, or C$_1$-C$_6$ haloalkyl; and R$^k$, at each occurrence, is independently C$_1$-C$_6$ alkyl or C$_1$-C$_6$ haloalkyl.

Exemplary compounds of formula (I) include, but are not limited to:

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4S)-4-({[1-(2,2-difluoro-1,3-benzodioxol-5-yl)cyclopropyl]carbonyl}amino)-7-methoxy-3,4-dihydro-2H-chromen-2-yl]benzoic acid;

1-(2,2-difluoro-1,3-benzodioxol-5-yl)-N-[(2R,4R)-2-(3,4-dimethoxyphenyl)-7-methoxy-3,4-dihydro-2H-chromen-4-yl]cyclopropanecarboxamide;

1-(2,2-difluoro-1,3-benzodioxol-5-yl)-N-[(2S,4S)-2-(3,4-dimethoxyphenyl)-7-methoxy-3,4-dihydro-2H-chromen-4-yl]cyclopropanecarboxamide;

methyl 3-[(2R,4S)-4-({[1-(2,2-difluoro-1,3-benzodioxol-5-yl)cyclopropyl]carbonyl}amino)-7-methoxy-3,4-dihydro-2H-chromen-2-yl]benzoate;

methyl 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoate;

methyl 3-[(2R,4S)-4-({[1-(2,2-difluoro-1,3-benzodioxol-5-yl)cyclopropyl]carbonyl}amino)-3,4-dihydro-2H-chromen-2-yl]benzoate;

methyl 3-[(2R,4R)-4-({[1-(2,2-difluoro-1,3-benzodioxol-5-yl)cyclopropyl]carbonyl}amino)-3,4-dihydro-2H-chromen-2-yl]benzoate;

3-[(2R,4R)-4-({[1-(2,2-difluoro-1,3-benzodioxol-5-yl)cyclopropyl]carbonyl}amino)-3,4-dihydro-2H-chromen-2-yl]benzoic acid;

3-[(2R,4S)-4-({[1-(2,2-difluoro-1,3-benzodioxol-5-yl)cyclopropyl]carbonyl}amino)-3,4-dihydro-2H-chromen-2-yl]benzoic acid;

methyl 3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoate;

methyl 3-[(2R,4S)-4-({[1-(2,2-difluoro-1,3-benzodioxol-5-yl)cyclopropyl]carbonyl}amino)-6-methyl-3,4-dihydro-2H-chromen-2-yl]benzoate;

3-[(2R,4S)-4-({[1-(2,2-difluoro-1,3-benzodioxol-5-yl)cyclopropyl]carbonyl}amino)-6-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid;

3-[(2R,4S)-4-({[1-(2,2-difluoro-1,3-benzodioxol-5-yl)cyclopropyl]carbonyl}amino)-7-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;

methyl 3-[(2R,4S)-4-({[1-(2,2-difluoro-1,3-benzodioxol-5-yl)cyclopropyl]carbonyl}amino)-7-methyl-3,4-dihydro-2H-chromen-2-yl]benzoate;

methyl 3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoate;

3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;

1-(2,2-difluoro-1,3-benzodioxol-5-yl)-N-[(2R,4R)-7-hydroxy-2-(3-methoxyphenyl)-3,4-dihydro-2H-chromen-4-yl]cyclopropanecarboxamide;

methyl 3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoate;

rac-1-(2,2-difluoro-1,3-benzodioxol-5-yl)-N-[(2R,4S)-7-methoxy-2-(pyridin-3-yl)-3,4-dihydro-2H-chromen-4-yl]cyclopropanecarboxamide;

3-[(2R,4R)-4-({[1-(2,2-difluoro-1,3-benzodioxol-5-yl)cyclopropyl]carbonyl}amino)-7-hydroxy-3,4-dihydro-2H-chromen-2-yl]benzoic acid;

ethyl rel-3-[(2S,4S)-4-({[1-(2,2-difluoro-1,3-benzodioxol-5-yl)cyclopropyl]carbonyl}amino)-3,4-dihydro-2H-pyrano[2,3-c]pyridin-2-yl]benzoate;

ethyl rel-3-[(2R,4R)-4-({[1-(2,2-difluoro-1,3-benzodioxol-5-yl)cyclopropyl]carbonyl}amino)-3,4-dihydro-2H-pyrano[2,3-c]pyridin-2-yl]benzoate;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

rac-3-[(2R,4R)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoic acid;

rac-3-[(2R,4S)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoic acid;

methyl rac-3-[(2R,4R)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoate;

rac-3-[(2R,4R)-4-({[1-(2,2-difluoro-1,3-benzodioxol-5-yl)cyclopropyl]carbonyl}amino)-3,4-dihydro-2H-pyrano[2,3-b]pyridin-2-yl]benzoic acid;

rac-3-[(2R,4S)-4-({[1-(2,2-difluoro-1,3-benzodioxol-5-yl)cyclopropyl]carbonyl}amino)-3,4-dihydro-2H-pyrano[2,3-b]pyridin-2-yl]benzoic acid;

rac-methyl 3-[(2R,4R)-4-({[1-(2,2-difluoro-1,3-benzodioxol-5-yl)cyclopropyl]carbonyl}amino)-3,4-dihydro-2H-pyrano[2,3-b]pyridin-2-yl]benzoate;

rac-methyl 3-[(2R,4S)-4-({[1-(2,2-difluoro-1,3-benzodioxol-5-yl)cyclopropyl]carbonyl}amino)-3,4-dihydro-2H-pyrano[2,3-b]pyridin-2-yl]benzoate;

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-fluoro-3,4-dihydro-2H-chromen-2-yl]cyclohexanecarboxylic acid;

methyl 3-[4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoate;

3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid;

methyl 3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoate;

rac-N-[(2R,4R)-2-cyclopropyl-7-methoxy-3,4-dihydro-2H-chromen-4-yl]-1-(2,2-difluoro-1,3-benzodioxol-5-yl)cyclopropanecarboxamide;

rac-N-[(2R,4S)-2-cyclopropyl-7-methoxy-3,4-dihydro-2H-chromen-4-yl]-1-(2,2-difluoro-1,3-benzodioxol-5-yl)cyclopropanecarboxamide;

4-({[1-(2,2-difluoro-1,3-benzodioxol-5-yl)cyclopropyl]carbonyl}amino)-3,4-dihydro-2H-chromene-7-carboxylic acid;

3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;

(2R,4R)-4-({[1-(2,2-difluoro-1,3-benzodioxol-5-yl)cyclopropyl]carbonyl}amino)-2-(3-methoxyphenyl)-3,4-dihydro-2H-chromene-6-carboxylic acid;

methyl 4-({[1-(2,2-difluoro-1,3-benzodioxol-5-yl)cyclopropyl]carbonyl}amino)-3,4-dihydro-2H-chromene-7-carboxylate;

methyl (2R,4R)-4-({[1-(2,2-difluoro-1,3-benzodioxol-5-yl)cyclopropyl]carbonyl}amino)-2-(3-methoxycyclohexyl)-3,4-dihydro-2H-chromene-6-carboxylate;

methyl (2R,4R)-4-({[1-(2,2-difluoro-1,3-benzodioxol-5-yl)cyclopropyl]carbonyl}amino)-2-(3-methoxyphenyl)-3,4-dihydro-2H-chromene-6-carboxylate;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide;

1-(2,2-difluoro-1,3-benzodioxol-5-yl)-N-[(2R,4R)-2-(3-{[(3R)-3-hydroxypyrrolidin-1-yl]carbonyl}phenyl)-7-methyl-3,4-dihydro-2H-chromen-4-yl]cyclopropanecarboxamide;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-(3,3,3-trifluoro-2-hydroxypropyl)benzamide;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-(2-hydroxy-2-methylpropyl)benzamide;

1-(2,2-difluoro-1,3-benzodioxol-5-yl)-N-[(2R,4R)-2-(3-{[3-(hydroxymethyl)piperidin-1-yl]carbonyl}phenyl)-7-methyl-3,4-dihydro-2H-chromen-4-yl]cyclopropanecarboxamide;

1-(2,2-difluoro-1,3-benzodioxol-5-yl)-N-[(2R,4R)-2-(3-{[2-(hydroxymethyl)morpholin-4-yl]carbonyl}phenyl)-7-methyl-3,4-dihydro-2H-chromen-4-yl]cyclopropanecarboxamide;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(1-hydroxycyclobutyl)methyl]benzamide;

1-(2,2-difluoro-1,3-benzodioxol-5-yl)-N-[(2R,4R)-2-(3-{[3-(hydroxymethyl)-3-methylazetidin-1-yl]carbonyl}phenyl)-7-methyl-3,4-dihydro-2H-chromen-4-yl]cyclopropanecarboxamide;

N-(7-bromo-3,4-dihydro-2H-chromen-4-yl)-1-(2,2-difluoro-1,3-benzodioxol-5-yl)cyclopropanecarboxamide;

rac-1-(2,2-difluoro-1,3-benzodioxol-5-yl)-N-[(2R,4R)-7-methoxy-2-(pyridin-3-yl)-3,4-dihydro-2H-chromen-4-yl]cyclopropanecarboxamide;

1-(2,2-difluoro-1,3-benzodioxol-5-yl)-N-{(2R)-2-[3-(hydroxymethyl)phenyl]-3,4-dihydro-2H-chromen-4-yl}cyclopropanecarboxamide;

1-(2,2-difluoro-1,3-benzodioxol-5-yl)-N-(7-methoxy-3,4-dihydro-2H-chromen-4-yl)cyclopropanecarboxamide;
1-(2,2-difluoro-1,3-benzodioxol-5-yl)-N-(7-methoxy-2-phenyl-3,4-dihydro-2H-chromen-4-yl)cyclopropanecarboxamide;
N-[2-(3,4-dichlorophenyl)-7-methoxy-3,4-dihydro-2H-chromen-4-yl]-1-(2,2-difluoro-1,3-benzodioxol-5-yl)cyclopropanecarboxamide;
1-(2,2-difluoro-1,3-benzodioxol-5-yl)-N-[2-(3,4-dimethoxyphenyl)-7-methoxy-3,4-dihydro-2H-chromen-4-yl]cyclopropanecarboxamide;
N-[2-(4-chlorophenyl)-7-methoxy-3,4-dihydro-2H-chromen-4-yl]-1-(2,2-difluoro-1,3-benzodioxol-5-yl)cyclopropanecarboxamide;
1-(2,2-difluoro-1,3-benzodioxol-5-yl)-N-{2-[4-(trifluoromethyl)phenyl]-3,4-dihydro-2H-chromen-4-yl}cyclopropanecarboxamide;
N-[2-(2-chlorophenyl)-3,4-dihydro-2H-chromen-4-yl]-1-(2,2-difluoro-1,3-benzodioxol-5-yl)cyclopropanecarboxamide;
N-[2-(3,4-dichlorophenyl)-3,4-dihydro-2H-chromen-4-yl]-1-(2,2-difluoro-1,3-benzodioxol-5-yl)cyclopropanecarboxamide;
1-(2,2-difluoro-1,3-benzodioxol-5-yl)-N-(2-phenyl-3,4-dihydro-2H-chromen-4-yl)cyclopropanecarboxamide;
N-[2-(4-chlorophenyl)-3,4-dihydro-2H-chromen-4-yl]-1-(2,2-difluoro-1,3-benzodioxol-5-yl)cyclopropanecarboxamide;
1-(2,2-difluoro-1,3-benzodioxol-5-yl)-N-[2-(3,4-dimethoxyphenyl)-3,4-dihydro-2H-chromen-4-yl]cyclopropanecarboxamide;
N-[2-(3-chlorophenyl)-3,4-dihydro-2H-chromen-4-yl]-1-(2,2-difluoro-1,3-benzodioxol-5-yl)cyclopropanecarboxamide;
1-(2,2-difluoro-1,3-benzodioxol-5-yl)-N-[2-(4-fluorophenyl)-3,4-dihydro-2H-chromen-4-yl]cyclopropanecarboxamide;
1-(2,2-difluoro-1,3-benzodioxol-5-yl)-N-[3-(3,4-dimethoxybenzyl)-6-methoxy-3,4-dihydro-2H-chromen-4-yl]cyclopropanecarboxamide;
N-(3-benzyl-3,4-dihydro-2H-chromen-4-yl)-1-(2,2-difluoro-1,3-benzodioxol-5-yl)cyclopropanecarboxamide;
N-[(4R)-2,2-diethyl-3,4-dihydro-2H-chromen-4-yl]-1-(2,2-difluoro-1,3-benzodioxol-5-yl)cyclopropanecarboxamide;
N-[(4R)-2,2-bis(fluoromethyl)-3,4-dihydro-2H-chromen-4-yl]-1-(2,2-difluoro-1,3-benzodioxol-5-yl)cyclopropanecarboxamide;
N-[(4R)-7-chloro-2,2-dimethyl-3,4-dihydro-2H-chromen-4-yl]-1-(2,2-difluoro-1,3-benzodioxol-5-yl)cyclopropanecarboxamide;
1-(2,2-difluoro-1,3-benzodioxol-5-yl)-N-[(4R)-8-fluoro-2,2-bis(fluoromethyl)-3,4-dihydro-2H-chromen-4-yl]cyclopropanecarboxamide;
1-(2,2-difluoro-1,3-benzodioxol-5-yl)-N-[(4R)-3,4-dihydrospiro[chromene-2,1'-cyclopentan]-4-yl]cyclopropanecarboxamide;
1-(2,2-difluoro-1,3-benzodioxol-5-yl)-N-[(4R)-7-fluoro-2,2-bis(fluoromethyl)-3,4-dihydro-2H-chromen-4-yl]cyclopropanecarboxamide;
1-(2,2-difluoro-1,3-benzodioxol-5-yl)-N-[(2S,4R)-2-(fluoromethyl)-2-methyl-7-(trifluoromethyl)-3,4-dihydro-2H-chromen-4-yl]cyclopropanecarboxamide;
1-(2,2-difluoro-1,3-benzodioxol-5-yl)-N-[(2R,4R)-2-(difluoromethyl)-2-methyl-3,4-dihydro-2H-chromen-4-yl]cyclopropanecarboxamide;
1-(2,2-difluoro-1,3-benzodioxol-5-yl)-N-[(2S,4R)-2-(difluoromethyl)-2-methyl-3,4-dihydro-2H-chromen-4-yl]cyclopropanecarboxamide;
N-[(2S,4R)-7-chloro-2-(difluoromethyl)-2-methyl-3,4-dihydro-2H-chromen-4-yl]-1-(2,2-difluoro-1,3-benzodioxol-5-yl)cyclopropanecarboxamide;
N-[(2R,4R)-7-chloro-2-(difluoromethyl)-2-methyl-3,4-dihydro-2H-chromen-4-yl]-1-(2,2-difluoro-1,3-benzodioxol-5-yl)cyclopropanecarboxamide;
1-(2,2-difluoro-1,3-benzodioxol-5-yl)-N-[(2S,4R)-2-methyl-2-(trifluoromethyl)-3,4-dihydro-2H-chromen-4-yl]cyclopropanecarboxamide;
1-(2,2-difluoro-1,3-benzodioxol-5-yl)-N-[(4R)-7-fluoro-2,2-dimethyl-3,4-dihydro-2H-chromen-4-yl]cyclopropanecarboxamide;
N-[(4R)-7-chloro-2,2-bis(fluoromethyl)-3,4-dihydro-2H-chromen-4-yl]-1-(2,2-difluoro-1,3-benzodioxol-5-yl)cyclopropanecarboxamide;
1-(2,2-difluoro-1,3-benzodioxol-5-yl)-N-[(4S)-6-fluoro-2,2-dimethyl-3,4-dihydro-2H-chromen-4-yl]cyclopropanecarboxamide;
1-(2,2-difluoro-1,3-benzodioxol-5-yl)-N-[(4S)-6-fluoro-3,4-dihydrospiro[chromene-2,1'-cyclobutan]-4-yl]cyclopropanecarboxamide;
N-[(4R)-8-chloro-7-fluoro-2,2-dimethyl-3,4-dihydro-2H-chromen-4-yl]-1-(2,2-difluoro-1,3-benzodioxol-5-yl)cyclopropanecarboxamide;
1-(2,2-difluoro-1,3-benzodioxol-5-yl)-N-[3-(3,4-dimethoxybenzyl)-7-methoxy-3,4-dihydro-2H-chromen-4-yl]cyclopropanecarboxamide;
tert-butyl 4-({[1-(2,2-difluoro-1,3-benzodioxol-5-yl)cyclopropyl]carbonyl}amino)-7-fluoro-3,4-dihydro-1'H-spiro[chromene-2,4'-piperidine]-1'-carboxylate;
1-(2,2-difluoro-1,3-benzodioxol-5-yl)-N-(7-fluoro-3,4-dihydrospiro[chromene-2,4'-piperidin]-4-yl)cyclopropanecarboxamide;
methyl 3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoate;
methyl 3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoate;
3-[(2R,4R)-7-(carboxymethoxy)-4-({[1-(2,2-difluoro-1,3-benzodioxol-5-yl)cyclopropyl]carbonyl}amino)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;
3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;
1-(2,2-difluoro-1,3-benzodioxol-5-yl)-N-{1'-[(2R)-2,3-dihydroxypropyl]-7-fluoro-3,4-dihydrospiro[chromene-2,4'-piperidin]-4-yl}cyclopropanecarboxamide;
benzyl 4'-({[1-(2,2-difluoro-1,3-benzodioxol-5-yl)cyclopropyl]carbonyl}amino)-7'-fluoro-3',4'-dihydro-1H-spiro[azetidine-3,2'-chromene]-1-carboxylate;
1-(2,2-difluoro-1,3-benzodioxol-5-yl)-N-[7-fluoro-1'-(methylsulfonyl)-3,4-dihydrospiro[chromene-2,4'-piperidin]-4-yl]cyclopropanecarboxamide;
N-(1'-acetyl-7-fluoro-3,4-dihydrospiro[chromene-2,4'-piperidin]-4-yl)-1-(2,2-difluoro-1,3-benzodioxol-5-yl)cyclopropanecarboxamide;
1-(2,2-difluoro-1,3-benzodioxol-5-yl)-N-(7'-fluoro-3',4'-dihydrospiro[azetidine-3,2'-chromen]-4'-yl)cyclopropanecarboxamide;

1-(2,2-difluoro-1,3-benzodioxol-5-yl)-N-[7'-fluoro-1-(methylsulfonyl)-3',4'-dihydrospiro[azetidine-3,2'-chromen]-4'-yl]cyclopropanecarboxamide;

N-(1-acetyl-7'-fluoro-3',4'-dihydrospiro[azetidine-3,2'-chromen]-4'-yl)-1-(2,2-difluoro-1,3-benzodioxol-5-yl)cyclopropanecarboxamide;

3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;

1-(2,2-difluoro-1,3-benzodioxol-5-yl)-N-[1'-(3-hydroxy-2,2-dimethylpropanoyl)-7-methoxy-3,4-dihydrospiro[chromene-2,4'-piperidin]-4-yl]cyclopropanecarboxamide;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;

methyl 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoate;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

methyl rac-3-[(2R,4R)-7-chloro-4-({[1-(2,2-difluoro-1,3-benzodioxol-5-yl)cyclopropyl]carbonyl}amino)-3,4-dihydro-2H-pyrano[2,3-b]pyridin-2-yl]benzoate;

methyl rac-3-[(2R,4R)-4-({[1-(2,2-difluoro-1,3-benzodioxol-5-yl)cyclopropyl]carbonyl}amino)-7-fluoro-3,4-dihydro-2H-pyrano[2,3-b]pyridin-2-yl]benzoate;

rac-3-[(2R,4R)-7-chloro-4-({[1-(2,2-difluoro-1,3-benzodioxol-5-yl)cyclopropyl]carbonyl}amino)-3,4-dihydro-2H-pyrano[2,3-b]pyridin-2-yl]benzoic acid;

tert-butyl 3-[4-({[1-(2,2-difluoro-1,3-benzodioxol-5-yl)cyclopropyl]carbonyl}amino)-7-methoxy-3,4-dihydro-2H-chromen-2-yl]azetidine-1-carboxylate;

N-[2-(azetidin-3-yl)-7-methoxy-3,4-dihydro-2H-chromen-4-yl]-1-(2,2-difluoro-1,3-benzodioxol-5-yl)cyclopropanecarboxamide;

1-(2,2-difluoro-1,3-benzodioxol-5-yl)-N-{7-methoxy-2-[1-(methylsulfonyl)azetidin-3-yl]-3,4-dihydro-2H-chromen-4-yl}cyclopropanecarboxamide;

methyl rac-3-[(2R,4S)-4-({[1-(2,2-difluoro-1,3-benzodioxol-5-yl)cyclopropyl]carbonyl}amino)-7-fluoro-3,4-dihydro-2H-pyrano[2,3-b]pyridin-2-yl]benzoate;

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;

methyl 4-[(2R,4R)-4-({[1-(2,2-difluoro-1,3-benzodioxol-5-yl)cyclopropyl]carbonyl}amino)-3,4-dihydro-2H-chromen-2-yl]benzoate;

4-[(2R,4R)-4-({[1-(2,2-difluoro-1,3-benzodioxol-5-yl)cyclopropyl]carbonyl}amino)-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

methyl 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoate;

1-(2,2-difluoro-1,3-benzodioxol-5-yl)-N-(7-hydroxy-2,2-dimethyl-3,4-dihydro-2H-chromen-4-yl)cyclopropanecarboxamide;

1-(2,2-difluoro-1,3-benzodioxol-5-yl)-N-[7-(difluoromethoxy)-2,2-dimethyl-3,4-dihydro-2H-chromen-4-yl]cyclopropanecarboxamide;

1-(2,2-difluoro-1,3-benzodioxol-5-yl)-N-[7-methoxy-2-(tetrahydrofuran-2-yl)-3,4-dihydro-2H-chromen-4-yl]cyclopropanecarboxamide;

methyl 4-[(2R,4R)-4-({[1-(2,2-difluoro-1,3-benzodioxol-5-yl)cyclopropyl]carbonyl}amino)-7-hydroxy-3,4-dihydro-2H-chromen-2-yl]benzoate;

4-[(2R,4R)-4-({[1-(2,2-difluoro-1,3-benzodioxol-5-yl)cyclopropyl]carbonyl}amino)-7-hydroxy-3,4-dihydro-2H-chromen-2-yl]benzoic acid;

4-({[1-(2,2-difluoro-1,3-benzodioxol-5-yl)cyclopropyl]carbonyl}amino)-7-methoxy-3,4-dihydrospiro[chromene-2,1'-cyclobutane]-3'-carboxylic acid;

ethyl rac-(2R,4S)-4-({[1-(2,2-difluoro-1,3-benzodioxol-5-yl)cyclopropyl]carbonyl}amino)-7-methoxy-3,4-dihydro-2H-chromene-2-carboxylate;

methyl rac-(2R,4S)-4-({[1-(2,2-difluoro-1,3-benzodioxol-5-yl)cyclopropyl]carbonyl}amino)-7-methoxy-3,4-dihydro-2H-chromene-2-carboxylate;

ethyl rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-5-carboxylate;

2-[(4S)-4-({[1-(2,2-difluoro-1,3-benzodioxol-5-yl)cyclopropyl]carbonyl}amino)-3,4-dihydro-2H-chromen-2-yl]-1,3-thiazole-5-carboxylic acid;

rac-(2R,4S)-4-({[1-(2,2-difluoro-1,3-benzodioxol-5-yl)cyclopropyl]carbonyl}amino)-7-methoxy-3,4-dihydro-2H-chromene-2-carboxylic acid;

ethyl rel-2-[(2R,4R)-4-({[1-(2,2-difluoro-1,3-benzodioxol-5-yl)cyclopropyl]carbonyl}amino)-3,4-dihydro-2H-chromen-2-yl]-1,3-thiazole-5-carboxylate;

2-[(4R)-4-({[1-(2,2-difluoro-1,3-benzodioxol-5-yl)cyclopropyl]carbonyl}amino)-3,4-dihydro-2H-chromen-2-yl]-1,3-thiazole-5-carboxylic acid;

methyl 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-2-fluorobenzoate;

methyl 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-3-fluorobenzoate;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-2-fluorobenzoic acid;

ethyl rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylate;

ethyl rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylate;

ethyl rel-2-[(2R,4R)-4-({[1-(2,2-difluoro-1,3-benzodioxol-5-yl)cyclopropyl]carbonyl}amino)-3,4-dihydro-2H-chromen-2-yl]-1,3-thiazole-4-carboxylate;

rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylic acid;

rel-2-[(2R,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylic acid;

rel-2-[(2R,4R)-4-({[1-(2,2-difluoro-1,3-benzodioxol-5-yl)cyclopropyl]carbonyl}amino)-3,4-dihydro-2H-chromen-2-yl]-1,3-thiazole-4-carboxylic acid;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-3-fluorobenzoic acid;

methyl rac-3-[(2R,4R)-4-({[1-(2,2-difluoro-1,3-benzodioxol-5-yl)cyclopropyl]carbonyl}amino)-7-methoxy-3,4-dihydro-2H-chromen-2-yl]bicyclo[1.1.1]pentane-1-carboxylate;

rac-3-[(2R,4R)-4-({[1-(2,2-difluoro-1,3-benzodioxol-5-yl)cyclopropyl]carbonyl}amino)-7-methoxy-3,4-dihydro-2H-chromen-2-yl]bicyclo[1.1.1]pentane-1-carboxylic acid;

ethyl rac-6-[(2R,4S)-4-({[1-(2,2-difluoro-1,3-benzodioxol-5-yl)cyclopropyl]carbonyl}amino)-3,4-dihydro-2H-chromen-2-yl]pyridine-3-carboxylate;

ethyl rac-6-[(2R,4R)-4-({[1-(2,2-difluoro-1,3-benzodioxol-5-yl)cyclopropyl]carbonyl}amino)-3,4-dihydro-2H-chromen-2-yl]pyridine-3-carboxylate;

ethyl 3-[4-({[1-(2,2-difluoro-1,3-benzodioxol-5-yl)cyclopropyl]carbonyl}amino)-3,4-dihydro-2H-chromen-2-yl]cyclobutanecarboxylate;

3-[4-({[1-(2,2-difluoro-1,3-benzodioxol-5-yl)cyclopropyl]carbonyl}amino)-3,4-dihydro-2H-chromen-2-yl]cyclobutanecarboxylic acid;

rac-6-[(2R,4S)-4-({[1-(2,2-difluoro-1,3-benzodioxol-5-yl)cyclopropyl]carbonyl}amino)-3,4-dihydro-2H-chromen-2-yl]pyridine-3-carboxylic acid;

rac-6-[(2R,4R)-4-({[1-(2,2-difluoro-1,3-benzodioxol-5-yl)cyclopropyl]carbonyl}amino)-3,4-dihydro-2H-chromen-2-yl]pyridine-3-carboxylic acid;

ethyl rel-2-[(2R,4R)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylate;

rel-2-[(2R,4R)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylic acid;

ethyl rel-2-[(2S,4S)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylate;

rel-2-[(2S,4S)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylic acid;

methyl rel-6-[(2R,4S)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylate;

methyl rel-6-[(2S,4R)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylate;

methyl rel-6-[(2S,4S)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylate;

methyl rel-6-[(2R,4R)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylate;

ethyl rac-(2R,4R)-4-({[1-(2,2-difluoro-1,3-benzodioxol-5-yl)cyclopropyl]carbonyl}amino)-7-methoxy-3,4-dihydro-2H-chromene-2-carboxylate;

rac-(2R,4R)-4-({[1-(2,2-difluoro-1,3-benzodioxol-5-yl)cyclopropyl]carbonyl}amino)-7-methoxy-3,4-dihydro-2H-chromene-2-carboxylic acid;

rel-6-[(2R,4R)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylic acid;

rac-(2R,4R)-4-({[1-(2,2-difluoro-1,3-benzodioxol-5-yl)cyclopropyl]carbonyl}amino)-N-(2-hydroxyethyl)-7-methoxy-N-propyl-3,4-dihydro-2H-chromene-2-carboxamide;

rac-(2R,4R)—N-benzyl-4-({[1-(2,2-difluoro-1,3-benzodioxol-5-yl)cyclopropyl]carbonyl}amino)-N-(2-hydroxyethyl)-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-(2-hydroxy-2-phenylethyl)-7-methoxy-N-methyl-3,4-dihydro-2H-chromene-2-carboxamide;

rac-1-(2,2-difluoro-1,3-benzodioxol-5-yl)-N-[(2R,4R)-2-{[4-(2-hydroxyethyl)piperazin-1-yl]carbonyl}-7-methoxy-3,4-dihydro-2H-chromen-4-yl]cyclopropanecarboxamide;

rac-(2R,4R)-4-({[1-(2,2-difluoro-1,3-benzodioxol-5-yl)cyclopropyl]carbonyl}amino)-N-(1-hydroxy-2-methylpropan-2-yl)-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-(2-hydroxy-1-phenylethyl)-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-(1,1-dioxidotetrahydro-2H-thiopyran-4-yl)-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-7-methoxy-N-[3-(trifluoromethyl)oxetan-3-yl]-3,4-dihydro-2H-chromene-2-carboxamide;

rac-1-(2,2-difluoro-1,3-benzodioxol-5-yl)-N-{(2R,4R)-2-[(4,4-difluoropiperidin-1-yl)carbonyl]-7-methoxy-3,4-dihydro-2H-chromen-4-yl}cyclopropanecarboxamide;

rac-1-(2,2-difluoro-1,3-benzodioxol-5-yl)-N-[(2R,4R)-7-methoxy-2-(1,4-oxazepan-4-ylcarbonyl)-3,4-dihydro-2H-chromen-4-yl]cyclopropanecarboxamide;

rac-(2R,4R)-4-({[1-(2,2-difluoro-1,3-benzodioxol-5-yl)cyclopropyl]carbonyl}amino)-7-methoxy-N-methyl-N-(oxetan-3-yl)-3,4-dihydro-2H-chromene-2-carboxamide;

rac-1-(2,2-difluoro-1,3-benzodioxol-5-yl)-N-[(2R,4R)-7-methoxy-2-(morpholin-4-ylcarbonyl)-3,4-dihydro-2H-chromen-4-yl]cyclopropanecarboxamide;

rac-(2R,4R)-4-({[1-(2,2-difluoro-1,3-benzodioxol-5-yl)cyclopropyl]carbonyl}amino)-N-[2-hydroxy-1-(2-methoxyphenyl)ethyl]-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-[2-(3-hydroxyphenyl)ethyl]-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-(1,3-dihydroxypropan-2-yl)-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-(2-hydroxy-2,3-dihydro-1H-inden-1-yl)-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-N-(2-hydroxyphenyl)-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-N-(2-hydroxyethyl)-7-methoxy-N-propyl-3,4-dihydro-2H-chromene-2-carboxamide;

rac-(2R,4S)—N-benzyl-4-({[1-(2,2-difluoro-1,3-benzodioxol-5-yl)cyclopropyl]carbonyl}amino)-N-(2-hydroxyethyl)-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-N-(2-hydroxy-2-phenylethyl)-7-methoxy-N-methyl-3,4-dihydro-2H-chromene-2-carboxamide;

rac-1-(2,2-difluoro-1,3-benzodioxol-5-yl)-N-{(2R,4S)-2-[(4-hydroxypiperidin-1-yl)carbonyl]-7-methoxy-3,4-dihydro-2H-chromen-4-yl}cyclopropanecarboxamide;

rac-1-(2,2-difluoro-1,3-benzodioxol-5-yl)-N-[(2R,4S)-2-{[4-(2-hydroxyethyl)piperazin-1-yl]carbonyl}-7-methoxy-3,4-dihydro-2H-chromen-4-yl]cyclopropanecarboxamid;

rac-(2R,4S)-4-({[1-(2,2-difluoro-1,3-benzodioxol-5-yl)cyclopropyl]carbonyl}amino)-N-(2-hydroxy-2-methylpropyl)-7-methoxy-3,4-dihydro-2H-chromene-2-carboxamide;
rac-(2R,4S)-4-({[1-(2,2-difluoro-1,3-benzodioxol-5-yl)cyclopropyl]carbonyl}amino)-N-(1-hydroxy-2-methylpropan-2-yl)-7-methoxy-3,4-dihydro-2H-chromene-2-carboxamid;
rac-(2R,4S)-4-({[1-(2,2-difluoro-1,3-benzodioxol-5-yl)cyclopropyl]carbonyl}amino)-N-(2-hydroxy-1-phenylethyl)-7-methoxy-3,4-dihydro-2H-chromene-2-carboxamide;
rac-(2R,4S)-4-({[1-(2,2-difluoro-1,3-benzodioxol-5-yl)cyclopropyl]carbonyl}amino)-N-(1,1-dioxidotetrahydro-2H-thiopyran-4-yl)-7-methoxy-3,4-dihydro-2H-chromene-2-carboxamide;
rac-(2R,4S)-4-({[1-(2,2-difluoro-1,3-benzodioxol-5-yl)cyclopropyl]carbonyl}amino)-7-methoxy-N-[3-(trifluoromethyl)oxetan-3-yl]-3,4-dihydro-2H-chromene-2-carboxamide;
rac-1-(2,2-difluoro-1,3-benzodioxol-5-yl)-N-{(2R,4S)-2-[(4,4-difluoropiperidin-1-yl)carbonyl]-7-methoxy-3,4-dihydro-2H-chromen-4-yl}cyclopropanecarboxamide;
rac-1-(2,2-difluoro-1,3-benzodioxol-5-yl)-N-[(2R,4S)-7-methoxy-2-(1,4-oxazepan-4-ylcarbonyl)-3,4-dihydro-2H-chromen-4-yl]cyclopropanecarboxamide;
rac-(2R,4S)-4-({[1-(2,2-difluoro-1,3-benzodioxol-5-yl)cyclopropyl]carbonyl}amino)-7-methoxy-N-methyl-N-(oxetan-3-yl)-3,4-dihydro-2H-chromene-2-carboxamide;
rac-1-(2,2-difluoro-1,3-benzodioxol-5-yl)-N-[(2R,4S)-7-methoxy-2-(morpholin-4-ylcarbonyl)-3,4-dihydro-2H-chromen-4-yl]cyclopropanecarboxamide;
rac-(2R,4S)-4-({[1-(2,2-difluoro-1,3-benzodioxol-5-yl)cyclopropyl]carbonyl}amino)-N-[2-hydroxy-1-(2-methoxyphenyl)ethyl]-7-methoxy-3,4-dihydro-2H-chromene-2-carboxamide;
rac-(2R,4S)-4-({[1-(2,2-difluoro-1,3-benzodioxol-5-yl)cyclopropyl]carbonyl}amino)-N-[2-(3-hydroxyphenyl)ethyl]-7-methoxy-3,4-dihydro-2H-chromene-2-carboxamide;
rac-(2R,4S)-4-({[1-(2,2-difluoro-1,3-benzodioxol-5-yl)cyclopropyl]carbonyl}amino)-N-(1,3-dihydroxypropan-2-yl)-7-methoxy-3,4-dihydro-2H-chromene-2-carboxamide;
rac-(2R,4S)-4-({[1-(2,2-difluoro-1,3-benzodioxol-5-yl)cyclopropyl]carbonyl}amino)-N-(2-hydroxy-2,3-dihydro-1H-inden-1-yl)-7-methoxy-3,4-dihydro-2H-chromene-2-carboxamide;
rac-1-{[(2R,4S)-4-({[1-(2,2-difluoro-1,3-benzodioxol-5-yl)cyclopropyl]carbonyl}amino)-7-methoxy-3,4-dihydro-2H-chromen-2-yl]carbonyl}pyrrolidine-3-carboxylic acid;
4-[(2R,4R)-4-({[1-(6-bromo-2,2-difluoro-1,3-benzodioxol-5-yl)cyclopropyl]carbonyl}amino)-7-(difluoromethoxy)-3,4-dihydro-2H-chromen-2-yl]benzoic acid;
methyl 4-((2R,4R)-4-(1-(6-bromo-2,2-difluorobenzo[d][1,3]dioxol-5-yl)cyclopropanecarboxamido)-7-methoxychroman-2-yl)benzoate; and
4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]-N-(methylsulfonyl)benzamide.

Compound names are assigned by using Name 2012 naming algorithm by Advanced Chemical Development or Struct=Name naming algorithm as part of CHEMDRAW® ULTRA v. 12.0.2.1076.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Chiral centers, of which the relative but not the absolute configuration is known, may be labelled arbitrarily, and the whole name is prefixed by rel- (for relative). For example, ethyl rel-3-[(2S,4S)-4-({[1-(2,2-difluoro-1,3-benzodioxol-5-yl)cyclopropyl]carbonyl}amino)-3,4-dihydro-2H-pyrano[2,3-c]pyridin-2-yl]benzoate means

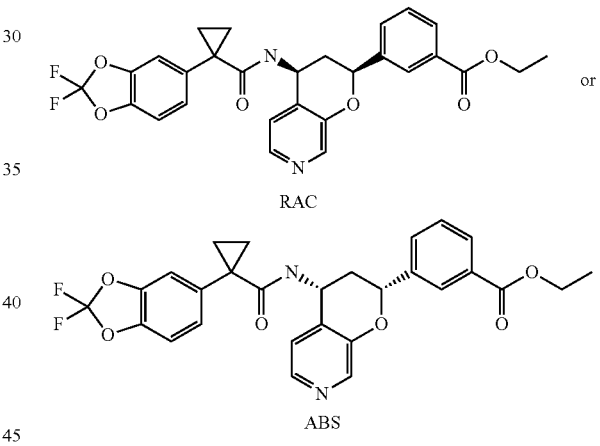

Certain names are prefixed by rac- (for racemic), denoting a racemic mixtures of two enantiomers in the ratio of about 1:1.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^1$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of formula (I) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds described herein in various embodiments, including compounds of general formula (I) and specific examples can be prepared by methodologies known in the art, for example, through the reaction schemes depicted in schemes 1-9. The variables $R^1$, $R^4$, $R^5$, $R^6$, $R^7$, $R^8$, $R^9$, $R^{10}$, $R^{11}$, $R^{12}$, $R^{13}$, $R^{14}$, $R''$, $G^{2A}$, X, Y, and m used in the following schemes have the meanings as set forth in the summary and detailed description sections, unless otherwise noted.

Abbreviations used in the descriptions of the schemes and the specific examples have the following meanings: n-BuLi for n-butyllithium, DMF for N,N-dimethylformamide, DMSO for dimethyl sulfoxide, dppf for 1,1'-bis(diphenylphosphino)ferrocene, HPLC for High Performance Liquid chromatography, LC/MS for liquid chromatography/mass spectrometry, Prep HPLC for Preparative High Performance Liquid chromatography, MeOH for methanol, MTBE for methyl tert-butyl ether, NMR is nuclear magnetic resonance, SFC for Supercritical Fluid Chromatography, TFA for trifluoroacetic acid, and THF for tetrahydrofuran.

Compounds of general formula (I) may be prepared utilizing general procedure as described in Scheme 1. Acids of formula (1) may be reacted with amines of formula (2) in the presence of 1-[bis(dimethylamino)methylene]-1H-1,2,3-triazolo[4,5-b]pyridinium 3-oxid hexafluorophosphate, and a base such as, but not limited to, diisopropylethyl amine, in a solvent such as, but not limited to, DMF, and at ambient temperature to provide amides of general formula (I).

Alternatively, compounds of general formula (I) may be prepared by (a) treatment of the acids (1) with oxalyl chloride in the presence of catalytic amount of DMF, and in a solvent such as, but not limited to, dichloromethane, at ambient temperature to provide the corresponding acid chloride (3), and (b) reacting the acid chloride (3) with the amines (2) in the presence of a base such as, but not limited to, triethylamine, in a solvent such as, but not limited to, dichloromethane, at ambient temperature.

Chromanones (4) may be treated with hydroxylamines or alkoxyamines such as methoxyamine to provide oximes of formula (5). The oxime group of (5) may be reduced using methodologies known by one skilled in the art, for example, by hydrogenoloysis in the presence of hydrogen and a catalyst such as, but not limited to, platinum on carbon, or Raney-Nickel, or platinum (IV) oxide, to provide the amines of general formula (2).

Alternatively, chromanones (4) may be treated with a reducing agent such as, but not limited to, sodium borohydride, to provide alcohols (6). Alcohols (6) may be converted to azides of general formula (7) by activation with a sulfonylating agent such as, but not limited to, methanesulfonic anhydride, followed by displacement with a nucleophilic azide source such as, but not limited to, tetrabutylammonium azide. Alternatively, alcohols (6) may be treated with diphenylphosphoryl azide in the presence of a base such as, but not limited to, 1,8-diazabicyclo[5.4.0]undec-7-

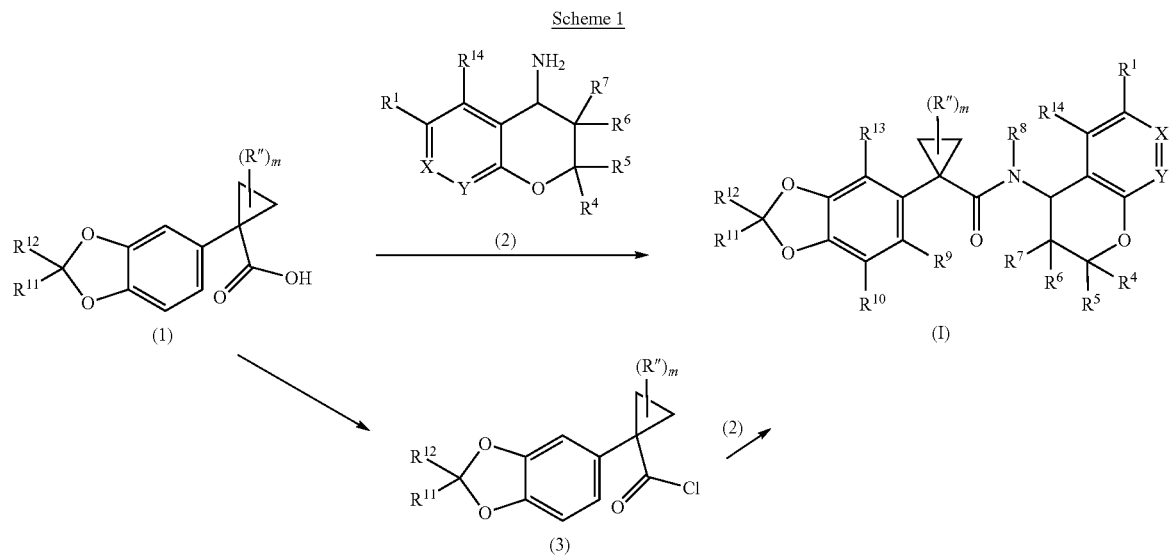

Scheme 1

The requisite amines of formula (2) may be prepared by any of several methods and synthetic intermediates selected by one of ordinary skill in the art as illustrated in Schemes 2-5. Racemic amines of general formula (2) may be prepared from the corresponding chromanones as shown in Scheme 2.

ene, to provide azides (7). Amines (2) may be prepared by reduction of azides (7) by treatment with a phosphine agent such as, but not limited to triphenylphosphine with an appropriate water miscible organic co-solvent such as, but not limited to, THF.

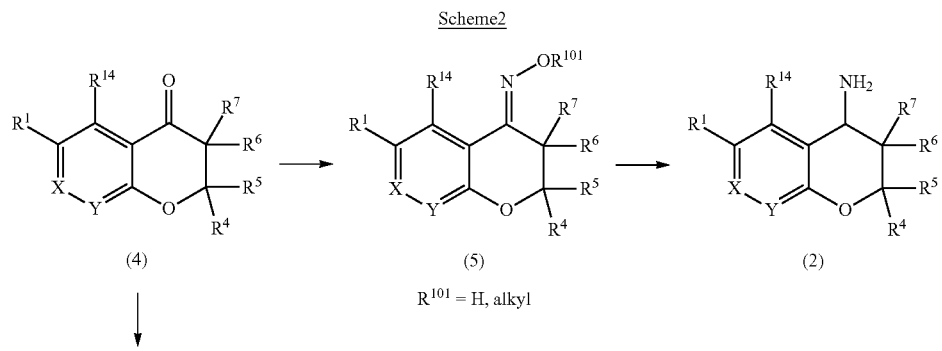

Scheme 2

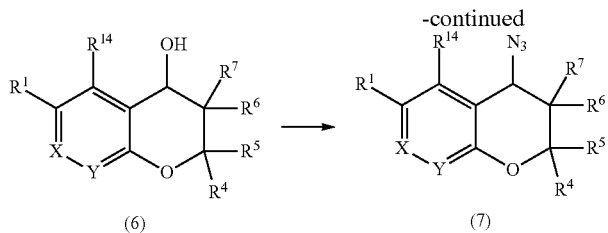

Chiral amines may be prepared using synthetic methods as outlined in Schemes 3 and 4. Chiral amines of formula (8), (15), and (16) may be converted to target compounds described herein using synthetic methods as outlined in Scheme 1.

Chromanones (4) may be treated with chiral hydride sources known to those skilled in the art (Corey, E. J. et al. *J. Org. Chem.* 1988, 53, 2861; Kawanami, S. et al. *Tetrahedron* 2003, 59, 8411; Corey, E. J. et al. *Tetrahedron Asymm.* 2002, 13, 1347) to provide chiral alcohols of general formula (9). Alcohols (9) may be converted to azides of formula (10) and subsequently to amines (8), by employing reagents and reaction conditions as described in Scheme 2.

Scheme 3

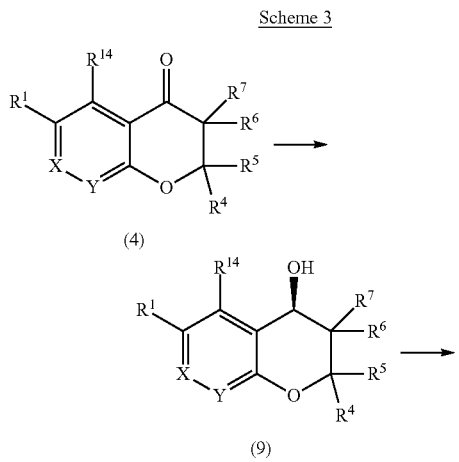

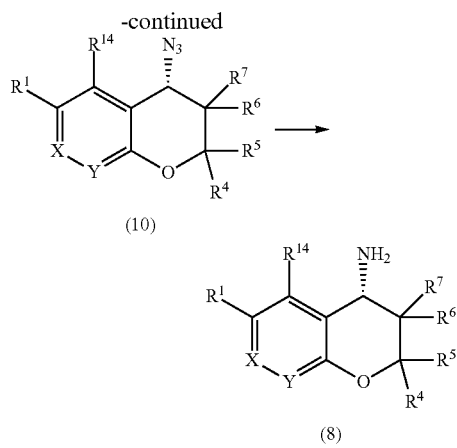

Alternatively, the hydrochloride salts of the chiral amines may be prepared according to the general procedure described by Ellman and co-workers (Tanuwidjaja, J.; Ellman, J. A. et al. *J. Org. Chem.* 2007, 72, 626) as illustrated in Scheme 4. Chromanones (4) may be condensed with a chiral sulfinamide such as tert-butanesulfinamide in the presence of a Lewis acid such as titanium(IV) ethoxide to provide N-sulfinyl imine intermediates (11) and (12). The diastereomeric mixture of (11) and (12) may be separated via chromatography. The respective N-sulfinyl imine intermediates (11) and (12) may undergo a subsequent reduction with reagents such as sodium borohydride to provide sulfinamides of general formula (13) and (14). Treatment of the sulfinamides (13) and (14) with HCl or acetyl chloride and methanol provides the hydrochloride salts of amines (15) and (16).

Scheme 4

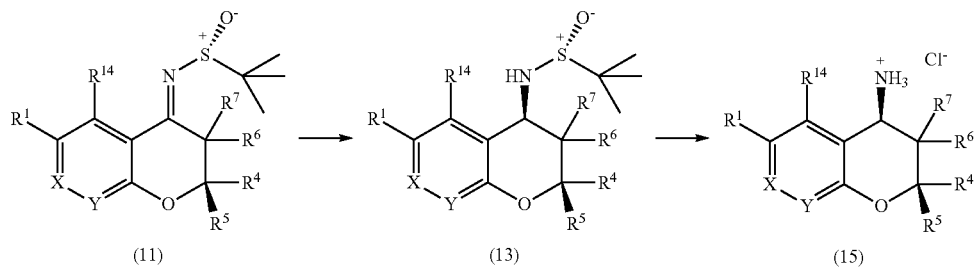

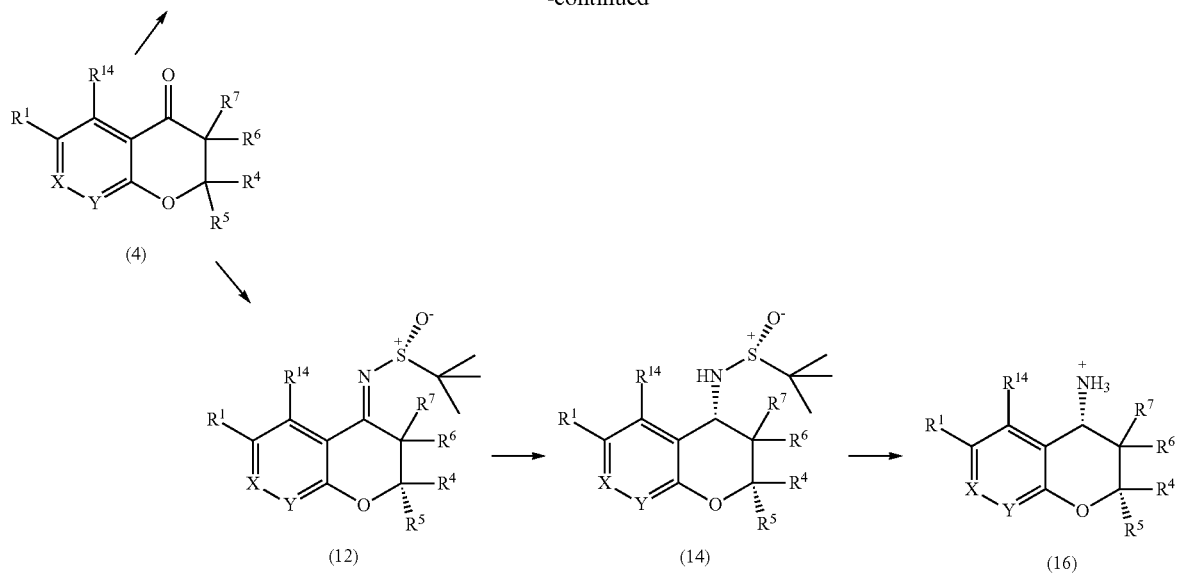

Stereoselective hydrogenolysis of oximes of formula (17) wherein $R^5$ is $G^{2A}$ may be achieved in the presence of a reducing agent such as platinum on carbon or platinum (IV) oxide/acetic acid, as illustrated in Scheme 5. The reduction provides selectively a single enantiomer of formula (18).

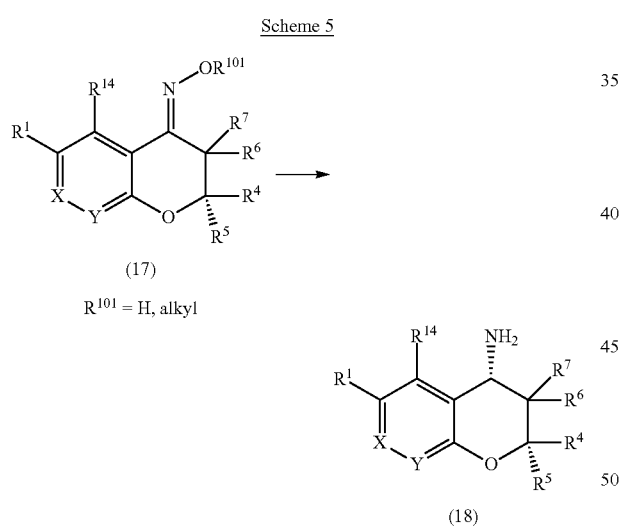

Alcohols of general formula (6) and (9) wherein $R^4$, $R^6$, and $R^7$ are hydrogen, and $R^5$ is alkyl or $G^{2A}$, may be prepared as shown in Scheme 6. Ethanones of general formula (20) may be treated with lithium bis(trimethylsilyl)amide in a solvent such as THF at about −78° C., followed by treatment with aldehydes of formula (19), to provide hydroxyketones of formula (21). Reduction of (21) with a reducing agent such as, but not limited to, sodium borohydride, optionally in presence of a complexing agent such as diethylmethoxyborane, provides the diols of formula (22). Cyclization of the diols (22) may be achieved in the presence of DBU at elevated temperature (e.g. about 60° C. to about 90° C.). The cis and trans isomers may be obtained via column chromatography of (23).

Chromanones (4) wherein $R^4$, $R^6$, and $R^7$ are hydrogen, and $R^5$ is alkyl or $G^{2A}$, may be prepared as shown in Scheme 7. Ethanones of general formula (20) may be reacted with lithium bis(trimethylsilyl)amide in a solvent such as THF at about −78° C., followed by treatment with acid chlorides of formula (24), to provide intermediates of formula (25). Cyclization of (25) in the presence of a base such as potassium carbonate in a solvent such as, but not limited to, DMF, at elevated temperature (e.g. about 90° C. to about 120° C.) provides chromenones (26). Transformation of the chromenones (26) to chromanones (26A) may be achieved by a) reduction of (26) with a suitable reducing agent to provide the corresponding chromanol (23), and b) oxidizing the chromanol with an oxidant such as, but not limited to, Jones reagent.

Scheme 7

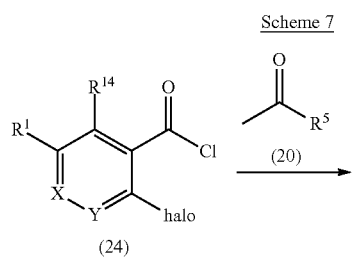

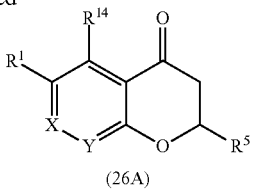

(26A)

Chromanones (4) wherein $R^4$, $R^6$, and $R^7$ are hydrogen, and $R^5$ is alkyl or $G^{2A}$, may be prepared as shown in Scheme 8. Hydroxyethanones (27) may be treated with aldehydes (28) in the presence of a base such as sodium hydroxide to provide intermediates (29). Cyclization of (29) to (26A) may be achieved by treatment with concentrated HCl at elevated temperature (e.g. about 100° C.).

Alternatively, chromanones (26A) may be prepared from a) treatment of hydroxyethanones (27) with lithium diisopropylamide and aldehydes (28) to provide intermediate (30), and b) cyclization of (30) in the presence of trifluoroacetic anhydride and DBU.

Scheme 8

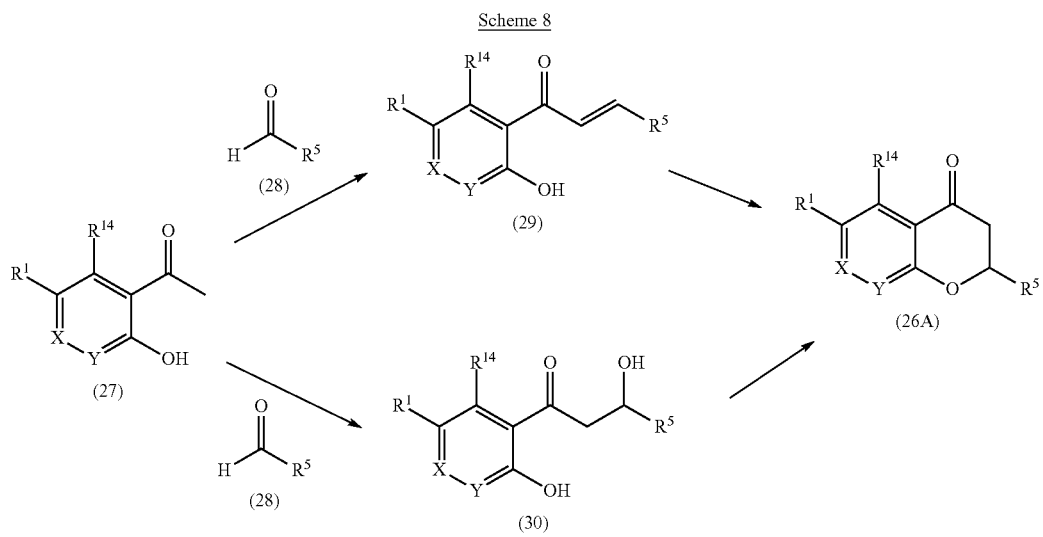

-continued

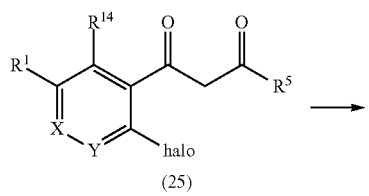

Chiral chormanones (32) wherein $R^5$ is aryl or heteroaryl may be prepared as shown in Scheme 9. Hydroxyethanones (27) may be treated with 1,1-dimethoxy-N,N-dimethylmethanamine at elevated temperature (about 100° C. to about 120° C.) or under microwave irradiation to provide chromenones (31). Treatment of (31) with aryl or heteroaryl boronic acid (or esters thereof) in the presence of (S)-4-(tert-butyl)-2-(pyridin-2-yl)-4,5-dihydrooxazole, and a catalyst such as bis(2,2,2-trifluroacetoxy)palladium provides the chiral chromanones (32).

Scheme 9

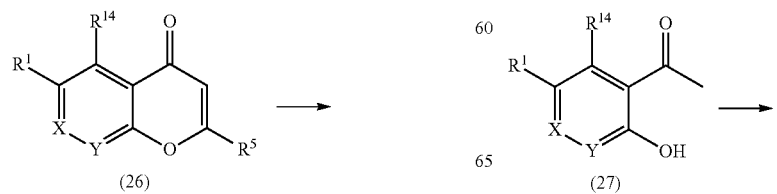

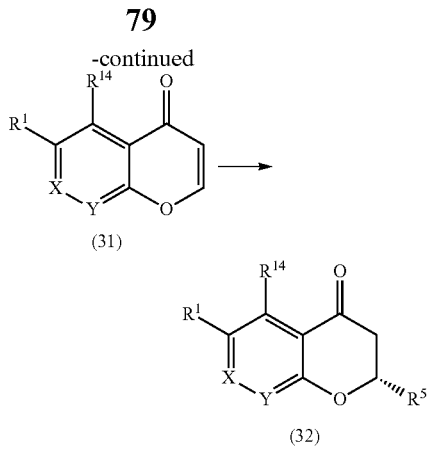

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be further processed in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

This invention also provides for pharmaceutical compositions comprising a therapeutically effective amount of a compound of formula (I), or a pharmaceutically acceptable salt thereof together with a pharmaceutically acceptable carrier, diluent, or excipient thereof. The phrase "pharmaceutical composition" refers to a composition suitable for administration in medical or veterinary use.

The pharmaceutical compositions that comprise a compound of formula (I), alone or in combination with one or more additional therapeutic agents, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which may serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate), and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula (I). In certain embodiments, the compound of formula (I) may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form may be a capsule, tablet, cachet, or lozenge itself, or it may be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition may, if desired, also contain other therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician may evaluate factors such as the circulating plasma levels of the compound, compound toxicities, and/or the progression of the disease, etc.

For administration, compounds may be administered at a rate determined by factors that may include, but are not limited to, the $LD_{50}$ of the compound, the pharmacokinetic profile of the compound, contraindicated drugs, and the side-effects of the compound at various concentrations, as applied to the mass and overall health of the subject. Administration may be accomplished via single or divided doses.

The compounds utilized in the pharmaceutical method of the invention may be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds with suitable non-irritating carriers or carriers such as cocoa butter, polyethylene glycol, or a suppository wax which are solid at room temperature but liquid at body temperature and therefore melt in the rectum or vaginal cavity and release the active compound.

Compounds may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes may be used. The present compositions in liposome form may contain, in addition to a compound of the invention, stabilizers, preservatives, excipients, and the like. Examples of lipids include, but are not limited to, natural and synthetic phospholipids, and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments, and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds and compositions using any amount and any route of administration may be administered to a subject for the treatment or prevention of cystic fibrosis, pancreatic insufficiency, Sjögren's Syndrome (SS), chronic obstructive lung disease (COLD), or chronic obstructive airway disease (COAD).

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, and via implantation. In certain embodiments, the compounds and compositions thereof may be delivered orally. The compounds may also be delivered rectally, bucally, intravaginally, ocularly, or by insufflation. CFTR-modulated disorders and conditions may be treated prophylactically, acutely, and chronically using compounds or pharmaceutically acceptable salts thereof and compositions thereof, depending on the nature of the disorder or condition. Typically, the host or subject in each of these methods is human, although other mammals may also benefit from the administration of compounds or pharmaceutically acceptable salts thereof and compositions thereof as set forth hereinabove.

Compounds of the invention are useful as modulators of CFTR. Thus, the compounds and compositions are particularly useful for treating or lessening the severity or progression of a disease, disorder, or a condition where hyperactivity or inactivity of CFTR is involved. Accordingly, the invention provides a method for treating cystic fibrosis, pancreatic insufficiency, Sjögren's Syndrome (SS), chronic obstructive lung disease (COLD), or chronic obstructive airway disease (COAD) in a subject, wherein the method comprises the step of administering to said subject a therapeutically effective amount of a compound of formula (I), (I-a), (I-b), (I-c), (I-d), (I-e), (I-f), (I-g), (I-h), (I-i), or (I-j) or a pharmaceutically acceptable salt thereof, or a preferred embodiment thereof as set forth above, with or without a pharmaceutically acceptable carrier. Particularly, the method is for the treatment or prevention of cystic fibrosis. In a more particular embodiment, the cystic fibrosis is caused by a Class I, II, III, IV, V, and/or VI mutation.

One embodiment is directed to a compound of the invention or a pharmaceutically acceptable salt thereof, or pharmaceutical compositions comprising a compound of the invention or a pharmaceutically acceptable salt thereof for use in medicine.

One embodiment is directed to a compound according to formula (I), (I-a), (I-b), (I-c), (I-d), (I-e), (I-f), (I-g), (I-h), (I-i), or (I-j) or a pharmaceutically acceptable salt thereof, or pharmaceutical compositions comprising a compound of the invention or pharmaceutically acceptable salt thereof, for use in the treatment of cystic fibrosis, pancreatic insufficiency, Sjögren's Syndrome (SS), chronic obstructive lung disease (COLD) or chronic obstructive airway disease (COAD). In a more particular embodiment, the cystic fibrosis is caused by a Class I, II, III, IV, V, and/or VI mutation.

In one embodiment, the present invention provides pharmaceutical compositions comprising a compound of the invention or a pharmaceutically acceptable salt thereof, and one or more additional therapeutic agents. In a particular embodiment, the additional therapeutic agent is a cystic fibrosis treatment agent other than a compound of the invention. In a more particular embodiment, the cystic fibrosis is caused by a Class I, II, III, IV, V, and/or VI mutation.

The present compounds or pharmaceutically acceptable salts thereof may be administered as the sole active agent or it may be co-administered with one or more additional therapeutic agents, including other compounds that demonstrate the same or a similar therapeutic activity and that are determined to be safe and efficacious for such combined administration. The present compounds may be co-administered to a subject. The term "co-administered" means the administration of two or more different therapeutic agents to a subject by combination in the same pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compounds of the invention or pharmaceutically acceptable salts thereof may be co-administered with a therapeutically effective amount of one or more additional therapeutic agents to treat a CFTR mediated disease, where examples of the therapeutic agents include, but are not limited to, antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), and CFTR amplifiers. In one embodiment, the CFTR mediated disease is cystic fibrosis. In one embodiment, the compounds of the invention or pharmaceutically acceptable salts thereof may be co-administered with one or more additional therapeutic agents selected from the group consisting of CFTR modulators and CFTR amplifiers. In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulators. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In one embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of potentiators include, but are not limited to, Ivacaftor (VX-770), CTP-656, NVS-QBW251, FD1860293, and N-(3-carbamoyl-5,5,7,7-tetramethyl-4,7-dihydro-5H-thieno[2,3-c]pyran-2-yl)-1H-pyrazole-5-carboxamide.

Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, and WO2013038390; and U.S. application Ser. Nos. 14/271,080 and 14/451,619.

In one embodiment, the potentiator can be selected from the group consisting of

Ivacaftor (VX-770, N-(2,4-di-tert-butyl-5-hydroxyphenyl)-4-oxo-1,4-dihydroquinoline-3-carboxamide);
CTP-656;
NVS-QBW251;
FD1860293;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-4,7-dihydro-5H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide
2-(1-hydroxycyclopropanecarboxamido)-5,5,7,7-tetramethyl-5,7-dihydro-4H-thieno[2,3-c]pyran-3-carboxamide;
5,5,7,7-tetramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-5-methyl-1H-pyrazole-3-carboxamide;
N-(3-carbamoyl-5,5,7,7-tetramethyl-5,7-dihydro-4H-thieno[2,3-c]pyran-2-yl)-5-cyclopropyl-1H-pyrazole-3-carboxamide;
N-(3-carbamoyl-5,5,7,7-tetramethyl-5,7-dihydro-4H-thieno[2,3-c]pyran-2-yl)-5-isopropyl-1H-pyrazole-3-carboxamide;
N-(3-carbamoyl-5,5,7,7-tetramethyl-5,7-dihydro-4H-thieno[2,3-c]pyran-2-yl)-5-(trifluoromethyl)-1H-pyrazole-3-carboxamide;
5-tert-butyl-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-5-ethyl-1H-pyrazole-3-carboxamide;
N-(3-carbamoyl-5,5,7,7-tetramethyl-5,7-dihydro-4H-thieno[2,3-c]pyran-2-yl)-3-ethyl-4-methyl-1H-pyrazole-5-carboxamide;
2-(2-hydroxypropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-4-chloro-1H-pyrazole-3-carboxamide;
N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;
4-bromo-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-4-chloro-5-methyl-1H-pyrazole-3-carboxamide;
N-(3-carbamoyl-5,5,7,7-tetramethyl-5,7-dihydro-4H-thieno[2,3-c]pyran-2-yl)-4-methyl-1H-pyrazole-3-carboxamide;
2-(2-hydroxy-3,3-dimethylbutanamido)-5,5,7,7-tetramethyl-5,7-dihydro-4H-thieno[2,3-c]pyran-3-carboxamide;
2-[(2-hydroxy-4-methyl-pentanoyl)amino]-5,5,7,7-tetramethyl-4H-thieno[2,3-c]pyran-3-carboxamide;
5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;
N-(3-carbamoyl-5,5,7,7-tetramethyl-4H-thieno[2,3-c]pyran-2-yl)-4-(3-methoxypropyl)-1H-pyrazole-3-carboxamide;
N-(3-carbamoyl-5,5,7,7-tetramethyl-4H-thieno[2,3-c]pyran-2-yl)-4-(2-ethoxyethyl)-1H-pyrazole-3-carboxamide;
2-[[(2S)-2-hydroxy-3,3-dimethyl-butanoyl]amino]-5,5,7,7-tetramethyl-4H-thieno[2,3-c]pyran-3-carboxamide;
2-[[(2R)-2-hydroxy-3,3-dimethyl-butanoyl]amino]-5,5,7,7-tetramethyl-4H-thieno[2,3-c]pyran-3-carboxamide;
2-[(2-hydroxy-2,3,3-trimethyl-butanoyl)amino]-5,5,7,7-tetramethyl-4H-thieno[2,3-c]pyran-3-carboxamide;

[5-[(3-carbamoyl-5,5,7,7-tetramethyl-4H-thieno[2,3-c]pyran-2-yl)carbamoyl]pyrazol-1-yl]methyl dihydrogen phosphate;

[3-[(3-carbamoyl-5,5,7,7-tetramethyl-4H-thieno[2,3-c]pyran-2-yl)carbamoyl]pyrazol-1-yl]methyl dihydrogen phosphate;

N-(3-carbamoyl-5,5,7,7-tetramethyl-4H-thieno[2,3-c]pyran-2-yl)-4-(1,4-dioxan-2-yl)-1H-pyrazole-3-carboxamide;

5,5,7,7-tetramethyl-2-[[(2S)-3,3,3-trifluoro-2-hydroxy-2-methyl-propanoyl]amino]-4H-thieno[2,3-c]pyran-3-carboxamide; and 2-[[(2S)-2-hydroxypropanoyl]amino]-5,5,7,7-tetramethyl-4H-thieno[2,3-c]pyran-3-carboxamide.

Non limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2665, VX-152, VX-440, FDL169, FDL304, FD2052160, and FD2035659. Examples of correctors are also disclosed in publications: US20140274933 and WO2014160478; and U.S. Application 62/073,586.

In one embodiment, the corrector(s) can be selected from the group consisting of Lumacaftor (VX-809);

1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);

VX-983;
GLPG2665;
VX-152;
VX-440;
FDL169
FDL304;
FD2052160;
FD2035659;

rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-4-[(2R,4S)-4-({[1-(2,2-difluoro-1,3-benzodioxol-5-yl)cyclopropyl]carbonyl}amino)tetrahydro-2H-pyran-2-yl]benzoic acid;

3-[(2S,4R)-4-({[1-(2,2-difluoro-1,3-benzodioxol-5-yl)cyclopropyl]carbonyl}amino)tetrahydro-2H-pyran-2-yl]benzoic acid;

3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid; and 4-[(2R,4S)-4-({[1-(2,2-difluoro-1,3-benzodioxol-5-yl)cyclopropyl]carbonyl}amino)tetrahydro-2H-pyran-2-yl]benzoic acid.

In one embodiment, the additional therapeutic agent is a CFTR amplifier. CFTR amplifiers enhance the effect of known CFTR modulators, such as potentiators and correctors. An example of a CFTR amplifier is PTI130. Examples of amplifiers are also disclosed in publications: WO2015138909 and WO2015138934.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., seine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in PCT Publication No. WO2009074575 and U.S. Pat. No. 8,999,976.

In one embodiment, the ENaC inhibitor is VX-371.

This invention also is directed to kits that comprise one or more compounds and/or salts of the invention, and, optionally, one or more additional therapeutic agents.

This invention also is directed to methods of use of the compounds, salts, compositions, and/or kits of the invention to, with or without one or more additional therapeutic agents, for example, modulate the Cystic Fibrosis Transmembrane Conductance Regulator (CFTR) protein, and treat a disease treatable by modulating the Cystic Fibrosis Transmembrane Conductance Regulator (CFTR) protein (including cystic fibrosis, Sjögren's syndrome, pancreatic insufficiency, chronic obstructive lung disease, and chronic obstructive airway disease).

This invention also is directed to a use of one or more compounds and/or salts of the invention in the preparation of a medicament. The medicament optionally can comprise one or more additional therapeutic agents. In some embodiments, the medicament is useful for treating cystic fibrosis, Sjögren's syndrome, pancreatic insufficiency, chronic obstructive lung disease, and chronic obstructive airway disease. In a particular embodiment, the medicament is for use in the treatment of cystic fibrosis. In a more particular embodiment, the cystic fibrosis is caused by a Class I, II, III, IV, V, and/or VI mutation.

This invention also is directed to a use of one or more compounds and/or salts of the invention in the manufacture of a medicament for the treatment of cystic fibrosis, Sjögren's syndrome, pancreatic insufficiency, chronic obstructive lung disease, and chronic obstructive airway disease. The medicament optionally can comprise one or more additional therapeutic agents. In a particular embodiment, the invention is directed to the use of one or more compounds and/or salts of the invention in the manufacture of a medicament for the treatment of cystic fibrosis. In a more particular embodiment, the cystic fibrosis is caused by a Class I, II, III, IV, V, and/or VI mutation.

Further benefits of Applicants' invention will be apparent to one skilled in the art from reading this patent application.

The following Examples may be used for illustrative purposes and should not be deemed to narrow the scope of the invention.

EXAMPLES

General Reverse Phase Purification Procedures

Preparative LC/MS Method TFA1

Samples were purified by reverse phase preparative HPLC on a Phenomenex Luna C8(2) 5 μm 100 Å AXIA column (50 mm×21.2 mm). A gradient of acetonitrile (A) and 0.1% trifluoroacetic acid in water (B) was used, at a flow rate of 30 mL/min (0-0.5 min 5% A, 0.5-6.5 min linear gradient 5-100% A, 6.5-8.5 min 100% A, 8.5-9.0 min linear gradient 100-5% A, 9.0-10 min 5% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Preparative LC/MS Method TFA2

Samples were purified by preparative HPLC on a Phenomenex Luna C8(2) 5 µm 100 Å AXIA column (30 mm×75 mm). A gradient of acetonitrile (A) and 0.1% trifluoroacetic acid in water (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A). Samples were injected in 1.5 mL DMSO:MeOH (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan Navigator using 70:30 MeOH:10 mM $NH_4OH$(aqueous) at a flow rate of 0.8 mL/min. Loop-injection mass spectra were acquired using a Finnigan Navigator running Navigator 1.8 software and a Gilson 215 liquid handler for fraction injection controlled by an Abbott developed Visual Basic application.

Preparative LC/MS Method TFA4

Samples were purified by reverse phase preparative HPLC on a Phenomenex Luna C8(2) 5 µm 100 Å AXIA column (50 mm×21.2 mm). A gradient of acetonitrile (A) and 0.1% trifluoroacetic acid in water (B) was used, at a flow rate of 30 mL/min (0-0.1 min 5% A, 0.1-0.5 min linear gradient 5-30% A, 0.5-6.5 min linear gradient 30-70% A, 6.5-7.0 min linear gradient 70-100% A, 7.0-8.5 min 100% A, 8.5-9.0 min linear gradient 100-5% A, 9.0-10 min 5% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Preparative LC/MS Method TFA6

Samples were purified by reverse phase preparative HPLC on a Phenomenex Luna C8(2) 5 µm 100 Å AXIA column (50 mm×21.2 mm). A gradient of acetonitrile (A) and 0.1% trifluoroacetic acid in water (B) was used, at a flow rate of 30 mL/min (0-0.5 min 15% A, 0.5-8.0 min linear gradient 15-100% A, 8.0-9.0 min 100% A, 7.0-8.9 min 100% A, 9.0-9.1 min linear gradient 100-15% A, 9.1-10 min 15% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Preparative LC/MS Method TFA8

Samples were purified by reverse phase preparative HPLC on a Phenomenex Luna C8(2) 5 µm 100 Å AXIA column (50 mm×21.2 mm). A gradient of acetonitrile (A) and 0.1% trifluoroacetic acid in water (B) was used, at a flow rate of 30 mL/min (0-0.5 min 35% A, 0.5-8.0 min linear gradient 35-100% A, 8.0-9.0 min 100% A, 7.0-8.9 min 100% A, 9.0-9.1 min linear gradient 100-35% A, 9.1-10 min 35% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Preparative LC/MS Method AA2

Samples were purified by preparative HPLC on a Phenomenex Luna C8(2) 5 µm 100 Å AXIA column (30 mm×75 mm). A gradient of acetonitrile (A) and 10 mM ammonium acetate in water (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A). Samples were injected in 1.5 mL DMSO:MeOH (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan Navigator using 70:30 MeOH:10 mM $NH_4OH$(aq) at a flow rate of 0.8 mL/min. Loop-injection mass spectra were acquired using a Finnigan Navigator running Navigator 1.8 software and a Gilson 215 liquid handler for fraction injection controlled by an Abbott developed Visual Basic application.

Preparative LC/MS Method AA7

Samples were purified by reverse phase preparative HPLC on a Phenomenex Luna C8(2) 5 µm 100 Å AXIA column (50 mm×21.2 mm). A gradient of acetonitrile (A) and 0.1% ammonium acetate in water (B) was used, at a flow rate of 30 mL/min (0-0.5 min 25% A, 0.5-8.0 min linear gradient 25-100% A, 8.0-9.0 min 100% A, 7.0-8.9 min 100% A, 9.0-9.1 min linear gradient 100-25% A, 9.1-10 min 25% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Preparative LC/MS Method AA8

Samples were purified by reverse phase preparative HPLC on a Phenomenex Luna C8(2) 5 μm 100 Å AXIA column (50 mm×21.2 mm). A gradient of acetonitrile (A) and 0.1% ammonium acetate in water (B) was used, at a flow rate of 30 mL/min (0-0.5 min 35% A, 0.5-8.0 min linear gradient 35-100% A, 8.0-9.0 min 100% A, 7.0-8.9 min 100% A, 9.0-9.1 min linear gradient 100-35% A, 9.1-10 min 35% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Example 1

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid To a solution of Example 6 (25 mg, 0.047 mmol) in tetrahydrofuran (233 μL) was added lithium hydroxide hydrate (233 μL of a 0.8 M solution in water). The resulting biphasic mixture was stirred vigorously for 16 hours at room temperature, followed by addition of more lithium hydroxide hydrate (233 μL of a 0.8 M solution). The reaction mixture was stirred for an additional 5 hours at room temperature, acidified by the addition of 6 M HCl (0.040 mL) and the resulting biphasic mixture loaded directly onto a 4 g silica gel cartridge and eluted with 30% ethyl acetate/heptanes over 15 minutes to give the title compound as a white solid. $^1$H NMR (400 MHz, CDCl$_3$) δ 8.20 (s, 1H), 8.06 (dd, J=7.9, 1.5 Hz, 1H), 7.71-7.61 (m, 1H), 7.48 (t, J=7.7 Hz, 1H), 7.13 (dd, J=8.2, 1.7 Hz, 1H), 7.09 (d, J=1.7 Hz, 1H), 7.01 (d, J=8.2 Hz, 1H), 6.96 (d, J=8.6 Hz, 1H), 6.52 (dd, J=8.6, 2.5 Hz, 1H), 6.45 (d, J=2.5 Hz, 1H), 5.49 (td, J=9.9, 6.0 Hz, 1H), 5.40 (d, J=8.9 Hz, 1H), 5.33-5.22 (m, 1H), 3.76 (s, 3H), 2.58 (ddd, J=13.3, 5.9, 2.0 Hz, 1H), 1.82-1.72 (m, 2H), 1.69-1.63 (m, 1H), 1.09 (q, J=2.8 Hz, 2H); MS (ESI−) m/z 522.1 (M−H)⁻.

Example 2

3-[(2R,4S)-4-({[1-(2,2-difluoro-1,3-benzodioxol-5-yl)cyclopropyl]carbonyl}amino)-7-methoxy-3,4-dihydro-2H-chromen-2-yl]benzoic acid To a solution of Example 5E (35 mg, 0.065 mmol) in tetrahydrofuran (326 μL) was added lithium hydroxide hydrate (326 μL of a 0.8 M solution). The resulting biphasic mixture was stirred vigorously for 16 hours at room temperature, followed by addition of more lithium hydroxide hydrate (326 μL of a 0.8 M solution). The reaction was stirred for an additional 5 hours at room temperature, acidified by the addition of 6 M HCl (0.050 mL) and the resulting biphasic mixture was loaded directly onto a 4 g silica gel cartridge and eluted with 30% ethyl acetate/heptanes over 15 minutes to give the title compound as a white solid. $^1$H NMR (400 MHz, CDCl$_3$) δ 8.13 (t, J=1.8 Hz, 1H), 8.12-8.04 (m, 1H), 7.72-7.61 (m, 1H), 7.51 (t, J=7.7 Hz, 1H), 7.20-7.11 (m, 2H), 7.04 (dd, J=8.4, 4.1 Hz, 2H), 6.53 (dd, J=8.5, 2.6 Hz, 1H), 6.45 (d, J=2.6 Hz, 1H), 5.60 (d, J=6.6 Hz, 1H), 5.01 (dd, J=5.5, 2.8 Hz, 1H), 4.84 (dd, J=11.6, 2.2 Hz, 1H), 3.76 (s, 3H), 2.35 (dt, J=14.4, 2.5 Hz, 1H), 2.16 (ddd, J=14.4, 11.4, 4.5 Hz, 1H), 1.70 (q, J=3.7 Hz, 2H), 1.09 (q, J=3.7 Hz, 2H); MS (ESI−) m/z 522.1 (M−H)⁻.

Example 3

1-(2,2-difluoro-1,3-benzodioxol-5-yl)-N-[(2R,4R)-2-(3,4-dimethoxyphenyl)-7-methoxy-3,4-dihydro-2H-chromen-4-yl]cyclopropanecarboxamide To 1-(2,2-difluorobenzo[d][1,3]dioxol-5-yl)cyclopropanecarboxylic acid (CAS 68015-98-5) (120 mg, 0.496 mmol) in DMF (1239 μL) was added HATU (1-[bis(dimethylamino)methylene]-1H-1,2,3-triazolo[4,5-b]pyridinium 3-oxid hexafluorophosphate) (245 mg, 0.644 mmol). The mixture was stirred for 5 minutes at room temperature, and then 2-(3,4-dimethoxyphenyl)-7-methoxychroman-4-amine (156 mg, 0.496 mmol) was added, followed by dropwise addition of triethylamine (276 μL, 1.982 mmol). After 45 minutes, the mixture was quenched with saturated aqueous sodium bicarbonate, and the aqueous layer removed. The resulting oil was triturated with water and filtered to give 283 mg of a white solid. The solid was dissolved in dichloromethane and purified using a 24 g silica gel cartridge with a gradient of 5-50% ethyl acetate/heptanes to give 189 mg of a mixture of the two diastereomers. The mixture was subjected to preparative supercritical fluid chromatography set to maintain a backpressure at 100 bar using a CHIRALPAK IA®, 21×250 mm, 5 micron, with the sample at a concentration of 20 mg/mL in methanol using 16% methanol in CO$_2$ at a flow rate of 70 mL/minute with a retention time of 7.2 minutes to give the title compound (111 mg, 0.206 mmol, 41.5% yield) as a white solid. $^1$H NMR (400 MHz, DMSO-d$_6$) δ 7.39 (d, J=1.6 Hz, 1H), 7.32 (d, J=8.4 Hz, 1H), 7.20 (dd, J=8.3, 1.7 Hz, 1H), 7.13 (d, J=9.1 Hz, 1H), 6.98-6.91 (m, 4H), 6.50 (dd, J=8.5, 2.6 Hz, 1H), 6.36 (d, J=2.5 Hz, 1H), 5.36-5.24 (m, 1H), 5.15 (dd, J=11.5, 1.9 Hz, 1H), 3.75 (d, J=1.4 Hz, 6H), 3.68 (s, 3H), 2.10 (q, J=11.8 Hz, 1H), 1.99 (ddd, J=12.9, 6.2, 2.1 Hz, 1H), 1.53-1.46 (m, 1H), 1.37 (ddd, J=8.4, 5.8, 2.8 Hz, 1H), 1.05 (dtdd, J=12.7, 9.6, 6.4, 3.3 Hz, 2H); MS (ESI+) m/z 402 (M+H)⁺. Absolute stereochemistry was assigned by X-ray diffraction analysis.

Example 4

1-(2,2-difluoro-1,3-benzodioxol-5-yl)-N-[(2S,4S)-2-(3,4-dimethoxyphenyl)-7-methoxy-3,4-dihydro-2H-chromen-4-yl]cyclopropanecarboxamide To 1-(2,2-difluorobenzo[d][1,3]dioxol-5-yl)cyclopropanecarboxylic acid (120 mg, 0.496 mmol) in DMF (1239 μL) was added HATU (1-[bis(dimethylamino)methylene]-1H-1,2,3-triazolo[4,5-b]pyridinium 3-oxid hexafluorophosphate) (245 mg, 0.644 mmol). The mixture was stirred for 5 minutes at room temperature, and then 2-(3,4-dimethoxyphenyl)-7-methoxychroman-4-amine (156 mg, 0.496 mmol) was added, followed by dropwise addition of triethylamine (276 μL, 1.982 mmol). After 45 minutes, the mixture was quenched with saturated aqueous sodium bicarbonate, the aqueous layer removed, the resulting oil triturated with water and filtered to give 283 mg of a white solid. The solid was dissolved in dichloromethane and purified using a 24 g silica gel cartridge with a gradient of 5-50% ethyl acetate/ heptanes to give 189 mg of a mixture of the two diastereomers. The mixture was subjected to preparative supercritical fluid chromatography set to maintain a backpressure at 100 bar using a CHIRALPAK® IA, 21×250 mm, 5 micron, with the sample at a concentration of 20 mg/mL in methanol using 16% methanol in $CO_2$ at a flow rate of 70 mL/minute with a retention time of 4.5 minutes to give the title compound (106 mg, 0.196 mmol, 39.7% yield) as a white solid. $^1$H NMR (400 MHz, DMSO-$d_6$) δ 7.39 (d, J=1.6 Hz, 1H), 7.32 (d, J=8.4 Hz, 1H), 7.20 (dd, J=8.3, 1.7 Hz, 1H), 7.13 (d, J=9.1 Hz, 1H), 6.98-6.91 (m, 4H), 6.50 (dd, J=8.5, 2.6 Hz, 1H), 6.36 (d, J=2.5 Hz, 1H), 5.36-5.24 (m, 1H), 5.15 (dd, J=11.5, 1.9 Hz, 1H), 3.75 (d, J=1.4 Hz, 6H), 3.68 (s, 3H), 2.10 (q, J=11.8 Hz, 1H), 1.99 (ddd, J=12.9, 6.2, 2.1 Hz, 1H), 1.53-1.46 (m, 1H), 1.37 (ddd, J=8.4, 5.8, 2.8 Hz, 1H), 1.05 (dtdd, J=12.7, 9.6, 6.4, 3.3 Hz, 2H); MS (ESI+) m/z 402 (M+H)$^+$.

Example 5 methyl 3-[(2R,4S)-4-({[1-(2,2-difluoro-1,3-benzodioxol-5-yl)cyclopropyl]carbonyl}amino)-7-methoxy-3,4-dihydro-2H-chromen-2-yl]benzoate

Example 5A 7-methoxy-4H-chromen-4-one 1,1-Dimethoxy-N,N-dimethylmethanamine (1.0 mL, 7.53 mmol) and 1-(2-hydroxy-4-methoxyphenyl)ethanone (1.251 g, 7.53 mmol) were heated in the microwave at 115° C. for 15 seconds to give a red solution which solidified upon cooling. The solid was triturated with heptane to give the enamine intermediate as red crystals. $^1$H NMR (400 MHz, DMSO-$d_6$) δ 14.96 (s, 1H), 7.82 (dd, J=10.6, 1.6 Hz, 2H), 6.37 (dd, J=8.8, 2.6 Hz, 1H), 6.32 (d, J=2.5 Hz, 1H), 5.84 (d, J=12.0 Hz, 1H), 3.75 (s, 3H), 3.17 (s, 3H), 2.95 (s, 3H). The enamine was dissolved in dichloromethane (40 mL) and treated with HCl (4 mL) at reflux for one hour. The aqueous layer was removed and extracted with 3×40 mL of dichloromethane. The combined extracts were washed with saturated aqueous sodium bicarbonate and dried over sodium sulfate, then filtered and the solvent removed under reduced pressure to give title compound (0.854 g, 4.85 mmol, 64.4% yield) as pale yellow crystals. $^1$H NMR (400 MHz, DMSO-$d_6$) δ 8.22 (d, J=6.0 Hz, 1H), 7.94 (d, J=8.9 Hz, 1H), 7.13 (d, J=2.4 Hz, 1H), 7.06 (dd, J=8.9, 2.4 Hz, 1H), 6.27 (d, J=6.0 Hz, 1H), 3.90 (s, 3H); MS (ESI+) m/z 177 (M+H)$^+$.

Example 5B (R)-methyl 3-(7-methoxy-4-oxochroman-2-yl)benzoate

A 4 mL vial was charged with bis(2,2,2-trifluoroacetoxy)palladium (9.44 mg, 0.028 mmol), (S)-4-(tert-butyl)-2-(pyridin-2-yl)-4,5-dihydrooxazole (6.96 mg, 0.034 mmol), ammonium hexafluorophosphate(V) (27.8 mg, 0.170 mmol), and 3-methoxycarbonylphenylboronic acid (204 mg, 1.135 mmol) were stirred in dichloroethane (1.0 mL) for 5 minutes, and a pale yellow color was observed. To this suspension was added Example 5A (100 mg, 0.568 mmol) and water (0.051 mL, 2.84 mmol) and the sides of the vial washed with more dichloromethane (1.0 mL). The vial was capped and the mixture stirred at 60° C. overnight. The mixture was filtered through a plug of silica gel and eluted with dichloromethane and then ethyl acetate. The solvent was removed and the crude material was chromatographed using a 12 g silica gel cartridge with a gradient of 5-50% ethyl acetate/heptanes over 20 minutes to give the title compound (133 mg, 0.426 mmol, 75% yield) as a white solid. $^1$H NMR (400 MHz, DMSO-$d_6$) δ 8.15 (t, J=1.8 Hz, 1H), 7.98 (dt, J=7.8, 1.4 Hz, 1H), 7.84 (dt, J=7.9, 1.5 Hz, 1H), 7.74 (d, J=8.5 Hz, 1H), 7.61 (t, J=7.8 Hz, 1H), 6.69 (d, J=8.6 Hz, 2H), 5.77 (dd, J=12.9, 2.9 Hz, 1H), 3.88 (s, 3H), 3.83 (s, 3H), 3.17 (dd, J=16.8, 13.0 Hz, 1H), 2.80 (dd, J=16.8, 3.0 Hz, 1H); MS (ESI+) m/z 313 (M+H)$^+$.

Example 5C (R)-methyl 3-(7-methoxy-4-(methoxyimino)chroman-2-yl)benzoate

Example 5B (100 mg, 0.320 mmol) and O-methylhydroxylamine hydrochloride (29.4 mg, 0.352 mmol) were stirred in pyridine (640 μL) at 60° C. overnight. Added an additional 0.3 equivalent (7 mg) of amine and heated at 60° C. for 12 hours. The mixture was concentrated and then diluted with ethyl acetate, washed with saturated aqueous sodium bicarbonate and saturated aqueous ammonium chloride sequentially. The solvent was removed and the crude material purified using a 12 g silica gel cartridge eluting with 5-20% ethyl acetate/heptanes over 20 minutes to give the title compound (107 mg, 0.313 mmol) as a light pink oil. $^1$H NMR (400 MHz, CDCl$_3$) δ 8.15 (t, J=1.9 Hz, 1H), 8.03 (dt, J=7.7, 1.5 Hz, 1H), 7.84 (d, J=8.8 Hz, 1H), 7.77-7.63 (m, 1H), 7.49 (t, J=7.7 Hz, 1H), 6.59 (dd, J=8.8, 2.6 Hz, 1H), 6.50 (d, J=2.5 Hz, 1H), 5.12 (dd, J=12.5, 3.1 Hz, 1H), 3.96 (s, 3H), 3.94 (s, 3H), 3.80 (s, 3H), 3.48 (dd, J=17.2, 3.1 Hz, 1H), 2.65 (dd, J=17.1, 12.5 Hz, 1H); MS (ESI+) m/z 342.0 (M+H)$^+$.

Example 5D 3-((2R)-4-amino-7-methoxychroman-2-yl)benzoate

Example 5C (50 mg, 0.146 mmol) and methanol (10 mL) were added to Ra—Ni 2800, water slurry (150 mg, 1.150 mmol) in a 50 mL pressure bottle and stirred for 16 hours at 30 psi of hydrogen gas and at ambient temperature. The reaction was filtered and the solvent removed. The residue (44 mg) was dissolved in methyl-tert-butyl ether. HCl (4.0 M in dioxane, 0.3 mL) was added dropwise, and the resulting suspension was filtered to give the hydrochloride salt of the title compound as a mixture of two diastereomers. $^1$H NMR (400 MHz, DMSO-$d_6$) δ 8.48 (s, 6H), 8.06 (dt, J=6.1, 1.8 Hz, 2H), 7.97 (ddd, J=9.2, 3.1, 1.4 Hz, 2H), 7.74 (dd, J=7.7, 1.7 Hz, 2H), 7.60 (t, J=7.7 Hz, 2H), 7.55 (d, J=8.6 Hz, 1H), 7.45 (d, J=8.6 Hz, 1H), 6.65 (ddd, J=8.7, 6.3, 2.6 Hz, 2H), 6.55 (d, J=2.6 Hz, 1H), 6.52 (d, J=2.6 Hz, 1H), 5.51 (dd, J=11.9, 2.3 Hz, 1H), 5.33 (dd, J=11.8, 1.8 Hz, 1H), 4.75 (dd, J=11.0, 6.4 Hz, 1H), 4.45 (dd, J=5.0, 2.4 Hz, 1H), 3.89 (s, 3H), 3.89 (s, 3H), 3.77 (s, 3H), 3.76 (s, 3H), 2.61 (ddd, J=13.1, 6.5, 1.9 Hz, 1H), 2.46 (t, J=2.4 Hz, 1H), 2.31 (ddd, J=15.0, 11.9, 5.0 Hz, 1H), 2.08 (dt, J=13.0, 11.4 Hz, 1H); MS (ESI−) m/z 297.1 (M-NH$_3$)$^−$.

Example 5E methyl 3-[(2R,4S)-4-({[1-(2,2-difluoro-1,3-benzodioxol-5-yl)cyclopropyl]carbonyl}amino)-7-methoxy-3,4-dihydro-2H-chromen-2-yl]benzoate To a suspension of the product from Example 5D (90 mg, 0.257 mmol) in 1.3 mL of dichloromethane was added N,N-diisopropylethylamine (135 μL, 0.772 mmol). After a solution was achieved, a solution of 1-(2,2-difluorobenzo[d][1,3]dioxol-5-yl)cyclopropanecarbonyl chloride (prepared as described in Example 8D) (84 mg, 0.322 mmol) in 1 mL of dichloromethane was added dropwise at ambient temperature and the reaction was stirred for 1 hour. The reaction mixture was diluted with 5 mL of methyl-tert-butyl ether and quenched with saturated aqueous sodium bicarbonate. After stirring for 10 minutes, the aqueous layer was removed and the organic layer was washed twice more with saturated aqueous sodium bicarbonate. The organics were dried over sodium sulfate then concentrated. The residue was chromatographed using a 40 g silica gel cartridge with 10-20% methyl-tert-butyl ether/heptanes over 3 minutes then 20% methyl-tert-butyl ether/heptanes for 17 minutes then a 20-30% methyl-tert-butyl ether/heptanes gradient over 10 minutes to provide the title compound as the first eluting isomer and Example 6 as the second eluting isomer. $^1$H NMR (500 MHz, CDCl$_3$) δ 8.06 (t, J=1.8 Hz, 1H), 8.01 (d, J=7.9 Hz, 1H), 7.59 (dt, J=7.9, 1.4 Hz, 1H), 7.48 (t, J=7.7 Hz, 1H), 7.15 (dd, J=8.2, 1.7 Hz, 1H), 7.12 (d, J=1.7 Hz, 1H), 7.07-6.99 (m, 2H), 6.52 (dd, J=8.5, 2.6 Hz, 1H), 6.44 (d, J=2.5 Hz, 1H), 5.58 (d, J=6.6 Hz, 1H), 5.06-4.96 (m, 1H), 4.81 (dd, J=11.5, 2.1 Hz, 1H), 3.94 (s, 3H), 3.75 (s, 3H), 2.31 (dt, J=14.3, 2.5 Hz, 1H), 2.15 (ddd, J=14.4, 11.5, 4.6 Hz, 1H), 1.71-1.66 (m, 2H), 1.10-1.05 (m, 2H); MS (ESI−) m/z 536.1 (M−H)$^−$. Relative stereochemistry confirmed by H NMR NOE analysis.

Example 6 methyl 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoate The title compound was isolated as the second eluting isomer from the column chromatography as described in Example 5E. $^1$H NMR (500 MHz, CDCl$_3$) δ 8.08 (s, 1H), 8.00 (d, J=7.7 Hz, 1H), 7.58 (dt, J=7.8, 1.4 Hz, 1H), 7.45 (t, J=7.7 Hz, 1H), 7.12 (dd, J=8.2, 1.7 Hz, 1H), 7.08 (d, J=1.7 Hz, 1H), 7.00 (d, J=8.2 Hz, 1H), 6.96 (dd, J=8.7, 1.0 Hz, 1H), 6.51 (dd, J=8.6, 2.6 Hz, 1H), 6.44 (d, J=2.6 Hz, 1H), 5.46-5.38 (m, 1H), 5.33 (d, J=8.8 Hz, 1H), 5.21 (dd, J=11.3, 1.9 Hz, 1H), 3.92 (s, 3H), 3.75 (s, 3H), 2.51 (ddd, J=13.3, 6.0, 2.0 Hz, 1H), 1.86-1.62 (m, 3H), 1.11-1.03 (m, 2H); MS (ESI−) m/z 536.1 (M−H)$^−$.

Example 7 methyl 3-[(2R,4S)-4-({[1-(2,2-difluoro-1,3-benzodioxol-5-yl)cyclopropyl]carbonyl}amino)-3,4-dihydro-2H-chromen-2-yl]benzoate The title compound (36 mg, 0.067 mmol, 21.76% yield) was collected as the first eluting isomer from the separation of the two isomers as described in Example 8D. $^1$H NMR (400 MHz, CDCl$_3$) δ 8.05 (d, J=2.1 Hz, 1H), 8.01 (dt, J=7.9, 1.6 Hz, 1H), 7.62-7.57 (m, 1H), 7.47 (dd, J=8.7, 6.8 Hz, 1H), 7.22 (td, J=7.7, 1.8 Hz, 1H), 7.18-7.10 (m, 3H), 7.03 (d, J=8.3 Hz, 1H), 6.93 (t, J=7.5 Hz, 2H), 5.63 (d, J=6.8 Hz, 1H), 5.05 (dt, J=6.8, 3.4 Hz, 1H), 4.84 (dd, J=11.3, 2.4 Hz, 1H), 3.94 (s, 3H), 2.32 (dt, J=14.4, 2.7 Hz, 1H), 2.19 (ddd, J=14.4, 11.3, 4.6 Hz, 1H), 1.72-1.66 (m, 2H), 1.12-1.05 (m, 2H); MS (ESI+) m/z 508 (M+H)$^+$.

Example 8 methyl 3-[(2R,4R)-4-({[1-(2,2-difluoro-1,3-benzodioxol-5-yl)cyclopropyl]carbonyl}amino)-3,4-dihydro-2H-chromen-2-yl]benzoate Example 8A (R)-methyl 3-(4-oxochroman-2-yl)benzoate A 20 mL vial was charged with bis(2,2,2-trifluoroacetoxy)palladium (56.9 mg, 0.171 mmol), (S)-4-(tert-butyl)-2-(pyridin-2-yl)-4,5-dihydrooxazole (41.9 mg, 0.205 mmol), ammonium hexafluorophosphate(V) (167 mg, 1.026 mmol), and 3-methoxycarbonylphenylboronic acid (1231 mg, 6.84 mmol). The reaction was stirred in dichloroethane (5 mL) for 5 minutes, and a pale yellow color was observed. To this suspension was added 4H-chromen-4-one (CAS 11013-97-1) (500 mg, 3.42 mmol) and water (0.308 mL, 17.11 mmol) and the sides of the vial washed with more dichloroethane (5 mL). The vial was capped and the mixture stirred at 60° C. for 16 hours. The mixture was filtered through a plug of silica gel and celite and eluted with ethyl acetate to give a red solution. The solvent was removed and the crude material was chromatographed using a 40 g silica gel cartridge with a gradient of 5-50% ethyl acetate/heptanes over 40 minutes to give the title compound (329 mg, 1.165 mmol, 34.1% yield) as a white solid. $^1$H NMR (400 MHz, DMSO-d$_6$) δ 8.16 (t, J=1.8 Hz, 1H), 7.98 (dt, J=7.7, 1.5 Hz, 1H), 7.84 (dt, J=7.9, 1.4 Hz, 1H), 7.81 (dd, J=7.8, 1.8 Hz, 1H), 7.65-7.58 (m, 2H), 7.17-7.10 (m, 2H), 5.80 (dd, J=13.1, 2.8 Hz, 1H), 3.88 (s, 3H), 3.28 (dd, J=16.8, 13.1 Hz, 1H), 2.88 (dd, J=16.8, 3.0 Hz, 1H); MS (ESI+) m/z 300 (M+NH$_4$)$^+$.

Example 8B (R)-methyl 3-(4-(hydroxyimino)chroman-2-yl)benzoate

Example 8A (200 mg, 0.708 mmol) was treated with hydroxylamine hydrochloride (59.1 mg, 0.850 mmol) and sodium acetate (69.7 mg, 0.850 mmol) in ethanol (3542 μL). The reaction was stirred at ambient temperature for 15 hours. The solvent was removed under a stream of nitrogen. The crude material was washed with water (2×2 mL) and dried under a stream of nitrogen to provide the title compound (210 mg, 0.706 mmol, 100% yield) as a white solid. $^1$H NMR (400 MHz, DMSO-d$_6$) δ 11.35 (s, 1H), 8.11 (t, J=1.8 Hz, 1H), 7.96 (dt, J=7.8, 1.4 Hz, 1H), 7.82 (td, J=7.7, 2.0, 1.6 Hz, 2H), 7.59 (t, J=7.7 Hz, 1H), 7.31 (ddd, J=8.6, 7.3, 1.7 Hz, 1H), 7.04-6.97 (m, 2H), 5.32 (dd, J=11.8, 3.2 Hz, 1H), 3.87 (s, 3H), 3.40 (dd, J=17.0, 3.3 Hz, 1H), 2.72 (dd, J=17.0, 11.8 Hz, 1H); MS (ESI+) m/z 298 (M+H)$^+$.

Example 8C methyl 3-((2R)-4-aminochroman-2-yl)benzoate

Example 8B (100 mg, 0.336 mmol) and methanol (10 ml) were added to Ra—Ni 2800, water slurry (350 mg, 2.68 mmol) in a 50 mL pressure bottle and shaken for 16 hours at 30 psi of H$_2$ at ambient temperature. The reaction was filtered and the solvent removed under reduced pressure to provide the title compound (94 mg, 0.332 mmol, 99% yield)

as a tan powder. $^1$H NMR (400 MHz, DMSO-d$_6$) δ 8.06-8.01 (m, 1H), 7.91 (ddt, J=7.8, 2.7, 1.4 Hz, 1H), 7.71 (ddt, J=7.1, 3.4, 1.5 Hz, 1H), 7.59-7.53 (m, 1.5H), 7.33 (dd, J=7.7, 1.6 Hz, 0.5H), 7.12 (dtd, J=13.9, 7.4, 1.7 Hz, 1H), 6.95-6.83 (m, 1.5H), 6.78 (dd, J=8.2, 1.2 Hz, 0.5H), 5.41 (dd, J=7.6, 5.7 Hz, 0.5H), 5.29 (dd, J=11.6, 2.1 Hz, 0.5H), 4.17 (dd, J=11.2, 5.8 Hz, 0.5H), 3.95 (t, J=3.8 Hz, 0.5H), 3.87 (d, J=1.6 Hz, 3H), 2.36 (ddd, J=13.1, 5.7, 2.1 Hz, 1H), 2.09-2.05 (m, 1H), 1.93-1.84 (m, 2H)

Example 8D methyl 3-[(2R,4R)-4-({[1-(2,2-difluoro-1,3-benzodioxol-5-yl)cyclopropyl]carbonyl}amino)-3,4-dihydro-2H-chromen-2-yl]benzoate To a solution of 1-(2,2-difluorobenzo[d][1,3]dioxol-5-yl)cyclopropanecarboxylic acid (75 mg, 0.310 mmol) in dichoromethane (774 µL) was added one quarter of a solution of oxalyl dichloride (108 µL, 1.239 mmol) in 200 µL of dichloromethane followed by 1 drop of DMF. The reaction bubbled vigorously. The remainder of the oxalyl chloride solution was added dropwise. The reaction was stirred for 30 minutes, and the solvent removed under a stream of nitrogen. The residue was chased with 2×0.5 mL of dichloromethane, drying under a stream of nitrogen. This residue was taken up in dichloromethane (774 µL) and added to a mixture of the product from Example 8C (88 mg, 0.310 mmol) and triethylamine (129 µl, 0.929 mmol) in dichloromethane (774 µL). After 15 minutes, the mixture was quenched with saturated aqueous sodium bicarbonate, concentrated, and the resulting oil purified on a 12 g silica gel cartridge and eluted with a gradient of 5-100% ethyl acetate/heptanes to give 137 mg of a mixture of the two diastereomers. The mixture of diastereomers were chromatographed again using 30% MTBE/heptanes to provide Example 7 as the first eluting isomer and the title compound as the second eluting isomer (36 mg, 0.066 mmol, 21.30% yield) as a clear foam. $^1$H NMR (501 MHz, CDCl$_3$) δ 8.08 (t, J=1.8 Hz, 1H), 8.00 (dt, J=7.7, 1.5 Hz, 1H), 7.59 (dt, J=7.8, 1.6 Hz, 1H), 7.45 (t, J=7.6 Hz, 1H), 7.18 (td, J=7.9, 1.6 Hz, 1H), 7.13 (dd, J=8.2, 1.8 Hz, 1H), 7.10-7.06 (m, 2H), 7.01 (d, J=8.3 Hz, 1H), 6.93 (td, J=7.6, 1.2 Hz, 1H), 6.90 (dd, J=8.1, 1.2 Hz, 1H), 5.50 (td, J=10.6, 10.1, 6.2 Hz, 1H), 5.39 (d, J=8.9 Hz, 1H), 5.23 (dd, J=11.6, 1.9 Hz, 1H), 3.92 (s, 2H), 2.52 (ddd, J=13.2, 6.0, 2.0 Hz, 1H), 1.82 (dt, J=13.2, 11.3 Hz, 1H), 1.77-1.73 (m, 1H), 1.67-1.62 (m, 1H), 1.13-1.05 (m, 2H); MS (ESI+) m/z 508 (M+H)$^+$.

Example 9

3-[(2R,4R)-4-({[1-(2,2-difluoro-1,3-benzodioxol-5-yl)cyclopropyl]carbonyl}amino)-3,4-dihydro-2H-chromen-2-yl]benzoic acid To a suspension of Example 8D in tetrahydrofuran (164 µL) and water (82 µL) was added lithium hydroxide (2.124 mg, 0.089 mmol). The reaction mixture was stirred at room temperature. After 2 hours, additional lithium hydroxide (2.209 mg, 0.092 mmol) was added and the reaction mixture was stirred at ambient temperature for 72 hours. The reaction was quenched with 10 drops of 1 M HCl and this crude material was chromatographed directly using a 4 g silica gel cartridge with a gradient of 5-100% ethyl acetate/heptane to give the title compound (15 mg, 0.030 mmol, 61.7% yield) as white foam. $^1$H NMR (500 MHz, CDCl$_3$) δ 8.19 (t, J=1.7 Hz, 1H), 8.06 (dt, J=7.7, 1.4 Hz, 1H), 7.67 (d, J=7.6 Hz, 1H), 7.49 (t, J=7.7 Hz, 1H), 7.21-7.17 (m, 1H), 7.14 (dd, J=8.1, 1.8 Hz, 1H), 7.11 (d, J=1.6 Hz, 1H), 7.08 (d, J=7.6 Hz, 1H), 7.02 (d, J=8.2 Hz, 1H), 6.96-6.89 (m, 2H), 5.56 (dd, J=16.7, 9.4 Hz, 1H), 5.45 (d, J=8.9 Hz, 1H), 5.29 (d, J=11.3 Hz, 1H), 2.59 (ddd, J=13.1, 5.9, 1.9 Hz, 1H), 1.85-1.76 (m, 2H), 1.71-1.64 (m, 2H), 1.12-1.08 (m, 2H); MS (ESI+) m/z 494 (M+H)$^+$.

Example 10

3-[(2R,4S)-4-({[1-(2,2-difluoro-1,3-benzodioxol-5-yl)cyclopropyl]carbonyl}amino)-3,4-dihydro-2H-chromen-2-yl]benzoic acid The title compound was prepared using the conditions similar to that described in Example 1, substituting Example 7 for Example 6. $^1$H NMR (500 MHz, CDCl$_3$) δ 8.12 (t, J=1.7 Hz, 1H), 8.08 (dt, J=7.8, 1.4 Hz, 1H), 7.65 (d, J=7.8 Hz, 1H), 7.51 (t, J=7.7 Hz, 1H), 7.22 (td, J=7.7, 1.6 Hz, 1H), 7.19-7.12 (m, 3H), 7.03 (d, J=8.2 Hz, 1H), 6.97-6.91 (m, 2H), 5.65 (d, J=6.8 Hz, 1H), 5.06 (t, J=6.8 Hz, 1H), 4.87 (dd, J=11.3, 2.2 Hz, 1H), 2.35 (dt, J=14.3, 2.6 Hz, 1H), 2.20 (ddd, J=14.0, 11.2, 4.5 Hz, 1H), 1.71 (q, J=3.6 Hz, 2H), 1.12-1.08 (m, 2H); MS (ESI+) m/z 494 (M+H)$^+$.

Example 11 methyl 3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoate Example 11A (R)-methyl 3-(6-methyl-4-oxochroman-2-yl)benzoate The mixture of bis(2,2,2-trifluoroacetoxy)palladium (51.9 mg, 0.156 mmol), (S)-4-(tert-butyl)-2-(pyridin-2-yl)-4,5-dihydrooxazole (38.3 mg, 0.187 mmol), ammonium hexafluorophosphate(V) (153 mg, 0.937 mmol), (3-(methoxycarbonyl)phenyl)boronic acid (1124 mg, 6.24 mmol) and dichloroethane (10 mL) in a 20 mL vial were stirred for 5 minutes at room temperature, followed by the addition of 6-methyl-4H-chromen-4-one (CAS 314041-54-8, MFCD00218598, 500 mg, 3.12 mmol) and water (0.26 mL, 14 mmol). The vial was capped and the mixture was stirred at 60° C. overnight. The reaction mixture was filtered through a plug of celite and eluted with ethyl acetate. The organics was washed with brine and dried over MgSO$_4$. The solvent was removed in vacuo and the crude material was chromatographed using a 40 g silica gel cartridge, eluting with a gradient of 5-40% ethyl acetate in heptane to provide the title compound (410 mg, 44.3%). $^1$H NMR (501 MHz, DMSO-d$_6$) δ 8.33 (t, J=1.7 Hz, 1H), 8.17 (dt, J=7.7, 1.5 Hz, 1H), 8.02 (dt, J=7.7, 1.5 Hz, 1H), 7.83-7.74 (m, 2H), 7.62 (dd, J=8.5, 2.4 Hz, 1H), 7.23 (d, J=8.4 Hz, 1H), 5.93 (dd, J=12.9, 2.9 Hz, 1H), 4.07 (s, 3H), 3.42 (dd, J=16.8, 13.0 Hz, 1H), 3.04 (dd, J=16.8, 3.0 Hz, 1H), 2.49 (s, 3H); MS (ESI+) m/z 297 (M+H)$^+$.

Example 11B (R)-methyl 3-(4-(hydroxyimino)-6-methylchroman-2-yl)benzoate

The mixture of Example 11A (390 mg, 1.316 mmol), hydroxylamine hydrochloride (183 mg, 2.63 mmol), sodium acetate (216 mg, 2.63 mmol) in methanol (10 mL) was stirred at 60° C. for 4 hours. The solvent was evaporated under pressure and the residue was dissolved in ethyl acetate, washed with brine, dried over MgSO$_4$, and filtered. The solvent was removed under reduced pressure to provide the title compound (393 mg, 95% yield) as white solid. $^1$H NMR (501 MHz, DMSO-d$_6$) δ 11.51 (s, 1H), 8.32 (t, J=1.7 Hz, 1H), 8.18 (dt, J=7.8, 1.5 Hz, 1H), 8.02 (dt, J=7.7, 1.3 Hz, 1H), 7.88-7.76 (m, 2H), 7.35 (dd, J=8.4, 2.2 Hz, 1H), 7.12 (d, J=8.3 Hz, 1H), 5.49 (dd, J=11.6, 3.1 Hz, 1H), 4.10 (s, 3H), 3.60 (dd, J=17.1, 3.3 Hz, 1H), 2.92 (dd, J=17.0, 11.6 Hz, 1H), 2.49 (s, 3H); MS (ESI+) m/z 312 (M+H)$^+$.

Example 11C methyl 3-((2R)-4-amino-6-methylchroman-2-yl) benzoate

Example 11B (390 mg, 1.253 mmol) was added to Ra—Ni 2800, water slurry (1.17 g) in a 100 mL pressure bottle. The mixture was charged with 30 psi of hydrogen and stirred at ambient temperature for 16 hours. LC/MS indicated that the reaction was completed. The mixture was filtered and the solvent evaporated under reduced pressure. The residue was dissolved in tert-butyl ethyl ether, followed by the addition of 4 M HCl in dioxane (2 ml) drop wise. The precipitated white solid was collected by filtration, washed with tert-butyl methyl ether, and dried to yield the hydrochloride salt of the title compound (355 mg, 1.063 mmol, 85% yield). LC/MS m/z 281 (M-NH$_2$)$^+$.

Example 11D methyl 3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoate To 1-(2,2-difluorobenzo[d][1,3]dioxol-5-yl)cyclopropanecarboxylic acid (332 mg, 1.372 mmol) in CH$_2$Cl$_2$ (6 mL) was added a few drops of DMF, followed by the drop wise addition of oxalyl dichloride (0.290 ml, 3.43 mmol). The mixture was stirred at room temperature for 30 minutes. LC/MS with methanol as solvent showed a completed methyl ester's peak. Solvent was removed in vacuo, excess oxalyl chloride removed via azeotrope with dichloroethane, and the crude material in CH$_2$Cl$_2$ (4 mL) was added to the product from Example 11C (340 mg, 1.143 mmol) and pyridine (543 mg, 6.86 mmol) in CH$_2$Cl$_2$ (6 mL). The mixture was stirred at room temperature for 2 hours and saturated NaHCO$_3$ aqueous solution and CH$_2$Cl$_2$ was added. The phases were separated and the aqueous layer was extracted with CH$_2$Cl$_2$. The combined organics were dried over MgSO$_4$, filtered, and concentrated under reduced pressure. Purification of the residue by chromatography using a 40 g silica gel cartridge, and eluting with 0-30% ethyl acetate in hexane provide Example 12 as the first eluting isomer, and the title compound as the second eluting isomer (133 mg, 0.255 mmol, 22.30% yield). $^1$H NMR (400 MHz, CDCl$_3$) δ 8.07 (t, J=1.7 Hz, 1H), 7.99 (dt, J=8.0, 1.4 Hz, 1H), 7.58 (dt, J=7.8, 1.4 Hz, 1H), 7.44 (t, J=7.7 Hz, 1H), 7.18-7.06 (m, 2H), 7.05-6.92 (m, 2H), 6.88-6.72 (m, 2H), 5.53-5.29 (m, 2H), 5.19 (dd, J=11.5, 1.9 Hz, 1H), 3.92 (s, 3H), 2.53 (ddd, J=13.4, 5.9, 2.0 Hz, 1H), 2.26 (s, 3H), 1.86-1.67 (m, 2H), 1.61 (d, J=16.1 Hz, 1H), 1.17-1.00 (m, 2H); MS (ESI+) m/z 522 (M+H)$^+$.

Example 12 methyl 3-[(2R,4S)-4-({[1-(2,2-difluoro-1,3-benzodioxol-5-yl)cyclopropyl]carbonyl}amino)-6-methyl-3,4-dihydro-2H-chromen-2-yl]benzoate The title compound was isolated as the first eluting isomer from the chromatography as described in Example 11D (97 mg, 16.27% yield). $^1$H NMR (400 MHz, CDCl$_3$) δ 8.05 (t, J=1.7 Hz, 1H), 8.00 (d, J=7.7 Hz, 1H), 7.61-7.56 (m, 1H), 7.47 (t, J=7.7 Hz, 1H), 7.19-7.12 (m, 2H), 7.05-6.99 (m, 2H), 6.93 (d, J=2.2 Hz, 1H), 6.81 (d, J=8.3 Hz, 1H), 5.62 (d, J=6.9 Hz, 1H), 5.01 (ddd, J=7.1, 4.6, 2.8 Hz, 1H), 4.80 (dd, J=11.2, 2.3 Hz, 1H), 3.94 (s, 3H), 2.34-2.23 (m, 4H), 2.17 (ddd, J=14.4, 11.1, 4.7 Hz, 1H), 1.74-1.64 (m, 2H), 1.13-1.04 (m, 2H); MS (ESI+) m/z 522 (M+H)$^+$.

Example 13

3-[(2R,4S)-4-({[1-(2,2-difluoro-1,3-benzodioxol-5-yl)cyclopropyl]carbonyl}amino)-6-methyl-3,4-dihydro-2H-chromen-2-yl]benzoic acid A mixture of Example 12 (96 mg, 0.184 mmol) and 2 M LiOH (2 mL) in methanol (6 mL) was stirred at 35° C. for 4 hours. Solvent was removed under reduced pressure and the residue dissolved in water (2 mL), and the pH was adjusted with 2 M HCl to pH 1-2. The precipitated white solid was collected by filtration, washed with water, and dried to provide the title compound (83 mg, 89% yield). $^1$H NMR (400 MHz, CDCl$_3$) δ 8.10 (t, J=1.7 Hz, 1H), 8.06 (d, J=7.8 Hz, 1H), 7.64 (d, J=7.7 Hz, 1H), 7.49 (t, J=7.8 Hz, 1H), 7.20-7.13 (m, 2H), 7.06-6.99 (m, 2H), 6.93 (d, J=2.1 Hz, 1H), 6.82 (d, J=8.4 Hz, 1H), 5.65 (d, J=6.8 Hz, 1H), 5.01 (dt, J=7.0, 3.5 Hz, 1H), 4.83 (dd, J=11.2, 2.3 Hz, 1H), 2.31 (dt, J=14.4, 2.8 Hz, 1H), 2.26 (s, 3H), 2.18 (ddd, J=14.7, 11.1, 4.7 Hz, 1H), 1.74-1.66 (m, 2H), 1.14-1.04 (m, 2H); MS (ESI+) m/z 508 (M+H)$^+$.

Example 14

3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid The mixture of Example 11D (35 mg, 0.067 mmol) and 2 M LiOH (1 mL) in methanol (4 mL) was stirred at 35° C. for 4 hours. Solvent was removed under reduced pressure and the residue dissolved in water (2 mL), and the pH was adjusted with 2 M HCl to pH 1-2. The white solid precipitated was collected by filtration, washed with water, and dried to yield title compound (30 mg, 88% yield). $^1$H NMR (400 MHz, CDCl$_3$) δ 8.18 (t, J=1.7 Hz, 1H), 8.05 (dt, J=7.9, 1.3 Hz, 1H), 7.65 (dt, J=7.6, 1.4 Hz, 1H), 7.47 (t, J=7.7 Hz, 1H), 7.17-7.10 (m, 2H), 7.02 (d, J=8.6 Hz, 1H), 6.98 (dd, J=8.3, 2.1 Hz, 1H), 6.84 (d, J=2.0 Hz, 1H), 6.80 (d, J=8.3 Hz, 1H), 5.49 (td, J=10.5, 9.8, 6.0 Hz, 1H), 5.42 (d, J=8.8 Hz, 1H), 5.25 (dd, J=11.6, 1.8 Hz, 1H), 2.59 (ddd, J=13.3, 5.9, 1.9 Hz, 1H), 2.26 (s, 3H), 1.85-1.75 (m, 2H), 1.68-1.58 (m, 1H), 1.18-1.04 (m, 2H); MS (ESI+) m/z 508 (M+H)$^+$.

Example 15

3-[(2R,4S)-4-({[1-(2,2-difluoro-1,3-benzodioxol-5-yl)cyclopropyl]carbonyl}amino)-7-methyl-3,4-dihydro-2H-chromen-2-yl]benzoic acid The title compound was prepared using the conditions similar to that described in Example 1, substituting Example 17 for Example 6. ¹H NMR (400 MHz, CDCl₃) δ 8.17-7.97 (m, 2H), 7.66-7.40 (m, 2H), 7.20-6.95 (m, 4H), 6.74 (t, J=3.4 Hz, 2H), 5.64 (d, J=6.8 Hz, 1H), 4.93 (ddd, J=70.0, 8.8, 3.0 Hz, 2H), 2.32 (dt, J=14.4, 2.6 Hz, 1H), 2.28 (s, 3H), 2.17 (ddd, J=14.9, 11.1, 4.7 Hz, 1H), 1.70 (q, J=3.9 Hz, 2H), 1.08 (q, J=3.9 Hz, 2H); MS (ESI+) m/z 508 (M+H)⁺.

Example 16

3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid The mixture of 18E (130 mg, 0.249 mmol) and 2 M LiOH (1 ml) in methanol (4 mL) was stirred at 35° C. for 4 hours, solvent was removed under pressure and the residue dissolved in water (2 mL), and adjusted with 2 M HCl to pH 1-2. The precipitated white solid was filtered, washed with water and dried to give title compound (114 mg, 90% yield). ¹H NMR (400 MHz, CDCl₃) δ 8.19 (s, 1H), 8.05 (d, J=7.7 Hz, 1H), 7.64 (d, J=7.6 Hz, 1H), 7.46 (t, J=7.7 Hz, 1H), 7.17-7.04 (m, 2H), 6.97 (dd, J=25.7, 7.9 Hz, 2H), 6.73 (d, J=9.0 Hz, 2H), 5.60-5.35 (m, 2H), 5.24 (d, J=11.3 Hz, 1H), 2.58 (dd, J=12.9, 5.9 Hz, 1H), 2.27 (s, 3H), 1.86-1.70 (m, 2H), 1.66 (d, J=11.9 Hz, 1H), 1.09 (q, J=2.8 Hz, 2H); MS (ESI+) m/z 508 (M+H)⁺.

Example 17 methyl 3-[(2R,4S)-4-({[1-(2,2-difluoro-1,3-benzodioxol-5-yl)cyclopropyl]carbonyl}amino)-7-methyl-3,4-dihydro-2H-chromen-2-yl]benzoate The title compound (290 mg, 26.5% yield) was isolated as the first eluting isomer from the separation of the isomers as described in Example 18E. ¹H NMR (400 MHz, CDCl₃) δ 8.05 (t, J=1.8 Hz, 1H), 8.01 (dt, J=7.7, 1.5 Hz, 1H), 7.58 (dt, J=7.5, 1.4 Hz, 1H), 7.47 (t, J=7.7 Hz, 1H), 7.19-7.10 (m, 2H), 7.03 (dd, J=8.2, 1.7 Hz, 2H), 6.75 (dd, J=6.2, 1.9 Hz, 2H), 5.61 (d, J=6.8 Hz, 1H), 5.01 (dt, J=7.1, 3.3 Hz, 1H), 4.81 (dd, J=11.3, 2.3 Hz, 1H), 3.94 (s, 3H), 2.34-2.29 (m, 1H), 2.29 (s, 3H), 2.16 (ddd, J=14.2, 11.3, 4.6 Hz, 1H), 1.73-1.65 (m, 2H), 1.11-1.03 (m, 2H); MS (ESI+) m/z 522 (M+H)⁺.

Example 18 methyl 3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoate Example 18A The mixture of 1-(2-hydroxy-4-methylphenyl)ethanone (2 ml, 14.12 mmol) and 1,1-dimethoxy-N,N-dimethylmethanamine (2.063 ml, 15.53 mmol) was heated at 120° C. for 2 hours, and then cooled down. The precipitated orange solid was filtered, washed with heptane, and dried to give intermediate (E)-3-(dimethylamino)-1-(2-hydroxy-4-methylphenyl)prop-2-en-1-one, which was dissolved in CH₂Cl₂ (120 mL) and treated with concentrated HCl (15 mL). The mixture was refluxed for 2 hours, and LC/MS indicated the reaction was complete. The water layer was removed and extracted with CH₂Cl₂ (10 mL×2). The combined organics was concentrated to give a crude orange color solid. Purification by chromatography on 80 g silica gel cartridge, eluting with ethyl acetate in heptane at 5-40% gradient gave title compound as white solid (1.82 g, 80% yield). ¹H NMR (400 MHz, CDCl₃) δ 8.09 (d, J=8.1 Hz, 1H), 7.81 (d, J=5.7 Hz, 1H), 7.24 (s, 1H), 7.23-7.19 (m, 1H), 6.30 (d, J=6.1 Hz, 1H), 2.48 (s, 3H); MS (ESI+) m/z 161 (M+H)⁺.

Example 18B (R)-methyl 3-(7-methyl-4-oxochroman-2-yl)benzoate

A 20 mL vial was charged with bis(2,2,2-trifluoroacetoxy)palladium (0.353 g, 1.061 mmol), (S)-4-(tert-butyl)-2-(pyridin-2-yl)-4,5-dihydrooxazole (0.260 g, 1.274 mmol), ammonium hexafluorophosphate(V) (1.038 g, 6.37 mmol), and (3-(methoxycarbonyl)phenyl)boronic acid (3.82 g, 21.23 mmol) were stirred in dichloroethane (10 mL) at room temperature for 5 minutes. To this suspension was added Example 18A (1.70 g, 10.61 mmol) and water (0.256 mL, 14.19 mmol). The vial was capped and the mixture was stirred at 60° C. overnight. The mixture was filtered through a plug of celite and eluted with ethyl acetate. The solvent was removed under pressure and the crude material was chromatographed using a 80 g silica gel cartridge, eluting with a gradient of 5-50% ethyl acetate in heptane to provide the title compound (2.6 g, 83% yield). ¹H NMR (400 MHz, CDCl₃) δ 8.22-8.13 (m, 1H), 8.11-8.01 (m, 1H), 7.83 (d, J=8.3 Hz, 1H), 7.77-7.60 (m, 1H), 7.52 (t, J=7.7 Hz, 1H), 6.89 (d, J=6.8 Hz, 2H), 5.51 (dd, J=13.2, 2.9 Hz, 1H), 4.13 (s, 0H), 3.95 (d, J=1.0 Hz, 3H), 3.76 (s, 0H), 3.05 (ddd, J=16.8, 13.3, 1.0 Hz, 1H), 2.88 (ddd, J=16.8, 2.9, 0.9 Hz, 1H), 2.38 (s, 3H); MS (ESI+) m/z 297 (M+H)⁺.

Example 18C (R)-methyl 3-(4-(methoxyimino)-7-methylchroman-2-yl)benzoate

The mixture of Example 18B (1.2 g, 4.05 mmol), sodium acetate (0.664 g, 8.10 mmol) and O-methylhydroxylamine, hydrochloric acid (0.676 g, 8.10 mmol) in methanol (10 mL) was stirred at 60° C. overnight. The solvent was evaporated under pressure and the residue washed with water, filtered, and dried to provide the title compound (1.3 g, 4.00 mmol, 99% yield) as white solid. ¹H NMR (400 MHz, CDCl₃) δ 8.14 (d, J=1.9 Hz, 1H), 8.03 (dt, J=7.7, 1.5 Hz, 1H), 7.90-7.76 (m, 1H), 7.67 (dt, J=7.7, 1.5 Hz, 1H), 7.49 (t, J=7.7 Hz, 1H), 6.81 (dd, J=4.4, 2.6 Hz, 2H), 5.10 (dd, J=12.5, 3.1 Hz, 1H), 3.97 (s, 3H), 3.93 (s, 3H), 3.48 (dd, J=17.3, 3.1 Hz, 1H), 2.65 (dd, J=17.2, 12.5 Hz, 1H), 2.32 (s, 3H); MS (ESI+) m/z 326 (M+H)⁺.

Example 18D

Methyl 3-((2R)-4-amino-7-methylchroman-2-yl)benzoate

Example 18C (820 mg, 2.52 mmol) was added to Ra—Ni 2800, water slurry (2.5 g) in a 100 mL pressure bottle and charged with 30 psi of hydrogen. The mixture was stirred at ambient temperature for 16 hours. The mixture was filtered and the solvent removed under pressure. The residue was dissolved in tert-butyl ethyl ether, followed by drop wise addition of 4 M HCl in dioxane (2 mL). The precipitated white solid was collected by filtration, washed with tert-butyl methyl ether, and dried to provide the hydrochloride salt of the title compound with a cis-/trans-isomer of about 1 to 1 (705 mg, 2.371 mmol, 94% yield). LC/MS m/z 281 (M-NH$_2$)$^+$.

Example 18E methyl 3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoate To 1-(2,2-difluorobenzo[d][1,3]dioxol-5-yl)cyclopropanecarboxylic acid (559 mg, 2.3 mmol) in DMF (5 ml) was added HATU (1-[bis(dimethylamino)methylene]-1H-1,2,3-triazolo[4,5-b]pyridinium 3-oxid hexafluorophosphate, 1196 mg, 3.15 mmol). The mixture was stirred for 10 minutes at room temperature, followed by addition of the product from Example 18D (700 mg, 2.1 mmol) and N-ethyl-N-isopropylpropan-2-amine (1.461 ml, 8.39 mmol) sequentially. The mixture was stirred at room temperature for 2 hours. LC/MS indicated the reaction was complete. Dichloromethane (40 mL) was added and the solution was washed with brine (20 mL×2). The organic layer was dried over MgSO$_4$ and concentrated under reduced pressure. The resulting residue was purified by chromatography on a 40 g silica gel cartridge, eluting with a gradient of 0-25% ethyl acetate in heptane to provide Example 17 as the first eluting isomer and the title compound as the second eluting isomer (400 mg, 36.6% yield). $^1$H NMR (400 MHz, CDCl$_3$) δ 8.07 (d, J=1.9 Hz, 1H), 7.99 (dt, J=7.9, 1.4 Hz, 1H), 7.58 (dt, J=7.8, 1.5 Hz, 1H), 7.44 (t, J=7.7 Hz, 1H), 7.15-7.05 (m, 2H), 6.97 (dd, J=21.0, 8.0 Hz, 2H), 6.74 (d, J=9.5 Hz, 2H), 5.49-5.39 (m, 1H), 5.36 (d, J=8.7 Hz, 1H), 5.20 (dd, J=11.3, 1.9 Hz, 1H), 3.92 (s, 3H), 2.51 (ddd, J=13.2, 6.0, 2.0 Hz, 1H), 2.28 (s, 3H), 1.67-1.59 (m, 1H), 1.57 (d, J=1.1 Hz, 2H), 1.07 (td, J=3.6, 2.2 Hz, 2H); MS (ESI+) m/z 522 (M+H)$^+$.

Example 19

3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid A mixture of Example 21D (80 mg, 0.149 mmol) and aqueous LiOH (2 M, 1 mL) in methanol (4 mL) was stirred at 35° C. for 4 hours; LC/MS indicated the reaction was complete. Solvent was removed under reduced pressure and water (2 mL) was added. To the mixture was added 2 M HCl to adjust pH to 1-2. The white solid was collected by filtration, washed with water, and dried to give the title compound (55 mg, 70.6% yield). $^1$H NMR (400 MHz, CDCl$_3$) δ 8.18 (s, 1H), 8.05 (d, J=7.7 Hz, 1H), 7.65 (d, J=7.6 Hz, 1H), 7.47 (t, J=7.7 Hz, 1H), 7.17-7.11 (m, 2H), 7.02 (dd, J=8.3, 3.7 Hz, 1H), 6.83 (d, J=9.0 Hz, 1H), 6.75 (dd, J=8.8, 3.0 Hz, 1H), 6.59 (d, J=3.0 Hz, 1H), 5.49 (dt, J=18.5, 7.4 Hz, 2H), 5.22 (d, J=11.4 Hz, 1H), 3.74 (s, 3H), 2.66-2.49 (m, 1H), 1.79 (ddd, J=11.9, 6.8, 4.0 Hz, 2H), 1.69-1.63 (m, 1H), 1.11 (d, J=5.0 Hz, 2H); MS (ESI+) m/z 524 (M+H)$^+$.

Example 20

1-(2,2-difluoro-1,3-benzodioxol-5-yl)-N-[(2R,4R)-7-hydroxy-2-(3-methoxyphenyl)-3,4-dihydro-2H-chromen-4-yl]cyclopropanecarboxamide Example 20A (R)-7-hydroxy-2-(3-methoxyphenyl)chroman-4-one A 250-mL round bottom flask was charged with (3-methoxyphenyl)boronic acid (1.991 g, 13.11 mmol), (S)-4-(tert-butyl)-2-(pyridin-2-yl)-4,5-dihydrooxazole (0.094 g, 0.463 mmol), bis(2,2,2-trifluoroacetoxy)palladium (0.128 g, 0.385 mmol), and ammonium hexafluorophosphate (0.377 g, 2.313 mmol), and dichloroethane (15.42 mL) was added. The reaction was stirred at ambient temperature for 5 minutes, at which point a yellow color was observed in the suspension. To the reaction mixture was added 7-hydroxy-4H-chromen-4-one (CAS 59887-89-7, MFCD00209371, 1.25 g, 7.71 mmol) and water (0.694 mL, 38.5 mmol) and an additional dichloroethane (10.28 mL) was used to wash down the sides of the flask. The reaction was stirred for 18 hours at 60° C., cooled to ambient temperature, diluted with dichloromethane, and filtered through a silica/celite filter, initially using 100% dichloromethane but then 20% ethyl acetate/80% dichloromethane to effectively remove the boronic acid. Combined filtrates was concentrated and the crude material loaded onto a 40 g silica gel column and eluted with 5-50% ethyl acetate/heptanes over 25 minutes to provide the title compound as a white solid. LC/MS m/z 271 (M+H)$^+$.

Example 20B (R)-7-hydroxy-2-(3-methoxyphenyl)chroman-4-one O-methyl oxime

Example 20A (1 g, 3.70 mmol) was dissolved in pyridine (3.70 mL) and O-methylhydroxylamine hydrochloride (0.927 g, 11.10 mmol) was added. The resulting suspension was heated at 60° C. for 2 hours, cooled to room temperature, and concentrated under reduced pressure. The crude material was partitioned between saturated aqueous ammonium chloride and methyl-tert-butyl ether. The crude material obtained from the concentration of the organic layer was purified using a 40 g silica gel cartridge, eluting with 5-20% ethyl acetate/heptanes over 30 minutes to provide the title compound (505 mg, 1.69 mmol) as a white solid. $^1$H NMR (400 MHz, CDCl$_3$) δ 7.80 (d, J=8.6 Hz, 1H), 7.31 (t, J=8.0 Hz, 1H), 7.13-6.96 (m, 2H), 6.98-6.82 (m, 1H), 6.48 (dd, J=8.7, 2.5 Hz, 1H), 6.43 (d, J=2.5 Hz, 1H), 5.91 (d, J=10.3 Hz, 1H), 5.03 (dd, J=12.4, 3.1 Hz, 1H), 3.95 (s, 3H), 3.83 (s, 3H), 3.43 (dd, J=17.3, 3.1 Hz, 1H), 2.66 (dd, J=17.3, 12.4 Hz, 1H); MS (ESI+) m/z 300.1 (M+H)$^+$.

Example 20C (2R,4R)-4-amino-2-(3-methoxyphenyl)chroman-7-ol

Example 20B (430 mg, 1.437 mmol) was dissolved in acetic acid (5 mL), and platinum (IV) oxide (48.9 mg, 0.215 mmol) was added. The resulting suspension was stirred under an atmosphere of hydrogen for 2 hours at room temperature. To the reaction mixture was added 15% more catalyst and it was stirred for 2 more hours. The solid was filtered and the filtrate concentrated. The residue was dissolved in methyl-tert-butyl ether (4 mL). To the solution was added HCl (4M solution in dioxane, 0.718 mL, 2.87 mmol). The resulting solid was collected by filtration and dried to constant weight to provide the hydrochloride salt of the title compound (407 mg, 1.32 mmol) as a solid. $^1$H NMR (400 MHz, DMSO-d$_6$) δ 9.71 (s, 1H), 8.67 (d, J=5.3 Hz, 3H), 7.45 (d, J=8.5 Hz, 1H), 7.36 (t, J=7.8 Hz, 1H), 7.05-6.91 (m, 3H), 6.47 (dd, J=8.6, 2.4 Hz, 1H), 6.31 (d, J=2.3 Hz, 1H), 5.16 (d, J=11.6 Hz, 1H), 4.67 (dt, J=11.0, 5.8 Hz, 1H), 3.78 (s, 3H), 2.50-2.46 (m, 1H), 1.99 (q, J=12.0 Hz, 1H); MS (ESI−) m/z 255.1 (M-NH$_2$).

Example 20D

1-(2,2-difluoro-1,3-benzodioxol-5-yl)-N-[(2R,4R)-7-hydroxy-2-(3-methoxyphenyl)-3,4-dihydro-2H-chromen-4-yl]cyclopropanecarboxamide To 1-(2,2-difluorobenzo[d][1,3]dioxol-5-yl)cyclopropanecarboxylic acid (40 mg, 0.165 mmol) in DMF (1 mL) was added HATU (1-[bis(dimethylamino)methylene]-1H-1,2,3-triazolo[4,5-b]pyridinium 3-oxid hexafluorophosphate) (82 mg, 0.215 mmol). The mixture was stirred for 5 minutes, and the product from Example 20C (50.8 mg, 0.165 mmol) was added, followed by addition of N-ethyl-N-isopropylpropan-2-amine (0.115 mL, 0.661 mmol). The mixture was stirred at ambient temperature for 2 hours, then purified by chromatography on a 25 g silica gel, eluting with a gradient of 5-50% ethyl acetatein heptanes to provide the title compound (25 mg, 0.050 mmol, 30.5% yield). $^1$H NMR (400 MHz, DMSO-$d_6$) δ 9.30 (s, 1H), 7.38 (d, J=1.6 Hz, 1H), 7.32-7.27 (m, 2H), 7.19 (dd, J=8.3, 1.7 Hz, 1H), 7.07 (d, J=8.9 Hz, 1H), 6.98-6.92 (m, 2H), 6.88 (dd, J=8.1, 2.6 Hz, 1H), 6.85-6.80 (m, 1H), 6.34 (dd, J=8.3, 2.4 Hz, 1H), 6.18 (d, J=2.4 Hz, 1H), 5.27 (td, J=9.9, 6.8 Hz, 1H), 5.16 (dd, J=10.8, 2.7 Hz, 1H), 3.75 (s, 3H), 2.09-1.95 (m, 2H), 1.49 (ddd, J=9.0, 5.4, 2.2 Hz, 1H), 1.41-1.30 (m, 1H), 1.10-0.98 (m, 2H); MS (ESI−) m/z 494 (M−H)$^-$.

Example 21 methyl 3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoate

Example 21A

(R)-methyl 3-(6-methoxy-4-oxochroman-2-yl)benzoate

A 20 mL vial was charged with bis(2,2,2-trifluoroacetoxy)palladium (0.377 g, 1.135 mmol), (S)-4-(tert-butyl)-2-(pyridin-2-yl)-4,5-dihydrooxazole (0.278 g, 1.362 mmol), ammonium hexafluorophosphate(V) (1.110 g, 6.81 mmol) and (3-(methoxycarbonyl)phenyl)boronic acid (3.06 g, 17.03 mmol). The mixture was stirred in dichloroethane (5 mL) for 5 minutes at room temperature, and a pale yellow color was observed. To this suspension was added 6-methoxy-4H-chromen-4-one (CAS 117408-98-7, 2.0 g, 11.35 mmol) and water (0.256 mL, 14.19 mmol) and the sides of the vial was washed with more dichloroethane (5 mL). The vial was capped and the mixture stirred at 60° C. overnight. The reaction gradually turned black, with Pd plated out on the sides of the vial. The mixture was filtered through a plug of silica gel and celite and eluted with ethyl acetate to give a red solution. The filtrate was concentrated under reduced pressure and the crude material was chromatographed using a 40 g silica gel cartridge, eluting with a gradient of 5-50% ethyl acetate/heptanes to provide the title compound (1.85 g, 5.92 mmol, 52.2% yield). $^1$H NMR (400 MHz, CDCl$_3$) δ 8.18 (t, J=1.7 Hz, 1H), 8.06 (dt, J=8.0, 1.4 Hz, 1H), 7.68 (dt, J=7.8, 1.5 Hz, 1H), 7.52 (t, J=7.8 Hz, 1H), 7.36 (d, J=3.1 Hz, 1H), 7.14 (dd, J=9.1, 3.1 Hz, 1H), 7.01 (d, J=9.0 Hz, 1H), 5.50 (dd, J=13.4, 3.0 Hz, 1H), 3.95 (s, 3H), 3.83 (s, 3H), 3.06 (dd, J=16.9, 13.4 Hz, 1H), 2.90 (dd, J=17.0, 3.0 Hz, 1H); MS (ESI+) m/z 329.9 (M+NH$_4$)$^+$.

Example 21B

(R)-methyl 3-(6-methoxy-4-(methoxyimino)chroman-2-yl)benzoate

The mixture of 21A (1.85 g, 5.92 mmol), sodium acetate (0.972 g, 11.85 mmol) and O-methylhydroxylamine, hydrochloric acid (0.989 g, 11.85 mmol) in methanol (10 mL) was stirred at 60° C. overnight. The solvent was evaporated under reduced pressure. The residue was dissolved in ethyl acetate, washed with water, and partitioned. The organic layers was dried over MgSO$_4$, filtered, and concentrated under reduced pressure. The residue was chromatographed on a 80 g silica gel cartridge, eluting with a gradient of 5-40% ethyl acetate/heptane to provided the title compound (1.7 g, 4.98 mmol, 84% yield) as white solid. LC/MS: TFA m/z 342 (M+H)$^+$.

Example 21C methyl 3-((2R,4R)-4-amino-6-methoxychroman-2-yl)benzoate

To Example 21B (1.5 g, 4.39 mmol) in acetic acid (10 mL) was added 5% platinum (857 mg, 0.220 mmol) on carbon. The reaction mixture was charged with 30 psi hydrogen and stirred at ambient temperature for 24 hours, and then filtered. The solvent was evaporated under reduced pressure and the residue dissolved in t-butyl methyl ether (10 mL). HCl (4M in dioxane, 2.5 mL) was added drop wise. The precipitated solid was collected by filtration and dried to provide the hydrochloride salt of the title compound (842 mg, 54.8% yield). LC/MS: m/z 297 (M-NH$_2$)$^+$.

Example 21D methyl 3-((2R,4R)-4-(1-(2,2-difluorobenzo[d][1,3]dioxol-5-yl)cyclopropanecarboxamido)-6-methoxychroman-2-yl)benzoate The mixture of 1-(2,2-difluorobenzo[d][1,3]dioxol-5-yl)cyclopropanecarboxylic acid (779 mg, 3.22 mmol) and HATU (1-[bis(dimethylamino)methylene]-1H-1,2,3-triazolo[4,5-b]pyridinium 3-oxid hexafluorophosphate (1427 mg, 3.75 mmol) in DMF (4 mL) was stirred for 10 minutes at room temperature, and the product from Example 21B (840 mg, 2.68 mmol) was added, followed by the addition of N-ethyl-N-isopropylpropan-2-amine (1.868 mL, 10.72 mmol). The mixture was stirred at ambient temperature for 2 hours. LC/MS indicated the reaction was complete. Purification of the mixture by chromatography on 80 g silica gel cartridge, eluting with a gradient of 5-40% ethyl acetate in heptane provided the title compound (835 mg, 57.9% yield). $^1$H NMR (400 MHz, CDCl$_3$) δ 8.07 (t, J=1.8 Hz, 1H), 7.99 (dt, J=7.9, 1.5 Hz, 1H), 7.59 (d, J=7.7 Hz, 1H), 7.44 (t, J=7.8 Hz, 1H), 7.15-7.10 (m, 2H), 7.01 (d, J=8.0 Hz, 1H), 6.83 (d, J=9.0 Hz, 1H), 6.75 (dd, J=8.9, 3.0 Hz, 1H), 6.59 (d, J=2.9 Hz, 1H), 5.49-5.33 (m, 2H), 5.20-5.13 (m, 1H), 3.92 (s, 3H), 3.74 (s, 3H), 2.52 (ddd, J=13.4, 5.9, 1.9 Hz, 1H), 1.84-1.72 (m, 2H), 1.66-1.61 (m, 1H), 1.11-1.06 (m, 2H); MS (ESI+) m/z 537.9 (M+H)$^+$.

Example 22 rac-1-(2,2-difluoro-1,3-benzodioxol-5-yl)-N-[(2R, 4S)-7-methoxy-2-(pyridin-3-yl)-3,4-dihydro-2H-chromen-4-yl]cyclopropanecarboxamide

Example 22A (E)-1-(2-hydroxy-4-methoxyphenyl)-3-(pyridin-3-yl)prop-2-en-1-one To a solution of 1-(2-hydroxy-4-methoxyphenyl)ethanone (10 g, 60.2 mmol) in 1 M aqueous NaOH (600 mL) was added nicotinaldehyde (16.95 mL, 181 mmol). The mixture was stirred for 16 hours at room temperature. The mixture was neutralized by dropwise addition of 1 M HCl (about 600 mL). The resulting precipitate was collected by filtration and dissolved in ethyl acetate and methanol. The solvent was removed in vacuo and the solid was then triturated with a small amount of methanol and filtered to provide the title compound (4.6 g, 18.04 mmol, 30.07% yield) as a yellow solid. $^1$HNMR (400 MHz, CDCl$_3$) δ 13.21 (s, 1H), 8.80 (s, 1H), 8.57 (d, J=4.4 Hz, 1H), 7.73-7.89 (m, 3H), 7.57 (d, J=16 Hz, 1H), 7.30 (t, J=7.2 Hz, 1H), 6.42-6.45 (m, 2H), 3.80 (s, 3H); MS (ESI+) m/z 256 (M+H)$^+$.

Example 22B 7-methoxy-2-(pyridin-3-yl)chroman-4-one

To a solution of the product from Example 22A (2.0 g, 7.83 mmol) in 96% ethanol (100 mL) was added concentrated HCl (10 mL, 120 mmol) and water (6 mL). The mixture was heated (block at 100° C.) at reflux for 72 hours, and cooled. The solvent was removed in vacuo. The crude material was purified by silica gel column chromatography, eluting with a gradient of 2-3% methanol/dichloromethane to afford the title compound (1.5 g, 5.13 mmol, 65.5% yield). $^1$HNMR (400 MHz, CDCl$_3$) δ 9.06 (s, 1H), 8.79 (s, 1H), 8.42 (d, J=7.2 Hz, 1H), 7.97 (s, 1H), 7.88-7.90 (m, 1H), 8.69-8.72 (m, 1H), 6.56 (s, 1H), 5.73 (d, J=10.4 Hz, 1H), 3.89 (s, 3H), 2.98-3.00 (m, 2H); MS (ESI+) m/z 256 (M+H)$^+$.

Example 22C 7-methoxy-2-(pyridin-3-yl)chroman-4-one oxime

A solution of the product from Example 22B (1.1 g, 4.31 mmol) in methanol (50 mL) was treated with hydroxylamine hydrochloride (0.359 g, 5.17 mmol) and sodium acetate (0.424 g, 5.17 mmol)). The mixture was stirred at 40° C. for 16 hours. The solvent was removed in vacuo. The crude material was washed with water (2×20 mL) and dried under a stream of nitrogen to provide the title compound (1.0 g, 3.31 mmol, 77% yield) as a brown solid. MS (ESI+) m/z 271 (M+H)$^+$.

Example 22D 7-methoxy-2-(pyridin-3-yl)chroman-4-amine

A solution of Example 22C (500 mg, 1.850 mmol) in ammonia-methanol solution (7 M, 50 mL) was treated with Raney nickel (109 mg, 1.850 mmol). The mixture was stirred at room temperature under 5 atmosphere of hydrogen for 5 hours. The mixture was filtered and the filtrate was concenrated to dryness. To the residue was added 1 M hydrogen chloride in ether. The precipitate was collected to afford the hydrochlorid salt of the title compound (235 mg, 0.917 mmol, 49.6% yield): $^1$HNMR (400 MHz, CD$_3$OD) δ 8.72-8.95 (m, 2H), 8.40 (s, 1H), 7.87 (s, 1H), 7.39 (t, J=8.8 Hz, 1H), 6.69-6.73 (m, 1H), 6.60-6.62 (m, 1H), 5.43-5.51 (m, 1H), 4.61 (s, 1H), 3.78 (d, J=2.4 Hz, 3H), 2.14-2.78 (m, 2H); MS (ESI+): m/z 257 (M+H)$^+$.

Example 22E rac-1-(2,2-difluoro-1,3-benzodioxol-5-yl)-N-[(2R, 4S)-7-methoxy-2-(pyridin-3-yl)-3,4-dihydro-2H-chromen-4-yl]cyclopropanecarboxamide To a solution of 1-(2,2-difluorobenzo[d][1,3]dioxol-5-yl)cyclopropanecarboxylic acid (45.5 mg, 0.188 mmol) in dichloromethane (1 mL) was added half of a solution of oxalyl dichloride (0.060 mL, 0.683 mmol) in 1 mL of dichloromethane followed by 1 drop of DMF. The reaction bubbled vigorously, then the remainder of the oxalyl chloride solution was added dropwise. The reaction was stirred for 30 minutes at room temperature. The solvent was removed under a stream of nitrogen, then chased with 2×1 mL of dichloromethane, drying under a stream of nitrogen. This reagent was taken up in dichloromethane (1 mL) and added to a mixture of the product from Example 22D (50 mg, 0.171 mmol) and triethylamine (0.095 mL, 0.683 mmol) in dichloromethane (1 mL). After 20 minutes of stirring at room temperature, the mixture was quenched with saturated aqueous sodium bicarbonate. The aqueous layer was removed and the organic phase concentrated. The resulting oil was dissolved in dichloromethane and purified on a 12 g silica gel cartridge, eluting with a gradient of 5-100% ethyl acetate/heptanes in 16 minutes to provide the crude product (71 mg) as an oil. The crude product was loaded onto a 2×0.25 mm plates and eluted with 100% ethyl acetate. The desired fractions were collected and concentrated to give 1-(2,2-difluorobenzo[d][1,3]dioxol-5-yl)-N-(7-methoxy-2-(pyridin-3-yl)chroman-4-yl)cyclopropanecarboxamide (45 mg, 0.094 mmol, 54.8% yield) as a pale foam. This material was further purified via preparative supercritical fluid chromatography set to maintain a back pressure at 100 bar using a CHIRALPAK® OD-H, 21×250 mm, 5 micron, with the sample at a concentration of 10 mg/mL in methanol using 16% methanol in CO$_2$ at a flow rate of 70 mL/minute to provide the title compound (retention time=3.8 minutes 18 mg, 0.037 mmol, 21.94% yield) and Example 57 (retention time=5.1 minutes). $^1$H NMR (400 MHz, DMSO-d$_6$) δ 8.57 (d, J=2.2 Hz, 1H), 8.55 (dd, J=4.7, 1.5 Hz, 1H), 7.77 (dt, J=8.0, 1.9 Hz, 1H), 7.53 (d, J=7.9 Hz, 1H), 7.43 (dd, J=5.5, 3.1 Hz, 2H), 7.32 (d, J=8.3 Hz, 1H), 7.21 (dd, J=8.4, 1.7 Hz, 1H), 7.02 (d, J=8.5 Hz, 1H), 6.52 (dd, J=8.5, 2.5 Hz, 1H), 6.46 (d, J=2.5 Hz, 1H), 5.30 (dd, J=9.5, 2.7 Hz, 1H), 4.88 (dt, J=8.6, 4.7 Hz, 1H), 3.70 (s, 3H), 2.20 (ddd, J=14.4, 9.7, 4.9 Hz, 1H), 2.10 (dt, J=14.1, 3.6 Hz, 1H), 1.40 (td, J=12.8, 9.4 Hz, 2H), 1.04 (d, J=2.9 Hz, 2H); MS (ESI+) m/z 481 (M+H)$^+$.

Example 23

3-[(2R,4R)-4-({[1-(2,2-difluoro-1,3-benzodioxol-5-yl)cyclopropyl]carbonyl}amino)-7-hydroxy-3,4-dihydro-2H-chromen-2-yl]benzoic acid

Example 23A 7-hydroxy-4H-chromen-4-one 1-(2,4-dihydroxyphenyl)ethanone (12.75 g, 84 mmol) was dissolved in triethylorthoformate (80 mL, 480 mmol), and concentrated perchloric acid (7 mL, 116 mmol) was added dropwise over 5 minutes. During the addition of acid, the temperature rose slowly but did not exceed 40° C. A dark red color was gradually formed. The reaction was stirred for 30 minutes and was then diluted with diethyl ether (300 mL), which resulted in the precipitation of a dark red solid. The solid was filtered and washed with ether (50 mL) and used without additional purification (a mixture of the perchlorate complex of the title compound and unreacted starting material was present). To 14 g of the crude intermediate mixture was added 150 mL of water, and the resulting suspension was stirred for 30 minutes at room temperature, during which point the red solid turned to a brownish color. The resulting solid was collected by filtration and washed with water (50 mL). The solid was dried to constant weight to provide the title compound (5.31 g, 32.7 mmol, 39%) as a light purple solid. $^1$H NMR (500 MHz, DMSO-$d_6$) δ 10.78 (s, 1H), 8.15 (d, J=6.0 Hz, 1H), 7.88 (d, J=8.7 Hz, 1H), 6.92 (dd, J=8.7, 2.3 Hz, 1H), 6.85 (d, J=2.3 Hz, 1H), 6.22 (d, J=6.0 Hz, 1H); MS (ESI+) m/z 163 (M+H)$^+$.

Example 23B (R)-methyl 3-(7-hydroxy-4-oxochroman-2-yl)benzoate

A 250 mL round bottle flask was charged with bis(2,2,2-trifluoroacetoxy)palladium (0.308 g, 0.925 mmol), (S)-4-(tert-butyl)-2-(pyridin-2-yl)-4,5-dihydrooxazole (0.227 g, 1.110 mmol), ammonium hexafluorophosphate(V) (0.905 g, 5.55 mmol), and 3-methoxycarbonylphenylboronic acid (5.99 g, 33.3 mmol) were stirred in dichloroethane (37 mL) for 5 minutes, and a pale yellow color was observed. To this suspension was added Example 23A (3.0 g, 18.50 mmol) and water (1.667 mL, 93 mmol) and additional dichloroethane (25 mL) was used to rinse the side of the flask. The reaction mixture was heated at 60° C. The reaction turned progressively darker and precipitation of Pd black could be seen along the sides of the flask. The reaction was allowed to stir overnight at the same temperature for a total reaction time of 18 hour. The reaction seemed to stall at ~50% conversion, so it was cooled to room temperature, filtered through a silica/celite plug using 100% dichloromethane to 90:10 dichloromethane:ethyl acetate. The mixture was heated with methyl t-butyl ether to give an off-white solid that was clean by LC-MS and used without additional purification (2 g). $^1$H NMR (400 MHz, DMSO-$d_6$) δ 10.63 (s, 1H), 8.12 (t, J=1.7 Hz, 1H), 7.97 (dt, J=7.5, 1.3 Hz, 1H), 7.82 (dd, J=8.1, 1.6 Hz, 1H), 7.67 (d, J=8.7 Hz, 1H), 7.60 (t, J=7.7 Hz, 1H), 6.54 (dd, J=8.6, 2.2 Hz, 1H), 6.40 (d, J=2.2 Hz, 1H), 5.71 (dd, J=12.8, 2.9 Hz, 1H), 3.88 (s, 3H), 3.12 (dd, J=16.8, 12.9 Hz, 1H), 2.76 (dd, J=16.7, 3.0 Hz, 1H); MS (ESI+) m/z=299.0 (M+H)$^+$.

Example 23C (R)-methyl 3-(7-hydroxy-4-(methoxyimino)chroman-2-yl)benzoate

Example 23B (2 g, 6.70 mmol) was dissolved in 13 mL of dry pyridine. O-methylhydroxylamine hydrochloride (1.15 g, 13.77 mmol) was added, and the resulting suspension was heated at 60° C. for 3 hours. Solvent was removed under reduced pressure and the crude residue partitioned between ethyl acetate and 1:1 saturated ammonium chloride solution in water. Combined organic extracts were concentrated and purified on an 80 g silica gel column, eluting with 20% ethyl acetate/heptanes to provide the title compound. $^1$H NMR (400 MHz, CDCl$_3$) δ 8.13 (d, J=2.1 Hz, 1H), 8.03 (dd, J=7.9, 1.8 Hz, 1H), 7.81 (dd, J=8.5, 1.5 Hz, 1H), 7.66 (d, J=7.7 Hz, 1H), 7.48 (t, J=7.7 Hz, 1H), 6.50 (dd, J=8.6, 2.6 Hz, 1H), 6.44 (d, J=2.5 Hz, 1H), 5.51 (d, J=9.5 Hz, 1H), 5.10 (dd, J=12.5, 3.1 Hz, 1H), 3.96 (s, 3H), 3.94 (d, J=1.4 Hz, 3H), 3.46 (dd, J=17.3, 3.2 Hz, 1H), 2.64 (dd, J=17.2, 12.4 Hz, 1H); MS (ESI+) m/z=300.1 (M+H)$^+$.

Example 23D methyl 3-((2R,4R)-4-amino-7-hydroxychroman-2-yl)benzoate

Example 23C (200 mg, 0.611 mmol) was dissolved in acetic acid (2.5 mL), and platinum(IV) oxide (13.87 mg, 0.061 mmol) was added. The resulting suspension was stirred under an atmosphere of H$_2$ for 18 hour at room temperature. The reaction mixture was diluted with ethyl acetate and filtered through a syringe filter. The filtrate was concentrated and suspended in methyl t-butyl ether (6 mL), followed by addition of 2 equivalents of HCl in dioxane, and was sonicated to ensure fine suspension, then stirred overnight at room temperature. The mixture was concentrated to provide the hydrochloride salt of the title compound (93 mg) as a light orange solid, which was used without additional purification. $^1$H NMR (400 MHz, DMSO-$d_6$) δ 9.74 (s, 1H), 8.66 (br. s, J=5.5 Hz, 3H), 8.04 (d, J=1.8 Hz, 1H), 7.98 (d, J=7.8 Hz, 1H), 7.74 (d, J=7.8 Hz, 1H), 7.62 (t, J=7.7 Hz, 1H), 7.46 (d, J=8.6 Hz, 1H), 6.49 (dd, J=8.5, 2.4 Hz, 1H), 6.34 (d, J=2.4 Hz, 1H), 5.32 (d, J=11.6 Hz, 1H), 4.69 (dt, J=11.2, 5.6 Hz, 1H), 3.88 (s, 3H), 2.57-2.52 (m, 1H), 2.03-1.95 (m, 1H); MS (ESI−) m/z=283.0 (M-NH$_3$)$^−$.

Example 23E

Methyl 3-((2R,4R)-4-(1-(2,2-difluorobenzo[d][1,3]dioxol-5-yl)cyclopropanecarboxamido)-7-hydroxychroman-2-yl)benzoate The title compound was prepared using the conditions described in Example 8D, substituting Example 23D for Example 8C, to generate the title compound. $^1$H NMR (400 MHz, CDCl$_3$) δ 8.06 (t, J=1.7 Hz, 1H), 7.99 (d, J=7.8 Hz, 1H), 7.56 (d, J=7.7 Hz, 1H), 7.44 (t, J=7.7 Hz, 1H), 7.11 (dd, J=8.2, 1.6 Hz, 1H), 7.07 (d, J=1.6 Hz, 1H), 7.00 (d, J=8.2 Hz, 1H), 6.92 (d, J=8.4 Hz, 1H), 6.43 (dd, J=8.5, 2.5 Hz, 1H), 6.38 (d, J=2.5 Hz, 1H), 5.40 (td, J=10.2, 9.8, 6.0 Hz, 1H), 5.32 (d, J=8.9 Hz, 1H), 5.22-5.16 (m, 1H), 5.04 (d, J=2.6 Hz, 1H), 3.92 (s, 3H), 2.49 (ddd, J=13.3, 5.9, 2.0 Hz, 1H), 1.87-1.69 (m, 2H), 1.07 (q, J=2.4 Hz, 2H); MS (ESI−): m/z=522.2 (M−H)$^−$.

Example 23F

3-[(2R,4R)-4-({[1-(2,2-difluoro-1,3-benzodioxol-5-yl)cyclopropyl]carbonyl}amino)-7-hydroxy-3,4-dihydro-2H-chromen-2-yl]benzoic acid Lithium hydroxide hydrate (16.16 mg, 0.385 mmol) was dissolved in 0.170 mL of water, and the resulting solution was added to a solution of Example 23E (48 mg, 0.064 mmol) in tetrahydrofuran (257 μL). The reaction was stirred vigorously at ambient temperature for 15 hours. The crude material was loaded directedly onto a 12 g silica gel cartridge, eluting with 10-50% ethyl acetate/heptanes over 20 minutes to provide the title compound. $^1$H NMR (400 MHz, CDCl$_3$) δ 8.13 (s, 1H), 8.04 (d, J=7.7 Hz, 1H), 7.61 (d, J=7.7 Hz, 1H), 7.46 (t, J=7.7 Hz, 1H), 7.14-7.06 (m, 2H), 7.01 (d, J=8.2 Hz, 1H), 6.91 (d, J=8.4 Hz, 1H), 6.49-6.37 (m, 2H), 5.43 (q, J=8.2, 7.0 Hz, 2H), 5.21 (d, J=11.1 Hz, 1H), 2.56-2.51 (m, 1H), 1.79-1.64 (m, 3H), 1.09 (q, J=2.2 Hz, 2H); MS (ESI−) m/z 507.9 (M−H)$^−$ Example 24 ethyl rel-3-[(2S,4S)-4-({[1-(2,2-difluoro-1,3-benzodioxol-5-yl)cyclopropyl]carbonyl}amino)-3,4-dihydro-2H-pyrano[2,3-c]pyridin-2-yl]benzoate Example 24A methyl 3-(3-(3-chloropyridin-4-yl)-3-oxopropanoyl)benzoate A solution of methyl 3-acetylbenzoate (2.278 g, 12.78 mmol) in tetrahydrofuran (35 mL) at −78° C. under N$_2$ was treated with 1 M lithium bis(trimethylsilyl)amide in tetrahydrofuran (28.1 mL, 28.1 mmol) under N$_2$. After stirring at −78° C. for 15 minutes, a solution of 3-chloroisonicotinoyl chloride (2.25 g, 12.78 mmol) in tetrahydrofuran (25 mL) was added dropwise. After stirring at −78° C. for 15 minutes, the mixture was treated all at once with 1 M HCl (50 mL) and allowed to warm to room temperature. The mixture was diluted with water (200 mL) and stirred for 15 minutes. The solid was collected by filtration, washed with water, and dried under vacuum with heating (60° C.) to provide the title compound (3.1 g, 9.76 mmol, 76% yield). $^1$H NMR (400 MHz, DMSO-d$_6$) δ ppm 8.84 (s, 1H), 8.73 (d, J=4.9 Hz, 1H), 8.57 (t, J=1.8 Hz, 1H), 8.36 (d, J=8.3 Hz, 1H), 8.22 (d, J=7.8 Hz, 1H), 7.79 (d, J=4.9 Hz, 1H), 7.74 (t, J=7.8 Hz, 1H), 7.11 (s, 1H), 3.91 (s, 3H).

Example 24B methyl 3-(4-oxo-4H-pyrano[2,3-c]pyridin-2-yl)benzoate

A mixture of the product from Example 24A (3.1 g, 9.76 mmol) and K$_2$CO$_3$ (1.348 g, 9.76 mmol) in N,N-dimethylformamide (30 mL) under N$_2$ was heated to 95° C. for 20 minutes, heated to 110° C. for 20 minutes, and heated to 120° C. for 20 minutes. The mixture was cooled to near 0° C., treated all at once with 1 M HCl (15 mL), treated with water (150 mL) and stirred at room temperature for 15 minutes. The solid was collected by filtration, washed with water and dried over night at 60° C. under vacuum to provide the title compound (2.38 g, 8.46 mmol, 87% yield). $^1$H NMR (400 MHz, DMSO-d$_6$) δ ppm 9.27 (s, 1H), 8.68 (d, J=5.1 Hz, 1H), 8.59 (s, 1H), 8.39 (d, J=7.8 Hz, 1H), 8.17 (d, J=7.8 Hz, 1H), 7.90 (d, J=5.1 Hz, 1H), 7.75 (t, J=7.7 Hz, 1H), 7.25 (s, 1H), 3.92 (s, 3H); MS (ESI) m/z 282 (M+H)$^+$.

Example 24C methyl 3-(4-hydroxy-3,4-dihydro-2H-pyrano[2,3-c]pyridin-2-yl)benzoate A solution of the product from Example 24B (1.2 g, 4.27 mmol) in methanol (7 mL) and CH$_2$Cl$_2$ (14 mL) was treated with cobalt(II) phthalocyanine (0.122 g, 0.213 mmol), treated with NaBH$_4$ (0.646 g, 17.07 mmol), stirred at room temperature for 20 minutes, treated with more NaBH$_4$ (about 0.3 g), stirred at room temperature for 20 minutes, quenched with 1 M HCl (30 mL) and basified to pH about 8 with solid NaHCO$_3$. The mixture was extracted with ethyl acetate (2 times, 1st extraction was filtered through celite). The combined ethyl acetate layers were washed with brine, dried (MgSO$_4$), filtered, concentrated and chromatographed on silica gel eluted with a gradient of 50%-100% ethyl acetate in heptanes to provide the title compound. $^1$H NMR (400 MHz, CDCl$_3$) δ ppm 8.36-8.16 (m, 2H), 8.11 (s, 1H), 8.04 (d, J=7.7 Hz, 1H), 7.65 (d, J=7.8 Hz, 1H), 7.54-7.46 (m, 2H), 5.27 (dd, J=11.9, 1.9 Hz, 1H), 5.11 (dd, J=10.9, 6.1 Hz, 1H), 3.94 (s, 3H), 2.57 (ddd, J=13.4, 6.2, 1.9 Hz, 1H), 2.16 (q, J=11.9 Hz, 1H); MS (ESI) m/z 286 (M+H)$^+$.

Example 24D methyl 3-(4-oxo-3,4-dihydro-2H-pyrano[2,3-c]pyridin-2-yl)benzoate

A solution of the product from Example 24C (240 mg, 0.841 mmol) in acetone (10 mL) was treated dropwise with Jones reagent until the starting material was consumed. The mixture was concentrated to 2 mL volume on the rotovap with minimal heating. The residue was partitioned between ethyl acetate and saturated NaHCO$_3$ solution. The layers were separated and the aqueous was extracted with ethyl acetate. The combined ethyl acetate layers were washed with brine, dried (MgSO$_4$), filtered, concentrated and chromatographed on silica gel eluted with a gradient of 15%-50% ethyl acetate in heptanes to provide the title compound. $^1$H NMR (400 MHz, CDCl$_3$) δ ppm 8.63 (s, 1H), 8.41 (d, J=5.1 Hz, 1H), 8.18 (t, J=1.8 Hz, 1H), 8.12-8.07 (m, 1H), 7.71-7.67 (m, 2H), 7.55 (t, J=7.8 Hz, 1H), 5.60 (dd, J=13.2, 3.0 Hz, 1H), 3.95 (s, 3H), 3.16 (dd, J=17.1, 13.3 Hz, 1H), 3.01 (dd, J=17.0, 3.0 Hz, 1H); MS (ESI) m/z 284 (M+H)$^+$.

Example 24E

A solution of the product from Example 24D (67 mg, 0.237 mmol), (R)-(+)-2-methyl-2-propanesulfinamide (43.0 mg, 0.355 mmol) and titanium(IV) ethoxide (298 μL, 1.419 mmol) in 2-methyl-tetrahydrofuran (1.5 mL) was heated at 70° C. over night. The mixture was cooled and partitioned between water and ethyl acetate. The layers were separated and the aqueous layer was extracted with ethyl acetate. The combined ethyl acetate layers were washed with brine, dried (MgSO$_4$), filtered, concentrated, and chromatographed on silica gel eluted with a gradient of 0%-100% ethyl acetate in [9:1 CH$_2$Cl$_2$:ethyl acetate] to provide Example 24E as the first eluting isomer and Example 24F as the second eluting isomer. $^1$H NMR (400 MHz, CDCl$_3$) δ ppm 8.56-8.49 (m, 1H), 8.35-8.29 (m, 1H), 8.15 (s, 1H), 8.07 (d, J=7.8 Hz, 1H), 7.78-7.72 (m, 1H), 7.67 (d, J=7.7 Hz, 1H), 7.50 (t, J=7.7 Hz, 1H), 5.32 (dd, J=12.8, 2.4 Hz, 1H), 4.40 (q, J=7.2 Hz, 2H), 3.97 (dd, J=17.7, 2.8 Hz, 1H), 3.37 (dd, J=17.7, 12.8 Hz, 1H), 1.41 (t, J=7.1 Hz, 3H), 1.34 (s, 9H); MS (ESI) m/z 399 (M−H)$^−$.

Example 24F

Example 24F was obtained as the second eluting isomer from the chromatography of the crude material as described in Example 24E. $^1$H NMR (500 MHz, CDCl$_3$) δ ppm 8.56-8.49 (m, 1H), 8.35-8.28 (m, 1H), 8.15 (s, 1H), 8.07 (dt, J=7.8, 1.4 Hz, 1H), 7.78-7.74 (m, 1H), 7.64 (d, J=7.8 Hz, 1H), 7.51 (t, J=7.8 Hz, 1H), 5.41 (dd, J=12.3, 2.8 Hz, 1H), 4.41 (q, J=7.1 Hz, 2H), 4.26 (dd, J=17.3, 2.9 Hz, 1H), 3.16

(dd, J=17.3, 12.2 Hz, 1H), 1.42 (t, J=7.2 Hz, 3H), 1.36 (s, 9H); MS (ESI) m/z 399 (M−H)⁻.

Example 24G

A solution of the product from Example 24F (17 mg, 0.042 mmol) in ethanol (1 mL) was cooled to 0° C., treated with NaBH₄ (4 mg), stirred at 0° C. for 15 minutes and partitioned between water and ethyl acetate. The layers were separated and the aqueous layer was extracted with ethyl acetate. The combined ethyl acetate layers were washed with brine, dried (MgSO₄), filtered, and concentrated to provide Example 24G. ¹H NMR (400 MHz, CDCl₃) δ ppm 8.35-8.15 (m, 2H), 8.11 (s, 1H), 8.05 (d, J=7.7 Hz, 1H), 7.71-7.67 (m, 1H), 7.65 (d, J=7.8 Hz, 1H), 7.51 (t, J=7.7 Hz, 1H), 5.29 (d, J=9.4 Hz, 1H), 4.89-4.81 (m, 1H), 4.41 (q, J=7.1 Hz, 2H), 3.58 (d, J=8.3 Hz, 1H), 2.53 (ddd, J=13.8, 6.2, 1.9 Hz, 1H), 2.20 (dt, J=13.6, 11.5 Hz, 1H), 1.41 (t, J=7.1 Hz, 3H), 1.25 (s, 9H); MS (ESI) m/z 403 (M+H)⁺.

Example 24H ethyl rel-3-((2S,4S)-4-amino-3,4-dihydro-2H-pyrano[2,3-c]pyridin-2-yl)benzoate hydrochloride A solution of the product from Example 24G (17 mg, 0.042 mmol) in ethanol (1 mL) was treated with 4 M HCl in dioxane (0.5 mL) and stirred at room temperature for 20 minutes. The mixture was concentrated to dryness and dried under vacuum with heating at 60° C. for 30 minutes to provide Example 24H. ¹H NMR (400 MHz, DMSO-d₆) δ ppm 9.26-9.06 (m, 3H), 8.60-8.34 (m, 2H), 8.09-7.97 (m, 3H), 7.78 (d, J=7.8 Hz, 1H), 7.65 (t, J=7.7 Hz, 1H), 5.60 (d, J=11.4 Hz, 1H), 5.04-4.92 (m, 1H), 4.35 (q, J=7.1 Hz, 2H), 2.71-2.64 (m, 1H), 2.20 (q, J=12.1 Hz, 1H), 1.34 (t, J=7.1 Hz, 3H); MS (ESI) m/z 299 (M+H)⁺.

Example 24I ethyl rel-3-[(2S,4S)-4-({[1-(2,2-difluoro-1,3-benzodioxol-5-yl)cyclopropyl]carbonyl}amino)-3,4-dihydro-2H-pyrano[2,3-c]pyridin-2-yl]benzoate A mixture of the product from Example 24H (14 mg, 0.042 mmol), 1-(2,2-difluoro-1,3-benzodioxol-5-yl)cyclopropanecarboxylic acid (10.13 mg, 0.042 mmol) and O-(7-azabenzotriazol-1-yl)-N,N,N',N'-tetramethyluronium hexafluorophosphate (17.49 mg, 0.046 mmol) in tetrahydrofuran (1 mL) was treated with triethylamine (17.49 μL, 0.125 mmol). The mixture was stirred at room temperature for 1 hour, diluted with ethyl acetate (30 mL), washed with 1 M HCl (10 mL), washed with saturated NaHCO₃ solution (10 mL), washed with brine, dried (MgSO₄), filtered, and concentrated. The residue was chromatographed on silica gel, eluting with a gradient of 50%-100% [1:1 CH₂Cl₂:ethyl acetate] in heptanes to provide the title compound. ¹H NMR (400 MHz, CDCl₃) δ ppm 8.25 (s, 1H), 8.17 (d, J=5.1 Hz, 1H), 8.06 (s, 1H), 8.03 (d, J=8.1 Hz, 1H), 7.59 (d, J=8.1 Hz, 1H), 7.47 (t, J=7.7 Hz, 1H), 7.17-7.02 (m, 4H), 5.57-5.45 (m, 2H), 5.34-5.26 (m, 1H), 4.39 (q, J=7.1 Hz, 2H), 2.49 (ddd, J=13.5, 5.9, 1.9 Hz, 1H), 1.92 (q, J=11.8 Hz, 1H), 1.81-1.62 (m, 2H), 1.40 (t, J=7.1 Hz, 3H), 1.19-1.08 (m, 2H); MS (ESI) m/z 523 (M+H)⁺.

Example 25 ethyl rel-3-[(2R,4R)-4-({[1-(2,2-difluoro-1,3-benzodioxol-5-yl)cyclopropyl]carbonyl}amino)-3,4-dihydro-2H-pyrano[2,3-c]pyridin-2-yl]benzoate Example 25A A solution of Example 24E (10.6 mg, 0.026 mmol) in ethanol (1 mL) was cooled to 0° C., treated with NaBH₄ (4 mg), stirred at 0° C. for 15 minutes and partitioned between water and ethyl acetate. The layers were separated and the aqueous layer was extracted with ethyl acetate. The combined ethyl acetate layers were washed with brine, dried (MgSO₄), filtered, and concentrated to provide Example 25A. ¹H NMR (400 MHz, CDCl₃) δ ppm 8.32-8.29 (m, 1H), 8.21 (d, J=5.0 Hz, 1H), 8.11 (s, 1H), 8.04 (d, J=8.0 Hz, 1H), 7.63 (d, J=7.8 Hz, 1H), 7.49 (t, J=7.7 Hz, 1H), 7.36 (d, J=4.9 Hz, 1H), 5.28 (dd, J=11.5, 2.1 Hz, 1H), 4.79 (td, J=11.0, 6.0 Hz, 1H), 4.40 (q, J=7.1 Hz, 2H), 3.35 (d, J=10.6 Hz, 1H), 2.95-2.85 (m, 1H), 2.16 (dt, J=13.7, 11.4 Hz, 1H), 1.41 (t, J=7.2 Hz, 3H), 1.32 (s, 9H); MS (ESI) m/z 403 (M+H)⁺.

Example 25B ethyl rel-3-((2R,4R)-4-amino-3,4-dihydro-2H-pyrano[2,3-c]pyridin-2-yl)benzoate hydrochloride A solution of the product from Example 25A (9.3 mg, 0.023 mmol) in ethanol (1 mL) was treated with 4 M HCl in dioxane (0.5 mL) and stirred at room temperature for 20 minutes. The mixture was concentrated to dryness and dried under vacuum with heating at 60° C. for 30 minutes to provide the title compound. ¹H NMR (400 MHz, DMSO-d₆) δ ppm 9.11 (bs, 3H), 8.48 (s, 1H), 8.39 (d, J=5.2 Hz, 1H), 8.06 (s, 1H), 8.05-7.98 (m, 1H), 7.95 (d, J=5.4 Hz, 1H), 7.78 (d, J=7.7 Hz, 1H), 7.65 (t, J=7.7 Hz, 1H), 5.57 (d, J=11.5 Hz, 1H), 5.01-4.90 (m, 1H), 4.35 (q, J=7.1 Hz, 2H), 2.70-2.63 (m, 1H), 2.18 (q, J=12.1 Hz, 1H), 1.34 (t, J=7.1 Hz, 3H); MS (ESI) m/z 299 (M+H)⁺.

Example 25C ethyl rel-3-[(2R,4R)-4-({[1-(2,2-difluoro-1,3-benzodioxol-5-yl)cyclopropyl]carbonyl}amino)-3,4-dihydro-2H-pyrano[2,3-c]pyridin-2-yl]benzoate A mixture of the product from Example 25B (7.7 mg, 0.023 mmol), O-(7-azabenzotriazol-1-yl)-N,N,N',N'-tetramethyluronium hexafluorophosphate (9.62 mg, 0.025 mmol) and 1-(2,2-difluoro-1,3-benzodioxol-5-yl)cyclopropanecarboxylic acid (5.57 mg, 0.023 mmol) in tetrahydrofuran (1 mL) was treated with triethylamine (9.62 μL, 0.069 mmol). The mixture was stirred at room temperature for 1 hour, diluted with ethyl acetate (30 mL), washed with 1 M HCl (10 mL), washed with saturated NaHCO₃ solution (10 mL), washed with brine, dried (MgSO₄), filtered, and concentrated. The crude product was chromatographed on silica gel eluting with a gradient of 50%-100% [1:1 CH₂Cl₂:ethyl acetate] in heptanes to provide the title compound. ¹H NMR (400 MHz, CDCl₃) δ ppm 8.26 (s, 1H), 8.17 (d, J=5.0 Hz, 1H), 8.06 (s, 1H), 8.03 (d, J=7.8 Hz, 1H), 7.58 (d, J=7.8 Hz, 1H), 7.47 (t, J=7.7 Hz, 1H), 7.15 (dd, J=8.2, 1.6 Hz, 1H), 7.10 (d, J=1.5 Hz, 1H), 7.06-7.02 (m, 2H), 5.52 (td, J=10.8, 10.1, 6.0 Hz, 1H), 5.43 (d, J=8.9 Hz, 1H), 5.28 (dd, J=11.7, 1.9 Hz, 1H), 4.39 (q, J=7.1 Hz, 2H), 2.50 (ddd, J=13.5, 6.0, 2.0 Hz, 1H), 1.89 (dt, J=13.3, 11.4 Hz, 1H), 1.80-1.63 (m, 2H), 1.40 (t, J=7.1 Hz, 3H), 1.17-1.08 (m, 2H); MS (ESI) m/z 523 (M+H)$^+$.

Example 26

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid

Example 26A methyl 3-((2R,4R)-4-(1-(2,2-difluorobenzo[d][1,3]dioxol-5-yl)cyclopropanecarboxamido)-7-(difluoromethoxy)chroman-2-yl)cyclohexanecarboxylate The title compound (9.0 mg, 0.016 mmol, 9.04% yield) was isolated as a second eluting compound from the purification of the crude product as described in Example 27E. LC/MS m/z 580 (M+H)$^+$.

Example 26B

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid The mixture of 26A (12 mg, 0.021 mmol) and 2 M LiOH (0.5 mL) in methanol (2 mL) was stirred at 35° C. for 4 hours. LC/MS showed the reaction was complete. Solvent was removed and water (1 mL) was added. The pH of the mixture was adjusted with 2 M HCl to pH 1-2. The precipitated white solid was collected by filtration, washed with water, and dried to provide the title compound (10 mg, 0.018 mmol, 85% yield). $^1$H NMR (400 MHz, CDCl$_3$) δ 7.21-7.10 (m, 2H), 7.07-6.92 (m, 2H), 6.64-6.58 (m, 1H), 6.54 (q, J=2.1 Hz, 1H), 6.47-6.22 (m, 1H), 5.29 (dt, J=26.3, 8.2 Hz, 2H), 3.95 (t, J=12.4 Hz, 1H), 2.30 (d, J=58.5 Hz, 2H), 2.04 (d, J=12.1 Hz, 3H), 1.80-1.60 (m, 4H), 1.51-1.23 (m, 5H), 1.11 (d, J=3.5 Hz, 2H); MS (ESI−) m/z 564.2 (M−H)$^−$.

Example 27

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid

Example 27A 7-(difluoromethoxy)-4H-chromen-4-one

To 7-hydroxy-4H-chromen-4-one (CAS 59887-89-7, MFCD00209371, 2.0 g, 12.33 mmol) and diethyl(bromodifluoromethyl)phosphonate (4.38 mL, 24.67 mmol) in acetonitrile (40 mL) and water (20.00 mL) was added 50% aqueous potassium hydroxide (8.30 g, 74.0 mmol) drop wise via syringe while stirring vigorously. The temperature rose to a maximum temperature of 38° C. during the addition. After the addition, LC/MS showed conversion done with a small by-product peak. Additional water was added to the mixture. The mixture was extracted with ethyl acetate (3×20 mL). The combined organics were washed with 1 M HCl (10 mL), dried over MgSO$_4$, filtered, and concentrated. The crude mixture was purified on 80 g silica gel cartridge, eluting with ethyl acetated in heptane (5-40%) to provide the title compound (1.31 g, 6.17 mmol, 50.1% yield). $^1$H NMR (500 MHz, CDCl$_3$) δ 8.22 (d, J=8.7 Hz, 1H), 7.84 (d, J=6.1 Hz, 1H), 7.21-7.10 (m, 2H), 6.64 (t, J=72.5 Hz, 1H), 6.34 (d, J=6.0 Hz, 1H); LC/MS m/z 213 (M+H)$^+$.

Example 27B (R)-methyl 3-(7-(difluoromethoxy)-4-oxochroman-2-yl)benzoate

A mixture of (3-(methoxycarbonyl)phenyl)boronic acid (901 mg, 5.01 mmol), (S)-4-(tert-butyl)-2-(pyridin-2-yl)-4,5-dihydrooxazole (49.1 mg, 0.240 mmol), bis(2,2,2-trifluoroacetoxy)-palladium (66.6 mg, 0.200 mmol), and ammonium exafluorophosphate (196 mg, 1.20 mmol) in (10 ml) dichloroethane was stirred at ambient temperature for 5 minutes, and to it was added Example 27A (850 mg, 4.0 mmol) and water (0.36 mL, 20.0 mmol). The mixture was heated at 60° C. for overnight. The reaction mixture diluted with dichloroethane and filtered through a plug of celite. The mixture washed with brine and concentrated. The crude material loaded onto a 40 g silica gel cartridge and eluted with 5-50% ethyl acetate/heptane to give the title product as white solid. Analytic Chiral SFC showed 93% ee. $^1$H NMR (501 MHz, CDCl$_3$) δ 8.17 (t, J=1.8 Hz, 1H), 8.08 (dt, J=7.8, 1.4 Hz, 1H), 7.96 (d, J=8.5 Hz, 1H), 7.70-7.62 (m, 1H), 7.53 (t, J=7.7 Hz, 1H), 6.88-6.79 (m, 2H), 6.60 (t, J=72.8 Hz, 1H), 5.56 (dd, J=13.3, 2.9 Hz, 1H), 3.95 (s, 3H), 3.08 (dd, J=16.9, 13.4 Hz, 1H), 2.92 (dd, J=16.9, 2.9 Hz, 1H); MS (ESI+) m/z 349 (M+H)$^+$.

Example 27C (R)-methyl 3-(7-(difluoromethoxy)-4-(methoxyimino)chroman-2-yl)benzoate The mixture of Example 27B (410 mg, 1.177 mmol), O-methylhydroxylamine hydrochloride (197 mg, 2.354 mmol) and sodium acetate (193 mg, 2.354 mmol) in methanol (10 mL) was heated at 60° C. for 4 hours. LC/MS indicated the reaction was complete. The solvent was evaporated in vacuo, and ethyl acetate (20 mL) was added. The mixture was washed with water, dried over MgSO$_4$, and concentrated in vacuo to provide the title compounds as white solid (395 mg, 1.047 mmol, 89% yield). $^1$H NMR (400 MHz, CDCl$_3$) δ 8.14 (t, J=1.6 Hz, 1H), 8.04 (dt, J=7.8, 1.3 Hz, 1H), 7.97-7.86 (m, 1H), 7.66 (dt, J=7.8, 1.4 Hz, 1H), 7.50 (t, J=7.7 Hz, 1H), 6.79-6.72 (m, 2H), 6.71 (s, 1H), 5.13 (dd, J=12.4, 3.0 Hz, 1H), 3.98 (s, 3H), 3.94 (s, 3H), 3.50 (dd, J=17.3, 3.1 Hz, 1H), 2.66 (dd, J=17.2, 12.5 Hz, 1H); MS (ESI+) m/z 378 (M+H)$^+$.

Example 27D

Methyl 3-((2R,4R)-4-amino-7-(difluoromethoxy) chroman-2-yl)benzoate

Platinum on carbon, 5% loading (199 mg, 0.051 mmol) was added to a solution of Example 27C (385 mg, 1.02 mmol) in acetic acid (5 mL) in a 50 mL round bottom flask. The flask was charged with a hydrogen balloon and stirred for 48 hours at room temperature. LC/MS indicated only about 60% conversion achieved. The reaction was filtered, and the filtrate concentrated. The resulting residue was purified on a 12 g silica gel cartridge, eluting with (95% ethyl acetate/5% methanol/2% triethyl amine) in heptane at 10-100% gradient to provide the title compound (63 mg, 34%), which contained about 15% over-reduced by product of methyl 3-((2R,4R)-4-amino-7-(difluoromethoxy)chroman-2-yl)cyclohexanecarboxylate. The resulting mixture was carried on without further purification. $^1$H NMR (400 MHz, CDCl$_3$) δ 8.19-8.07 (m, 1H), 8.03 (dt, J=7.8, 1.4 Hz, 1H), 7.69-7.58 (m, 1H), 7.56-7.44 (m, 2H), 6.75 (dd, J=8.6, 2.4 Hz, 1H), 6.68 (d, J=2.1 Hz, 1H), 6.50-6.26 (m, 1H), 5.23 (dd, J=11.8, 1.9 Hz, 1H), 4.26 (dd, J=11.3, 5.8 Hz, 1H), 3.94 (s, 3H), 3.73-3.66 (m, 1H), 2.43 (ddd, J=13.4, 5.8, 1.9 Hz, 1H); MS (ESI+) m/z 333 (M-NH$_2$)$^+$.

Example 27E methyl 3-((2R,4R)-4-(1-(2,2-difluorobenzo[d][1,3] dioxol-5-yl)cyclopropanecarboxamido)-7-(difluoromethoxy)chroman-2-yl)benzoate A mixture of 1-(2,2-difluorobenzo[d][1,3]dioxol-5-yl)cyclopropanecarboxylic acid (41.6 mg, 0.172 mmol) and HATU (1-[bis(dimethylamino)methylene]-1H-1,2,3-triazolo[4,5-b]pyridinium 3-oxid hexafluorophosphate) (98 mg, 0.258 mmol) in DMF (1 mL) was stirred for 5 minutes, and Example 27D (60 mg, 0.172 mmol) was added, followed by addition of N-ethyl-N-isopropylpropan-2-amine (0.120 mL, 0.687 mmol). The mixture was stirred at ambient temperature for 2 hours and LC/MS showed the reaction was complete. The crude product was purified by preparative LC method TFA2 to provide the title compound (43 mg, 43.7% yield) as the first eluting compound and Example 26A as the second eluenting compound.

Example 27F 3-((2R,4R)-4-(1-(2,2-difluorobenzo[d][1,3]dioxol-5-yl)cyclopropanecarboxamido)-7-(difluoromethoxy) chroman-2-yl)benzoic acid A mixture of Example 27E (40 mg, 0.07 mmol) in methanol (2 mL) and 2 M aqueous LiOH was stirred at 35° C. for 4 hours. LC/MS showed the reaction was complete. Solvent was removed and water (1 mL) added, and the pH of the mixture was adjusted pH to 1-2 with 2 M HCl. The precipitated white solid was collected by filtration, washed with water, and dried to provide the title compound (32 mg, 0.057 mmol, 82% yield). $^1$H NMR (400 MHz, DMSO-d$_6$) δ 7.99 (s, 1H), 7.88 (d, J=7.9 Hz, 1H), 7.53 (d, J=7.7 Hz, 1H), 7.48-6.99 (m, 7H), 6.74 (d, J=8.2 Hz, 1H), 6.65 (s, 1H), 5.38 (d, J=10.8 Hz, 2H), 2.23-2.01 (m, 2H), 1.45 (ddd, J=44.1, 9.1, 3.1 Hz, 2H), 1.06 (d, J=3.7 Hz, 2H); MS (ESI−) m/z 558 (M−H)$^-$.

Example 28 rac-3-[(2R,4R)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoic acid A solution of Example 30 (23 mg, 0.043 mmol) in tetrahydrofuran (1.5 mL) and methanol (1.5 mL) was treated with 1 M NaOH (15 drops). The mixture was stirred at 50° C. for 15 minutes, heated to 60° C. for 30 minutes, cooled, diluted with water (10 mL), treated with 1 M HCl (1 mL) and extracted with ethyl acetate (30 mL). The ethyl acetate layer was washed with brine, dried (MgSO$_4$), filtered, and concentrated to provide the title compound (22 mg, 0.042 mmol, 98% yield). $^1$H NMR (400 MHz, CDCl$_3$) δ ppm 8.17 (t, J=1.7 Hz, 1H), 8.06 (d, J=7.8 Hz, 1H), 7.67 (d, J=7.7 Hz, 1H), 7.47 (t, J=7.7 Hz, 1H), 7.35 (d, J=8.2 Hz, 1H), 7.11 (dd, J=8.2, 1.7 Hz, 1H), 7.07 (d, J=1.5 Hz, 1H), 7.02 (d, J=8.2 Hz, 1H), 6.41 (d, J=8.3 Hz, 1H), 5.48 (td, J=9.8, 6.2 Hz, 1H), 5.39-5.29 (m, 2H), 3.89 (s, 3H), 2.58-2.51 (m, 1H), 1.85 (dt, J=13.3, 10.9 Hz, 1H), 1.78-1.62 (m, 2H), 1.13-1.05 (m, 2H); MS (ESI) m/z 523 (M+H)$^+$.

Example 29 rac-3-[(2R,4S)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoic acid

Example 29A methyl rac-3-[(2R,4S)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoate The product from Example 37G was chromatographed on silica gel, eluting with a gradient of 50%-65% [9:1 CH$_2$Cl$_2$: ethyl acetate] in heptanes to provide the title compound as the first eluting isomer. $^1$HNMR (400 MHz, CDCl$_3$) δ ppm 8.06 (t, J=1.6 Hz, 1H), 8.02 (d, J=7.8 Hz, 1H), 7.61 (dt, J=7.7, 1.5 Hz, 1H), 7.47 (t, J=7.7 Hz, 1H), 7.40 (d, J=8.2 Hz, 1H), 7.15 (dd, J=8.1, 1.7 Hz, 1H), 7.12 (d, J=1.7 Hz, 1H), 7.05 (d, J=8.2 Hz, 1H), 6.41 (d, J=8.2 Hz, 1H), 5.50 (d, J=6.9 Hz, 1H), 5.00 (ddd, J=7.1, 4.4, 2.8 Hz, 1H), 4.96 (dd, J=11.5, 2.4 Hz, 1H), 3.94 (s, 3H), 3.88 (s, 3H), 2.29 (dt, J=14.4, 2.7 Hz, 1H), 2.19 (ddd, J=14.4, 11.3, 4.5 Hz, 1H), 1.68 (q, J=3.4 Hz, 2H), 1.09 (q, J=3.3 Hz, 2H); MS (ESI) m/z 537 (M−H)$^-$.

Example 29B rac-3-[(2R,4S)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoic acid The title compound was prepared using the procedure similar to Example 28, substituting the product from Example 29A for the product from Example 30. $^1$H NMR (400 MHz, CDCl$_3$) δ ppm 8.13 (s, 1H), 8.08 (d, J=7.8 Hz, 1H), 7.67 (d, J=7.6 Hz, 1H), 7.50 (t, J=7.7 Hz, 1H), 7.41 (d, J=8.2 Hz, 1H), 7.16 (d, J=8.9 Hz, 1H), 7.13 (s, 1H), 7.05 (d, J=8.1 Hz, 1H), 6.41 (d, J=8.2 Hz, 1H), 5.53 (d, J=6.9 Hz, 1H), 5.05-4.95 (m, 2H), 3.89 (s, 3H), 2.32 (d, J=14.6 Hz, 1H), 2.28-2.10 (m, 1H), 1.69 (q, J=3.2 Hz, 2H), 1.10 (q, J=3.3 Hz, 2H); MS (ESI) m/z 523 (M−H).

Example 30 methyl rac-3-[(2R,4R)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoate The product from Example 37G was chromatographed on silica gel, eluting with a gradient of 50%-65% [9:1 CH$_2$Cl$_2$: ethyl acetate] in heptanes to provide the title compound as the second eluting isomer. 1H NMR (501 MHz, CDCl$_3$) δ ppm 8.08 (t, J=1.8 Hz, 1H), 8.00 (dt, J=7.8, 1.4 Hz, 1H), 7.62-7.59 (m, 1H), 7.44 (t, J=7.7 Hz, 1H), 7.34 (dd, J=8.3, 0.9 Hz, 1H), 7.09 (dd, J=8.2, 1.7 Hz, 1H), 7.05 (d, J=1.7 Hz, 1H), 7.01 (d, J=8.2 Hz, 1H), 6.40 (d, J=8.3 Hz, 1H), 5.46-5.39 (m, 1H), 5.32 (dd, J=11.2, 2.0 Hz, 1H), 5.26 (d, J=8.9 Hz, 1H), 3.92 (s, 3H), 3.88 (s, 3H), 2.48 (ddd, J=13.5, 6.2, 2.1 Hz, 1H), 1.86 (dt, J=13.5, 10.9 Hz, 1H), 1.75-1.68 (m, 1H), 1.68-1.61 (m, 1H), 1.12-1.04 (m, 2H); MS (ESI) m/z 537 (M−H)−.

Example 31 rac-3-[(2R,4R)-4-({[1-(2,2-difluoro-1,3-benzodioxol-5-yl)cyclopropyl]carbonyl}amino)-3,4-dihydro-2H-pyrano[2,3-b]pyridin-2-yl]benzoic acid The title compound was prepared using the procedure similar to that described in Example 28, substituting the product from Example 33F for the product from Example 30. $^1$H NMR (400 MHz, CDCl$_3$) δ ppm 8.31 (s, 1H), 8.25 (d, J=4.3 Hz, 1H), 8.04 (d, J=7.7 Hz, 1H), 7.58-7.51 (m, 2H), 7.44 (t, J=7.7 Hz, 1H), 7.13 (dd, J=8.2, 1.5 Hz, 1H), 7.10 (d, J=1.3 Hz, 1H), 7.03-6.97 (m, 2H), 5.64-5.56 (m, 1H), 5.51 (d, J=9.1 Hz, 1H), 5.44 (d, J=11.2 Hz, 1H), 2.61 (ddd, J=13.5, 6.0, 2.0 Hz, 1H), 1.89-1.65 (m, 3H), 1.18-1.08 (m, 2H); MS (ESI) m/z 495 (M+H)+.

Example 32 rac-3-[(2R,4S)-4-({[1-(2,2-difluoro-1,3-benzodioxol-5-yl)cyclopropyl]carbonyl}amino)-3,4-dihydro-2H-pyrano[2,3-b]pyridin-2-yl]benzoic acid The title compound was prepared using the procedure similar to that described in Example 28, substituting the product from Example 34 for the product from Example 30. $^1$H NMR (400 MHz, CDCl$_3$) δ ppm 8.28 (s, 2H), 8.05 (d, J=7.6 Hz, 1H), 7.60 (dd, J=7.5, 1.8 Hz, 1H), 7.53 (d, J=7.7 Hz, 1H), 7.46 (t, J=7.7 Hz, 1H), 7.16 (dd, J=8.0, 1.7 Hz, 1H), 7.12 (d, J=1.6 Hz, 1H), 7.03 (d, J=8.2 Hz, 1H), 6.99 (dd, J=7.3, 5.0 Hz, 1H), 5.77 (d, J=6.8 Hz, 1H), 5.18-5.08 (m, 2H), 2.44 (dt, J=14.3, 2.6 Hz, 1H), 2.16 (ddd, J=15.0, 11.4, 4.6 Hz, 1H), 1.72 (q, J=3.6 Hz, 2H), 1.12 (q, J=3.7 Hz, 2H); MS (ESI) m/z 495 (M+H)+.

Example 33 rac-methyl 3-[(2R,4R)-4-({[1-(2,2-difluoro-1,3-benzodioxol-5-yl)cyclopropyl]carbonyl}amino)-3,4-dihydro-2H-pyrano[2,3-b]pyridin-2-yl]benzoate Example 33A methyl 3-(3-(2-chloropyridin-3-yl)-3-oxopropanoyl)benzoate A solution of methyl 3-acetylbenzoate (108 mg, 0.606 mmol) in tetrahydrofuran (1 mL) was added to a −78° C. solution of 1 M lithium bis(trimethylsilyl)amide in tetrahydrofuran (1.3 mL, 1.3 mmol) under N$_2$. After stirring at −78 C for 15 minutes, a solution of 2-chloronicotinoyl chloride (107 mg, 0.606 mmol) in tetrahydrofuran (1 mL) was added dropwise. The mixture was stirred at room temperature for 15 minutes and quenched with 1 M HCl (about 2 mL). The mixture was allowed to warm to room temperature and then extracted with ethyl acetate (about 30 mL). The ethyl acetate layer was washed with brine, dried (MgSO$_4$), filtered, and concentrated. The crude product solidified on standing overnight. This residue was treated with 1:1 heptanes:ethyl acetate and the mixture was diluted with heptanes. The solid was collected by filtration, washed with 5:1 heptanes:ethyl acetate, and dried under vacuum to provide the title compound (55.5 mg, 0.175 mmol, 28.8% yield). MS (ESI) m/z 318 (M+H)+.

Example 33B methyl 3-(4-oxo-4H-pyrano[2,3-b]pyridin-2-yl)benzoate

A mixture of the product from Example 33A (3.06 g, 9.63 mmol) and K$_2$CO$_3$ (1.331 g, 9.63 mmol) in N,N-dimethylformamide (30 mL) was heated at 100° C. for 30 minutes, cooled to near 0° C., treated all at once with 1 M HCl (15 mL) and then diluted with water (150 mL). The mixture was stirred at room temperature for 15 minutes and the solid was collected by filtration, washed with water, and dried under vacuum with heating at 60° C. for 2 hours to provide the title compound (2.53 g, 9.00 mmol, 93% yield). $^1$H NMR (400 MHz, DMSO-d$_6$) δ ppm 8.81 (dd, J=4.6, 2.0 Hz, 1H), 8.59 (t, J=1.8 Hz, 1H), 8.51 (dd, J=7.7, 2.1 Hz, 1H), 8.37 (dd, J=8.3, 1.7 Hz, 1H), 8.17 (dt, J=7.8, 1.3 Hz, 1H), 7.74 (t, J=7.8 Hz, 1H), 7.65 (dd, J=7.8, 4.7 Hz, 1H), 7.21 (s, 1H), 3.92 (s, 3H); MS (ESI) m/z 282 (M+H)+.

Example 33C methyl 3-(4-oxo-3,4-dihydro-2H-pyrano[2,3-b]pyridin-2-yl)benzoate

A solution of the product from Example 33B (0.49 g, 1.742 mmol) in methanol (3 mL) and CH$_2$Cl$_2$ (6 mL) was treated with cobalt(II) phthalocyanine (0.050 g, 0.087 mmol), treated with NaBH$_4$ (0.527 g, 13.94 mmol), stirred at room temperature for 10 minutes, and partitioned between ethyl acetate (30 mL) and 1 M HCl (15 mL). The mixture was neutralized with saturated NaHCO$_3$ solution. The layers were separated and the aqueous layer was extracted with ethyl acetate (2×25 mL). The combined ethyl acetate layers were washed with brine, dried (MgSO$_4$), filtered, and concentrated. This material was dissolved in CH$_2$Cl$_2$ (about 10 mL), treated with pyridinium chlorochromate (0.751 g, 3.48 mmol) and stirred for 20 minutes. The residue was partitioned between saturated NaHCO$_3$ solution and CH$_2$Cl$_2$. This material was filtered through celite. The layers were separated and the aqueous was extracted with CH$_2$Cl$_2$ (2×). The combined CH$_2$Cl$_2$ layers were dried (MgSO$_4$), filtered, treated with silica gel (about 3 g), and concentrated to dryness. Chromatography of the residue on silica gel and eluting with a gradient of 30%-100% ethyl acetate in heptanes provided the title compound (115 mg, 0.406 mmol, 23.30% yield). $^1$H NMR (400 MHz, CDCl$_3$) δ ppm 8.52 (dd, J=4.9, 2.1 Hz, 1H), 8.29 (dd, J=7.6, 2.1 Hz, 1H), 8.20 (d, J=1.8 Hz, 1H), 8.07 (dt, J=7.8, 1.3 Hz, 1H), 7.73 (dt, J=7.8, 1.5 Hz, 1H), 7.52 (t, J=7.7 Hz, 1H), 7.14 (dd, J=7.6, 4.7 Hz, 1H), 5.69 (dd, J=12.9, 3.2 Hz, 1H), 3.94 (s, 3H), 3.13 (dd, J=16.9, 12.8 Hz, 1H), 3.00 (dd, J=16.9, 3.2 Hz, 1H); MS (ESI) m/z 284 (M+H)+.

Example 33D methyl 3-(4-(methoxyimino)-3,4-dihydro-2H-pyrano[2,3-b]pyridin-2-yl)benzoate A solution of the product from Example 33C (115 mg, 0.406 mmol) and O-methylhydroxylamine hydrochloride (102 mg, 1.218 mmol) in pyridine (1 mL) was heated at 60 OC for 2 hours. The mixture was cooled, concentrated, and partitioned between tert-butyl methyl ether and water. The tert-butyl methyl ether layer was isolated and the water layer was extracted with tert-butyl methyl ether. The combined tert-butyl methyl ether layers were washed with brine, dried (MgSO$_4$), filtered, concentrated, and chromatographed on silica gel eluted with a gradient of 25%-100% ethyl acetate in heptanes to provide the title compound (99 mg, 0.317 mmol, 78% yield). $^1$H NMR (400 MHz, CDCl$_3$) δ ppm 8.31-8.26 (m, 2H), 8.17 (t, J=1.8 Hz, 1H), 8.03 (dt, J=7.8, 1.4 Hz, 1H), 7.73 (dt, J=7.8, 1.5 Hz, 1H), 7.49 (t, J=7.8 Hz, 1H), 7.01 (dd, J=7.4, 5.0 Hz, 1H), 5.30 (dd, J=12.1, 3.1 Hz, 1H), 4.01 (s, 3H), 3.93 (s, 3H), 3.53 (dd, J=17.2, 3.2 Hz, 1H), 2.71 (dd, J=17.2, 12.1 Hz, 1H); MS (ESI) m/z 313 (M+H)$^+$.

Example 33E methyl 3-(4-amino-3,4-dihydro-2H-pyrano[2,3-b]pyridin-2-yl)benzoate

The product from Example 33D (99 mg, 0.317 mmol) and methanol (10 mL) was added to Ra—Ni 2800, water slurry (0.5 g, 3.83 mmol) in a 50 mL pressure bottle and shaken in an atmosphere of 30 psi H$_2$ for 16 hours at room temperature. The mixture was filtered, and the filtrate was concentrated to provide the title compound.

Example 33F rac-methyl 3-[(2R,4R)-4-({[1-(2,2-difluoro-1,3-benzodioxol-5-yl)cyclopropyl]carbonyl}amino)-3,4-dihydro-2H-pyrano[2,3-b]pyridin-2-yl]benzoate The title compound was isolated as the second eluting isomer from the chromatography column while prepared and purified using procedure similar to that described in Example 24I, substituting the product from Example 33E for the product from Example 24H. $^1$H NMR (400 MHz, CDCl$_3$) δ ppm 8.15 (dd, J=5.2, 2.0 Hz, 1H), 8.09 (t, J=1.8 Hz, 1H), 8.00 (dt, J=7.8, 1.4 Hz, 1H), 7.64 (dt, J=7.6, 1.5 Hz, 1H), 7.51-7.40 (m, 2H), 7.12 (dd, J=8.2, 1.7 Hz, 1H), 7.08 (d, J=1.6 Hz, 1H), 7.02 (d, J=8.2 Hz, 1H), 6.95 (dd, J=7.5, 4.8 Hz, 1H), 5.54 (td, J=10.3, 6.2 Hz, 1H), 5.42-5.35 (m, 2H), 3.92 (s, 3H), 2.51 (ddd, J=13.4, 6.0, 2.0 Hz, 1H), 1.86 (dt, J=13.4, 11.3 Hz, 1H), 1.80-1.62 (m, 2H), 1.17-1.04 (m, 2H); MS (ESI) m/z 509 (M+H)$^+$.

Example 34 rac-methyl 3-[(2R,4S)-4-({[1-(2,2-difluoro-1,3-benzodioxol-5-yl)cyclopropyl]carbonyl}amino)-3,4-dihydro-2H-pyrano[2,3-b]pyridin-2-yl]benzoate The title compound was isolated as the first eluting isomer from the chromatography column while prepared and purified using procedure similar to that described in Example 24I, substituting the product from Example 33E for the product from Example 24H. $^1$H NMR (400 MHz, CDCl$_3$) δ ppm 8.19 (dd, J=4.8, 1.9 Hz, 1H), 8.05 (t, J=1.7 Hz, 1H), 8.01 (dt, J=7.9, 1.4 Hz, 1H), 7.61 (dt, J=7.9, 1.4 Hz, 1H), 7.54 (dt, J=7.5, 1.9 Hz, 1H), 7.46 (t, J=7.7 Hz, 1H), 7.16 (dd, J=8.2, 1.7 Hz, 1H), 7.12 (d, J=1.6 Hz, 1H), 7.05 (d, J=8.2 Hz, 1H), 6.95 (dd, J=7.5, 4.8 Hz, 1H), 5.61 (d, J=7.2 Hz, 1H), 5.13-5.03 (m, 2H), 3.93 (s, 3H), 2.32 (dt, J=14.5, 2.9 Hz, 1H), 2.19 (ddd, J=14.8, 10.9, 4.6 Hz, 1H), 1.70 (q, J=3.6 Hz, 2H), 1.11 (q, J=3.7 Hz, 2H); MS (ESI) m/z 509 (M+H)$^+$.

Example 35

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid Example 35A methyl 3-((2R,4R)-4-amino-7-methoxychroman-2-yl)cyclohexanecarboxylate The title compound was prepared using the conditions described in Example 20C, substituting Example 5C for Example 20B. The title compound was the by-product of over reduction of the phenyl ring. Isolation of the title compound was achieved by formation of its hydrochloride salt, prepared by the addition of HCl (2.0 equivalents, 4M in dioxane) to a solution of the crude amine (30 mg) in methyl tert-butyl ether (2 mL), which afforded the hydrochloride salt of the title compound as colorless solid. The solid was collected by filtration and dried to constant weight to give the title compound (15 mg, 0.047 mmol, 53%).

Example 35B methyl 3-((2R,4R)-4-(1-(2,2-difluorobenzo[d][1,3]dioxol-5-yl)cyclopropanecarboxamido)-7-methoxychroman-2-yl)cyclohexanecarboxylate The title compound was prepared using the procedures similar to that described in Example 20D, substituting the product from Example 35A for the product from Example 20C. $^1$H NMR (400 MHz, CDCl$_3$) δ 7.18-7.11 (m, 2H), 7.02 (dd, J=8.2, 1.4 Hz, 1H), 6.87 (d, J=8.6 Hz, 1H), 6.43 (dd, J=8.6, 2.6 Hz, 1H), 6.31 (d, J=2.4 Hz, 1H), 5.31 (d, J=8.8 Hz, 1H), 5.27-5.11 (m, 1H), 3.89 (dd, J=11.4, 5.3 Hz, 1H), 3.73 (s, 3H), 3.67 (s, 3H), 2.39-0.83 (m, 14H); MS (ESI-) m/z 542.2 (M-H)$^-$.

Example 35C

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid The title compound was prepared using the conditions similar to that described in Example 1 substituting Example 35B for Example 6. $^1$H NMR (400 MHz, CDCl$_3$) δ 7.20-7.07 (m, 2H), 7.02 (d, J=8.1 Hz, 1H), 6.87 (d, J=8.6 Hz, 1H), 6.43 (dd, J=8.6, 2.5 Hz, 1H), 6.31 (t, J=1.9 Hz, 1H), 5.34 (d, J=8.7 Hz, 1H), 5.30-5.14 (m, 1H), 3.91 (td, J=11.5, 5.1 Hz, 1H), 3.73 (s, 3H), 2.41-1.03 (m, 16H); MS (ESI-) m/z 528.3 (M-H)$^-$.

Example 36

3-[(2R,4R)-4-({[1-(2,2-difluoro-1,3-benzodioxol-5-yl)cyclopropyl]carbonyl}amino)-7-fluoro-3,4-dihydro-2H-chromen-2-yl]cyclohexanecarboxylic acid

Example 36A methyl 3-((2R,4R)-4-amino-7-fluorochroman-2-yl)cyclohexanecarboxylate The title compound was isolated as the second eluting compound from the purification of Example 39E (19 mg, 8.0% yield). LC/MS m/z 532 (M+H)+.

Example 36B

3-[(2R,4R)-4-({[1-(2,2-difluoro-1,3-benzodioxol-5-yl)cyclopropyl]carbonyl}amino)-7-fluoro-3,4-dihydro-2H-chromen-2-yl]cyclohexanecarboxylic acid Example 36A (19 mg, 0.036 mmol) and 2 M NaOH aqueous solution (0.5 mL) in methanol (2 mL) was stirred at 35 (° C.) for 2 hours. The solvent was removed and water (1 mL) was added. The pH of the mixture was adjusted with 2 M HCl to 1-2. The precipitated white solid was collected by filtration, washed with water, and dried to yield title compound (14.5 mg, 83% yield). $^1$H NMR (501 MHz, CDCl$_3$) δ 7.16 (dt, J=8.2, 1.5 Hz, 1H), 7.12 (q, J=1.7 Hz, 1H), 7.03 (d, J=8.0 Hz, 1H), 6.92 (t, J=7.5 Hz, 1H), 6.55 (td, J=8.3, 2.6 Hz, 1H), 6.46 (ddt, J=10.1, 4.8, 2.6 Hz, 1H), 5.37-5.30 (m, 1H), 5.29-5.19 (m, 1H), 3.92 (d, J=11.4 Hz, 1H), 2.35 (s, 1H), 2.23 (dd, J=13.1, 6.2 Hz, 1H), 2.07-1.85 (m, 3H), 1.77-1.60 (m, 4H), 1.35 (dt, J=22.7, 14.4 Hz, 4H), 1.17-1.02 (m, 3H); MS (ESI+) m/z 517.9 (M+H)+.

Example 37 methyl 3-[4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoate

Example 37A methyl 3-(3-(2,6-dichloropyridin-3-yl)-3-oxopropanoyl)benzoate

The title compound was prepared using the procedure similar to that described in Example 24A, substituting 2,6-dichloronicotinoyl chloride for 3-chloroisonicotinoyl chloride.

Example 37B methyl 3-(7-chloro-4-oxo-4H-pyrano[2,3-b]pyridin-2-yl)benzoate

The title compound was prepared using the procedure similar to that described in Example 33B, substituting the product from Example 37A for the product from Example 33A.

Example 37C methyl 3-(7-methoxy-4-oxo-4H-pyrano[2,3-b]pyridin-2-yl)benzoate

A solution of KOtBu (889 mg, 7.92 mmol) in methanol (25 mL) was treated with the product from Example 37B (500 mg, 1.584 mmol) and the resulting suspension was stirred for 10 minutes at 100° C. The mixture was cooled in an ice bath and quenched all at once with 1 M HCl (20 mL). The mixture was diluted with water (80 mL) and the mixture was stirred for 5 minutes. The solid was collected by filtration, washed with water, and dried under vacuum at 60 OC for 90 minutes to provide the title compound (420 mg, 1.349 mmol, 85% yield).

Example 37D methyl 3-(7-methoxy-4-oxo-3,4-dihydro-2H-pyrano[2,3-b]pyridin-2-yl)benzoate The title compound was prepared using the procedure similar to that described in Example 33C, substituting the product from Example 37C for the product from Example 33B. $^1$H NMR (400 MHz, CDCl$_3$) δ ppm 8.20 (t, J=1.8 Hz, 1H), 8.16 (d, J=8.5 Hz, 1H), 8.07 (dt, J=7.8, 1.5 Hz, 1H), 7.71 (dt, J=7.8, 1.6 Hz, 1H), 7.52 (t, J=7.8 Hz, 1H), 6.53 (d, J=8.5 Hz, 1H), 5.64 (dd, J=13.3, 3.1 Hz, 1H), 4.00 (s, 3H), 3.94 (s, 3H), 3.09 (dd, J=17.0, 13.3 Hz, 1H), 2.87 (dd, J=16.9, 3.1 Hz, 1H); MS (ESI) m/z 314 (M+H)+.

Example 37E methyl 3-(7-methoxy-4-(methoxyimino)-3,4-dihydro-2H-pyrano[2,3-b]pyridin-2-yl)benzoate The title compound was prepared using the procedure similar to that described in Example 33D, substituting the product from Example 37D for the product from Example 33C, provided the title compound. $^1$H NMR (400 MHz, CDCl$_3$) δ ppm 8.19-8.11 (m, 2H), 8.03 (dt, J=7.8, 1.4 Hz, 1H), 7.70 (dt, J=7.7, 1.4 Hz, 1H), 7.48 (t, J=7.7 Hz, 1H), 6.47 (d, J=8.5 Hz, 1H), 5.26 (dd, J=12.4, 3.1 Hz, 1H), 3.95 (s, 3H), 3.94 (s, 3H), 3.93 (s, 3H), 3.47 (dd, J=17.2, 3.2 Hz, 1H), 2.69 (dd, J=17.1, 12.3 Hz, 1H); MS (ESI) m/z 343 (M+H)+.

Example 37F methyl 3-(4-amino-7-methoxy-3,4-dihydro-2H-pyrano[2,3-b]pyridin-2-yl)benzoate The title compound was prepared using the procedure similar to that described in Example 33E, substituting the product from Example 37E for the product from Example 33D. MS (ESI) m/z 315 (M+H)+.

Example 37G methyl 3-[4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoate The title compound was prepared using the procedure similar to that described in Example 24I, substituting the product from Example 37F for the product from Example 24H. The crude product was chromatographed on silica gel eluting with 30% ethyl acetate in heptanes to provide the title compound as mixture of cis and trans isomers. $^1$H NMR (400 MHz, CDCl$_3$) δ 8.10-8.05 (m, 1H), 8.04-7.97 (m, 1H), 7.64-7.58 (m, 1H), 7.50-7.38 (m, 1.5H), 7.37-7.32 (m, 0.5H), 7.17-6.97 (m, 3H), 6.43-6.38 (m, 1H), 5.50 (d, J=6.8 Hz, 0.5H), 5.47-5.38 (m, 0.5H), 5.32 (d, J=10.7 Hz, 0.5H), 5.26 (d, J=8.8 Hz, 0.5H), 5.03-4.93 (m, 1H), 3.94 (s, 1.5H), 3.92 (s, 1.5H), 3.88 (s, 3H), 2.48 (dd, J=12.8, 5.4 Hz, 0.5H), 2.29 (d, J=14.4 Hz, 0.5H), 2.19 (ddd, J=14.8, 11.6, 4.4 Hz, 0.5H), 1.93-1.79 (m, 0.5H), 1.77-1.57 (m, 2H), 1.13-1.05 (m, 2H).

Example 38

3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid A mixture of Example 39E (90 mg, 0.171 mmol) and 2 M NaOH aqueous solution (2 mL) in methanol (6 mL) was stirred at 35° C. for 4 hours, solvent was removed and water (1 mL) added. The mixture was adjusted with 2 M HCl to pH 1-2 and the precipitated white solid was washed with water and dried to provide the title compound (64 mg, 73.1% yield). $^1$H NMR (400 MHz, CDCl$_3$) δ 8.19 (s, 1H), 8.07 (d, J=7.8 Hz, 1H), 7.64 (d, J=7.9 Hz, 1H), 7.48 (t, J=7.7 Hz, 1H), 7.18-7.07 (m, 2H), 7.02 (dt, J=8.5, 3.4 Hz, 2H), 6.71-6.52 (m, 2H), 5.61-5.44 (m, 1H), 5.40 (d, J=8.9 Hz, 1H), 5.35-5.22 (m, 1H), 2.58 (dd, J=13.2, 6.3 Hz, 1H), 1.79 (dd, J=12.6, 4.9 Hz, 2H), 1.71-1.61 (m, 1H), 1.10 (q, J=2.2 Hz, 2H); MS (ESI+) m/z 511.9 (M+H)$^+$.

Example 39 methyl 3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoate Example 39A 7-fluoro-4H-chromen-4-one A mixture of 1-(4-fluoro-2-hydroxyphenyl)ethanone (1. g, 6.49 mmol) and 1,1-dimethoxy-N,N-dimethylmethanamine (0.948 mL, 7.14 mmol) was heated at 120° C. for 2 hours, and cooled down. The precipitated orange solid was filtered, washed with heptane, and dried to yield (E)-3-(dimethylamino)-1-(4-fluoro-2-hydroxyphenyl)prop-2-en-1-one which was dissolved in dichloromethane (120 mL) and treated with concentrated HCl (15 mL). The mixture was refluxed for 2 hours. Water layer was removed and organic layer was washed with brine (50 mL×2). The organics was concentrated and the residue was purified by chromatography on 80 g silica gel cartridge, eluting with 5-30% ethyl acetate in heptane to provide the title compound (760 mg, 71.4% yield) as white solid. $^1$H NMR (400 MHz, CDCl$_3$) δ 8.23 (dd, J=9.6, 6.2 Hz, 1H), 7.83 (d, J=6.0 Hz, 1H), 7.19-7.08 (m, 2H), 6.33 (d, J=6.1 Hz, 1H); MS (ESI+) m/z 165 (M+H)$^+$.

Example 39B (R)-methyl 3-(7-fluoro-4-oxochroman-2-yl)benzoate

A mixture of bis(2,2,2-trifluoroacetoxy)palladium (136 mg, 0.408 mmol), (S)-4-(tert-butyl)-2-(pyridin-2-yl)-4,5-dihydrooxazole (100 mg, 0.490 mmol), ammonium hexafluorophosphate(V) (399 mg, 2.449 mmol), (3-(methoxycarbonyl)phenyl)boronic acid (1102 mg, 6.12 mmol) and dichloroethane (10 mL) in a vial (20 mL) were stirred for 5 minutes, and then Example 39A (670 mg, 4.08 mmol) and water (0.256 mL, 14.19 mmol) were added. The vial was capped and the mixture stirred at 60° C. overnight. The mixture was filtered through a plug of celite and eluted with ethyl acetate. The organic layers were removed in vacuo and the crude material was chromatographed on a 80 g silica gel cartridge, eluting with ethyl acetate in heptane at 5-40% gradient to provide the title compound (767 mg, 62.6% yield). LC/MS m/z 300 (M+H)$^+$.

Example 39C (R)-methyl 3-(7-fluoro-4-(methoxyimino)chroman-2-yl)benzoate

The mixture of Example 39B (760 mg, 2.53 mmol), sodium acetate (415 mg, 5.06 mmol) and O-methylhydroxylamine, hydrochloric acid (423 mg, 5.06 mmol) in methanol (10 mL) was stirred at 60° C. overnight. Solvent was removed under pressure and the residue dissolved in ethyl acetate and washed with water, the organic layers dried over MgSO$_4$, filtered, and concentrated under pressure. The residue was purified by chromatography on a 80 g silica gel cartridge, eluting with ethyl acetate in heptane at 5-35% gradient to provide the title compound (752 mg, 90% yield) as white solid. $^1$H NMR (400 MHz, CDCl$_3$) δ 8.13 (t, J=1.8 Hz, 1H), 8.04 (dt, J=7.9, 1.5 Hz, 1H), 7.92 (dd, J=8.7, 6.5 Hz, 1H), 7.66 (dt, J=7.8, 1.5 Hz, 1H), 7.50 (t, J=7.7 Hz, 1H), 6.77-6.62 (m, 2H), 5.13 (dd, J=12.4, 3.1 Hz, 1H), 3.98 (s, 3H), 3.94 (s, 3H), 3.49 (dd, J=17.2, 3.1 Hz, 1H), 2.66 (dd, J=17.2, 12.4 Hz, 1H); MS (ESI+) m/z 330 (M+H)$^+$.

Example 39D methyl 3-((2R,4R)-4-amino-7-fluorochroman-2-yl)benzoate

To Example 39C (300 mg, 0.911 mmol) in acetic acid (10 mL) was added 5% platinum on carbon (355 mg, 0.091 mmol). The mixture was charged with a hydrogen balloon and stirred at ambient temperature for 48 hours, LC/MS indicated ⅔ starting material converted to product, but reduced benzoic acid ring was detected. The mixture was purged with nitrogen, diluted with ethyl acetate and filtered through a plug of celite. The filtrate was concentrated under reduced pressure and the residue dissolved in tert-butyl methyl ether, followed by drop wise addition of 4 M HCl (1 mL). The precipitated white solid was collected by filtration and dried to provide the title compound (153 mg, 49.6% yield), which contained about 12% methyl 3-((2R,4R)-4-amino-7-fluorochroman-2-yl)cyclohexanecarboxylate.

Example 39E methyl 3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoate A mixture of 1-(2,2-difluorobenzo[d][1,3]dioxol-5-yl)cyclopropanecarboxylic acid (108 mg, 0.444 mmol) and HATU (1-[bis(dimethylamino)methylene]-1H-1,2,3-triazolo[4,5-b]pyridinium 3-oxid hexafluorophosphate) (220 mg, 0.577 mmol) in DMF (3 mL) was stirred for 5 minutes, followed by addition of Example 39D (150 mg, 0.48 mmol), followed by addition of N-ethyl-N-isopropylpropan-2-amine (0.31 mL, 1.78 mmol). The mixture was stirred at ambient temperature for 2 hours; LC/MS indicated the reaction was complete. Ethyl acetate (20 mL) and water (10 mL) were added. The mixture was partitioned. The organic layer was washed with saturated NaHCO$_3$ aqueous solution and brine sequentially, dried over MgSO$_4$, filtered, and concentrated. The residue was purified by chromatography on a 40 g silica gel cartridge, eluting with ethyl acetate in heptane at 0-30% gradient to provide the title compound as the first eluting compound (140 mg, 60.0% yield) and Example 36A as the second eluting compound. $^1$H NMR (400 MHz, CDCl$_3$) δ 8.13-7.91 (m, 2H), 7.57 (dt, J=7.8, 1.5 Hz, 1H), 7.45 (t, J=7.7 Hz, 1H), 7.14-6.99 (m, 4H), 6.69-6.58 (m, 2H), 5.44 (td, J=10.1, 6.4 Hz, 1H), 5.33 (d, J=8.9 Hz, 1H), 5.23 (dd, J=11.5, 1.9 Hz, 1H), 3.93 (s, 3H), 3.48 (q, J=7.0 Hz, 1H), 2.50 (ddd, J=13.4, 6.0, 2.0 Hz, 1H), 1.77-1.60 (m, 2H), 1.10-1.06 (m, 2H); MS (ESI+) m/z 525.9 (M+H); The $^1$HNMR and Analytical Chiral SFC (5-30% methanol:CO$_2$, 10 minutes at 3 mL/minutes 150 bar, Column ChiralCel OJ-H) indicated the isolated product was a cis-stereoisomer with 94% ee purity.

Example 40 rac-N-[(2R,4R)-2-cyclopropyl-7-methoxy-3,4-di-hydro-2H-chromen-4-yl]-1-(2,2-difluoro-1,3-benzo-dioxol-5-yl)cyclopropanecarboxamide Example 40A 3-cyclopropyl-1-(2-hydroxy-4-methoxyphenyl)prop-2-en-1-one To a solution of 1 M NaOH (300 mL) was added 1-(2-hydroxy-4-methoxyphenyl)ethanone (5 g, 30.1 mmol), followed by addition of cyclopropanecarbaldehyde (6.33 g, 90 mmol). The mixture was stirred over 48 hours at ambient temperature. The mixture was adjusted to pH 5 by 1 M HCl, extracted with ethyl acetate (100 mL×3), dried over Na$_2$SO$_4$, filtered, and concentrated. The residue was purified by silica gel column chromatography, eluted with a gradient of 15-50% petroleum ether:ethyl acetate to provide the title compound (1.5 g, 22.84%) as white oil. MS (ESI+) m/z 219 (M+H)$^+$.

Example 40B 2-cyclopropyl-7-methoxychroman-4-one

To a solution of Example 40A (2 g, 9.16 mmol) in 200 mL of ethanol and 10 mL of water was added concentrated HCl (21 mL). The reaction was refluxed for 16 hours. Ethanol was removed under reduced pressure and 50 mL of water was added. The mixture was extracted with ethyl acetate (50 mL×2). The combined organic layers were dried over Na$_2$SO$_4$, filtered, and concentrated. The residue was purified by silica gel column chromatography, eluted with a gradient of 10-15% petroleum ether:ethyl acetate to provide the title compound (1.4 g, 70.0%) as white solid. $^1$H NMR (400 MHz, CDCl$_3$) δ 7.80 (s, J=8.8 Hz, 1H), 6.56 (dd, J=9.2 Hz, 2.4 Hz, 1H), 6.45 (d, J=2.4 Hz, 1H), 3.83 (s, 3H), 3.69-3.75 (m, 1H), 2.70-2.83 (m, 2H), 1.20-1.26 (m, 1H), 0.71-0.74 (m, 2H), 0.66-0.69 (m, 1H), 0.62-0.64 (m, 1H); MS (ESI+) m/z 219 (M+H)$^+$.

Example 40C 2-cyclopropyl-7-methoxychroman-4-one oxime

To a solution of Example 40B (940 mg, 4.31 mmol) in methanol (20 mL) was added sodium acetate (424 mg, 5.17 mmol) and hydroxylamine hydrochloride (359 mg, 5.17 mmol). The mixture was stirred at 40° C. for 16 hours. The solvent was removed under reduced pressure. The resulting white solid was collected by filtration, washed with water (30 mL), and dried under reduced pressure to provide the title compound (980 mg, 86%) as white solid. MS (ESI+) m/z 234 (M+H)$^+$.

Example 40D 2-cyclopropyl-7-methoxychroman-4-amine

A solution of Example 40C (500 mg, 2.144 mmol) in ammonia-methanol solution (50 mL) was treated with nickel (126 mg, 2.144 mmol). The mixture was stirred at room temperature under hydrogen for 5 hours. The mixture was filtered and concentrated to dryness. To the residue was added 1 M hydrogen chloride in ether and then the organics were concentrated to afford the hydrochloride acid salt of the title compound (480 mg, 1.761 mmol, 82% yield). $^1$HNMR (400 MHz, CD$_3$OD) δ: 7.25-7.29 (m, 1H), 6.43-6.46 (m, 1H), 4.48-4.63 (m, 1H), 3.76 (d, J=2.4 Hz, 3H), 3.42-3.53 (m, 1H), 1.88-2.56 (m, 2H), 1.10-1.16 (m, 1H), 0.38-0.71 (m, 4H); MS (ESI+) m/z 203 (M-NH$_2$)$^+$.

Example 40E rac-N-[(2R,4R)-2-cyclopropyl-7-methoxy-3,4-di-hydro-2H-chromen-4-yl]-1-(2,2-difluoro-1,3-benzo-dioxol-5-yl)cyclopropanecarboxamide To 1-(2,2-difluorobenzo[d][1,3]dioxol-5-yl)cyclopropanecarboxylic acid (142 mg, 0.587 mmol) in dichloromethane (1.5 mL) was added half of a solution of oxalyl dichloride (0.205 mL, 2.346 mmol) in dichloromethane (1 mL), followed by 1 drop of DMF. The reaction bubbled vigorously, then the remainder of the oxalyl chloride solution was added dropwise. The reaction was stirred for 30 minutes at room temperature, then the solvent removed under a stream of nitrogen, then chased with 2×1 mL of dichloromethane, drying under a stream of nitrogen. The intermediate was taken up in dichloromethane (1.5 mL) and added to a mixture of the product from Example 40D (150 mg, 0.587 mmol) and triethylamine (0.327 mL, 2.346 mmol) in dichloromethane (1.5 mL). The mixture was stirred at room temperature for 20 minutes. The mixture was quenched with saturated aqueous bicarbonate, and the aqueous layer removed. The organic phase was concentrated and the resulting oil dissolved in dichloromethane and purified on a 24 g silica gel cartridge, eluting with a gradient of 5-60% ethyl acetate/heptanes in 20 minutes to provide 110 mg of a mixture of diastereomers. The mixture was further purified via preparative supercritical fluid chromatography set to maintain a backpressure at 100 bar using a Lux Cellulose® (21×250 mm, 5 micron), with the sample at a concentration of 25 mg/mL in methanol using 16% methanol in CO$_2$ at a flow rate of 70 mL/minute to provide the title compound (retention time=4.4 minutes, 24 mg, 0.054 mmol, 9.23% yield) and Example 41 (retention time=3.7 minutes). $^1$H NMR (400 MHz, DMSO-d$_6$) δ 7.38-7.32 (m, 2H), 7.29 (d, J=8.4 Hz, 1H), 7.16 (dd, J=8.4, 1.7 Hz, 1H), 6.96 (d, J=8.5 Hz, 1H), 6.43 (dd, J=8.5, 2.5 Hz, 1H), 6.33 (d, J=2.5 Hz, 1H), 4.93 (dt, J=8.3, 4.4 Hz, 1H), 3.67 (s, 3H), 3.37 (td, J=9.2, 2.6 Hz, 1H), 1.89 (dt, J=14.0, 3.3 Hz, 1H), 1.81 (ddd, J=14.0, 9.6, 5.0 Hz, 1H), 1.41-1.31 (m, 2H), 1.08-0.97 (m, 3H), 0.60-0.46 (m, 2H), 0.36-0.28 (m, 1H), 0.14 (dt, J=9.5, 4.6 Hz, 1H); MS (ESI+) m/z 444 (M+H)$^+$.

Example 41 rac-N-[(2R,4S)-2-cyclopropyl-7-methoxy-3,4-dihydro-2H-chromen-4-yl]-1-(2,2-difluoro-3-benzodioxol-5-yl)cyclopropanecarboxamide The title compound (retention time=3.7 minutes, 21 mg, 0.047 mmol, 8.07% yield) was isolated from the preparative supercritical fluid chromatography as described in Example 40E. $^1$H NMR (400 MHz, DMSO-$d_6$) δ 7.38-7.32 (m, 2H), 7.29 (d, J=8.4 Hz, 1H), 7.16 (dd, J=8.4, 1.7 Hz, 1H), 6.96 (d, J=8.5 Hz, 1H), 6.43 (dd, J=8.5, 2.5 Hz, 1H), 6.33 (d, J=2.5 Hz, 1H), 4.93 (dt, J=8.3, 4.4 Hz, 1H), 3.67 (s, 3H), 3.37 (td, J=9.2, 2.6 Hz, 1H), 1.89 (dt, J=14.0, 3.3 Hz, 1H), 1.81 (ddd, J=14.0, 9.6, 5.0 Hz, 1H), 1.41-1.31 (m, 2H), 1.08-0.97 (m, 3H), 0.60-0.46 (m, 2H), 0.36-0.28 (m, 1H), 0.14 (dt, J=9.5, 4.6 Hz, 1H); MS (ESI+) m/z 444 (M+H)$^+$.

Example 42

4-({[1-(2,2-difluoro-1,3-benzodioxol-5-yl)cyclopropyl]carbonyl}amino)-3,4-dihydro-2H-chromene-7-carboxylic acid To a suspension of the product from Example 45 (25 mg, 0.058 mmol) in tetrahydrofuran (193 µL) and water (97 µL) was added lithium hydroxide (2.8 mg, 0.117 mmol). The reaction mixture was stirred at room temperature overnight. The solvent was removed under a stream of nitrogen and the reaction was quenched with 10 drops of 1N HCl. This crude material was chromatographed directly on a 4 g silica gel cartridge, eluting with a gradient of 5-100% ethyl acetate/heptane to provide the title compound (10 mg, 0.024 mmol, 41.3% yield) as a white solid. $^1$H NMR (400 MHz, DMSO-$d_6$) δ 7.45-7.37 (m, 3H), 7.31 (d, J=8.3 Hz, 1H), 7.23-7.18 (m, 2H), 7.12 (d, J=8.1 Hz, 1H), 5.11 (q, J=7.9 Hz, 1H), 4.24-4.10 (m, 2H), 2.02-1.85 (m, 2H), 1.48 (ddd, J=9.8, 6.0, 2.9 Hz, 1H), 1.37 (ddd, J=8.6, 5.9, 2.9 Hz, 1H), 1.05 (dtdd, J=12.6, 9.3, 6.2, 3.3 Hz, 2H). MS (ESI+) m/z 418 (M+H)$^+$.

Example 43

3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid

Example 43A ethyl 3-(3-((2R,4R)-4-(1-(2,2-difluorobenzo[d][1,3]dioxol-5-yl)cyclopropanecarboxamido)-7-methylchroman-2-yl)benzamido)-1-methylcyclopentanecarboxylate In a 4 mL vial, 300 µL of a stock solution containing the product from Example 16 (0.13 M, 0.039 mmol, 1.0 eq) and diisopropylethylamine (0.39 M, 0.12 mmol, 3.0 equivalents) in dimethyl acetamide was added to a stock solution containing 2-(3H-[1,2,3]triazolo[4,5-b]pyridin-3-yl)-1,1,3,3-tetramethylisouronium hexafluorophosphate(V) (0.15 M in dimethyl acetamide, 300 µL, 0.046 mmol, 1.2 equivalents). A stock solution of ethyl 3-amino-1-methylcyclopentanecarboxylate (0.40 M in dimethyl acetamide, 145 µL, 0.058 mmol, 1.5 equivalents) was added and the reaction was stirred at room temperature until complete as determined by LC. The vial was loaded directly into a Gilson GX-271 autosampler and purified using preparative LC method TFA8 to provide the title compound.

Example 43B 3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid Example 43A was dissolved in methanol (1 mL). A stock solution of potassium hydroxide (4.0 M in water, 100 µL) was added and the reaction was heated at 50° C. for 30 minutes, after which the reaction was deemed complete by LC. Solvent was removed under a stream of nitrogen and the residue was reconstituted in acetonitrile (600 µL) and 4 M HCl in dioxane (400 µL). The vial was loaded directly into a Gilson GX-271 autosampler and purified using preparative LC method TFA6 to provide the title compound (15.7 mg, 66% yield). $^1$H NMR (400 MHz, 90° C., DMSO-$d_6$:D$_2$O=9:1 (v/v)) δ 7.88-7.79 (m, 1H), 7.76 (dt, J=7.7, 1.5 Hz, 1H), 7.55 (dt, J=7.6, 1.4 Hz, 1H), 7.46 (t, J=7.7 Hz, 1H), 7.32 (d, J=1.6 Hz, 1H), 7.27-7.15 (m, 2H), 6.95-6.86 (m, 2H), 6.71 (dd, J=7.7, 1.7 Hz, 1H), 6.65-6.61 (m, 2H), 5.38-5.18 (m, 2H), 4.33 (p, J=7.7 Hz, 1H), 2.50-2.44 (m, 1H), 2.26-2.12 (m, 4H), 2.11-1.97 (m, 3H), 1.76-1.61 (m, 2H), 1.55-1.45 (m, 2H), 1.42-1.36 (m, 1H), 1.30 (s, 3H), 1.12-1.00 (m, 2H); MS (APCI+) m/z 633.5 (M+H)$^+$.

Example 44

(2R,4R)-4-({[1-(2,2-difluoro-1,3-benzodioxol-5-yl)cyclopropyl]carbonyl}amino)-2-(3-methoxyphenyl)-3,4-dihydro-2H-chromene-6-carboxylic acid The title compound was prepared using the conditions similar to that described in Example 1, substituting Example 47E for Example 6. $^1$H NMR (400 MHz, CDCl$_3$) δ 8.00-7.84 (m, 2H), 7.29 (t, J=7.9 Hz, 1H), 7.21 (d, J=8.3 Hz, 1H), 7.14 (s, 1H), 7.03 (d, J=8.2 Hz, 1H), 6.98-6.81 (m, 4H), 5.50 (q, J=8.9 Hz, 1H), 5.40 (d, J=8.9 Hz, 1H), 5.26 (d, J=11.1 Hz, 1H), 3.81 (s, 3H), 2.61-2.46 (m, 1H), 1.92-1.74 (m, 2H), 1.63 (d, J=6.3 Hz, 1H), 1.16-1.07 (m, 2H), MS (ESI+) m/z 524 (M+H)$^+$.

Example 45 methyl 4-({[1-(2,2-difluoro-1,3-benzodioxol-5-yl)cyclopropyl]carbonyl}amino)-3,4-dihydro-2H-chromene-7-carboxylate A 50 mL pressure bottle was charged with the product from Example 56 (40 mg, 0.088 mmol), Pd-dppf (Heraeus) (1.294 mg, 1.769 µmol), DMF (2 mL), methanol (2 mL), and triethylamine (0.025 mL, 0.177 mmol). The reaction was degassed with argon several times followed by carbon monoxide. The mixture was heated at 100° C. for 16 hours at 70 psi carbon monoxide. To the reaction mixture were added DMF (2 mL) and fresh catalyst, degassed with argon and carbon monoxide was repeated, and the mixture was heated for 16 hours at 100° C. at 70 psi carbon monoxide. Solvent was removed under reduced pressure to give brown oil. The residue was quenched with water to get a brown solid. The aqueous layer was removed and the resulting solid dissolved in dichloromethane and chromatographed on a 12 g silica gel cartridge, eluting with a gradient of 5-100% ethyl acetate/heptanes over 20 minutes to provide the title compound (32 mg, 0.074 mmol, 84% yield) as white solid. $^1$H NMR (501 MHz, DMSO-d$_6$) δ 7.47-7.38 (m, 3H), 7.31 (d, J=8.3 Hz, 1H), 7.25-7.19 (m, 2H), 7.16 (dd, J=8.0, 1.0 Hz, 1H), 5.12 (td, J=8.6, 6.0 Hz, 1H), 4.22 (ddd, J=11.2, 5.1, 3.7 Hz, 1H), 4.16 (ddd, J=11.5, 9.5, 2.9 Hz, 1H), 3.80 (s, 3H), 2.03-1.86 (m, 2H), 1.48 (ddd, J=9.9, 6.1, 3.1 Hz, 1H), 1.37 (ddd, J=9.2, 6.2, 3.2 Hz, 1H), 1.05 (dtdd, J=12.8, 9.4, 6.4, 3.4 Hz, 2H); MS (ESI+) m/z 432 (M+H)$^+$.

Example 46 methyl (2R,4R)-4-({[1-(2,2-difluoro-1,3-benzodioxol-5-yl)cyclopropyl]carbonyl}amino)-2-(3-methoxycyclohexyl)-3,4-dihydro-2H-chromene-6-carboxylate Example 46A (2R,4R)-methyl 4-amino-2-(3-methoxycyclohexyl)chroman-6-carboxylate The title compound was obtained from Example 47D as a by-product from the reduction.

Example 46B methyl (2R,4R)-4-({[1-(2,2-difluoro-1,3-benzodioxol-5-yl)cyclopropyl]carbonyl}amino)-2-(3-methoxycyclohexyl)-3,4-dihydro-2H-chromene-6-carboxylate The title compound was obtained according to the preparation of Example 47E, substituting Example 46A for Example 47D (17 mg, 0.031 mmol, 21.78% yield). $^1$H NMR (501 MHz, CDCl$_3$) δ 7.79 (dd, J=8.4, 2.2 Hz, 1H), 7.73 (dd, J=2.1, 1.1 Hz, 1H), 7.22 (dt, J=8.3, 1.3 Hz, 1H), 7.18 (d, J=1.7 Hz, 1H), 7.04 (d, J=8.2 Hz, 1H), 6.78 (dd, J=8.6, 1.7 Hz, 1H), 5.35 (d, J=8.9 Hz, 1H), 5.28 (td, J=10.2, 9.0, 5.9 Hz, 1H), 4.03 (dddd, J=15.8, 11.7, 5.2, 1.6 Hz, 1H), 3.90 (s, 3H), 3.36 (d, J=3.6 Hz, 3H), 3.15 (tq, J=11.0, 4.4 Hz, 1H), 2.30-2.26 (m, 1H), 2.11-2.05 (m, 1H), 1.83 (dddd, J=30.6, 10.1, 6.9, 3.5 Hz, 3H), 1.72-1.61 (m, 3H), 1.30-1.23 (m, 2H), 1.16-1.02 (m, 5H); MS (ESI+) m/z 544 (M+H)$^+$.

Example 47 methyl (2R,4R)-4-({[1-(2,2-difluoro-1,3-benzodioxol-5-yl)cyclopropyl]carbonyl}amino)-2-(3-methoxyphenyl)-3,4-dihydro-2H-chromene-6-carboxylate Example 47A (R)-6-bromo-2-(3-methoxyphenyl)chroman-4-one A 20 mL vial was charged with bis(2,2,2-trifluoroacetoxy)palladium (0.295 g, 0.889 mmol), (S)-4-(tert-butyl)-2-(pyridin-2-yl)-4,5-dihydrooxazole (0.218 g, 1.066 mmol), ammonium hexafluorophosphate(V) (0.869 g, 5.33 mmol) and (3-methoxyphenyl)boronic acid (2.70 g, 17.77 mmol) were stirred in dichloroethane (5 mL) for 5 minutes, and a pale yellow color was observed. To this suspension was added 6-bromo-4H-chromen-4-one (CAS 51483-92-2) (2.0 g, 8.89 mmol) and water (0.256 mL, 14.19 mmol) and the sides of the vial washed with more dichloroethane (5 mL). The vial was capped and the mixture stirred at 60° C. for 16 hours. The mixture was filtered through a plug of silica gel and celite and eluted with ethyl acetate to give a light yellow color solution. The solvent was removed under reduced pressure and the crude material was chromatographed on a 40 g silica gel cartridge, eluting with a gradient of 5-50% ethyl acetate/heptanes to provide the title compound (2.10 g, 6.30 mmol, 70.9% yield). $^1$H NMR (400 MHz, CDCl$_3$) δ 8.04 (d, J=2.6 Hz, 1H), 7.58 (dd, J=8.9, 2.6 Hz, 1H), 7.35 (t, J=8.0 Hz, 1H), 7.08-6.87 (m, 4H), 5.45 (dd, J=13.1, 3.1 Hz, 1H), 3.84 (s, 3H), 3.07 (dd, J=17.0, 13.1 Hz, 1H), 2.91 (dd, J=17.0, 3.1 Hz, 1H).

Example 47B (R)-methyl 2-(3-methoxyphenyl)-4-oxochroman-6-carboxylate

A 250 mL stainless steel pressure bottle was charged with Example 47A (2.0 g, 6.00 mmol), Pd-dppf (Heraeus) (0.088 g, 0.120 mmol), methanol (20 mL) and triethylamine (1.673 mL, 12.01 mmol). The reactor was degassed with argon several times followed by carbon monoxide and the reaction heated to 100° C. for 16 hours at 60 psi carbon monoxide. To the reaction mixture were added DMF (2 mL) and fresh catalyst, degassed with argon and carbon monoxide was repeated, and the mixture was heated for 16 hours at 100° C. at 60 psi carbon monoxide. The reaction was filtered and the solvent removed under reduced pressure. The crude product was purified on a 40 g silica gel cartridge, eluting with 5-30% heptane in ethyl acetate over 40 minutes to provide the title compound (450 mg, 1.441 mmol, 24.00% yield). $^1$H NMR (400 MHz, CDCl$_3$) δ 8.63 (d, J=2.2 Hz, 1H), 8.18 (dd, J=8.7, 2.3 Hz, 1H), 7.36 (dd, J=8.7, 7.2 Hz, 1H), 7.11 (d, J=8.7 Hz, 1H), 7.08-7.00 (m, 2H), 6.97-6.89 (m, 1H), 5.52 (dd, J=13.1, 3.0 Hz, 1H), 3.92 (s, 3H), 3.85 (s, 3H), 3.11 (dd, J=16.9, 13.0 Hz, 1H), 2.95 (dd, J=17.0, 3.1 Hz, 1H); MS (ESI+) m/z 313 (M+H)$^+$.

Example 47C (R)-methyl 4-(methoxyimino)-2-(3-methoxyphenyl)chroman-6-carboxylate A mixture of Example 47B (450 mg, 1.441 mmol), sodium acetate (236 mg, 2.88 mmol) and O-methylhydroxylamine hydrochloric acid salt (120 mg, 1.441 mmol) in methanol (10 mL) was stirred at 60° C. for 16 hours. The solvent was evaporated under reduced pressure and the residue dissolved in ethyl acetate, and washed with water. The organics were dried over magnesium sulfate, filtered, and concentrated. The crude material was purified by preparative LC method AA2 to provide the title compound (204 mg, 0.598 mmol, 41.5% yield). $^1$H NMR (400 MHz, CDCl$_3$) δ 8.63 (d, J=2.2 Hz, 1H), 7.95 (dd, J=8.6, 2.2 Hz, 1H), 7.33 (t, J=7.9 Hz, 1H), 7.06-6.97 (m, 3H), 6.94-6.85 (m, 1H), 5.09 (dd, J=12.3, 3.1 Hz, 1H), 4.01 (s, 3H), 3.91 (s, 3H), 3.83 (s, 3H), 3.54-3.46 (m, 1H), 2.70 (dd, J=17.2, 12.3 Hz, 1H); MS (ESI+) m/z 342 (M+H)$^+$.

Example 47D (2R,4R)-methyl 4-amino-2-(3-methoxyphenyl)chroman-6-carboxylate

To the mixture of Example 47C (204 mg, 0.598 mmol) in acetic acid (3 mL) was added platinum (IV) oxide (13.57 mg, 0.060 mmol). The mixture was purged with hydrogen and stirred at ambient temperature for 18 hours. The solvent was evaporated under reduced pressure and the residue dissolved in ethyl acetate, and then washed with water. The organics were dried over magnesium sulfate, filtered, and concentrated. The crude material was purified by preparative LC method AA2 to provide the title compound (105 mg, 0.335 mmol, 56.1% yield) as white solid, LC/MS m/z 297 (M-NH$_2$)+; and Example 46A (42 mg, 0.131 mmol, 22.00% yield). LC/MS m/z 303 (M-NH$_2$)$^+$.

Example 47E methyl (2R,4R)-4-({[1-(2,2-difluoro-1,3-benzodi-oxol-5-yl)cyclopropyl]carbonyl}amino)-2-(3-methoxyphenyl)-3,4-dihydro-2H-chromene-6-carboxylate To 1-(2,2-difluorobenzo[d][1,3]dioxol-5-yl)cyclopropanecarboxylic acid (34.8 mg, 0.144 mmol) in DMF (3 mL) was added HATU (1-[bis(dimethylamino)methylene]-1H-1,2,3-triazolo[4,5-b]pyridinium 3-oxid hexafluorophosphate) (82 mg, 0.215 mmol). The mixture was stirred for 5 minutes, and then Example 47D (45 mg, 0.144 mmol) was added, followed by addition of N-ethyl-N-isopropylpropan-2-amine (0.100 mL, 0.574 mmol). The mixture was stirred at ambient temperature for 2 hours. The reaction was purified on a 12 g silica gel cartridge and eluted with a gradient of 5-100% ethyl acetate/heptanes over 20 minutes to prodide the title compound (45 mg, 0.084 mmol, 58.3% yield). $^1$H NMR (400 MHz, CDCl$_3$) δ 7.91-7.75 (m, 2H), 7.29 (d, J=7.8 Hz, 1H), 7.18 (dd, J=8.1, 1.7 Hz, 1H), 7.13 (d, J=1.7 Hz, 1H), 7.02 (d, J=8.2 Hz, 1H), 6.97-6.83 (m, 4H), 5.46 (td, J=10.1, 6.0 Hz, 1H), 5.36 (d, J=8.9 Hz, 1H), 5.23 (dd, J=11.5, 2.0 Hz, 1H), 3.92 (s, 3H), 3.80 (s, 3H), 2.52 (ddd, J=13.3, 5.9, 2.1 Hz, 1H), 1.89-1.75 (m, 2H), 1.67-1.59 (m, 1H), 1.10 (dtd, J=9.5, 6.5, 3.2 Hz, 2H); MS (ESI+) m/z 537.9 (M+H)$^+$.

Example 48

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide Example 48A 3-((2R,4R)-4-(1-(2,2-difluorobenzo[d][1,3]dioxol-5-yl)cyclopropanecarboxamido)-7-methylchroman-2-yl)-N—(((R)-2,2-dimethyl-1,3-dioxolan-4-yl)methyl)benzamide In a 4 mL vial, 300 μL of a stock solution containing the product from Example 16 (0.13 M, 0.039 mmol, 1.0 equivalent) and diisopropylethylamine (0.39 M, 0.12 mmol, 3.0 equivalents) in dimethyl acetamide was added to a stock solution containing 2-(3H-[1,2,3]triazolo[4,5-b]pyridin-3-yl)-1,1,3,3-tetramethylisouronium hexafluorophosphate(V) (0.15 M in dimethyl acetamide, 300 μL, 0.046 mmol, 1.2 equivalents). A stock solution of (R)-(2,2-dimethyl-1,3-dioxolan-4-yl)methanamine (0.40 M in dimethyl acetamide, 145 μL, 0.058 mmol, 1.5 equivalents) was added and the reaction was stirred at room temperature until complete as determined by LC. The material was loaded directly into a Gilson GX-271 autosampler and purified using preparative LC method TFA8 to provide the title compound.

Example 48B

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide Example 48A was dissolved in acetonitrile (3 mL). Trifluoroacetic acid (100 μL) was added and the reaction immediately deemed complete by LC. The material was loaded directly into a Gilson GX-271 autosampler and purified using preparative LC method TFA8 to yield the title compound (25.3 mg, 94% yield). $^1$H NMR (400 MHz, 90° C., DMSO-d$_6$:D$_2$O=9:1 (v/v)) δ 7.87 (t, J=1.7 Hz, 1H), 7.78 (dt, J=7.7, 1.5 Hz, 1H), 7.61-7.52 (m, 1H), 7.47 (t, J=7.7 Hz, 1H), 7.31 (d, J=1.6 Hz, 1H), 7.27-7.15 (m, 2H), 6.92 (d, J=7.7 Hz, 1H), 6.71 (dd, J=7.7, 1.7 Hz, 1H), 6.68-6.60 (m, 1H), 5.37-5.19 (m, 2H), 3.77-3.63 (m, 1H), 3.51-3.37 (m, 3H), 3.33-3.28 (m, 1H), 2.25-2.16 (m, 4H), 2.13-2.03 (m, 1H), 1.53-1.46 (m, 1H), 1.43-1.36 (m, 1H), 1.15-0.97 (m, 2H); MS (APCI+) m/z 581.5 (M+H)$^+$.

Example 49

1-(2,2-difluoro-1,3-benzodioxol-5-yl)-N-[(2R,4R)-2-(3-{[(3R)-3-hydroxypyrrolidin-1-yl]carbonyl}phenyl)-7-methyl-3,4-dihydro-2H-chromen-4-yl]cyclopropanecarboxamide In a 4 mL vial, 300 μL of a stock solution containing the product from Example 16 (0.13 M, 0.039 mmol, 1.0 equivalent) and diisopropylethylamine (0.39 M, 0.12 mmol, 3.0 equivalents) in dimethyl acetamide was added to a stock solution containing 2-(3H-[1,2,3]triazolo[4,5-b]pyridin-3-yl)-1,1,3,3-tetramethylisouronium hexafluorophosphate (V) (0.15 M in dimethyl acetamide, 300 μL, 0.046 mmol, 1.2 equivalents). A stock solution of (R)-pyrrolidin-3-ol (0.40 M in dimethyl acetamide, 145 μL, 0.058 mmol, 1.5 equivalents) was added and the reaction was stirred at room temperature until complete as determined by LC. The material was loaded directly into a Gilson GX-271 autosampler and purified using preparative LC AA8 to yield the title compound (21.7 mg, 97% yield). $^1$H NMR (400 MHz, 90° C., DMSO-d$_6$:D$_2$O=9:1 (v/v)) δ 7.56-7.40 (m, 4H), 7.31 (d, J=1.6 Hz, 1H), 7.27-7.15 (m, 2H), 6.91 (d, J=8.0 Hz, 1H), 6.71 (dd, J=7.7, 1.7 Hz, 1H), 6.63 (d, J=1.6 Hz, 1H), 5.36-5.19 (m, 2H), 4.30 (s, 1H), 3.67-3.37 (m, 2H), 2.24-2.14 (m, 4H), 2.12-2.03 (m, 1H), 1.96 (dp, J=13.0, 5.3, 4.7 Hz, 1H), 1.83 (tt, J=9.2, 3.9 Hz, 1H), 1.54-1.46 (m, 1H), 1.43-1.36 (m, 1H), 1.11-0.98 (m, 2H); MS (APCI+) m/z 577.4 (M+H)$^+$.

Example 50

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-(3,3,3-trifluoro-2-hydroxypropyl)benzamide Example 50 was prepared according to the procedure for the preparation of Example 49, substituting 3-amino-1,1,1-trifluoropropan-2-ol for (R)-pyrrolidin-3-ol (23.1 mg, 97% yield). $^1$H NMR (400 MHz, 90° C., DMSO-d$_6$:D$_2$O=9:1 (v/v)) δ 7.90 (t, J=1.8 Hz, 1H), 7.88-7.76 (m, 1H), 7.60 (d, J=7.7 Hz, 1H), 7.51 (t, J=7.7 Hz, 1H), 7.34 (d, J=1.6 Hz, 1H), 7.30-7.18 (m, 2H), 6.94 (d, J=7.7 Hz, 1H), 6.79-6.71 (m, 1H), 6.66 (s, 1H), 5.39-5.22 (m, 2H), 4.25 (pd, J=7.5, 4.6

Hz, 1H), 3.67 (dd, J=13.9, 4.7 Hz, 1H), 3.44 (dd, J=14.0, 7.6 Hz, 1H), 2.25 (s, 4H), 2.15-2.05 (m, 1H), 1.57-1.49 (m, 1H), 1.45-1.37 (m, 1H), 1.17-1.00 (m, 2H); MS (APCI+) m/z 619.4 (M+H)+.

Example 51

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-(2-hydroxy-2-methylpropyl)benzamide Example 51 was prepared according to the procedure for the preparation of Example 49, substituting 1-amino-2-methylpropan-2-ol for (R)-pyrrolidin-3-ol (19.1 mg, 86% yield). $^1$H NMR (400 MHz, 90° C., DMSO-d$_6$:D$_2$O=9:1 (v/v)) δ 7.90 (t, J=1.8 Hz, 1H), 7.81 (dt, J=7.6, 1.6 Hz, 1H), 7.62-7.56 (m, 1H), 7.50 (t, J=7.7 Hz, 1H), 7.34 (d, J=1.5 Hz, 1H), 7.29-7.20 (m, 2H), 6.94 (d, J=7.8 Hz, 1H), 6.74 (dd, J=7.6, 1.7 Hz, 1H), 6.66 (d, J=1.7 Hz, 1H), 5.39-5.22 (m, 2H), 3.32 (s, 2H), 2.29-2.19 (m, 4H), 2.16-2.05 (m, 1H), 1.56-1.49 (m, 1H), 1.46-1.38 (m, 1H), 1.17 (s, 6H), 1.12-1.01 (m, 2H); MS (APCI+) m/z 579.5 (M+H)+.

Example 52

1-(2,2-difluoro-1,3-benzodioxol-5-yl)-N-[(2R,4R)-2-(3-{[3-(hydroxymethyl)piperidin-1-yl]carbonyl}phenyl)-7-methyl-3,4-dihydro-2H-chromen-4-yl]cyclopropanecarboxamide Example 52 was prepared according to the procedure for the preparation of Example 49, substituting piperidin-3-ylmethanol for (R)-pyrrolidin-3-ol (23.0 mg, 99% yield). $^1$H NMR (400 MHz, 90° C., DMSO-d$_6$:D$_2$O=9:1 (v/v)) δ 7.55-7.39 (m, 3H), 7.38-7.17 (m, 4H), 6.94 (d, J=7.9 Hz, 1H), 6.78-6.70 (m, 1H), 6.70-6.61 (m, 1H), 5.38-5.20 (m, 2H), 4.22-3.71 (m, 2H), 3.40-3.32 (m, 1H), 3.03-2.91 (m, 1H), 2.78 (dd, J=13.0, 10.1 Hz, 1H), 2.28-2.15 (m, 4H), 2.15-2.01 (m, 2H), 1.84-1.74 (m, 1H), 1.74-1.59 (m, 2H), 1.56-1.48 (m, 1H), 1.48-1.36 (m, 2H), 1.36-1.22 (m, 1H), 1.17-1.00 (m, 2H); MS (APCI+) m/z 605.5 (M+H)+.

Example 53

1-(2,2-difluoro-1,3-benzodioxol-5-yl)-N-[(2R,4R)-2-(3-{[2-(hydroxymethyl)morpholin-4-yl]carbonyl}phenyl)-7-methyl-3,4-dihydro-2H-chromen-4-yl]cyclopropanecarboxamide Example 53 was prepared according to the procedure for the preparation of Example 49, substituting morpholin-2-ylmethanol for (R)-pyrrolidin-3-ol (16.5 mg, 70% yield). $^1$H NMR (400 MHz, 90° C., DMSO-d$_6$:D$_2$O=9:1 (v/v)) δ 7.55-7.44 (m, 4H), 7.38 (dt, J=7.1, 1.8 Hz, 1H), 7.34 (d, J=1.6 Hz, 1H), 7.29-7.20 (m, 2H), 6.94 (d, J=7.7 Hz, 1H), 6.76-6.70 (m, 1H), 6.66 (s, 1H), 5.36-5.23 (m, 2H), 4.11-3.92 (m, 1H), 3.92-3.75 (m, 2H), 3.58-3.35 (m, 4H), 3.19-3.05 (m, 1H), 2.94-2.84 (m, 1H), 2.27-2.15 (m, 4H), 2.13-2.05 (m, 1H), 1.56-1.49 (m, 1H), 1.46-1.39 (m, 1H), 1.15-1.02 (m, 2H); MS (APCI+) m/z 607.5 (M+H)+.

Example 54

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(1-hydroxycyclobutyl)methyl]benzamide Example 54 was prepared according to the procedure for the preparation of Example 49, substituting 1-(aminomethyl)cyclobutanol for (R)-pyrrolidin-3-ol (21.7 mg, 95% yield). $^1$H NMR (400 MHz, 90° C., DMSO-d$_6$:D$_2$O=9:1 (v/v)) δ 7.90 (t, J=1.7 Hz, 1H), 7.81 (dt, J=7.7, 1.5 Hz, 1H), 7.59 (dt, J=7.8, 1.5 Hz, 1H), 7.50 (t, J=7.7 Hz, 1H), 7.34 (d, J=1.5 Hz, 1H), 7.29-7.17 (m, 2H), 6.94 (d, J=7.9 Hz, 1H), 6.74 (dd, J=7.9, 1.8 Hz, 1H), 6.66 (d, J=1.6 Hz, 1H), 5.39-5.22 (m, 2H), 3.48 (s, 2H), 2.29-2.18 (m, 4H), 2.16-2.05 (m, 3H), 2.01-1.92 (m, 2H), 1.78-1.65 (m, 1H), 1.62-1.46 (m, 2H), 1.46-1.37 (m, 1H), 1.14-1.02 (m, 2H); MS (APCI+) m/z 591.5 (M+H)+.

Example 55

1-(2,2-difluoro-1,3-benzodioxol-5-yl)-N-[(2R,4R)-2-(3-{[3-(hydroxymethyl)-3-methylazetidin-1-yl]carbonyl}phenyl)-7-methyl-3,4-dihydro-2H-chromen-4-yl]cyclopropanecarboxamide Example 54 was prepared according to the procedure for the preparation of Example 49, substituting (3-methylazetidin-3-yl)methanol for (R)-pyrrolidin-3-ol, and purified by preparative LC method AA7 (22.6 mg, 99% yield). $^1$H NMR (400 MHz, 90° C., DMSO-d$_6$:D$_2$O=9:1 (v/v)) δ 7.70-7.65 (m, 1H), 7.57 (ddt, J=11.8, 7.9, 1.6 Hz, 2H), 7.48 (t, J=7.6 Hz, 1H), 7.33 (d, J=1.6 Hz, 1H), 7.28-7.19 (m, 2H), 6.94 (d, J=7.9 Hz, 1H), 6.73 (dd, J=7.9, 1.7 Hz, 1H), 6.68-6.64 (m, 1H), 5.36-5.24 (m, 2H), 4.08-3.93 (m, 2H), 3.85-3.66 (m, 2H), 3.43 (s, 2H), 2.29-2.16 (m, 4H), 2.16-2.05 (m, 1H), 1.56-1.48 (m, 1H), 1.46-1.38 (m, 1H), 1.24 (s, 3H), 1.16-1.00 (m, 2H); MS (APCI+) m/z 591.5 (M+H)+.

Example 56

N-(7-bromo-3,4-dihydro-2H-chromen-4-yl)-1-(2,2-difluoro-1,3-benzodioxol-5-yl)cyclopropanecarboxamide Example 56A 7-bromochroman-4-one oxime 7-bromochroman-4-one (CAS 18442-22-3, 0.523 g, 2.303 mmol) was treated with hydroxylamine hydrochloride (0.192 g, 2.76 mmol) and sodium acetate (0.227 g, 2.76 mmol) in ethanol (5 mL). The reaction was stirred at 30° C. for 16 hours, then at 100° C. for 100 hours. The solvent was removed under a stream of nitrogen and the crude material was triturated with water, filtered, washed with water, and dried to provide the title compound (0.429 g, 1.772 mmol, 77% yield) as a white solid. $^1$H NMR (400 MHz, DMSO-d$_6$) δ 11.36 (s, 1H), 7.70 (d, J=8.1 Hz, 1H), 7.17-7.09 (m, 2H), 4.20 (t, J=6.2 Hz, 2H), 2.83 (t, J=6.2 Hz, 2H).

Example 56B 7-bromochroman-4-amine

A solution of the product from Example 56A (360 mg, 1.487 mmol) in tetrahydrofuran (20 mL) was added to Ra—Ni 2800, water slurry (194 mg, 1.487 mmol) in a 50 mL pressure bottle. The mixture was shaken for 32 hours at 30 psi hydrogen and at room temperature. The reaction was filtered and the solvent removed to provide the title compound. $^1$H NMR (400 MHz, DMSO-d$_6$) δ 7.33 (d, J=8.2 Hz, 1H), 7.03 (dd, J=8.3, 2.1 Hz, 1H), 6.93 (d, J=2.2 Hz, 1H), 4.25 (ddd, J=11.2, 8.3, 2.9 Hz, 1H), 4.16 (ddd, J=10.8, 6.8, 3.4 Hz, 1H), 3.89 (d, J=5.7 Hz, 1H), 2.00 (dq, J=9.1, 4.3 Hz, 1H), 1.75 (dtd, J=13.4, 6.4, 3.0 Hz, 1H).

Example 56C

N-(7-bromo-3,4-dihydro-2H-chromen-4-yl)-1-(2,2-difluoro-1,3-benzodioxol-5-yl)cyclopropanecarboxamide To 1-(2,2-difluorobenzo[d][1,3]dioxol-5-yl)cyclopropanecarboxylic acid (80 mg, 0.330 mmol) in DMF (826 µL) was added HATU (1-[bis(dimethylamino)methylene]-1H-1,2,3-triazolo[4,5-b]pyridinium 3-oxid hexafluorophosphate) (163 mg, 0.429 mmol). The mixture was stirred for 5 minutes, and then the product from Example 56B (75 mg, 0.330 mmol) was added, followed by dropwise addition of triethylamine (184 µL, 1.321 mmol). After 45 minutes the mixture was quenched with water, the aqueous layer removed, the resulting oil was dissolved in dichloromethane and purified on a 12 g silica gel cartridge, eluting with a gradient of 5-100% ethyl acetate/heptanes to provide the title compound (120 mg, 0.265 mmol, 80% yield) as a white solid. $^1$H NMR (501 MHz, DMSO-$d_6$) δ 7.39 (d, J=1.7 Hz, 1H), 7.36 (d, J=8.5 Hz, 1H), 7.31 (d, J=8.3 Hz, 1H), 7.19 (dd, J=8.3, 1.8 Hz, 1H), 7.01 (dd, J=8.3, 2.0 Hz, 1H), 6.96 (dd, J=8.2, 0.9 Hz, 1H), 6.91 (d, J=1.9 Hz, 1H), 5.01 (td, J=8.2, 6.0 Hz, 1H), 4.20-4.09 (m, 2H), 1.97-1.84 (m, 2H), 1.48-1.42 (m, 1H), 1.36 (ddd, J=8.7, 5.9, 3.0 Hz, 1H), 1.04 (dtdd, J=12.7, 9.4, 6.3, 3.2 Hz, 2H); MS (ESI−) m/z 450 (M−H)$^-$.

Example 57 rac-1-(2,2-difluoro-1,3-benzodioxol-5-yl)-N-[(2R,4R)-7-methoxy-2-(pyridin-3-yl)-3,4-dihydro-2H-chromen-4-yl]cyclopropanecarboxamide The title compound was isolated from the preparative supercritical fluid chromatography with a retention time of 5.1 minutes as described in Example 22E. $^1$H NMR (400 MHz, DMSO-$d_6$) δ 8.63 (d, J=2.3 Hz, 1H), 8.55 (dd, J=4.7, 1.6 Hz, 1H), 7.80 (dt, J=8.1, 1.9 Hz, 1H), 7.43 (dd, J=7.9, 4.8 Hz, 1H), 7.40 (d, J=1.7 Hz, 1H), 7.32 (d, J=8.3 Hz, 1H), 7.21 (dd, J=8.3, 1.8 Hz, 1H), 7.17 (d, J=8.9 Hz, 1H), 6.96 (d, J=8.3 Hz, 1H), 6.53 (dd, J=8.6, 2.6 Hz, 1H), 6.40 (d, J=2.5 Hz, 1H), 5.41-5.29 (m, 2H), 3.69 (s, 3H), 2.18-2.03 (m, 2H), 1.53-1.45 (m, 1H), 1.42-1.35 (m, 1H), 1.11-1.02 (m, 2H); MS (ESI+) m/z 481 (M+H)$^+$.

Example 58

1-(2,2-difluoro-1,3-benzodioxol-5-yl)-N-{(2R)-2-[3-(hydroxymethyl)phenyl]-3,4-dihydro-2H-chromen-4-yl}cyclopropanecarboxamide To a solution of methyl 3-((2R)-4-(1-(2,2-difluorobenzo[d][1,3]dioxol-5-yl)cyclopropanecarboxamido)chroman-2-yl)benzoate (25 mg, 0.049 mmol) as a mixture of disatereomers from Example 8D in tetrahydrofuran (164 µL) and methanol (82 µL) was added sodium tetrahydroborate (1.864 mg, 0.049 mmol). The reaction was stirred at room temperature. After 30 minutes more sodium tetrahydroborate (1.864 mg, 0.049 mmol) was added. After 2 hours, added more sodium borohydride about every 8 hours for 48 hours. The reaction was quenched with 2 mL of aqueous ammonium acetate, then extracted with methyl-tert-butyl ether and purified on a 12 g silica gel cartridge, eluting with a gradient of 5-100% ethyl acetate/heptanes to provide the title compound (20 mg, 0.042 mmol, 85% yield) as a 6:4 ratio of diastereomer mixture. $^1$H NMR (500 MHz, CDCl$_3$) δ 7.42-7.36 (m, 2H), 7.36-7.29 (m, 2H), 7.23-7.05 (m, 5H), 7.01 (dd, J=8.2, 5.6 Hz, 1H), 6.95-6.87 (m, 2H), 5.63 (d, J=7.0 Hz, 0.6H), 5.52-5.45 (m, 0.4H), 5.39 (d, J=8.9 Hz, 0.4H), 5.19 (dd, J=11.4, 1.9 Hz, 0.4H), 5.05 (ddd, J=7.3, 4.4, 2.9 Hz, 0.6H), 4.81 (dd, J=11.0, 2.4 Hz, 0.6H), 4.75-4.69 (m, 2H), 2.50 (ddd, J=13.2, 6.0, 2.0 Hz, 0.4H), 2.30 (dt, J=14.3, 2.8 Hz, 0.6H), 2.21 (ddd, J=14.2, 11.0, 4.7 Hz, 0.6H), 1.72-1.64 (m, 2.4H), 1.12-1.03 (m, 2H); MS (ESI+) m/z 480 (M+H)$^+$.

Example 59

1-(2,2-difluoro-1,3-benzodioxol-5-yl)-N-(7-methoxy-3,4-dihydro-2H-chromen-4-yl)cyclopropanecarboxamide To a solution of 1-(2,2-difluorobenzo[d][1,3]dioxol-5-yl)cyclopropanecarboxylic acid (40 mg, 0.165 mmol) in DMF (413 µL) was added HATU (1-[bis(dimethylamino)methylene]-1H-1,2,3-triazolo[4,5-b]pyridinium 3-oxid hexafluorophosphate) (82 mg, 0.215 mmol). The mixture was stirred for 5 minutes, and then 7-methoxychroman-4-amine, sulfuric acid salt (45.8 mg, 0.165 mmol) was added, followed by dropwise addition of triethylamine (92 µL, 0.661 mmol). After 45 minutes the mixture was quenched with saturated aqueous bicarbonate, and the aqueous layer removed. The resulting oil was triturated with water to give a pink goo, which was dissolved in dichloromethane and purified on a 12 g silica gel cartridge, eluted with a gradient of 5-50% ethyl acetate/heptanes to provide the title compound (61 mg, 0.151 mmol, 92% yield) as a white solid. $^1$H NMR (400 MHz, DMSO-$d_6$) δ 7.39 (d, J=1.7 Hz, 1H), 7.31 (d, J=8.4 Hz, 1H), 7.26 (d, J=8.4 Hz, 1H), 7.20 (dd, J=8.3, 1.8 Hz, 1H), 6.92 (d, J=8.5 Hz, 1H), 6.44 (dd, J=8.5, 2.6 Hz, 1H), 6.27 (d, J=2.5 Hz, 1H), 4.98 (q, J=7.2 Hz, 1H), 4.18-4.04 (m, 2H), 3.66 (s, 3H), 1.94-1.83 (m, 2H), 1.45 (ddd, J=9.6, 5.8, 2.7 Hz, 1H), 1.36 (ddd, J=8.6, 5.6, 2.8 Hz, 1H), 1.11-0.97 (m, 2H); MS (ESI+) m/z 404 (M+H)$^+$.

Example 60

1-(2,2-difluoro-1,3-benzodioxol-5-yl)-N-(7-methoxy-2-phenyl-3,4-dihydro-2H-chromen-4-yl)cyclopropanecarboxamide In a 4 mL vial, 300 µL of a stock solution containing 1-(2,2-difluorobenzo[d][1,3]dioxol-5-yl)cyclopropanecarboxylic acid (0.25 M, 0.073 mmol, 1.0 equivalent) and diisopropylethylamine (0.74 M, 0.22 mmol, 3.0 equivalents) in dimethyl acetamide was added to a stock solution containing 2-(3H-[1,2,3]triazolo[4,5-b]pyridin-3-yl)-1,1,3,3-tetramethylisouronium hexafluorophosphate(V) (0.30 M in dimethyl acetamide, 300 µL, 0.089 mmol, 1.2 equivalents). A stock solution of 7-methoxy-2-phenyl-chroman-4-ylamine hydrochloride (0.40 M in dimethyl acetamide, 278 µL, 0.111 mmol, 1.5 equivalents) was added and the reaction was stirred at 50° C. until complete as determined by LC. The material was loaded directly into a Gilson GX-271 autosampler and purified using preparative LC method TFA4 to provide the title compound (27.1 mg, 76% yield). $^1$H NMR (400 MHz, DMSO-$d_6$:D$_2$O=9:1 (v/v)) δ 7.44-7.25 (m, 7H), 7.25-7.12 (m, 2H), 6.95 (dd, J=8.6, 1.1 Hz, 1H), 6.52 (dd, J=8.5, 2.6 Hz, 1H), 6.36 (d, J=2.5 Hz, 1H), 5.38-5.27 (m, 1H), 5.22 (dd, J=11.3, 2.5 Hz, 1H), 3.69 (s, 3H), 2.19-1.93 (m, 2H), 1.50 (dt, J=8.5, 3.0 Hz, 1H), 1.44-1.32 (m, 1H), 1.12-1.00 (m, 2H); MS (APCI+) m/z 480.4 (M+H)+.

Example 61

N-[2-(3,4-dichlorophenyl)-7-methoxy-3,4-dihydro-2H-chromen-4-yl]-1-(2,2-difluoro-1,3-benzodioxol-5-yl)cyclopropanecarboxamide Example 61 (33.7 mg, 83% yield) was prepared according to the procedure similar to that as described in Example 60, substituting 2-(3,4-dichloro-phenyl)-7-methoxy-chroman-4-ylamine hydrochloride for 7-methoxy-2-phenyl-chroman-4-ylamine hydrochloride. $^1$H NMR (400 MHz, DMSO-d$_6$:D$_2$O=9:1 (v/v)) δ 7.69-7.63 (m, 2H), 7.49-7.39 (m, 1H), 7.37 (d, J=1.7 Hz, 1H), 7.30 (d, J=8.4 Hz, 1H), 7.21 (dd, J=8.3, 1.7 Hz, 1H), 7.15 (d, J=8.9 Hz, 1H), 6.95 (dd, J=8.5, 1.0 Hz, 1H), 6.54 (dd, J=8.6, 2.6 Hz, 1H), 6.41 (d, J=2.5 Hz, 1H), 5.38-5.17 (m, 2H), 3.69 (s, 3H), 2.16-1.95 (m, 2H), 1.50 (dt, J=8.8, 3.2 Hz, 1H), 1.42-1.33 (m, 1H), 1.15-0.99 (m, 2H); MS (APCI+) m/z 548.3 (M+H)+.

Example 62

1-(2,2-difluoro-1,3-benzodioxol-5-yl)-N-[2-(3,4-dimethoxyphenyl)-7-methoxy-3,4-dihydro-2H-chromen-4-yl]cyclopropanecarboxamide Example 62 hydrochloride (39.4 mg, 98% yield) was prepared according to the procedure similar to that as described in Example 60, substituting 2-(3,4-dimethoxyphenyl)-7-methoxy-chroman-4-ylamine for 7-methoxy-2-phenyl-chroman-4-ylamine. $^1$H NMR (400 MHz, DMSO-d$_6$:D$_2$O=9:1 (v/v)) δ 7.38 (d, J=1.7 Hz, 1H), 7.30 (d, J=8.3 Hz, 1H), 7.22 (dd, J=8.4, 1.7 Hz, 1H), 7.15 (d, J=8.9 Hz, 1H), 7.07-6.90 (m, 4H), 6.51 (dd, J=8.6, 2.6 Hz, 1H), 6.35 (d, J=2.5 Hz, 1H), 5.36-5.22 (m, 1H), 5.19-5.04 (m, 1H), 3.77-3.75 (m, 6H), 3.68 (s, 3H), 2.20-1.95 (m, 2H), 1.57-1.46 (m, 1H), 1.46-1.32 (m, 1H), 1.21-0.98 (m, 2H); MS (APCI+) m/z 540.4 (M+H)+.

Example 63

N-[2-(4-chlorophenyl)-7-methoxy-3,4-dihydro-2H-chromen-4-yl]-1-(2,2-difluoro-1,3-benzodioxol-5-yl)cyclopropanecarboxamide Example 63 (26.5 mg, 69% yield) was prepared according to the procedure similar to that as described in Example 60, substituting 2-(4-chloro-phenyl)-7-methoxy-chroman-4-ylamine hydrochloride for 7-methoxy-2-phenyl-chroman-4-ylamine hydrochloride. $^1$H NMR (400 MHz, DMSO-d$_6$:D$_2$O=9:1 (v/v)) δ 7.56-7.39 (m, 4H), 7.37 (d, J=1.7 Hz, 1H), 7.30 (d, J=8.3 Hz, 1H), 7.25-7.13 (m, 2H), 6.94 (dd, J=8.6, 1.0 Hz, 1H), 6.53 (dd, J=8.6, 2.6 Hz, 1H), 6.37 (d, J=2.5 Hz, 1H), 5.38-5.27 (m, 1H), 5.27-5.16 (m, 1H), 3.69 (s, 3H), 2.09-1.99 (m, 2H), 1.53-1.46 (m, 1H), 1.42-1.35 (m, 1H), 1.14-1.00 (m, 2H); MS (APCI+) m/z 514.2 (M+H)+.

Example 64

1-(2,2-difluoro-1,3-benzodioxol-5-yl)-N-{2-[4-(trifluoromethyl)phenyl]-3,4-dihydro-2H-chromen-4-yl}cyclopropanecarboxamide Example 64 (34.8 mg, 91% yield) was prepared according to the procedure similar to that as described in Example 60, substituting 2-(4-trifluoromethyl-phenyl)-chroman-4-ylamine hydrochloride for 7-methoxy-2-phenyl-chroman-4-ylamine hydrochloride. $^1$H NMR (400 MHz, DMSO-d$_6$:D$_2$O=9:1 (v/v)) δ 7.78 (d, J=8.1 Hz, 2H), 7.66 (d, J=8.0 Hz, 2H), 7.38 (d, J=1.6 Hz, 1H), 7.29 (dd, J=8.5, 1.9 Hz, 2H), 7.25-7.12 (m, 2H), 7.12-7.03 (m, 1H), 6.98-6.90 (m, 1H), 6.90-6.78 (m, 1H), 5.49-5.33 (m, 2H), 2.21-2.01 (m, 2H), 1.55-1.48 (m, 1H), 1.44-1.35 (m, 1H), 1.11-1.03 (m, 2H); MS (APCI+) m/z 518.4 (M+H)+.

Example 65

N-[2-(2-chlorophenyl)-3,4-dihydro-2H-chromen-4-yl]-1-(2,2-difluoro-1,3-benzodioxol-5-yl)cyclopropanecarboxamide Example 65 (35.8 mg, 99% yield) was prepared according to the procedure similar to that as described in Example 60, substituting 2-(2-chloro-phenyl)-chroman-4-ylamine hydrochloride for 7-methoxy-2-phenyl-chroman-4-ylamine hydrochloride. The crude material was purified using preparative LC method TFA1. $^1$H NMR (400 MHz, DMSO-d$_6$:D$_2$O=9:1 (v/v)) δ 7.55 (dd, J=7.4, 1.9 Hz, 1H), 7.48-7.24 (m, 4H), 7.24-7.07 (m, 4H), 6.98-6.76 (m, 2H), 5.38 (dd, J=11.0, 2.2 Hz, 1H), 4.97 (t, J=3.8 Hz, 1H), 2.36 (d, J=14.0 Hz, 1H), 2.29-2.16 (m, 1H), 2.06-1.89 (m, 1H), 1.56-1.31 (m, 2H), 1.18-0.96 (m, 2H).

Example 66

N-[2-(3,4-dichlorophenyl)-3,4-dihydro-2H-chromen-4-yl]-1-(2,2-difluoro-1,3-benzodioxol-5-yl)cyclopropanecarboxamide Example 66 (15.2 mg, 39% yield) was prepared according to the procedure similar to that as described in Example 60, substituting 2-(3,4-dichloro-phenyl)-chroman-4-ylamine for 7-methoxy-2-phenyl-chroman-4-ylamine hydrochloride. The crude material was purified using preparative LC method TFA1. $^1$H NMR (400 MHz, DMSO-d$_6$:D$_2$O=9:1 (v/v)) δ 7.64-7.51 (m, 2H), 7.43-7.28 (m, 2H), 7.24-7.01 (m, 5H), 6.94-6.76 (m, 2H), 5.39-5.28 (m, 0.5H), 5.26-5.23 (m, 0.5H), 5.19 (dd, J=8.6, 4.0 Hz, 0.5H), 4.99-4.86 (m, 0.5H), 2.31-1.98 (m, 2H), 1.55-1.38 (m, 2H), 1.11-0.99 (m, 2H); MS (APCI+) m/z 468.3 (M+H)+.

Example 67

1-(2,2-difluoro-1,3-benzodioxol-5-yl)-N-(2-phenyl-3,4-dihydro-2H-chromen-4-yl)cyclopropanecarboxamide Example 67 (15.2 mg, 45% yield) was prepared according to the procedure similar to that as described in Example 60, substituting 2-phenyl-chroman-4-ylamine hydrochloride for 7-methoxy-2-phenyl-chroman-4-ylamine hydrochloride. The crude material was purified using preparative LC method TFA1. $^1$H NMR (400 MHz, DMSO-d$_6$:D$_2$O=9:1 (v/v)) δ 7.56-7.00 (m, 11H), 6.98-6.77 (m, 2H), 5.46-5.32 (m, 0.7H), 5.30-5.19 (m, 1H), 4.90 (t, J=3.9 Hz, 0.3H), 2.25-2.00 (m, 2H), 1.56-1.33 (m, 2H), 1.12-1.02 (m, 2H); MS (APCI+) m/z 450.4 (M+H)+.

Example 68

N-[2-(4-chlorophenyl)-3,4-dihydro-2H-chromen-4-yl]-1-(2,2-difluoro-1,3-benzodioxol-5-yl)cyclopropanecarboxamide Example 68 (27.1 mg, 75% yield) was prepared according to the procedure similar to that as described in Example 60, substituting 2-(4-chloro-phenyl)-chroman-4-ylamine hydrochloride for 7-methoxy-2-phenyl-chroman-4-ylamine hydrochloride. The crude material was purified using preparative LC method TFA1. $^1$H NMR (400 MHz, DMSO-$d_6$:$D_2O$=9:1 (v/v)) δ 7.59-7.40 (m, 4H), 7.38 (d, J=1.7 Hz, 1H), 7.34-7.25 (m, 2H), 7.22 (dd, J=8.3, 1.7 Hz, 1H), 7.19-7.10 (m, 1H), 7.10-7.00 (m, 1H), 6.93 (td, J=7.5, 1.2 Hz, 1H), 6.80 (dd, J=8.2, 1.2 Hz, 1H), 5.46-5.32 (m, 1H), 5.32-5.21 (m, 1H), 2.19-2.00 (m, 2H), 1.55-1.48 (m, 1H), 1.43-1.35 (m, 1H), 1.14-1.00 (m, 2H); MS (APCI+) m/z 484.3 (M+H)+.

Example 69

1-(2,2-difluoro-1,3-benzodioxol-5-yl)-N-[2-(3,4-dimethoxyphenyl)-3,4-dihydro-2H-chromen-4-yl]cyclopropanecarboxamide Example 69 (33.4 mg, 88% yield) was prepared according to the procedure similar to that as described in Example 60, substituting 2-(3,4-dimethoxy-phenyl)-chroman-4-ylamine for 7-methoxy-2-phenyl-chroman-4-ylamine hydrochloride. The crude material was purified using preparative LC method TFA1. $^1$H NMR (400 MHz, DMSO-$d_6$:$D_2O$=9:1 (v/v)) δ 7.31 (d, J=5.3 Hz, 1H), 7.29-7.07 (m, 3H), 7.07-6.91 (m, 3H), 6.91-6.72 (m, 3H), 5.37-5.27 (m, 0.5H), 5.14 (dd, J=11.1, 2.4 Hz, 0.5H), 5.06 (dd, J=9.3, 3.3 Hz, 0.5H), 4.94 (t, J=4.7 Hz, 0.5H), 3.82-3.72 (m, 6H), 2.26-2.07 (m, 2H), 1.59-1.32 (m, 2H), 1.14-0.98 (m, 2H); MS (APCI+) m/z 510.4 (M+H)+.

Example 70

N-[2-(3-chlorophenyl)-3,4-dihydro-2H-chromen-4-yl]-1-(2,2-difluoro-1,3-benzodioxol-5-yl)cyclopropanecarboxamide Example 70 (31.0 mg, 86% yield) was prepared according to the procedure similar to that as described in Example 60, substituting 2-(3-chloro-phenyl)-chroman-4-ylamine hydrochloride for 7-methoxy-2-phenyl-chroman-4-ylamine hydrochloride. The crude material was purified using preparative LC method TFA1. $^1$H NMR (400 MHz, DMSO-$d_6$:$D_2O$=9:1 (v/v)) δ 7.47-7.24 (m, 5H), 7.24-7.00 (m, 4H), 6.95-6.71 (m, 2H), 5.30 (dd, J=10.9, 6.1 Hz, 0.4H), 5.23 (dd, J=11.3, 2.4 Hz, 0.4H), 5.16 (dd, J=8.0, 4.5 Hz, 0.6H), 4.90 (t, J=4.9 Hz, 0.6H), 2.27-1.95 (m, 2H), 1.55-1.32 (m, 2H), 1.10-0.96 (m, 2H); MS (APCI+) m/z 484.3 (M+H)+.

Example 71

1-(2,2-difluoro-1,3-benzodioxol-5-yl)-N-[2-(4-fluorophenyl)-3,4-dihydro-2H-chromen-4-yl]cyclopropanecarboxamide Example 71 (32.8 mg, 95% yield) was prepared according to the procedure similar to that as described in Example 60, substituting 2-(4-fluoro-phenyl)-chroman-4-ylamine for 7-methoxy-2-phenyl-chroman-4-ylamine hydrochloride. The crude material was purified using preparative LC method TFA1. $^1$H NMR (400 MHz, DMSO-$d_6$:$D_2O$=9:1 (v/v)) δ 7.51-7.35 (m, 2H), 7.31 (d, J=5.8 Hz, 1H), 7.27-7.01 (m, 6H), 6.96-6.73 (m, 2H), 5.32 (dd, J=11.1, 6.2 Hz, 0.5H), 5.22 (dd, J=11.4, 2.3 Hz, 0.5H), 5.15 (t, J=6.3 Hz, 0.5H), 4.93 (t, J=4.8 Hz, 0.5H), 2.27-2.02 (m, 2H), 1.55-1.37 (m, 2H), 1.07 (dd, J=7.0, 2.9 Hz, 2H); MS (APCI+) m/z 468.3 (M+H)+.

Example 72

1-(2,2-difluoro-1,3-benzodioxol-5-yl)-N-[3-(3,4-dimethoxybenzyl)-6-methoxy-3,4-dihydro-2H-chromen-4-yl]cyclopropanecarboxamide A stock solution of 1-(2,2-difluorobenzo[d][1,3]dioxol-5-yl)cyclopropanecarboxylic acid and N,N-diisopropylethylamine (0.218 M and 0.654 M in dimethylacetamide, respectively, 284 μL, 0.061 mmol 1-(2,2-difluorobenzo[d][1,3]dioxol-5-yl)cyclopropanecarboxylic acid (1.0 equivalent) and 0.18 mmol N,N-diisopropylethylamine (3.0 equivalents)), 2-(3H-[1,2,3]triazolo[4,5-b]pyridin-3-yl)-1,1,3,3-tetramethylisouronium hexafluorophosphate(V) (0.26 M in dimethylacetamide, 284 μL, 0.074 mmol, 1.2 equivalents), and 3-(3,4-dimethoxy-benzyl)-6-methoxy-chroman-4-ylamine (Von P. Pfeiffer et al., *Justus Liebigs Annalen der Chemie* (1949), 564, 208-19) (0.40 M in dimethylacetamide, 232 μL, 0.093 mmol, 1.5 equivalents) were aspirated from their respective source vials, mixed through a PFA (perfluoroalkoxy) mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 μL min$^{-1}$ (10 minute residence time). Upon exiting the reactor, the reaction was loaded directly into an injection loop and purified using preparative LC method TFA1 to yield the title compound (10.69 mg, 49% yield). $^1$H NMR (400 MHz, DMSO-$d_6$:$D_2O$=9:1 (v/v)) δ 7.42 (d, J=8.9 Hz, 1H), 7.36 (d, J=1.6 Hz, 1H), 7.31 (d, J=8.3 Hz, 1H), 7.20 (dd, J=8.3, 1.8 Hz, 1H), 6.86 (d, J=8.1 Hz, 1H), 6.77-6.61 (m, 4H), 6.50 (d, J=2.9 Hz, 1H), 4.91-4.79 (m, 1H), 4.02-3.93 (m, 1H), 3.75 (s, 6H), 3.64 (s, 3H), 3.46 (s, 0H), 2.70-2.60 (m, 1H), 2.36-2.21 (m, 2H), 1.51-1.32 (m, 2H), 1.15-0.97 (m, 2H); MS (APCI+) m/z 554.1 (M+H)+.

Example 73

N-(3-benzyl-3,4-dihydro-2H-chromen-4-yl)-1-(2,2-difluoro-1,3-benzodioxol-5-yl)cyclopropanecarboxamide Example 73 (5.56 mg, 19% yield) was prepared according to the procedure similar to that as described in Example 72, substituting 3-benzyl-chroman-4-ylamine (Von P. Pfeiffer et al., *Justus Liebigs Annalen der Chemie* (1949), 564, 208-19) for 3-(3,4-dimethoxy-benzyl)-6-methoxy-chroman-4-ylamine. $^1$H NMR (400 MHz, DMSO-$d_6$:$D_2O$=9:1 (v/v)) δ 7.52-7.40 (m, 1H), 7.40-6.96 (m, 9H), 6.94-6.82 (m, 1H), 6.81-6.68 (m, 1H), 4.95-4.82 (m, 1H), 4.05-3.79 (m, 2H), 2.76-2.60 (m, 1H), 2.40-2.17 (m, 2H), 1.52-1.36 (m, 2H), 1.21-0.98 (m, 2H); MS (APCI+) m/z 464.2 (M+H)+.

Example 74

N-[(4R)-2,2-diethyl-3,4-dihydro-2H-chromen-4-yl]-1-(2,2-difluoro-1,3-benzodioxol-5-yl)cyclopropanecarboxamide Example 74 (2.9 mg, 11% yield) was prepared according to the procedure similar to that as described in Example 72, substituting (4R)-2,2-diethylchroman-4-amine (2S,3S)-2,3-dihydroxybutanedioic acid (WO2010045402A1) for 3-(3,4-dimethoxy-benzyl)-6-methoxy-chroman-4-ylamine. $^1$H NMR (400 MHz, DMSO-$d_6$:$D_2O$=9:1 (v/v)) δ 7.40 (d, J=1.6 Hz, 1H), 7.31 (d, J=8.3 Hz, 1H), 7.23 (dd, J=8.3, 1.8 Hz, 1H), 7.16-7.05 (m, 1H), 7.05-6.94 (m, 1H), 6.89-6.77 (m, 1H), 6.75-6.66 (m, 1H), 5.16-5.03 (m, 1H), 1.87-1.73 (m, 2H), 1.64-1.32 (m, 6H), 1.16-1.07 (m, 1H), 1.07-0.99 (m, 1H), 0.90-0.76 (m, 7H); MS (APCI+) m/z 430.2 (M+H)+.

Example 75

N-[(4R)-2,2-bis(fluoromethyl)-3,4-dihydro-2H-chromen-4-yl]-1-(2,2-difluoro-1,3-benzodioxol-5-yl)cyclopropanecarboxamide Example 75 (10.1 mg, 42% yield) was prepared according to the procedure similar to that as described in Example 72, substituting (4R)-2,2-bis(fluoromethyl)chroman-4-amine (2S,3S)-2,3-dihydroxybutanedioic acid (WO2010045402A1) for 3-(3,4-dimethoxy-benzyl)-6-methoxy-chroman-4-ylamine. $^1$H NMR (400 MHz, DMSO-$d_6$:$D_2O$=9:1 (v/v)) δ 7.41 (d, J=1.6 Hz, 1H), 7.32 (d, J=8.3 Hz, 1H), 7.24 (dd, J=8.3, 1.8 Hz, 1H), 7.20-7.10 (m, 1H), 7.08-6.98 (m, 1H), 6.93 (td, J=7.5, 1.2 Hz, 1H), 6.81 (dd, J=8.2, 1.1 Hz, 1H), 5.21-5.08 (m, 1H), 4.69-4.39 (m, 4H), 2.14-1.92 (m, 2H), 1.55-1.47 (m, 1H), 1.44-1.36 (m, 1H), 1.15-1.00 (m, 2H); MS (APCI+) m/z 438.2 (M+H)+.

Example 76

N-[(4R)-7-chloro-2,2-dimethyl-3,4-dihydro-2H-chromen-4-yl]-1-(2,2-difluoro-1,3-benzodioxol-5-yl)cyclopropanecarboxamide Example 76 (3.3 mg, 12% yield) was prepared according to the procedure similar to that as described in Example 72, substituting (4R)-7-chloro-2,2-dimethyl-chroman-4-amine (2S,3S)-2,3-dihydroxybutanedioic acid (WO2010045402A1) for 3-(3,4-dimethoxy-benzyl)-6-methoxy-chroman-4-ylamine. $^1$H NMR (400 MHz, DMSO-$d_6$:$D_2O$=9:1 (v/v)) δ 7.39 (d, J=1.7 Hz, 1H), 7.31 (d, J=8.3 Hz, 1H), 7.22 (dd, J=8.3, 1.8 Hz, 1H), 7.08-6.97 (m, 1H), 6.90 (dd, J=8.4, 2.2 Hz, 1H), 6.75 (d, J=2.1 Hz, 1H), 5.07 (t, J=9.1 Hz, 1H), 1.83 (d, J=9.1 Hz, 2H), 1.56-1.46 (m, 1H), 1.42-1.35 (m, 1H), 1.33 (s, 3H), 1.21 (s, 3H), 1.13-1.02 (m, 2H); MS (APCI+) m/z 436.1 (M+H)+.

Example 77

1-(2,2-difluoro-1,3-benzodioxol-5-yl)-N-[(4R)-8-fluoro-2,2-bis(fluoromethyl)-3,4-dihydro-2H-chromen-4-yl]cyclopropanecarboxamide Example 77 (1.4 mg, 5% yield) was prepared according to the procedure similar to that as described in Example 72, substituting (4R)-8-fluoro-2,2-bis(fluoromethyl)chroman-4-amine (2S,3S)-2,3-dihydroxybutanedioic acid (WO2010045402A1) for 3-(3,4-dimethoxy-benzyl)-6-methoxy-chroman-4-ylamine. 1H NMR (400 MHz, DMSO-$d_6$:$D_2O$=9:1 (v/v)) δ 7.41 (d, J=1.7 Hz, 1H), 7.32 (d, J=8.3 Hz, 1H), 7.27-7.19 (m, 1H), 7.17-7.04 (m, 1H), 6.98-6.80 (m, 2H), 5.23-5.12 (m, 1H), 4.74-4.43 (m, 4H), 2.19-1.96 (m, 2H), 1.56-1.46 (m, 1H), 1.46-1.35 (m, 1H), 1.21-1.03 (m, 2H); MS (APCI+) m/z 456.1 (M+H)+.

Example 78

1-(2,2-difluoro-1,3-benzodioxol-5-yl)-N-[(4R)-3,4-dihydrospiro[chromene-2,1'-cyclopentan]-4-yl]cyclopropanecarboxamide Example 78 (2.9 mg, 10% yield) was prepared according to the procedure similar to that as described in Example 72, substituting (4R)-spiro[chromane-2,1'-cyclopentane]-4-amine (2S,3S)-2,3-dihydroxybutanedioic acid (WO2010045402A1) for 3-(3,4-dimethoxy-benzyl)-6-methoxy-chroman-4-ylamine. 1H NMR (400 MHz, DMSO-$d_6$:$D_2O$=9:1 (v/v)) δ 7.39 (d, J=1.6 Hz, 1H), 7.31 (d, J=8.3 Hz, 1H), 7.28-7.17 (m, 2H), 7.15-7.05 (m, 1H), 7.05-6.95 (m, 1H), 6.90-6.78 (m, 1H), 6.66 (dd, J=8.1, 1.2 Hz, 1H), 5.11 (dd, J=11.6, 6.2 Hz, 1H), 2.06 (t, J=12.2 Hz, 1H), 1.86-1.46 (m, 10H), 1.44-1.35 (m, 1H), 1.13-1.02 (m, 2H); MS (APCI+) m/z 428.2 (M+H)+.

Example 79

1-(2,2-difluoro-1,3-benzodioxol-5-yl)-N-[(4R)-7-fluoro-2,2-bis(fluoromethyl)-3,4-dihydro-2H-chromen-4-yl]cyclopropanecarboxamide Example 79 (4.2 mg, 15% yield) was prepared according to the procedure similar to that as described in Example 72, substituting (4R)-7-fluoro-2,2-bis(fluoromethyl)chroman-4-amine hydrochloride (WO2010045402A1) for 3-(3,4-dimethoxy-benzyl)-6-methoxy-chroman-4-ylamine. $^1$H NMR (400 MHz, DMSO-$d_6$:$D_2O$=9:1 (v/v)) δ 7.41 (d, J=1.6 Hz, 1H), 7.32 (d, J=8.3 Hz, 1H), 7.24 (dd, J=8.4, 1.7 Hz, 1H), 7.12-6.99 (m, 1H), 6.78 (td, J=8.5, 2.6 Hz, 1H), 6.68 (dd, J=10.3, 2.6 Hz, 1H), 5.11 (dd, J=11.3, 6.4 Hz, 1H), 4.71-4.40 (m, 4H), 2.14-1.92 (m, 2H), 1.55-1.46 (m, 1H), 1.44-1.37 (m, 1H), 1.15-1.03 (m, 2H); MS (APCI+) m/z 456.1 (M+H)+.

Example 80

1-(2,2-difluoro-1,3-benzodioxol-5-yl)-N-[(2S,4R)-2-(fluoromethyl)-2-methyl-7-(trifluoromethyl)-3,4-dihydro-2H-chromen-4-yl]cyclopropanecarboxamide Example 80 (7.64 mg, 25% yield) was prepared according to the procedure similar to that as described in Example 72, substituting (2S,4R)-2-(fluoromethyl)-2-methyl-7-(trifluoromethyl)chroman-4-amine hydrochloride (WO2010045402A1) for 3-(3,4-dimethoxy-benzyl)-6-methoxy-chroman-4-ylamine. $^1$H NMR (400 MHz, DMSO-$d_6$:$D_2O$=9:1 (v/v)) δ 7.41 (d, J=1.6 Hz, 1H), 7.32 (d, J=8.3 Hz, 1H), 7.28-7.16 (m, 3H), 7.10-7.01 (m, 1H), 5.15 (dd, J=11.8, 6.4 Hz, 1H), 4.61-4.46 (m, 1H), 4.46-4.32 (m, 1H), 2.11 (dd, J=13.7, 6.4 Hz, 1H), 2.02-1.93 (m, 1H), 1.55-1.47 (m, 1H), 1.44-1.37 (m, 1H), 1.33 (d, J=2.0 Hz, 3H), 1.15-1.01 (m, 2H); MS (APCI+) m/z 488.1 (M+H)+.

Example 81

1-(2,2-difluoro-1,3-benzodioxol-5-yl)-N-[(2R,4R)-2-(difluoromethyl)-2-methyl-3,4-dihydro-2H-chromen-4-yl]cyclopropanecarboxamide Example 81 (10.7 mg, 40% yield) was prepared according to the procedure similar to that as described in Example 72, substituting (2R,4R)-2-difluoromethyl-2-methyl-chroman-4-ylamine hydrochloride (WO2010045402A1) for 3-(3,4-dimethoxy-benzyl)-6-methoxy-chroman-4-ylamine. $^1$H NMR (400 MHz, DMSO-d$_6$:D$_2$O=9:1 (v/v)) δ 7.41 (d, J=1.7 Hz, 1H), 7.38 (d, J=8.7 Hz, 1H), 7.32 (d, J=8.4 Hz, 1H), 7.24 (dd, J=8.3, 1.7 Hz, 1H), 7.20-7.10 (m, 1H), 7.10-6.98 (m, 1H), 6.98-6.87 (m, 1H), 6.78 (dd, J=8.2, 1.1 Hz, 1H), 6.02 (t, J=55.1 Hz, 1H), 5.26-5.12 (m, 1H), 2.11-1.96 (m, 1H), 1.82 (dd, J=12.9, 6.0 Hz, 1H), 1.56-1.48 (m, 1H), 1.46-1.37 (m, 1H), 1.31 (s, 3H), 1.17-1.00 (m, 2H); MS (APCI+) m/z 438.1 (M+H)$^+$.

Example 82

1-(2,2-difluoro-1,3-benzodioxol-5-yl)-N-[(2S,4R)-2-(difluoromethyl)-2-methyl-3,4-dihydro-2H-chromen-4-yl]cyclopropanecarboxamide Example 82 (9.4 mg, 35% yield) was prepared according to the procedure similar to that as described in Example 72, substituting (2S,4R)-2-difluoromethyl-2-methyl-chroman-4-ylamine hydrochloride (WO2010045402A1) for 3-(3,4-dimethoxy-benzyl)-6-methoxy-chroman-4-ylamine. $^1$H NMR (400 MHz, DMSO-d$_6$:D$_2$O=9:1 (v/v)) δ 7.41 (d, J=1.6 Hz, 1H), 7.32 (d, J=8.3 Hz, 1H), 7.28-7.19 (m, 2H), 7.19-7.09 (m, 1H), 7.06-6.96 (m, 1H), 6.96-6.85 (m, 1H), 6.79 (dd, J=8.1, 1.1 Hz, 1H), 6.09 (t, J=54.8 Hz, 1H), 5.16 (dt, J=12.2, 6.5 Hz, 1H), 2.14 (dd, J=14.0, 6.2 Hz, 1H), 2.07-1.91 (m, 1H), 1.54-1.46 (m, 1H), 1.44-1.36 (m, 1H), 1.32 (s, 3H), 1.14-1.00 (m, 2H); MS (APCI+) m/z 438.1 (M+H)$^+$.

Example 83

N-[(2S,4R)-7-chloro-2-(difluoromethyl)-2-methyl-3,4-dihydro-2H-chromen-4-yl]-1-(2,2-difluoro-1,3-benzodioxol-5-yl)cyclopropanecarboxamide Example 83 (9.7 mg, 33% yield) was prepared according to the procedure similar to that as described in Example 72, substituting (2S,4R)-7-chloro-2-difluoromethyl-2-methyl-chroman-4-ylamine hydrochloride (WO2010045402A1) for 3-(3,4-dimethoxy-benzyl)-6-methoxy-chroman-4-ylamine. $^1$H NMR (400 MHz, DMSO-d$_6$:D$_2$O=9:1 (v/v)) δ 7.41 (d, J=1.6 Hz, 1H), 7.32 (d, J=8.3 Hz, 1H), 7.28-7.19 (m, 2H), 7.03 (dd, J=8.3, 1.0 Hz, 1H), 6.97 (dd, J=8.3, 2.1 Hz, 1H), 6.88 (d, J=2.0 Hz, 1H), 6.12 (t, J=54.7 Hz, 1H), 5.17-5.04 (m, 1H), 2.16 (dd, J=14.1, 6.3 Hz, 1H), 2.09-1.91 (m, 1H), 1.56-1.45 (m, 1H), 1.45-1.36 (m, 1H), 1.33 (s, 3H), 1.15-1.00 (m, 2H); MS (APCI+) m/z 472.1 (M+H)$^+$.

Example 84

N-[(2R,4R)-7-chloro-2-(difluoromethyl)-2-methyl-3,4-dihydro-2H-chromen-4-yl]-1-(2,2-difluoro-1,3-benzodioxol-5-yl)cyclopropanecarboxamide Example 84 (11.2 mg, 38% yield) was prepared according to the procedure similar to that as described in Example 72, substituting (2R,4R)-7-chloro-2-difluoromethyl-2-methyl-chroman-4-ylamine hydrochloride (WO2010045402A1) for 3-(3,4-dimethoxy-benzyl)-6-methoxy-chroman-4-ylamine. $^1$H NMR (400 MHz, DMSO-d$_6$:D$_2$O=9:1 (v/v)) δ 7.41 (d, J=1.6 Hz, 1H), 7.38 (d, J=8.7 Hz, 1H), 7.32 (d, J=8.3 Hz, 1H), 7.24 (dd, J=8.3, 1.7 Hz, 1H), 7.12-7.02 (m, 1H), 6.99 (dd, J=8.3, 2.1 Hz, 1H), 6.87 (d, J=2.0 Hz, 1H), 6.04 (t, J=55.0 Hz, 1H), 5.15 (dt, J=12.4, 6.4 Hz, 1H), 2.11-1.96 (m, 1H), 1.83 (dd, J=13.0, 6.1 Hz, 1H), 1.57-1.46 (m, 1H), 1.45-1.37 (m, 1H), 1.31 (s, 3H), 1.17-1.00 (m, 2H); MS (APCI+) m/z 472.1 (M+H)$^+$.

Example 85

1-(2,2-difluoro-1,3-benzodioxol-5-yl)-N-[(2S,4R)-2-methyl-2-(trifluoromethyl)-3,4-dihydro-2H-chromen-4-yl]cyclopropanecarboxamide Example 85 (9.1 mg, 32% yield) was prepared according to the procedure similar to that as described in Example 72, substituting (2S,4R)-2-methyl-2-trifluoromethyl-chroman-4-ylamine hydrochloride (WO2010045402A1) for 3-(3,4-dimethoxy-benzyl)-6-methoxy-chroman-4-ylamine. $^1$H NMR (400 MHz, DMSO-d$_6$:D$_2$O=9:1 (v/v)) δ 7.43 (d, J=1.5 Hz, 1H), 7.32 (d, J=8.3 Hz, 1H), 7.26 (dd, J=8.3, 1.7 Hz, 1H), 7.22-7.12 (m, 1H), 7.09-7.00 (m, 1H), 7.00-6.90 (m, 1H), 6.84 (dd, J=8.2, 1.1 Hz, 1H), 5.13 (dd, J=12.0, 6.2 Hz, 1H), 2.28 (dd, J=14.6, 6.1 Hz, 1H), 2.21-2.05 (m, 1H), 1.60-1.45 (m, 4H), 1.45-1.33 (m, 1H), 1.21-1.01 (m, 2H); MS (APCI+) m/z 456.1 (M+H)$^+$.

Example 86

1-(2,2-difluoro-1,3-benzodioxol-5-yl)-N-[(4R)-7-fluoro-2,2-dimethyl-3,4-dihydro-2H-chromen-4-yl]cyclopropanecarboxamide Example 86 (4.1 mg, 15% yield) was prepared according to the procedure similar to that as described in Example 72, substituting (R)-7-fluoro-2,2-dimethylchroman-4-amine (2S,3S)-2,3-dihydroxysuccinate (WO2010045402A1) for 3-(3,4-dimethoxy-benzyl)-6-methoxy-chroman-4-ylamine. $^1$H NMR (400 MHz, DMSO-d$_6$:D$_2$O=9:1 (v/v)) δ 7.39 (d, J=1.7 Hz, 1H), 7.31 (d, J=8.3 Hz, 1H), 7.22 (dd, J=8.3, 1.7 Hz, 1H), 7.09-6.97 (m, 1H), 6.69 (td, J=8.6, 2.7 Hz, 1H), 6.52 (dd, J=10.6, 2.6 Hz, 1H), 5.07 (t, J=8.8 Hz, 1H), 1.83 (d, J=9.0 Hz, 2H), 1.56-1.45 (m, 1H), 1.44-1.35 (m, 1H), 1.33 (s, 3H), 1.21 (s, 3H), 1.19-0.99 (m, 2H); MS (APCI+) m/z 420.1 (M+H)$^+$.

Example 87

N-[(4R)-7-chloro-2,2-bis(fluoromethyl)-3,4-dihydro-2H-chromen-4-yl]-1-(2,2-difluoro-1,3-benzodioxol-5-yl)cyclopropanecarboxamide Example 87 (2.7 mg, 9% yield) was prepared according to the procedure similar to that as described in Example 72, substituting (R)-7-chloro-2,2-bis-fluoromethyl-chroman-4-ylamine (2S,3S)-2,3-dihydroxy-succinic acid (WO2010045402A1) for 3-(3,4-dimethoxy-benzyl)-6-methoxy-chroman-4-ylamine. $^1$H NMR (400 MHz, DMSO-d$_6$:D$_2$O=9:1 (v/v)) δ 7.41 (d, J=1.7 Hz, 1H), 7.32 (d, J=8.3 Hz, 1H), 7.24 (dd, J=8.4, 1.7 Hz, 1H), 7.05 (d, J=8.3 Hz, 1H), 6.98 (dd, J=8.4, 2.1 Hz, 1H), 6.90 (d, J=2.0 Hz, 1H), 5.11 (dd, J=11.2, 6.4 Hz, 1H), 4.71-4.40 (m, 4H), 2.15-1.93

(m, 2H), 1.56-1.45 (m, 1H), 1.45-1.34 (m, 1H), 1.15-1.02 (m, 2H); MS (APCI+) m/z 472.1 (M+H)+.

Example 88

1-(2,2-difluoro-1,3-benzodioxol-5-yl)-N-[(4S)-6-fluoro-2,2-dimethyl-3,4-dihydro-2H-chromen-4-yl]cyclopropanecarboxamide Example 88 (1.8 mg, 7% yield) was prepared according to the procedure similar to that as described in Example 72, substituting (S)-6-fluoro-2,2-dimethyl-chroman-4-ylamine with (2R,3R)-2,3-dihydroxy-succinic acid (WO2010045402A1) for 3-(3,4-dimethoxy-benzyl)-6-methoxy-chroman-4-ylamine. $^1$H NMR (400 MHz, DMSO-$d_6$:$D_2O$=9:1 (v/v)) δ 7.41 (d, J=1.7 Hz, 1H), 7.32 (d, J=8.3 Hz, 1H), 7.23 (dd, J=8.3, 1.7 Hz, 1H), 6.94 (td, J=8.6, 3.3 Hz, 1H), 6.78-6.66 (m, 2H), 5.14-5.01 (m, 1H), 1.87-1.73 (m, 2H), 1.56-1.44 (m, 1H), 1.43-1.36 (m, 1H), 1.32 (s, 3H), 1.20 (s, 3H), 1.14-1.03 (m, 2H); MS (APCI+) m/z 420.1 (M+H)+.

Example 89

1-(2,2-difluoro-1,3-benzodioxol-5-yl)-N-[(4S)-6-fluoro-3,4-dihydrospiro[chromene-2,1'-cyclobutan]-4-yl]cyclopropanecarboxamide Example 89 (2.0 mg, 8% yield) was prepared according to the procedure similar to that as described in Example 72, substituting (S)-6-fluorospiro[chroman-2,1'-cyclobutan]-4-amine (2R,3R)-2,3-dihydroxysuccinate (WO2010045402A1) for 3-(3,4-dimethoxy-benzyl)-6-methoxy-chroman-4-ylamine. $^1$H NMR (400 MHz, DMSO-$d_6$:$D_2O$=9:1 (v/v)) δ 7.43 (d, J=1.6 Hz, 1H), 7.33 (d, J=8.3 Hz, 1H), 7.25 (dd, J=8.3, 1.7 Hz, 1H), 6.94 (td, J=8.6, 3.2 Hz, 1H), 6.75 (dd, J=9.0, 4.8 Hz, 1H), 6.71-6.63 (m, 1H), 5.07 (dd, J=11.5, 5.9 Hz, 1H), 2.30-2.19 (m, 1H), 2.16-1.96 (m, 4H), 1.94-1.62 (m, 3H), 1.56-1.45 (m, 1H), 1.44-1.37 (m, 1H), 1.15-1.05 (m, 2H); MS (APCI+) m/z 432.1 (M+H)+.

Example 90

N-[(4R)-8-chloro-7-fluoro-2,2-dimethyl-3,4-dihydro-2H-chromen-4-yl]-1-(2,2-difluoro-1,3-benzodioxol-5-yl)cyclopropanecarboxamide Example 90 (5.3 mg, 19% yield) was prepared according to the procedure similar to that as described in Example 72, substituting (R)-8-chloro-7-fluoro-2,2-dimethyl-chroman-4-ylamine (WO2010045402A1) for 3-(3,4-dimethoxy-benzyl)-6-methoxy-chroman-4-ylamine. $^1$H NMR (400 MHz, DMSO-$d_6$:$D_2O$=9:1 (v/v)) δ 7.39 (d, J=1.7 Hz, 1H), 7.31 (d, J=8.3 Hz, 1H), 7.22 (dd, J=8.3, 1.8 Hz, 1H), 7.08-6.96 (m, 1H), 6.90 (t, J=8.8 Hz, 1H), 5.10 (t, J=9.1 Hz, 1H), 1.93-1.80 (m, 2H), 1.56-1.44 (m, 1H), 1.44-1.35 (m, 4H), 1.24 (s, 3H), 1.20-1.00 (m, 2H); MS (APCI+) m/z 454.1 (M+H)+.

Example 91

1-(2,2-difluoro-1,3-benzodioxol-5-yl)-N-[3-(3,4-dimethoxybenzyl)-7-methoxy-3,4-dihydro-2H-chromen-4-yl]cyclopropanecarboxamide A stock solution of 1-(2,2-difluorobenzo[d][1,3]dioxol-5-yl)cyclopropanecarboxylic acid and N,N-diisopropylethyl-amine (0.218 M and 0.654 M in dimethylacetamide, respectively, 284 μL, 0.061 mmol 1-(2,2-difluorobenzo[d][1,3]dioxol-5-yl)cyclopropanecarboxylic acid (1.0 equivalent) and 0.18 mmol N,N-diisopropylethylamine (3.0 equivalents)), 2-(3H-[1,2,3]triazolo[4,5-b]pyridin-3-yl)-1,1,3,3-tetramethylisouronium hexafluorophosphate(V) (0.26 M in dimethylacetamide, 284 μL, 0.074 mmol, 1.2 equivalents), and 3-(3,4-dimethoxy-benzyl)-7-methoxy-chroman-4-ylamine (Von P. Pfeiffer et al., *Justus Liebigs Annalen der Chemie* (1949), 564, 208-19) (0.40 M in dimethylacetamide, 232 μL, 0.093 mmol, 1.5 equivalents) were mixed in a 4 mL vial at room temperature. The reaction was deemed complete by LC and the reaction mixture was loaded directly into an injection loop and purified using preparative LC method TFA1 to provide the title compound (9.9 mg, 29% yield). $^1$H NMR (400 MHz, DMSO-$d_6$:$D_2O$=9:1 (v/v)) δ 7.38-7.24 (m, 3H), 7.19 (dd, J=8.3, 1.7 Hz, 1H), 6.90 (d, J=8.7 Hz, 1H), 6.86 (d, J=8.2 Hz, 1H), 6.73 (d, J=2.0 Hz, 1H), 6.65 (dd, J=8.1, 2.0 Hz, 1H), 6.48 (dd, J=8.6, 2.6 Hz, 1H), 6.27 (d, J=2.5 Hz, 1H), 4.80 (t, J=8.5 Hz, 1H), 4.00 (dd, J=11.3, 2.7 Hz, 1H), 3.74 (s, 5H), 3.67 (s, 3H), 2.68-2.56 (m, 1H), 2.35-2.19 (m, 2H), 1.48-1.36 (m, 2H), 1.14-1.07 (m, 1H), 1.03-0.97 (m, 1H); MS (APCI+) m/z 554.0 (M+H)+.

Example 92 tert-butyl 4-({[1-(2,2-difluoro-1,3-benzodioxol-5-yl)cyclopropyl]carbonyl}amino)-7-fluoro-3,4-dihydro-1'H-spiro[chromene-2,4'-piperidine]-1'-carboxylate Example 92A tert-butyl 7-fluoro-4-hydroxyspiro[chroman-2,4'-piperidine]-1'-carboxylate A solution of tert-butyl 7-fluoro-4-oxospiro[chroman-2,4'-piperidine]-1'-carboxylate (CAS#936648-33-8, MFCD12912048) (500 mg, 1.491 mmol) in methanol (7 mL) was cooled to 0° C., treated with NaBH$_4$ (113 mg, 2.98 mmol) and stirred at room temperature for 10 minutes. The mixture was concentrated to about 2 mL volume and quenched with 10% acetic acid in water (10 mL). The mixture was extracted with ethyl acetate (2 times). The combined ethyl acetate layers were washed with saturated NaHCO$_3$ solution, washed with brine, dried (MgSO$_4$), filtered, concentrated, and chromatographed on silica gel eluted with a gradient of 20%-100% ethyl acetate in heptanes to provide the title compound (0.5 g, 1.482 mmol, 99% yield). $^1$H NMR (400 MHz, CDCl$_3$) δ ppm 7.38 (dd, J=8.6, 6.7 Hz, 1H), 6.65 (td, J=8.4, 2.5 Hz, 1H), 6.55 (dd, J=10.2, 2.5 Hz, 1H), 4.82 (t, J=6.7 Hz, 1H), 3.83 (bs, 2H), 3.19 (dt, J=29.3, 13.2 Hz, 2H), 2.29 (s, 1H), 2.11 (dd, J=13.7, 6.0 Hz, 1H), 1.97-1.91 (m, 1H), 1.88 (dd, J=13.8, 7.9 Hz, 1H), 1.77 (dq, J=13.7, 3.1 Hz, 1H), 1.65 (ddd, J=13.5, 11.8, 4.6 Hz, 1H), 1.56 (ddd, J=13.7, 11.9, 4.8 Hz, 1H), 1.46 (s, 9H).

Example 92B tert-butyl 4-azido-7-fluorospiro[chroman-2,4'-piperidine]-1'-carboxylate A solution of the product from Example 92A (0.5 g, 1.482 mmol) in tetrahydrofuran (8 mL) was cooled to 0° C. and treated with 1,8-diazabicyclo[5.4.0]undec-7-ene (0.447 ml, 2.96 mmol) followed by diphenylphosphoryl azide (0.544 ml, 2.52 mmol). The mixture was stirred at 0° C. for 2 hours and then at room temperature for 2 days. The mixture was partitioned between tert-butyl methyl ether (30 mL) and 1 M NaOH (10 mL). The layers were separated and the organic layer was washed with 1 M NaOH (10 mL), washed with 1% aqueous citric acid (2×20 mL), washed with brine, dried (MgSO$_4$), filtered, concentrated, and chromatographed on silica gel eluted with a gradient of 10%-33% ethyl acetate in heptanes to provide the title compound. $^1$H NMR (400 MHz, CDCl$_3$) δ ppm 7.39-7.18 (m, 2H), 6.69 (td, J=8.4, 2.6 Hz, 1H), 6.60 (dd, J=10.1, 2.6 Hz, 1H), 4.59 (t, J=6.8 Hz, 1H), 3.89 (s, 3H), 3.19 (dt, J=22.9, 12.3 Hz, 2H), 2.13 (dd, J=13.9, 6.0 Hz, 1H), 2.00 (dd, J=13.9, 7.6 Hz, 1H), 1.93 (dt, J=14.1, 2.9 Hz, 1H), 1.77 (dq, J=13.9, 3.0 Hz, 1H), 1.72-1.52 (m, 2H), 1.47 (s, 9H).

Example 92C tert-butyl 4-amino-7-fluorospiro[chroman-2,4'-piperidine]-1'-carboxylate A solution of the product from Example 92B (0.23 g, 0.635 mmol) was dissolved in tetrahydrofuran (5 mL), treated with water (0.5 mL), treated with triphenylphosphine (0.333 g, 1.269 mmol) and heated at 65° C. for 1 hour. The mixture was cooled and concentrated. The residue was dissolved in tert-butyl methyl ether (20 mL), washed with brine, dried (MgSO$_4$), filtered, concentrated, and chromatographed on silica gel eluted with a gradient of 0%-100% [3:1 ethyl acetate:ethanol] in ethyl acetate, then eluted with 75:25:2 ethyl acetate:ethanol:saturated NH$_4$OH solution to provide the title compound (0.15 g, 0.446 mmol, 70.3% yield). $^1$H NMR (400 MHz, CDCl$_3$) δ ppm 7.41 (dd, J=8.6, 6.7 Hz, 1H), 6.64 (td, J=8.4, 2.6 Hz, 1H), 6.54 (dd, J=10.2, 2.6 Hz, 1H), 4.01 (dd, J=10.9, 6.2 Hz, 1H), 3.94-3.77 (m, 2H), 3.31 (t, J=12.4 Hz, 1H), 3.07 (t, J=12.3 Hz, 1H), 2.07 (dd, J=13.4, 6.2 Hz, 1H), 1.85-1.61 (m, 6H), 1.54-1.41 (m, 10H).

Example 92D tert-butyl 4-({[1-(2,2-difluoro-1,3-benzodioxol-5-yl)cyclopropyl]carbonyl}amino)-7-fluoro-3,4-dihydro-1'H-spiro[chromene-2,4'-piperidine]-1'-carboxylate A mixture of the product from Example 92C (0.15 g, 0.446 mmol), O-(7-azabenzotriazol-1-yl)-N,N,N',N'-tetramethyluronium hexafluorophosphate (0.186 g, 0.490 mmol) and 1-(2,2-difluoro-1,3-benzodioxol-5-yl)cyclopropanecarboxylic acid (0.108 g, 0.446 mmol) in tetrahydrofuran (2 mL) was treated with triethylamine (0.124 ml, 0.892 mmol) and stirred at room temperature for 3 hours. The mixture was diluted with ethyl acetate (30 mL), washed with 5% aqueous citric acid (20 mL), washed with saturated NaHCO$_3$ solution (10 mL), washed with brine, dried (MgSO$_4$), filtered, concentrated, and chromatographed on silica gel eluted with a gradient of 50%-100% [9:1 CH$_2$Cl$_2$:ethyl acetate] in heptanes, then eluted with a gradient of 0%-100% ethyl acetate in [9:1 CH$_2$Cl$_2$:ethyl acetate] to provide the title compound (220 mg, 0.392 mmol, 88% yield). $^1$H NMR (400 MHz, CDCl$_3$) δ ppm 7.15 (dd, J=8.2, 1.8 Hz, 1H), 7.11 (d, J=1.7 Hz, 1H), 7.05-6.98 (m, 2H), 6.59 (td, J=8.3, 2.6 Hz, 1H), 6.52 (dd, J=10.1, 2.6 Hz, 1H), 5.33 (d, J=8.9 Hz, 1H), 5.27-5.15 (m, 1H), 3.84 (s, 2H), 3.26 (t, J=12.3 Hz, 1H), 3.12-2.98 (m, 1H), 2.11 (dd, J=13.4, 6.3 Hz, 1H), 1.82 (d, J=12.6 Hz, 1H), 1.77-1.48 (m, 6H), 1.46 (s, 9H), 1.16-1.04 (m, 2H); MS (ESI) m/z 559 (M–H)⁻.

Example 93

1-(2,2-difluoro-1,3-benzodioxol-5-yl)-N-(7-fluoro-3,4-dihydrospiro[chromene-2,4'-piperidin]-4-yl)cyclopropanecarboxamide A solution of the product from Example 92D (210 mg, 0.375 mmol) in trifluoroacetic acid (2 mL) was heated at 60° C. for 2 minutes, concentrated, and partitioned between tert-butyl methyl ether (30 mL) and 1 M NaOH (10 mL). The tert-butyl methyl ether layer was washed with brine, dried (MgSO$_4$), filtered, and concentrated to provide the title compound. $^1$H NMR (400 MHz, CDCl$_3$) δ ppm 7.14 (dd, J=8.2, 1.7 Hz, 1H), 7.11 (d, J=1.6 Hz, 1H), 7.04-6.98 (m, 2H), 6.58 (td, J=8.4, 2.6 Hz, 1H), 6.52 (dd, J=10.2, 2.6 Hz, 1H), 5.33 (d, J=8.8 Hz, 1H), 5.26-5.18 (m, 1H), 3.14-3.04 (m, 1H), 2.94-2.79 (m, 3H), 2.14 (dd, J=13.4, 6.3 Hz, 1H), 1.85-1.46 (m, 8H), 1.14-1.05 (m, 2H); MS (ESI) m/z 461 (M+H)⁺.

Example 94 methyl 3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoate To the product from Example 23E (60 mg, 0.115 mmol), and 2-methoxyethanol (13.08 mg, 0.172 mmol) in dichloromethane (2 mL) was added triphenylphosphine (60.1 mg, 0.229 mmol), followed by portion wise addition of di-t-butyl azodicarboxylate (52.8 mg, 0.229 mmol). The mixture was stirred at ambient temperature for 2 hours. Solvent was removed in vacuo and residue was purified on silica gel cartridge eluted with a gradient of 5-50% ethyl acetate in heptane to yield title compound (60 mg, 0.103 mmol, 90% yield). $^1$H NMR (400 MHz, CDCl$_3$) δ 8.07 (t, J=1.7 Hz, 1H), 7.99 (dt, J=7.7, 1.4 Hz, 1H), 7.61-7.52 (m, 1H), 7.44 (t, J=7.7 Hz, 1H), 7.14-7.05 (m, 2H), 7.00 (d, J=8.2 Hz, 1H), 6.95 (d, J=8.6 Hz, 1H), 6.55 (dd, J=8.7, 2.5 Hz, 1H), 6.45 (d, J=2.5 Hz, 1H), 5.41 (td, J=10.3, 9.8, 6.2 Hz, 1H), 5.31 (d, J=8.8 Hz, 1H), 5.20 (dd, J=11.2, 1.9 Hz, 1H), 4.11-4.02 (m, 2H), 3.92 (s, 3H), 3.72 (dd, J=5.6, 3.8 Hz, 2H), 3.43 (s, 3H), 2.50 (ddd, J=13.3, 6.1, 2.0 Hz, 1H), 1.85-1.70 (m, 2H), 1.65-1.59 (m, 1H), 1.06 (q, J=2.4 Hz, 2H); MS (ESI–) m/z 580 (M–H)⁻.

Example 95 methyl 3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoate The title compound was prepared using the conditions similar to that described in Example 94 substituting phenylmethanol for 2-methoxyethanol. $^1$H NMR (400 MHz, CDCl$_3$) δ 8.07 (t, J=1.7 Hz, 1H), 8.00 (dt, J=7.6, 1.4 Hz, 1H), 7.57 (dt, J=7.7, 1.5 Hz, 1H), 7.47-7.28 (m, 6H), 7.14-7.06 (m, 2H), 6.98 (dd, J=15.3, 8.4 Hz, 2H), 6.58 (dd, J=8.6, 2.5 Hz, 1H), 6.52 (d, J=2.5 Hz, 1H), 5.42 (td, J=10.3, 9.8, 6.0 Hz, 1H), 5.33 (d, J=8.8 Hz, 1H), 5.24-5.16 (m, 1H), 5.01 (s, 2H), 3.92 (s, 3H), 2.50 (ddd, J=13.4, 6.1, 2.0 Hz, 1H), 1.83-1.71 (m, 1H), 1.66-1.61 (m, 1H), 1.07 (td, J=3.6, 2.1 Hz, 2H); MS (ESI–) m/z 612 (M–H)⁻.

Example 96

3-[(2R,4R)-7-(carboxymethoxy)-4-({[1-(2,2-difluoro-1,3-benzodioxol-5-yl)cyclopropyl]carbonyl}amino)-3,4-dihydro-2H-chromen-2-yl]benzoic acid

Example 96A methyl 3-((2R,4R)-4-(1-(2,2-difluorobenzo[d][1,3]dioxol-5-yl)cyclopropanecarboxamido)-7-(2-methoxy-2-oxoethoxy)chroman-2-yl)benzoate The title compound was prepared using conditions similar to that described in Example 94, substituting methyl 2-hydroxyacetate for 2-methoxyethanol. LC/MS m/z 596 (M+H)$^+$.

Example 96B

3-[(2R,4R)-7-(carboxymethoxy)-4-({[1-(2,2-difluoro-1,3-benzodioxol-5-yl)cyclopropyl]carbonyl}amino)-3,4-dihydro-2H-chromen-2-yl]benzoic acid Example 96A (60 mg, 0.10 mmol) and lithium hydroxide (24 mg, 1.0 mmol) in methanol (2 mL) and water (0.5 mL) were stirred at ambient temperature for 1 hour and LC/MS indicated the reaction was complete. Purification of the mixture by preparative LC method TFA2 provided the title compound. $^1$H NMR (400 MHz, DMSO-d$_6$) δ 8.00 (s, 1H), 7.91 (d, J=7.7 Hz, 1H), 7.65 (d, J=7.7 Hz, 1H), 7.52 (t, J=7.7 Hz, 1H), 7.39 (d, J=1.7 Hz, 1H), 7.31 (d, J=8.3 Hz, 1H), 7.24-7.11 (m, 2H), 6.96 (d, J=8.6 Hz, 1H), 6.51 (dd, J=8.6, 2.6 Hz, 1H), 6.35 (d, J=2.5 Hz, 1H), 5.42-5.25 (m, 2H), 4.61 (s, 2H), 2.16-1.94 (m, 2H), 1.53-1.32 (m, 2H), 1.05 (d, J=3.2 Hz, 2H), MS (ESI–) m/z 566 (M–H)$^-$.

Example 97

3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid The mixture of Example 94 (50 mg, 0.086 mmol) and lithium hydroxide (12.35 mg, 0.516 mmol) in methanol (2 mL) and water (0.5 mL) was stirred at ambient temperature for 1 hour and LC/MS showed the reaction was complete. Purification of the reaction mixture by preparative LC method AA2 provided the title compound. $^1$H NMR (501 MHz, CDCl$_3$) δ 8.17 (s, 1H), 8.04 (s, 1H), 7.61 (s, 1H), 7.44 (s, 1H), 7.16-7.04 (m, 2H), 7.00 (d, J=8.2 Hz, 1H), 6.94 (d, J=8.6 Hz, 1H), 6.53 (d, J=8.6 Hz, 1H), 6.44 (s, 1H), 5.46 (s, 1H), 5.39 (d, J=8.8 Hz, 1H), 5.23 (s, 1H), 4.13-3.97 (m, 2H), 3.71 (t, J=4.7 Hz, 2H), 3.43 (s, 3H), 2.54 (s, 1H), 1.76 (d, J=9.6 Hz, 2H), 1.08 (d, J=3.3 Hz, 2H); MS (ESI–) m/z 566 (M–H)$^-$.

Example 98

3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid The mixture of Example 95 (60 mg, 0.098 mmol) and lithium hydroxide (14.05 mg, 0.587 mmol) in methanol (2 ml) and water (0.5 ml) was stirred at ambient temperature for 2 hour and LC/MS showed the reaction done. Purification of the reaction mixture by preparative LC method AA2 provided the title compound (43 mg, 73.3% yield). $^1$H NMR (400 MHz, CDCl$_3$) δ 8.15 (s, 1H), 8.01 (s, 1H), 7.55 (s, 1H), 7.45-7.30 (m, 6H), 7.09 (t, J=9.0 Hz, 2H), 7.02-6.84 (m, 2H), 6.51 (d, J=30.6 Hz, 2H), 5.41 (s, 2H), 5.16 (s, 1H), 4.97 (s, 2H), 2.52 (s, 1H), 1.75 (s, 2H), 1.26 (s, 1H), 1.07 (s, 2H); MS (ESI–) m/z 598 (M–H)$^-$.

Example 99

1-(2,2-difluoro-1,3-benzodioxol-5-yl)-N-{1'-[(2R)-2,3-dihydroxypropyl]-7-fluoro-3,4-dihydrospiro[chromene-2,4'-piperidin]-4-yl}cyclopropanecarboxamide A solution of the product from Example 93 (9.8 mg, 0.021 mmol) in methanol (0.3 mL) was treated with an excess of (S)-glycidol (20 mg), stirred at room temperature for 30 minutes and heated at 65° C. for 45 minutes. The mixture was cooled, diluted with ethyl acetate (2 mL), diluted with heptanes (2 mL), and directly chromatographed on silica gel eluted with a gradient of 0%-100% [3:1 ethyl acetate: methanol] in ethyl acetate to provide the title compound (5.6 mg, 10.48 μmol, 49.2% yield). $^1$H NMR (400 MHz, CDCl$_3$) δ ppm 7.18-7.10 (m, 2H), 7.07-6.97 (m, 2H), 6.60 (td, J=8.4, 2.5 Hz, 1H), 6.52 (dd, J=10.2, 2.4 Hz, 1H), 5.37-5.29 (m, 1H), 5.21 (q, J=8.7 Hz, 1H), 3.89-3.82 (m, 1H), 3.79-3.74 (m, 1H), 3.52 (dd, J=11.4, 4.0 Hz, 1H), 2.90-2.78 (m, 1H), 2.74-2.53 (m, 3H), 2.46 (dt, J=12.8, 3.4 Hz, 1H), 2.42-1.97 (m, 5H), 1.89 (d, J=13.9 Hz, 1H), 1.81-1.65 (m, 4H), 1.55 (dd, J=13.3, 10.5 Hz, 1H), 1.11 (dd, J=3.1, 1.6 Hz, 2H); MS (ESI) m/z 533 (M–H)$^-$.

Example 100 benzyl 4'-({[1-(2,2-difluoro-1,3-benzodioxol-5-yl)cyclopropyl]carbonyl}amino)-7'-fluoro-3',4'-dihydro-1H-spiro[azetidine-3,2'-chromene]-1-carboxylate

Example 100A benzyl 3-(2-(4-fluoro-2-hydroxyphenyl)-2-oxoethyl)-3-hydroxyazetidine-1-carboxylate A solution of diisopropylamine (1.573 mL, 11.04 mmol) in tetrahydrofuran (11 mL) was cooled to –10° C., treated dropwise with 2.5 M n-BuLi in hexanes (4.41 mL, 11.04 mmol), stirred at –10° C. for 5 minutes, treated dropwise with a solution of 4'-fluoro-2'-hydroxyacetophenone (0.81 g, 5.26 mmol) in tetrahydrofuran (5 mL), stirred between –10° C. and 0° C. for 1 hour, cooled to –60° C., treated dropwise with a solution of benzyl 3-oxoazetidine-1-carboxylate (1.402 g, 6.83 mmol) in tetrahydrofuran (5 mL) over 15 minutes, stirred between –60° C. and –50° C. for 10 minutes, treated with a 10% aqueous solution of KH$_2$PO$_4$ (50 mL) and allowed to warm to room temperature. The mixture was extracted with ethyl acetate (twice). The combined ethyl acetate layers were washed with brine, dried (MgSO$_4$), filtered, concentrated, and chromatographed on silica gel eluted with a gradient of 20%-100% ethyl acetate in heptanes to provide the title compound (1.35 g, 3.76 mmol, 71.5% yield). $^1$H NMR (400 MHz, CDCl$_3$) δ ppm 12.08 (s, 1H), 7.72 (dd, J=8.8, 6.3 Hz, 1H), 7.40-7.26 (m, 5H), 6.71-6.63 (m, 2H), 5.10 (s, 2H), 4.11 (d, J=9.5 Hz, 2H), 3.95 (d, J=9.4 Hz, 2H), 3.79 (s, 1H), 3.50 (s, 2H); MS (ESI) m/z 342 (M+H)$^+$.

Example 100B benzyl 7'-fluoro-4'-oxospiro[azetidine-3,2'-chroman]-1-carboxylate A solution of the product from Example 100A (1.25 g, 3.48 mmol) in pyridine (2.81 mL, 34.8 mmol) was cooled to 0° C., treated dropwise with trifluoroacetic anhydride (0.737 mL, 5.22 mmol) over 20 minutes, stirred at 0° C. for 30 minutes, treated dropwise with more trifluoroacetic anhydride (0.5 mL), stirred at 0° C. for 30 minutes, treated with more trifluoroacetic anhydride (0.7 mL), and stirred at room temperature for 2 hours. The mixture was diluted with ethanol (10 mL), treated with 1,8-diazabicyclo[5.4.0]undec-7-ene (6 mL), stirred at 50° C. for 5 minutes, treated with more 1,8-diazabicyclo[5.4.0]undec-7-ene (1 mL), stirred at 50° C. for 15 minutes, and stirred at room temperature overnight. Mixture was diluted with tert-butyl methyl ether (75 mL) and washed with water (25 mL), washed with 1 M HCl (2×25 mL), washed with 1 M NaOH (2×25 mL), washed with brine, dried (MgSO$_4$), filtered, concentrated, and chromatographed on silica gel eluted with a gradient of 15%-50% ethyl acetate in heptanes to provide the title compound (0.54 g, 1.582 mmol, 45.5% yield). $^1$H NMR (400 MHz, CDCl$_3$) δ ppm 7.89 (dd, J=8.8, 6.5 Hz, 1H), 7.39-7.28 (m, 5H), 6.79 (td, J=8.4, 2.4 Hz, 1H), 6.74 (dd, J=9.6, 2.3 Hz, 1H), 5.11 (s, 2H), 4.16 (d, J=9.7 Hz, 2H), 4.04 (d, J=9.7 Hz, 2H), 3.02 (s, 2H); MS (ESI) m/z 342 (M+H)$^+$.

Example 100C benzyl 7'-fluoro-4'-hydroxyspiro[azetidine-3,2'-chroman]-1-carboxylate The title compound was prepared using the procedure similar to that as described in Example 92A, substituting the product from Example 100B for tert-butyl 7-fluoro-4-oxospiro[chroman-2,4'-piperidine]-1'-carboxylate. $^1$H NMR (400 MHz, CDCl$_3$) δ ppm 7.37-7.27 (m, 6H), 6.69 (td, J=8.3, 2.5 Hz, 1H), 6.62 (dd, J=10.0, 2.6 Hz, 1H), 5.12 (s, 2H), 4.87-4.83 (m, 1H), 4.38 (d, J=9.5 Hz, 1H), 4.19 (d, J=9.5 Hz, 1H), 4.07 (d, J=9.5 Hz, 2H), 2.38 (dd, J=14.0, 4.9 Hz, 1H), 2.26 (dd, J=14.0, 4.6 Hz, 1H), 1.77 (s, 1H); MS (ESI) m/z 344 (M+H)$^+$.

Example 100D benzyl 4'-azido-7'-fluorospiro[azetidine-3,2'-chroman]-1-carboxylate The title compound was prepared using the procedure similar to that as described in Example 92B, substituting the product from Example 100C for the product from Example 92A. $^1$H NMR (400 MHz, CDCl$_3$) δ ppm 7.39-7.29 (m, 5H), 7.21 (dd, J=8.6, 6.3 Hz, 1H), 6.72 (td, J=8.3, 2.6 Hz, 1H), 6.66 (dd, J=9.9, 2.5 Hz, 1H), 5.12 (s, 2H), 4.65 (t, J=4.8 Hz, 1H), 4.35 (d, J=9.6 Hz, 1H), 4.19 (d, J=9.6 Hz, 1H), 4.09-4.04 (m, 2H), 2.38 (dd, J=14.1, 4.6 Hz, 1H), 2.28 (dd, J=14.1, 4.9 Hz, 1H); MS (ESI) m/z 369 (M+H)$^+$.

Example 100E benzyl 4'-amino-7'-fluorospiro[azetidine-3,2'-chroman]-1-carboxylate The title compound was prepared using the procedure similar to that as described in Example 92C, substituting the product from Example 100D for the product from Example 92B. $^1$H NMR (400 MHz, CDCl$_3$) δ ppm 7.79 (bs, 1H), 7.56 (bs, 1H), 7.41-7.29 (m, 6H), 6.67 (td, J=8.4, 2.6 Hz, 1H), 6.57 (dd, J=10.0, 2.6 Hz, 1H), 5.12 (s, 2H), 4.24-4.14 (m, 2H), 4.08 (d, J=9.4 Hz, 1H), 4.04 (dd, J=8.9, 5.4 Hz, 1H), 3.99 (d, J=9.3 Hz, 1H), 2.36 (dd, J=13.4, 5.3 Hz, 1H), 1.99 (dd, J=13.3, 9.0 Hz, 1H).

Example 100F benzyl 4'-({[1-(2,2-difluoro-1,3-benzodioxol-5-yl)cyclopropyl]carbonyl}amino)-7'-fluoro-3',4'-dihydro-1H-spiro[azetidine-3,2'-chromene]-1-carboxylate A mixture of the product from Example 100E (86 mg, 0.251 mmol), O-(7-azabenzotriazol-1-yl)-N,N,N',N'-tetramethyluronium hexafluorophosphate (201 mg, 0.528 mmol) and 1-(2,2-difluoro-1,3-benzodioxol-5-yl)cyclopropanecarboxylic acid (122 mg, 0.502 mmol) in tetrahydrofuran (2 mL) was treated with triethylamine (140 μL, 1.005 mmol), and stirred at room temperature for 1 hour. The mixture was diluted with ethyl acetate (30 mL), washed with 10% aqueous citric acid (10 mL), washed with saturated NaHCO$_3$ solution (10 mL), washed with brine, dried (MgSO$_4$), filtered, concentrated and chromatographed on silica gel eluting with a gradient of 50%-100% [9:1 CH$_2$Cl$_2$:ethyl acetate] in heptanes to provide the title compound (90 mg, 0.159 mmol, 63.2% yield). $^1$H NMR (400 MHz, CDCl$_3$) δ ppm 7.40-7.29 (m, 5H), 7.16-7.07 (m, 2H), 6.97 (dd, J=8.6, 6.2 Hz, 2H), 6.63 (td, J=8.4, 2.6 Hz, 1H), 6.55 (dd, J=9.8, 2.6 Hz, 1H), 5.33-5.27 (m, 1H), 5.20-5.09 (m, 3H), 4.09-3.95 (m, 4H), 2.41 (dd, J=13.5, 5.7 Hz, 1H), 1.97 (dd, J=13.5, 9.1 Hz, 1H), 1.76-1.65 (m, 2H), 1.15-1.06 (m, 2H); MS (ESI) m/z 565 (M–H)$^-$.

Example 101

1-(2,2-difluoro-1,3-benzodioxol-5-yl)-N-[7-fluoro-1'-(methylsulfonyl)-3,4-dihydrospiro[chromene-2,4'-piperidin]-4-yl]cyclopropanecarboxamide A solution of the product from Example 93 (11.1 mg, 0.024 mmol) in CH$_2$Cl$_2$ (0.3 mL) was treated with triethylamine (0.03 mL), and methanesulfonyl chloride (2 drops). The mixture was stirred at room temperature for 15 minutes and partitioned between ethyl acetate (30 mL) and 1 M HCl (10 mL). The layers were separated. The ethyl acetate layer was washed with saturated NaHCO$_3$ solution (10 mL), washed with brine, dried (MgSO$_4$), filtered, concentrated, and chromatographed on silica gel eluted with a gradient of 25%-100% ethyl acetate in heptanes to provide the title compound (11.6 mg, 0.022 mmol, 89% yield). $^1$H NMR (400 MHz, CDCl$_3$) δ ppm 7.15 (dd, J=8.2, 1.7 Hz, 1H), 7.11 (d, J=1.6 Hz, 1H), 7.06-7.00 (m, 2H), 6.62 (td, J=8.4, 2.6 Hz, 1H), 6.53 (dd, J=10.0, 2.6 Hz, 1H), 5.32 (d, J=8.7 Hz, 1H), 5.27-5.18 (m, 1H), 3.67-3.55 (m, 2H), 3.16 (dt, J=11.8, 7.4 Hz, 1H), 2.92 (td, J=12.0, 2.9 Hz, 1H), 2.81 (s, 3H), 2.12

(dd, J=13.4, 6.3 Hz, 1H), 1.98 (d, J=14.0 Hz, 1H), 1.84-1.79 (m, 2H), 1.77-1.65 (m, 3H), 1.15-1.07 (m, 2H); MS (ESI) m/z 537 (M−H)⁻.

Example 102

N-(1'-acetyl-7-fluoro-3,4-dihydrospiro[chromene-2,4'-piperidin]-4-yl)-1-(2,2-difluoro-1,3-benzodioxol-5-yl)cyclopropanecarboxamide A solution of the product from Example 93 (11.1 mg, 0.024 mmol) in pyridine (0.3 mL) was treated with acetic anhydride (2 drops) and stirred at room temperature for 30 minutes. The mixture was partitioned between tert-butyl methyl ether (30 mL) and 1 M HCl (15 mL). The layers were separated and the tert-butyl methyl ether layer was washed with 1 M NaOH (10 mL), washed with brine, dried (MgSO₄), filtered, concentrated, and chromatographed on silica gel eluted with a gradient of 25%-100% [3:1 ethyl acetate:ethanol] in ethyl acetate to provide the title compound (10 mg, 0.020 mmol, 83% yield). $^1$H NMR (500 MHz, CDCl₃) δ ppm 7.15 (dt, J=8.1, 1.8 Hz, 1H), 7.11 (s, 1H), 7.02 (dd, J=16.6, 7.1 Hz, 2H), 6.61 (td, J=8.4, 2.6 Hz, 1H), 6.53 (ddd, J=10.1, 5.2, 2.6 Hz, 1H), 5.33 (t, J=7.9 Hz, 1H), 5.25-5.18 (m, 1H), 4.36 (dd, J=18.9, 14.3 Hz, 1H), 3.65-3.51 (m, 1.5H), 3.35 (ddd, J=13.9, 12.1, 3.0 Hz, 0.5H), 3.17-3.09 (m, 0.5H), 2.89 (td, J=12.8, 3.1 Hz, 0.5H), 2.14-2.06 (m, 4H), 1.89 (ddd, J=19.2, 14.1, 3.0 Hz, 1H), 1.79-1.47 (m, 6H), 1.14-1.06 (m, 2H); MS (ESI) m/z 501 (M−H)⁻.

Example 103

1-(2,2-difluoro-1,3-benzodioxol-5-yl)-N-(7'-fluoro-3',4'-dihydrospiro[azetidine-3,2'-chromen]-4'-yl)cyclopropanecarboxamide A mixture of the product from Example 100F (81 mg, 0.143 mmol), 10% Pd on carbon (15 mg) and isopropyl alcohol (1 mL) was stirred under an atmosphere of H₂ using a balloon for 1 hour at room temperature, heated at 60° C. for 5 minutes, and stirred again at room temperature for 15 minutes. The mixture was filtered and the filtrate was concentrated to provide the title compound (63.2 mg, 0.146 mmol, 102% yield). $^1$H NMR (400 MHz, CDCl₃) δ ppm 7.15 (dd, J=8.2, 1.7 Hz, 1H), 7.12 (d, J=1.6 Hz, 1H), 7.02 (d, J=8.2 Hz, 1H), 6.97 (dd, J=8.5, 6.4 Hz, 1H), 6.60 (td, J=8.4, 2.6 Hz, 1H), 6.54 (dd, J=9.9, 2.5 Hz, 1H), 5.32 (d, J=8.4 Hz, 1H), 5.21-5.13 (m, 1H), 3.85-3.72 (m, 2H), 3.65 (d, J=8.0 Hz, 1H), 3.57 (d, J=8.2 Hz, 1H), 2.52 (dd, J=13.4, 5.7 Hz, 1H), 1.90 (dd, J=13.4, 9.4 Hz, 1H), 1.75-1.65 (m, 2H), 1.15-1.06 (m, 2H); MS (ESI) m/z 433 (M+H)⁺.

Example 104

1-(2,2-difluoro-1,3-benzodioxol-5-yl)-N-[7'-fluoro-1-(methylsulfonyl)-3',4'-dihydrospiro[azetidine-3,2'-chromen]-4'-yl]cyclopropanecarboxamide The title compound was prepared using procedure similar to that described in Example 101, substituting the product from Example 103 for the product from Example 93. $^1$H NMR (400 MHz, CDCl₃) δ ppm 7.16 (dd, J=8.2, 1.7 Hz, 1H), 7.12 (d, J=1.6 Hz, 1H), 7.04 (d, J=8.2 Hz, 1H), 6.99 (dd, J=8.6, 6.3 Hz, 1H), 6.65 (td, J=8.3, 2.5 Hz, 1H), 6.56 (dd, J=9.7, 2.5 Hz, 1H), 5.31 (d, J=8.0 Hz, 1H), 5.21-5.13 (m, 1H), 4.02 (d, J=8.1 Hz, 1H), 3.99 (s, 2H), 3.91 (d, J=8.7 Hz, 1H), 2.91 (s, 3H), 2.50 (dd, J=13.4, 5.7 Hz, 1H), 1.97 (dd, J=13.4, 9.5 Hz, 1H), 1.77-1.65 (m, 2H), 1.13 (s, 2H); MS (ESI) m/z 511 (M+H)⁺.

Example 105

N-(1-acetyl-7'-fluoro-3',4'-dihydrospiro[azetidine-3,2'-chromen]-4'-yl)-1-(2,2-difluoro-1,3-benzodioxol-5-yl)cyclopropanecarboxamide The title compound was prepared using procedure similar to that described in Example 102, substituting the product from Example 103 for the product from Example 93, provided the title compound. $^1$H NMR (400 MHz, CDCl₃) δ ppm 7.18-7.11 (m, 2H), 7.01 (ddd, J=25.6, 8.4, 6.2 Hz, 2H), 6.65 (td, J=8.4, 2.4 Hz, 1H), 6.56 (dt, J=9.7, 2.9 Hz, 1H), 5.38-5.28 (m, 1H), 5.23-5.14 (m, 1H), 4.16-3.98 (m, 4H), 2.47-2.40 (m, 1H), 2.01-1.93 (m, 1H), 1.89 (s, 3H), 1.77-1.64 (m, 2H), 1.17-1.07 (m, 2H); MS (ESI) m/z 475 (M+H)⁺.

Example 106

3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid Example 106A methyl 3-((2R,4R)-4-(1-(2,2-difluorobenzo[d][1,3]dioxol-5-yl)cyclopropanecarboxamido)-7-(2-fluoroethoxy)chroman-2-yl)benzoate To Example 23E (65 mg, 0.124 mmol) and 2-fluoroethanol (11.93 mg, 0.186 mmol) in CH₂Cl₂ (2 ml) was added triphenylphosphine (65.1 mg, 0.248 mmol), followed by addition of di-tert-butyl azodicarboxylate (57.2 mg, 0.248 mmol) in portion. The mixture was stirred at ambient temperature for 2 hours and LC/MS indicated the reaction was complete. Solvent was removed and residue purified by chromatography on a 1 2 g silica gel cartridge, eluting with ethyl acetate in heptane at 5-40% gradient to provide the title compound (63 mg, 90%). LC/MS m/z 570 (M+H)⁺.

Example 106B

3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid Example 106A (60 mg, 0.105 mmol) and 2 M lithium hydroxide aqueous (0.5 mL) in methanol (2 mL) was stirred at ambient temperature overnight. Solvent was removed and water (1 mL) added to the mixture. The mixture was adjusted with 2 M HCl to pH 1-2. The precipitated white solid was collected by filtration and dried to yield the title compound (43 mg, 74% yield). $^1$H NMR (501 MHz, CDCl₃) δ 8.19 (s, 1H), 8.05 (s, 1H), 7.64 (s, 1H), 7.50 (s, 1H), 7.16-7.04 (m, 2H), 7.00 (d, J=8.2 Hz, 1H), 6.94 (d, J=8.6 Hz, 1H), 6.53 (d, J=8.6 Hz, 1H), 6.45 (s, 1H), 5.50 (s, 1H), 5.39 (d, J=8.8 Hz, 1H), 5.28 (s, 1H), 4.78 (d, 1H), 4.66 (d, 1H), 4.18 (s, 1H), 4.12 (s, 1H), 2.6-2.55 (m, 2H), 1.76 (m, 2H), 1.08 (m, 2H); MS (ESI−) m/z 554 (M−H)⁻.

Example 107

1-(2,2-difluoro-1,3-benzodioxol-5-yl)-N-[1'-(3-hydroxy-2,2-dimethylpropanoyl)-7-methoxy-3,4-dihydrospiro[chromene-2,4'-piperidin]-4-yl]cyclopropanecarboxamide

Example 107A

1'-(3-hydroxy-2,2-dimethylpropanoyl)-7-methoxyspiro[chroman-2,4'-piperidin]-4-one To 3-hydroxy-2,2-dimethylpropanoic acid (112 mg, 0.952 mmol) in DMF (4 mL) was added HATU (1-[bis(dimethylamino)methylene]-1H-1,2,3-triazolo[4,5-b]pyridinium 3-oxid hexafluorophosphate) (543 mg, 1.427 mmol). The mixture was stirred for 5 minutes at room temperature, followed by the sequential addition of 7-methoxyspiro[chroman-2,4'-piperidin]-4-one, hydrochloric acid (CAS 1031416-37-1, MFCD11973587) (270 mg, 0.952 mmol) and N-ethyl-N-isopropylpropan-2-amine (0.663 mL, 3.81 mmol). The mixture was stirred at room temperature for 2 hours. Purification by chromatography on silica gel, eluting with 5-50% ethyl acetate in heptane provided the title compound (305 mg, 92% yield). LC/MS m/z 348 (M+H)$^+$.

Example 107B (E)-3-hydroxy-1-(7-methoxy-4-(methoxyimino)spiro[chroman-2,4'-piperidin]-1'-yl)-2,2-dimethylpropan-1-one A mixture of Example 107A, O-methylhydroxylamine, hydrochloric acid (144 mg, 1.727 mmol) and sodium acetate (142 mg, 1.727 mmol) in methanol (10 mL) was stirred at 60° C. for overnight. Solvent was removed and the residue was taken up in ethyl acetate, and then washed with water. The organic layers was dried over MgSO$_4$, filtered, and concentrated. Purification by preparative LC method AA2 provided the title compound (300 mg, 92% yield). LC/MS m/z 377 (M+H)$^+$.

Example 107C 1-(4-amino-7-methoxyspiro[chroman-2,4'-piperidin]-1'-yl)-3-hydroxy-2,2-dimethylpropan-1-one Example 107B (300 mg, 0.797 mmol) and 5% platinum (155 mg, 0.040 mmol) in acetic acid (5 mL) was charged with 30 psi hydrogen for 24 hours. The reaction mixture was filtered and solvent was removed under reduced pressure. The residue was purified by preparative LC method TFA2 to provide the trifluoroacetic acid salt of the title compound (110 mg, 0.316 mmol, 39.6% yield). LC/MS m/z 350 (M+2H)$^+$.

Example 107D 1-(2,2-difluoro-1,3-benzodioxol-5-yl)-N-[1'-(3-hydroxy-2,2-dimethylpropanoyl)-7-methoxy-3,4-dihydrospiro[chromene-2,4'-piperidin]-4-yl]cyclopropanecarboxamide To 1-(2,2-difluorobenzo[d][1,3]dioxol-5-yl)cyclopropanecarboxylic acid (57.6 mg, 0.238 mmol) in DMF (4 mL) was added HATU (1-[bis(dimethylamino)methylene]-1H-1,2,3-triazolo[4,5-b]pyridinium 3-oxid hexafluorophosphate) (123 mg, 0.324 mmol). The mixture was stirred for 5 minutes at room temperature, followed by the sequential addition of Example 107C (100 mg, 0.216 mmol) and N-ethyl-N-isopropylpropan-2-amine (0.151 ml, 0.865 mmol). The mixture was stirred at room temperature for 2 hours. LC/MS showed the reaction was complete. Purification of the reaction mixture by chromatography on 24 g silica gel cartridge, eluting with 5-50% ethyl acetate in heptane provided the title compound (35 mg, 28.3% yield). $^1$H NMR (500 MHz, CDCl$_3$) δ 7.14 (dd, J=8.2, 1.7 Hz, 1H), 7.11 (d, J=1.7 Hz, 1H), 7.02 (d, J=8.2 Hz, 1H), 6.94 (d, J=8.7 Hz, 1H), 6.49 (dd, J=8.6, 2.6 Hz, 1H), 6.36 (d, J=2.5 Hz, 1H), 5.35 (d, J=8.5 Hz, 1H), 5.23-5.11 (m, 1H), 4.15 (d, J=60.1 Hz, 2H), 3.75 (s, 3H), 3.50 (dd, J=9.9, 5.6 Hz, 2H), 3.27 (d, J=69.6 Hz, 2H), 2.56 (s, 1H), 2.12 (dd, J=13.4, 6.3 Hz, 1H), 1.93 (dq, J=14.2, 2.6 Hz, 1H), 1.81-1.49 (m, 6H), 1.26 (d, J=1.9 Hz, 6H), 1.10 (td, J=3.3, 1.8 Hz, 2H); MS (ESI+) m/z 573 (M+H)$^+$.

Example 108

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid

Example 108A 7-(trifluoromethyl)-4H-chromen-4-one

A mixture of 1-(2-hydroxy-4-(trifluoromethyl)phenyl)ethanone (400 mg, 1.959 mmol) and 1,1-dimethoxy-N,N-dimethylmethanamine (0.286 ml, 2.155 mmol) was heated at 120° C. for 2 hours, and cooled down. The precipitated orange solid was collected by filtration, washed with heptane, and dried to yield (E)-3-(dimethylamino)-1-(4-trifluoromethyl-2-hydroxyphenyl)prop-2-en-1-one which was dissolved in dichloromethane (120 mL) and treated with concentrated HCl (15 mL). The mixture was refluxed for 2 hours. The aqueous layer was removed and organic layer was washed with brine (50 mL×2), and concentrated. The residue was purified by chromatography on a 80 g silica gel cartridge, eluting with 5-30% ethyl acetate in heptane to yield the title compound (310 mg, 73.9% yield) as white solid.

Example 108B (R)-methyl 3-(4-oxo-7-(trifluoromethyl)chroman-2-yl)benzoate

A mixture of bis(2,2,2-trifluoroacetoxy)palladium (46.6 mg, 0.140 mmol), (S)-4-(tert-butyl)-2-(pyridin-2-yl)-4,5-dihydrooxazole (34.3 mg, 0.168 mmol), ammonium hexafluorophosphate(V) (137 mg, 0.841 mmol), (3-(methoxycarbonyl)phenyl)boronic acid (504 mg, 2.80 mmol) and dichloroethane (5 mL) in a vial (20 mL) were stirred for 5 minutes at room temperature. Example 108A (300 mg, 1.41 mmol) and water (0.256 mL, 14.19 mmol) were added to the mixture. The vial was capped and the mixture stirred at 60° C. overnight. The mixture was filtered through a plug of celite and eluted with ethyl acetate. The organic layers were removed in vacuo and the crude material was chromatographed using a 80 g silica gel cartridge, eluting with 5-40% ethyl acetate in heptane to provide the title compound (230 mg, 46.9% yield).

Example 108 C (R)-methyl 3-(4-(methoxyimino)-7-(trifluoromethyl)chroman-2-yl)benzoate A mixture of Example 108B (230 mg, 2.53 mmol), sodium acetate (108 mg, 1.31 mmol) and O-methylhydroxylamine, hydrochloric acid (110 mg, 1.31 mmol) in methanol (10 mL) was stirred at 60° C. overnight. The solvent was evaporated under reduced pressure and the residue dissolved in ethyl acetate and washed with water, dried over MgSO$_4$, filtered, and concentrated. The title compound (225 mg, 90% yield) was carried on to next step without further purification. LC/MS m/z 380 (M+H)$^+$.

Example 108D methyl 3-((2R,4R)-4-amino-7-(trifluoromethyl)chroman-2-yl)benzoate To a mixture of Example 108C (270 mg, 0.712 mmol) and acetic acid (30 mL) was added 5% platinum/carbon wet (90 mg, 0.190 mmol) in a 50 mL pressure bottle and stirred for 32 hours at 30 psi of hydrogen and at ambient temperature. The reaction mixture was filtered, and the filtrate was concentrated under reduced pressure. The resulting oil was purified by preparative LC method TFA2 to provide the title compound and methyl 3-((2R,4R)-4-amino-7-(trifluoromethyl)chroman-2-yl)cyclohexanecarboxylate.

Example 108E methyl 3-((2R,4R)-4-(1-(2,2-difluorobenzo[d][1,3]dioxol-5-yl)cyclopropanecarboxamido)-7-(trifluoromethyl)chroman-2-yl)benzoate A mixture of 1-(2,2-difluorobenzo[d][1,3]dioxol-5-yl)cyclopropanecarboxylic acid (76 mg, 0.313 mmol) and HATU (1-[bis(dimethylamino)methylene]-1H-1,2,3-triazolo[4,5-b]pyridinium 3-oxid hexafluorophosphate) (162 mg, 0.427 mmol) in DMF (4 mL) was stirred for 5 minutes at room temperature, followed by the sequential addition of Example 108D (150 mg, 0.48 mmol) and N-ethyl-N-isopropylpropan-2-amine (0.198 mL, 1.14 mmol). The mixture was stirred at ambient temperature for 2 hours. LC/MS indicated the reaction was complete. Purification by chromatography on 12 g silica gel cartridge, eluting with 5-40% ethyl acetate in heptane to provide the title compound (45 mg, 27.5% yield). $^1$H NMR (400 MHz, CDCl$_3$) δ 8.07 (t, J=1.9 Hz, 1H), 8.05-7.99 (m, 1H), 7.59 (dt, J=7.7, 1.6 Hz, 1H), 7.47 (t, J=7.7 Hz, 1H), 7.21-7.15 (m, 3H), 7.14-7.08 (m, 2H), 7.03 (d, J=8.2 Hz, 1H), 5.60-5.48 (m, 1H), 5.40 (d, J=9.0 Hz, 1H), 5.28 (dd, J=11.5, 2.0 Hz, 1H), 3.94 (s, 3H), 3.69-3.63 (m, 1H), 2.53 (ddd, J=13.5, 6.2, 2.1 Hz, 1H), 1.89-1.79 (m, 2H), 1.12 (td, J=6.6, 3.2 Hz, 2H); MS (ESI−) m/z 574 (M−H)$^-$

Example 108F

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid A mixture of Example 108E (40 mg, 0.07 mmol) and 2 M NaOH (0.2 mL) in methanol (1 mL) was stirred at 35° C. for 2 hours and the solvent was removed in vacuo. Water (0.5 mL) was added to the residue and the pH was adjusted to 1-2. The precipitated solid was collected by filtration, washed with water, and dried to provide the title compound (33 mg, 85%). $^1$H NMR (400 MHz, CDCl$_3$) δ 8.18 (s, 1H), 8.12-8.03 (m, 1H), 7.65 (d, J=7.8 Hz, 1H), 7.49 (t, J=7.8 Hz, 1H), 7.20-7.06 (m, 6H), 5.71-5.52 (m, 1H), 5.45 (d, J=9.0 Hz, 1H), 5.32 (d, J=10.9 Hz, 1H), 2.58 (dd, J=13.3, 6.0 Hz, 1H), 1.84-1.77 (m, 1H), 1.73-1.60 (m, 2H), 1.15-1.07 (m, 2H); MS (ESI−) m/z 560 (M−H)$^-$.

Example 109

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid

Example 109A methyl 3-((2R,4R)-4-(1-(2,2-difluorobenzo[d][1,3]dioxol-5-yl)cyclopropanecarboxamido)-7-(trifluoromethyl)chroman-2-yl)cyclohexanecarboxylate To 1-(2,2-difluorobenzo[d][1,3]dioxol-5-yl)cyclopropanecarboxylic acid (52.2 mg, 0.215 mmol) in DMF (1 mL) was added HATU (1-[bis(dimethylamino)methylene]-1H-1,2,3-triazolo[4,5-b]pyridinium 3-oxid hexafluorophosphate) (112 mg, 0.294 mmol). The mixture was stirred for 5 minutes at room temperature, followed by sequential addition of methyl 3-((2R,4R)-4-amino-7-(trifluoromethyl)chroman-2-yl)cyclohexanecarboxylate (70 mg, 0.196 mmol) and N-ethyl-N-isopropylpropan-2-amine (0.136 ml, 0.784 mmol). The mixture was stirred at ambient temperature for 2 hours. LC/MS showed the reaction was complete. Purification by chromatography on 12 g silica gel cartridge, eluting with 5-40% ethyl acetate in heptane provided the title compound (40 mg, 0.069 mmol, 35.1% yield). MS (ESI+) m/z 581.9 (M+H)$^+$.

Example 109B

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid A mixture of Example 109A (36 mg, 0.062 mmol) and aqueous NaOH aqueous (2 M, 0.2 mL) in methanol (1 mL) was stirred at 35° C. for 2 hours. The solvent was removed, and water (0.5 mL) was added. The pH of the mixture was adjusted to 1~2. The precipitated solid was collected by filtration, washed with water, and dried to provide the title compound (28 mg, 80%). $^1$H NMR (400 MHz, CDCl$_3$) δ 7.21-6.97 (m, 6H), 5.49-5.24 (m, 2H), 3.98 (dt, J=11.4, 6.3 Hz, 1H), 2.38 (d, J=10.9 Hz, 1H), 2.25 (dd, J=13.2, 5.3 Hz, 2H), 2.10-1.86 (m, 3H), 1.72 (ddd, J=27.0, 10.1, 3.8 Hz, 4H), 1.58-1.41 (m, 2H), 1.35 (q, J=12.8, 11.7 Hz, 2H), 1.12 (d, J=3.5 Hz, 2H); MS (ESI+) m/z 567.9 (M+H)$^+$.

Example 110 methyl 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoate

Example 110A (R)-methyl 4-(7-methoxy-4-oxochroman-2-yl)benzoate

A 20 mL vial was charged with bis(2,2,2-trifluoroacetoxy)palladium (0.264 g, 0.795 mmol), (S)-4-(tert-butyl)-2-(pyridin-2-yl)-4,5-dihydrooxazole (0.195 g, 0.954 mmol), ammonium hexafluorophosphate(V) (0.777 g, 4.77 mmol) and (4-(methoxycarbonyl)phenyl)boronic acid (2.86 g, 15.89 mmol). The reaction was stirred in dichloroethane (5 mL) for 5 minutes, and a pale brown color suspension was observed. To this suspension was added Example 5A (1.4 g, 7.95 mmol) and water (0.716 mL, 39.7 mmol) and the sides of the vial washed with more dichloroethane (5 mL). The vial was capped and the mixture stirred at 60° C. overnight. The mixture was filtered through a plug of silica gel and celite and eluted with ethyl acetate to give a red solution. The solvent was removed under reduced pressure and the crude material was chromatographed using a 24 g silica gel cartridge with a gradient of 5-60% ethyl acetate/heptanes over 20 minutes, a white solid precipitated in the middle of fractions collection and clogged up the line into the IR detection unit. The output line was unclogged and the white solid was filtered, the filtrate was concentrated and chromatographed again using a 12 g cartridge eluting with 100% dichloromethane to give a white solid which was combined to give the title compound (1.6 g, 5.12 mmol, 64.5% yield)). $^1$H NMR (400 MHz, DMSO-$d_6$) δ 8.02 (dd, J=8.4, 2.1 Hz, 2H), 7.75-7.72 (m, 1H), 7.70 (d, J=8.4 Hz, 2H), 6.72-6.66 (m, 2H), 5.77 (dd, J=12.9, 3.1 Hz, 1H), 3.87 (s, 3H), 3.83 (d, J=2.0 Hz, 3H), 3.14 (dd, J=16.8, 12.9 Hz, 1H), 2.82 (dd, J=16.7, 3.1 Hz, 1H); MS (ESI+) m/z 313 (M+H)$^+$.

Example 110B (R)-methyl 4-(7-methoxy-4-(methoxyimino)chroman-2-yl)benzoate

A solution of the product from Example 110A (0.6 g, 1.921 mmol), O-methylhydroxylamine hydrochloride (0.241 g, 2.88 mmol) in pyridine (1.921 mL) in a 20 mL vial was stirred at ambient temperature for 5 minutes and 65° C. for 1 hour. The solvent was removed under reduced pressure. The crude material was dissolved in 10% methanol/dichloromethane and washed with water. The organic layer was separated, and concentrated in vacuo. The resulted white solid was rinsed with 10% dichloromethane/hexane and collected by filtration to give title compounds as white solid (0.581 g, 1.702 mmol, 89% yield). $^1$H NMR (400 MHz, DMSO-$d_6$) δ 8.03-7.96 (m, 2H), 7.71 (d, J=8.7 Hz, 1H), 7.69-7.63 (m, 2H), 6.62 (dd, J=8.8, 2.5 Hz, 1H), 6.59 (d, J=2.5 Hz, 1H), 5.32 (dd, J=11.8, 3.2 Hz, 1H), 3.88 (s, 3H), 3.87 (s, 3H), 3.76 (s, 3H), 3.36 (d, J=3.4 Hz, 1H), 2.71 (dd, J=17.1, 11.9 Hz, 1H); MS (ESI+) m/z 342 (M+H)$^+$.

Example 110C methyl 4-((2R,4R)-4-amino-7-methoxychroman-2-yl)benzoate

To a mixture of Example 110B (580 mg, 1.69 mmol) and acetic acid (20 mL) was added platinum (180 mg, 0.923 mmol) in a 50 mL pressure bottle and stirred for 32 hours at 30 psi of hydrogen and at ambient temperature. The reaction mixture was filtered, and the filtrate was concentrated under reduced pressure. The resulting oil was purified by flash chromatography on a 24 g cartridge, and eluted with 5-70% ethyl acetate/heptane over 20 minutes to provide the title compound (240 mg, 0.766 mmol, 45.1% yield) as white solid. $^1$H NMR (400 MHz, DMSO-$d_6$) δ 8.06-7.97 (m, 2H), 7.64-7.57 (m, 2H), 7.47 (d, J=8.5 Hz, 1H), 6.52 (dd, J=8.6, 2.6 Hz, 1H), 6.38 (d, J=2.5 Hz, 1H), 5.29 (dd, J=11.9, 1.7 Hz, 1H), 4.07 (dd, J=11.0, 5.7 Hz, 1H), 3.87 (s, 3H), 3.70 (s, 3H), 2.28 (ddd, J=13.1, 5.7, 1.9 Hz, 1H), 1.72 (dt, J=13.0, 11.4 Hz, 1H); MS (ESI+) m/z 314 (M+H)$^+$.

Example 110D methyl 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoate To 1-(2,2-difluorobenzo[d][1,3]dioxol-5-yl)cyclopropanecarboxylic acid (83 mg, 0.345 mmol) in DMF (1 mL) was added HATU (1-[bis(dimethylamino)methylene]-1H-1,2,3-triazolo[4,5-b]pyridinium 3-oxid hexafluorophosphate) (183 mg, 0.483 mmol). The solution was stirred for 15 minutes at room temperature, followed by sequential addition of Example 110C (108 mg, 0.345 mmol) and triethylamine (0.144 mL, 1.034 mmol). The mixture was stirred at ambient temperature for 5 hours and water (10 mL) was added. The resulted white precipitate was filtered and purified by flash chromatography on a 12 g cartridge, eluted with 5-60% ethyl acetate/heptane over 20 minutes to provide the title compound (126 mg, 0.234 mmol, 68.0% yield) as a white solid. $^1$H NMR (400 MHz, DMSO-$d_6$) δ 8.00-7.94 (m, 2H), 7.58-7.52 (m, 2H), 7.37 (d, J=1.7 Hz, 1H), 7.29 (d, J=8.3 Hz, 1H), 7.18 (dd, J=8.4, 1.7 Hz, 1H), 7.15 (d, J=8.9 Hz, 1H), 6.93 (dd, J=8.5, 1.1 Hz, 1H), 6.51 (dd, J=8.6, 2.6 Hz, 1H), 6.39 (d, J=2.5 Hz, 1H), 5.33 (q, J=9.5, 8.4 Hz, 2H), 3.84 (s, 3H), 3.67 (s, 3H), 2.11-1.99 (m, 2H), 1.54-1.41 (m, 1H), 1.41-1.29 (m, 1H), 1.07-0.96 (m, 2H); MS (ESI−) m/z 536 (M−H)$^-$.

Example 111

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid To a solution of the product from Example 110D (81 mg, 0.151 mmol) in ethanol (1 mL) and tetrahydrofuran (0.4 mL) was added 3 N sodium hydroxide (0.201 mL, 0.603 mmol). The reaction was stirred at room temperature for 16 hours. The reaction was quenched with HCl (1 N, 1 mL), and water (2 mL) was added. The organics were removed under a stream of nitrogen to give an off-white precipitate. The precipitate was collected by filtration, washed with water, and then purified by flash chromatography on a 12 g silica gel cartridge, and eluted with a gradient of 5-90% ethyl acetate/heptanes over 20 minutes to provide the title compound (65 mg, 0.124 mmol, 82% yield) as a white solid. $^1$H NMR (400 MHz, DMSO-$d_6$) δ 12.93 (s, 1H), 7.95 (d, J=8.2 Hz, 2H), 7.51 (d, J=8.3 Hz, 2H), 7.37 (d, J=1.7 Hz, 1H), 7.29 (d, J=8.3 Hz, 1H), 7.21-7.12 (m, 2H), 6.93 (d, J=8.5 Hz, 1H), 6.50 (dd, J=8.6, 2.6 Hz, 1H), 6.39 (d, J=2.5 Hz, 1H), 5.39-5.28 (m, 2H), 3.67 (s, 3H), 2.04 (td, J=7.9, 2.3 Hz, 2H), 1.51-1.43 (m, 1H), 1.41-1.33 (m, 1H), 1.03 (q, J=2.6 Hz, 2H); MS (ESI+) m/z 522 (M−H)$^-$.

Example 112 methyl rac-3-[(2R,4R)-7-chloro-4-({[1-(2,2-difluoro-1,3-benzodioxol-5-yl)cyclopropyl]carbonyl}amino)-3,4-dihydro-2H-pyrano[2,3-b]pyridin-2-yl]benzoate Example 112A methyl 3-(3-(6-chloro-2-fluoropyridin-3-yl)-3-hydroxypropanoyl)benzoate A solution of methyl 3-acetylbenzoate (1 g, 5.61 mmol) in tetrahydrofuran (25 mL) was cooled to −78° C., treated dropwise with 1 M lithium bis(trimethylsilyl)amide in tetrahydrofuran (7.30 ml, 7.30 mmol), stirred at −78° C. for 15 minutes, treated dropwise with a solution of 6-chloro-2-fluoronicotinaldehyde (0.895 g, 5.61 mmol) in tetrahydrofuran (10 mL), stirred at −78° C. for 15 minutes, treated with saturated NH$_4$Cl solution (30 mL) and the mixture was allowed to warm to near room temperature. The mixture was extracted with ethyl acetate (30 mL) and the layers were separated. The aqueous layer was extracted with ethyl acetate (20 mL). The combined organic layers were washed with brine, dried (MgSO$_4$), filtered, and concentrated. The residue was chromatographed on silica gel and eluted with a gradient of 20%-100% ethyl acetate in heptanes to provide the title compound (1.35 g, 4.00 mmol, 71.2% yield). $^1$H NMR (400 MHz, CDCl$_3$) δ ppm 8.56 (t, J=1.8 Hz, 1H), 8.28 (dt, J=7.7, 1.5 Hz, 1H), 8.15 (dt, J=7.9, 1.6 Hz, 1H), 8.10-8.05 (m, 1H), 7.59 (t, J=7.8 Hz, 1H), 7.30 (dd, J=7.8, 1.0 Hz, 1H), 5.53 (dt, J=9.4, 2.9 Hz, 1H), 3.96 (s, 3H), 3.89 (d, J=3.9 Hz, 1H), 3.55 (dd, J=18.0, 2.4 Hz, 1H), 3.29 (dd, J=18.0, 9.3 Hz, 1H); MS (ESI) m/z 338 (M+H)$^+$.

Example 112B

A solution of the product from Example 112A (1.35 g, 4.00 mmol) in tetrahydrofuran (40 mL) under N$_2$ was cooled to −78° C., treated with 1 M diethylmethoxyborane in tetrahydrofuran (4.40 ml, 4.40 mmol), stirred at −78° C. for 15 minutes, treated with NaBH$_4$ (0.166 g, 4.40 mmol), stirred at −78° C. for 30 minutes, treated with acetic acid (4 mL) and allowed to warm to room temperature. The mixture was concentrated to near dryness. The residue was portioned between tert-butyl methyl ether (about 30 mL) and 0.5 M NaOH (40 mL). The layers were separated and the organic layer was washed with 1 M NaOH (twice), washed with brine, dried (MgSO$_4$), filtered, and concentrated to provide the title compound (1.38 g, 4.06 mmol, 102% yield) as a mixture of isomers. NMR of major isomer: $^1$H NMR (400 MHz, CDCl$_3$) δ ppm 8.05-7.96 (m, 2H), 7.96-7.92 (m, 1H), 7.59-7.54 (m, 1H), 7.42 (t, J=7.7 Hz, 1H), 7.23 (d, J=7.7 Hz, 1H), 5.25 (t, J=6.2 Hz, 1H), 5.18-5.12 (m, 1H), 4.47 (s, 1H), 3.91 (s, 3H), 3.55 (s, 1H), 2.05-2.00 (m, 2H); MS (ESI) m/z 340 (M+H)$^+$.

Example 112C methyl rac-3-((2R,4R)-7-chloro-4-hydroxy-3,4-dihydro-2H-pyrano[2,3-b]pyridin-2-yl)benzoate A solution of the product from Example 112B (1.38 g, 4.06 mmol) in 2-methyl-tetrahydrofuran (40 mL) was treated with 1,8-diazabicyclo[5.4.0]undec-7-ene (about 3 mL) and heated at 75° C. for 16 hours and then, heated at 80° C. for 24 hours. The mixture was cooled, diluted with ethyl acetate and washed with 10% citric acid solution. This acidic aqueous layer was extracted with ethyl acetate. The combined organic layers were washed with brine, dried (MgSO$_4$), filtered, and concentrated. The residue was chromatographed on silica gel and eluted with a gradient of 25%-100% ethyl acetate in heptanes to provide the title compound as the first eluting isomer. $^1$H NMR (400 MHz, CDCl$_3$) δ ppm 8.08 (s, 1H), 8.00 (dt, J=7.8, 1.5 Hz, 1H), 7.85 (dd, J=7.8, 1.1 Hz, 1H), 7.65 (d, J=6.7 Hz, 1H), 7.46 (t, J=7.7 Hz, 1H), 6.99 (d, J=7.9 Hz, 1H), 5.35 (dd, J=11.9, 1.9 Hz, 1H), 5.12 (dd, J=10.0, 5.8 Hz, 1H), 3.92 (s, 3H), 2.55 (ddd, J=13.4, 6.0, 2.0 Hz, 1H), 2.11 (ddd, J=13.3, 12.0, 10.8 Hz, 1H).

Example 112D methyl rac-3-((2R,4S)-7-chloro-4-hydroxy-3,4-dihydro-2H-pyrano[2,3-b]pyridin-2-yl)benzoate The title compound was isolated as the second eluting isomer from the column chromatography as described in Example 112C. $^1$H NMR (400 MHz, CDCl$_3$) δ ppm 8.07 (s, 1H), 7.98 (d, J=7.9 Hz, 1H), 7.66 (d, J=7.8 Hz, 1H), 7.63 (d, J=7.7 Hz, 1H), 7.43 (t, J=7.7 Hz, 1H), 6.95 (d, J=7.7 Hz, 1H), 5.53 (dd, J=11.9, 2.2 Hz, 1H), 4.87 (t, J=3.0 Hz, 1H), 3.90 (s, 3H), 3.25 (s, 1H), 2.32 (dt, J=14.7, 2.5 Hz, 1H), 2.12-2.03 (m, 1H).

Example 112E methyl rac-3-((2R,4R)-4-azido-7-chloro-3,4-dihydro-2H-pyrano[2,3-b]pyridin-2-yl)benzoate A solution of the product from Example 112D (122 mg, 0.382 mmol) in tetrahydrofuran (2 mL) under N$_2$ was cooled to 0° C., treated with 1,8-diazabicyclo[5.4.0]undec-7-ene (115 μL, 0.763 mmol) treated with diphenylphosphoryl azide (140 μL, 0.649 mmol) and stirred over the weekend at room temperature. The mixture was partitioned between ethyl acetate and saturated NaHCO$_3$ solution. The ethyl acetate layer was washed with 10% citric acid solution, washed with brine, dried (MgSO$_4$), filtered, and concentrated. The residue was chromatographed on silica gel and eluted with a gradient of 10%-100% ethyl acetate in heptanes to provide the title compound (104.7 mg, 0.304 mmol, 80% yield). $^1$H NMR (400 MHz, CDCl$_3$) δ ppm 8.12 (s, 1H), 8.05 (d, J=7.7 Hz, 1H), 7.75 (d, J=7.9 Hz, 1H), 7.69 (d, J=7.7 Hz, 1H), 7.50 (t, J=7.8 Hz, 1H), 7.06 (d, J=7.9 Hz, 1H), 5.40 (d, J=11.4 Hz, 1H), 4.85 (dd, J=11.3, 6.0 Hz, 1H), 3.94 (s, 3H), 2.65 (ddd, J=13.5, 6.0, 1.9 Hz, 1H), 2.33-2.17 (m, 1H); MS (ESI) m/z 345 (M+H)$^+$.

Example 112F methyl rac-3-((2R,4R)-4-amino-7-chloro-3,4-dihydro-2H-pyrano[2,3-b]pyridin-2-yl)benzoate A solution of the product from Example 112E (104.7 mg, 0.304 mmol) and triphenylphosphine (159 mg, 0.607 mmol) in tetrahydrofuran (1 mL) and H$_2$O (219 μL, 12.15 mmol) was heated at 70° C. for 2 hours. 2-methyl-tetrahydrofuran was added and the reaction was heated at 90° C. so that tetrahydrofuran was removed from the reaction and the mixture was heated at 90° C. overnight. The mixture was cooled and partitioned between tert-butyl methyl ether (20 mL) and 1 M HCl (5 mL). The layers were separated and the aqueous was washed with tert-butyl methyl ether. The aqueous layer treated with ethyl acetate (20 mL) was basified to pH>7 with 1 M NaOH and extracted. The ethyl acetate layer was washed with brine, dried (MgSO$_4$), filtered, and concentrated to provide the title compound (64 mg, 0.201 mmol, 66.1% yield). $^1$H NMR (501 MHz, CDCl$_3$) δ ppm 8.11 (t, J=1.8 Hz, 1H), 8.02 (dt, J=7.8, 1.4 Hz, 1H), 7.91 (dd, J=7.9, 1.1 Hz, 1H), 7.69 (d, J=7.9 Hz, 1H), 7.48 (t, J=7.7 Hz, 1H), 7.01 (d, J=7.9 Hz, 1H), 5.38 (dd, J=11.9, 2.0 Hz, 1H), 4.28 (dd, J=11.2, 5.6 Hz, 1H), 3.93 (s, 3H), 2.48 (ddd, J=13.5, 5.6, 2.0 Hz, 1H), 1.94 (dt, J=13.5, 11.6 Hz, 1H); MS (ESI) m/z 319 (M+H)$^+$.

Example 112G methyl rac-3-[(2R,4R)-7-chloro-4-({[1-(2,2-difluoro-1,3-benzodioxol-5-yl)cyclopropyl]carbonyl}amino)-3,4-dihydro-2H-pyrano[2,3-b]pyridin-2-yl]benzoate The title compound was prepared using the procedure similar to that described in Example 100F, substituting the product from Example 112F for the product from Example 100E. $^1$H NMR (400 MHz, CDCl$_3$) δ ppm 8.06 (d, J=1.7 Hz, 1H), 8.00 (d, J=7.9 Hz, 1H), 7.61 (d, J=7.7 Hz, 1H), 7.47-7.40 (m, 2H), 7.11 (dd, J=8.3, 1.6 Hz, 1H), 7.08 (d, J=1.6 Hz, 1H), 7.02 (d, J=8.1 Hz, 1H), 6.96 (d, J=7.9 Hz, 1H), 5.50 (td, J=10.5, 10.1, 6.1 Hz, 1H), 5.38 (d, J=3.9 Hz, 1H), 5.36 (s, 1H), 3.92 (s, 3H), 2.50 (ddd, J=13.6, 6.1, 2.0 Hz, 1H), 1.84 (dt, J=13.6, 11.4 Hz, 1H), 1.77-1.63 (m, 2H), 1.16-1.06 (m, 2H); MS (ESI) m/z 543 (M+H)$^+$.

Example 113 methyl rac-3-[(2R,4R)-4-({[1-(2,2-difluoro-1,3-benzodioxol-5-yl)cyclopropyl]carbonyl}amino)-7-fluoro-3,4-dihydro-2H-pyrano[2,3-b]pyridin-2-yl]benzoate

Example 113A methyl 3-(3-(2,6-difluoropyridin-3-yl)-3-hydroxypropanoyl)benzoate The title compound was prepared using procedure similar to that described in Example 112A, substituting 2,6-difluoronicotinaldehyde (CAS#155601-65-3) for 6-chloro-2-fluoronicotinaldehyde. $^1$H NMR (400 MHz, CDCl$_3$) δ ppm 8.87 (t, J=1.8 Hz, 1H), 8.59 (dt, J=7.9, 1.5 Hz, 1H), 8.54-8.49 (m, 1H), 8.47 (dt, J=8.0, 1.5 Hz, 1H), 7.90 (t, J=7.8 Hz, 1H), 7.21 (dd, J=8.1, 2.8 Hz, 1H), 5.86 (dt, J=9.3, 2.8 Hz, 1H), 4.27 (s, 3H), 4.18 (d, J=3.7 Hz, 1H), 3.85 (dd, J=18.0, 2.5 Hz, 1H), 3.61 (dd, J=18.0, 9.3 Hz, 1H); MS (ESI) m/z 339 (M+NH$_4$)$^+$.

Example 113B methyl 3-(3-(2,6-difluoropyridin-3-yl)-1,3-dihydroxypropyl)benzoate The title compound was prepared using procedure similar to that described in Example 112B, substituting the product from Example 113A for the product from Example 112A. MS (ESI) m/z 341 (M+NH$_4$)$^+$.

Example 113C methyl rac-3-((2R,4S)-7-fluoro-4-hydroxy-3,4-dihydro-2H-pyrano[2,3-b]pyridin-2-yl)benzoate The title compound was isolated as the first eluting isomer when prepared using procedure similar to that described in Example 112C, substituting the product from Example 113B for the product from Example 112B. $^1$H NMR (400 MHz, CDCl$_3$) δ ppm 8.09 (s, 1H), 8.03-7.95 (m, 2H), 7.65 (d, J=7.7 Hz, 1H), 7.47 (t, J=7.7 Hz, 1H), 6.59 (dd, J=8.1, 2.7 Hz, 1H), 5.36 (dd, J=11.9, 2.0 Hz, 1H), 5.17-5.08 (m, 1H), 3.92 (s, 3H), 2.60 (bs, 1H), 2.56 (ddd, J=13.4, 6.1, 2.1 Hz, 1H), 2.12 (ddd, J=13.4, 12.0, 10.6 Hz, 1H); MS (ESI) m/z 304 (M+H)$^+$.

Example 113D methyl rac-3-((2R,4S)-7-fluoro-4-hydroxy-3,4-dihydro-2H-pyrano[2,3-b]pyridin-2-yl)benzoate The title compound was isolated as the second eluting isomer when prepared using procedure similar to that described in Example 112C, substituting the product from Example 113B for the product from Example 112B. $^1$H NMR (400 MHz, CDCl$_3$) δ ppm 8.14 (t, J=1.8 Hz, 1H), 8.03 (dt, J=7.7, 1.3 Hz, 1H), 7.80 (t, J=8.0 Hz, 1H), 7.70 (d, J=7.8 Hz, 1H), 7.48 (t, J=7.7 Hz, 1H), 6.61 (dd, J=8.0, 2.8 Hz, 1H), 5.55 (dd, J=12.0, 2.2 Hz, 1H), 4.90 (q, J=3.3 Hz, 1H), 3.93 (s, 3H), 2.34 (dt, J=14.5, 2.5 Hz, 1H), 2.23 (d, J=4.0 Hz, 1H), 2.14 (ddd, J=14.9, 11.9, 3.4 Hz, 1H); MS (ESI) m/z 304 (M+H)$^+$.

Example 113E methyl rac-3-((2R,4R)-4-azido-7-fluoro-3,4-dihydro-2H-pyrano[2,3-b]pyridin-2-yl)benzoate The title compound was prepared using procedure similar to that described in Example 112E, substituting the product from Example 113D for the product from Example 112D. $^1$H NMR (400 MHz, CDCl$_3$) δ ppm 8.13 (t, J=1.8 Hz, 1H), 8.06 (dt, J=7.8, 1.5 Hz, 1H), 7.88 (td, J=8.0, 1.0 Hz, 1H), 7.70 (d, J=7.7 Hz, 1H), 7.51 (t, J=7.7 Hz, 1H), 6.66 (dd, J=8.2, 2.8 Hz, 1H), 5.41 (dd, J=11.8, 2.0 Hz, 1H), 4.84 (dd, J=11.1, 6.0 Hz, 1H), 3.94 (s, 3H), 2.66 (ddd, J=13.5, 6.0, 2.1 Hz, 1H), 2.26 (dt, J=13.4, 11.4 Hz, 1H); MS (ESI) m/z 329 (M+H)$^+$.

Example 113F methyl rac-3-((2R,4R)-4-amino-7-fluoro-3,4-dihydro-2H-pyrano[2,3-b]pyridin-2-yl)benzoate The title compound was prepared using procedure similar to that described in Example 112F, substituting the product from Example 113E for the product from Example 112E. $^1$H NMR (400 MHz, CDCl$_3$) δ ppm 8.12 (s, 1H), 8.05-8.00 (m, 2H), 7.68 (d, J=7.6 Hz, 1H), 7.48 (t, J=7.7 Hz, 1H), 6.60 (dd, J=8.1, 2.9 Hz, 1H), 5.39 (d, J=12.1 Hz, 1H), 4.33-4.23 (m, 1H), 3.93 (s, 3H), 2.49 (ddd, J=13.1, 5.3, 1.4 Hz, 1H), 1.94 (dt, J=13.7, 11.6 Hz, 1H).

Example 113G methyl rac-3-[(2R,4R)-4-({[1-(2,2-difluoro-1,3-benzodioxol-5-yl)cyclopropyl]carbonyl}amino)-7-fluoro-3,4-dihydro-2H-pyrano[2,3-b]pyridin-2-yl]benzoate A solution of the product from Example 113F (3.5 mg, 0.012 mmol) in CH$_2$Cl$_2$ (0.5 mL) was treated with 1-(2,2-difluorobenzo[d][1,3]dioxol-5-yl)cyclopropanecarbonyl chloride (CAS#1004294-65-8) (3.92 mg, 0.015 mmol), and triethylamine (4.84 μL, 0.035 mmol). The mixture was stirred overnight at room temperature. The mixture was partitioned between tert-butyl methyl ether and 10% citric acid. The layers were separated and the tert-butyl methyl ether layer was washed with saturated NaHCO$_3$ solution, washed with brine, dried (MgSO$_4$), filtered, and concentrated. The residue was chromatographed on silica gel and eluted with a gradient of 50%-100% [9:1 CH$_2$Cl$_2$:ethyl acetate] in heptane to provide the title compound (1.7 mg, 3.23 μmol, 27.9% yield). $^1$H NMR (400 MHz, CDCl$_3$) δ ppm 8.07 (s, 1H), 8.01 (d, J=7.8 Hz, 1H), 7.61 (d, J=7.7 Hz, 1H), 7.55 (t, J=8.0 Hz, 1H), 7.45 (t, J=7.7 Hz, 1H), 7.11 (dd, J=8.2, 1.6 Hz, 1H), 7.07 (d, J=1.6 Hz, 1H), 7.02 (d, J=8.2 Hz, 1H), 6.57 (dd, J=8.1, 2.8 Hz, 1H), 5.54-5.46 (m, 1H), 5.42-5.30 (m, 2H), 3.92 (s, 3H), 2.52 (ddd, J=13.7, 6.1, 2.1 Hz, 1H), 1.86 (dt, J=13.2, 11.1 Hz, 1H), 1.78-1.63 (m, 2H), 1.11 (q, J=2.5 Hz, 2H); MS (ESI) m/z 525 (M−H)−.

Example 114 rac-3-[(2R,4R)-7-chloro-4-({[1-(2,2-difluoro-1,3-benzodioxol-5-yl)cyclopropyl]carbonyl}amino)-3,4-dihydro-2H-pyrano[2,3-b]pyridin-2-yl]benzoic acid The title compound was prepared using the procedure similar to that described in Example 28, substituting the product from Example 112G for the product from Example 30. $^1$H NMR (400 MHz, CDCl$_3$) δ ppm 8.16 (s, 1H), 8.06 (d, J=8.2 Hz, 1H), 7.68 (d, J=7.7 Hz, 1H), 7.47 (t, J=7.8 Hz, 1H), 7.43 (dd, J=8.0, 1.1 Hz, 1H), 7.13 (dd, J=8.1, 1.7 Hz, 1H), 7.09 (d, J=1.7 Hz, 1H), 7.03 (d, J=8.2 Hz, 1H), 6.96 (d, J=8.0 Hz, 1H), 5.57 (td, J=10.3, 6.0 Hz, 1H), 5.47-5.39 (m, 2H), 2.57 (ddd, J=13.5, 6.0, 2.0 Hz, 1H), 1.84 (dt, J=13.4, 11.3 Hz, 1H), 1.79-1.66 (m, 2H), 1.18-1.08 (m, 2H); MS (ESI) m/z 527 (M−H)−.

Example 115 tert-butyl 3-[4-({[1-(2,2-difluoro-1,3-benzodioxol-5-yl)cyclopropyl]carbonyl}amino)-7-methoxy-3,4-dihydro-2H-chromen-2-yl]azetidine-1-carboxylate

Example 115A tert-butyl 3-(1-hydroxy-3-(2-hydroxy-4-methoxyphenyl)-3-oxopropyl)azetidine-1-carboxylate The title compound was prepared using the procedure similar to that described in Example 100A, substituting 1-(2-hydroxy-4-methoxyphenyl)ethanone for 4'-fluoro-2'-hydroxyacetophenone, and substituting tert-butyl 3-formylazetidine-1-carboxylate for benzyl 3-oxoazetidine-1-carboxylate. $^1$H NMR (400 MHz, CDCl$_3$) δ ppm 12.47 (s, 1H), 7.58 (d, J=8.8 Hz, 1H), 6.47-6.42 (m, 2H), 4.37-4.30 (m, 1H), 4.04-3.91 (m, 3H), 3.85 (s, 3H), 3.72 (dd, J=8.6, 5.6 Hz, 1H), 3.27 (d, J=3.6 Hz, 1H), 3.03 (dd, J=17.2, 2.6 Hz, 1H), 2.93 (dd, J=17.1, 9.0 Hz, 1H), 2.70-2.60 (m, 1H), 1.44 (s, 9H); MS (ESI) m/z 350 (M−H)−.

Example 115B tert-butyl 3-(7-methoxy-4-oxochroman-2-yl)azetidine-1-carboxylate The title compound was prepared using the procedure similar to that described in Example 100B, substituting the product from Example 115A for the product from Example 100A. $^1$H NMR (400 MHz, CDCl$_3$) δ ppm 7.82 (d, J=8.8 Hz, 1H), 6.60 (dd, J=8.8, 2.3 Hz, 1H), 6.44 (d, J=2.3 Hz, 1H), 4.56 (q, J=7.7 Hz, 1H), 4.15-3.99 (m, 4H), 3.84 (s, 3H), 2.91-2.81 (m, 1H), 2.57 (d, J=7.8 Hz, 2H), 1.46 (s, 9H); MS (ESI) m/z 665 (2M−H)−.

Example 115C tert-butyl 3-(7-methoxy-4-(methoxyimino)chroman-2-yl)azetidine-1-carboxylate A solution of the product from Example 115B (54 mg, 0.162 mmol) and O-methylhydroxylamine hydrochloride (40.6 mg, 0.486 mmol) in pyridine (1 mL) was heated at 60 OC for 90 minutes and then concentrated to remove the pyridine. The residue was partitioned between ethyl acetate (~30 mL) and water (~10 mL). The layers were separated and the ethyl acetate layer was washed with brine, dried (MgSO$_4$), filtered, and concentrated to provide the title compound (57 mg, 0.157 mmol, 97% yield). $^1$H NMR (400 MHz, CDCl$_3$) δ ppm 7.78 (d, J=8.8 Hz, 1H), 6.54 (dd, J=8.8, 2.5 Hz, 1H), 6.41 (d, J=2.6 Hz, 1H), 4.15 (ddd, J=12.1, 7.4, 3.1 Hz, 1H), 4.08-3.95 (m, 3H), 3.94 (s, 3H), 3.85 (ddd, J=8.9, 6.1, 2.8 Hz, 1H), 3.79 (s, 3H), 3.15 (dd, J=17.0, 3.0 Hz, 1H), 2.80 (qt, J=8.0, 5.6 Hz, 1H), 2.22 (dd, J=17.0, 12.0 Hz, 1H), 1.45 (s, 9H); MS (ESI) m/z 307 (M-tBu)+.

Example 115D tert-butyl 3-(4-amino-7-methoxychroman-2-yl)azetidine-1-carboxylate The title compound (as 1:1 mixture of cis and trans isomers) was prepared using the procedure similar to that described in Example 33E, substituting the product from Example 115C for the product from Example 33D. $^1$H NMR (400 MHz, CDCl$_3$) δ ppm 7.32 (d, J=8.5 Hz, 0.5H), 7.26 (s, 0.5H), 7.11 (d, J=8.4 Hz, 0.5H), 6.98 (s, 0.5H), 6.53 (dd, J=8.8, 2.6 Hz, 0.5H), 6.51 (dd, J=8.6, 2.5 Hz, 0.5H), 6.40 (d, J=2.5 Hz, 0.5H), 6.36 (d, J=2.5 Hz, 0.5H), 4.34 (td, J=7.9, 4.6 Hz, 0.5H), 4.20 (dd, J=10.3, 7.6 Hz, 0.5H), 4.10-3.80 (m, 6H), 3.76 (s, 3H), 2.82-2.69 (m, 1H), 2.11 (ddd, J=13.1, 6.0, 1.7 Hz, 0.5H), 1.75-1.69 (m, 1H), 1.45 (s, 5H), 1.43 (s, 4H); MS (ESI) m/z 355 (M+H)+.

Example 115E tert-butyl 3-[4-({[1-(2,2-difluoro-1,3-benzodioxol-5-yl)cyclopropyl]carbonyl}amino)-7-methoxy-3,4-dihydro-2H-chromen-2-yl]azetidine-1-carboxylate Using the procedure similar to that as described in Example 100F, substituting the product from Example 115D for the product from Example 100E, and the crude product was chromatographed on silica gel eluted with a gradient of 5%-100% ethyl acetate in CH$_2$Cl$_2$, provide the title compound as a 1:1 mixture of cis and trans isomers. $^1$H NMR (400 MHz, CDCl$_3$) δ ppm 7.15 (dd, J=8.1, 1.7 Hz, 0.5H), 7.13-7.09 (m, 1H), 7.07 (d, J=1.7 Hz, 0.5H), 7.02 (d, J=8.2 Hz, 0.5H), 7.01-6.96 (m, 1H), 6.89 (d, J=8.6 Hz, 0.5H), 6.49-6.45 (m, 1H), 6.35-6.32 (m, 1H), 5.44 (d, J=6.5 Hz, 0.5H), 5.33 (d, J=8.7 Hz, 0.5H), 5.28-5.20 (m, 0.5H), 4.92 (ddd, J=6.8, 4.6, 2.4 Hz, 0.5H), 4.19 (ddd, J=11.6, 6.9, 1.6 Hz, 0.5H), 4.06-3.95 (m, 2H), 3.93-3.88 (m, 1H), 3.86-3.75 (m, 1.5H), 3.74 (s, 1.5H), 3.73 (s, 1.5H), 2.78-2.64 (m, 1H), 2.22 (ddd, J=12.9, 6.0, 1.6 Hz, 0.5H), 2.01 (dt, J=14.2, 2.2 Hz, 0.5H), 1.76-1.61 (m, 2H), 1.46 (s, 4.5H), 1.44 (s, 4.5H), 1.07 (dq, J=11.6, 2.4, 2.0 Hz, 2H); MS (ESI) m/z 557 (M−H)−.

Example 116

N-[2-(azetidin-3-yl)-7-methoxy-3,4-dihydro-2H-chromen-4-yl]-1-(2,2-difluoro-1,3-benzodioxol-5-yl)cyclopropanecarboxamide A solution of the product from Example 115E (65.6 mg, 0.117 mmol) in trifluoroacetic acid (1 mL) was heated to 55° C. for 2 minutes, and concentrated to dryness. The residue was partitioned between 1 M NaOH (5 mL) and CH$_2$Cl$_2$ (25 mL). The aqueous layer was extracted with CH$_2$Cl$_2$ (10 mL). The combined CH$_2$Cl$_2$ layers were dried (MgSO$_4$), filtered, and concentrated to provide the title compound (40 mg, 0.087 mmol, 74.3% yield). $^1$H NMR (400 MHz, CDCl$_3$) δ ppm 7.15 (dd, J=8.1, 1.6 Hz, 0.5H), 7.12-7.09 (m, 1H), 7.08 (d, J=1.7 Hz, 0.5H), 7.04-6.96 (m, 1.5H), 6.89 (dd, J=8.6, 1.0 Hz, 0.5H), 6.46 (ddd, J=8.6, 3.8, 2.6 Hz, 1H), 6.37 (d, J=2.6 Hz, 0.5H), 6.35 (d, J=2.6 Hz, 0.5H), 5.45 (d, J=6.7 Hz, 0.5H), 5.33 (d, J=8.8 Hz, 0.5H), 5.24 (td, J=9.8, 8.7, 6.1 Hz, 0.5H), 4.91 (ddd, J=6.9, 4.7, 2.6 Hz, 0.5H), 4.23 (ddd, J=11.7, 7.0, 1.7 Hz, 0.5H), 3.90 (ddd, J=11.5, 7.0, 2.0 Hz, 0.5H), 3.86-3.55 (m, 4H), 3.74 (s, 1.5H), 3.74 (s, 1.5H), 3.01-2.87 (m, 1H), 2.21 (ddd, J=12.9, 6.2, 1.6 Hz, 0.5H), 1.97 (dt, J=14.3, 2.3 Hz, 0.5H), 1.75-1.60 (m, 2H), 1.12-1.01 (m, 2H); MS (ESI) m/z 459 (M+H)$^+$.

Example 117

1-(2,2-difluoro-1,3-benzodioxol-5-yl)-N-{7-methoxy-2-[1-(methylsulfonyl)azetidin-3-yl]-3,4-dihydro-2H-chromen-4-yl}cyclopropanecarboxamide The title compound as a 1:1 mixture of cis and trans isomers was prepared using procedure similar to that described in Example 101, substituting the product from Example 116 for the product from Example 93, and the crude product was chromatographed on silica gel eluted with a gradient of 5%-100% ethyl acetate in CH$_2$Cl$_2$. $^1$H NMR (400 MHz, CDCl$_3$) δ ppm 7.16 (dd, J=8.1, 1.7 Hz, 0.5H), 7.13-7.10 (m, 1H), 7.07 (d, J=1.8 Hz, 0.5H), 7.05-6.97 (m, 1.5H), 6.90 (dd, J=8.6, 1.0 Hz, 0.5H), 6.51-6.47 (m, 1H), 6.32 (d, J=2.8 Hz, 0.5H), 6.31 (d, J=2.7 Hz, 0.5H), 5.44 (d, J=6.4 Hz, 0.5H), 5.34 (d, J=8.7 Hz, 0.5H), 5.28-5.21 (m, 0.5H), 4.92 (ddd, J=6.6, 4.6, 2.3 Hz, 0.5H), 4.22 (ddd, J=11.8, 6.0, 1.6 Hz, 0.5H), 4.04-3.82 (m, 4.5H), 3.74 (s, 1.5H), 3.74 (s, 1.5H), 2.90 (s, 1.5H), 2.89 (s, 1.5H), 2.87-2.77 (m, 1H), 2.22 (ddd, J=13.0, 6.1, 1.6 Hz, 0.5H), 2.01 (dt, J=14.1, 2.2 Hz, 0.5H), 1.76-1.63 (m, 2H), 1.12-1.04 (m, 2H); MS (ESI) m/z 535 (M−H)$^−$.

Example 118 methyl rac-3-[(2R,4S)-4-({[1-(2,2-difluoro-1,3-benzodioxol-5-yl)cyclopropyl]carbonyl}amino)-7-fluoro-3,4-dihydro-2H-pyrano[2,3-b]pyridin-2-yl]benzoate Example 118A methyl rac-3-((2R,4S)-4-azido-7-fluoro-3,4-dihydro-2H-pyrano[2,3-b]pyridin-2-yl)benzoate The title compound was prepared using the procedure similar to that described in Example 112E, substituting the product from Example 113C for the product from Example 112D. $^1$H NMR (400 MHz, CDCl$_3$) δ ppm 8.13 (s, 1H), 8.04 (d, J=7.7 Hz, 1H), 7.74 (t, J=7.9 Hz, 1H), 7.68 (d, J=7.7 Hz, 1H), 7.50 (t, J=7.8 Hz, 1H), 6.66 (dd, J=8.1, 2.8 Hz, 1H), 5.46 (dd, J=11.7, 2.3 Hz, 1H), 4.75 (t, J=3.1 Hz, 1H), 3.93 (s, 3H), 2.31 (dt, J=14.4, 2.5 Hz, 1H), 2.19 (ddd, J=14.7, 11.6, 3.9 Hz, 1H); MS (ESI) m/z 329 (M+H)$^+$.

Example 118B methyl rac-3-((2R,4S)-4-amino-7-fluoro-3,4-dihydro-2H-pyrano[2,3-b]pyridin-2-yl)benzoate The title compound was prepared using the procedure similar to that described in Example 112F, substituting the product from Example 118A for the product from Example 112E. $^1$H NMR (400 MHz, CDCl$_3$) δ ppm 8.13 (s, 1H), 8.02 (d, J=7.9 Hz, 1H), 7.75 (t, J=8.0 Hz, 1H), 7.69 (d, J=7.9 Hz, 1H), 7.48 (t, J=7.8 Hz, 1H), 6.59 (dd, J=8.0, 2.8 Hz, 1H), 5.57 (dd, J=10.5, 2.9 Hz, 1H), 4.15 (t, J=3.5 Hz, 1H), 3.93 (s, 3H), 2.21-2.07 (m, 2H); MS (ESI) m/z 303 (M+H)$^+$.

Example 118C methyl rac-3-[(2R,4S)-4-({[1-(2,2-difluoro-1,3-benzodioxol-5-yl)cyclopropyl]carbonyl}amino)-7-fluoro-3,4-dihydro-2H-pyrano[2,3-b]pyridin-2-yl]benzoate The title compound was prepared using the procedure similar to that described in Example 1 OF, substituting the product from Example 118B for the product from Example 100E. $^1$H NMR (400 MHz, CDCl$_3$) δ ppm 7.97 (d, J=7.6 Hz, 1H), 7.93 (s, 0H), 7.58 (t, J=8.0 Hz, 1H), 7.44 (d, J=8.2 Hz, 1H), 7.39 (t, J=7.6 Hz, 1H), 7.18 (dd, J=8.1, 1.6 Hz, 1H), 7.15 (d, J=1.5 Hz, 1H), 7.06 (d, J=8.2 Hz, 1H), 6.44 (dd, J=8.2, 2.6 Hz, 1H), 5.89 (d, J=7.0 Hz, 1H), 5.09-4.96 (m, 2H), 3.94 (s, 3H), 2.28 (dt, J=14.4, 2.7 Hz, 1H), 2.12-1.99 (m, 1H), 1.75-1.63 (m, 2H), 1.19-1.05 (m, 2H); MS (ESI) m/z 525 (M−H)$^−$.

Example 119

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid Example 119A 8-fluoro-4H-chromen-4-one The title compound was prepared using the conditions similar to that described in Example 39A, substituting 1-(3-fluoro-2-hydroxyphenyl)ethanone for 1-(4-fluoro-2-hydroxyphenyl)ethanone.

Example 119B (R)-methyl 3-(8-fluoro-4-oxochroman-2-yl)benzoate

The title compound was prepared using the conditions similar to that described in Example 39B, substituting Example 119A for Example 39A.

Example 119C (R)-methyl 3-(8-fluoro-4-(methoxyimino)chroman-2-yl)benzoate

The title compound was prepared using the conditions similar to that described in Example 39C, substituting Example 119B for Example 39B.

Example 119D methyl 3-((2R,4R)-4-amino-8-fluorochroman-2-yl)benzoate

The title compound was prepared using the conditions similar to that described in Example 39D, substituting Example 119C for Example 39C.

Example 119E methyl 4-((2R,4R)-4-(1-(2,2-difluorobenzo[d][1,3]dioxol-5-yl)cyclopropanecarboxamido)-8-fluorochroman-2-yl)benzoate The title compound was prepared using the conditions similar to that described in Example 39E, substituting Example 119D for Example 39D.

Example 119F

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid The title compound was prepared using the conditions similar to that described in Example 38, substituting Example 119E for Example 39E. $^1$H NMR (400 MHz, CDCl$_3$) δ 8.17 (s, 1H), 8.05 (s, 1H), 7.67 (s, 1H), 7.47 (s, 1H), 7.19-7.05 (m, 3H), 7.02 (d, J=8.1 Hz, 1H), 6.86-6.81 (m, 2H), 5.56 (s, 1H), 5.37 (dd, J=46.4, 10.0 Hz, 2H), 2.58 (s, 1H), 1.82 (d, J=30.1 Hz, 2H), 1.66 (d, J=15.0 Hz, 1H), 1.10 (d, J=3.6 Hz, 2H); MS (ESI−) m/z=510 (M−H)$^-$.

Example 120 methyl 4-[(2R,4R)-4-({[1-(2,2-difluoro-1,3-benzodioxol-5-yl)cyclopropyl]carbonyl}amino)-3,4-dihydro-2H-chromen-2-yl]benzoate

Example 120A (R)-methyl 4-(4-oxochroman-2-yl)benzoate

A mixture of bis(2,2-trifluoroacetoxy)palladium (0.341 g, 1.026 mmol), (S)-4-(tert-butyl)-2-(pyridin-2-yl)-4,5-dihydrooxazole (0.252 g, 1.232 mmol), ammonium hexafluorophosphate(V) (1.004 g, 6.16 mmol), methyl 4-(4,4,5,5-tetramethyl-1,3,2-dioxaborolan-2-yl)benzoate (4.04 g, 15.40 mmol) and dichloroethane (8 mL) in a 20 ml vial was stirred at room temperature for 5 minutes, followed by the addition of 4H-chromen-4-one (CAS 11013-97-1, 1.5 g, 10.26 mmol) and water (0.256 mL, 14.19 mmol). The vial was capped and the mixture was stirred at 60° C. overnight. The reaction mixture gradually turned to black with Pd plated out on the sides of the vial. The mixture was filtered through a plug of celite and eluted with ethyl acetate to give a red solution, which was washed with water and dried over MgSO$_4$. After filtration, the solvent was removed in vacuo. The crude material was chromatographed using a 100 g silica gel cartridge and eluted with a gradient of 5-40% ethyl acetate in heptane to yield title compound (1.66 g, 57.3% yield). $^1$H NMR (400 MHz, CDCl$_3$) δ 8.16-8.06 (m, 2H), 7.94 (dd, J=8.0, 1.7 Hz, 1H), 7.62-7.47 (m, 3H), 7.14-7.02 (m, 2H), 5.56 (dd, J=13.1, 3.1 Hz, 1H), 3.94 (s, 3H), 3.13-2.86 (m, 2H); LC/MS (ESI+)=283 (M+1)$^+$.

Example 120B (R)-Methyl 4-(4-(methoxyimino)chroman-2-yl)benzoate

A mixture of Example 120A (1.65 g, 5.85 mmol), sodium acetate (0.959 g, 11.69 mmol) and O-methylhydroxylamine, hydrochloric acid (0.976 g, 11.69 mmol) in methanol (20 mL) was stirred at 60° C. overnight. Solvent was removed under reduced pressure and the residue dissolved in ethyl acetate and washed with water. The organic layer was dried over MgSO$_4$, filtered, and concentrated. The residue was washed with ether to provide the title compound (1.758 g, 97% yield). $^1$H NMR (400 MHz, CDCl$_3$) δ 8.16-8.04 (m, 2H), 7.93 (dd, J=8.2, 1.7 Hz, 1H), 7.62-7.47 (m, 2H), 7.32-7.26 (m, 1H), 7.01-6.95 (m, 2H), 5.13 (dd, J=12.4, 3.2 Hz, 1H), 3.99 (s, 3H), 3.93 (s, 3H), 3.48 (dd, J=17.2, 3.2 Hz, 1H), 2.66 (dd, J=17.2, 12.3 Hz, 1H); MS(ESI+): m/z=312 (M+H)$^+$.

Example 120C

Methyl 4-((2R,4R)-4-aminochroman-2-yl)benzoate

The product from Example 120B (1.75 g, 5.62 mmol) was treated with 5% platinum (0.05 equivalent) on carbon in acetic acid (10 mL). The reaction mixture was stirred for 24 hours at room temperature under hydrogen (1 atmosphere). LC/MS showed the conversion was over 95%, with a little over reduced by-product detected. The reaction mixture was filtered through a celite pad and the solvent removed under reduced pressure. Tert-butyl methylether was added to the residue, followed by drop wise addition of 4 M HCl in tetrahydrofuran solution (2 mL). The mixture was stirred for 1 hour at room temperature. The precipitated white solid was collected by filtration, washed with ether, and dried to provide the hydrochloride salt of the title compound (1.2 g, 66.8% yield). $^1$H NMR (400 MHz, CDCl$_3$) δ 8.08 (d, J=7.9 Hz, 2H), 7.50 (dd, J=23.2, 7.8 Hz, 3H), 7.20 (t, J=7.8 Hz, 1H), 7.07-6.84 (m, 2H), 5.22 (d, J=11.4 Hz, 1H), 4.36 (dd, J=10.8, 5.8 Hz, 1H), 3.93 (s, 3H), 2.46 (dd, J=13.2, 5.8 Hz, 1H), 2.00-1.85 (m, 1H); MS(ESI+) m/z=267 (M-NH$_2$)$^+$.

Example 120D

Methyl 4-((2R,4R)-4-(1-(2,2-difluorobenzo[d][1,3]dioxol-5-yl)cyclopropanecarboxamido)chroman-2-yl)benzoate To 1-(2,2-difluorobenzo[d][1,3]dioxol-5-yl)cyclopropanecarboxylic acid (300 mg, 1.239 mmol) in DMF (2 mL) was added HATU (1-[bis(dimethylamino)methylene]-1H-1,2,3-triazolo[4,5-b]pyridinium 3-oxid hexafluorophosphate, 642 mg, 1.689 mmol). The mixture was stirred for 5 minutes at room temperature, followed by the addition of Example 120C (319 mg, 1.0 mmol), and N-ethyl-N-isopropylpropan-2-amine (0.785 mL, 4.50 mmol). The mixture was stirred at room temperature for 2 hours, LC/MS showed the conversion was complete. The reaction mixture was directly loaded on a 50 g silica gel cartridge, eluting with 5-50%, ethyl acetate in heptane to provide the title compound (320 mg, 56.0% yield). $^1$H NMR (400 MHz, CDCl$_3$) δ 8.07-8.02 (m, 2H), 7.50-7.44 (m, 2H), 7.21-7.15 (m, 1H), 7.14-7.05 (m, 3H), 7.00 (d, J=8.2 Hz, 1H), 6.96-6.87 (m, 2H), 5.53-5.44 (m, 1H), 5.38 (d, J=8.8 Hz, 1H), 5.24 (dd, J=11.3, 1.9 Hz, 1H), 3.93 (s, 3H), 2.52 (ddd, J=13.3, 6.1, 2.1 Hz, 1H), 1.84-1.72 (m, 2H), 1.26 (s, 1H), 1.08 (td, J=3.5, 2.1 Hz, 2H); MS (ESI−) m/z=506.1 (M−H)$^-$.

Example 121

4-[(2R,4R)-4-({[1-(2,2-difluoro-1,3-benzodioxol-5-yl)cyclopropyl]carbonyl}amino)-3,4-dihydro-2H-chromen-2-yl]benzoic acid To Example 120D (300 mg, 0.591 mmol) in methanol (4 mL) and water (1.0 mL) was added lithium hydroxide (85 mg, 3.55 mmol). The mixture was stirred at 35° C. for 4 hours. LC/MS showed reaction was complete. Solvent was removed under reduced pressure. Water (4 mL) added to the residue and the pH of the mixture was adjusted to pH 1-2 with the addition of 2 M HCl. The precipitated white solid was collected by filtration, and dried to provide the title compound (252 mg, 0.511 mmol, 86% yield). $^1$H NMR (501 MHz, CDCl$_3$) δ 8.11 (d, J=7.8 Hz, 2H), 7.47 (d, J=7.9 Hz, 2H), 7.17 (t, J=7.6 Hz, 1H), 7.13-6.98 (m, 4H), 6.90 (dd, J=13.1, 5.7 Hz, 2H), 5.49 (s, 1H), 5.42 (d, J=8.6 Hz, 1H), 5.23 (d, J=11.1 Hz, 1H), 2.53 (s, 1H), 1.76 (d, J=10.9 Hz, 2H), 1.66 (d, J=10.4 Hz, 1H), 1.08 (s, 2H); MS (ESI−) m/z=492 (M−H)$^−$.

Example 122

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid To Example 123E (130 mg, 0.227 mmol) in methanol (2 mL) and water (0.5 mL) was added lithium hydroxide (32.6 mg, 1.360 mmol). The mixture was stirred at 35° C. for 4 hours, LC/MS showed the conversion was complete. Solvent was removed under reduced pressure and water (2 mL) was added. The pH of the mixture was adjusted to pH 1-2 with the addition of 2 M HCl. The precipitated white solid was collected by filtration, and dried to provide the title compound (110 mg, 0.197 mmol, 87% yield). $^1$H NMR (400 MHz, CDCl$_3$) δ 8.17-8.03 (m, 2H), 7.49 (d, J=8.2 Hz, 2H), 7.16-6.99 (m, 4H), 6.73-6.67 (m, 2H), 6.38 (d, J=73.6 Hz, 1H), 5.48 (td, J=10.4, 6.1 Hz, 1H), 5.36 (d, J=8.8 Hz, 1H), 5.31-5.21 (m, 1H), 2.52 (ddd, J=13.3, 6.0, 2.2 Hz, 1H), 1.86-1.71 (m, 2H), 1.68-1.60 (m, 1H), 1.10 (q, J=3.7, 2.4 Hz, 2H); MS (ESI−) m/z=558 (M−H)$^−$.

Example 123 methyl 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoate Example 123A (R)-methyl 4-(7-hydroxy-4-oxochroman-2-yl)benzoate A mixture of bis(2,2,2-trifluoroacetoxy)palladium (271 mg, 0.816 mmol), (S)-4-(tert-butyl)-2-(pyridin-2-yl)-4,5-dihydrooxazole (200 mg, 0.979 mmol), ammonium hexafluorophosphate(V) (798 mg, 4.90 mmol), (4-(methoxycarbonyl)phenyl)boronic acid (2203 mg, 12.24 mmol) and dichloroethane (8 mL) in a 20 mL vial was stirred for 5 minutes at room temperature, followed by the addition of 7-hydroxy-4H-chromen-4-one (CAS 59887-89-7, MFCD00209371, 1323 mg, 8.16 mmol) and water (256 mg, 14.19 mmol). The vial was capped and the mixture was stirred at 60° C. overnight. The reaction gradually turned black, with Pd plated out on the sides of the vial. The mixture was filtered through a plug of celite and eluted with ethyl acetate to give a red solution which was washed with brine. The solvent was removed in vacuo and the crude material was chromatographed using a 100 g silica gel cartridge and eluted with a gradient of 5-40% ethyl acetate in heptane to provide the title compound (1.62 g, 66.6% yield). $^1$H NMR (400 MHz, CDCl$_3$) δ 8.15-8.04 (m, 2H), 7.87 (d, J=8.7 Hz, 1H), 7.60-7.49 (m, 2H), 6.62-6.45 (m, 2H), 5.87 (s, 1H), 5.53 (dd, J=12.8, 3.2 Hz, 1H), 3.94 (s, 3H), 3.07-2.80 (m, 2H); MS (ESI+) m/z=299 (M+H)$^+$.

Example 123B (R)-methyl 4-(7-hydroxy-4-(methoxyimino)chroman-2-yl)benzoate

The mixture of Example 123A (960 mg, 3.22 mmol), sodium acetate (528 mg, 6.44 mmol) and O-methylhydroxylamine, hydrochloric acid (538 mg, 6.44 mmol) in methanol (10 mL) was stirred at 60° C. overnight. Solvent was removed under reduced pressure. The residue was dissolved in ethyl acetate and washed with water. The organic layers was dried over MgSO$_4$, filtered, and concentrated. The residue was washed with ether to provide the title compound (810 mg, 2.475 mmol, 77% yield). $^1$H NMR (400 MHz, CDCl$_3$) δ 8.15-8.03 (m, 2H), 7.81 (d, J=8.7 Hz, 1H), 7.58-7.43 (m, 2H), 6.50 (dd, J=8.6, 2.5 Hz, 1H), 6.45 (d, J=2.5 Hz, 1H), 5.21 (d, J=3.0 Hz, 1H), 5.12 (dd, J=12.2, 3.2 Hz, 1H), 3.95 (s, 3H), 3.93 (s, 3H), 3.45 (dd, J=17.2, 3.2 Hz, 1H), 2.63 (dd, J=17.2, 12.2 Hz, 1H); MS (ESI+) m/z 328 (M+H)$^+$.

Example 123C

Methyl 4-((2R,4R)-4-amino-7-hydroxychroman-2-yl)benzoate

A mixture of Example 123B (570 mg, 1.741 mmol) was treated with 5% platinum (0.05 equivalent) on carbon in acetic acid (5 mL). The reaction was stirred at room temperature under hydrogen (1 atmosphere) for 24 hours, LC/MS showed conversion over 95%. The mixture was filtered through a celite pad and solvent removed under reduced pressure. The residue was purified by preparative LC method TFA2 to provide the trifluroroacetic acid salt of the title compound (300 mg, 44% yield). LC/MS m/z 283 (M-NH$_2$)$^+$.

Example 123D methyl 4-((2R,4R)-4-(1-(2,2-difluorobenzo[d][1,3] dioxol-5-yl)cyclopropanecarboxamido)-7-hydroxychroman-2-yl)benzoate A mixture of 1-(2,2-difluorobenzo[d][1,3]dioxol-5-yl)cyclopropanecarboxylic acid (162 mg, 0.668 mmol) and HATU (1-[bis(dimethylamino)methylene]-1H-1,2,3-triazolo[4,5-b]pyridinium 3-oxid hexafluorophosphate, 380 mg, 1.0 mmol) in DMF (2 mL) was stirred for 5 minutes at room temperature, followed by the addition of Example 123C (200 mg, 0.334 mmol) and N-ethyl-N-isopropylpropan-2-amine (0.466 ml, 2.67 mmol). The mixture was stirred at room temperature for 2 hours, LC/MS showed reaction complete. The mixture was loaded on to a 25 g silica gel cartridge eluting with 5-50% ethyl acetate in heptane provide the title compound (204 mg, 58.3% yield). $^1$H NMR (400 MHz, CDCl$_3$) δ 8.11-7.90 (m, 2H), 7.42 (d, J=8.0 Hz, 2H), 7.16-7.02 (m, 2H), 6.94 (dd, J=37.7, 8.3 Hz, 2H), 6.49-6.32 (m, 2H), 5.67 (s, 1H), 5.36 (dt, J=15.3, 8.7 Hz, 2H), 5.18 (d, J=10.7 Hz, 1H), 3.93 (s, 3H), 2.56-2.36 (m, 1H), 1.80-1.70 (m, 2H), 1.26 (d, J=2.2 Hz, 1H), 1.10-1.04 (m, 2H); MS (ESI−) m/z=521.9 (M−H)$^−$.

Example 123E

Methyl 4-((2R,4R)-4-(1-(2,2-difluorobenzo[d][1,3]dioxol-5-yl)cyclopropanecarboxamido)-7-(difluoromethoxy)chroman-2-yl)benzoate To Example 123D (190 mg, 0.363 mmol) and diethyl (bromodifluoromethyl)phosphonate (0.129 ml, 0.726 mmol) in a mixture of acetonitrile (2 mL) and water (1 mL) was added 50% aqueous potassium hydroxide (244 mg, 2.178 mmol) drop wise via syringe while stirring vigorously. After the addition was completed, LC/MS showed conversion was complete with a small by-product peak. Additional water was added to the mixture and the mixture was extracted with ethyl acetate (3×20 mL). The combined organic extracts were washed with 1 M HCl (5 mL) and water, dried over $MgSO_4$, filtered, and concentrated. The residue was purified by preparative LC method TFA2 to provide the title compound (150 mg, 72% yield). $^1$H NMR (400 MHz, $CDCl_3$) δ 8.09-8.00 (m, 2H), 7.49-7.41 (m, 2H), 7.15-6.99 (m, 4H), 6.75-6.66 (m, 2H), 5.50-5.40 (m, 1H), 5.33 (d, J=8.9 Hz, 1H), 5.25 (dd, J=11.3, 2.0 Hz, 1H), 3.93 (s, 3H), 2.50 (ddd, J=13.4, 6.1, 2.1 Hz, 1H), 1.84-1.71 (m, 2H), 1.65 (d, J=2.8 Hz, 1H), 1.11-1.06 (m, 2H); MS (ESI–) m/z=572 (M–H)⁻.

Example 124

1-(2,2-difluoro-1,3-benzodioxol-5-yl)-N-(7-hydroxy-2,2-dimethyl-3,4-dihydro-2H-chromen-4-yl)cyclopropanecarboxamide

Example 124A 7-hydroxy-2,2-dimethylchroman-4-one O-methyl oxime

The mixture of 7-hydroxy-2,2-dimethylchroman-4-one (cas#17771-33-4) (680 mg, 3.54 mmol), sodium acetate (580 mg, 7.08 mmol) and O-methylhydroxylamine, hydrochloric acid (591 mg, 7.08 mmol) in methanol (10 mL) was stirred at 60° C. overnight. Solvent was evaporated under reduced pressure. The resulting residue was dissolved in ethyl acetate, and washed with brine, dried over $MgSO_4$, and filtered. The solvent was removed under reduced pressure to give the title compound (740 mg, 95%). LC/MS (ESI+) m/z 222 (M+H)⁺.

Example 124B 4-amino-2,2-dimethylchroman-7-ol hydrochloride

To Example 124A (740 mg, 3.34 mmol) and acetic acid (10 mL) in a 50 mL pressure bottle was added 5% Pt/C wet (240 mg, 0.506 mmol). The mixture was stirred at 30 psi of hydrogen and at room temperature for 40 hours. The reaction mixture was filtered, and the solvent was removed. Diethyl ether (10 mL) was added to the resulting residue, followed by drop wise addition of 4N HCl in dioxane (1 mL). The white solid was collected by filtration and dried to yield title compound (460 mg, 60%). LC/MS (ESI+) m/z=177 (M-$NH_2$)⁺.

Example 124C 1-(2,2-difluoro-1,3-benzodioxol-5-yl)-N-(7-hydroxy-2,2-dimethyl-3,4-dihydro-2H-chromen-4-yl)cyclopropanecarboxamide To 1-(2,2-difluorobenzo[d][1,3]dioxol-5-yl)cyclopropanecarboxylic acid (CAS 68015-98-5) (485 mg, 2.0 mmol) in N,N-dimethylformamide (4 mL) was added HATU (1-[bis(dimethylamino)methylene]-1H-1,2,3-triazolo[4,5-b]pyridinium 3-oxid hexafluorophosphate) (1142 mg, 3.00 mmol). The mixture was stirred at room temperature for 5 minutes, and Example 124B was added, followed by addition of N-ethyl-N-isopropylpropan-2-amine (1.395 mL, 8.01 mmol). The mixture was stirred at room temperature for 2 hours. The mixture was purification by chromatography, eluting with a gradient of 0-50% ethyl acetate in heptane, to yield the title compound (505 mg, 1.210 mmol, 60.4% yield). $^1$H NMR (400 MHz, $CDCl_3$) δ 7.20-7.07 (m, 2H), 7.01 (d, J=8.2 Hz, 1H), 6.88 (dd, J=8.5, 1.0 Hz, 1H), 6.36 (dd, J=8.4, 2.5 Hz, 1H), 6.23 (d, J=2.6 Hz, 1H), 5.41-5.25 (m, 2H), 5.23-5.08 (m, 1H), 2.11 (dd, J=13.2, 6.2 Hz, 1H), 1.76-1.63 (m, 2H), 1.50 (dd, J=13.2, 10.5 Hz, 1H), 1.32 (s, 3H), 1.26 (s, 3H), 1.09 (td, J=3.2, 1.5 Hz, 2H); MS (ESI) m/z 417.7 (M+H)⁺.

Example 125

1-(2,2-difluoro-1,3-benzodioxol-5-yl)-N-[7-(difluoromethoxy)-2,2-dimethyl-3,4-dihydro-2H-chromen-4-yl]cyclopropanecarboxamide The product of Example 124C (150 mg, 0.359 mmol) and diethyl(bromodifluoromethyl)phosphonate (0.128 mL, 0.719 mmol) in a mixture of acetonitrile (10 mL) and water (5 mL) were cooled to <5° C. in an ice-water bath. Potassium hydroxide (0.185 mL, 2.156 mmol, 50% water solution) was added drop wise via syringe while stirring vigorously. The mixture was stirred at room temperature for 30 minutes. The reaction mixture was diluted with water (5 mL) and extracted with methyl tert-butyl ether (3×10 mL). The combined extracts were washed with 1M HCl (5 mL) and purified by LC/MS method TFA1 to provide the title compound (85 mg, 50.6%). $^1$H NMR (400 MHz, $CDCl_3$) δ 7.15 (dd, J=8.1, 1.7 Hz, 1H), 7.11 (d, J=1.6 Hz, 1H), 7.03 (dd, J=8.3, 1.2 Hz, 2H), 6.63-6.59 (m, 1H), 6.51 (d, J=2.4 Hz, 1H), 6.44, (1H), 5.35 (d, J=8.8 Hz, 1H), 5.26-5.17 (m, 1H), 2.12 (dd, J=13.2, 6.2 Hz, 1H), 1.76-1.64 (m, 2H), 1.52 (dd, J=13.2, 10.9 Hz, 1H), 1.35 (s, 3H), 1.29 (s, 3H), 1.15-1.05 (m, 2H); MS(ESI+) m/z=468 (M+H)⁺.

Example 126

1-(2,2-difluoro-1,3-benzodioxol-5-yl)-N-[7-methoxy-2-(tetrahydrofuran-2-yl)-3,4-dihydro-2H-chromen-4-yl]cyclopropanecarboxamide

Example 126A 2-acetyl-5-methoxyphenyl tetrahydrofuran-2-carboxylate

Oxalyl chloride (14.83 mL, 175 mmol) was added drop wise via syringe to a mixture of tetrahydrofuran-2-carboxylic acid (18.5 g, 159 mmol) and N,N-dimethylformamide (0.116 g, 1.593 mmol) in $CH_2Cl_2$ (100 mL) at 0° C. under a nitrogen atmosphere. The mixture was stirred for another 1 hour and then was added dropwise via syringe to a mixture of 1-(2-hydroxy-4-methoxyphenyl)ethanone (CAS 552-41-0) (26.5 g, 159 mmol) and triethylamine (66.6 mL, 478 mmol) in $CH_2Cl_2$ (100 mL) at 0° C. The resulting mixture was stirred at room temperature for about 3 hours. The reaction mixture was diluted with ethyl acetate, washed with brine, dried over $Na_2SO_4$, filtered, and concentrated under reduced pressure. The residue was chromatographed on silica gel eluting with 0-90% ethyl acetate in hexanes to provide the title compound (36.5 g, 138 mmol, 87% yield). $^1$H NMR (400 MHz, CDCl$_3$) δ 7.84 (d, J=8.8 Hz, 1H), 6.85 (dd, J=8.8, 2.5 Hz, 1H), 6.65 (d, J=2.5 Hz, 1H), 4.78 (dd, J=8.5, 5.4 Hz, 1H), 4.18-4.09 (m, 1H), 4.06-3.98 (m, 1H), 3.88 (s, 3H), 2.54 (s, 1H), 2.58-2.45 (m, 3H), 2.47-2.33 (m, 1H), 2.23-2.08 (m, 1H), 2.10-1.95 (m, 1H); MS (ESI+) m/z 265 (M+H)$^+$.

Example 126B 1-(2-hydroxy-4-methoxyphenyl)-3-(tetrahydrofuran-2-yl)propane-1,3-dione A solution of the product from Example 126A (18 g, 68.1 mmol) in tetrahydrofuran (200 mL) under an atmosphere of N$_2$ was cooled to −70° C. and treated with a 1 M solution of lithium bis(trimethylsilyl)amide in tetrahydrofuran (170 mL, 170 mmol). The reaction mixture was stirred for 2 hours at room temperature. The organic layer was washed with sat NH$_4$Cl (3×20 mL), dried with Na$_2$SO$_4$, filtered, and concentrated to provide the titled compound (18 g, 54.5 mmol, 80% yield). MS (ESI+) m/z 265 (M+H)$^+$.

Example 126C 7-methoxy-2-(tetrahydrofuran-2-yl)-4H-chromen-4-one

A solution of the product from Example 126B (10 g, 37.8 mmol) in CH$_2$Cl$_2$ (100 mL) was treated with iron(III) chloride (18.41 g, 114 mmol). The resulting suspension was stirred at room temperature overnight. The reaction was filtered and concentrated to provide the title compound (9.32 g, 31.0 mmol, 82% yield). MS (ESI+) m/z 247 (M+H)$^+$.

Example 126D 7-methoxy-2-(tetrahydrofuran-2-yl)chroman-4-one

The product from Example 126C (12 g, 48.7 mmol) was treated with Pd/C (3.37 g) and triethyl amine (34.0 mL, 244 mmol) in ethyl acetate (100 mL). The reaction was stirred at room temperature overnight. The mixture was filtered and the solvent removed in vacuo. The crude material was purified by chromatography on silica gel, eluting with 0-90% ethyl acetate in petroleum ether to provide the title compound (1.7 g, 6.85 mmol, 14.05% yield). $^1$H NMR (400 MHz, CDCl$_3$) δ 7.83 (d, J=8.8 Hz, 1H), 6.59 (dd, J=8.8, 2.4 Hz, 1H), 6.46 (d, J=2.3 Hz, 1H), 4.45-4.38 (m, 1H), 4.20-4.12 (m, 1H), 3.98-3.91 (m, 1H), 3.85 (s, 3H), 3.89-3.82 (m, 1H), 2.79 (dd, J=16.9, 12.2 Hz, 1H), 2.71 (dd, J=16.8, 3.8 Hz, 1H), 2.17-2.08 (m, 1H), 2.02-1.86 (m, 3H); MS (ESI+) m/z 249 (M+H)$^+$.

Example 126E 7-methoxy-2-(tetrahydrofuran-2-yl)chroman-4-one oxime

The product from Example 126D (700 mg, 2.82 mmol) was treated with hydroxylamine hydrochloride (294 mg, 4.23 mmol) and sodium acetate (347 mg, 4.23 mmol) in methanol (1 mL). The reaction was stirred at ambient temperature for 3 hours. The mixture was concentrated to dryness and the residue was purified by chromatography on silica gel, eluting with 0-90% ethyl acetate in petroleum ether to provide the title compound (742 mg, 2.82 mmol, 100% yield). MS (ESI+) m/z 264 (M+H)$^+$.

Example 126F 7-methoxy-2-(tetrahydrofuran-2-yl)chroman-4-amine hydrochloride

Methanol (10 mL) was treated for 1 minute with a stream of NH$_3$ gas. The product from Example 126E (0.742 g, 2.82 mmol) was added followed by nickel (0.165 g, 2.82 mmol). The mixture was stirred at room temperature under 5 atmospheres of H$_2$ for 24 hours. The mixture was filtered and the filtrate was concentrated to dryness. The residue was treated with HCl in diethyl ether, then concentrated to provide the titled compound (0.762 g, 2.67 mmol, 95% yield). MS (ESI+) m/z 233 (M-NH$_3$)$^+$.

Example 126G 1-(2,2-difluoro-1,3-benzodioxol-5-yl)-N-[7-methoxy-2-(tetrahydrofuran-2-yl)-3,4-dihydro-2H-chromen-4-yl]cyclopropanecarboxamide A mixture of the product from Example 126F (50.7 mg, 0.177 mmol), 1-(2,2-difluorobenzo[d][1,3]dioxol-5-yl)cyclopropanecarboxylic acid (55.9 mg, 0.231 mmol) and HATU (1-[bis(dimethylamino)methylene]-1H-1,2,3-triazolo[4,5-b]pyridinium 3-oxid hexafluorophosphate) (101 mg, 0.266 mmol) in tetrahydrofuran (2 mL) under N$_2$ was treated with triethylamine (99 µL, 0.710 mmol) and stirred overnight at room temperature. The mixture was partitioned between methyl tert-butyl ether (30 mL) and 10% citric acid (15 mL). The layers were separated and the methyl tert-butyl ether layer was washed with saturated NaHCO$_3$ solution (about 15 mL), washed with brine, dried (MgSO$_4$), filtered, and concentrated. The residue was purified by chromatography on silica gel eluting with a gradient of 50-100% [9:1 CH$_2$Cl$_2$:ethyl acetate] in heptane to provide the title compound (67.9 mg, 0.143 mmol, 81% yield). $^1$H NMR (400 MHz, CDCl$_3$) δ 7.18-7.07 (m, 2H), 7.05-6.98 (m, 1.5H), 6.93 (d, J=8.7 Hz, 0.5H), 6.50-6.43 (m, 1.5H), 6.40 (d, J=2.4 Hz, 0.5H), 5.70 (d, J=8.9 Hz, 0.5H), 5.46 (d, J=6.8 Hz, 0.5H), 5.31-5.22 (m, 0.5H), 5.03-4.95 (m, 0.5H), 4.10-3.83 (m, 2H), 3.82-3.65 (m, 4H), 2.29 (ddd, J=13.2, 6.2, 2.3 Hz, 0.5H), 2.10-1.83 (m, 4.5H), 1.77-1.57 (m, 3H), 1.15-1.00 (m, 2H); MS (ESI−) m/z 472 (M−H)$^−$.

Example 127 methyl 4-[(2R,4R)-4-({[1-(2,2-difluoro-1,3-benzodioxol-5-yl)cyclopropyl]carbonyl}amino)-7-hydroxy-3,4-dihydro-2H-chromen-2-yl]benzoate The title compound was prepared as described in Example 123D.

Example 128

4-[(2R,4R)-4-({[1-(2,2-difluoro-1,3-benzodioxol-5-yl)cyclopropyl]carbonyl}amino)-7-hydroxy-3,4-dihydro-2H-chromen-2-yl]benzoic acid To the product of Example 127 (33 mg, 0.063 mmol) in methanol (2 mL) and water (0.5 mL) was added lithium hydroxide (15.10 mg, 0.630 mmol). The mixture was stirred at 35° C. for 4 hours. Solvent was removed and water (1 mL)

was added. The pH of the reaction mixture was adjusted with 2M HCl to about 1-2. The white solid precipitated was collected by filtration and dried to yield title compound (30 mg, 93% yield). $^1$H NMR (400 MHz, DMSO-d$_6$) δ 9.38 (s, 1H), 7.96 (d, J=8.0 Hz, 2H), 7.51 (d, J=8.1 Hz, 2H), 7.38 (s, 1H), 7.31 (d, J=8.4 Hz, 1H), 7.19 (d, J=7.9 Hz, 1H), 7.12 (d, J=9.0 Hz, 1H), 6.84 (d, J=8.5 Hz, 1H), 6.37 (dd, J=8.5, 2.5 Hz, 1H), 6.21 (d, J=2.9 Hz, 1H), 5.30 (q, J=8.8, 7.6 Hz, 2H), 2.08-1.97 (m, 2H), 1.49 (dt, J=8.8, 3.2 Hz, 1H), 1.40-1.33 (m, 1H), 1.06-1.00 (m, 2H); MS (ESI−) m/z=508 (M−H)$^-$.

Example 129

4-({[1-(2,2-difluoro-1,3-benzodioxol-5-yl)cyclopropyl]carbonyl}amino)-7-methoxy-3,4-dihydrospiro[chromene-2,1'-cyclobutane]-3'-carboxylic acid

Example 129A methyl 7-methoxy-4-oxospiro[chroman-2,1'-cyclobutane]-3'-carboxylate To 1-(2-hydroxy-4-methoxyphenyl)ethanone (CAS 552-41-0) (500 mg, 3.01 mmol) in methanol (10 mL) was added methyl 3-oxocyclobutanecarboxylate (1157 mg, 9.03 mmol) and pyrrolidine (0.754 mL, 9.03 mmol) at room temperature. The mixture was stirred at room temperature overnight. The reaction mixture was extracted with CH$_2$Cl$_2$ and the organic layer washed with water, dried over NaSO$_4$, filtered, and concentrated. Purification by flash chromatography on silica gel, eluting with ethyl acetate in heptane (0-30%) yielded title compound (200 mg, 24%).

Example 129B methyl 7-methoxy-4-(methoxyimino)spiro[chroman-2,1'-cyclobutane]-3'-carboxylate The mixture of Example 129A (196 mg, 0.709 mmol), sodium acetate (116 mg, 1.419 mmol) and O-methylhydroxylamine, hydrochloric acid (118 mg, 1.419 mmol) in methanol (10 mL) was stirred at 60° C. overnight. The solvent was evaporated under reduced pressure and the residue was dissolved in ethyl acetate, and washed with brine. The organic layers was dried over MgSO$_4$, and filtered. The solvent was removed under pressure to give crude product of title compound (203 mg, 94%), which was used without further purification. $^1$H NMR (400 MHz, CDCl$_3$) δ 7.75 (dd, J=8.9, 5.8 Hz, 1H), 6.51 (ddt, J=8.4, 5.6, 2.5 Hz, 1H), 6.42 (td, J=6.1, 2.8 Hz, 1H), 3.96 (t, J=4.4 Hz, 3H), 3.75 (dt, J=32.6, 2.8 Hz, 6H), 2.95 (d, J=7.2 Hz, 2H), 2.56-2.28 (m, 4H); MS (ESI+) m/z 306 (M+H)$^+$.

Example 129C methyl 4-amino-7-methoxyspiro[chroman-2,1'-cyclobutane]-3'-carboxylate To a solution of Example 129B (200 mg, 0.655 mmol) in methanol (10 mL) was added Raney nickel (1 g, 17.04 mmol) in a 50 mL pressure bottle. The mixture was stirred at 30 psi of hydrogen and at room temperature for 52 hours. The reaction mixture was filtered and concentrated to dryness to provide the title compound (150 mg, 83%). MS (ESI+) m/z 261 (M−NH$_2$)$^+$.

Example 129D methyl 4-(1-(2,2-difluorobenzo[d][1,3]dioxol-5-yl)cyclopropanecarboxamido)-7-methoxyspiro[chroman-2,1'-cyclobutane]-3'-carboxylate To 1-(2,2-difluorobenzo[d][1,3]dioxol-5-yl)cyclopropanecarboxylic acid (34.9 mg, 0.144 mmol) in N,N-dimethylformamide (4 mL) was added HATU (1-[bis(dimethylamino)methylene]-1H-1,2,3-triazolo[4,5-b]pyridinium 3-oxid hexafluorophosphate) (82 mg, 0.216 mmol). The mixture was stirred for 5 minutes, and then Example 129C (40 mg, 0.144 mmol) was added, following by addition of N-ethyl-N-isopropylpropan-2-amine (0.100 mL, 0.577 mmol). The mixture was stirred at room temperature for 2 hours. The mixture was purified by chromatography, eluting with 0-50% ethyl acetate in heptane to provide the title compound (60 mg, 83% yield). $^1$H NMR (400 MHz, CDCl$_3$) δ 7.18-7.07 (m, 2H), 7.00 (d, J=8.1 Hz, 1H), 6.94 (dd, J=8.6, 0.9 Hz, 1H), 6.46 (dd, J=8.6, 2.6 Hz, 1H), 6.34 (d, J=2.5 Hz, 1H), 5.32 (d, J=8.5 Hz, 1H), 5.17-5.05 (m, 1H), 3.73 (d, J=9.6 Hz, 6H), 3.29 (tt, J=9.3, 7.7 Hz, 1H), 2.47-2.32 (m, 4H), 2.26 (dd, J=13.3, 5.8 Hz, 1H), 1.79 (dd, J=13.4, 8.4 Hz, 1H), 1.69 (t, J=3.6 Hz, 2H), 1.12-1.05 (m, 2H); MS(ESI−) m/z 500.2 (M−H)$^-$.

Example 129E 4-({[1-(2,2-difluoro-1,3-benzodioxol-5-yl)cyclopropyl]carbonyl}amino)-7-methoxy-3,4-dihydrospiro[chromene-2,1'-cyclobutane]-3'-carboxylic acid To a solution of Example 129D (58 mg, 0.116 mmol) in methanol (4 mL) and water (1 mL) was added lithium hydroxide (27 mg, 1.16 mmol). The mixture was stirred at 35° C. for 4 hours and solvent removed under reduced pressure, and then water (1 mL) was added. The mixture was adjusted with 2N HCl to pH 1-2. The white solid precipitated was collected and washed with water and dried to yield title compound as solid (53 mg, 94%). $^1$H NMR (400 MHz, CDCl$_3$) δ 7.19-7.08 (m, 2H), 7.01 (t, J=7.9 Hz, 1H), 6.95-6.83 (m, 1H), 6.46 (ddd, J=8.6, 4.4, 2.5 Hz, 1H), 6.33 (dd, J=6.9, 2.5 Hz, 1H), 5.39 (dd, J=8.5, 5.6 Hz, 1H), 5.14 (dtd, J=17.2, 9.2, 8.6, 6.1 Hz, 1H), 3.73 (d, J=6.5 Hz, 3H), 3.31 (p, J=8.3 Hz, 1H), 2.91-2.58 (m, 1H), 2.52-2.28 (m, 4H), 1.84-1.64 (m, 3H), 1.14-1.05 (m, 2H); MS (ESI−) m/z=486.2 (M−H)$^-$.

Example 130

Ethyl rac-(2R,4S)-4-({[1-(2,2-difluoro-1,3-benzodioxol-5-yl)cyclopropyl]carbonyl}amino)-7-methoxy-3,4-dihydro-2H-chromene-2-carboxylate

Example 130A ethyl 7-methoxy-4-oxo-4H-chromene-2-carboxylate 1-(2-hydroxy-4-methoxyphenyl)ethanone (CAS 552-41-0) (10 g, 60.2 mmol) was dissolved in ethanol (175 mL). Diethyl oxalate (41.1 mL, 301 mmol) was added, followed by a 2.5 M solution of sodium ethoxide in ethanol (94 mL, 241 mmol). The mixture was heated at 75° C. for 1 hour, cooled to room temperature, acidified with HCl (7.31 mL, 241 mmol), then concentrated in vacuo. This intermediate was dissolved in CH$_2$Cl$_2$ (200 mL), treated with concentrated HCl (20 mL) and stirred at room temperature for 3 hours. The organic layer was isolated and dried over sodium sulfate, filtered, and concentrated. The residue was triturated with methyl tert-butyl ether and the solid was collected by filtration to provide the title compound as an off-white solid. $^1$H NMR (400 MHz, DMSO-$d_6$) δ 7.94 (d, J=8.9 Hz, 1H), 7.22 (d, J=2.4 Hz, 1H), 7.10 (dd, J=8.9, 2.4 Hz, 1H), 6.88 (s, 1H), 4.40 (q, J=7.1 Hz, 2H), 3.93 (s, 3H), 1.36 (t, J=7.1 Hz, 3H).

Example 130B ethyl 7-methoxy-4-oxochroman-2-carboxylate

A mixture of the product from Example 130A (2.16 g, 8.70 mmol), ammonium formate (1.646 g, 26.1 mmol) and 10% Pd/C (0.695 g, 0.653 mmol) in ethanol (40 mL) was heated at 85° C. overnight under an $N_2$ atmosphere (balloon). The mixture was cooled, filtered to remove the solids, and concentrated. The residue was purified by chromatography on silica gel eluting with a gradient of 50-100% $CH_2Cl_2$ in heptane to provide the title compound (0.8 g, 3.20 mmol, 36.7% yield). $^1$H NMR (501 MHz, CDCl$_3$) δ 7.81 (d, J=8.8 Hz, 1H), 6.61 (dd, J=8.8, 2.4 Hz, 1H), 6.56 (d, J=2.4 Hz, 1H), 5.06 (dd, J=8.5, 5.9 Hz, 1H), 4.27 (q, J=7.1 Hz, 2H), 3.85 (s, 3H), 3.04-2.95 (m, 2H), 1.30 (t, J=7.1 Hz, 3H); MS (ESI+) m/z 251 (M+H)$^+$.

Example 130C ethyl 7-methoxy-4-(methoxyimino)chroman-2-carboxylate

A solution of the product from Example 130B (0.8 g, 3.20 mmol) and O-methylhydroxylamine hydrochloride (0.801 g, 9.59 mmol) in pyridine (10 mL) was heated at 60° C. for 75 minutes, cooled, concentrated and partitioned between ethyl acetate and water. The ethyl acetate layer was washed with brine, dried (MgSO$_4$), filtered, and concentrated to provide the title compound (0.8 g, 2.86 mmol, 90% yield). $^1$H NMR (400 MHz, CDCl$_3$) δ 7.78 (d, J=8.7 Hz, 1H), 6.56 (dd, J=8.7, 2.5 Hz, 1H), 6.53 (d, J=2.3 Hz, 1H), 4.70 (dd, J=9.9, 4.3 Hz, 1H), 4.27 (q, J=7.1 Hz, 2H), 3.96 (s, 3H), 3.79 (s, 3H), 3.33 (dd, J=17.2, 4.3 Hz, 1H), 2.91 (dd, J=17.2, 10.0 Hz, 1H), 1.30 (t, J=7.1 Hz, 3H); MS (ESI+) m/z 280 (M+H)$^+$.

Example 130D methyl 4-amino-7-methoxychroman-2-carboxylate and ethyl 4-amino-7-methoxychroman-2-carboxylate A solution of the product from Example 130C in methanol (20 mL) was added to Ra—Ni 2800, water slurry, (6 g, 46.0 mmol) in a 50 mL pressure bottle and shaken for 4 hours at 30 psi of hydrogen and at room temperature. The mixture was filtered and concentrated to provide the title compounds. MS (ESI+) m/z 220 (M-NH$_3$)$^+$ for methyl ester and m/z 235 (M-NH$_3$)$^+$ for ethyl ester.

Example 130E ethyl rac-(2R,4S)-4-({[1-(2,2-difluoro-1,3-benzodioxol-5-yl)cyclopropyl]carbonyl}amino)-7-methoxy-3,4-dihydro-2H-chromene-2-carboxylate A mixture of the product from Example 130D (650 mg, 2.59 mmol), 1-(2,2-difluorobenzo[d][1,3]dioxol-5-yl)cyclopropanecarboxylic acid (689 mg, 2.85 mmol) and HATU (1-[bis(dimethylamino)methylene]-1H-1,2,3-triazolo[4,5-b]pyridinium 3-oxid hexafluorophosphate) (1475 mg, 3.88 mmol) in N,N-dimethylformamide (20 mL) under $N_2$ was treated with triethylamine (1082 μL, 7.76 mmol) and stirred at room temperature for 90 minutes. The mixture was partitioned between methyl tert-butyl ether (30 mL) and 1 M HCl (15 mL). The layers were separated and the ethyl acetate layer was washed sequentially with saturated NaHCO$_3$ solution (10 mL) and brine, dried (MgSO$_4$), filtered, and concentrated. The residue was purified by chromatography on silica gel eluting with a gradient of 10 to 100% ethyl acetate in heptane to provide the title compound as the first eluting product. This product was further purified by chromatography on silica gel eluting with a gradient of 25-100% [9:1 CH$_2$Cl$_2$:ethyl acetate] in heptanes. $^1$H NMR (400 MHz, CDCl$_3$) δ 7.13 (dd, J=8.2, 1.7 Hz, 1H), 7.10 (d, J=1.6 Hz, 1H), 7.00 (d, J=8.1 Hz, 1H), 6.96 (d, J=8.4 Hz, 1H), 6.50 (dd, J=8.4, 2.5 Hz, 1H), 6.48 (d, J=2.5 Hz, 1H), 5.42 (d, J=6.9 Hz, 1H), 5.02-4.96 (m, 1H), 4.44 (dd, J=9.2, 3.5 Hz, 1H), 4.29 (q, J=7.1 Hz, 2H), 3.75 (s, 3H), 2.31-2.18 (m, 2H), 1.74-1.65 (m, 2H), 1.33 (t, J=7.1 Hz, 3H), 1.12-1.04 (m, 2H); MS (ESI−) m/z 474 (M−H)$^-$.

Example 131 methyl rac-(2R,4S)-4-({[1-(2,2-difluoro-1,3-benzodioxol-5-yl)cyclopropyl]carbonyl}amino)-7-methoxy-3,4-dihydro-2H-chromene-2-carboxylate The title compound was isolated as the second eluting isomer from the first chromatography as described in Example 130E. This product was further purified by chromatography on silica gel eluting with a gradient of 25-100% [9:1 CH$_2$Cl$_2$:ethyl acetate] in heptanes. $^1$H NMR (400 MHz, CDCl$_3$) δ 7.15 (dd, J=8.2, 1.6 Hz, 1H), 7.12 (d, J=1.6 Hz, 1H), 7.02 (d, J=8.2 Hz, 1H), 6.98 (d, J=8.5 Hz, 1H), 6.52 (dd, J=8.5, 2.5 Hz, 1H), 6.49 (d, J=2.5 Hz, 1H), 5.44 (d, J=6.8 Hz, 1H), 5.02-4.96 (m, 1H), 4.48 (dd, J=9.7, 3.1 Hz, 1H), 3.84 (s, 3H), 3.76 (s, 3H), 2.36-2.29 (m, 1H), 2.22 (ddd, J=14.2, 9.7, 4.8 Hz, 1H), 1.71 (tq, J=7.3, 4.2 Hz, 2H), 1.09 (p, J=6.1, 5.6 Hz, 2H); MS (ESI−) m/z 460 (M−H)$^-$.

Example 132 ethyl rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-5-carboxylate Example 132A (E)-methyl 2-(3-(tert-butoxy)-2-(2-hydroxybenzoyl)-3-oxoprop-1-en-1-yl)thiazole-5-carboxylate A mixture of tert-butyl 3-(2-hydroxyphenyl)-3-oxopropanoate (0.704 g, 2.98 mmol, CAS#936182-86-4, Biddle, et al., Journal of the American Chemical Society 2007, 129 (13), p 3830-3831), methyl 2-formylthiazole-5-carboxylate (CAS#1408075-35-3, 0.51 g, 2.98 mmol), piperidine (0.015 mL, 0.149 mmol) and acetic acid (8.53 μL, 0.149 mmol) in benzene was heated at reflux using Dean-Starke trap overnight. The mixture was concentrated and purified by chromatography on silica gel, and eluting with a gradient of 15-100% ethyl acetate in heptane to provide the title compound (0.26 g, 0.668 mmol, 22.41% yield). $^1$H NMR (400 MHz, CDCl$_3$) δ 11.66 (s, 1H), 8.33 (s, 1H), 7.85 (s, 1H), 7.53-7.46 (m, 2H), 7.09-7.06 (m, 1H), 6.87-6.82 (m, 1H), 3.90 (s, 3H), 1.45 (s, 9H); MS (ESI−) m/z 388 (M−H)⁻.

Example 132B methyl 2-(4-oxochroman-2-yl)thiazole-5-carboxylate

A solution of the product from Example 132A (0.25 g, 0.642 mmol) and 1-[3,5-bis(trifluoromethyl)phenyl]-3-[(1R, 2R)-(−)-2-(dimethylamino)cyclohexyl]thiourea (0.053 g, 0.128 mmol) in toluene (4 mL) was stirred at room temperature for 2 days. The mixture was treated with DL-10-camphorsulfonic acid (0.149 g, 0.642 mmol) and was heated at 95° C. for 3 hours. The mixture was cooled and partitioned between ethyl acetate and saturated NaHCO₃ solution. The ethyl acetate layer was washed with brine, dried (MgSO₄), filtered, and concentrated. The resulting residue was purified by chromatography on silica gel, and eluting with a gradient of 10 to 100% ethyl acetate in heptane to provide the title compound (0.14 g, 0.484 mmol, 75% yield). ¹H NMR (400 MHz, CDCl₃) δ 8.38 (s, 1H), 7.95 (dd, J=7.8, 1.6 Hz, 1H), 7.58 (ddd, J=8.8, 7.3, 1.7 Hz, 1H), 7.16-7.10 (m, 2H), 5.86 (dd, J=10.3, 4.3 Hz, 1H), 3.94 (s, 3H), 3.33 (dd, J=17.0, 4.3 Hz, 1H), 3.24 (dd, J=17.0, 10.3 Hz, 1H); MS (ESI+) m/z 290 (M+H)⁺.

Example 132C ethyl rel-2-((S)-4-(((R)-tert-butylsulfinyl)imino)chroman-2-yl)thiazole-5-carboxylate A solution of product from Example 132B (70 mg, 0.242 mmol), titanium(IV) ethoxide (331 mg, 1.452 mmol), and (R)-(+)-2-methyl-2-propanesulfinamide (44.0 mg, 0.363 mmol) in tetrahydrofuran (1 mL) was heated at 70° C. overnight. The mixture was cooled and partitioned between ethyl acetate (30 mL) and water (15 mL). The solid present was removed by filtration through diatomaceous earth. The ethyl acetate layer was isolated, washed with brine, dried (MgSO₄), filtered, and concentrated. The resulting residue was purified by chromatography on silica gel, eluting with a gradient of 50-100% [9:1 CH₂Cl₂:ethyl acetate] in heptanes, then further eluted with a gradient of 0-50% ethyl acetate in [9:1 CH₂Cl₂:ethyl acetate] to provide the title compound (35.6 mg, 0.088 mmol, 36.2% yield) as the first eluting isomer. The stereochemistry was arbitrarily assigned. ¹H NMR (400 MHz, CDCl₃) δ 8.36 (s, 1H), 8.02 (d, J=8.1 Hz, 1H), 7.46 (t, J=7.7 Hz, 1H), 7.07 (dd, J=7.8, 3.7 Hz, 2H), 5.59 (dd, J=11.3, 3.3 Hz, 1H), 4.39 (q, J=7.1 Hz, 2H), 4.05 (dd, J=17.5, 3.4 Hz, 1H), 3.56 (dd, J=17.5, 11.4 Hz, 1H), 1.40 (t, J=7.0 Hz, 3H), 1.33 (s, 9H); MS (ESI+) m/z 407 (M+H)⁺.

Example 132D ethyl rel-2-((2S,4S)-4-aminochroman-2-yl)thiazole-5-carboxylate

A solution of the product from Example 132C (35.6 mg, 0.088 mmol) in ethanol (2 mL) was cooled to 0° C., treated with NaBH₄ (3.31 mg, 0.088 mmol), stirred at 0° C. for 15 minutes, treated with more NaBH₄ (5 mg), and stirred at 0° C. for 75 minutes. The reaction was treated with 4 M HCl in dioxane (219 μL, 0.876 mmol) and stirred at room temperature for 40 minutes. The mixture was partitioned between water (10 mL) and methyl tert-butyl ether (30 mL). The aqueous layer was basified with solid NaHCO₃ and extracted with ethyl acetate (30 mL). The ethyl acetate layer was washed with brine, dried (MgSO₄), filtered, and concentrated to provide the title compound (26.2 mg, 0.086 mmol, 98% yield). The stereochemistry was arbitrarily assigned. ¹H NMR (400 MHz, CDCl₃) δ 8.38 (s, 1H), 7.56 (d, J=7.8 Hz, 1H), 7.24 (t, J=7.7 Hz, 1H), 7.05 (t, J=7.3 Hz, 1H), 6.98 (d, J=8.2 Hz, 1H), 5.53 (dd, J=11.0, 2.3 Hz, 1H), 4.41 (q, J=7.2 Hz, 2H), 4.35 (dd, J=10.6, 5.8 Hz, 1H), 2.83 (ddd, J=13.1, 5.6, 2.2 Hz, 1H), 2.09-1.99 (m, 1H), 1.42 (t, J=7.1 Hz, 3H); MS (ESI+) m/z 305 (M+H)⁺.

Example 132E ethyl rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-5-carboxylate The title compound was prepared using procedure similar to that as described in Example 130E, substituting the product from Example 132D for the product from Example 130D. ¹H NMR (400 MHz, CDCl₃) δ 8.24 (s, 1H), 7.21 (t, J=7.6 Hz, 1H), 7.15-7.10 (m, 3H), 7.01 (d, J=8.1 Hz, 1H), 6.99-6.96 (m, 1H), 6.94 (d, J=8.3 Hz, 1H), 5.56 (d, J=8.6 Hz, 1H), 5.53-5.45 (m, 2H), 4.38 (q, J=7.1 Hz, 2H), 2.87 (ddd, J=13.4, 6.1, 2.8 Hz, 1H), 2.05-1.94 (m, 1H), 1.78-1.66 (m, 2H), 1.39 (t, J=7.1 Hz, 3H), 1.09 (d, J=3.0 Hz, 2H); MS (ESI−) m/z 527 (M−H)⁻.

Example 133

2-[(4S)-4-({[1-(2,2-difluoro-1,3-benzodioxol-5-yl)cyclopropyl]carbonyl}amino)-3,4-dihydro-2H-chromen-2-yl]-1,3-thiazole-5-carboxylic acid A solution of product from Example 132E (36 mg, 0.068 mmol) in tetrahydrofuran (1 mL) was diluted with methanol (1 mL) and then treated with 1 M NaOH (0.5 mL). The mixture was stirred at room temperature for 15 minutes and acidified by the addition of 1 M HCl (2 mL). The mixture was extracted with ethyl acetate (30 mL). The layers were separated and the ethyl acetate layer was washed with brine, dried (MgSO₄), filtered, and concentrated to provide the title compound (31 mg, 0.062 mmol, 91% yield) as a 2:1 ratio of cis:trans isomers. The stereochemistry of the chiral center bearing the amino group was arbitrarily assigned as "S". ¹H NMR (501 MHz, CDCl₃) δ 8.46 (s, 0.35H), 8.36 (s, 0.65H), 7.28-7.21 (m, 1H), 7.19 (dd, J=8.2, 1.7 Hz, 0.35H), 7.17-7.12 (m, 2.65H), 7.05-6.98 (m, 2.35H), 6.96 (dd, J=8.2, 1.0 Hz, 0.65H), 5.63 (d, J=7.0 Hz, 0.35H), 5.59-5.49 (m, 1.95H), 5.28 (dd, J=10.0, 2.8 Hz, 0.35H), 5.14-5.10 (m, 0.35H), 2.91 (ddd, J=13.4, 6.0, 2.7 Hz, 0.65H), 2.67-2.58 (m, 0.35H), 2.35 (ddd, J=14.5, 10.2, 5.0 Hz, 0.35H), 2.01 (dt, J=13.3, 9.9 Hz, 0.65H), 1.82-1.68 (m, 2H), 1.17-1.08 (m, 2H); MS (ESI−) m/z 499 (M−H)⁻.

Example 134 rac-(2R,4S)-4-({[1-(2,2-difluoro-1,3-benzodioxol-5-yl)cyclopropyl]carbonyl}amino)-7-methoxy-3,4-dihydro-2H-chromene-2-carboxylic acid A solution of product from Example 130E in tetrahydrofuran (2 mL) was diluted with methanol (2 mL) and then treated with 1 M NaOH (2 mL). The mixture was stirred at room temperature for 15 minutes and acidified by the addition of 1 M HCl. The mixture was extracted with ethyl acetate (30 mL). The layers were separated and the ethyl acetate layer was washed with brine, dried (MgSO$_4$), filtered, and concentrated to provide the titled compound. $^1$H NMR (400 MHz, CDCl$_3$) δ 7.16 (dd, J=8.2, 1.6 Hz, 1H), 7.13 (d, J=1.5 Hz, 1H), 7.03 (d, J=8.1 Hz, 1H), 6.95 (d, J=8.5 Hz, 1H), 6.52 (dd, J=8.5, 2.5 Hz, 1H), 6.49 (d, J=2.4 Hz, 1H), 5.52 (d, J=7.1 Hz, 1H), 5.03 (q, J=5.5 Hz, 1H), 4.58 (dd, J=7.9, 3.7 Hz, 1H), 3.76 (s, 3H), 2.38-2.23 (m, 2H), 1.78-1.70 (m, 2H), 1.16-1.08 (m, 2H); MS (ESI−) m/z 446 (M−H)$^-$.

Example 135 ethyl rel-2-[(2R,4R)-4-({[1-(2,2-difluoro-1,3-benzodioxol-5-yl)cyclopropyl]carbonyl}amino)-3,4-dihydro-2H-chromen-2-yl]-1,3-thiazole-5-carboxylate

Example 135A ethyl rel-2-((R)-4-(((R)-tert-butylsulfinyl)imino) chroman-2-yl)thiazole-5-carboxylate The title compound was isolated as the second eluting isomer from the chromatography purification described in Example 132C. Stereochemistry was arbitrarily assigned. $^1$H NMR (400 MHz, CDCl$_3$) δ 8.35 (s, 1H), 8.03 (dd, J=7.9, 1.5 Hz, 1H), 7.50-7.45 (m, 2H), 7.10-7.04 (m, 2H), 5.71 (dd, J=8.6, 4.2 Hz, 1H), 4.38 (q, J=7.1 Hz, 1H), 4.15 (dd, J=17.1, 4.2 Hz, 1H), 3.66 (dd, J=17.1, 8.7 Hz, 1H), 1.40 (t, J=7.1 Hz, 3H), 1.36 (s, 9H); MS (ESI+) m/z 407 (M+H)$^+$.

Example 135B ethyl rel-2-((2R,4R)-4-aminochroman-2-yl)thiazole-5-carboxylate The title compound was prepared using procedure similar to that described in Example 132D, substituting the product from Example 135A for the product from Example 132C. Stereochemistry was arbitrarily assigned. $^1$H NMR (400 MHz, CDCl$_3$) δ 8.37 (s, 1H), 7.54 (d, J=7.7 Hz, 1H), 7.22 (t, J=7.2 Hz, 1H), 7.03 (t, J=7.0 Hz, 1H), 6.96 (dd, J=8.2, 0.9 Hz, 1H), 5.51 (dd, J=11.1, 2.4 Hz, 1H), 4.39 (q, J=7.1 Hz, 2H), 4.33 (dd, J=10.6, 5.7 Hz, 1H), 2.81 (ddd, J=13.3, 5.7, 2.4 Hz, 1H), 2.01 (dt, J=13.2, 10.9 Hz, 1H), 1.40 (t, J=7.1 Hz, 3H); MS (ESI+) m/z 305 (M+H)$^+$.

Example 135C ethyl rel-2-[(2R,4R)-4-({[1-(2,2-difluoro-1,3-benzodioxol-5-yl)cyclopropyl]carbonyl}amino)-3,4-dihydro-2H-chromen-2-yl]-1,3-thiazole-5-carboxylate The title compound was prepared using procedure similar to that described in Example 130E, substituting the product from Example 135B for the product from Example 130D. Stereochemistry was arbitrarily assigned. $^1$H NMR (400 MHz, CDCl$_3$) δ 8.24 (s, 1H), 7.21 (td, J=7.9, 7.5, 1.1 Hz, 1H), 7.16-7.10 (m, 3H), 7.01 (d, J=8.1 Hz, 1H), 6.98 (dd, J=7.5, 1.1 Hz, 1H), 6.93 (dd, J=8.3, 1.0 Hz, 1H), 5.58-5.44 (m, 3H), 4.38 (q, J=7.1 Hz, 2H), 2.87 (ddd, J=13.4, 6.1, 2.8 Hz, 1H), 2.00 (dt, J=13.4, 9.8 Hz, 1H), 1.78-1.65 (m, 2H), 1.39 (t, J=7.1 Hz, 3H), 1.13-1.05 (m, 2H); MS (ESI+) m/z 529 (M+H)$^+$.

Example 136

2-[(4R)-4-({[1-(2,2-difluoro-1,3-benzodioxol-5-yl) cyclopropyl]carbonyl}amino)-3,4-dihydro-2H-chromen-2-yl]-1,3-thiazole-5-carboxylic acid The title compound was isolated as 2:1 ratio of cis:trans isomers, using procedure similar to that as described in Example 133, substituting the product from Example 135C for the product from Example 132E. The stereochemistry of the chiral center bearing the amino group was arbitrarily assigned as "R". $^1$H NMR (400 MHz, CDCl$_3$) δ 8.44 (s, 0.35H), 8.34 (s, 0.65H), 7.26-7.10 (m, 3.5H), 7.04-6.93 (m, 3.5H), 5.60 (d, J=6.9 Hz, 0.35H), 5.57-5.46 (m, 1.95H), 5.25 (dd, J=9.7, 2.1 Hz, 0.35H), 5.14-5.08 (m, 0.35H), 2.92-2.85 (m, 0.65H), 2.64-2.58 (m, 0.35H), 2.37-2.29 (m, 0.35H), 1.99 (dt, J=12.9, 9.7 Hz, 0.65H), 1.80-1.66 (m, 2H), 1.15-1.07 (m, 2H); MS (ESI−) m/z 499 (M−H)$^-$.

Example 137 methyl 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-2-fluorobenzoate

Example 137A (R)-methyl 2-fluoro-4-(7-methoxy-4-oxochroman-2-yl)benzoate

In a 20 mL vial was charged with bis(2,2,2-trifluoroacetoxy)palladium (84 mg, 0.253 mmol), (S)-4-(tert-butyl)-2-(pyridin-2-yl)-4,5-dihydrooxazole (61.9 mg, 0.303 mmol), ammonium hexafluorophosphate(V) (247 mg, 1.515 mmol) and (3-fluoro-4-(methoxycarbonyl)phenyl)boronic acid (500 mg, 2.53 mmol). The mixture was stirred in dichloroethane (10 mL) for 5 minutes, and 7-methoxy-4H-chromen-4-one (CAS 5751-52-0) (534 mg, 3.03 mmol) and water (0.256 mL, 14.19 mmol) were added. The mixture was stirred at 60° C. overnight, filtered through a plug of diatomaceous earth and eluted and washed with ethyl acetate to give a red solution. The solvent was removed under vacuum and the crude material chromatographed on 24 g silica gel cartridge, eluting with ethyl acetate in heptane at a gradient of 0-40% to yield title compound (235 mg, 0.711 mmol, 28.2%). $^1$H NMR (400 MHz, CDCl$_3$) δ 8.00 (t, J=7.7 Hz, 1H), 7.87 (d, J=8.8 Hz, 1H), 7.35-7.27 (m, 2H), 6.65 (dd, J=8.9, 2.4 Hz, 1H), 6.53 (d, J=2.4 Hz, 1H), 5.51 (dd, J=12.3, 3.6 Hz, 1H), 3.95 (s, 3H), 3.86 (s, 3H), 3.03-2.81 (m, 2H). MS(ESI+): m/z=331 (M+H)$^+$

Example 137B (R)-methyl 2-fluoro-4-(7-methoxy-4-(methoxyimino)chroman-2-yl)benzoate The mixture of Example 137A (230 mg, 0.696 mmol), sodium acetate (114 mg, 1.393 mmol) and O-methylhydroxylamine hydrochloride (116 mg, 1.393 mmol) in methanol (10 mL) was stirred at 60° C. for 4 hours. Solvent was removed under reduced pressure. The resulting residue was dissolved in ethyl acetate, washed with water, dried over MgSO$_4$, and filtered. The solvent was removed under reduced pressure. The resulting white solid was washed with diethyl ether to provide the title compound (228 mg, 0.634 mmol, 91% yield). $^1$H NMR (400 MHz, CDCl$_3$) δ 7.97 (dd, J=8.3, 7.4 Hz, 1H), 7.83 (d, J=8.8 Hz, 1H), 7.32-7.29 (m, 1H), 7.27 (s, 1H), 6.59 (dd, J=8.8, 2.6 Hz, 1H), 6.50 (d, J=2.5 Hz, 1H), 5.11 (dd, J=12.2, 3.2 Hz, 1H), 3.96 (s, 3H), 3.94 (s, 3H), 3.80 (s, 3H), 3.46 (dd, J=17.1, 3.2 Hz, 1H), 2.60 (dd, J=17.2, 12.1 Hz, 1H); MS(ESI+) m/z=360 (M+H)$^+$.

Example 137C methyl 4-((2R,4R)-4-amino-7-methoxychroman-2-yl)-2-fluorobenzoate, hydrochloric Acid The mixture of Example 137B (220 mg, 0.612 mmol) and platinum (119 mg, 0.031 mmol) on carbon in methanol (6 mL) was charged with a hydrogen balloon and stirred at room temperature for 24 hours, LC/MS showed about 50% conversion. The balloon was refilled. The reaction mixture was charged with more platinum catalyst (0.05 equivalent) and stirred for another 24 hours, at which time LC/MS showed 95% conversion. The reaction mixture was filtered through a diatomaceous earth pad and solvent was removed under reduced pressure. To the residue was added 4 M HCl in dioxane drop wise. The precipitated white solid was filtered and dried to yield title compound (110 mg, 48.9%). MS (ESI+) m/z=315 (M-NH$_2$)$^+$.

Example 137D methyl 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-2-fluorobenzoate To 1-(2,2-difluorobenzo[d][1,3]dioxol-5-yl)cyclopropanecarboxylic acid (87 mg, 0.359 mmol) in N,N-dimethylformamide (4 mL) was added HATU (1-[bis(dimethylamino)methylene]-1H-1,2,3-triazolo[4,5-b]pyridinium 3-oxid hexafluorophosphate) (186 mg, 0.489 mmol). The mixture was stirred for 5 minutes, and then Example 137C (120 mg, 0.326 mmol) was added, followed by the addition of N-ethyl-N-isopropylpropan-2-amine (0.227 mL, 1.305 mmol). The mixture was stirred at room temperature for 2 hours. Purification by chromatography on silica gel and eluting with a gradient of 5-40% ethyl acetate in heptane provided the title compound (120 mg, 66.2% yield). $^1$H NMR (400 MHz, CDCl$_3$) δ 7.94 (t, J=7.7 Hz, 1H), 7.24-7.17 (m, 2H), 7.12-7.03 (m, 2H), 7.00 (d, J=8.2 Hz, 1H), 6.95 (d, J=8.6 Hz, 1H), 6.52 (dd, J=8.7, 2.5 Hz, 1H), 6.44 (d, J=2.5 Hz, 1H), 5.38 (td, J=10.0, 9.5, 5.8 Hz, 1H), 5.30 (d, J=8.6 Hz, 1H), 5.19 (dd, J=11.1, 2.0 Hz, 1H), 3.94 (s, 3H), 3.76 (s, 3H), 2.51 (ddd, J=13.4, 6.1, 2.2 Hz, 1H), 1.79-1.70 (m, 2H), 1.29-1.23 (m, 1H), 1.07 (d, J=3.8 Hz, 2H); MS(ESI-) m/z 554 (M-H)$^+$.

Example 138 methyl 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-3-fluorobenzoate The title compound (115 mg, 66.2% yield) was prepared using the procedures similar to that described in Examples 137A-137D, substituting (2-fluoro-4-(methoxycarbonyl)phenyl)boronic acid for (3-fluoro-4-(methoxycarbonyl)phenyl)boronic acid. $^1$H NMR (400 MHz, CDCl$_3$) δ 7.83 (dd, J=8.1, 1.5 Hz, 1H), 7.72 (dd, J=10.7, 1.6 Hz, 1H), 7.57 (t, J=7.5 Hz, 1H), 7.12-7.06 (m, 2H), 7.01-6.95 (m, 2H), 6.53 (dt, J=8.7, 3.2 Hz, 1H), 6.43 (d, J=2.6 Hz, 1H), 5.51-5.45 (m, 1H), 5.42 (dt, J=10.2, 4.9 Hz, 1H), 5.30 (d, J=8.7 Hz, 1H), 3.94 (d, J=2.6 Hz, 3H), 3.76 (s, 3H), 2.53 (ddd, J=13.4, 6.2, 2.1 Hz, 1H), 1.82-1.69 (m, 2H), 1.27 (d, J=3.6 Hz, 1H), 1.07 (q, J=2.4, 1.5 Hz, 2H); MS(ESI-) m/z=554 (M-H)$^-$.

Example 139

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-2-fluorobenzoic acid To a solution of Example 137D (105 mg, 0.189 mmol) in methanol (2 mL) was added 4N LiOH (0.5 mL). The mixture was stirred at 35° C. for 2 hours. The solvent was removed and water (0.5 mL) was added to the resulting residue. The pH of the mixture was adjusted with 2N HCl to pH 1-2. The resulting white solid was collected by filtration and dried to yield the title compound (97 mg, 95% yield). $^1$H NMR (501 MHz, CDCl$_3$) δ 8.00 (s, 1H), 7.23 (d, J=9.5 Hz, 2H), 7.14-7.06 (m, 2H), 7.01 (dd, J=8.2, 4.6 Hz, 1H), 6.94 (d, J=8.5 Hz, 1H), 6.51 (dd, J=8.6, 2.5 Hz, 1H), 6.44 (d, J=2.6 Hz, 1H), 5.46-5.30 (m, 2H), 5.20 (d, J=11.1 Hz, 1H), 3.76 (s, 3H), 2.54 (d, J=12.6 Hz, 1H), 1.67 (s, 1H), 1.09 (d, J=3.5 Hz, 2H); MS (ESI-) m/z 540 (M-H)$^+$.

Example 140 ethyl rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylate Example 140A ethyl 2-(1-hydroxy-3-(2-hydroxyphenyl)-3-oxopropyl)thiazole-4-carboxylate A solution of diisopropylamine (923 µL, 6.48 mmol) in tetrahydrofuran (10 mL) was cooled to −78° C. under N$_2$, treated with 2.5 M n-butyllithium in hexanes (2.246 mL, 5.62 mmol), stirred at 0° C. for 15 minutes, treated with 2'-hydroxyacetophenone (286 µL, 2.376 mmol), stirred for 1 hour at 0° C., cooled to −78° C., treated with a solution of ethyl 2-formylthiazole-4-carboxylate (CAS #73956-17-9) (400 mg, 2.160 mmol) in tetrahydrofuran (5 mL), stirred at −78° C. for 10 minutes, quenched with 10% aqueous solution of KH$_2$PO$_4$ (50 mL) and allowed to warm to room temperature. The mixture was extracted with ethyl acetate (twice). The combined ethyl acetate layers were washed with brine, dried (MgSO$_4$), filtered, and concentrated. The residue was purified by chromatography on silica gel eluting with a gradient of 25-100% ethyl acetate in heptane to provide the title compound (0.38 g, 1.183 mmol, 54.8% yield).

Example 140B ethyl 2-(4-oxochroman-2-yl)thiazole-4-carboxylate

A solution of 40% w/w diethyl azodicarboxylate in toluene (0.619 mL, 1.360 mmol) and triphenylphosphine (0.357 g, 1.360 mmol) in tetrahydrofuran (10 mL) was stirred at room temperature for 15 minutes. A solution of the product from Example 140A (0.38 g, 1.183 mmol) in tetrahydrofuran (10 mL) was added drop wise over 10 minutes. The mixture was stirred at 0° C. for 1 hour and then at room temperature for 30 minutes. The reaction was not proceeding. In a separate flask, a solution of triphenylphosphine (0.357 g, 1.360 mmol) in tetrahydrofuran (10 mL) under N$_2$ was cooled to 0° C. and treated with 40% w/w diethyl azodicarboxylate in toluene (0.619 mL, 1.360 mmol) over 3 minutes, stirred for 15 minutes and transferred to the original reaction mixture drop wise over 15 minutes. The mixture was stirred at 0° C. for 1 hour. The mixture was concentrated. The residue was purified by chromatography on silica gel eluting with a gradient of 10 to 100% ethyl acetate in heptane. The isolated impure product was further purified by chromatography on silica gel eluting with a gradient of [9:1 $CH_2Cl_2$:ethyl acetate] in heptanes to provide the title compound (70 mg, 0.231 mmol, 19.52% yield). $^1$H NMR (400 MHz, $CDCl_3$) δ 8.24 (s, 1H), 7.96-7.92 (m, 1H), 7.56 (t, J=7.8 Hz, 1H), 7.14-7.08 (m, 2H), 5.88 (dd, J=11.7, 3.7 Hz, 1H), 4.44 (q, J=7.1 Hz, 2H), 3.34 (dd, J=17.0, 3.7 Hz, 1H), 3.19 (dd, J=17.0, 11.7 Hz, 1H), 1.42 (t, J=7.1 Hz, 3H); MS (ESI+) m/z 304 (M+H)$^+$, m/z 321 (M+$NH_4$)+.

Example 140C ethyl rel-2-((S)-4-(((R)-tert-butylsulfinyl)imino)chroman-2-yl)thiazole-4-carboxylate The title compound was isolated as the first eluting isomer from the procedure similar to that described in Example 132C, substituting the product from Example 140B for the product from Example 132B. Stereochemistry was arbitrarily assigned. $^1$H NMR (501 MHz, $CDCl_3$) δ 8.26 (s, 1H), 8.07 (dd, J=8.0, 1.7 Hz, 1H), 7.48 (ddd, J=8.5, 7.3, 1.6 Hz, 1H), 7.12-7.07 (m, 2H), 5.66 (dd, J=12.7, 3.0 Hz, 1H), 4.48 (qd, J=7.1, 2.7 Hz, 2H), 4.14 (dd, J=17.5, 3.1 Hz, 1H), 3.38 (dd, J=17.5, 12.7 Hz, 1H), 1.45 (t, J=7.1 Hz, 3H), 1.35 (s, 9H); MS (ESI+) m/z 407 (M+H)$^+$.

Example 140D ethyl rel-2-((2S,4S)-4-aminochroman-2-yl)thiazole-4-carboxylate

A solution of product from Example 140C (31 mg, 0.076 mmol) in ethanol (2 mL) was cooled to 0° C., treated with $NaBH_4$ (8.66 mg, 0.229 mmol), stirred at 0° C. for 15 minutes, and stirred at room temperature for 1 hour. The mixture was treated with 4 M HCl in dioxane (191 μL, 0.763 mmol) and stirred at room temperature for 40 minutes. The mixture was partitioned between water (10 mL) and methyl tert-butyl ether (30 mL). The aqueous layer was basified with solid $NaHCO_3$ and extracted with ethyl acetate (twice, 2×30 mL). The combined ethyl acetate layers were washed with brine, dried ($MgSO_4$), filtered, and concentrated to provide the title compound (20 mg, 0.066 mmol, 86% yield). Stereochemistry was arbitrarily assigned. $^1$H NMR (501 MHz, $CDCl_3$) δ 8.23 (s, 1H), 7.57 (d, J=7.5 Hz, 1H), 7.26-7.21 (m, 1H), 7.07-7.03 (m, 2H), 6.97 (dd, J=8.2, 1.1 Hz, 1H), 5.60 (dd, J=11.4, 2.2 Hz, 1H), 4.47 (q, J=7.1 Hz, 2H), 4.36-4.30 (m, 1H), 2.88 (ddd, J=13.0, 5.6, 2.2 Hz, 1H), 1.45 (t, J=7.1 Hz, 3H); MS (ESI+) m/z 305 (M+H)$^+$.

Example 140E ethyl rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylate The title compound was prepared using the procedure similar to that described in Example 126G, substituting the product from Example 140D for the product from Example 126F, and purification by chromatography on silica gel eluting with a gradient of 0-50% ethyl acetate in [9:1 $CH_2Cl_2$:ethyl acetate]. Stereochemistry was arbitrarily assigned. $^1$H NMR (500 MHz, $CDCl_3$) δ 8.21 (s, 1H), 7.27-7.20 (m, 1H), 7.17 (dd, J=8.2, 1.7 Hz, 1H), 7.16-7.10 (m, 2H), 7.04 (d, J=8.2 Hz, 1H), 7.00 (td, J=7.6, 1.1 Hz, 1H), 6.97 (dd, J=8.2, 1.0 Hz, 1H), 5.59 (dd, J=11.1, 2.4 Hz, 1H), 5.51 (td, J=10.0, 6.2 Hz, 1H), 5.39 (d, J=8.9 Hz, 1H), 4.48 (q, J=7.1 Hz, 2H), 2.97 (ddd, J=13.2, 6.0, 2.4 Hz, 1H), 1.94 (dt, J=13.2, 11.0 Hz, 1H), 1.81-1.77 (m, 1H), 1.72-1.68 (m, 1H), 1.46 (t, J=7.1 Hz, 3H), 1.15-1.09 (m, 2H); MS (ESI−) m/z 527 (M−H)$^-$.

Example 141 ethyl rel-2-[(2R,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylate Example 141A ethyl rel-2-((R)-4-(((R)-tert-butylsulfinyl)imino)chroman-2-yl)thiazole-4-carboxylate The title compound was isolated as the second eluting isomer from the procedure similar to that described in Example 132C, substituting the product from Example 140B for the product from Example 132B. Stereochemistry was arbitrarily assigned. $^1$H NMR (501 MHz, $CDCl_3$) δ 8.23 (s, 1H), 8.06 (dd, J=8.4, 1.6 Hz, 1H), 7.48 (ddd, J=8.9, 7.6, 1.7 Hz, 1H), 7.11-7.06 (m, 2H), 5.74 (dd, J=10.1, 3.8 Hz, 1H), 4.46 (qd, J=7.1, 1.0 Hz, 2H), 4.28 (dd, J=17.1, 3.8 Hz, 1H), 3.48 (dd, J=17.2, 10.1 Hz, 1H), 1.45 (t, J=7.1 Hz, 3H), 1.35 (s, 9H); MS (ESI+) m/z 407 (M+H)$^+$.

Example 141B ethyl rel-2-((2R,4R)-4-aminochroman-2-yl)thiazole-4-carboxylate and ethyl rel-2-((2R,4S)-4-aminochroman-2-yl)thiazole-4-carboxylate Using the procedure similar to that described in Example 140D, substituting the product from Example 141A for the product from Example 140C, provided the titled compound as a 4:1 mixture of cis and trans isomers. Stereochemistry was arbitrarily assigned. NMR of peaks of major cis isomer: $^1$H NMR (501 MHz, $CDCl_3$) δ 8.23 (s, 1H), 7.57 (d, J=7.6 Hz, 1H), 7.26-7.21 (m, 1H), 7.05 (td, J=7.6, 1.1 Hz, 1H), 6.97 (dd, J=8.2, 1.1 Hz, 1H), 5.60 (dd, J=11.4, 2.2 Hz, 1H), 4.47 (q, J=7.1 Hz, 2H), 4.36-4.29 (m, 1H), 2.88 (ddd, J=13.1, 5.7, 2.2 Hz, 1H), 2.03-1.95 (m, 1H), 1.45 (t, J=7.1 Hz, 3H); MS (ESI+) m/z 305 (M+H)$^+$.

Example 141C ethyl rel-2-[(2R,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylate The title compound was prepared using the procedure similar to that described in Example 126G, substituting the product from Example 141B for the product from Example 126F. Purification by chromatography on silica gel eluting with a gradient of 0-50% ethyl acetate in [9:1 $CH_2Cl_2$:ethyl acetate] provided the title compound as the first eluting isomer. Stereochemistry was arbitrarily assigned. $^1$H NMR (500 MHz, $CDCl_3$) δ 8.23 (s, 1H), 7.30-7.25 (m, 1H), 7.22 (dd, J=8.2, 1.7 Hz, 1H), 7.20-7.17 (m, 2H), 7.04 (d, J=8.2 Hz, 1H), 7.03-6.98 (m, 2H), 5.62 (d, J=6.7 Hz, 1H), 5.30

(dd, J=11.2, 2.6 Hz, 1H), 5.14-5.09 (m, 1H), 4.49 (q, J=7.1 Hz, 2H), 2.74 (dt, J=14.2, 2.8 Hz, 1H), 2.25 (ddd, J=14.3, 11.2, 4.9 Hz, 1H), 1.78 (ddd, J=10.0, 6.7, 3.4 Hz, 1H), 1.70 (ddd, J=9.9, 6.8, 3.6 Hz, 1H), 1.47 (t, J=7.1 Hz, 3H), 1.20 (ddd, J=10.3, 6.7, 3.6 Hz, 1H), 1.07 (ddd, J=9.7, 6.8, 3.3 Hz, 1H); MS (ESI+) m/z 529 (M+H)$^+$.

Example 142 ethyl rel-2-[(2R,4R)-4-({[1-(2,2-difluoro-1,3-benzo-dioxol-5-yl)cyclopropyl]carbonyl}amino)-3,4-di-hydro-2H-chromen-2-yl]-1,3-thiazole-4-carboxylate The title compound was isolated as the second eluting isomer from the chromatography of the crude material as described in Example 141C. Stereochemistry was arbitrarily assigned. $^1$H NMR (400 MHz, CDCl$_3$) δ 8.20 (s, 1H), 7.25-7.20 (m, 1H), 7.16 (dd, J=8.2, 1.7 Hz, 1H), 7.14-7.10 (m, 2H), 7.02 (d, J=8.2 Hz, 1H), 7.01-6.94 (m, 2H), 5.58 (dd, J=11.1, 2.4 Hz, 1H), 5.54-5.46 (m, 1H), 5.38 (d, J=8.9 Hz, 1H), 4.47 (q, J=7.1 Hz, 2H), 2.96 (ddd, J=13.2, 6.0, 2.3 Hz, 1H), 1.93 (dt, J=13.1, 11.0 Hz, 1H), 1.78 (dd, J=10.1, 3.7 Hz, 1H), 1.69 (dd, J=9.5, 3.5 Hz, 1H), 1.45 (t, J=7.1 Hz, 3H), 1.15-1.07 (m, 2H); MS (ESI-) m/z 527 (M-H)$^-$.

Example 143 rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylic acid The title compound was prepared using procedure similar to that described in Example 152, substituting the product from Example 140E for the product from Example 151G. Stereochemistry was arbitrarily assigned. $^1$H NMR (500 MHz, CDCl$_3$) δ 8.33 (s, 1H), 7.27-7.23 (m, 1H), 7.18 (dd, J=8.2, 1.6 Hz, 1H), 7.15-7.12 (m, 2H), 7.05 (d, J=8.2 Hz, 1H), 7.03-6.99 (m, 1H), 6.98 (d, J=8.2 Hz, 1H), 5.58 (dd, J=11.1, 1.7 Hz, 1H), 5.56-5.51 (m, 1H), 5.44 (d, J=8.8 Hz, 1H), 2.99 (dd, J=12.3, 5.0 Hz, 1H), 2.00-1.90 (m, 1H), 1.81 (dd, J=9.8, 3.2 Hz, 1H), 1.72 (dd, J=9.8, 3.1 Hz, 1H), 1.19-1.11 (m, 2H); MS (ESI-) m/z 499 (M-H)$^-$.

Example 144 rel-2-[(2R,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylic acid The title compound was prepared using procedure similar to that described in Example 152, substituting the product from Example 141C for the product from Example 151G. Stereochemistry was arbitrarily assigned. $^1$H NMR (501 MHz, CDCl$_3$) δ 8.32 (s, 1H), 7.29-7.25 (m, 1H), 7.20 (dd, J=8.2, 1.7 Hz, 1H), 7.18-7.15 (m, 2H), 7.03 (d, J=8.2 Hz, 1H), 7.02-6.98 (m, 2H), 5.63 (d, J=6.8 Hz, 0H), 5.29 (dd, J=10.5, 2.6 Hz, 1H), 5.15-5.11 (m, 1H), 2.69 (dt, J=14.3, 3.0 Hz, 1H), 2.33 (ddd, J=14.6, 10.7, 3.9 Hz, 2H), 1.77 (ddd, J=9.7, 6.5, 3.1 Hz, 1H), 1.72 (ddd, J=9.6, 6.3, 3.1 Hz, 1H), 1.17 (ddd, J=9.9, 6.5, 3.5 Hz, 1H), 1.09 (ddd, J=9.2, 6.4, 3.0 Hz, 1H); MS (ESI+) m/z 501 (M+H)$^+$.

Example 145 rel-2-[(2R,4R)-4-({[1-(2,2-difluoro-1,3-benzodioxol-5-yl)cyclopropyl]carbonyl}amino)-3,4-dihydro-2H-chromen-2-yl]-1,3-thiazole-4-carboxylic acid The title compound was prepared using procedure similar to that described in Example 152, substituting the product from Example 142 for the product from Example 151G. $^1$H NMR (500 MHz, CDCl$_3$) δ 8.33 (s, 1H), 7.27-7.23 (m, 1H), 7.18 (dd, J=8.2, 1.7 Hz, 1H), 7.16-7.12 (m, 2H), 7.05 (d, J=8.2 Hz, 1H), 7.04-7.00 (m, 1H), 6.98 (d, J=8.2 Hz, 1H), 5.57 (dd, J=11.0, 1.8 Hz, 1H), 5.56-5.51 (m, 1H), 5.43 (d, J=8.7 Hz, 1H), 2.99 (ddd, J=13.3, 5.8, 1.8 Hz, 1H), 2.00-1.90 (m, 1H), 1.83-1.78 (m, 1H), 1.75-1.70 (m, 1H), 1.18-1.11 (m, 2H); MS (ESI-) m/z 499 (M-H)$^-$.

Example 146

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-3-fluorobenzoic acid The mixture of Example 138 (100 mg, 0.180 mmol) and 2N aqueous LiOH (0.5 mL) in methanol (2 mL) was stirred at 35° C. for 2 hours. Solvent was removed and water was added (0.5 mL). The pH of the mixture was adjusted with 2N HCl to pH 1-2. The precipitated white solid was collected by filtration and dried to yield title compound (85 mg, 87% yield). $^1$H NMR (500 MHz, CDCl$_3$) δ 7.92 (ddd, J=18.8, 8.0, 1.5 Hz, 1H), 7.79 (td, J=10.2, 1.6 Hz, 1H), 7.64 (dt, J=20.9, 7.5 Hz, 1H), 7.19-7.07 (m, 2H), 7.04-6.95 (m, 2H), 6.54 (ddd, J=8.6, 4.5, 2.5 Hz, 1H), 6.45 (dd, J=6.3, 2.5 Hz, 1H), 5.50 (dd, J=11.3, 2.0 Hz, 1H), 5.44 (td, J=9.7, 6.1 Hz, 1H), 5.34 (d, J=8.8 Hz, 1H), 3.76 (d, J=1.6 Hz, 3H), 2.55 (ddd, J=13.4, 6.2, 2.1 Hz, 1H), 1.82-1.70 (m, 2H), 1.66 (ddd, J=9.7, 4.3, 2.0 Hz, 1H), 1.14-1.03 (m, 2H); MS (ESI-) m/z 540 (M-H)$^+$.

Example 147 methyl rac-3-[(2R,4R)-4-({[1-(2,2-difluoro-1,3-benzodioxol-5-yl)cyclopropyl]carbonyl}amino)-7-methoxy-3,4-dihydro-2H-chromen-2-yl]bicyclo[1.1.1]pentane-1-carboxylate Example 147A methyl 3-(7-methoxy-4-oxochroman-2-yl)bicyclo[1.1.1]pentane-1-carboxylate The title compound was prepared and purified using the procedures similar to that described in Example 129A, substituting methyl 3-formylbicyclo[1.1.1]pentane-1-carboxylate for methyl 3-oxocyclobutanecarboxylate.

Example 147B methyl 3-[4-({[1-(2,2-difluoro-1,3-benzodioxol-5-yl)cyclopropyl]carbonyl}amino)-7-methoxy-3,4-dihydro-2H-chromen-2-yl]bicyclo[1.1.1]pentane-1-carboxylate The title compound was prepared and purified using the procedures similar to that described in Example 129 B, substituting Example 147A for Example 129A (73% yield). $^1$H NMR (500 MHz, CDCl$_3$) δ 7.76 (d, J=8.8 Hz, 1H), 6.52 (dd, J=8.8, 2.5 Hz, 1H), 6.40 (d, J=2.5 Hz, 1H), 4.06 (dd, J=11.2, 3.5 Hz, 1H), 3.96 (s, 3H), 3.79 (s, 3H), 3.69 (s, 3H), 3.06 (dd, J=17.0, 3.5 Hz, 1H), 2.43-2.28 (m, 1H), 2.13-2.01 (m, 6H); MS (ESI+) m/z=332 (M+H)$^+$.

Example 147C methyl rac-3-((2R,4R)-4-amino-7-methoxychroman-2-yl)bicyclo[1.1.1]pentane-1-carboxylate hydrochloride Example 147B (150 mg, 0.453 mmol) in acetic acid was charged with a hydrogen balloon and reduced to amine using 5% platinum (177 mg, 0.045 mmol) on carbon as catalyst and was stirred for 18 hours at room temperature. The reaction mixture was filtered through a diatomaceous earth pad and the solvent removed under pressure. To the residue was added methyl tert-butyl ether (2 mL), followed by slow addition of 4M HCl in dioxane (0.5 mL). The precipitated white solid was collected by filtration and dried to provide title compound (105 mg, 0.309 mmol, 68.3% yield). MS (ESI+) m/z=287 (M-NH$_2$)+.

Example 147D methyl rac-3-[(2R,4R)-4-({[1-(2,2-difluoro-1,3-benzodioxol-5-yl)cyclopropyl]carbonyl}amino)-7-methoxy-3,4-dihydro-2H-chromen-2-yl]bicyclo[1.1.1]pentane-1-carboxylate To 1-(2,2-difluorobenzo[d][1,3]dioxol-5-yl)cyclopropanecarboxylic acid (78 mg, 0.324 mmol) in N,N-dimethylformamide (2 mL) was added HATU (1-[bis(dimethylamino)methylene]-1H-1,2,3-triazolo[4,5-b]pyridinium 3-oxid hexafluorophosphate) (168 mg, 0.441 mmol). The mixture was stirred at room temperature for 5 minutes, followed by addition of Example 147C (100 mg, 0.294 mmol) and N-ethyl-N-isopropylpropan-2-amine (0.205 mL, 1.177 mmol). The mixture was stirred at room temperature for 2 hours. Purification by chromatography, eluting with 0-40% ethyl acetate in heptane to provide the title compound (68 mg, 43.8%). $^1$H NMR (500 MHz, CDCl$_3$) δ 7.19-7.12 (m, 2H), 7.03 (d, J=8.2 Hz, 1H), 6.86 (dd, J=8.5, 1.0 Hz, 1H), 6.44 (dd, J=8.6, 2.6 Hz, 1H), 6.32 (d, J=2.6 Hz, 1H), 5.32 (d, J=8.8 Hz, 1H), 5.26-5.17 (m, 1H), 4.07 (dd, J=11.9, 1.6 Hz, 1H), 3.73 (s, 3H), 3.69 (s, 3H), 2.21 (ddd, J=13.0, 6.2, 1.8 Hz, 1H), 2.08-1.99 (m, 6H), 1.97-1.84 (m, 1H), 1.74 (ddd, J=9.0, 5.4, 2.2 Hz, 1H), 1.69-1.63 (m, 1H), 1.08 (tdd, J=9.6, 6.2, 3.0 Hz, 2H); MS(ESI-) m/z 526 (M-H)$^+$.

Example 148 rac-3-[(2R,4R)-4-({[1-(2,2-difluoro-1,3-benzodioxol-5-yl)cyclopropyl]carbonyl}amino)-7-methoxy-3,4-dihydro-2H-chromen-2-yl]bicyclo[1.1.1]pentane-1-carboxylic acid To Example 147D (23 mg, 0.044 mmol) in a 4 mL vial was added methanol (1.5 mL), followed by addition of 4N LiOH solution in water (0.5 mL). The mixture was stirred at 35° C. for 2 hours. Solvent was removed and water was added (1 mL), followed by addition of 2N HCl drop wise to adjust pH to 1-2. The white solid precipitated was collected by filtration and dried to yield the title compound (21.5 mg, 96%). 1H NMR (500 MHz, CDCl$_3$) δ 7.17 (dd, J=8.2, 1.7 Hz, 1H), 7.15-7.05 (m, 2H), 7.03 (d, J=8.1 Hz, 1H), 6.86 (dd, J=8.5, 1.0 Hz, 1H), 6.47-6.41 (m, 1H), 6.32 (d, J=2.5 Hz, 1H), 5.33 (d, J=8.8 Hz, 1H), 5.27-5.15 (m, 1H), 4.08 (dd, J=11.7, 1.6 Hz, 1H), 3.74 (d, J=1.5 Hz, 3H), 2.22 (ddd, J=12.9, 6.2, 1.8 Hz, 1H), 2.11-2.02 (m, 6H), 1.74 (ddd, J=8.9, 5.4, 2.2 Hz, 1H), 1.65 (dpd, J=19.3, 7.6, 6.5, 3.1 Hz, 2H), 1.12-1.05 (m, 2H), MS(ESI-) m/z 512 (M-H)

Example 149 ethyl rac-6-[(2R,4S)-4-({[1-(2,2-difluoro-1,3-benzodioxol-5-yl)cyclopropyl]carbonyl}amino)-3,4-dihydro-2H-chromen-2-yl]pyridine-3-carboxylate

Example 149A tert-butyl 3-(2-hydroxyphenyl)-3-oxopropanoate

To a solution of diisopropylamine (26.6 mL, 190 mmol) in anhydrous tetrahydrofuran (100 mL) under nitrogen and at −78° C. was added 1.6 M n-butyl lithium in hexanes (110 mL, 176 mmol). After the resulting suspension had been stirred a while, a solution of tert-butyl acetate (20.1 mL, 150 mmol) in tetrahydrofuran (30 mL) was added over 15 minutes. Then, after the solution had been stirred at −78° C. about 100 minutes, a solution of methyl salicylate (6.45 mL, 50.0 mmol) in tetrahydrofuran (50 mL) was added to the reaction mixture over nearly 20 minutes. The reaction mixture was permitted to warm to room temperature overnight and the reaction mixture was then quenched with 1 M aqueous citric acid (80 mL). The aqueous phase was separated and extracted twice with ethyl acetate. The combined organic phases were washed with brine, concentrated and chromatographed on silica (30 to 50% CH$_2$Cl$_2$/heptane) to give some purified material and additional fractions which were still impure. The impure fractions were concentrated and chromatographed on silica (eluted with 25 to 50% CH$_2$Cl$_2$/heptane). The desired fractions from both columns were combined and concentrated to give title compound (9.55 g). $^1$H NMR (500 MHz, CDCl$_3$) δ ppm 1.49 (s, 9H), 3.95 (s, 2H), 6.95 (ddd, J=8.0, 7.3, 1.1 Hz, 1H), 7.04 (dd, J=8.4, 1.1 Hz, 1H), 7.53 (ddd, J=8.4, 7.3, 1.7 Hz, 1H), 7.71 (dd, J=8.0, 1.7 Hz, 1H), 11.95 (s, 1H); MS (DCI) m/z 237 (M+H)$^+$, 254 (M+NH4)$^+$.

Example 149B tert-Butyl 3-(5-bromopyridin-2-yl)-2-(2-hydroxybenzoyl)acrylate The mixture of Example 149A (1.66 g, 7.0 mmol), 5-bromopicolinaldehyde (1.33 g, 7.15 mmol), piperidine (30 µL, 0.30 mmol) and acetic acid (17.5 µL, 0.31 mmol) was heated at gentle reflux in anhydrous toluene (30 mL), within a round-bottomed flask with a Dean-Stark apparatus attached, for 40 minutes. The heat was increased to very slowly azeotrope water over. After an hour, the heat was reduced back to gentle reflux, 3 Å molecular sieves (3.5 grams) were added. After 30 minutes of refluxing the reaction mixture was cooled to room temperature. The sieves were filtered off with a thorough chloroform rinse, and the filtrate was concentrated to a dark syrup which was chromatographed on silica (20% methyl tert-butyl ether/heptane) to give an impure solid which was slurried in heptane. The title compound was collected by filtration, with a heptane rinse, as a yellow powder (1.105 g). $^1$H NMR (400 MHz, CDCl$_3$) δ ppm 1.41 (s, 9H), 6.74-6.79 (m, 1H), 7.00-7.04 (m, 1H), 7.28 (d, J=8.2 Hz, 1H), 7.40-7.45 (m, 2H), 7.68 (s, 1H), 7.76-7.80 (m, 1H), 8.40 (d, J=2.3 Hz, 1H), 11.73 (s, 1H); MS (ESI) m/z 406 (M+H)$^+$.

Example 149C

2-(5-bromopyridin-2-yl)chroman-4-one

A mixture of Example 149B (1.103 g, 2.72 mmol) and 1-(3,5-bis(trifluoromethyl)phenyl)-3-((1R,2R)-2-(dimethylamino)cyclohexyl)thiourea (170 mg, 0.41 mmol) were stirred in anhydrous toluene (15 mL) for 3 hours at room temperature and then at 40° C. overnight. (rac)-Camphorsulfonic acid (316 mg, 1.36 mmol) was added and the solution was heated at 90° C. for two days and cooled to room temperature. The reaction mixture was placed on a silica column and chromatographed (20 to 35% methyl tert-butyl ether/heptane) to give title compound (414 mg). $^1$H NMR (400 MHz, CDCl$_3$) δ ppm 3.11-3.15 (m, 2H), 5.57 (dd, J=7.7 Hz, 1H), 7.04-7.10 (m, 2H), 7.50-7.56 (m, 2H), 7.90 (dd, J=8.4, 2.4 Hz, 1H), 7.92-7.95 (m, 1H), 8.66-8.68 (m, 1H); MS (DCI) m/z 306 (M+H)$^+$.

Example 149D ethyl 6-(4-oxochroman-2-yl)nicotinate

To Example 149C (410 mg, 1.35 mmol) and dichloro[1,1'-bis(diphenylphosphino)ferrocene]palladium(II) (49 mg, 0.068 mmol) in a 50 mL pressure bottle were added ethanol (10 mL) and triethylamine (0.377 mL, 2.70 mmol). The reactor was degassed with argon several times, then filled with carbon monoxide and heated at 100° C. for 16 hours at 70 psi. The sample was concentrated and filtered through silica (80% CH$_2$Cl$_2$/heptane), and the filtrate was concentrated and chromatographed on silica (60 to 100% CH$_2$Cl$_2$/heptane) to give title compound as an orange solid (242 mg). $^1$H NMR (400 MHz, CDCl$_3$) δ ppm 1.42 (t, J=7.1 Hz, 3H), 3.12 (dd, J=17.0, 11.6 Hz, 1H), 3.20 (dd, J=17.0, 4.0 Hz, 1H), 4.43 (q, J=7.1 Hz, 2H), 5.67 (dd, J=11.6, 4.0 Hz, 1H), 7.05-7.13 (m, 2H), 7.54 (ddd, J=8.6, 7.2, 1.8 Hz, 1H), 7.74 (d, J=8.2 Hz, 1H), 7.94 (dd, J=7.8, 1.8 Hz, 1H), 8.38 (dd, J=8.2, 2.2 Hz, 1H), 9.20 (d, J=2.2 Hz, 1H); MS (DCI) m/z 298 (M+H)$^+$.

Example 149E ethyl 6-(4-(ethoxyimino)chroman-2-yl)nicotinate

A mixture of Example 149D (239 mg, 0.80 mmol), O-ethylhydroxylamine hydrochloride (117 mg, 1.20 mmol) and potassium acetate (118 mg, 1.20 mmol) were heated in ethanol (3 mL) at 50° C. for 90 minutes and then cooled to room temperature, concentrated, and chromatographed on silica (30% methyl tert-butyl ether/heptane) to give title compound as an orange syrup (262 mg). $^1$H NMR (500 MHz, CDCl$_3$) δ ppm 1.31 (t, J=7.1 Hz, 3H), 1.42 (t, J=7.1 Hz, 3H), 2.75 (dd, J=17.2, 11.8 Hz, 1H), 3.71 (dd, J=17.2, 3.5 Hz, 1H), 4.21-4.26 (m, 2H), 4.43 (q, J=7.1 Hz, 2H), 5.26 (dd, J=11.8, 3.5 Hz, 1H), 6.97-7.03 (m, 2H), 7.29 (ddd, J=8.2, 7.2, 1.7 Hz, 1H), 7.70-7.73 (m, 1H), 7.95 (dd, J=7.9, 1.7 Hz, 1H), 8.36 (dd, J=8.2, 2.1 Hz, 1H), 9.20 (dd, J=2.1, 0.8 Hz, 1H); MS (DCI) m/z 341 (M+H)$^+$.

Example 149F ethyl 6-(4-aminochroman-2-yl)nicotinate

Example 149E (259 mg, 0.76 mmol) and ethanol (25 mL) were added to Ra—Ni 2800 water slurry (2.6 g, 20 mmol) in a 50 mL pressure bottle and stirred or shaken for 16 hours under hydrogen at 30 psi and at room temperature. The reaction mixture was filtered, concentrated, and chromatographed on silica (0 to 3% concentrated aqueous NH$_4$OH in acetonitrile) to give title compound as a syrup (119 mg). MS (ESI) m/z 299 (M+H)$^+$.

Example 149G ethyl rac-6-((2R,4S)-4-(1-(2,2-difluorobenzo[d][1,3]dioxol-5-yl)cyclopropanecarboxamido)chroman-2-yl)nicotinate 1-(2,2-Difluorobenzo[d][1,3]dioxol-5-yl)cyclopropanecarboxylic acid (132 mg, 0.55 mmol), carbonyl diimidazole (89 mg, 0.55 mmol) and 1-hydroxy-7-azabenzotriazole (8 mg, 0.06 mmol) were stirred in anhydrous acetonitrile (1.3 mL) for 100 minutes and then transferred to a flask containing Example 149F (115 mg, 0.39 mmol) with an acetonitrile (0.2 mL) rinse. After several minutes, diisopropylethylamine (50 µL, 0.29 mmol) was added and the solution was stirred at room temperature for 3.5 hours. Then the solution was concentrated and chromatographed on silica (5 to 20% methyl tert-butyl ether in 1:1 CH$_2$Cl$_2$/heptane) to give the title compound as the first eluting isomer (84 mg), and Example 150 (85 mg) as the second eluting isomer. $^1$H NMR (501 MHz, CDCl$_3$) δ ppm 1.04-1.12 (m, 2H), 1.42 (t, J=7.1 Hz, 3H), 1.66-1.73 (m, 2H), 2.23 (ddd, J=14.1, 10.3, 4.9 Hz, 1H), 2.47 (ddd, J=14.1, 4.1, 2.9 Hz, 1H), 4.43 (q, J=7.1 Hz, 2H), 5.01-5.06 (m, 2H), 5.62 (d, J=7.4 Hz, 1H), 6.91-7.04 (m, 4H), 7.13-7.16 (m, 2H), 7.18 (dd, J=8.2, 1.7 Hz, 1H), 7.23 (ddd, J=8.6, 7.2, 1.7 Hz, 1H), 7.62 (d, J=8.2 Hz, 1H), 8.32 (dd, J=8.2, 2.1 Hz, 1H), 9.19-9.21 (m, 1H); MS (ESI) m/z 523 (M+H)$^+$.

Example 150 ethyl rac-6-[(2R,4R)-4-({[1-(2,2-difluoro-1,3-benzodioxol-5-yl)cyclopropyl]carbonyl}amino)-3,4-dihydro-2H-chromen-2-yl]pyridine-3-carboxylate The title compound was obtained as the second eluting isomer from the chromatography described in Example 149G. $^1$H NMR (500 MHz, CDCl$_3$) δ ppm 1.04-1.11 (m, 2H), 1.43 (t, J=7.1 Hz, 3H), 1.64-1.68 (m, 1H), 1.73-1.77 (m, 1H), 1.84 (ddd, J=13.3, 10.9, 10.8 Hz, 1H), 2.78 (ddd, J=13.3, 6.2, 2.3 Hz, 1H), 4.43 (q, J=7.1 Hz, 2H), 5.33 (dd, J=10.8, 2.3 Hz, 1H), 5.41 (d, J=8.9 Hz, 1H), 5.48-5.55 (m, 1H), 6.91-7.03 (m, 3H), 7.08-7.13 (m, 3H), 7.17-7.22 (m, 1H), 7.63 (d, J=8.2 Hz, 1H), 8.32 (dd, J=8.2, 2.1 Hz, 1H), 9.14 (dd, J=2.1, 0.8 Hz, 1H); MS (ESI) m/z 523 (M+H)$^+$.

Example 151 ethyl 3-[4-({[1-(2,2-difluoro-1,3-benzodioxol-5-yl)cyclopropyl]carbonyl}amino)-3,4-dihydro-2H-chromen-2-yl]cyclobutanecarboxylate

Example 151A ethyl 3-methylenecyclobutanecarboxylate

A mixture of 3-methylenecyclobutanecarboxylic acid (CAS#15760-36-8) (2.06 g, 18.37 mmol), ethyl iodide (1.782 mL, 22.05 mmol) and Cs$_2$CO$_3$ (13.17 g, 40.4 mmol) in N,N-dimethylformamide (100 mL) under N$_2$ was stirred at room temperature overnight. The mixture was poured slowly into a stirred 0° C. mixture of 0.2 M HCl (500 mL)

and methyl tert-butyl ether (1000 mL). The layers were separated and the methyl tert-butyl ether layer was washed with water (500 mL×2), washed with brine, dried (MgSO$_4$), filtered, and concentrated to provide the title compound (2.5 g, 17.83 mmol, 97% yield). $^1$H NMR (500 MHz, CDCl$_3$) δ 4.83 (p, J=2.3 Hz, 2H), 4.19 (q, J=7.1 Hz, 2H), 3.18-3.11 (m, 1H), 3.07-3.00 (m, 2H), 2.97-2.89 (m, 2H), 1.30 (t, J=7.1 Hz, 3H).

Example 151B ethyl 3-(hydroxymethyl)cyclobutanecarboxylate

A solution of product from Example 151A (2.5 g, 17.83 mmol) in tetrahydrofuran (20 mL) was treated with borane-methyl sulfide complex (4.46 mL, 8.92 mmol) and the mixture was stirred at room temperature for approximately 3 hours. A suspension of sodium perborate (1.751 g, 21.40 mmol) in water (15 mL) was added (slowly at first) followed by dioxane (15 mL). The mixture was heated to 65° C. for 2 hours and allowed to slowly cool to room temperature overnight. The mixture was partitioned between ethyl acetate (100 mL) and water (50 mL). The layers were separated and the aqueous was extracted with ethyl acetate (50 mL). The combined ethyl acetate layers were washed with brine, dried (MgSO$_4$), filtered, and concentrated to provide the title compound (2.8 g, 17.70 mmol, 99% yield) as a 1:1 mixture of cis and trans isomers. MS (DCI+) m/z 176 (M+NH$_4$)$^+$.

Example 151C ethyl 3-formylcyclobutanecarboxylate

Following a procedure described in Kasar, et al. WO2012154204A1, 2012, a solution of oxalyl chloride (3.10 mL, 35.4 mmol) in CH$_2$Cl$_2$ (115 mL) was cooled to −78° C. under N$_2$, treated dropwise with a solution of dimethylsulfoxide (5.02 mL, 70.8 mmol) in CH$_2$Cl$_2$ (10 mL), followed by the addition of a solution of the product from Example 151B (2.8 g, 17.70 mmol) in CH$_2$Cl$_2$ (40 mL). The mixture was stirred at −78° C. for 2 hours, treated with triethylamine (24.67 mL, 177 mmol), stirred at −78° C. for 20 minutes, quenched with saturated NH$_4$Cl solution (100 mL), and allowed to warm to room temperature. The layers were separated and the aqueous was extracted with CH$_2$Cl$_2$ (twice). The combined CH$_2$Cl$_2$ layers were dried (MgSO$_4$), filtered, and concentrated. The residue was purified by chromatography on silica gel eluting with a gradient 0-90% of ethyl acetate in heptanes to provide the titled compound.

Example 151D ethyl 3-(4-oxochroman-2-yl)cyclobutanecarboxylate

A mixture of 2'-hydroxyacetophenone (212 mg, 1.560 mmol) and the product from Example 151C (203 mg, 1.300 mmol) in ethanol (1 mL) was treated with pyrrolidine (107 μL, 1.300 mmol) and stirred at room temperature overnight. Mixture was partitioned between ethyl acetate (30 mL) and 1 M HCl (10 mL). The ethyl acetate layer was washed with brine, dried (MgSO$_4$), filtered, and concentrated. The residue was purified by chromatography on silica gel eluting with a gradient of 10 to 30% ethyl acetate in heptane to provide the titled compound (0.27 g, 0.984 mmol, 76% yield). $^1$H NMR (400 MHz, CDCl$_3$) δ 7.93-7.88 (m, 1H), 7.55-7.47 (m, 1H), 7.07-6.99 (m, 2H), 4.49-4.37 (m, 1H), 4.24-4.14 (m, 2H), 3.23-3.04 (m, 1H), 2.83-2.74 (m, 0.5H), 2.70-2.57 (m, 2.5H), 2.52-2.24 (m, 4H), 1.33-1.27 (m, 3H); MS (ESI+) m/z 275 (M+H)$^+$.

Example 151E ethyl 3-(4-(methoxyimino)chroman-2-yl)cyclobutanecarboxylate

A solution of the product from Example 151D (270 mg, 0.984 mmol) and O-methylhydroxylamine hydrochloride (247 mg, 2.95 mmol) in pyridine (2 mL) was heated at 65° C. for 1 hour. The mixture was cooled, concentrated, and partitioned between ethyl acetate (50 mL) and water (15 mL). The ethyl acetate layer was washed with brine, dried (MgSO$_4$), filtered, concentrated, and dried under vacuum to provide the title compound (0.27 g, 0.890 mmol, 90% yield). $^1$H NMR (400 MHz, CDCl$_3$) δ 8.50 (td, J=6.5, 3.1 Hz, 0.1H), 7.90 (ddd, J=7.9, 6.5, 1.5 Hz, 0.9H), 7.36-7.22 (m, 1H), 6.98-6.89 (m, 2H), 4.18 (dq, J=14.2, 7.1 Hz, 2H), 4.08-3.95 (m, 4H), 3.22-2.99 (m, 1.5H), 2.78-2.65 (m, 0.5H), 2.62-2.21 (m, 5H), 1.34-1.25 (m, 3H); MS (ESI+) m/z 304 (M+H)$^+$.

Example 151F ethyl 3-(4-aminochroman-2-yl)cyclobutanecarboxylate

A solution of the product from Example 151E (0.27 g, 0.890 mmol) in ethanol (20 mL) was added to Ra—Ni 2800, water slurry, (3 g, 23.00 mmol) in a 50 mL pressure bottle and stirred at room temperature under an atmosphere of H$_2$ for 16 hours at a pressure of 30 pounds per square inch. The mixture was filtered to remove the solids and the filtrate was concentrated to provide the title compound (230 mg, 0.835 mmol, 94% yield) as a mixture of isomers. $^1$H NMR (400 MHz, CDCl$_3$) δ 7.44 (t, J=7.4 Hz, 0.5H), 7.23 (dt, J=7.6, 1.6 Hz, 0.5H), 7.20-7.11 (m, 1H), 6.96-6.79 (m, 2H), 4.23-3.98 (m, 4H), 3.21-2.98 (m, 1H), 2.65 (dt, J=15.0, 7.4 Hz, 0.5H), 2.57-2.21 (m, 5H), 2.12 (dtd, J=12.8, 6.4, 1.7 Hz, 0.5H), 1.76 (ddd, J=7.6, 5.9, 3.1 Hz, 1H), 1.32-1.24 (m, 3H); MS (ESI+) m/z 259 (M-NH$_3$)$^+$.

Example 151G ethyl 3-[4-({[1-(2,2-difluoro-1,3-benzodioxol-5-yl)cyclopropyl]carbonyl}amino)-3,4-dihydro-2H-chromen-2-yl]cyclobutanecarboxylate The title compound was prepared using the procedure similar to that described in Example 126G, substituting the product from Example 151F for the product from Example 126F. The crude material was purified by chromatography on silica gel, eluting with a gradient of 15-50% ethyl acetate in heptanes to provide the title compound. $^1$H NMR (400 MHz, CDCl$_3$) δ 7.20-7.07 (m, 3.5H), 7.06-6.98 (m, 1.5H), 6.91-6.77 (m, 2H), 5.55-5.50 (m, 0.5H), 5.39 (dd, J=8.7, 5.4 Hz, 0.5H), 5.36-5.26 (m, 0.5H), 5.05-4.98 (m, 0.5H), 4.22-3.99 (m, 2.5H), 3.74-3.64 (m, 0.5H), 3.15-2.96 (m, 1H), 2.69-2.53 (m, 0.5H), 2.51-2.14 (m, 4H), 1.96 (ddt, J=12.7, 7.8, 2.3 Hz, 0.5H), 1.80-1.66 (m, 1H), 1.34-1.23 (m, 3H), 1.14-1.04 (m, 2H), 0.93-0.81 (m, 3H); MS (ESI+) m/z 500 (M+H)$^+$.

Example 152

3-[4-({[1-(2,2-difluoro-1,3-benzodioxol-5-yl)cyclopropyl]carbonyl}amino)-3,4-dihydro-2H-chromen-2-yl]cyclobutanecarboxylic acid A solution of the product from Example 151G (50 mg, 0.100 mmol) in tetrahydrofuran (1.5 mL) was diluted with methanol (1.5 mL), treated with 1 M NaOH (1 mL) and stirred at room temperature for 15 minutes. The mixture was treated with 1 M HCl (5 mL) and extracted with ethyl acetate (30 mL). The ethyl acetate layer was washed with brine, dried (MgSO$_4$), filtered, and concentrated to provide the title compound (47 mg, 0.100 mmol, 100% yield). $^1$H NMR (400 MHz, CDCl$_3$) δ 7.21-7.08 (m, 3.5H), 7.06-6.98 (m, 1.5H), 6.91-6.78 (m, 2H), 5.54 (d, J=6.8 Hz, 0.5H), 5.42 (dd, J=8.8, 2.3 Hz, 0.5H), 5.31 (s, 0.5H), 5.05-4.98 (m, 0.5H), 4.10-4.00 (m, 0.5H), 3.75-3.63 (m, 0.5H), 3.22-3.03 (m, 1H), 2.74-2.57 (m, 0.5H), 2.55-2.17 (m, 5H), 2.00-1.92 (m, 0.5H), 1.81-1.64 (m, 3H), 1.15-1.03 (m, 2H); MS (ESI+) m/z 472 (M+H)$^+$.

Example 153 rac-6-[(2R,4S)-4-({[1-(2,2-difluoro-1,3-benzodioxol-5-yl)cyclopropyl]carbonyl}amino)-3,4-dihydro-2H-chromen-2-yl]pyridine-3-carboxylic acid The product from Example 149G (18 mg, 35 μmol) was dissolved in anhydrous tetrahydrofuran (140 μL) and methanol (35 μL), treated with two drops of 3 M aqueous NaOH (about 40 μL) and stirred at room temperature for two hours. The reaction mixture was concentrated, acidified with a drop of concentrated aqueous HCl and partitioned between brine and methyl tert-butyl ether. The aqueous phase was separated and extracted with more methyl tert-butyl ether. The combined organic phases were dried (Na$_2$SO$_4$), filtered, and concentrated. When it was discovered that the reaction was incomplete, the material was resubjected to the reaction conditions, stirred overnight and worked up as before to give the title compound (17 mg). $^1$H NMR (501 MHz, CDCl$_3$) δ ppm 1.09-1.16 (m, 2H), 1.73-1.78 (m, 2H), 2.25-2.34 (m, 1H), 2.52-2.59 (m, 1H), 5.06-5.11 (m, 1H), 5.16 (bs, 1H), 5.20-5.26 (m, 1H), 5.75 (d, J=7.2 Hz, 1H), 6.96-7.05 (m, 3H), 7.15-7.29 (m, 4H), 7.75 (d, J=7.6 Hz, 1H), 8.45 (d, J=7.3 Hz, 1H), 9.23-9.28 (m, 1H); MS (ESI) m/z 493 (M−H)$^−$.

Example 154 rac-6-[(2R,4R)-4-({[1-(2,2-difluoro-1,3-benzodioxol-5-yl)cyclopropyl]carbonyl}amino)-3,4-dihydro-2H-chromen-2-yl]pyridine-3-carboxylic acid The product from Example 150 (18 mg, 35 μmol) was dissolved in anhydrous THF (170 μL) and methanol (70 μL), treated with three drops of 3 M aqueous NaOH (about 70 μL) and stirred at room temperature overnight. The reaction mixture was concentrated, acidified with a drop of concentrated aqueous HCl and partitioned between brine and methyl tert-butyl ether. The aqueous phase was separated and extracted with more methyl tert-butyl ether. The combined organic phases were dried (Na$_2$SO$_4$), and filtered with a methyl tert-butyl ether rinse. The filter disc was then washed through with methanol, and the filtrate concentrated to give the title compound (6 mg). MS (ESI) m/z=493 (M−H)$^−$.

Example 155 ethyl rel-2-[(2R,4R)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylate

Example 155A ethyl 2-(1-hydroxy-3-(2-hydroxy-4-methoxyphenyl)-3-oxopropyl)thiazole-4-carboxylate Using the procedure similar to that described in Example 140A, substituting a solution of 2'-hydroxy-4'-methoxyacetophenone (269 mg, 1.620 mmol) in tetrahydrofuran for 2'-hydroxyacetophenone, and quenching with saturated NH$_4$Cl solution in place of a 10% aqueous solution of KH$_2$PO$_4$, provided the titled compound. $^1$H NMR (501 MHz, CDCl$_3$) δ 12.33 (s, 1H), 8.19 (s, 1H), 7.68 (d, J=9.0 Hz, 1H), 6.48 (dd, J=8.9, 2.5 Hz, 1H), 6.45 (d, J=2.5 Hz, 1H), 5.61 (ddd, J=8.7, 4.7, 2.7 Hz, 1H), 4.45 (q, J=7.1 Hz, 2H), 4.30 (d, J=4.7 Hz, 1H), 3.90 (dd, J=17.9, 2.8 Hz, 1H), 3.87 (s, 3H), 3.49 (dd, J=17.8, 8.8 Hz, 1H), 1.43 (t, J=7.1 Hz, 3H); MS (ESI+) m/z 352 (M+H)$^+$.

Example 155B ethyl 2-(7-methoxy-4-oxochroman-2-yl)thiazole-4-carboxylate

A solution of the product from Example 155A (0.38 g, 1.081 mmol) and triphenylphosphine (0.567 g, 2.163 mmol) in tetrahydrofuran (12 mL) was cooled to 0° C., treated portion wise with 40% w/w diethyl azodicarboxylate in toluene (0.739 mL, 1.622 mmol) over 20 minutes, stirred at room temperature for 1 hour, treated with silica gel (3 g) and concentrated to dryness. This silica gel suspension was subjected to chromatography on silica gel, eluting with a gradient of 15-50% ethyl acetate in heptane to provide impure product. The impure product was further purified by chromatography on silica gel eluting with a gradient of 50-100% [9:1 CH$_2$Cl$_2$:ethyl acetate] in heptanes to provide the titled compound (0.15 g, 0.450 mmol, 41.6% yield). $^1$H NMR (400 MHz, CDCl$_3$) δ 8.26 (s, 1H), 7.90 (d, J=8.8 Hz, 1H), 6.68 (dd, J=8.8, 2.4 Hz, 1H), 6.57 (d, J=2.4 Hz, 1H), 5.89 (dd, J=11.5, 3.8 Hz, 1H), 4.46 (q, J=7.1 Hz, 2H), 3.89 (s, 3H), 3.28 (dd, J=17.0, 3.8 Hz, 1H), 3.14 (dd, J=17.0, 11.6 Hz, 1H), 1.44 (t, J=7.1 Hz, 3H); MS (ESI+) m/z 334 (M+H)$^+$.

Example 155C ethyl rel-2-((R)-4-(((S)-tert-butylsulfinyl)imino)-7-methoxychroman-2-yl)thiazole-4-carboxylate The title compound was prepared using the procedure similar to that described in Example 132C, substituting the product from Example 155B for the product from Example 132B, and substituting (S)-(−)-2-methyl-2-propanesulfinamide for (R)-(+)-2-methyl-2-propanesulfinamide. Purification by chromatography on silica gel eluting with a gradient of 0-100% [9:1 CH$_2$Cl$_2$:ethyl acetate] in [1:1 CH$_2$Cl$_2$:ethyl acetate] provided the title compound as the first eluting isomer. This compound contained some impurities and was further purified by chromatography on silica gel eluting with a gradient of 20-100% ethyl acetate in heptanes to provide the title compound. $^1$H NMR (501 MHz, CDCl$_3$) δ 8.26 (s, 1H), 8.01 (d, J=8.9 Hz, 1H), 6.67 (dd, J=9.0, 2.5 Hz, 1H), 6.54 (d, J=2.5 Hz, 1H), 5.66 (dd, J=12.6, 3.1 Hz, 1H), 4.48 (qd, J=7.1, 3.2 Hz, 2H), 4.06 (dd, J=17.4, 3.1 Hz, 1H), 3.88 (s, 3H), 3.34 (dd, J=17.4, 12.6 Hz, 1H), 1.45 (t, J=7.1 Hz, 3H), 1.34 (s, 9H); MS (ESI+) m/z 437 (M+H)$^+$. Stereochemistry was arbitrarily assigned.

Example 155D ethyl rel-2-((2R,4R)-4-amino-7-methoxychroman-2-yl)thiazole-4-carboxylate Using the procedure similar to that described in Example 140D, substituting the product from Example 155C for the product from Example 140C, provided the title compound. MS (ESI+) m/z 318 (M-NH$_3$)$^+$. Stereochemistry was arbitrarily assigned.

Example 155E ethyl rel-2-[(2R,4R)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylate Using the procedure similar to that described in Example 126G, substituting the product from Example 155D for the product from Example 126F, and purification by chromatography on silica gel eluting with a gradient of 0-50% ethyl acetate in [9:1 CH$_2$Cl$_2$:ethyl acetate], provided the title compound. $^1$H NMR (400 MHz, CDCl$_3$) δ 8.19 (s, 1H), 7.17-6.97 (m, 4H), 6.57 (dd, J=8.6, 2.5 Hz, 1H), 6.48 (d, J=2.4 Hz, 1H), 5.55 (dd, J=10.8, 2.2 Hz, 1H), 5.46-5.37 (m, 1H), 5.31 (d, J=8.9 Hz, 1H), 4.47 (q, J=7.1 Hz, 2H), 3.80 (s, 3H), 2.93 (ddd, J=13.3, 5.9, 2.2 Hz, 1H), 1.99-1.87 (m, 1H), 1.79-1.62 (m, 2H), 1.45 (t, J=7.1 Hz, 3H), 1.09 (m, 2H); MS (ESI-) m/z 557 (M-H)$^-$.

Example 156 rel-2-[(2R,4R)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylic acid Using the procedure similar to that described in Example 152, substituting the product from Example 155E for the product from Example 151G, provided the title compound. $^1$H NMR (400 MHz, CDCl$_3$) δ 8.30 (s, 1H), 7.17-7.10 (m, 2H), 7.05-6.98 (m, 2H), 6.58 (dd, J=8.6, 2.2 Hz, 1H), 6.49 (d, J=2.2 Hz, 1H), 5.54 (d, J=10.9 Hz, 1H), 5.48-5.40 (m, 1H), 5.35 (d, J=8.5 Hz, 1H), 3.80 (s, 3H), 2.95 (dd, J=13.2, 5.8 Hz, 1H), 1.98-1.87 (m, 1H), 1.81-1.63 (m, 2H), 1.16-1.07 (m, 2H); MS (ESI-) m/z 529 (M-H)$^-$.

Example 157 ethyl rel-2-[(2S,4S)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylate Example 157A ethyl rel-2-((S)-4-(((S)-tert-butylsulfinyl)imino)-7-methoxychroman-2-yl)thiazole-4-carboxylate The impure title compound was obtained as the second eluting isomer from the first chromatography described in Example 155C. This material was further purified by chromatography on silica gel eluting with a gradient of 20-100% ethyl acetate in heptanes to provide the title compound. $^1$H NMR (501 MHz, CDCl$_3$) δ 8.23 (s, 1H), 8.02 (d, J=8.9 Hz, 1H), 6.65 (dd, J=8.9, 2.5 Hz, 1H), 6.53 (d, J=2.5 Hz, 1H), 5.73 (dd, J=10.1, 3.8 Hz, 1H), 4.52-4.40 (m, 2H), 4.20 (dd, J=17.1, 3.8 Hz, 1H), 3.88 (s, 3H), 3.41 (dd, J=17.1, 10.1 Hz, 1H), 1.45 (t, J=7.1 Hz, 3H), 1.32 (s, 9H); MS (ESI+) m/z 437 (M+H)$^+$. Stereochemistry was arbitrarily assigned.

Example 157B ethyl rel-2-((2S,4S)-4-amino-7-methoxychroman-2-yl)thiazole-4-carboxylate Using the procedure similar to that described in Example 140D, substituting the product from Example 157A for the product from Example 140C, provided the title compound. $^1$H NMR (400 MHz, CDCl$_3$) δ 8.21 (s, 1H), 7.44 (d, J=8.5 Hz, 1H), 6.61 (dd, J=8.6, 2.5 Hz, 1H), 6.50 (d, J=2.5 Hz, 1H), 5.56 (d, J=9.8 Hz, 1H), 4.45 (q, J=7.1 Hz, 2H), 4.29-4.21 (m, 1H), 3.81 (s, 3H), 2.86-2.79 (m, 1H), 2.00-1.89 (m, 1H), 1.43 (t, J=7.1 Hz, 3H); MS (ESI+) m/z 318 (M-NH$_3$)+.

Example 157C ethyl rel-2-[(2S,4S)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylate Using the procedure similar to that described in Example 126G, substituting the product from Example 157B for the product from Example 126F, and purification by chromatography on silica gel eluting with a gradient of 0-50% ethyl acetate in [9:1 CH$_2$Cl$_2$:ethyl acetate], provided the title compound. $^1$H NMR (400 MHz, CDCl$_3$) δ 8.19 (s, 1H), 7.15-7.07 (m, 2H), 7.04-6.98 (m, 2H), 6.57 (dd, J=8.6, 2.6 Hz, 1H), 6.48 (d, J=2.5 Hz, 1H), 5.55 (dd, J=10.8, 1.8 Hz, 1H), 5.45-5.38 (m, 1H), 5.31 (d, J=8.6 Hz, 1H), 4.47 (q, J=7.1 Hz, 2H), 3.80 (s, 3H), 2.93 (ddd, J=13.3, 6.0, 2.3 Hz, 1H), 1.99-1.86 (m, 1H), 1.82-1.64 (m, 2H), 1.45 (t, J=7.1 Hz, 3H), 1.14-1.05 (m, 2H); MS (ESI-) m/z 557 (M-H)$^-$.

Example 158 rel-2-[(2S,4S)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylic acid Using the procedure similar to that described in Example 152, substituting the product from Example 157C for the product from Example 151G, provided the title compound. $^1$H NMR (400 MHz, CDCl$_3$) δ 8.29 (s, 1H), 7.17-6.97 (m, 4H), 6.57 (dd, J=8.6, 2.5 Hz, 1H), 6.49 (d, J=2.4 Hz, 1H), 5.53 (d, J=11.0 Hz, 1H), 5.48-5.39 (m, 1H), 5.34 (d, J=12.7 Hz, 1H), 3.80 (s, 3H), 2.94 (dd, J=12.1, 4.7 Hz, 1H), 2.00-1.87 (m, 1H), 1.81-1.66 (m, 2H), 1.15-1.06 (m, 2H); MS (ESI-) m/z 529 (M-H)$^-$.

Example 159 methyl rel-6-[(2R,4S)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylate

Example 159A tert-butyl 3-(2-hydroxy-4-methoxyphenyl)-3-oxopropanoate

To a solution of diisopropylamine (36.3 mL, 259 mmol) in anhydrous tetrahydrofuran (130 mL) under nitrogen and at −78° C. was added 1.6 M n-butyl lithium in hexanes (150 mL, 240 mmol). After the resulting suspension had been stirred 15 minutes, a solution of tert-butyl acetate (28.2 mL, 210 mmol) in tetrahydrofuran (40 mL) was added over 15 minutes. Then, after the solution had been stirred at −78° C. for 100 minutes, a solution of methyl 4-methoxysalicylate (12.75 g, 70.0 mmol) in THF (70 mL) was added to the reaction mixture over 20 minutes. The reaction mixture was permitted to warm to room temperature overnight, the flask placed in a water bath and the reaction mixture quenched with 1 M aqueous citric acid (110 mL). The aqueous phase was separated and extracted twice with ethyl acetate. The combined organic phases were washed with brine, dried ($Na_2SO_4$), filtered, and concentrated. The resulting residue was chromatographed on silica (25 to 60% $CH_2Cl_2$/heptanes) to give the impure product which was chromatographed on silica (25 to 70% $CH_2Cl_2$/heptane) to give title compound as a light oil (4.88 g). $^1$H NMR (400 MHz, $CDCl_3$) δ ppm 1.48 (s, 9H), 3.85 (s, 2H), 3.87 (s, 3H), 6.44-6.51 (m, 2H), 7.60 (d, J=8.8 Hz, 1H), 12.42 (s, 1H); MS (DCI) m/z 267 (M+H)$^+$, 284 (M+NH$_2$)+.

Example 159B tert-butyl 2-(5-bromopyridin-2-yl)-7-methoxy-4-oxochroman-3-carboxylate Example 159A (799 mg, 3.0 mmol), 5-bromopicolinaldehyde (558 mg, 3.0 mmol), piperidine (30 μL, 0.30 mmol) and acetic acid (18 μL, 0.31 mmol) were stirred at room temperature in anhydrous acetonitrile (9.0 mL) and anhydrous methanol (3.0 mL) for 4.5 hours and then concentrated. The residue was chromatographed twice on silica (15% methyl tert-butyl ether/heptane) to give 836 mg of a mixture of the (E/Z)-tert-butyl 3-(5-bromopyridin-2-yl)-2-(2-hydroxy-4-methoxybenzoyl)acrylates and cyclized product. The mixture was stirred with piperidine (30 μL, 0.30 mmol) in methanol (6 mL) and acetonitrile (3 mL), and after one hour water (3 mL) was added. The white precipitate was collected by filtration and washed with 1:1 methanol/water, and a second crop was similarly isolated. Both crops were dried under vacuum to give title compound (836 mg). $^1$H NMR (400 MHz, $CDCl_3$) δ ppm 1.40 (s, 9H), 3.84 (s, 3H), 4.22 (d, J=10.2 Hz, 1H), 5.80 (d, J=10.2 Hz, 1H), 6.48 (d, J=2.4 Hz, 1H), 6.62 (dd, J=8.8, 2.4 Hz, 1H), 7.43 (d, J=8.3 Hz, 1H), 7.83-7.89 (m, 2H), 8.67-8.68 (m, 1H); MS (DCI) m/z 434/436 (M+H)$^+$.

Example 159C 2-(5-bromopyridin-2-yl)-7-methoxychroman-4-one

Example 159B 792 mg, 1.8 mmol) and (rac)-camphorsulfonic acid (210 mg, 0.90 mmol were heated under nitrogen in anhydrous toluene (10 mL) at 85° C. overnight and brought to room temperature. The reaction mixture was diluted with heptane (2 mL) and placed directly on silica for chromatography (20% methyl tert-butyl ether in 1:1 $CH_2Cl_2$/heptane) to give title compound as a white powder (350 mg). 1H NMR (501 MHz, $CDCl_3$) δ ppm 3.02-3.12 (m, 2H), 3.85 (s, 3H), 5.56 (dd, J=10.1, 5.4 Hz, 1H), 6.52 (d, J=2.4 Hz, 1H), 6.63 (dd, J=8.8, 2.4 Hz, 1H), 7.51 (d, J=8.3 Hz, 1H), 7.87 (d, J=8.8 Hz, 1H), 7.90 (dd, J=8.3, 2.3 Hz, 1H), 8.67 (d, J=2.3 Hz, 1H); MS (DCI) m/z 334/336 (M+H)$^+$.

Example 159D methyl 6-(7-methoxy-4-oxochroman-2-yl)nicotinate

To Example 159C (349 mg, 1.044 mmol) and dichloro[1,1'-bis(diphenylphosphino)ferrocene]palladium(II) (15 mg, 0.021 mmol) in a 50 mL Hast C reactor were added methanol (10 mL) and triethylamine (0.29 mL, 2.1 mmol). The reactor was degassed with argon several times, then filled with carbon monoxide and heated at 100° C. for 11 hr at 60 psi. The sample was concentrated and partitioned between water and methyl tert-butyl ether. The aqueous phase was separated and extracted with methyl tert-butyl ether and the combined organic phases were washed again with water then with brine, dried ($Na_2SO_4$), filtered, concentrated, and chromatographed (25 to 50% methyl tert-butyl ether/heptane) to give impure title compound (79 mg). 1H NMR (500 MHz, $CDCl_3$) δ ppm 3.07 (dd, J=17.0, 11.6 Hz, 1H), 3.12 (dd, J=17.0, 4.1 Hz, 1H), 3.86 (s, 3H), 3.97 (s, 3H), 5.65 (dd, J=11.6, 4.1 Hz, 1H), 6.56 (d, J=2.4 Hz, 1H), 6.64 (dd, J=8.8, 2.4 Hz, 1H), 7.72 (d, J=8.2 Hz, 1H), 7.88 (d, J=8.8 Hz, 1H), 8.38 (dd, J=8.2, 2.1 Hz, 1H), 9.20-9.21 (m, 1H); MS (DCI) m/z 314 (M+H)$^+$.

Example 159E methyl 6-(4-(ethoxyimino)-7-methoxychroman-2-yl)nicotinate

The impure methyl 6-(7-methoxy-4-oxochroman-2-yl)nicotinate from Example 159D (77 mg, <0.25 mmol), O-ethylhydroxylamine hydrochloride (22 mg, 0.23 mmol) and potassium acetate (36 mg, 0.37 mmol) were heated in ethanol (1 mL) at 50° C. for 20 minutes. Additional O-ethylhydroxylamine hydrochloride (13 mg, 0.13 mmol) was added and the mixture was heated at 50° C. for another 3 hours. The suspension was brought to room temperature, concentrated, and chromatographed on silica (30% methyl tert-butyl ether/heptane) to give title compound as an impure solid (about 75 mg). $^1$H NMR (400 MHz, $CDCl_3$) δ ppm 1.30 (t, J=7.1 Hz, 3H), 2.72 (dd, J=17.2, 11.8 Hz, 1H), 3.68 (dd, J=17.2, 3.5 Hz, 1H), 3.81 (s, 3H), 3.97 (s, 3H), 4.20 (d, J=7.1 Hz, 2H), 5.26 (dd, J=11.8, 3.5 Hz, 1H), 6.53 (d, J=2.5 Hz, 1H), 6.59 (dd, J=8.8, 2.5 Hz, 1H), 7.70 (d, J=8.2 Hz, 1H), 7.85 (d, J=8.8 Hz, 1H), 8.36 (dd, J=8.2, 2.1 Hz, 1H), 9.19-9.22 (m, 1H); MS (DCI) m/z 357 (M+H)$^+$.

Example 159F methyl 6-(4-amino-7-methoxychroman-2-yl)nicotinate

The impure methyl 6-(4-(ethoxyimino)-7-methoxychroman-2-yl)nicotinate from Example 159E (72 mg, 0.2 mmol) and methanol (10 mL) were added to a Ra—Ni 2800 water slurry (700 mg, 5.4 mmol) in a 50 mL pressure bottle and shaken for 36 hours under hydrogen at 30 psi and room temperature. The sample was filtered, concentrated, and chromatographed on silica (0 to 5% conc. aqueous $NH_4OH$/acetonitrile) to give the title compound as an amber syrup (38 mg); MS (DCI) m/z 315 (M+H)$^+$.

Example 159G methyl rel-6-[(2R,4S)-4-({[1-(2,2-difluoro-1,3-ben-zodioxol-5-yl)cyclopropyl]carbonyl}amino)-7-methoxy-3,4-dihydro-2H-chromen-2-yl]pyridine-3-carboxylate The mixture of 1-(2,2-difluorobenzo[d][1,3]dioxol-5-yl)cyclopropanecarboxylic acid (40 mg, 0.16 mmol), carbonyl diimidazole (27 mg, 0.17 mmol) and 1-hydroxy-7-azabenzotriazole (2.4 mg, 18 μmol) were stirred in anhydrous acetonitrile (350 μL) for 100 minutes and then transferred to a flask containing Example 159F (about 37 mg, 0.12 mmol) with an acetonitrile (100 μL) rinse. After several minutes, diisopropylethylamine (16 μL, 92 μmol) was added and the solution was stirred at room temperature for four hours before being concentrated. The residue was chromatographed on silica (5 to 25% methyl tert-butyl ether in 1:1 $CH_2Cl_2$/heptane) to give a mixture of diastereomers. The appropriate fractions were combined, concentrated, and subjected to preparative supercritical fluid chromatography set to maintain a maximum back pressure of 10 MPa using a Whelk-O S.S (21×250 mm) column, with the sample at a concentration of 5 mg/mL in methanol, using a co-solvent of 15% methanol and 0.1% diethylamine in $CO_2$ at a flow rate of 70 mL/minute to provide Example 159G (retention time=11.50 minutes). The stereochemistry was arbitrarily assigned. $^1$H NMR (400 MHz, $CD_2Cl_2$) δ ppm 1.04-1.09 (m, 2H), 1.60-1.64 (m, 2H), 2.16 (ddd, J=14.2, 10.4, 4.8 Hz, 1H), 2.44 (ddd, J=14.2, 3.8, 2.6 Hz, 1H), 3.75 (s, 3H), 3.93 (s, 3H), 4.92 (ddd, J=7.1, 4.8, 3.8 Hz, 1H), 5.01 (dd, J=10.4, 2.6 Hz, 1H), 5.56 (d, J=7.1 Hz, 1H), 6.46 (d, J=2.5 Hz, 1H), 6.51 (dd, J=8.5, 2.5 Hz, 1H), 7.00-7.07 (m, 2H), 7.15-7.22 (m, 2H), 7.62 (d, J=8.2 Hz, 1H), 8.30 (dd, J=8.2, 2.1 Hz, 1H), 9.14 (d, J=2.1 Hz, 1H); MS (ESI) m/z=537 (M-H)$^-$.

Example 160 methyl rel-6-[(2S,4R)-4-({[1-(2,2-difluoro-1,3-ben-zodioxol-5-yl)cyclopropyl]carbonyl}amino)-7-methoxy-3,4-dihydro-2H-chromen-2-yl]pyridine-3-carboxylate The title compound (retention time=14.20 minutes) was isolated from the preparative supercritical fluid chromatography described Example 159 G. The stereochemistry was arbitrarily assigned. $^1$H NMR (400 MHz, $CD_2Cl_2$) δ ppm 1.05-1.08 (m, 2H), 1.60-1.63 (m, 2H), 2.16 (ddd, J=14.1, 10.4, 4.8 Hz, 1H), 2.44 (ddd, J=14.1, 3.9, 2.7 Hz, 1H), 3.75 (s, 3H), 3.93 (s, 3H), 4.92 (ddd, J=7.1, 4.8, 3.9 Hz, 1H), 5.01 (dd, J=10.4, 2.7 Hz, 1H), 5.55 (d, J=7.1 Hz, 1H), 6.46 (d, J=2.6 Hz, 1H), 6.50 (dd, J=8.5, 2.6 Hz, 1H), 7.01-7.05 (m, 2H), 7.15-7.21 (m, 2H), 7.62 (d, J=8.2 Hz, 1H), 8.30 (dd, J=8.2, 2.2 Hz, 1H), 9.14-9.15 (m, 1H); MS (ESI) m/z 537 (M-H)$^-$.

Example 161 methyl rel-6-[(2S,4S)-4-({[1-(2,2-difluoro-1,3-ben-zodioxol-5-yl)cyclopropyl]carbonyl}amino)-7-methoxy-3,4-dihydro-2H-chromen-2-yl]pyridine-3-carboxylate The title compound (retention time=16.19 minutes) was isolated from the preparative supercritical fluid chromatography described Example 159G. MS (ESI) m/z 537 (M-H)$^-$. The stereochemistry was arbitrarily assigned.

Example 162 methyl rel-6-[(2R,4R)-4-({[1-(2,2-difluoro-1,3-ben-zodioxol-5-yl)cyclopropyl]carbonyl}amino)-7-methoxy-3,4-dihydro-2H-chromen-2-yl]pyridine-3-carboxylate The title compound (retention time=19.80 minutes) was isolated from the preparative supercritical fluid chromatography described Example 159G. MS (ESI) m/z 537 (M-H)$^-$. The stereochemistry was arbitrarily assigned.

Example 163 ethyl rac-(2R,4R)-4-({[1-(2,2-difluoro-1,3-benzodi-oxol-5-yl)cyclopropyl]carbonyl}amino)-7-methoxy-3,4-dihydro-2H-chromene-2-carboxylate Example 163A rac-(2R,4R)-ethyl 4-amino-7-methoxychroman-2-carboxylate hydrochloride A solution of the product from Example 130C (1.5 g, 5.37 mmol) in acetic acid (5 mL) was treated with platinum(IV) oxide (0.244 g, 1.074 mmol). The flask was sparged with $N_2$ then the reaction was stirred under a balloon of $H_2$ overnight at room temperature. The solids were removed by filtration and the filtrate was concentrated. The resulting colorless oil was dissolved in methyl tert-butyl ether (10 mL) and acidified with 3 M HCl in cyclopentyl methyl ether (0.326 mL, 10.74 mmol). The mixture was concentrated and placed under vacuum overnight at 50° C. to provide the title compound as a 13:1 ratio of cis:trans. Only the peaks of the major cis isomer only are reported in the NMR: $^1$H NMR (501 MHz, DMSO-$d_6$) δ 7.44 (d, J=8.6 Hz, 1H), 6.56 (dd, J=8.6, 2.6 Hz, 1H), 6.43 (d, J=2.5 Hz, 1H), 4.87 (dd, J=10.6, 2.6 Hz, 1H), 4.30 (dd, J=9.8, 5.8 Hz, 1H), 4.20 (qd, J=7.1, 1.4 Hz, 2H), 3.72 (s, 3H), 2.46 (ddd, J=13.1, 5.7, 2.6 Hz, 1H), 1.94-1.85 (m, 1H), 1.24 (t, J=7.1 Hz, 3H).

Example 163B ethyl rac-(2R,4R)-4-({[1-(2,2-difluoro-1,3-benzodi-oxol-5-yl)cyclopropyl]carbonyl}amino)-7-methoxy-3,4-dihydro-2H-chromene-2-carboxylate A solution of the product from Example 163A (2.1 g, 7.30 mmol) and triethylamine (3.05 mL, 21.89 mmol) in $CH_2Cl_2$ (29 mL) at 0° C. was treated drop wise with a solution of 1-(2,2-difluorobenzo[d][1,3]dioxol-5-yl)cyclopropanecarbonyl chloride (prepared as described in Example 8D) in $CH_2Cl_2$ (5 mL) and then stirred at 30 minutes at 0° C. The mixture was partitioned between 1M HCl (10 mL) and $CH_2Cl_2$. The layers were separated and the aqueous was extracted with $CH_2Cl_2$. The combined $CH_2Cl_2$ layers were concentrated. The residue was purified by chromatography on silica gel eluting with a gradient of 0-40% ethyl acetate in heptanes to provide a product which was a 14:1 mixture of cis and trans isomers. 1.5 g of this product was precipitated from ethyl acetate/heptanes to provide the diastereomerically pure title compound. $^1$H NMR (400 MHz, $CDCl_3$) δ 7.10 (d, J=8.1 Hz, 1H), 7.08 (s, 1H), 7.00 (d, J=8.2

Hz, 1H), 6.95 (d, J=8.5 Hz, 1H), 6.49 (dd, J=8.6, 2.5 Hz, 1H), 6.44 (d, J=2.4 Hz, 1H), 5.56 (d, J=8.3 Hz, 1H), 5.21 (q, J=7.3 Hz, 1H), 4.71 (dd, J=8.0, 3.6 Hz, 1H), 4.22-4.07 (m, 2H), 3.74 (s, 3H), 2.53 (ddd, J=13.8, 6.0, 3.7 Hz, 1H), 1.99 (dt, J=15.1, 7.8 Hz, 1H), 1.74-1.68 (m, 1H), 1.66-1.61 (m, 1H), 1.26 (t, J=7.1 Hz, 3H), 1.13-1.02 (m, 2H); MS (ESI−) m/z 474 (M−H)⁻.

Example 164 rac-(2R,4R)-4-({[1-(2,2-difluoro-1,3-benzodioxol-5-yl)cyclopropyl]carbonyl}amino)-7-methoxy-3,4-dihydro-2H-chromene-2-carboxylic acid Using the procedure similar to that described in Example 152, substituting the product from Example 163B for the product from Example 151G, provided the title compound. $^1$H NMR (400 MHz, CDCl$_3$) δ 7.14 (dd, J=8.1, 1.7 Hz, 1H), 7.12 (d, J=1.4 Hz, 1H), 7.02 (d, J=8.1 Hz, 1H), 6.93 (d, J=8.6 Hz, 1H), 6.51 (dd, J=8.6, 2.5 Hz, 1H), 6.47 (d, J=2.5 Hz, 1H), 5.48 (d, J=7.9 Hz, 1H), 5.21 (q, J=7.7 Hz, 1H), 4.80 (dd, J=8.6, 3.5 Hz, 1H), 3.75 (s, 3H), 2.59 (ddd, J=13.6, 5.7, 3.5 Hz, 1H), 2.14-2.06 (m, 1H), 1.80-1.71 (m, 1H), 1.71-1.62 (m, 1H), 1.14-1.06 (m, 2H); MS (ESI−) m/z 446 (M−H)⁻.

Example 165 rel-6-[(2R,4R)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylic acid Example 165A (S)—N-(1-(2-hydroxy-4-methoxyphenyl)ethylidene)-2-methylpropane-2-sulfinamide A solution of 2'-hydroxy-4'-methoxyacetophenone (1 g, 6.02 mmol) and (S)-(−)-2-methyl-2-propanesulfinamide (0.802 g, 6.62 mmol) in 2-methyl-tetrahydrofuran (10 mL) was treated with titanium(IV) ethoxide (5.15 g, 22.57 mmol), heated at 90° C. under N$_2$ for 2 hours, cooled and partitioned between ethyl acetate and water. The mixture was filtered through diatomaceous earth to remove the solids. The ethyl acetate layer was washed with brine, dried (MgSO$_4$), filtered, concentrated, and chromatographed on silica gel, eluting with a gradient of 30% to 100% ethyl acetate in heptane provided the title compound (377 mg, 1.400 mmol, 23.26% yield). $^1$H NMR (400 MHz, CDCl$_3$) δ 13.62 (s, 1H), 7.55 (d, J=8.9 Hz, 1H), 6.48-6.43 (m, 2H), 3.84 (s, 3H), 2.76 (s, 3H), 1.32 (s, 9H); MS (ESI+) m/z 435 (M+H); MS (ESI−) m/z 433 (M−H)⁻.

Example 165B methyl rel-6-((S)-3-(((S)-tert-butylsulfinyl)imino)-1-hydroxy-3-(2-hydroxy-4-methoxyphenyl)propyl)nicotinate A solution of diisopropylamine (163 µL, 1.143 mmol) in tetrahydrofuran (2 mL) under N$_2$ at −20° C. was treated with 2.5 M n-butyl lithium in hexanes (437 µL, 1.091 mmol) and stirred for 15 minutes. In a separate flask, a solution of the product from Example 165A (140 mg, 0.520 mmol) in tetrahydrofuran (2 mL) under N$_2$ at −20° C. was treated over 1 minute with the solution of lithium diisopropylamine. The resulting mixture was stirred at −20° C. for 1 hour, cooled to −78° C., treated with a solution of methyl 6-formylnicotinate (86 mg, 0.520 mmol) in tetrahydrofuran (1.5 mL), warmed to 0° C., cooled to −30° C., treated with a solution of 10% acetic acid in tetrahydrofuran (about 1.5 mL) and allowed to warm to room temperature. The mixture was partitioned between ethyl acetate and saturated NaHCO$_3$ solution. The ethyl acetate layer was washed with brine, dried (MgSO$_4$), filtered, concentrated, and chromatographed on silica gel (ethyl acetate/heptanes) to provide the title compound (52 mg, 23% yield) as the second eluting isomer. $^1$H NMR (400 MHz, CDCl$_3$) δ 13.25 (s, 1H), 9.19 (d, J=1.9 Hz, 1H), 8.22 (dd, J=8.2, 2.1 Hz, 1H), 7.57 (d, J=8.2 Hz, 1H), 7.38 (d, J=9.1 Hz, 1H), 6.40 (d, J=2.6 Hz, 1H), 6.28 (dd, J=9.1, 2.6 Hz, 1H), 5.34 (q, J=5.1 Hz, 1H), 4.92 (d, J=5.2 Hz, 1H), 3.96 (s, 3H), 3.80 (s, 3H), 3.82-3.71 (m, 2H), 1.39 (s, 9H); MS (ESI+) m/z 435 (M+H)⁺. Stereochemistry was arbitrarily assigned.

Example 165C methyl rel-6-((R)-4-(((S)-tert-butylsulfinyl)imino)-7-methoxychroman-2-yl)nicotinate A solution of the product from Example 165B (52 mg, 0.120 mmol) and triphenylphosphine (31.4 mg, 0.120 mmol) in CH$_2$Cl$_2$ (1 mL) at 0° C. was treated drop wise with a 40 weight % solution diethyl azodicarboxylate in toluene (54.5 µL, 0.120 mmol) over 3 minutes, stirred at 0° C. for 10 minutes, allowed to stir at ambient temperature for 1 hour, concentrated and directly chromatographed on silica gel eluting with ethyl acetate in heptanes to provide the titled compound (18 mg, 0.043 mmol, 36.1% yield). $^1$H NMR (400 MHz, CDCl$_3$) δ 9.20-9.18 (m, 1H), 8.37 (dd, J=8.2, 2.1 Hz, 1H), 7.98 (d, J=8.9 Hz, 1H), 7.70 (d, J=8.2 Hz, 1H), 6.62 (dd, J=8.9, 2.5 Hz, 1H), 6.53 (d, J=2.5 Hz, 1H), 5.40 (dd, J=12.5, 3.0 Hz, 1H), 3.97 (s, 3H), 3.92 (dd, J=17.5, 3.1 Hz, 1H), 3.85 (s, 3H), 3.28 (dd, J=17.5, 12.5 Hz, 1H), 1.30 (s, 9H); MS (ESI+) m/z 417 (M+H)⁺. Stereochemistry was arbitrarily assigned.

Example 165D methyl rel-6-((2R,4R)-4-amino-7-methoxychroman-2-yl)nicotinate

A solution of the product from Example 165C (17.4 mg, 0.042 mmol) in methanol (1 mL) was cooled to 0° C., treated with NaBH$_4$ (4.74 mg, 0.125 mmol), stirred at 0° C. for 30 minutes, treated with 4 M HCl in dioxane (209 µL, 0.836 mmol), stirred at 0° C. for 5 minutes and then stirred at ambient temperature for 30 minutes. The mixture was partitioned between methyl tert-butyl ether (30 mL) and water (15 mL). The aqueous layer was basified to pH 8 with solid NaHCO$_3$ and extracted with ethyl acetate. The ethyl acetate layer was washed with brine, dried (MgSO$_4$), filtered, and concentrated to provide the title compound (12 mg, 0.038 mmol, 91% yield). $^1$H NMR (501 MHz, CDCl$_3$) δ 9.18 (d, J=1.5 Hz, 1H), 8.36 (dd, J=8.2, 2.1 Hz, 1H), 7.72 (d, J=8.2 Hz, 1H), 7.42 (d, J=8.6 Hz, 1H), 6.59 (d, J=8.5 Hz, 1H), 6.50 (d, J=2.5 Hz, 1H), 5.32 (d, J=10.8 Hz, 1H), 4.29 (s, 1H), 3.97 (s, 3H), 3.80 (s, 3H), 2.68 (dd, J=12.5, 4.0 Hz, 1H), 1.83 (q, J=11.5 Hz, 1H). Stereochemistry was arbitrarily assigned.

Example 165E methyl rel-6-((2R,4R)-4-(1-(2,2-difluorobenzo[d][1,3]dioxol-5-yl)cyclopropanecarboxamido)-7-methoxychroman-2-yl)nicotinate Using the procedure similar to that described in Example 126G, substituting the product from Example 165D for the product from Example 126F, and purification by chromatography on silica gel eluting with a gradient of 30-100% ethyl acetate in heptane, provided the titled compound. $^1$H NMR (400 MHz, CDCl$_3$) δ 9.14 (d, J=1.9 Hz, 1H), 8.31 (dd, J=8.2, 2.1 Hz, 1H), 7.61 (d, J=8.2 Hz, 1H), 7.10 (dd, J=8.2, 1.6 Hz, 1H), 7.06 (d, J=1.6 Hz, 1H), 7.01 (d, J=4.6 Hz, 1H), 6.99 (d, J=4.3 Hz, 1H), 6.53 (dd, J=8.6, 2.6 Hz, 1H), 6.47 (d, J=2.5 Hz, 1H), 5.43 (dt, J=9.4, 4.3 Hz, 1H), 5.36-5.30 (m, 2H), 3.98 (s, 3H), 3.77 (s, 3H), 2.76 (ddd, J=13.3, 6.1, 2.4 Hz, 1H), 1.85 (dt, J=13.3, 10.4 Hz, 1H), 1.77-1.62 (m, 2H), 0.92-0.80 (m, 2H); MS (ESI−) m/z 537 (M−H)$^−$.

Example 165F rel-6-[(2R,4R)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylic acid Using the procedure similar to that described in Example 152, substituting the product from Example 165E for the product from Example 151G, provided the title compound. $^1$H NMR (400 MHz, CDCl$_3$) δ 9.24 (s, 1H), 8.40 (d, J=8.2 Hz, 1H), 7.68 (d, J=8.2 Hz, 1H), 7.13 (dd, J=8.2, 1.5 Hz, 1H), 7.10 (d, J=1.5 Hz, 1H), 7.04-7.00 (m, 2H), 6.56 (dd, J=8.6, 2.5 Hz, 1H), 6.50 (d, J=2.4 Hz, 1H), 5.52-5.32 (m, 3H), 3.80 (s, 3H), 2.82 (ddd, J=13.4, 6.0, 1.9 Hz, 1H), 1.91-1.67 (m, 3H), 1.15-1.06 (m, 2H); MS (ESI−) m/z 523 (M−H)$^−$.

Example 166 rac-(2R,4R)-4-({[1-(2,2-difluoro-1,3-benzodioxol-5-yl)cyclopropyl]carbonyl}amino)-N-(2-hydroxy-ethyl)-7-methoxy-N-propyl-3,4-dihydro-2H-chromene-2-carboxamide A stock solution Example 164 and diisopropylethylamine (0.089 M and 0.26 M in dimethylacetamide, respectively, 344 μL, 0.031 mmol Example 164 (1.0 equivalent) and 0.092 mmol diisopropylethylamine (3.0 equivalents)), 2-(3H-[1,2,3]triazolo[4,5-b]pyridin-3-yl)-1,1,3,3-tetramethylisouronium hexafluorophosphate(V) (0.11 M in dimethylacetamide, 344 μL, 0.037 mmol, 1.2 equivalents), and 2-propylamino-ethanol (0.40 M in dimethylacetamide, 117 μL, 0.046 mmol, 1.5 equivalents) were aspirated from their respective source vials, mixed through a PFA mixing tube (0.2 mm inner diameter), and loaded into an injection loop. The reaction segment was injected into the flow reactor (Hastelloy coil, 0.75 mm inner diameter, 1.8 mL internal volume) set at 75° C., and passed through the reactor at 180 μL min$^{-1}$ (10 minute residence time). Upon exiting the reactor, the reaction was loaded directly into an injection loop and purified using preparative LC method TFA1 to yield the title compound (11.4 mg, 70% yield). $^1$H NMR (400 MHz, 120° C., DMSO-d$_6$:D$_2$O=9:1 (v/v)) δ 7.27 (d, J=1.5 Hz, 1H), 7.25-7.12 (m, 2H), 6.95 (dd, J=8.5, 1.0 Hz, 1H), 6.46 (dd, J=8.5, 2.6 Hz, 1H), 6.29 (d, J=2.6 Hz, 1H), 5.11 (t, J=7.3 Hz, 2H), 3.69 (s, 3H), 3.60-3.18 (m, 6H), 2.23-2.11 (m, 1H), 2.11-1.96 (m, 1H), 1.74-1.33 (m, 4H), 1.14-0.90 (m, 2H), 0.82 (t, J=7.5 Hz, 3H); MS (APCI+) m/z 533.1 (M+H)$^+$.

Example 167 rac-(2R,4R)—N-benzyl-4-({[1-(2,2-difluoro-1,3-benzodioxol-5-yl)cyclopropyl]carbonyl}amino)-N-(2-hydroxyethyl)-7-methoxy-3,4-dihydro-2H-chromene-2-carboxamide Example 167 was prepared according to the procedure for the preparation of Example 166, substituting 2-benzylamino-ethanol for 2-propylamino-ethanol and purified using preparative LC method TFA6 to provide the title compound (7.3 mg, 41% yield). $^1$H NMR (400 MHz, 120° C., DMSO-d$_6$:D$_2$O=9:1 (v/v)) δ 7.35-7.12 (m, 8H), 6.96 (d, J=8.5 Hz, 1H), 6.47 (dd, J=8.5, 2.6 Hz, 1H), 6.36-6.09 (m, 1H), 5.23-5.05 (m, 2H), 4.73-4.36 (m, 2H), 3.68 (s, 3H), 3.59-3.46 (m, 3H), 3.47-3.23 (m, 1H), 2.30-1.95 (m, 2H), 1.55-1.34 (m, 2H), 1.13-0.97 (m, 2H); MS (APCI+) m/z 581.0 (M+H)$^+$.

Example 168 rac-(2R,4R)-4-({[1-(2,2-difluoro-1,3-benzodioxol-5-yl)cyclopropyl]carbonyl}amino)-N-(2-hydroxy-2-phenylethyl)-7-methoxy-N-methyl-3,4-dihydro-2H-chromene-2-carboxamide Example 168 was prepared according to the procedure for the preparation of Example 166, substituting 2-methylamino-1-phenyl-ethanol for 2-propylamino-ethanol and purified using preparative LC method TFA6 to provide the title compound (15.5 mg, 87% yield). $^1$H NMR (400 MHz, 120° C., DMSO-d$_6$:D$_2$O=9:1 (v/v)) δ 7.42-7.12 (m, 8H), 6.94 (td, J=8.5, 0.9 Hz, 1H), 6.46 (dt, J=8.5, 2.2 Hz, 1H), 6.28 (dd, J=11.6, 2.5 Hz, 1H), 5.05 (s, 2H), 4.80 (dd, J=7.2, 5.3 Hz, 1H), 3.69 (d, J=3.4 Hz, 3H), 3.63-3.36 (m, 2H), 2.92 (s, 3H), 2.17-1.90 (m, 2H), 1.44 (tdd, J=12.2, 7.3, 3.3 Hz, 2H), 1.05 (tt, J=5.2, 2.6 Hz, 2H); MS (APCI+) m/z 581.0 (M+H)$^+$.

Example 169 rac-1-(2,2-difluoro-1,3-benzodioxol-5-yl)-N-[(2R,4R)-2-{[4-(2-hydroxyethyl)piperazin-1-yl]carbonyl}-7-methoxy-3,4-dihydro-2H-chromen-4-yl]cyclopropanecarboxamide Example 169 was prepared according to the procedure for the preparation of Example 166, substituting 2-piperazin-1-yl-ethanol for 2-propylamino-ethanol and purified using preparative LC method TFA6 to provide the title compound (15.2 mg, 73% yield). $^1$H NMR (400 MHz, 120° C., DMSO-d$_6$:D$_2$O=9:1 (v/v)) δ 7.27 (d, J=1.6 Hz, 1H), 7.24-7.14 (m, 2H), 6.94 (dd, J=8.6, 1.0 Hz, 1H), 6.48 (dd, J=8.6, 2.6 Hz, 1H), 6.31 (d, J=2.5 Hz, 1H), 5.20-5.07 (m, 2H), 3.91-3.72 (m, 6H), 3.68 (s, 3H), 3.29 (s, 4H), 3.25-3.19 (m, 2H), 2.24-2.11 (m, 1H), 2.11-1.95 (m, 1H), 1.55-1.34 (m, 2H), 1.15-0.99 (m, 2H); MS (APCI+) m/z 560.0 (M+H)$^+$.

Example 170 rac-(2R,4R)-4-({[1-(2,2-difluoro-1,3-benzodioxol-5-yl)cyclopropyl]carbonyl}amino)-N-(1-hydroxy-2-methylpropan-2-yl)-7-methoxy-3,4-dihydro-2H-chromene-2-carboxamide Example 170 was prepared according to the procedure for the preparation of Example 166, substituting 2-amino-2-methyl-propan-1-ol for 2-propylamino-ethanol and purified using preparative LC method TFA6 to provide the title compound (5.6 mg, 35% yield). $^1$H NMR (400 MHz, 90° C., DMSO-d$_6$:D$_2$O=9:1 (v/v)) δ 7.31 (d, J=1.6 Hz, 1H), 7.28-7.15 (m, 2H), 6.93 (dd, J=8.5, 1.0 Hz, 1H), 6.49 (dd, J=8.6, 2.6 Hz, 1H), 6.40 (d, J=2.5 Hz, 1H), 5.09 (dd, J=9.3, 6.5 Hz, 1H), 4.54 (dd, J=10.0, 2.9 Hz, 1H), 3.70 (s, 3H), 3.45-3.30 (m, 2H), 2.23 (ddd, J=13.5, 6.3, 2.9 Hz, 1H), 1.91 (dt, J=13.5, 9.8 Hz, 1H), 1.55-1.33 (m, 2H), 1.21 (s, 3H), 1.17 (s, 3H), 1.14-0.97 (m, 2H); MS (APCI+) m/z 519.1 (M+H)+.

Example 171 rac-(2R,4R)-4-({[1-(2,2-difluoro-1,3-benzodioxol-5-yl)cyclopropyl]carbonyl}amino)-N-(2-hydroxy-1-phenylethyl)-7-methoxy-3,4-dihydro-2H-chromene-2-carboxamide Example 171 was prepared according to the procedure for the preparation of Example 166, substituting 2-amino-2-phenyl-ethanol for 2-propylamino-ethanol and purified using preparative LC method TFA6 to provide the title compound (14.2 mg, 81% yield). $^1$H NMR (400 MHz, 90° C., DMSO-$d_6$:$D_2O$=9:1 (v/v)) δ 7.33 (d, J=4.4 Hz, 2H), 7.29-7.06 (m, 6H), 7.01-6.82 (m, 1H), 6.55-6.47 (m, 1H), 6.45 (d, J=2.5 Hz, 1H), 5.10 (dd, J=9.1, 6.2 Hz, 1H), 4.85 (td, J=5.9, 2.7 Hz, 1H), 4.77-4.62 (m, 1H), 3.76-3.60 (m, 5H), 2.32-2.15 (m, 1H), 2.06-1.87 (m, 1H), 1.52-1.29 (m, 2H), 1.10-0.93 (m, 2H); MS (APCI+) m/z 567.0 (M+H)+.

Example 172 rac-(2R,4R)-4-({[1-(2,2-difluoro-1,3-benzodioxol-5-yl)cyclopropyl]carbonyl}amino)-N-(1,1-dioxidotetrahydro-2H-thiopyran-4-yl)-7-methoxy-3,4-dihydro-2H-chromene-2-carboxamide Example 172 was prepared according to the procedure for the preparation of Example 166, substituting 1,1-dioxothian-4-amine for 2-propylamino-ethanol and purified using preparative LC method TFA6 to provide the title compound (9.0 mg, 51% yield). $^1$H NMR (400 MHz, 90° C., DMSO-$d_6$:$D_2O$=9:1 (v/v)) δ 7.32 (d, J=1.7 Hz, 1H), 7.26 (d, J=8.2 Hz, 1H), 7.20 (dd, J=8.3, 1.7 Hz, 1H), 6.93 (d, J=8.6 Hz, 1H), 6.48 (dd, J=8.5, 2.6 Hz, 1H), 6.43 (d, J=2.5 Hz, 1H), 5.09 (dd, J=9.5, 6.2 Hz, 1H), 4.60 (dd, J=10.1, 3.0 Hz, 1H), 3.92 (p, J=7.3, 6.9 Hz, 1H), 3.70 (s, 3H), 3.24-2.96 (m, 4H), 2.29-2.17 (m, 1H), 2.14-1.86 (m, 5H), 1.53-1.36 (m, 2H), 1.13-0.99 (m, 2H).\; MS (APCI+) m/z 578.2 (M+H)+.

Example 173 rac-(2R,4R)-4-({[1-(2,2-difluoro-1,3-benzodioxol-5-yl)cyclopropyl]carbonyl}amino)-7-methoxy-N-[3-(trifluoromethyl)oxetan-3-yl]-3,4-dihydro-2H-chromene-2-carboxamide Example 173 was prepared according to the procedure for the preparation of Example 166, substituting 3-(trifluoromethyl)oxetan-3-amine for 2-propylamino-ethanol and purified using preparative LC method TFA6 to provide the title compound (2.3 mg, 13% yield). $^1$H NMR (400 MHz, 90° C., DMSO-$d_6$:$D_2O$=9:1 (v/v)) δ 7.32 (d, J=1.7 Hz, 1H), 7.28-7.14 (m, 2H), 6.94 (d, J=8.5 Hz, 1H), 6.51 (dd, J=8.5, 2.6 Hz, 1H), 6.46 (d, J=2.6 Hz, 1H), 5.12 (dd, J=9.6, 6.2 Hz, 1H), 4.82-4.60 (m, 5H), 3.71 (s, 3H), 2.30-2.18 (m, 1H), 2.07-1.87 (m, 1H), 1.54-1.34 (m, 2H), 1.15-0.97 (m, 2H); MS (APCI+) m/z 571.0 (M+H)+.

Example 174 rac-1-(2,2-difluoro-1,3-benzodioxol-5-yl)-N-{(2R,4R)-2-[(4,4-difluoropiperidin-1-yl)carbonyl]-7-methoxy-3,4-dihydro-2H-chromen-4-yl}cyclopropanecarboxamide Example 174 was prepared according to the procedure for the preparation of Example 166, substituting 4,4-difluoropiperidine hydrochloride for 2-propylamino-ethanol and purified using preparative LC method TFA6 to provide the title compound (7.3 mg, 41% yield). $^1$H NMR (400 MHz, 90° C., DMSO-$d_6$:$D_2O$=9:1 (v/v)) δ 7.31 (d, J=1.8 Hz, 1H), 7.25 (d, J=8.3 Hz, 1H), 7.19 (dd, J=8.4, 1.8 Hz, 1H), 6.97 (d, J=8.5 Hz, 1H), 6.49 (dd, J=8.6, 2.6 Hz, 1H), 6.32 (d, J=2.5 Hz, 1H), 5.21-5.06 (m, 2H), 3.69 (d, J=0.9 Hz, 3H), 3.61 (s, 4H), 2.26-1.83 (m, 6H), 1.54-1.35 (m, 2H), 1.15-0.97 (m, 2H); MS (APCI+) m/z 551.0 (M+H)+.

Example 175 rac-1-(2,2-difluoro-1,3-benzodioxol-5-yl)-N-[(2R,4R)-7-methoxy-2-(1,4-oxazepan-4-ylcarbonyl)-3,4-dihydro-2H-chromen-4-yl]cyclopropanecarboxamide Example 175 was prepared according to the procedure for the preparation of Example 166, substituting 1,4-oxazepane hydrochloride for 2-propylamino-ethanol and purified using preparative LC method TFA6 to provide the title compound (14.1 mg, 86% yield). $^1$H NMR (400 MHz, 90° C., DMSO-$d_6$:$D_2O$=9:1 (v/v)) δ 7.30 (d, J=1.7 Hz, 1H), 7.24 (d, J=8.3 Hz, 1H), 7.18 (dd, J=8.3, 1.7 Hz, 1H), 6.97 (d, J=8.6 Hz, 1H), 6.48 (dd, J=8.6, 2.6 Hz, 1H), 6.30 (d, J=2.5 Hz, 1H), 5.12 (t, J=7.2 Hz, 2H), 3.85-3.40 (m, 11H), 2.21-1.98 (m, 2H), 1.98-1.68 (m, 2H), 1.53-1.32 (m, 2H), 1.14-0.96 (m, 2H); MS (APCI+) m/z 531.0 (M+H)+.

Example 176 rac-(2R,4R)-4-({[1-(2,2-difluoro-1,3-benzodioxol-5-yl)cyclopropyl]carbonyl}amino)-7-methoxy-N-methyl-N-(oxetan-3-yl)-3,4-dihydro-2H-chromene-2-carboxamide Example 176 was prepared according to the procedure for the preparation of Example 166, substituting N-methyloxetan-3-amine for 2-propylamino-ethanol and purified using preparative LC method TFA6 to provide the title compound (16.2 mg, >99% yield). $^1$H NMR (400 MHz, 90° C., DMSO-$d_6$:$D_2O$=9:1 (v/v)) δ 7.32 (d, J=1.7 Hz, 1H), 7.26 (d, J=8.3 Hz, 1H), 7.21 (dd, J=8.3, 1.7 Hz, 1H), 6.93 (d, J=8.6 Hz, 1H), 6.52 (dd, J=8.6, 2.6 Hz, 1H), 6.36 (d, J=2.5 Hz, 1H), 5.14 (dd, J=10.0, 6.0 Hz, 1H), 4.89 (dd, J=10.7, 2.8 Hz, 1H), 4.51-4.20 (m, 2H), 3.81-3.61 (m, 5H), 3.44 (d, J=6.5 Hz, 1H), 2.68 (s, 3H), 2.40-2.30 (m, 1H), 2.16-1.97 (m, 1H), 1.58-1.29 (m, 2H), 1.14-0.98 (m, 2H); MS (APCI+) m/z 517.1 (M+H)+.

Example 177 rac-1-(2,2-difluoro-1,3-benzodioxol-5-yl)-N-[(2R,4R)-7-methoxy-2-(morpholin-4-ylcarbonyl)-3,4-dihydro-2H-chromen-4-yl]cyclopropanecarboxamide Example 177 was prepared according to the procedure for the preparation of Example 166, substituting morpholine for 2-propylamino-ethanol and purified using preparative LC method TFA6 to provide the title compound (10.2 mg, 64% yield). $^1$H NMR (400 MHz, 90° C., DMSO-$d_6$:$D_2O$=9:1 (v/v)) δ 7.30 (d, J=1.8 Hz, 1H), 7.24 (d, J=8.3 Hz, 1H), 7.18 (dd, J=8.3, 1.7 Hz, 1H), 6.96 (dd, J=8.6, 1.0 Hz, 1H), 6.48 (dd, J=8.6, 2.6 Hz, 1H), 6.31 (d, J=2.6 Hz, 1H), 5.16-5.05 (m, 2H), 3.87 (s, 0H), 3.69 (s, 3H), 3.65-3.55 (m, 4H), 3.49 (s, 4H), 2.22-2.09 (m, 1H), 2.09-1.96 (m, 1H), 1.54-1.35 (m, 2H), 1.15-0.96 (m, 2H); MS (APCI+) m/z 517.1 (M+H)+.

Example 178 rac-(2R,4R)-4-({[1-(2,2-difluoro-1,3-benzodioxol-5-yl)cyclopropyl]carbonyl}amino)-N-[2-hydroxy-1-(2-methoxyphenyl)ethyl]-7-methoxy-3,4-dihydro-2H-chromene-2-carboxamide Example 178 was prepared according to the procedure for the preparation of Example 166, substituting 2-amino-2-(2-methoxy-phenyl)-ethanol for 2-propylamino-ethanol and purified using preparative LC method TFA6 to provide the title compound (5.5 mg, 30% yield). $^1$H NMR (400 MHz, 90° C., DMSO-$d_6$:D$_2$O=9:1 (v/v)) spectrum contains diastereomer peaks δ 7.35-7.07 (m, 4H), 7.07-6.80 (m, 4H), 6.56-6.48 (m, 1H), 6.48-6.38 (m, 1H), 5.21-5.03 (m, 2H), 4.69 (ddd, J=16.6, 10.0, 3.0 Hz, 1H), 3.89-3.78 (m, 3H), 3.76-3.68 (m, 3H), 3.68-3.47 (m, 2H), 2.31-2.17 (m, 1H), 2.06-1.84 (m, 1H), 1.53-1.31 (m, 2H), 1.10-0.95 (m, 2H); MS (APCI+) m/z 597.0 (M+H)$^+$.

Example 179 rac-(2R,4R)-4-({[1-(2,2-difluoro-1,3-benzodioxol-5-yl)cyclopropyl]carbonyl}amino)-N-[2-(3-hydroxyphenyl)ethyl]-7-methoxy-3,4-dihydro-2H-chromene-2-carboxamide Example 179 was prepared according to the procedure for the preparation of Example 166, substituting 3-(2-aminoethyl)phenol hydrochloride for 2-propylamino-ethanol and purified using preparative LC method TFA6 to provide the title compound (11.8 mg, 68% yield). $^1$H NMR (400 MHz, 90° C., DMSO-$d_6$:D$_2$O=9:1 (v/v)) δ 7.30 (d, J=1.6 Hz, 1H), 7.27-7.13 (m, 2H), 7.06 (td, J=7.3, 1.4 Hz, 1H), 6.93 (dd, J=8.6, 1.0 Hz, 1H), 6.66-6.55 (m, 3H), 6.48 (dd, J=8.6, 2.6 Hz, 1H), 6.39 (d, J=2.6 Hz, 1H), 5.15-5.01 (m, 1H), 4.57 (dd, J=10.0, 3.1 Hz, 1H), 3.70 (s, 3H), 3.30 (t, J=7.3 Hz, 2H), 2.66 (t, J=7.3 Hz, 2H), 2.28-2.14 (m, 1H), 1.96-1.80 (m, 1H), 1.55-1.32 (m, 2H), 1.16-0.97; MS (APCI+) m/z 567.0 (M+H)$^+$.

Example 180 rac-(2R,4R)-4-({[1-(2,2-difluoro-1,3-benzodioxol-5-yl)cyclopropyl]carbonyl}amino)-N-(1,3-dihydroxypropan-2-yl)-7-methoxy-3,4-dihydro-2H-chromene-2-carboxamide Example 180 was prepared according to the procedure for the preparation of Example 166, substituting 2-amino-propane-1,3-diol for 2-propylamino-ethanol and purified using preparative LC method TFA6 to provide the title compound (11.3 mg, 71% yield). $^1$H NMR (400 MHz, 90° C., DMSO-$d_6$:D$_2$O=9:1 (v/v)) δ 7.32 (d, J=1.7 Hz, 1H), 7.28-7.15 (m, 2H), 6.92 (dd, J=8.6, 1.0 Hz, 1H), 6.49 (dd, J=8.6, 2.6 Hz, 1H), 6.41 (d, J=2.6 Hz, 1H), 5.10 (dd, J=9.8, 6.3 Hz, 1H), 4.62 (dd, J=10.5, 2.9 Hz, 1H), 3.77 (p, J=5.5 Hz, 1H), 3.70 (s, 3H), 3.60-3.37 (m, 4H), 2.32-2.18 (m, 1H), 2.01-1.84 (m, 1H), 1.55-1.34 (m, 2H), 1.15-0.97 (m, 2H); MS (APCI+) m/z 521.0 (M+H)$^+$.

Example 181 rac-(2R,4R)-4-({[1-(2,2-difluoro-1,3-benzodioxol-5-yl)cyclopropyl]carbonyl}amino)-N-(2-hydroxy-2,3-dihydro-1H-inden-1-yl)-7-methoxy-3,4-dihydro-2H-chromene-2-carboxamide Example 181 was prepared according to the procedure for the preparation of Example 166, substituting 1-amino-indan-2-ol for 2-propylamino-ethanol and purified using preparative LC method TFA6 to provide the title compound (11.3 mg, 70% yield). $^1$H NMR (400 MHz, 90° C., DMSO-$d_6$:D$_2$O=9:1 (v/v)) spectrum contains diastereomer peaks δ 7.34-6.77 (m, 8H), 6.57-6.44 (m, 1H), 6.41-6.31 (m, 1H), 5.20-5.06 (m, 2H), 4.86-4.73 (m, 1H), 4.52-4.36 (m, 1H), 3.72-3.62 (m, 3H), 3.15-3.01 (m, 1H), 2.92-2.79 (m, 1H), 2.44-2.26 (m, 1H), 2.15-1.96 (m, 1H), 1.56-1.36 (m, 2H), 1.15-0.96 (m, 2H); MS (APCI+) m/z 579.0 (M+H)$^+$.

Example 182 rac-(2R,4S)-4-({[1-(2,2-difluoro-1,3-benzodioxol-5-yl)cyclopropyl]carbonyl}amino)-N-(2-hydroxyphenyl)-7-methoxy-3,4-dihydro-2H-chromene-2-carboxamide A stock solution Example 134 and diisopropylethylamine (0.089 M and 0.26 M in dimethylacetamide, respectively, 344 μL, 0.031 mmol Example 134 (1.0 equivalent) and 0.092 mmol diisopropylethylamine (3.0 equivalents)), 2-(3H-[1,2,3]triazolo[4,5-b]pyridin-3-yl)-1,1,3,3-tetramethylisouronium hexafluorophosphate(V) (0.11 M in dimethylacetamide, 344 μL, 0.037 mmol, 1.2 equivalents), and 2-aminophenol (0.40 M in dimethylacetamide, 117 μL, 0.046 mmol, 1.5 equivalents) were aspirated from their respective source vials, mixed through a PFA mixing tube (0.2 mm inner diameter), and loaded into an injection loop. The reaction segment was injected into the flow reactor (Hastelloy coil, 0.75 mm inner diameter, 1.8 mL internal volume) set at 75° C., and passed through the reactor at 180 μL min$^{-1}$ (10 minute residence time). Upon exiting the reactor, the reaction was loaded directly into an injection loop and purified using preparative LC method TFA6 to yield the title compound (5.7 mg, 34% yield). $^1$H NMR (400 MHz, 90° C., DMSO-$d_6$:D$_2$O=9:1 (v/v)) δ 7.93 (dd, J=8.1, 1.6 Hz, 1H), 7.32 (d, J=1.8 Hz, 1H), 7.28-7.13 (m, 2H), 7.05-6.91 (m, 2H), 6.88 (dd, J=8.1, 1.5 Hz, 1H), 6.79 (td, J=7.7, 1.5 Hz, 1H), 6.54 (dd, J=8.5, 2.6 Hz, 1H), 6.49 (d, J=2.5 Hz, 1H), 4.96-4.90 (m, 1H), 4.81 (dd, J=8.4, 3.7 Hz, 1H), 3.73 (s, 3H), 2.31-2.07 (m, 2H), 1.53-1.33 (m, 2H), 1.15-0.97 (m, 2H); MS (APCI+) m/z 539.0 (M+H)$^+$.

Example 183 rac-(2R,4S)-4-({[1-(2,2-difluoro-1,3-benzodioxol-5-yl)cyclopropyl]carbonyl}amino)-N-(2-hydroxyethyl)-7-methoxy-N-propyl-3,4-dihydro-2H-chromene-2-carboxamide Example 183 was prepared according to the procedure for the preparation of Example 182, substituting 2-propylamino-ethanol for 2-aminophenol to provide the title compound (9.6 mg, 59% yield). $^1$H NMR (400 MHz, 120° C., DMSO-$d_6$:D$_2$O=9:1 (v/v)) δ 7.25 (d, J=1.6 Hz, 1H), 7.22-7.12 (m, 2H), 6.95 (dd, J=8.4, 0.8 Hz, 1H), 6.45 (dd, J=8.5, 2.6 Hz, 1H), 6.30 (d, J=2.6 Hz, 1H), 5.05-4.86 (m, 2H), 3.68 (s, 3H), 3.63-3.20 (m, 6H), 2.15-1.91 (m, 2H), 1.70-1.45 (m, 2H), 1.45-1.31 (m, 2H), 1.13-0.89 (m, 2H), 0.82 (t, J=7.4 Hz, 3H); MS (APCI+) m/z 533.1 (M+H)$^+$.

Example 184 rac-(2R,4S)—N-benzyl-4-({[1-(2,2-difluoro-1,3-benzodioxol-5-yl)cyclopropyl]carbonyl}amino)-N-(2-hydroxyethyl)-7-methoxy-3,4-dihydro-2H-chromene-2-carboxamide Example 184 was prepared according to the procedure for the preparation of Example 182, substituting 2-benzylamino-ethanol for 2-aminophenol to provide the title compound (7.4 mg, 41% yield). $^1$H NMR (400 MHz, 120° C., DMSO-d$_6$:D$_2$O=9:1 (v/v)) δ 7.39-7.11 (m, 8H), 6.96 (d, J=8.5 Hz, 1H), 6.47 (dd, J=8.5, 2.6 Hz, 1H), 6.31-6.20 (m, 1H), 5.15-5.07 (m, 1H), 4.99 (t, J=4.9 Hz, 1H), 4.64 (s, 2H), 3.68 (s, 3H), 3.56 (t, J=5.9 Hz, 2H), 3.49-3.31 (m, 2H), 2.20-1.97 (m, 2H), 1.41 (td, J=11.4, 10.5, 8.1 Hz, 2H), 1.11-0.95 (m, 2H); MS (APCI+) m/z 581.0 (M+H)$^+$.

Example 185 rac-(2R,4S)-4-({[1-(2,2-difluoro-1,3-benzodioxol-5-yl)cyclopropyl]carbonyl}amino)-N-(2-hydroxy-2-phenylethyl)-7-methoxy-N-methyl-3,4-dihydro-2H-chromene-2-carboxamide Example 185 was prepared according to the procedure for the preparation of Example 182, substituting 2-methyl-amino-1-phenyl-ethanol for 2-aminophenol to provide the title compound (11.2 mg, 63% yield). $^1$H NMR (400 MHz, 90° C., DMSO-d$_6$:D$_2$O=9:1 (v/v)) δ 7.44-7.06 (m, 8H), 6.96 (t, J=7.8 Hz, 1H), 6.48 (dd, J=8.5, 2.5 Hz, 1H), 6.37-6.24 (m, 1H), 5.10-4.86 (m, 2H), 4.81 (t, J=6.4 Hz, 1H), 3.69 (s, 3H), 3.60-3.34 (m, 2H), 2.91 (d, J=23.4 Hz, 3H), 2.07-1.89 (m, 2H), 1.56-1.13 (m, 2H), 1.07-0.99 (m, 2H); MS (APCI+) m/z 581.0 (M+H)$^+$.

Example 186 rac-1-(2,2-difluoro-1,3-benzodioxol-5-yl)-N-{(2R,4S)-2-[(4-hydroxypiperidin-1-yl)carbonyl]-7-methoxy-3,4-dihydro-2H-chromen-4-yl}cyclopropanecarboxamide Example 186 was prepared according to the procedure for the preparation of Example 182, substituting piperidin-4-ol for 2-aminophenol to provide the title compound (6.8 mg, 42% yield). $^1$H NMR (400 MHz, 120° C., DMSO-d$_6$:D$_2$O=9:1 (v/v)) δ 7.26 (d, J=1.7 Hz, 1H), 7.22-7.12 (m, 2H), 6.94 (d, J=8.5 Hz, 1H), 6.45 (dd, J=8.5, 2.6 Hz, 1H), 6.30 (d, J=2.5 Hz, 1H), 5.05-4.91 (m, 2H), 3.86-3.73 (m, 3H), 3.68 (s, 3H), 3.26-3.11 (m, 2H), 2.14-1.91 (m, 2H), 1.83-1.66 (m, 2H), 1.39 (dt, J=11.7, 9.5 Hz, 4H), 1.11-0.97 (m, 2H); MS (APCI+) m/z 531.0 (M+H)$^+$.

Example 187 rac-1-(2,2-difluoro-1,3-benzodioxol-5-yl)-N-[(2R,4S)-2-{[4-(2-hydroxyethyl)piperazin-1-yl]carbonyl}-7-methoxy-3,4-dihydro-2H-chromen-4-yl]cyclopropanecarboxamide Example 187 was prepared according to the procedure for the preparation of Example 182, substituting 2-piperazin-1-yl-ethanol for 2-aminophenol to provide the title compound (15.9 mg, 77% yield). $^1$H NMR (400 MHz, 120° C., DMSO-d$_6$:D$_2$O=9:1 (v/v)) δ 7.27 (d, J=1.7 Hz, 1H), 7.22-7.13 (m, 2H), 7.03-6.92 (m, 1H), 6.48 (dd, J=8.5, 2.6 Hz, 1H), 6.34 (d, J=2.5 Hz, 1H), 5.03 (dd, J=8.1, 3.7 Hz, 1H), 4.97 (t, J=5.5 Hz, 1H), 3.93-3.74 (m, 6H), 3.69 (s, 3H), 3.31 (t, J=5.3 Hz, 4H), 3.27-3.20 (m, 2H), 2.21-1.92 (m, 2H), 1.54-1.31 (m, 2H), 1.13-0.97 (m, 2H); MS (APCI+) m/z 560.0 (M+H)$^+$.

Example 188 rac-(2R,4S)-4-({[1-(2,2-difluoro-1,3-benzodioxol-5-yl)cyclopropyl]carbonyl}amino)-N-(2-hydroxy-2-methylpropyl)-7-methoxy-3,4-dihydro-2H-chromene-2-carboxamide Example 188 was prepared according to the procedure for the preparation of Example 182, substituting 1-amino-2-methyl-propan-2-ol for 2-aminophenol to provide the title compound (9.0 mg, 56% yield). $^1$H NMR (400 MHz, DMSO-d$_6$:D$_2$O=9:1 (v/v)) δ 7.31 (d, J=1.8 Hz, 1H), 7.28-7.13 (m, 2H), 6.97 (d, J=8.5 Hz, 1H), 6.50 (dd, J=8.5, 2.6 Hz, 1H), 6.45 (d, J=2.5 Hz, 1H), 4.89 (t, J=5.4 Hz, 1H), 4.61 (dd, J=8.6, 3.5 Hz, 1H), 3.71 (s, 3H), 3.19-3.00 (m, 2H), 2.22-1.95 (m, 2H), 1.51-1.32 (m, 2H), 1.13-0.97 (m, 8H); MS (APCI+) m/z 519.1 (M+H)$^+$.

Example 189 rac-(2R,4S)-4-({[1-(2,2-difluoro-1,3-benzodioxol-5-yl)cyclopropyl]carbonyl}amino)-N-(1-hydroxy-2-methylpropan-2-yl)-7-methoxy-3,4-dihydro-2H-chromene-2-carboxamide Example 189 was prepared according to the procedure for the preparation of Example 182, substituting 2-amino-2-methyl-propan-1-ol for 2-aminophenol to provide the title compound (8.8 mg, 55% yield). $^1$H NMR (400 MHz, 90° C., DMSO-d$_6$:D$_2$O=9:1 (v/v)) δ 7.30 (d, J=1.7 Hz, 1H), 7.27-7.13 (m, 2H), 6.96 (d, J=8.6 Hz, 1H), 6.50 (dd, J=8.5, 2.6 Hz, 1H), 6.43 (d, J=2.5 Hz, 1H), 4.87 (t, J=5.3 Hz, 1H), 4.47 (dd, J=8.8, 3.4 Hz, 1H), 3.71 (s, 3H), 3.45-3.33 (m, 2H), 2.18-1.90 (m, 2H), 1.51-1.32 (m, 2H), 1.25 (s, 3H), 1.22 (s, 3H), 1.19-0.95 (m, 2H); MS (APCI+) m/z 519.1 (M+H)$^+$.

Example 190 rac-(2R,4S)-4-({[1-(2,2-difluoro-1,3-benzodioxol-5-yl)cyclopropyl]carbonyl}amino)-N-(2-hydroxy-1-phenylethyl)-7-methoxy-3,4-dihydro-2H-chromene-2-carboxamide Example 190 was prepared according to the procedure for the preparation of Example 182, substituting 2-amino-2-phenyl-ethanol for 2-aminophenol to provide the title compound (11.4 mg, 65% yield). $^1$H NMR (400 MHz, 90° C., DMSO-d$_6$:D$_2$O=9:1 (v/v)) spectrum contains diastereomer peaks δ 7.37-6.91 (m, 9H), 6.57-6.43 (m, 2H), 4.95-4.80 (m, 2H), 4.74-4.53 (m, 1H), 3.76-3.59 (m, 5H), 2.21-1.93 (m, 2H), 1.51-1.31 (m, 2H), 1.12-0.94 (m, 2H); MS (APCI+) m/z 567.0 (M+H)$^+$.

Example 191 rac-(2R,4S)-4-({[1-(2,2-difluoro-1,3-benzodioxol-5-yl)cyclopropyl]carbonyl}amino)-N-(1,1-dioxidotetrahydro-2H-thiopyran-4-yl)-7-methoxy-3,4-dihydro-2H-chromene-2-carboxamide Example 191 was prepared according to the procedure for the preparation of Example 182, substituting 1,1-dioxothian-4-amine for 2-aminophenol to provide the title compound (9.8 mg, 55% yield). $^1$H NMR (400 MHz, 90° C., DMSO-d$_6$:D$_2$O=9:1 (v/v)) δ 7.30 (d, J=1.7 Hz, 1H), 7.28-7.13 (m, 2H), 6.96 (d, J=8.6 Hz, 1H), 6.55-6.39 (m, 2H), 4.88 (t, J=5.4 Hz, 1H), 4.54 (dd, J=8.8, 3.5 Hz, 1H), 3.99 (p, J=7.2

Hz, 1H), 3.71 (s, 3H), 3.24-3.10 (m, 2H), 3.10-2.92 (m, 2H), 2.19-1.90 (m, 6H), 1.52-1.32 (m, 2H), 1.14-0.96 (m, 2H); MS (APCI+) m/z 579.0 (M+H)+.

Example 192 rac-(2R,4S)-4-({[1-(2,2-difluoro-1,3-benzodioxol-5-yl)cyclopropyl]carbonyl}amino)-7-methoxy-N-[3-(trifluoromethyl)oxetan-3-yl]-3,4-dihydro-2H-chromene-2-carboxamide Example 192 was prepared according to the procedure for the preparation of Example 182, substituting 3-(trifluoromethyl)oxetan-3-amine for 2-aminophenol to provide the title compound (3.3 mg, 19% yield). $^1$H NMR (400 MHz, DMSO-d$_6$:D$_2$O=9:1 (v/v)) δ 7.30 (d, J=1.7 Hz, 1H), 7.28-7.13 (m, 2H), 6.98 (d, J=8.6 Hz, 1H), 6.51 (dd, J=8.4, 2.6 Hz, 1H), 6.49-6.42 (m, 1H), 4.90 (t, J=5.2 Hz, 1H), 4.80 (d, J=7.9 Hz, 2H), 4.69 (d, J=8.6 Hz, 2H), 4.63 (dd, J=9.1, 3.4 Hz, 1H), 3.71 (s, 3H), 2.22-1.93 (m, 2H), 1.52-1.32 (m, 2H), 1.13-0.96 (m, 2H); MS (APCI+) m/z 571.0 (M+H)+.

Example 193 rac-1-(2,2-difluoro-1,3-benzodioxol-5-yl)-N-{(2R,4S)-2-[(4,4-difluoropiperidin-1-yl)carbonyl]-7-methoxy-3,4-dihydro-2H-chromen-4-yl}cyclopropanecarboxamide Example 193 was prepared according to the procedure for the preparation of Example 182, substituting 4,4-difluoropiperidine hydrochloride for 2-aminophenol to provide the title compound (9.8 mg, 58% yield). $^1$H NMR (400 120° C., MHz, DMSO-d$_6$:D$_2$O=9:1 (v/v)) δ 7.33-7.26 (m, 1H), 7.26-7.13 (m, 2H), 6.97 (d, J=8.5 Hz, 1H), 6.49 (dd, J=8.5, 2.6 Hz, 1H), 6.35 (d, J=2.5 Hz, 1H), 5.03 (dd, J=8.7, 3.4 Hz, 1H), 4.98 (t, J=5.1 Hz, 1H), 3.70 (s, 3H), 3.68-3.60 (m, 4H), 2.22-1.93 (m, 6H), 1.53-1.31 (m, 2H), 1.12-0.97 (m, 2H); MS (APCI+) m/z 551.0 (M+H)+.

Example 194 rac-1-(2,2-difluoro-1,3-benzodioxol-5-yl)-N-[(2R,4S)-7-methoxy-2-(1,4-oxazepan-4-ylcarbonyl)-3,4-dihydro-2H-chromen-4-yl]cyclopropanecarboxamide Example 194 was prepared according to the procedure for the preparation of Example 182, substituting 1,4-oxazepane hydrochloride for 2-aminophenol to provide the title compound (8.7 mg, 53% yield). $^1$H NMR (400 MHz, 120° C., DMSO-d$_6$:D$_2$O=9:1 (v/v)) δ 7.28 (d, J=1.5 Hz, 1H), 7.25-7.12 (m, 2H), 6.98 (d, J=8.5 Hz, 1H), 6.48 (dd, J=8.5, 2.6 Hz, 1H), 6.33 (d, J=2.6 Hz, 1H), 5.04-4.93 (m, 2H), 3.70 (s, 7H), 3.64-3.55 (m, 4H), 2.17-1.93 (m, 2H), 1.93-1.73 (m, 2H), 1.49-1.33 (m, 2H), 1.12-0.96 (m, 2H); MS (APCI+) m/z 531.0 (M+H)+.

Example 195 rac-(2R,4S)-4-({[1-(2,2-difluoro-1,3-benzodioxol-5-yl)cyclopropyl]carbonyl}amino)-7-methoxy-N-methyl-N-(oxetan-3-yl)-3,4-dihydro-2H-chromene-2-carboxamide Example 195 was prepared according to the procedure for the preparation of Example 182, substituting N-methyloxetan-3-amine for 2-aminophenol to provide the title compound (13.7 mg, 86% yield). $^1$H NMR (400 MHz, 90° C., DMSO-d$_6$:D$_2$O=9:1 (v/v)) δ 7.31 (d, J=1.7 Hz, 1H), 7.29-7.14 (m, 2H), 6.94 (d, J=8.6 Hz, 1H), 6.51 (dd, J=8.6, 2.6 Hz, 1H), 6.37 (d, J=2.6 Hz, 1H), 4.99-4.83 (m, 2H), 4.47-4.27 (m, 2H), 3.80-3.55 (m, 5H), 3.55-3.34 (m, 1H), 2.72-2.60 (m, 3H), 2.21 (d, J=5.8 Hz, 2H), 1.53-1.32 (m, 2H), 1.21-0.98 (m, 2H); MS (APCI+) m/z 517.1 (M+H)+.

Example 196 rac-1-(2,2-difluoro-1,3-benzodioxol-5-yl)-N-[(2R,4S)-7-methoxy-2-(morpholin-4-ylcarbonyl)-3,4-dihydro-2H-chromen-4-yl]cyclopropanecarboxamide Example 196 was prepared according to the procedure for the preparation of Example 182, substituting morpholine for 2-aminophenol to provide the title compound (9.5 mg, 60% yield). $^1$H NMR (400 MHz, 90° C., DMSO-d$_6$:D$_2$O=9:1 (v/v)) δ 7.31 (d, J=1.7 Hz, 1H), 7.27-7.14 (m, 2H), 6.97 (d, J=8.4 Hz, 1H), 6.49 (dd, J=8.5, 2.6 Hz, 1H), 6.34 (d, J=2.6 Hz, 1H), 5.07-4.93 (m, 2H), 3.70 (s, 3H), 3.60 (td, J=4.8, 1.6 Hz, 4H), 3.51 (t, J=4.9 Hz, 4H), 2.14-1.92 (m, 2H), 1.52-1.32 (m, 2H), 1.13-0.97 (m, 2H); MS (APCI+) m/z 517.1 (M+H)+.

Example 197 rac-(2R,4S)-4-({[1-(2,2-difluoro-1,3-benzodioxol-5-yl)cyclopropyl]carbonyl}amino)-N-[2-hydroxy-1-(2-methoxyphenyl)ethyl]-7-methoxy-3,4-dihydro-2H-chromene-2-carboxamide Example 197 was prepared according to the procedure for the preparation of Example 182, substituting 2-amino-2-(2-methoxy-phenyl)-ethanol for 2-aminophenol to provide the title compound (11.3 mg, 70% yield). $^1$H NMR (400 MHz, 90° C., DMSO-d$_6$:D$_2$O=9:1 (v/v)) spectrum contains diastereomer peaks δ 7.33-7.12 (m, 5H), 7.04-6.85 (m, 3H), 6.56-6.41 (m, 2H), 5.22-5.10 (m, 1H), 4.94-4.76 (m, 1H), 4.70-4.51 (m, 1H), 3.80 (d, J=17.0 Hz, 3H), 3.75-3.68 (m, 3H), 3.68-3.49 (m, 2H), 2.23-1.92 (m, 2H), 1.51-1.32 (m, 2H), 1.13-0.97 (m, 2H); MS (APCI+) m/z 597.0 (M+H)+.

Example 198 rac-(2R,4S)-4-({[1-(2,2-difluoro-1,3-benzodioxol-5-yl)cyclopropyl]carbonyl}amino)-N-[2-(3-hydroxyphenyl)ethyl]-7-methoxy-3,4-dihydro-2H-chromene-2-carboxamide Example 198 was prepared according to the procedure for the preparation of Example 182, substituting 3-(2-aminoethyl)phenol hydrochloride for 2-aminophenol to provide the title compound (12.7 mg, 73% yield). $^1$H NMR (400 MHz, 90° C., DMSO-d$_6$:D$_2$O=9:1 (v/v)) δ 7.30 (d, J=1.7 Hz, 1H), 7.27-7.13 (m, 2H), 7.05 (t, J=7.7 Hz, 1H), 6.96 (d, J=8.5 Hz, 1H), 6.65-6.55 (m, 3H), 6.49 (dd, J=8.5, 2.6 Hz, 1H), 6.42 (d, J=2.6 Hz, 1H), 4.86 (t, J=5.1 Hz, 1H), 4.51 (dd, J=9.2, 3.4 Hz, 1H), 3.71 (s, 3H), 3.35 (t, J=7.3 Hz, 2H), 2.68 (t, J=7.3 Hz, 2H), 2.12 (dt, J=14.0, 4.1 Hz, 1H), 2.05-1.87 (m, 1H), 1.51-1.32 (m, 2H), 1.21-0.95 (m, 2H); MS (APCI+) m/z 567.0 (M+H)+.

Example 199 rac-(2R,4S)-4-({[1-(2,2-difluoro-1,3-benzodioxol-5-yl)cyclopropyl]carbonyl}amino)-N-(1,3-dihydroxypropan-2-yl)-7-methoxy-3,4-dihydro-2H-chromene-2-carboxamide Example 199 was prepared according to the procedure for the preparation of Example 182, substituting 2-amino-propane-1,3-diol for 2-aminophenol to provide the title compound (10.7 mg, 67% yield). $^1$H NMR (400 MHz, 90° C., DMSO-d$_6$:D$_2$O=9:1 (v/v)) δ 7.30 (d, J=1.7 Hz, 1H), 7.28-7.13 (m, 2H), 6.98 (d, J=8.5 Hz, 1H), 6.50 (dd, J=8.5, 2.6 Hz, 1H), 6.44 (d, J=2.5 Hz, 1H), 4.88 (t, J=4.9 Hz, 1H), 4.55 (dd, J=9.3, 3.3 Hz, 1H), 3.80 (h, J=5.3 Hz, 1H), 3.71 (d, J=1.0 Hz, 3H), 3.59-3.36 (m, 4H), 2.15 (dt, J=14.0, 4.2 Hz, 1H), 2.07-1.90 (m, 1H), 1.51-1.32 (m, 2H), 1.21-0.95 (m, 2H); MS (APCI+) m/z 521.0 (M+H)$^+$.

Example 200 rac-(2R,4S)-4-({[1-(2,2-difluoro-1,3-benzodioxol-5-yl)cyclopropyl]carbonyl}amino)-N-(2-hydroxy-2,3-dihydro-1H-inden-1-yl)-7-methoxy-3,4-dihydro-2H-chromene-2-carboxamide Example 200 was prepared according to the procedure for the preparation of Example 182, substituting 1-amino-indan-2-ol for 2-aminophenol to provide the title compound (11.3 mg, 70% yield). $^1$H NMR (400 MHz, 90° C., DMSO-d$_6$:D$_2$O=9:1 (v/v)) spectrum contains diastereomer peaks δ 7.37-6.90 (m, 8H), 6.57-6.45 (m, 1H), 6.39 (dd, J=6.5, 2.6 Hz, 1H), 5.23 (d, J=5.3 Hz, 1H), 5.04-4.89 (m, 1H), 4.83-4.67 (m, 1H), 4.54-4.40 (m, 1H), 3.69 (d, 3H), 3.10 (dd, J=16.4, 5.2 Hz, 1H), 2.92-2.78 (m, 1H), 2.32-1.98 (m, 2H), 1.55-1.34 (m, 2H), 1.22-0.97 (m, 2H).; MS (APCI+) m/z 579.0 (M+H)$^+$.

Example 201 rac-1-{[(2R,4S)-4-({[1-(2,2-difluoro-1,3-benzodioxol-5-yl)cyclopropyl]carbonyl}amino)-7-methoxy-3,4-dihydro-2H-chromen-2-yl]carbonyl}pyrrolidine-3-carboxylic acid A stock solution Example 134 and diisopropylethylamine (0.044 M and 0.13 M in dimethylacetamide, respectively, 1.0 mL, 0.044 mmol Example 134 (1.0 equivalent) and 0.13 mmol diisopropylethylamine (3.0 equivalents)) and 2-(3H-[1,2,3]triazolo[4,5-b]pyridin-3-yl)-1,1,3,3-tetramethylisouronium hexafluorophosphate(V) (0.054 M in dimethylacetamide, 1.0 mL, 0.054 mmol, 1.2 equivalents) were combined and stirred at room temperature for 10 minutes. Pyrrolidine-3-carboxylic acid (0.40 M in dimethylacetamide, 167 μL, 0.067 mmol, 1.5 equivalents) was added and the reaction was stirred at 75° C. for 30 minutes. The reaction was loaded directly into an injection loop and purified using preparative LC method TFA6 to yield the title compound (5.7 mg, 34% yield). $^1$H NMR (400 MHz, 120° C., DMSO-d$_6$:D$_2$O=9:1 (v/v)) spectrum contains diastereomer peaks δ 7.26 (s, 1H), 7.20-7.14 (m, 2H), 6.95 (d, J=8.5 Hz, 1H), 6.46 (dd, J=8.5, 2.6 Hz, 1H), 6.32 (t, J=2.5 Hz, 1H), 4.94 (s, 1H), 4.80 (dd, J=7.9, 4.2 Hz, 1H), 3.68 (s, 3H), 3.62-3.34 (m, 4H), 2.07 (d, J=39.1 Hz, 5H), 1.43-1.37 (m, 2H), 1.04-0.99 (m, 2H); MS (APCI+) m/z 545.4 (M+H)$^+$.

Example 202

4-[(2R,4R)-4-({[1-(6-bromo-2,2-difluoro-1,3-benzodioxol-5-yl)cyclopropyl]carbonyl}amino)-7-(difluoromethoxy)-3,4-dihydro-2H-chromen-2-yl]benzoic acid Example 202A (R)-methyl 4-(4-((benzyloxy)imino)-7-methoxychroman-2-yl)benzoate Example 110A (29.52 g, 95 mmol) was dissolved in 190 mL of dry pyridine. O-benzylhydroxylamine hydrochloride (15.84 g, 99 mmol) was added, and the solution was heated at 50° C. for 16 hours. The reaction flask was cooled to room temperature, concentrated in vacuo, and partitioned between ethyl acetate (300 mL) and saturated aqueous ammonium chloride (150 mL). The organic layer was washed with 1M HCl (3×100 mL) and brine (100 mL) then concentrated and triturated with heptanes to give a solid mass, which was filtered then crushed with a mortar/pestle and dried to constant weight to give 35 g of the title compound, which was used without additional purification. Analytical data for the major isomer are show here. $^1$H NMR (501 MHz, CDCl$_3$) δ 8.06 (d, J=8.3 Hz, 2H), 7.84 (d, J=8.8 Hz, 1H), 7.54-7.46 (m, 2H), 7.40-7.28 (m, 5H), 6.57 (dd, J=8.8, 2.5 Hz, 1H), 6.48 (d, J=2.5 Hz, 1H), 5.19 (d, J=2.0 Hz, 2H), 5.11 (dd, J=12.3, 3.2 Hz, 1H), 3.92 (s, 3H), 3.78 (s, 3H), 3.48 (dd, J=17.2, 3.2 Hz, 1H), 2.67 (dd, J=17.2, 12.2 Hz, 1H); MS (ESI+) m/z 418.1 (M+H)$^+$.

Example 202B methyl 4-((2R,4R)-4-amino-7-methoxychroman-2-yl)benzoate hydrochloride Example 202A (20 g 47.9 mmol) was dissolved in 300 mL of acetic acid and 5% Pt/C wet (1.5 g wet weight, 58.9% water, 0.884 g or 4.42% dry basis) in a 300-mL stainless steel reactor. The headspace was inerted with argon and then pressurized to 30 psi with hydrogen. The mixture was shaken at room temperature under 30 psi of hydrogen for 18 hours. The reaction was monitored by HPLC for disappearance of the starting material. Once about 95% conversion was achieved (18 hours, monitored by LC-MS), the reactor was vented and the reaction mixture was filtered through 0.45 μm GHP Acrodisc membrane. The solvent was removed in vacuo to give 60 g of crude material. The crude material was heated at 70° C. in 250 mL of 4:1 methyl tert-butyl ether:heptanes until a clear solution resulted. HCl (3M in cyclopropyl methyl ether, 47.9 mL, 144 mmol) was added drop wise at the same temperature, and a white solid precipitated from the reaction mixture. The flask was allowed to cool to room temperature over 1 hour, and the resulting off-white solid was removed via filtration using a fritted funnel. The solid was washed with methyl tert-butyl ether (2×100 mL) and dried in the funnel. The resulting white solid was further heated at 70° C. in toluene (20 mL) for 30 minutes to remove additional impurities. After cooling to room temperature, the resulting solid was filtered using a fritted funnel and washed with 75 mL of toluene and 100 mL of heptanes then dried to constant weight to give 19.8 g of the title compound (79% yield). $^1$H NMR (400 MHz, DMSO-d$_6$) δ 8.67 (s, 3H), 8.08-7.95 (m, 2H), 7.58 (dd, J=8.4, 6.1 Hz, 3H), 6.62 (dd, J=8.7, 2.6 Hz, 1H), 6.50 (d, J=2.5 Hz, 1H), 5.33 (dd, J=11.8, 1.6 Hz, 1H), 4.70 (dd, J=11.1, 6.2 Hz, 1H), 3.84 (s, 3H), 3.70 (s, 3H), 2.60-2.50 (m, 1H), 1.96 (q, J=11.8 Hz, 1H); MS (ESI+) m/z 297.1 (M-NH$_3$)$^+$.

Example 202C methyl 1-(6-bromo-2,2-difluorobenzo[d][1,3]dioxol-5-yl)cyclopropanecarboxylate 1-(2,2-difluorobenzo[d][1,3]dioxol-5-yl)cyclopropanecarboxylic acid (2 g, 8.26 mmol) was suspended in acetonitrile (16.52 mL) and N-bromosuccinimide (1.911 g, 10.74 mmol) was added, followed by iron (III) chloride (0.670 g, 4.13 mmol). The reaction was stirred at room temperature for 16 hours. The reaction mixture was diluted with ethyl acetate and washed with water, saturated sodium thiosulfate, and brine then dried over sodium sulfate then concentrated to give a dark crude oil. The crude material was dissolved in a 2:1 mixture of tetrahydrofuran and methanol (20 mL total) and TMS-diazomethane (2M in diethyl ether, 5.37 mL, 10.74 mmol) was added drop wise. After the addition was complete, TLC indicated that complete conversion to the methyl ester had occurred. The solvent was removed in vacuo and the resulting crude residue was purified by flash column chromatography, eluting with 0-10% ethyl acetate/heptanes over 20 minutes on a 40 g silica gel column to give 1.56 g of the title compound as a colorless oil. $^1$H NMR (400 MHz, CDCl$_3$) δ 7.29 (s, 1H), 7.04 (s, 1H), 3.64 (s, 3H), 1.78 (m, 2H), 1.21-1.09 (m, 2H).

Example 202D 1-(6-bromo-2,2-difluorobenzo[d][1,3]dioxol-5-yl)cyclopropanecarboxylic acid Example 202C (1.354 g, 4.04 mmol) was dissolved in tetrahydrofuran (10.10 mL) and potassium trimethylsilanolate (0.778 g, 6.06 mmol) was added. The resulting light yellow solution was heated at 40° C. for 2 hours. The flask was cooled to room temperature and stirred with 1M HCl (10 mL) for 5 minutes and partitioned between ethyl acetate and water. The organic extracts were dried over sodium sulfate, filtered, and concentrated to give 1.25 g of the title compound as a white solid. $^1$H NMR (400 MHz, CDCl$_3$) δ 7.29 (s, 1H), 7.04 (s, 1H), 1.97-1.73 (m, 2H), 1.27 (br s, 2H); MS (ESI+) m/z 338.3 (M+H$_2$O)$^+$.

Example 202E 1-(6-bromo-2,2-difluorobenzo[d][1,3]dioxol-5-yl)cyclopropanecarbonyl chloride Example 202D (1 g, 3.11 mmol) was dissolved in dichloromethane (7.79 mL). The resulting solution was treated with oxalyl dichloride (0.791 mL, 9.34 mmol) and N,N-dimethylformamide (4.55 mg, 0.062 mmol). The solution was stirred for 1 hour at room temperature, and concentrated. The resulting crude oil was dissolved in 10 mL of dichloromethane and concentrated in vacuo. The obtained acid chloride was used immediately in the amide coupling reaction after preparation of the compound as a solution in 5 mL of dry dichloromethane.

Example 202F methyl 4-((2R,4R)-4-(1-(6-bromo-2,2-difluorobenzo[d][1,3]dioxol-5-yl)cyclopropanecarboxamido)-7-methoxychroman-2-yl)benzoate A solution of Example 202B (1.092 g, 3.12 mmol) in dichloromethane (15.61 mL) in a 100-mL round-bottomed flask was cooled to <5° C. in an ice-water bath, and triethylamine (1.305 mL, 9.37 mmol) was added. A freshly prepared solution of Example 202E (1.06 g, 3.12 mmol) in 2 mL of dichloromethane was added drop wise via syringe, and the reaction was stirred for 15 minutes at the same temperature. The reaction mixture was diluted with methyl tert-butyl ether (30 mL) and was stirred with 1M HCl (10 mL) for 5 minutes at room temperature. After standard aqueous workup, the resulting crude solid was slurried with hot ethyl acetate/heptanes mixture (1:4, 10 mL) at 75° C. for 30 minutes and was then cooled to room temperature. The resulting white solid was collected via filtration using a fritted funnel and was dried to constant weight to give 1.25 g of the title compound. $^1$H NMR (501 MHz, CDCl$_3$) δ 8.07 (d, J=8.4 Hz, 2H), 7.60-7.43 (m, 2H), 7.33 (s, 1H), 7.12 (d, J=24.1 Hz, 2H), 6.55 (dd, J=8.6, 2.6 Hz, 1H), 6.47 (d, J=2.5 Hz, 1H), 5.47 (td, J=9.7, 6.2 Hz, 1H), 5.32-5.16 (m, 2H), 3.96 (s, 3H), 3.79 (s, 3H), 2.56 (ddd, J=13.3, 6.1, 2.1 Hz, 1H), 1.93 (br s, 1H), 1.83 (dt, J=13.4, 11.0 Hz, 2H), 1.12 (br s, 2H); MS(ESI+) m/z 297.1 (M-Amide+H)$^+$.

Example 202G methyl 4-((2R,4R)-4-(1-(6-bromo-2,2-difluorobenzo[d][1,3]dioxol-5-yl)cyclopropanecarboxamido)-7-hydroxychroman-2-yl)benzoate Example 202F (1 g, 1.622 mmol) and tetrabutylammonium iodide (1.798 g, 4.87 mmol were dissolved in 10 mL of dry dichloromethane and the solution was cooled to <−20° C. in an acetone-dry ice bath. Boron trichloride (1M in dichloromethane, 4.87 mL, 4.87 mmol) solution was added drop wise over 5 minutes, and the reaction was kept at the same temperature for 1 hour. The resulting solution was poured into ice water and extracted with dichloromethane (3×20 mL). The combined extracts were concentrated in vacuo to approximately 5 mL and were then diluted with 20 mL of methyl tert-butyl ether. The volatiles were removed in vacuo and the resulting crude material was slurried with 15 mL of methyl tert-butyl ether and concentrated partially in vacuo then followed by addition of methyl tert-butyl ether, concentrated again and slurried with methyl tert-butyl ether. The slurry was washed with water (2×20 mL) and the organic layer was then concentrated in vacuo and filtered through a 1-inch pad of silica, eluting with methyl tert-butyl ether. The solvent was removed in vacuo to give a crude white solid, which was used without additional purification. $^1$H NMR (501 MHz, CDCl$_3$) δ 8.05 (d, J=8.4 Hz, 2H), 7.45 (d, J=8.1 Hz, 2H), 7.32 (s, 1H), 7.09 (br s, 2H), 6.49 (d, J=0.7 Hz, 1H), 6.43 (s, 1H), 6.00-5.78 (br s, 1H), 5.44 (q, J=8.8 Hz, 1H), 5.29 (d, J=8.7 Hz, 1H), 5.20 (dd, J=11.3, 2.0 Hz, 1H), 3.95 (s, 3H), 2.53 (ddd, J=13.3, 6.0, 2.0 Hz, 1H), 1.93 (br s, 1H), 1.81 (dt, J=13.1, 10.8 Hz, 2H), 1.11 (br s, 2H); MS (ESI+) m/z 283.1 (M-Amide+H)$^+$.

Example 202H 4-((2R,4R)-4-(1-(6-bromo-2,2-difluorobenzo[d][1,3]dioxol-5-yl)cyclopropanecarboxamido)-7-(difluoromethoxy)chroman-2-yl)benzoic acid Example 202G (0.980 g, 1.627 mmol) was suspended in acetonitrile (8.13 mL). The suspension was cooled to <−25° C. in an acetone-dry ice bath and diethyl(bromodifluoromethyl)phosphonate (0.434 mL, 2.440 mmol) was added, followed by drop wise addition of aqueous potassium hydroxide (4 M, 8.13 mL, 32.5 mmol) at such a rate that the temperature was maintained below −15° C. After the addition was complete (2 minutes), the reaction was stirred for an additional 15 minutes, at which point it was warmed to room temperature. Methanol (5 mL) was added, and the reaction was heated at 40° C. for 15 minutes. The flask was cooled to room temperature, diluted with 10 mL of isopropyl acetate and washed with KOH (2 M, 3×10 mL), 20 mL of 1M HCl, and brine then dried over sodium sulfate, filtered, and concentrated. The residue was purified via flash column chromatography, eluting with 0-100% ethyl acetate/heptanes over 20 minutes on a 40 g silica gel column to afford 275 mg of the title compound as a white solid. $^1$H NMR (400 MHz, DMSO-$d_6$; 90° C.) δ 7.96 (d, J=8.2 Hz, 2H), 7.65 (s, 1H), 7.52 (d, J=8.1 Hz, 2H), 7.44 (s, 1H), 7.21 (d, J=8.5 Hz, 1H), 7.05 (t, J=72 Hz, 1H; CF$_2$H) 7.01 (d, J=8.7 Hz, 1H), 6.72 (dd, J=8.5, 2.6 Hz, 1H), 6.63 (d, J=2.6 Hz, 1H), 5.46-5.30 (m, 2H), 2.22-1.95 (m, 2H), 1.68 (dt, J=9.7, 3.0 Hz, 1H), 1.57 (dt, J=8.7, 2.9 Hz, 1H), 1.08 (s, 2H); MS (ESI+) m/z=636.0 (M−H)$^−$.

Example 203

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]-N-(methylsulfonyl)benzamide A mixture of the product from Example 122 (0.100 g, 0.178 mmol), TBTU (O-(benzotriazol-1-yl)-N,N,N',N'-tetramethyluronium tetrafluoroborate) (0.086 g, 0.268 mmol), and triethylamine (0.080 mL, 0.572 mmol) in tetrahydrofuran (2 mL) was stirred at room temperature for 90 minutes, at which time a cloudy white mixture was seen. The mixture was then treated with lithium chloride (2.5 mg, 0.059 mmol) and methanesulfonamide (22 mg, 0.228 mmol), and the reaction stirred overnight at room temperature. After this time, the reaction mixture was concentrated in vacuo, and the residue was purified by reverse-phase preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A), yielding the title compound as a white solid (45 mg, 40% yield). $^1$H NMR (400 MHz, DMSO-$d_6$) δ 12.15 (s, 1H), 7.97 (d, J=8.3 Hz, 2H), 7.61-7.17 (m, 6H), 7.09-7.01 (m, 2H), 6.77-6.68 (m, 2H), 5.50-5.32 (m, 2H), 3.38 (s, 3H), 2.13-2.02 (m, 2H), 1.52-1.34 (m, 2H). 1.06 (m, 2H); MS (ESI$^+$) m/z 636.9 (M+H)$^+$.

Determination of Biological Activity
Cellular Assays
Cell Surface Expression-Horse Radish Peroxidase (CSE-HRP) Assay:

A cellular assay for measuring the F508delCFTR cell surface expression after correction with test compounds was developed in human lung derived epithelial cell line (CFBE4lo-) (Veit G et al, (2012) Mol Biol Cell. 23(21): 4188-4202). This was achieved by expressing the F508delCFTR mutation along with a horseradish peroxidase (HRP) in the fourth exofacial loop and then measuring the HRP activity using luminescence readout from these cells, CFBE4lo-F508delCFTR-HRP, that were incubated overnight with the test corrector compounds. Briefly, for this primary assay, the CFBE4lo-F508delCFTR-HRP cells were plated in 384-well plates (Greiner Bio-one; Cat 781080) at 4,000 cells/well along with 0.5 μg/mL doxycycline to induce the F508delCFTR-HRP expression and further incubated at 37° C., 5% CO$_2$ for 72 hours. The test compounds were then added at the required concentrations and further incubated for 18-24 hours at 33° C. The highest concentration tested was 20 μM with an 8-point concentration response curve using a 3-fold dilution. Three replicate plates were run to determine one EC$_{50}$. All plates contained negative controls (dimethyl sulfoxide, DMSO) and positive controls (3 μM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) as well as on-plate concentration response of the positive control. Post incubation, the plates were washed 5× times with Dulbecco's phosphate buffered saline (DPBS), followed by the addition of the HRP substrate, luminol (50 μL), and measuring the HRP activity using luminescence readout on EnVision® Multilabel Plate Reader (Perkin Elmer; product number 2104-0010). The raw counts from the experiment are analyzed using Accelrys® Assay Explorer v3.3.

Z' greater than 0.5 was used as passing quality control criteria for the plates.

The Z' is defined as:

$$1-[3*SD_{Positive\ Control}+3*SD_{Negative\ Control}/Absolute\ (Mean_{Positive\ Control}-Mean_{Negative\ Control})]$$

wherein "SD" is standard deviation.

The % activity measured at each of the 8 test concentrations of the test compound was normalized to the on-plate positive control using the following formula:

% activity=[(test compound response−DMSO response)/(positive control response−DMSO response)]*100

The maximum % activity achieved for the test compound at any tested concentration is presented in Table 1 along with the EC$_{50}$ calculated using the following general sigmoidal curve with variable Hill slope equation (described as Model 42 in the Accelrys® Assay Explorer v3.3 software):

$$y=(a-d)/(1+(x/c)^b)+d$$

General sigmoidal curve with concentration, response, top, bottom, EC$_{50}$ and Hill slope.

This model describes a sigmoidal curve with an adjustable baseline, a. The equation can be used to fit curves where response is either increasing or decreasing with respect to the independent variable, "x".

"x" is a concentration of drug under test.
"y" is the response.
"a" is the maximum response, and "d" is the minimum response
"c" is the inflection point (EC$_{50}$) for the curve. That is, "y" is halfway between the lower and upper asymptotes when x=c.
"b" is the slope-factor or Hill coefficient. The sign of b is positive when the response increases with increasing dose and is negative when the response decreases with increasing dose (inhibition).

TABLE 1

| CSE-HRP data | | |
|---|---|---|
| Example | EC$_{50}$ (μM) | Maximum % activity (%) |
| 1 | 0.28 | 102 |
| 2 | 2.71 | 122 |
| 3 | 0.39 | 135 |
| 4 | 1.19 | 73 |
| 5 | 2.45 | 92 |
| 6 | 0.38 | 120 |
| 7 | 5.84 | 58 |
| 8 | 1.75 | 98 |
| 9 | 0.42 | 84 |
| 10 | 4.1 | 112 |
| 11 | 0.91 | 102 |
| 12 | 5.47 | 58 |
| 13 | 4.57 | 118 |
| 14 | 0.85 | 78 |
| 15 | 2.47 | 101 |
| 16 | 0.37 | 108 |
| 17 | 2.64 | 78 |

TABLE 1-continued

CSE-HRP data

| Example | EC$_{50}$ (μM) | Maximum % activity (%) |
|---|---|---|
| 18 | 0.35 | 113 |
| 19 | 0.63 | 103 |
| 20 | 4.62 | 30 |
| 21 | 0.80 | 142 |
| 22 | 1.77 | 109 |
| 23 | 20 | 12 |
| 24 | 8.37 | 63 |
| 25 | 3.91 | 41 |
| 26 | 0.34 | 93 |
| 27 | 0.12 | 113 |
| 28 | 3.24 | 98 |
| 29 | 5.71 | 106 |
| 30 | 1.88 | 78 |
| 31 | 10.7 | 21 |
| 32 | 20 | 16 |
| 33 | 7.65 | 38 |
| 34 | 20 | 15 |
| 35 | 1.16 | 82 |
| 36 | 1.82 | 78 |
| 37 | 3.05 | 88 |
| 38 | 0.61 | 93 |
| 39 | 1.72 | 82 |
| 40 | 2.68 | 107 |
| 41 | 2.58 | 73 |
| 42 | 20 | 5 |
| 43 | 0.85 | 78 |
| 44 | 20 | 14 |
| 45 | 1.33 | 89 |
| 46 | 5.14 | 27 |
| 47 | 4 | 43 |
| 48 | 1 | 104 |
| 49 | 0.97 | 105 |
| 50 | 0.86 | 101 |
| 51 | 0.97 | 83 |
| 52 | 1.01 | 93 |
| 53 | 1.76 | 90 |
| 54 | 0.86 | 92 |
| 55 | 2.11 | 101 |
| 56 | 3.12 | 124 |
| 57 | 1.69 | 112 |
| 58 | 2.54 | 101 |
| 59 | 3.66 | 101 |
| 60 | 0.7 | 131 |
| 61 | 2.04 | 132 |
| 62 | 0.69 | 135 |
| 63 | 0.63 | 106 |
| 64 | 1.61 | 78 |
| 65 | 10.1 | 45 |
| 66 | 6.1 | 89 |
| 67 | 5.89 | 128 |
| 68 | 0.87 | 89 |
| 69 | 2.12 | 109 |
| 70 | 6.84 | 94 |
| 71 | 2.84 | 91 |
| 72 | 2.5 | 71 |
| 73 | 7.63 | 57 |
| 74 | 5.53 | 98 |
| 75 | 3.28 | 75 |
| 76 | 2.99 | 105 |
| 78 | 5.28 | 95 |
| 79 | 7.25 | 117 |
| 80 | 1.55 | 114 |
| 81 | 4.5 | 98 |
| 82 | 2.72 | 97 |
| 83 | 2.72 | 106 |
| 84 | 2.24 | 91 |
| 85 | 6.81 | 108 |
| 86 | 3.5 | 101 |
| 87 | 4.63 | 146 |
| 90 | 3.44 | 42 |
| 91 | 2.71 | 82 |
| 92 | 2.57 | 71 |
| 93 | 2.8 | 26 |
| 94 | 0.94 | 119 |
| 95 | 0.92 | 98 |
| 96 | 20 | 15 |
| 97 | 0.38 | 90 |
| 98 | 0.57 | 102 |
| 99 | 3.89 | 56 |
| 100 | 3.08 | 40 |
| 101 | 6.65 | 60 |
| 102 | 4.86 | 89 |
| 103 | 8.53 | 28 |
| 104 | 6.58 | 49 |
| 105 | 7.46 | 34 |
| 106 | 0.31 | 88 |
| 107 | 1.13 | 99 |
| 108 | 0.34 | 115 |
| 109 | 0.45 | 94 |
| 110 | 0.28 | 115 |
| 111 | 0.044 | 113 |
| 112 | 20 | 5 |
| 113 | 3.55 | 49 |
| 114 | 4.76 | 61 |
| 115 | 1.94 | 77 |
| 116 | 7.64 | 59 |
| 117 | 6.01 | 82 |
| 118 | 8.15 | 25 |
| 119 | 0.88 | 71 |
| 120 | 0.50 | 110 |
| 121 | 0.13 | 102 |
| 122 | 0.026 | 122 |
| 123 | 0.050 | 115 |
| 124 | 6.76 | 26 |
| 125 | 2.14 | 115 |
| 126 | 1.38 | 79 |
| 127 | 2.81 | 65 |
| 128 | 4.57 | 66 |
| 129 | 6.20 | 44 |
| 130 | 2.56 | 79 |
| 131 | 3.60 | 70 |
| 132 | 3.44 | 86 |
| 133 | 7.02 | 25 |
| 134 | >20 | 4 |
| 135 | 1.51 | 97 |
| 136 | 3.36 | 90 |
| 137 | 0.14 | 131 |
| 138 | 0.05 | 119 |
| 139 | 0.10 | 115 |
| 140 | 2.28 | 53 |
| 141 | 3.05 | 54 |
| 142 | 1.18 | 87 |
| 143 | 8.50 | 27 |
| 144 | >20 | 11 |
| 145 | 2.45 | 96 |
| 146 | 0.03 | 129 |
| 147 | 2.04 | 78 |
| 148 | 2.12 | 77 |
| 149 | 1.53 | 85 |
| 150 | 0.42 | 106 |
| 151 | 6.12 | 64 |
| 152 | 6.35 | 59 |
| 153 | 1.90 | 84 |
| 154 | 0.67 | 106 |
| 155 | 0.37 | 108 |
| 156 | 1.23 | 112 |
| 157 | 1.52 | 77 |
| 158 | 6.65 | 101 |
| 159 | 1.36 | 92 |
| 160 | 0.60 | 104 |
| 161 | 2.26 | 82 |
| 162 | 0.17 | 105 |
| 163 | 3.59 | 42 |
| 164 | >20 | 2 |
| 165 | 0.09 | 123 |
| 166 | 2.00 | 65 |
| 167 | 1.08 | 66 |
| 168 | 1.16 | 67 |
| 169 | 4.90 | 38 |
| 170 | 1.55 | 65 |
| 171 | 2.29 | 40 |
| 172 | 4.08 | 66 |

TABLE 1-continued

CSE-HRP data

| Example | EC$_{50}$ (µM) | Maximum % activity (%) |
|---|---|---|
| 173 | 2.15 | 27 |
| 174 | 1.73 | 55 |
| 175 | 3.20 | 54 |
| 176 | 9.63 | 30 |
| 177 | 2.91 | 56 |
| 178 | 0.74 | 64 |
| 179 | 0.80 | 69 |
| 180 | 5.93 | 59 |
| 181 | 1.59 | 57 |
| 182 | 0.80 | 46 |
| 183 | 0.86 | 67 |
| 184 | 0.58 | 73 |
| 185 | 0.64 | 77 |
| 186 | 1.36 | 66 |
| 187 | 1.95 | 76 |
| 188 | 4.65 | 43 |
| 189 | 3.83 | 58 |
| 190 | 2.79 | 39 |
| 191 | 4.10 | 51 |
| 192 | 4.40 | 29 |
| 193 | 0.47 | 68 |
| 194 | 0.88 | 68 |
| 195 | 7.53 | 37 |
| 196 | 1.24 | 67 |
| 197 | 2.10 | 73 |
| 198 | 1.71 | 67 |
| 199 | 6.89 | 27 |
| 200 | 2.35 | 61 |
| 201 | 7.92 | 35 |
| 202 | 0.01 | 142 |
| 202F | 0.04 | 131 |
| 203 | 0.69 | 157 |

Transepithelial Clamp Circuit on Human Bronchial Epithelial Cells Conductance Assay:

A cell based assay using the primary human bronchial epithelial cells (hBE) was used as a secondary assay to test novel F508delCFTR correctors for their activity on primary hBE cells with F508del/F508del CFTR mutation. The assay used a TECC-24 (Transepithelial Clamp Circuit for 24 wells) instrument that measures the functionality of the mutated channel by measuring the equivalent short circuit current (Ieq) generated by the polarized epithelial cells. The instrument works by measuring the transepithelial potential difference (Vt) and transepithelial resistance (Rt) in an open circuit format, and the Ieq is calculated by using Ohms law (Ieq=Vt/Rt). The assay was run in a 24-well format and all 24-wells were measured at the same time point giving a higher throughput for this assay.

Primary human bronchial epithelial (hBE) cells from F508del/F508delCFTR patients were expanded from $1\times10^6$ to $250\times10^6$ cells (Neuberger T, Burton B, Clark H and VanGoor F; *Cystic Fibrosis*, Methods in Mole Biol 741; eds. Amaral M D and Kunzelmann K, 2011). For this purpose, cells isolated from CF patients with the homozygous mutation were seeded onto 24 well Corning (Cat #3378) filter plates that were coated with 3T3 conditioned media and grown at an air-liquid interface for 35 days using an Ultroser® G supplemented differentiation media. Apical surface mucus was removed 72 hours before the experiment using 3 mM dithiothreitol (DTT) in phosphate buffered saline (PBS). The apical surface was washed again 24 hours before the experiment using PBS. The cells were incubated with the desired dose response of the corrector compounds 18-24 hours at 37° C., 5% $CO_2$. The corrector compounds are only added on the basolateral side of the epithelial cells. On the day of measuring the corrector activity on the TECC, the cells were switched into a bicarbonate and serum free F-12 Coon's medium and allowed to equilibrate for 90 minutes in a $CO_2$ free incubator. At the time of measurement, the apical and basolateral sides of the filter were bathed with the F-12 Coon's modification media (with 20 mM 4-(2-hydroxyethyl)-1-piperazineethanesulfonic acid (HEPES), pH 7.4 (using 1 M tris(hydroxymethyl)aminormethane (Tris)), and the measurements were made at 36.5° C. Transepithelial voltage (Vt) and transepithelial resistance (Rt) were measured using a 24 channel transepithelial current clamp (TECC-24). Current responses to the sequential addition of benzamil (apical 6 µM addition; for inhibiting epithelial ENaC channel), forskolin (apical and basolateral 10 µM addition; for activating the CFTR channel), control potentiator (N-(3-carbamoyl-5,5,7,7-tetramethyl-4,7-dihydro-5H-thieno[2,3-c]pyran-2-yl)-1H-pyrazole-5-carboxamide; apical and basolateral 1 µM addition; for potentiating the CFTR channel) and bumetanide (basolateral 20 µM addition; for inhibiting the Na:2Cl:K co-transporter, an indirect measure of inhibiting the Cl-secretion driven by CFTR channel) were measured.

All plates contained negative controls (dimethyl sulfoxide, DMSO) which coupled with the control potentiator (N-(3-carbamoyl-5,5,7,7-tetramethyl-4,7-dihydro-5H-thieno[2,3-c]pyran-2-yl)-1H-pyrazole-5-carboxamide) sets the null response and positive controls (3 µM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) coupled with the control potentiator sets the 100% response to measure the correction of the mutated CFTR channel. The maximum percent activity is reported relative to the positive control value.

The % activity measured at each of the 6 test concentrations of the test compound was normalized to the on-plate positive control using the following formula:

% activity=[(test compound response−DMSO response)/(positive control response−DMSO response)]*100

The following log(agonist) vs response using a four parameters variable slope was used to calculate EC$_{50}$ (4 PL in Prism v 5 software):

$$F(x)=D+(A-D)/(1+(x/C)^B)$$

Where:
"x" is a concentration of drug under test.
"F(x)" is the response.
"A" is the maximum response, and "D" is the minimum response
"C" is the inflection point (EC$_{50}$) for the curve. That is, "F(x)" is halfway between the lower and upper asymptotes when x=C.
"B" is the slope-factor or Hill coefficient. The sign of B is positive when the response increases with increasing dose and is negative when the response decreases with increasing dose (inhibition).

The maximum percent activity and EC$_{50}$ values for tested corrector compounds are presented in Table 2.

TABLE 2 hBE-TECC data

| Example | EC$_{50}$ (µM) | Maximum % activity (%) |
|---|---|---|
| 1 | 0.29 | 95 |
| 9 | 0.16 | 92 |
| 19 | 0.21 | 111 |
| 26 | 0.11 | 88 |

TABLE 2-continued

| | hBE-TECC data | |
|---|---|---|
| Example | $EC_{50}$ (μM) | Maximum % activity (%) |
| 27 | 0.075 | 117 |
| 28 | 3.4 | 51 |
| 38 | 0.61 | 106 |
| 108 | 0.086 | 96 |
| 109 | 0.055 | 70 |
| 111 | 0.005 | 90 |
| 119 | 0.45 | 80 |
| 121 | 0.038 | 87 |
| 122 | 0.004 | 87 |
| 139 | 0.0313 | 100 |
| 146 | 0.004 | 98 |
| 148 | 1.1 | 44 |

CYP3A4 Induction:

Cryopreserved primary human hepatocytes were thawed and cultured overnight prior to treatment. Cultured hepatocytes were treated with either test compounds (10 μM), vehicle control (0.1% v/v DMSO), or prototypical inducer of CYP3A4 (rifampin 10 μM) for 48 hours, with culture medium being refreshed every 24 hours. Following the 48 hour treatment, hepatocytes were harvested for RNA isolation and reverse transcription, followed by CYP3A4 mRNA quantitation using RT-PCR (real time reverse transcript polymerase chain reaction).

CYP3A4 mRNA level was used as a measure of CYP3A4 expression in hepatocytes, which was not expected to change in hepatocytes treated with vehicle control (0.1% v/v DMSO), but was expected to be significantly increased in hepatocytes treated with prototypical inducer (Rifampin). CYP3A4 mRNA levels measured in compound treated hepatocytes were expressed as a percentage of the response of positive control (Rifampin 10 μM).

Fold Induction=Fold of Treated/Fold of Vehicle Control

% positive control=(Fold Induction of Treated−1)/(Fold Induction of Prototypical Inducer−1)

In test compound treated hepatocytes, CYP3A4 mRNA level increase by less than 20% of the response of positive control (Rifampin) is considered low risk for CYP3A4 induction.

TABLE 3

| Examples | CYP3A4 Hepatocytes mRNA % of positive control |
|---|---|
| 1 | 14 |
| 3 | 49.3 |
| 9 | 16.1 |
| 14 | 3.54 |
| 19 | 9.38 |
| 28 | 9.41 |
| 38 | 40.2 |
| 108 | 39.6 |
| 109 | 42.2 |
| 111 | −0.105 |
| 122 | 10.6 |
| 146 | 11.6 |
| Rifampin (positive control) | 100 |

It is understood that the foregoing detailed description and accompanying examples are merely illustrative and are not to be taken as limitations upon the scope of the invention, which is defined solely by the appended claims and their equivalents. Various changes and modifications to the embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

We claim:

1. A compound having formula (I) or a pharmaceutically acceptable salt thereof

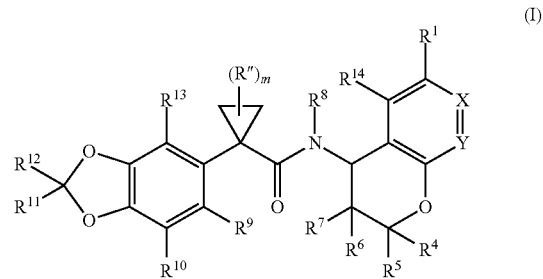

(I)

wherein
X is $CR^2$ and Y is $CR^3$; or
X is N and Y is $CR^3$; or
X is $CR^2$ and Y is N;
m is 0, 1, 2, or 3;
R″ are optional substituents on the cyclopropyl ring, and at each occurrence, are each independently halogen, $C_1$-$C_6$ haloalkyl, or $C_1$-$C_6$ alkyl;
$R^1$ and $R^2$, are each independently hydrogen, halogen, $C_1$-$C_6$ haloalkyl, $C_1$-$C_6$ alkyl, —$OR^{1A}$, —$C(O)OR^{1B}$, —$NR^{1A}R^{2A}$, or —$C(O)NR^{1A}R^{2A}$;
$R^{1A}$ and $R^{2A}$, at each occurrence, are each independently hydrogen, $C_1$-$C_6$ haloalkyl, $G^{1A}$, or $C_1$-$C_6$ alkyl; wherein the $C_1$-$C_6$ haloalkyl and the $C_1$-$C_6$ alkyl are each optionally substituted with one or two substituents independently selected from the group consisting of —$OR^{ZA}$, —$SR^{ZA}$, —$S(O)_2R^{ZA}$, —$C(O)R^{ZA}$, —$C(O)OR^{ZA}$, —$C(O)N(R^{ZA})_2$, —$N(R^{ZA})_2$, —$N(R^{ZA})C(O)R^{ZB}$, —$N(R^{ZA})S(O)_2R^{ZB}$, —$N(R^{ZA})C(O)OR^{ZB}$, —$N(R^{ZA})C(O)N(R^{ZA})_2$, —CN, and $G^{1A}$; or $R^{1A}$ and $R^{2A}$ together with the nitrogen atom to which they are attached form a 4-6 membered heterocycle wherein the 4-6 membered heterocycle is optionally substituted with 1, 2, or 3 substituents independently selected from the group consisting of halogen, $C_1$-$C_6$ alkyl, $C_1$-$C_6$ haloalkyl, —$OR^j$, and $N(R^j)_2$; wherein
$R^{ZA}$, at each occurrence, is independently hydrogen, $C_1$-$C_6$ haloalkyl, $C_1$-$C_6$ alkyl, $G^{1A}$, or ($C_1$-$C_6$ alkylenyl)-$G^{1A}$; and
$R^{ZB}$, at each occurrence, is independently $C_1$-$C_6$ haloalkyl, $C_1$-$C_6$ alkyl, $G^{1A}$, or —($C_1$-$C_6$ alkylenyl)-$G^{1A}$;
$R^{1B}$ is hydrogen, $C_1$-$C_6$ haloalkyl, or $C_1$-$C_6$ alkyl;
$R^3$ and $R^{14}$, are each independently hydrogen, halogen, $C_1$-$C_6$ haloalkyl, $C_1$-$C_6$ alkyl, —OH, or —O—($C_1$-$C_6$ alkyl);
$R^4$ is hydrogen, $C_1$-$C_6$ haloalkyl, or $C_1$-$C_6$ alkyl;
$R^5$ is hydrogen, —$C(O)R^i$, —$C(O)OH$, —$C(O)O(C_1$-$C_6$ alkyl), —$C(O)N(R^h)_2$, $C_1$-$C_6$ haloalkyl, $C_1$-$C_6$ alkyl, or $G^{2A}$; wherein the $C_1$-$C_6$ haloalkyl and the $C_1$-$C_6$ alkyl are each optionally substituted with one or two substituents independently selected from the group consisting of —$OR^h$, —$OC(O)N(R^h)_2$, —$C(O)R^h$, —$C(O)$ OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^{2A}$; or R$^4$ and R$^5$, together with the carbon atom to which they are attached, form a C$_3$-C$_6$ cycloalkyl or a 4-6 membered heterocycle; wherein the C$_3$-C$_6$ cycloalkyl and the 4-6 membered heterocycle are each optionally substituted with 1, 2, or 3 independently selected R$^p$ groups;

G$^{2A}$, at each occurrence, is independently cycloalkyl, cycloalkenyl, heterocycle, aryl, or heteroaryl, each of which is independently unsubstituted or substituted with 1, 2, or 3 independently selected R$^q$ groups;

R$^p$ and R$^q$, at each occurrence, are each independently C$_1$-C$_6$ alkyl, halogen, C$_1$-C$_6$ haloalkyl, —CN, oxo, NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^h$, —C(O)OR$^h$, —C(O)N(R$^h$)$_2$, —C(O)N(R$^h$)S(O)$_2$R$^h$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, or G$^A$, wherein the C$_1$-C$_6$ haloalkyl and the C$_1$-C$_6$ alkyl are each optionally substituted with one or two substituents independently selected from the group consisting of —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^h$, —C(O)OR$^h$, —C(O)N(R$^h$)$_2$, —C(O)N(R$^h$)S(O)$_2$R$^h$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, —CN, and G$^A$;

R$^h$, at each occurrence, is independently hydrogen, C$_1$-C$_6$ haloalkyl, C$_1$-C$_6$ alkyl, or G$^A$, wherein the C$_1$-C$_6$ haloalkyl and the C$_1$-C$_6$ alkyl are each optionally substituted with one or two substituents independently selected from the group consisting of —OR$^j$, —OC(O)N(R$^j$)$_2$, —SR$^j$, —C(O)OR$^j$, —C(O)N(R$^j$)$_2$, —N(R$^j$)$_2$, —CN, and G$^A$;

R$^i$, at each occurrence, is independently C$_1$-C$_6$ haloalkyl, C$_1$-C$_6$ alkyl, or G$^A$, wherein the C$_1$-C$_6$ haloalkyl and the C$_1$-C$_6$ alkyl are each optionally substituted with one or two substituents independently selected from the group consisting of —OR$^j$, —OC(O)N(R$^j$)$_2$, —SR$^j$, —C(O)OR$^j$, —C(O)N(R$^j$)$_2$, —N(R$^j$)$_2$, —CN, and G$^A$;

R$^6$ is hydrogen, halogen, C$_1$-C$_6$ haloalkyl, or C$_1$-C$_6$ alkyl;

R$^7$ is hydrogen, halogen, —OR$^j$, —N(R$^j$)$_2$, —N(R$^j$)C(O)R$^k$, C$_1$-C$_6$ haloalkyl, C$_1$-C$_6$ alkyl, C$_2$-C$_6$ alkenyl, or —(C$_1$-C$_6$ alkylenyl)-G$^{3A}$;

R$^8$ is hydrogen, C$_1$-C$_6$ haloalkyl, or C$_1$-C$_6$ alkyl;

R$^9$, R$^{10}$, and R$^{13}$, are each independently hydrogen, halogen, —OR$^j$, C$_1$-C$_6$ haloalkyl, or C$_1$-C$_6$ alkyl;

R$^{11}$ and R$^{12}$ are each independently hydrogen, C$_1$-C$_3$ alkyl, or halogen;

G$^{1A}$, G$^{3A}$, and G$^A$, at each occurrence, are each independently cycloalkyl, cycloalkenyl, heterocycle, aryl, or heteroaryl, each of which is independently unsubstituted or substituted with 1, 2, or 3 independently selected R$^s$ groups; wherein R$^s$, at each occurrence, is independently C$_1$-C$_6$ alkyl, C$_2$-C$_6$ alkenyl, C$_2$-C$_6$ alkynyl, halogen, C$_1$-C$_6$ haloalkyl, —CN, oxo, NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^j$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$ alkylenyl)-OR$^j$, —(C$_1$-C$_6$ alkylenyl)-OC(O)R$^k$, —(C$_1$-C$_6$ alkylenyl)-OC(O)N(R$^j$)$_2$, —(C$_1$-C$_6$ alkylenyl)-SR$^j$, —(C$_1$-C$_6$ alkylenyl)-S(O)$_2$R$^j$, —(C$_1$-C$_6$ alkylenyl)-S(O)$_2$N(R$^j$)$_2$, —(C$_1$-C$_6$ alkylenyl)-C(O)R$^j$, —(C$_1$-C$_6$ alkylenyl)-C(O)OR$^j$, —(C$_1$-C$_6$ alkylenyl)-C(O)N(R$^j$)$_2$, —(C$_1$-C$_6$ alkylenyl)-N(R$^j$)$_2$, —(C$_1$-C$_6$ alkylenyl)-N(R$^j$)C(O)R$^k$, —(C$_1$-C$_6$ alkylenyl)-N(R$^j$)S(O)$_2$R$^k$, —(C$_1$-C$_6$ alkylenyl)-N(R$^j$)C(O)O(R$^k$), —(C$_1$-C$_6$ alkylenyl)-N(R$^j$)C(O)N(R$^j$)$_2$, or —(C$_1$-C$_6$ alkylenyl)-CN;

R$^j$, at each occurrence, is independently hydrogen, C$_1$-C$_6$ alkyl, or C$_1$-C$_6$ haloalkyl; and R$^k$, at each occurrence, is independently C$_1$-C$_6$ alkyl or C$_1$-C$_6$ haloalkyl.

2. The compound of claim 1 having formula (I-a) or a pharmaceutically acceptable salt thereof

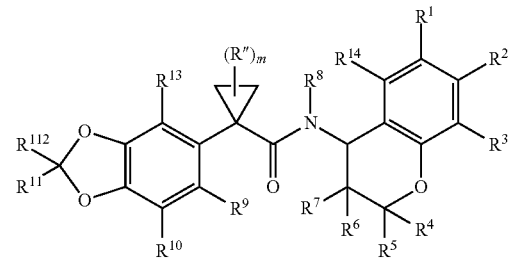

(I-a)

wherein R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, m, and R", are as set forth in claim 1.

3. The compound of claim 1 having formula (I-b) or a pharmaceutically acceptable salt thereof

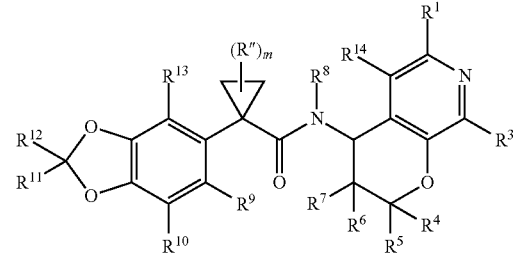

(I-b)

wherein R$^1$, R$^3$, R$^4$, R$^5$, R$^6$, R$^7$, R$^8$, R$^9$, R$^{10}$, R$^{11}$, R$^{12}$, R$^{13}$, R$^{14}$, m, and R", are as set forth in claim 1.

4. The compound of claim 1 having formula (I-c) or a pharmaceutically acceptable salt thereof

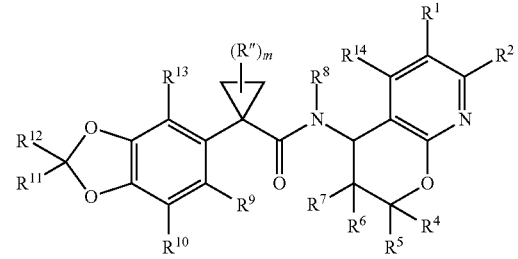

(I-c)

wherein R$^1$, R$^2$, R$^4$, R$^5$, R$^6$, R$^7$, R$^8$, R$^9$, R$^{10}$, R$^{11}$, R$^{12}$, R$^{13}$, R$^{14}$, m, and R", are as set forth in claim 1.

5. The compound of claim 1 or a pharmaceutically acceptable salt thereof, wherein R$^8$ is hydrogen.

6. The compound of claim 1 or a pharmaceutically acceptable salt thereof, wherein
R$^8$ is hydrogen; and
m is 0.

7. The compound of claim 1 or a pharmaceutically acceptable salt thereof,
wherein
R$^8$ is hydrogen;
m is 0; and
R$^9$, R$^{10}$, and R$^{13}$ are each independently hydrogen or halogen.

8. The compound of claim 1 or a pharmaceutically acceptable salt thereof,
wherein
R$^8$ is hydrogen;
m is 0; and
R$^9$, R$^{10}$, and R$^{13}$ are hydrogen.

9. The compound of claim 1 or a pharmaceutically acceptable salt thereof,
wherein
R$^8$ is hydrogen;
m is 0;
R$^9$, R$^{10}$, and R$^{13}$ are each independently hydrogen or halogen; and
R$^{11}$ and R$^{12}$ are hydrogen, or R$^{11}$ and R$^{12}$ are halogen.

10. The compound of claim 1 or a pharmaceutically acceptable salt thereof,
wherein
R$^8$ is hydrogen;
m is 0;
R$^9$, R$^{10}$, and R$^{13}$ are hydrogen; and
R$^{11}$ and R$^{12}$ are halogen.

11. The compound of claim 1 or a pharmaceutically acceptable salt thereof,
wherein
R$^8$ is hydrogen;
m is 0;
R$^9$, R$^{10}$, and R$^{13}$ are hydrogen;
R$^{11}$ and R$^{12}$ are halogen; and
R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl.

12. The compound of claim 1 or a pharmaceutically acceptable salt thereof,
wherein
R$^8$ is hydrogen;
m is 0;
R$^9$, R$^{10}$, and R$^{13}$ are hydrogen;
R$^{11}$ and R$^{12}$ are halogen;
R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl; and
R$^2$ is hydrogen, halogen, C$_1$-C$_6$ haloalkyl, C$_1$-C$_6$ alkyl, —OR$^{1A}$, or —C(O)OR$^{1B}$; wherein R$^{1A}$ is hydrogen, C$_1$-C$_3$ haloalkyl, or C$_1$-C$_3$ alkyl wherein the C$_1$-C$_3$ alkyl is optionally substituted with one substituent selected from the group consisting of —OR$^{ZA}$, —C(O)OH, and G$^{1A}$; and R$^{1B}$ is hydrogen or C$_1$-C$_3$ alkyl.

13. The compound of claim 1 or a pharmaceutically acceptable salt thereof,
wherein
R$^8$ is hydrogen;
m is 0;
R$^9$, R$^{10}$, and R$^{13}$ are hydrogen;
R$^{11}$ and R$^{12}$ are halogen;
R$^1$ is hydrogen, halogen, C$_1$-C$_6$ haloalkyl, C$_1$-C$_6$ alkyl, —OR$^{1A}$, or —C(O)OR$^{1B}$; wherein R$^{1A}$ is C$_1$-C$_3$ haloalkyl or C$_1$-C$_3$ alkyl; and R$^{1B}$ is hydrogen or C$_1$-C$_3$ alkyl; and
R$^3$ is hydrogen or halogen.

14. The compound of claim 1 or a pharmaceutically acceptable salt thereof,
wherein
R$^8$ is hydrogen;
m is 0;
R$^9$, R$^{10}$, and R$^{13}$ are hydrogen;
R$^{11}$ and R$^{12}$ are halogen; and
R$^{14}$ is hydrogen or halogen.

15. The compound of claim 1 or a pharmaceutically acceptable salt thereof,
wherein
R$^4$ is hydrogen, C$_1$-C$_6$ haloalkyl, or C$_1$-C$_6$ alkyl;
R$^5$ is hydrogen, C$_1$-C$_6$ haloalkyl, C$_1$-C$_6$ alkyl, or G$^{2A}$;
R$^6$ is hydrogen or C$_1$-C$_3$ alkyl; and
R$^7$ is hydrogen or C$_1$-C$_3$ alkyl.

16. The compound of claim 1 or a pharmaceutically acceptable salt thereof,
wherein
R$^4$ and R$^5$, together with the carbon atom to which they are attached, form a C$_3$-C$_6$ cycloalkyl or a 4-6 membered heterocycle; wherein the C$_3$-C$_6$ cycloalkyl and the 4-6 membered heterocycle are each optionally substituted with 1, 2, or 3 independently selected R$^p$ groups;
R$^6$ is hydrogen or C$_1$-C$_3$ alkyl; and
R$^7$ is hydrogen or C$_1$-C$_3$ alkyl.

17. The compound of claim 1 or a pharmaceutically acceptable salt thereof,
wherein
R$^4$ is hydrogen or C$_1$-C$_3$ alkyl;
R$^5$ is hydrogen or C$_1$-C$_3$ alkyl;
R$^6$ is hydrogen or C$_1$-C$_3$ alkyl; and
R$^7$ is —(C$_1$-C$_6$ alkylenyl)-G$^{3A}$.

18. The compound of claim 1 having formula (I-d) or a pharmaceutically acceptable salt thereof (I-d)

wherein
X is CR$^2$ and Y is CR$^3$; or
X is N and Y is CR$^3$; or
X is CR$^2$ and Y is N;
R$^1$ and R$^2$, are each independently hydrogen, halogen, C$_1$-C$_6$ haloalkyl, C$_1$-C$_6$ alkyl, —OR$^{1A}$, —C(O)OR$^{1B}$, —NR$^{1A}$R$^{2A}$, or —C(O)NR$^{1A}$R$^{2A}$;
R$^{1A}$ and R$^{2A}$, at each occurrence, are each independently hydrogen, C$_1$-C$_6$ haloalkyl, G$^{1A}$, or C$_1$-C$_6$ alkyl; wherein the C$_1$-C$_6$ haloalkyl and the C$_1$-C$_6$ alkyl are each optionally substituted with one or two substituents independently selected from the group consisting of —OR$^{ZA}$, —SR$^{ZA}$, —S(O)$_2$R$^{ZA}$, —C(O)R$^{ZA}$, —C(O)

OR$^{ZA}$, —C(O)N(R$^{ZA}$)$_2$, —N(R$^{ZA}$)$_2$, —N(R$^{ZA}$)C(O) R$^{ZB}$, —N(R$^{ZA}$)S(O)$_2$R$^{ZB}$, —N(R$^{ZA}$)C(O)OR$^{ZB}$, —N(R$^{ZA}$)C(O)N(R$^{ZA}$)$_2$, —CN, and G$^{1A}$; or R$^{1A}$ and R$^{2A}$ together with the nitrogen atom to which they are attached form a 4-6 membered heterocycle wherein the 4-6 membered heterocycle is optionally substituted with 1, 2, or 3 substituents independently selected from the group consisting of halogen, C$_1$-C$_6$ alkyl, C$_1$-C$_6$ haloalkyl, —OR$^j$, and N(R$^j$)$_2$; wherein
  R$^{ZA}$, at each occurrence, is independently hydrogen, C$_1$-C$_6$ haloalkyl, C$_1$-C$_6$ alkyl, G$^{1A}$, or (C$_1$-C$_6$ alkylenyl)-G$^{1A}$; and
  R$^{ZB}$, at each occurrence, is independently C$_1$-C$_6$ haloalkyl, C$_1$-C$_6$ alkyl, G$^{1A}$, or —(C$_1$-C$_6$ alkylenyl)-G$^{1A}$;
R$^{1B}$ is hydrogen, C$_1$-C$_6$ haloalkyl, or C$_1$-C$_6$ alkyl;
R$^3$ and R$^{14}$ are each independently hydrogen or halogen;
R$^4$ is hydrogen, C$_1$-C$_6$ haloalkyl, or C$_1$-C$_6$ alkyl;
R$^5$ is hydrogen, —C(O)R$^i$, —C(O)OH, —C(O)N(R$^h$)$_2$, C$_1$-C$_6$ haloalkyl, C$_1$-C$_6$ alkyl, or G$^{2A}$; wherein the C$_1$-C$_6$ haloalkyl and the C$_1$-C$_6$ alkyl are each optionally substituted with one or two substituents independently selected from the group consisting of —OR$^h$, —OC(O)N(R$^h$)$_2$, —C(O)R$^h$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^{2A}$; or
R$^4$ and R$^5$, together with the carbon atom to which they are attached, form a C$_3$-C$_6$ cycloalkyl or a 4-6 membered heterocycle; wherein the C$_3$-C$_6$ cycloalkyl and the 4-6 membered heterocycle are each optionally substituted with 1, 2, or 3 independently selected R$^p$ groups;
G$^{2A}$, at each occurrence, is independently cycloalkyl, cycloalkenyl, heterocycle, aryl, or heteroaryl, each of which is independently unsubstituted or substituted with 1, 2, or 3 independently selected R$^q$ groups;
R$^p$ and R$^q$, at each occurrence, are each independently C$_1$-C$_6$ alkyl, halogen, C$_1$-C$_6$ haloalkyl, —CN, oxo, NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^h$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, or G$^A$, wherein the C$_1$-C$_6$ haloalkyl and the C$_1$-C$_6$ alkyl are each optionally substituted with one or two substituents independently selected from the group consisting of —OR$^h$, —OC(O)R$^i$, —OC(O)N(R$^h$)$_2$, —S(O)$_2$R$^h$, —S(O)$_2$N(R$^h$)$_2$, —C(O)R$^h$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, —CN, and G$^A$;
R$^h$, at each occurrence, is independently hydrogen, C$_1$-C$_6$ haloalkyl, C$_1$-C$_6$ alkyl, or G$^A$, wherein the C$_1$-C$_6$ haloalkyl and the C$_1$-C$_6$ alkyl are each optionally substituted with one or two substituents independently selected from the group consisting of —OR$^j$, —OC(O)N(R$^j$)$_2$, —SR$^j$, —C(O)OR$^j$, —C(O)N(R$^j$)$_2$, —N(R$^j$)$_2$, —CN, and G$^A$;
R$^i$, at each occurrence, is independently C$_1$-C$_6$ haloalkyl, C$_1$-C$_6$ alkyl, or G$^A$, wherein the C$_1$-C$_6$ haloalkyl and the C$_1$-C$_6$ alkyl are each optionally substituted with one or two substituents independently selected from the group consisting of —OR$^j$, —OC(O)N(R$^j$)$_2$, —SR$^j$, —C(O)OR$^j$, —C(O)N(R$^j$)$_2$, —N(R$^j$)$_2$, —CN, and G$^A$;
R$^6$ is hydrogen, halogen, C$_1$-C$_6$ haloalkyl, or C$_1$-C$_6$ alkyl;
R$^7$ is hydrogen, halogen, —OR$^j$, —N(R$^j$)$_2$, —N(R$^j$)C(O) R$^k$, C$_1$-C$_6$ haloalkyl, C$_1$-C$_6$ alkyl, C$_2$-C$_6$ alkenyl, or —(C$_1$-C$_6$ alkylenyl)-G$^{3A}$;

R$^9$, R$^{10}$, and R$^{13}$, are each independently hydrogen or halogen;
G$^{1A}$, G$^{3A}$, and G$^A$, at each occurrence, are each independently cycloalkyl, cycloalkenyl, heterocycle, aryl, or heteroaryl, each of which is independently unsubstituted or substituted with 1, 2, or 3 independently selected R$^s$ groups; wherein
  R$^s$, at each occurrence, is independently C$_1$-C$_6$ alkyl, C$_2$-C$_6$ alkenyl, C$_2$-C$_6$ alkynyl, halogen, C$_1$-C$_6$ haloalkyl, —CN, oxo, NO$_2$, —OR$^j$, —OC(O)R$^k$, —OC(O)N(R$^j$)$_2$, —S(O)$_2$R$^j$, —S(O)$_2$N(R$^j$)$_2$, —C(O)R$^j$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O (R$^k$), —N(R$^j$)C(O)N(R$^j$)$_2$, —(C$_1$-C$_6$ alkylenyl)-OR$^j$, —(C$_1$-C$_6$ alkylenyl)-OC(O)R$^k$, —(C$_1$-C$_6$ alkylenyl)-OC(O)N(R$^j$)$_2$, —(C$_1$-C$_6$ alkylenyl)-SR$^j$, —(C$_1$-C$_6$ alkylenyl)-S(O)$_2$R$^j$, —(C$_1$-C$_6$ alkylenyl)-S(O)$_2$N (R$^j$)$_2$, —(C$_1$-C$_6$ alkylenyl)-C(O)R$^j$, —(C$_1$-C$_6$ alkylenyl)-C(O)OR$^j$, —(C$_1$-C$_6$ alkylenyl)-C(O)N(R$^j$)$_2$, —(C$_1$-C$_6$ alkylenyl)-N(R$^j$)$_2$, —(C$_1$-C$_6$ alkylenyl)-N (R$^j$)C(O)R$^k$, —(C$_1$-C$_6$ alkylenyl)-N(R$^j$)S(O)$_2$R$^k$, —(C$_1$-C$_6$ alkylenyl)-N(R$^j$)C(O)O(R$^k$), —(C$_1$-C$_6$ alkylenyl)-N(R$^j$)C(O)N(R$^j$)$_2$, or —(C$_1$-C$_6$ alkylenyl)-CN;
R$^j$, at each occurrence, is independently hydrogen, C$_1$-C$_6$ alkyl, or C$_1$-C$_6$ haloalkyl; and
R$^k$, at each occurrence, is independently C$_1$-C$_6$ alkyl or C$_1$-C$_6$ haloalkyl.

19. The compound of claim 18 having formula (I-e) or a pharmaceutically acceptable salt thereof,

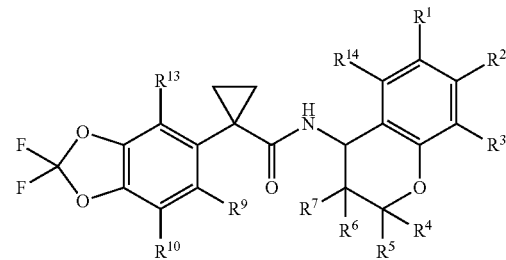

(I-e)

wherein R$^1$, R$^2$, R$^4$, R$^5$, R$^6$, R$^7$, R$^9$, R$^{10}$, R$^{13}$, and R$^{14}$ are as set forth in claim 18.

20. The compound of claim 18 having formula (I-f) or a pharmaceutically acceptable salt thereof,

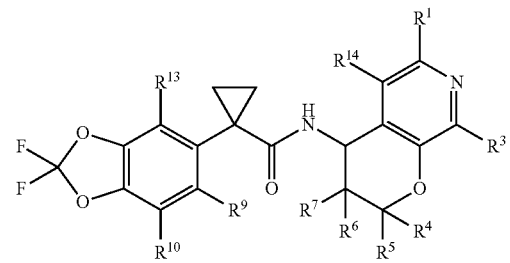

(I-f)

wherein R$^1$, R$^3$, R$^4$, R$^5$, R$^6$, R$^7$, R$^9$, R$^{10}$, R$^{13}$, and R$^{14}$ are as set forth in claim 18.

21. The compound of claim 18 having formula (I-g) or a pharmaceutically acceptable salt thereof, (I-g)

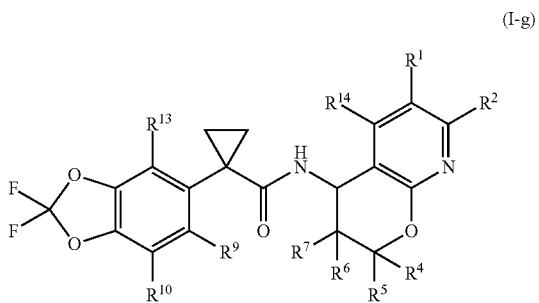

wherein $R^1$, $R^2$, $R^4$, $R^5$, $R^6$, $R^7$, $R^9$, $R^{10}$, $R^{13}$, and $R^{14}$ are as set forth in claim 18.

22. The compound of claim 18 or a pharmaceutically acceptable salt thereof,
wherein
$R^9$, $R^{10}$, and $R^{13}$ are hydrogen.

23. The compound of claim 22, or a pharmaceutically acceptable salt thereof,
wherein
$R^1$ is hydrogen, halogen, $C_1$-$C_6$ haloalkyl, $C_1$-$C_6$ alkyl, —$OR^{1A}$, or —$C(O)OR^{1B}$; wherein $R^{1A}$ is $C_1$-$C_3$ haloalkyl or $C_1$-$C_3$ alkyl; and $R^{1B}$ is hydrogen or $C_1$-$C_3$ alkyl.

24. The compound of claim 23, or a pharmaceutically acceptable salt thereof,
wherein
$R^4$ is hydrogen, $C_1$-$C_6$ haloalkyl, or $C_1$-$C_6$ alkyl;
$R^5$ is hydrogen, $C_1$-$C_6$ haloalkyl, or $C_1$-$C_6$ alkyl;
$R^6$ is hydrogen or $C_1$-$C_3$ alkyl; and
$R^7$ is hydrogen or $C_1$-$C_3$ alkyl.

25. The compound of claim 23, or a pharmaceutically acceptable salt thereof,
wherein
$R^4$ is hydrogen or $C_1$-$C_3$ alkyl;
$R^5$ is $G^{2A}$ wherein $G^{2A}$ is phenyl, $C_3$-$C_6$ cycloalkyl, 4-6 membered heterocycle, or 5-6 membered heteroaryl; each of which is optionally substituted with 1, 2, or 3 independently selected $R^q$ groups;
$R^6$ is hydrogen or $C_1$-$C_3$ alkyl; and
$R^7$ is hydrogen or $C_1$-$C_3$ alkyl.

26. The compound of claim 25 or a pharmaceutically acceptable salt thereof, wherein $G^{2A}$ is phenyl which is optionally substituted with 1, 2, or 3 independently selected $R^q$ group.

27. The compound of claim 25 or a pharmaceutically acceptable salt thereof,
wherein $G^{2A}$ is phenyl which is optionally substituted with 1, 2, or 3 $R^q$ groups; wherein
each $R^q$ is independently
$C_1$-$C_6$ alkyl wherein the $C_1$-$C_6$ alkyl is optionally substituted with one —OH;
halogen;
$C_1$-$C_6$ haloalkyl;
—$OR^h$ wherein $R^h$ is hydrogen or $C_1$-$C_3$ alkyl,
—$C(O)R^h$ wherein $R^h$ is $G^A$; wherein $G^A$ is 4-6 membered heterocycle;
—$C(O)OR^h$ wherein $R^h$ is hydrogen or $C_1$-$C_6$ alkyl,
—$C(O)N(R^h)_2$, wherein $R^h$ at each occurrence, is independently hydrogen, $C_3$-$C_6$ cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or
—$SO_2R^h$ wherein $R^h$ is $C_1$-$C_6$ haloalkyl or $C_1$-$C_6$ alkyl.

28. The compound of claim 25 or a pharmaceutically acceptable salt thereof,
wherein $G^{2A}$ is $C_3$-$C_6$ cycloalkyl which is optionally substituted with 1, 2, or 3 $R^q$ groups;
wherein each $R^q$ is independently
$C_1$-$C_6$ alkyl wherein the $C_1$-$C_6$ alkyl is optionally substituted with one —OH;
halogen;
$C_1$-$C_6$ haloalkyl;
—$OR^h$ wherein $R^h$ is hydrogen or $C_1$-$C_3$ alkyl,
—$C(O)R^h$ wherein $R^h$ is $G^A$; wherein $G^A$ is 4-6 membered heterocycle;
—$C(O)OR^h$ wherein $R^h$ is hydrogen or $C_1$-$C_6$ alkyl,
—$C(O)N(R^h)_2$, wherein $R^h$ at each occurrence, is independently hydrogen, $C_3$-$C_6$ cycloalkyl, $C_1$-$C_6$ haloalkyl, or $C_1$-$C_6$ alkyl; wherein the $C_1$-$C_6$ haloalkyl and $C_1$-$C_6$ alkyl are each optionally substituted with 1 or 2 —OH groups; or
—$SO_2R^h$ wherein $R^h$ is $C_1$-$C_6$ haloalkyl or $C_1$-$C_6$ alkyl.

29. The compound of claim 25 or a pharmaceutically acceptable salt thereof,
wherein $G^{2A}$ is cyclopropyl or cyclohexyl, each of which is optionally substituted with one $R^q$ wherein $R^q$ is
—$OR^h$ wherein $R^h$ is $C_1$-$C_3$ alkyl, or
—$C(O)OR^h$ wherein $R^h$ is hydrogen or $C_1$-$C_6$ alkyl.

30. The compound of claim 25 or a pharmaceutically acceptable salt thereof,
wherein
$G^{2A}$ is cyclohexyl which is substituted with one $R^q$; and
$R^q$ is —$C(O)OR^h$ wherein $R^h$ is hydrogen or $C_1$-$C_3$ alkyl.

31. The compound of claim 25 or a pharmaceutically acceptable salt thereof,
wherein
$G^{2A}$ is a 4-6 membered heterocycle which is optionally substituted with 1, 2, or 3 independently selected $R^q$ groups.

32. The compound of claim 25 or a pharmaceutically acceptable salt thereof,
wherein
$G^{2A}$ is 5-6 membered heteroaryl which is optionally substituted with 1, 2, or 3 independently selected $R^q$ groups.

33. The compound of claim 23 or a pharmaceutically acceptable salt thereof,
wherein
$R^4$ and $R^5$, together with the carbon atom to which they are attached, form a $C_3$-$C_6$ cycloalkyl or a 4-6 membered heterocycle; wherein the $C_3$-$C_6$ cycloalkyl and the 4-6 membered heterocycle are each optionally substituted with 1, 2, or 3 independently selected $R^p$ groups; and
$R^6$ and $R^7$ are each independently hydrogen or $C_1$-$C_3$ alkyl.

34. The compound of claim 33 or a pharmaceutically acceptable salt thereof,
wherein
$R^4$ and $R^5$, together with the carbon atom to which they are attached, form a $C_3$-$C_6$ cycloalkyl which is optionally substituted with for 2 $R^p$ groups, wherein each $R^p$ is independently
$C_1$-$C_6$ alkyl wherein the $C_1$-$C_6$ alkyl is optionally substituted with 1 or 2 —OH groups,
—$C(O)R^h$ wherein $R^h$ is $C_1$-$C_6$ alkyl;
—$C(O)OR^h$ wherein $R^h$ is hydrogen, $C_1$-$C_6$ alkyl, or —$CH_2$-phenyl; or
—$SO_2R^h$ wherein $R^h$ is $C_1$-$C_6$ haloalkyl or $C_1$-$C_6$ alkyl.

35. The compound of claim 33 or a pharmaceutically acceptable salt thereof,
wherein
$R^4$ and $R^5$, together with the carbon atom to which they are attached, form a 4-6 membered heterocycle which is optionally substituted with 1 or 2 $R^p$ groups, wherein each $R^p$ is independently
$C_1$-$C_6$ alkyl wherein the $C_1$-$C_6$ alkyl is optionally substituted with 1 or 2 —OH groups,
—C(O)$R^h$ wherein $R^h$ is $C_1$-$C_6$ alkyl;
—C(O)O$R^h$ wherein $R^h$ is hydrogen, $C_1$-$C_6$ alkyl, or —CH$_2$-phenyl; or
—SO$_2$$R^h$ wherein $R^h$ is $C_1$-$C_6$ haloalkyl or $C_1$-$C_6$ alkyl.

36. The compound of claim 23 or a pharmaceutically acceptable salt thereof,
wherein
$R^4$ hydrogen or $C_1$-$C_3$ alkyl;
$R^5$ is hydrogen or $C_1$-$C_3$ alkyl;
$R^6$ is hydrogen or $C_1$-$C_3$ alkyl; and
$R^7$ is —($C_1$-$C_6$ alkylenyl)-$G^{3A}$.

37. The compound of claim 36, or a pharmaceutically acceptable salt thereof,
wherein
$R^7$ is —(CH$_2$)-$G^{3A}$ wherein $G^{3A}$ is phenyl which is optionally substituted with 1, 2, or 3 $R^s$ groups; and each $R^s$ is independently $C_1$-$C_3$ alkyl, halogen, $C_1$-$C_3$ haloalkyl, or —O$R^j$ wherein $R^j$ is hydrogen or $C_1$-$C_3$ alkyl.

38. The compound of claim 1 having formula (I-h) or a pharmaceutically acceptable salt thereof

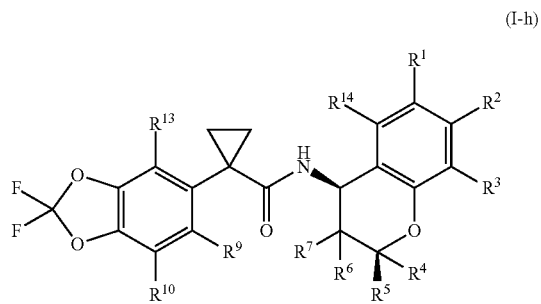

(I-h)

wherein
$R^1$ is hydrogen, halogen, $C_1$-$C_6$ haloalkyl, $C_1$-$C_6$ alkyl, —O$R^{1A}$, or —C(O)O$R^{1B}$; wherein $R^{1A}$ is $C_1$-$C_3$ haloalkyl or $C_1$-$C_3$ alkyl;
$R^2$ is hydrogen, halogen, $C_1$-$C_6$ haloalkyl, $C_1$-$C_6$ alkyl, —O$R^{1A}$, or —C(O)O$R^{1B}$; wherein $R^{1A}$ is hydrogen, $C_1$-$C_3$ haloalkyl, or $C_1$-$C_3$ alkyl; wherein the $C_1$-$C_3$ alkyl is optionally substituted with one substituent selected from the group consisting of —O$R^{ZA}$, —C(O)OH, and $G^{1A}$; wherein $G^{1A}$ is phenyl which is optionally substituted with 1, 2, or 3 $R^s$ groups wherein each $R^s$ is independently $C_1$-$C_3$ alkyl, $C_1$-$C_3$ haloalkyl, halogen, or —OCH$_3$; and $R^{ZA}$ is $C_1$-$C_3$ haloalkyl or $C_1$-$C_3$ alkyl;
$R^{1B}$ is hydrogen or $C_1$-$C_3$ alkyl;
$R^3$ and $R^{14}$ are each independently hydrogen or halogen;
$R^4$ is hydrogen, $C_1$-$C_3$ haloalkyl, or $C_1$-$C_3$ alkyl;
$R^5$ is $G^{2A}$;
$G^{2A}$ is $C_3$ cycloalkyl, 4-6 membered heterocycle, phenyl, or 5-6 membered heteroaryl, each of which is independently unsubstituted or substituted with 1, 2, or 3 independently selected $R^q$ groups;

$R^q$, at each occurrence, is independently $C_1$-$C_6$ alkyl, halogen, $C_1$-$C_6$ haloalkyl, —CN, oxo, NO$_2$, —O$R^h$, —OC(O)$R^i$, —OC(O)N($R^h$)$_2$, —S$R^h$, —S(O)$_2$$R^h$, —S(O)$_2$N($R^h$)$_2$, —C(O)$R^h$, —C(O)O$R^h$, —C(O)N($R^h$)$_2$, —N($R^h$)$_2$, —N($R^h$)C(O)$R^i$, —N($R^h$)S(O)$_2$$R^i$, —N($R^h$)C(O)O($R^i$), —N($R^h$)C(O)N($R^h$)$_2$, or $G^A$, wherein the $C_1$-$C_6$ haloalkyl and the $C_1$-$C_6$ alkyl are each optionally substituted with one or two substituents independently selected from the group consisting of —O$R^h$, —OC(O)$R^i$, —OC(O)N($R^h$)$_2$, —S$R^h$, —S(O)$_2$$R^h$, —S(O)$_2$N($R^h$)$_2$, —C(O)$R^h$, —C(O)O$R^h$, —C(O)N($R^h$)$_2$, —N($R^h$)$_2$, —N($R^h$)C(O)$R^i$, —N($R^h$)S(O)$_2$$R^i$, —N($R^h$)C(O)O($R^i$), —N($R^h$)C(O)N($R^h$)$_2$, —CN, and $G^A$;

$R^h$, at each occurrence, is independently hydrogen, $C_1$-$C_6$ haloalkyl, $C_1$-$C_6$ alkyl, or $G^A$, wherein the $C_1$-$C_6$ haloalkyl and the $C_1$-$C_6$ alkyl are each optionally substituted with one or two substituents independently selected from the group consisting of —O$R^j$, —OC(O)N($R^j$)$_2$, —S$R^j$, —C(O)O$R^j$, —C(O)N($R^j$)$_2$, —N($R^j$)$_2$, —CN, and $G^A$;

$R^i$, at each occurrence, is independently $C_1$-$C_6$ haloalkyl, $C_1$-$C_6$ alkyl, or $G^A$, wherein the $C_1$-$C_6$ haloalkyl and the $C_1$-$C_6$ alkyl are each optionally substituted with one or two substituents independently selected from the group consisting of —O$R^j$, —OC(O)N($R^j$)$_2$, —S$R^j$, —C(O)O$R^j$, —C(O)N($R^j$)$_2$, —N($R^j$)$_2$, —CN, and $G^A$;

$R^6$ is hydrogen or $C_1$-$C_3$ alkyl;
$R^7$ is hydrogen or $C_1$-$C_3$ alkyl;
$R^9$, $R^{10}$, and $R^{13}$, are each independently hydrogen or halogen;
$G^A$, at each occurrence, is independently cycloalkyl, cycloalkenyl, heterocycle, aryl, or heteroaryl, each of which is independently unsubstituted or substituted with 1, 2, or 3 independently selected $R^s$ groups; wherein $R^s$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, NO$_2$, O$R^j$, —OC(O)$R^k$, —OC(O)N($R^j$)$_2$, —S$R^j$, —S(O)$_2$$R^j$, —S(O)$_2$N($R^j$)$_2$, —C(O)$R^j$, —C(O)O$R^j$, —C(O)N($R^j$)$_2$, —N($R^j$)$_2$, —N($R^j$)C(O)$R^k$, —N($R^j$)S(O)$_2$$R^k$, —N($R^j$)C(O)O($R^k$), —N($R^j$)C(O)N($R^j$)$_2$, ($C_1$-$C_6$ alkylenyl)-O$R^j$, —($C_1$-$C_6$ alkylenyl)-OC(O)$R^k$, —($C_1$-$C_6$ alkylenyl)-OC(O)N($R^j$)$_2$, alkylenyl)-S$R^j$, alkylenyl)-S(O)$_2$$R^j$, —($C_1$-$C_6$ alkylenyl)-S(O)$_2$N($R^j$)$_2$, —($C_1$-$C_6$ alkylenyl)-C(O)$R^j$, alkylenyl)-C(O)O$R^j$, —($C_1$-$C_6$ alkylenyl)-C(O)N($R^j$)$_2$, —($C_1$-$C_6$ alkylenyl)-N($R^j$)$_2$, —($C_1$-$C_6$ alkylenyl)-N($R^j$)C(O)$R^k$, —($C_1$-$C_6$ alkylenyl)-N($R^j$)S(O)$_2$$R^k$, —($C_1$-$C_6$ alkylenyl)-N($R^j$)C(O)O($R^k$), —($C_1$-$C_6$ alkylenyl)-N($R^j$)C(O)N($R^j$)$_2$, or —($C_1$-$C_6$ alkylenyl)-CN;

$R^j$, at each occurrence, is independently hydrogen, $C_1$-$C_6$ alkyl, or $C_1$-$C_6$ haloalkyl; and
$R^k$, at each occurrence, is independently $C_1$-$C_6$ alkyl or $C_1$-$C_6$ haloalkyl.

39. The compound of claim 38 or a pharmaceutically acceptable salt thereof,
wherein
$G^{2A}$ is phenyl, cyclopropyl, cyclohexyl, pyridinyl, azetidinyl, or tetrahydrofuranyl, each of which is optionally substituted with 1, 2, or 3 independently selected $R^q$ groups.

40. The compound of claim 38 or a pharmaceutically acceptable salt thereof, wherein
$R^1$ is hydrogen, halogen, $C_1$-$C_3$ haloalkyl, $C_1$-$C_3$ alkyl, or —O$R^{1A}$; wherein $R^{1A}$ is $C_1$-$C_3$ alkyl; and
$R^2$ is hydrogen, halogen, $C_1$-$C_3$ haloalkyl, $C_1$-$C_3$ alkyl, or —O$R^{1A}$; wherein $R^{1A}$ is $C_1$-$C_3$ haloalkyl, or $R^{1A}$ is $C_1$-$C_3$ alkyl wherein the $C_1$-$C_3$ alkyl is optionally substituted with one —$OR^{ZA}$ wherein $R^{ZA}$ is $C_1$-$C_3$ alkyl.

41. The compound of claim 40 or a pharmaceutically acceptable salt thereof,
wherein
$R^4$ is hydrogen;
$R^6$ is hydrogen; and
$R^7$ is hydrogen.

42. The compound of claim 41 or a pharmaceutically acceptable salt thereof,
wherein $G^{2A}$ is phenyl substituted with 1, 2, or 3 $R^q$ groups; wherein one of $R^q$ groups is $C(O)OR^h$ wherein $R^h$ is hydrogen or $C_1$-$C_6$ alkyl; or one of $R^q$ groups is —$C(O)N(H)(R^h)$, wherein $R^h$ is cyclopentyl, or $R^h$ is $C_1$-$C_6$ alkyl substituted with 1 or 2 —OH groups; and the other optional $R^q$ groups are independently selected from the group consisting of $C_1$-$C_3$ alkyl, halogen, and $C_1$-$C_3$ haloalkyl.

43. The compound of claim 41 or a pharmaceutically acceptable salt thereof,
wherein
$G^{2A}$ is phenyl or cyclohexyl; each of which is substituted with one $C(O)OR^h$ wherein $R^h$ is hydrogen or $C_1$-$C_3$ alkyl.

44. The compound of claim 41 or a pharmaceutically acceptable salt thereof,
wherein
$G^{2A}$ is phenyl substituted with one $C(O)OR^h$ wherein $R^h$ is hydrogen.

45. The compound of claim 41 or a pharmaceutically acceptable salt thereof,
wherein
$G^{2A}$ is cyclohexyl substituted with one $C(O)OR^h$ wherein $R^h$ is hydrogen.

46. The compound of claim 45 or a pharmaceutically acceptable salt thereof,
wherein
$R^3$, $R^{14}$, $R^9$, $R^{10}$, and $R^{13}$ are hydrogen.

47. A compound having formula (I-i) or a pharmaceutically acceptable salt thereof

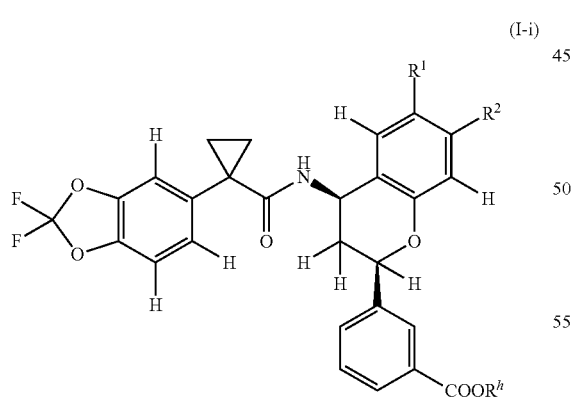

(I-i)

wherein
$R^1$ is hydrogen, halogen, $C_1$-$C_3$ haloalkyl, $C_1$-$C_3$ alkyl, or —$OR^{14}$; wherein $R^{14}$ is $C_1$-$C_3$ alkyl; and
$R^2$ is hydrogen, halogen, $C_1$-$C_3$ haloalkyl, $C_1$-$C_3$ alkyl, or —$OR^{14}$; wherein $R^{14}$ is $C_1$-$C_3$ haloalkyl, or $C_1$-$C_3$ alkyl wherein the $C_1$-$C_3$ alkyl is optionally substituted with one —$OR^{ZA}$, and $R^{ZA}$ is $C_1$-$C_3$ alkyl; and
$R^h$ is hydrogen or $C_1$-$C_3$ alkyl.

48. A compound having formula (I-j) or a pharmaceutically acceptable salt thereof

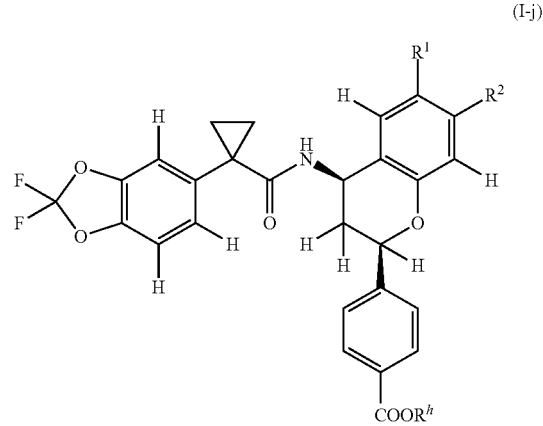

(I-j)

wherein
$R^1$ is hydrogen, halogen, $C_1$-$C_3$ haloalkyl, $C_1$-$C_3$ alkyl, or —$OR^{14}$; wherein $R^{14}$ is $C_1$-$C_3$ alkyl; and
$R^2$ is hydrogen, halogen, $C_1$-$C_3$ haloalkyl, $C_1$-$C_3$ alkyl, or —$OR^{14}$; wherein $R^{14}$ is $C_1$-$C_3$ haloalkyl, or $C_1$-$C_3$ alkyl wherein the $C_1$-$C_3$ alkyl is optionally substituted with one —$OR^{ZA}$, and $R^{ZA}$ is $C_1$-$C_3$ alkyl; and
$R^h$ is hydrogen or $C_1$-$C_3$ alkyl.

49. The compound of claim 47, or a pharmaceutically acceptable salt thereof
wherein
$R^1$ is hydrogen, $C_1$-$C_3$ alkyl, or —$OR^{14}$; wherein $R^{14}$ is $C_1$-$C_3$ alkyl; and
$R^h$ is hydrogen.

50. The compound of claim 1 or a pharmaceutically acceptable salt thereof,
wherein the compound is selected from the group consisting of
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;
3-[(2R,4S)-4-({[1-(2,2-difluoro-1,3-benzodioxol-5-yl)cyclopropyl]carbonyl}amino)-7-methoxy-3,4-dihydro-2H-chromen-2-yl]benzoic acid;
1-(2,2-difluoro-1,3-benzodioxol-5-yl)-N-[(2R,4R)-2-(3,4-dimethoxyphenyl)-7-methoxy-3,4-dihydro-2H-chromen-4-yl]cyclopropanecarboxamide;
1-(2,2-difluoro-1,3-benzodioxol-5-yl)-N-[(2S,4S)-2-(3,4-dimethoxyphenyl)-7-methoxy-3,4-dihydro-2H-chromen-4-yl]cyclopropanecarboxamide;
methyl 3-[(2R,4S)-4-({[1-(2,2-difluoro-1,3-benzodioxol-5-yl)cyclopropyl]carbonyl}amino)-7-methoxy-3,4-dihydro-2H-chromen-2-yl]benzoate;
methyl 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoate;
methyl 3-[(2R,4S)-4-({[1-(2,2-difluoro-1,3-benzodioxol-5-yl)cyclopropyl]carbonyl}amino)-3,4-dihydro-2H-chromen-2-yl]benzoate;
methyl 3-[(2R,4R)-4-({[1-(2,2-difluoro-1,3-benzodioxol-5-yl)cyclopropyl]carbonyl}amino)-3,4-dihydro-2H-chromen-2-yl]benzoate;
3-[(2R,4R)-4-({[1-(2,2-difluoro-1,3-benzodioxol-5-yl)cyclopropyl]carbonyl}amino)-3,4-dihydro-2H-chromen-2-yl]benzoic acid;

3-[(2R,4S)-4-({[1-(2,2-difluoro-1,3-benzodioxol-5-yl)cyclopropyl]carbonyl}amino)-3,4-dihydro-2H-chromen-2-yl]benzoic acid;
methyl 3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoate;
methyl 3-[(2R,4S)-4-({[1-(2,2-difluoro-1,3-benzodioxol-5-yl)cyclopropyl]carbonyl}amino)-6-methyl-3,4-dihydro-2H-chromen-2-yl]benzoate;
3-[(2R,4S)-4-({[1-(2,2-difluoro-1,3-benzodioxol-5-yl)cyclopropyl]carbonyl}amino)-6-methyl-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid;
3-[(2R,4S)-4-({[1-(2,2-difluoro-1,3-benzodioxol-5-yl)cyclopropyl]carbonyl}amino)-7-methyl-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;
methyl 3-[(2R,4S)-4-({[1-(2,2-difluoro-1,3-benzodioxol-5-yl)cyclopropyl]carbonyl}amino)-7-methyl-3,4-dihydro-2H-chromen-2-yl]benzoate;
methyl 3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoate;
3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;
1-(2,2-difluoro-1,3-benzodioxol-5-yl)-N-[(2R,4R)-7-hydroxy-2-(3-methoxyphenyl)-3,4-dihydro-2H-chromen-4-yl]cyclopropanecarboxamide;
methyl 3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoate;
rac-1-(2,2-difluoro-1,3-benzodioxol-5-yl)-N-[(2R,4S)-7-methoxy-2-(pyridin-3-yl)-3,4-dihydro-2H-chromen-4-yl]cyclopropanecarboxamide;
3-[(2R,4R)-4-({[1-(2,2-difluoro-1,3-benzodioxol-5-yl)cyclopropyl]carbonyl}amino)-7-hydroxy-3,4-dihydro-2H-chromen-2-yl]benzoic acid;
ethyl rel-3-[(2S,4S)-4-({[1-(2,2-difluoro-1,3-benzodioxol-5-yl)cyclopropyl]carbonyl}amino)-3,4-dihydro-2H-pyrano[2,3-c]pyridin-2-yl]benzoate;
ethyl rel-3-[(2R,4R)-4-({[1-(2,2-difluoro-1,3-benzodioxol-5-yl)cyclopropyl]carbonyl}amino)-3,4-dihydro-2H-pyrano[2,3-c]pyridin-2-yl]benzoate;
3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;
3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;
rac-3-[(2R,4R)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoic acid;
rac-3-[(2R,4S)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoic acid;
methyl rac-3-[(2R,4R)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoate;
rac-3-[(2R,4R)-4-({[1-(2,2-difluoro-1,3-benzodioxol-5-yl)cyclopropyl]carbonyl}amino)-3,4-dihydro-2H-pyrano[2,3-b]pyridin-2-yl]benzoic acid;
rac-3-[(2R,4S)-4-({[1-(2,2-difluoro-1,3-benzodioxol-5-yl)cyclopropyl]carbonyl}amino)-3,4-dihydro-2H-pyrano[2,3-b]pyridin-2-yl]benzoic acid;
rac-methyl 3-[(2R,4R)-4-({[1-(2,2-difluoro-1,3-benzodioxol-5-yl)cyclopropyl]carbonyl}amino)-3,4-dihydro-2H-pyrano[2,3-b]pyridin-2-yl]benzoate;
rac-methyl 3-[(2R,4S)-4-({[1-(2,2-difluoro-1,3-benzodioxol-5-yl)cyclopropyl]carbonyl}amino)-3,4-dihydro-2H-pyrano[2,3-b]pyridin-2-yl]benzoate;
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;
3-[(2R,4R)-4-({[1-(2,2-difluoro-1,3-benzodioxol-5-yl)cyclopropyl]carbonyl}amino)-7-fluoro-3,4-dihydro-2H-chromen-2-yl]cyclohexanecarboxylic acid;
methyl 3-[4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoate;
3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid;
methyl 3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoate;
rac-N-[(2R,4R)-2-cyclopropyl-7-methoxy-3,4-dihydro-2H-chromen-4-yl]-1-(2,2-difluoro-1,3-benzodioxol-5-yl)cyclopropanecarboxamide;
rac-N-[(2R,4S)-2-cyclopropyl-7-methoxy-3,4-dihydro-2H-chromen-4-yl]-1-(2,2-difluoro-1,3-benzodioxol-5-yl)cyclopropanecarboxamide;
4-({[1-(2,2-difluoro-1,3-benzodioxol-5-yl)cyclopropyl]carbonyl}amino)-3,4-dihydro-2H-chromene-7-carboxylic acid;
3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;
(2R,4R)-4-({[1-(2,2-difluoro-1,3-benzodioxol-5-yl)cyclopropyl]carbonyl}amino)-2-(3-methoxyphenyl)-3,4-dihydro-2H-chromene-6-carboxylic acid;
methyl 4-({[1-(2,2-difluoro-1,3-benzodioxol-5-yl)cyclopropyl]carbonyl}amino)-3,4-dihydro-2H-chromene-7-carboxylate;
methyl (2R,4R)-4-({[1-(2,2-difluoro-1,3-benzodioxol-5-yl)cyclopropyl]carbonyl}amino)-2-(3-methoxycyclohexyl)-3,4-dihydro-2H-chromene-6-carboxylate;
methyl (2R,4R)-4-({[1-(2,2-difluoro-1,3-benzodioxol-5-yl)cyclopropyl]carbonyl}amino)-2-(3-methoxyphenyl)-3,4-dihydro-2H-chromene-6-carboxylate;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2, 3-dihydroxypropyl]benzamide;
1-(2,2-difluoro-1,3-benzodioxol-5-yl)-N-[(2R,4R)-2-(3-{[(3R)-3-hydroxypyrrolidin-1-yl]carbonyl}phenyl)-7-methyl-3,4-dihydro-2H-chromen-4-yl]cyclopropanecarboxamide;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-(3,3,3-trifluoro-2-hydroxypropyl)benzamide;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-(2-hydroxy-2-methylpropyl)benzamide;

1-(2,2-difluoro-1,3-benzodioxol-5-yl)-N-[(2R,4R)-2-(3-{[3-(hydroxymethyl)piperidin-1-yl]carbonyl}phenyl)-7-methyl-3,4-dihydro-2H-chromen-4-yl]cyclopropanecarboxamide;

1-(2,2-difluoro-1,3-benzodioxol-5-yl)-N-[(2R,4R)-2-(3-{[2-(hydroxymethyl)morpholin-4-yl]carbonyl}phenyl)-7-methyl-3,4-dihydro-2H-chromen-4-yl]cyclopropanecarboxamide;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(1-hydroxycyclobutyl)methyl]benzamide;

1-(2,2-difluoro-1,3-benzodioxol-5-yl)-N-[(2R,4R)-2-(3-{[3-(hydroxymethyl)-3-methylazetidin-1-yl]carbonyl}phenyl)-7-methyl-3,4-dihydro-2H-chromen-4-yl]cyclopropanecarboxamide;

N-(7-bromo-3,4-dihydro-2H-chromen-4-yl)-1-(2,2-difluoro-1,3-benzodioxol-5-yl)cyclopropanecarboxamide;

rac-1-(2,2-difluoro-1,3-benzodioxol-5-yl)-N-[(2R,4R)-7-methoxy-2-(pyridin-3-yl)-3,4-dihydro-2H-chromen-4-yl]cyclopropanecarboxamide;

1-(2,2-difluoro-1,3-benzodioxol-5-yl)-N-{(2R)-2-[3-(hydroxymethyl)phenyl]-3,4-dihydro-2H-chromen-4-yl}cyclopropanecarboxamide;

1-(2,2-difluoro-1,3-benzodioxol-5-yl)-N-(7-methoxy-3,4-dihydro-2H-chromen-4-yl)cyclopropanecarboxamide;

1-(2,2-difluoro-1,3-benzodioxol-5-yl)-N-(7-methoxy-2-phenyl-3,4-dihydro-2H-chromen-4-yl)cyclopropanecarboxamide;

N-[2-(3,4-dichlorophenyl)-7-methoxy-3,4-dihydro-2H-chromen-4-yl]-1-(2,2-difluoro-1,3-benzodioxol-5-yl)cyclopropanecarboxamide;

1-(2,2-difluoro-1,3-benzodioxol-5-yl)-N-[2-(3,4-dimethoxyphenyl)-7-methoxy-3,4-dihydro-2H-chromen-4-yl]cyclopropanecarboxamide;

N-[2-(4-chlorophenyl)-7-methoxy-3,4-dihydro-2H-chromen-4-yl]-1-(2,2-difluoro-1,3-benzodioxol-5-yl)cyclopropanecarboxamide;

1-(2,2-difluoro-1,3-benzodioxol-5-yl)-N-{2-[4-(trifluoromethyl)phenyl]-3,4-dihydro-2H-chromen-4-yl}cyclopropanecarboxamide;

N-[2-(2-chlorophenyl)-3,4-dihydro-2H-chromen-4-yl]-1-(2,2-difluoro-1,3-benzodioxol-5-yl)cyclopropanecarboxamide;

N-[2-(3,4-dichlorophenyl)-3,4-dihydro-2H-chromen-4-yl]-1-(2,2-difluoro-1,3-benzodioxol-5-yl)cyclopropanecarboxamide;

1-(2,2-difluoro-1,3-benzodioxol-5-yl)-N-(2-phenyl-3,4-dihydro-2H-chromen-4-yl)cyclopropanecarboxamide;

N-[2-(4-chlorophenyl)-3,4-dihydro-2H-chromen-4-yl]-1-(2,2-difluoro-1,3-benzodioxol-5-yl)cyclopropanecarboxamide;

1-(2,2-difluoro-1,3-benzodioxol-5-yl)-N-[2-(3,4-dimethoxyphenyl)-3,4-dihydro-2H-chromen-4-yl]cyclopropanecarboxamide;

N-[2-(3-chlorophenyl)-3,4-dihydro-2H-chromen-4-yl]-1-(2,2-difluoro-1,3-benzodioxol-5-yl)cyclopropanecarboxamide;

1-(2,2-difluoro-1,3-benzodioxol-5-yl)-N-[2-(4-fluorophenyl)-3,4-dihydro-2H-chromen-4-yl]cyclopropanecarboxamide;

1-(2,2-difluoro-1,3-benzodioxol-5-yl)-N-[3-(3,4-dimethoxybenzyl)-6-methoxy-3,4-dihydro-2H-chromen-4-yl]cyclopropanecarboxamide;

N-(3-benzyl-3,4-dihydro-2H-chromen-4-yl)-1-(2,2-difluoro-1,3-benzodioxol-5-yl)cyclopropanecarboxamide;

N-[(4R)-2,2-diethyl-3,4-dihydro-2H-chromen-4-yl]-1-(2,2-difluoro-1,3-benzodioxol-5-yl)cyclopropanecarboxamide;

N-[(4R)-2,2-bis(fluoromethyl)-3,4-dihydro-2H-chromen-4-yl]-1-(2,2-difluoro-1,3-benzodioxol-5-yl)cyclopropanecarboxamide;

N-[(4R)-7-chloro-2,2-dimethyl-3,4-dihydro-2H-chromen-4-yl]-1-(2,2-difluoro-1,3-benzodioxol-5-yl)cyclopropanecarboxamide;

1-(2,2-difluoro-1,3-benzodioxol-5-yl)-N-[(4R)-8-fluoro-2,2-bis(fluoromethyl)-3,4-dihydro-2H-chromen-4-yl]cyclopropanecarboxamide;

1-(2,2-difluoro-1,3-benzodioxol-5-yl)-N-[(4R)-3,4-dihydrospiro[chromene-2,1'-cyclopentan]-4-yl]cyclopropanecarboxamide;

1-(2,2-difluoro-1,3-benzodioxol-5-yl)-N-[(4R)-7-fluoro-2,2-bis(fluoromethyl)-3,4-dihydro-2H-chromen-4-yl]cyclopropanecarboxamide;

1-(2,2-difluoro-1,3-benzodioxol-5-yl)-N-[(2S,4R)-2-(fluoromethyl)-2-methyl-7-(trifluoromethyl)-3,4-dihydro-2H-chromen-4-yl]cyclopropanecarboxamide;

1-(2,2-difluoro-1,3-benzodioxol-5-yl)-N-[(2R,4R)-2-(difluoromethyl)-2-methyl-3,4-dihydro-2H-chromen-4-yl]cyclopropanecarboxamide;

1-(2,2-difluoro-1,3-benzodioxol-5-yl)-N-[(2S,4R)-2-(difluoromethyl)-2-methyl-3,4-dihydro-2H-chromen-4-yl]cyclopropanecarboxamide;

N-[(2S,4R)-7-chloro-2-(difluoromethyl)-2-methyl-3,4-dihydro-2H-chromen-4-yl]-1-(2,2-difluoro-1,3-benzodioxol-5-yl)cyclopropanecarboxamide;

N-[(2R,4R)-7-chloro-2-(difluoromethyl)-2-methyl-3,4-dihydro-2H-chromen-4-yl]-1-(2,2-difluoro-1,3-benzodioxol-5-yl)cyclopropanecarboxamide;

1-(2,2-difluoro-1,3-benzodioxol-5-yl)-N-[(2S,4R)-2-methyl-2-(trifluoromethyl)-3,4-dihydro-2H-chromen-4-yl]cyclopropanecarboxamide;

1-(2,2-difluoro-1,3-benzodioxol-5-yl)-N-[(4R)-7-fluoro-2,2-dimethyl-3,4-dihydro-2H-chromen-4-yl]cyclopropanecarboxamide;

N-[(4R)-7-chloro-2,2-bis(fluoromethyl)-3,4-dihydro-2H-chromen-4-yl]-1-(2,2-difluoro-1,3-benzodioxol-5-yl)cyclopropanecarboxamide;

1-(2,2-difluoro-1,3-benzodioxol-5-yl)-N-[(4S)-6-fluoro-2,2-dimethyl-3,4-dihydro-2H-chromen-4-yl]cyclopropanecarboxamide;

1-(2,2-difluoro-1,3-benzodioxol-5-yl)-N-[(4S)-6-fluoro-3,4-dihydrospiro[chromene-2,1'-cyclobutan]-4-yl]cyclopropanecarboxamide;

N-[(4R)-8-chloro-7-fluoro-2,2-dimethyl-3,4-dihydro-2H-chromen-4-yl]-1-(2,2-difluoro-1,3-benzodioxol-5-yl)cyclopropanecarboxamide;

1-(2,2-difluoro-1,3-benzodioxol-5-yl)-N-[3-(3,4-dimethoxybenzyl)-7-methoxy-3,4-dihydro-2H-chromen-4-yl]cyclopropanecarboxamide;

tert-butyl 4-({[1-(2,2-difluoro-1,3-benzodioxol-5-yl)cyclopropyl]carbonyl}amino)-7-fluoro-3,4-dihydro-1'H-spiro[chromene-2,4'-piperidine]-1'-carboxylate;

1-(2,2-difluoro-1,3-benzodioxol-5-yl)-N-(7-fluoro-3,4-dihydrospiro[chromene-2,4'-piperidin]-4-yl)cyclopropanecarboxamide;

methyl 3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoate;

methyl 3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoate;

3-[(2R,4R)-7-(carboxymethoxy)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;

3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;

1-(2,2-difluoro-1,3-benzodioxol-5-yl)-N-{1'-[(2R)-2,3-dihydroxypropyl]-7-fluoro-3,4-dihydrospiro[chromene-2,4'-piperidin]-4-yl}cyclopropanecarboxamide;

benzyl 4'-({[1-(2,2-difluoro-1,3-benzodioxol-5-yl)cyclopropyl]carbonyl}amino)-7'-fluoro-3',4'-dihydro-1H-spiro[azetidine-3,2'-chromene]-1-carboxylate;

1-(2,2-difluoro-1,3-benzodioxol-5-yl)-N-[7-fluoro-1'-(methylsulfonyl)-3,4-dihydrospiro[chromene-2,4'-piperidin]-4-yl]cyclopropanecarboxamide;

N-(1'-acetyl-7-fluoro-3,4-dihydrospiro[chromene-2,4'-piperidin]-4-yl)-1-(2,2-difluoro-1,3-benzodioxol-5-yl)cyclopropanecarboxamide;

1-(2,2-difluoro-1,3-benzodioxol-5-yl)-N-(7'-fluoro-3',4'-dihydrospiro[azetidine-3,2'-chromen]-4'-yl)cyclopropanecarboxamide;

1-(2,2-difluoro-1,3-benzodioxol-5-yl)-N-[7'-fluoro-1-(methylsulfonyl)-3',4'-dihydrospiro[azetidine-3,2'-chromen]-4'-yl]cyclopropanecarboxamide;

N-(1-acetyl-7'-fluoro-3',4'-dihydrospiro[azetidine-3,2'-chromen]-4'-yl)-1-(2,2-difluoro-1,3-benzodioxol-5-yl)cyclopropanecarboxamide;

3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;

1-(2,2-difluoro-1,3-benzodioxol-5-yl)-N-[1'-(3-hydroxy-2,2-dimethylpropanoyl)-7-methoxy-3,4-dihydrospiro[chromene-2,4'-piperidin]-4-yl]cyclopropanecarboxamide;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;

methyl 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoate;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

methyl rac-3-[(2R,4R)-7-chloro-4-({[1-(2,2-difluoro-1,3-benzodioxol-5-yl)cyclopropyl]carbonyl}amino)-3,4-dihydro-2H-pyrano[2,3-b]pyridin-2-yl]benzoate;

methyl rac-3-[(2R,4R)-4-({[1-(2,2-difluoro-1,3-benzodioxol-5-yl)cyclopropyl]carbonyl}amino)-7-fluoro-3,4-dihydro-2H-pyrano[2,3-b]pyridin-2-yl]benzoate;

rac-3-[(2R,4R)-7-chloro-4-({[1-(2,2-difluoro-1,3-benzodioxol-5-yl)cyclopropyl]carbonyl}amino)-3,4-dihydro-2H-pyrano[2,3-b]pyridin-2-yl]benzoic acid;

tert-butyl 3-[4-({[1-(2,2-difluoro-1,3-benzodioxol-5-yl)cyclopropyl]carbonyl}amino)-7-methoxy-3,4-dihydro-2H-chromen-2-yl]azetidine-1-carboxylate;

N-[2-(azetidin-3-yl)-7-methoxy-3,4-dihydro-2H-chromen-4-yl]-1-(2,2-difluoro-1,3-benzodioxol-5-yl)cyclopropanecarboxamide;

1-(2,2-difluoro-1,3-benzodioxol-5-yl)-N-{7-methoxy-2-[1-(methylsulfonyl)azetidin-3-yl]-3,4-dihydro-2H-chromen-4-yl}cyclopropanecarboxamide;

methyl rac-3-[(2R,4S)-4-({[1-(2,2-difluoro-1,3-benzodioxol-5-yl)cyclopropyl]carbonyl}amino)-7-fluoro-3,4-dihydro-2H-pyrano[2,3-b]pyridin-2-yl]benzoate;

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;

methyl 4-[(2R,4R)-4-({[1-(2,2-difluoro-1,3-benzodioxol-5-yl)cyclopropyl]carbonyl}amino)-3,4-dihydro-2H-chromen-2-yl]benzoate;

4-[(2R,4R)-4-({[1-(2,2-difluoro-1,3-benzodioxol-5-yl)cyclopropyl]carbonyl}amino)-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

methyl 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoate;

1-(2,2-difluoro-1,3-benzodioxol-5-yl)-N-(7-hydroxy-2,2-dimethyl-3,4-dihydro-2H-chromen-4-yl)cyclopropanecarboxamide;

1-(2,2-difluoro-1,3-benzodioxol-5-yl)-N-[7-(difluoromethoxy)-2,2-dimethyl-3,4-dihydro-2H-chromen-4-yl]cyclopropanecarboxamide;

1-(2,2-difluoro-1,3-benzodioxol-5-yl)-N-[7-methoxy-2-(tetrahydrofuran-2-yl)-3,4-dihydro-2H-chromen-4-yl]cyclopropanecarboxamide;

methyl 4-[(2R,4R)-4-({[1-(2,2-difluoro-1,3-benzodioxol-5-yl)cyclopropyl]carbonyl}amino)-7-hydroxy-3,4-dihydro-2H-chromen-2-yl]benzoate;

4-[(2R,4R)-4-({[1-(2,2-difluoro-1,3-benzodioxol-5-yl)cyclopropyl]carbonyl}amino)-7-hydroxy-3,4-dihydro-2H-chromen-2-yl]benzoic acid;

4-({[1-(2,2-difluoro-1,3-benzodioxol-5-yl)cyclopropyl]carbonyl}amino)-7-methoxy-3,4-dihydrospiro[chromene-2,1'-cyclobutane]-3'-carboxylic acid;

ethyl rac-(2R,4S)-4-({[1-(2,2-difluoro-1,3-benzodioxol-5-yl)cyclopropyl]carbonyl}amino)-7-methoxy-3,4-dihydro-2H-chromene-2-carboxylate;

methyl rac-(2R,4S)-4-({[1-(2,2-difluoro-1,3-benzodioxol-5-yl)cyclopropyl]carbonyl}amino)-7-methoxy-3,4-dihydro-2H-chromene-2-carboxylate;

ethyl rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-5-carboxylate;

2-[(4S)-4-({[1-(2,2-difluoro-1,3-benzodioxol-5-yl)cyclopropyl]carbonyl}amino)-3,4-dihydro-2H-chromen-2-yl]-1,3-thiazole-5-carboxylic acid;

rac-(2R,4S)-4-({[1-(2,2-difluoro-1,3-benzodioxol-5-yl)cyclopropyl]carbonyl}amino)-7-methoxy-3,4-dihydro-2H-chromene-2-carboxylic acid;

ethyl rel-2-[(2R,4R)-4-({[1-(2,2-difluoro-1,3-benzodioxol-5-yl)cyclopropyl]carbonyl}amino)-3,4-dihydro-2H-chromen-2-yl]-1,3-thiazole-5-carboxylate;

2-[(4R)-4-({[1-(2,2-difluoro-1,3-benzodioxol-5-yl)cyclopropyl]carbonyl}amino)-3,4-dihydro-2H-chromen-2-yl]-1,3-thiazole-5-carboxylic acid;

methyl 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-2-fluorobenzoate;

methyl 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-3-fluorobenzoate;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-2-fluorobenzoic acid;

ethyl rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylate;

ethyl rel-2-[(2R,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylate;

ethyl rel-2-[(2R,4R)-4-({[1-(2,2-difluoro-1,3-benzodioxol-5-yl)cyclopropyl]carbonyl}amino)-3,4-dihydro-2H-chromen-2-yl]-1,3-thiazole-4-carboxylate;

rel-2-[(2S,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylic acid;

rel-2-[(2R,4S)-4-({[1-(2,2-difluoro-1,3-benzodioxol-5-yl)cyclopropyl]carbonyl}amino)-3,4-dihydro-2H-chromen-2-yl]-1,3-thiazole-4-carboxylic acid;

rel-2-[(2R,4R)-4-({[1-(2,2-difluoro-1,3-benzodioxol-5-yl)cyclopropyl]carbonyl}amino)-3,4-dihydro-2H-chromen-2-yl]-1,3-thiazole-4-carboxylic acid;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-3-fluorobenzoic acid;

methyl rac-3-[(2R,4R)-4-({[1-(2,2-difluoro-1,3-benzodioxol-5-yl)cyclopropyl]carbonyl}amino)-7-methoxy-3,4-dihydro-2H-chromen-2-yl]bicyclo[1.1.1]pentane-1-carboxylate;

rac-3-[(2R,4R)-4-({[1-(2,2-difluoro-1,3-benzodioxol-5-yl)cyclopropyl]carbonyl}amino)-7-methoxy-3,4-dihydro-2H-chromen-2-yl]bicyclo[1.1.1]pentane-1-carboxylic acid;

ethyl rac-6-[(2R,4S)-4-({[1-(2,2-difluoro-1,3-benzodioxol-5-yl)cyclopropyl]carbonyl}amino)-3,4-dihydro-2H-chromen-2-yl]pyridine-3-carboxylate;

ethyl rac-6-[(2R,4R)-4-({[1-(2,2-difluoro-1,3-benzodioxol-5-yl)cyclopropyl]carbonyl}amino)-3,4-dihydro-2H-chromen-2-yl]pyridine-3-carboxylate;

ethyl 3-[4-({[1-(2,2-difluoro-1,3-benzodioxol-5-yl)cyclopropyl]carbonyl}amino)-3,4-dihydro-2H-chromen-2-yl]cyclobutanecarboxylate;

3-[4-({[1-(2,2-difluoro-1,3-benzodioxol-5-yl)cyclopropyl]carbonyl}amino)-3,4-dihydro-2H-chromen-2-yl]cyclobutanecarboxylic acid;

rac-6-[(2R,4S)-4-({[1-(2,2-difluoro-1,3-benzodioxol-5-yl)cyclopropyl]carbonyl}amino)-3,4-dihydro-2H-chromen-2-yl]pyridine-3-carboxylic acid;

rac-6-[(2R,4R)-4-({[1-(2,2-difluoro-1,3-benzodioxol-5-yl)cyclopropyl]carbonyl}amino)-3,4-dihydro-2H-chromen-2-yl]pyridine-3-carboxylic acid;

ethyl rel-2-[(2R,4R)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylate;

rel-2-[(2R,4R)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylic acid;

ethyl rel-2-[(2S,4S)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylate;

rel-2-[(2S,4S)-4-({[1-(2,2-difluoro-1,3-benzodioxol-5-yl)cyclopropyl]carbonyl}amino)-7-methoxy-3,4-dihydro-2H-chromen-2-yl]-1,3-thiazole-4-carboxylic acid;

methyl rel-6-[(2R,4S)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylate;

methyl rel-6-[(2S,4R)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylate;

methyl rel-6-[(2S,4S)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylate;

methyl rel-6-[(2R,4R)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylate;

ethyl rac-(2R,4R)-4-({[1-(2,2-difluoro-1,3-benzodioxol-5-yl)cyclopropyl]carbonyl}amino)-7-methoxy-3,4-dihydro-2H-chromene-2-carboxylate;

rac-(2R,4R)-4-({[1-(2,2-difluoro-1,3-benzodioxol-5-yl)cyclopropyl]carbonyl}amino)-7-methoxy-3,4-dihydro-2H-chromene-2-carboxylic acid;

rel-6-[(2R,4R)-4-({[1-(2,2-difluoro-1,3-benzodioxol-5-yl)cyclopropyl]carbonyl}amino)-7-methoxy-3,4-dihydro-2H-chromen-2-yl]pyridine-3-carboxylic acid;

rac-(2R,4R)-4-({[1-(2,2-difluoro-1,3-benzodioxol-5-yl)cyclopropyl]carbonyl}amino)-N-(2-hydroxyethyl)-7-methoxy-N-propyl-3,4-dihydro-2H-chromene-2-carboxamide;

rac-(2R,4R)—N-benzyl-4-({[1-(2,2-difluoro-1,3-benzodioxol-5-yl)cyclopropyl]carbonyl}amino)-N-(2-hydroxyethyl)-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-(2-hydroxy-2-phenylethyl)-7-methoxy-N-methyl-3,4-dihydro-2H-chromene-2-carboxamide;

rac-1-(2,2-difluoro-1,3-benzodioxol-5-yl)-N-[(2R,4R)-2-{[4-(2-hydroxyethyl)piperazin-1-yl]carbonyl}-7-methoxy-3,4-dihydro-2H-chromen-4-yl]cyclopropanecarboxamide;

rac-(2R,4R)-4-({[1-(2,2-difluoro-1,3-benzodioxol-5-yl)cyclopropyl]carbonyl}amino)-N-(1-hydroxy-2-methylpropan-2-yl)-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-(2-hydroxy-1-phenylethyl)-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-(1,1-dioxidotetrahydro-2H-thiopyran-4-yl)-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-7-methoxy-N-[3-(trifluoromethyl)oxetan-3-yl]-3,4-dihydro-2H-chromene-2-carboxamide;

rac-1-(2,2-difluoro-1,3-benzodioxol-5-yl)-N-{(2R,4R)-2-[(4,4-difluoropiperidin-1-yl)carbonyl]-7-methoxy-3,4-dihydro-2H-chromen-4-yl}cyclopropanecarboxamide;

rac-1-(2,2-difluoro-1,3-benzodioxol-5-yl)-N-[(2R,4R)-7-methoxy-2-(1,4-oxazepan-4-ylcarbonyl)-3,4-dihydro-2H-chromen-4-yl]cyclopropanecarboxamide;

rac-(2R,4R)-4-({[1-(2,2-difluoro-1,3-benzodioxol-5-yl)cyclopropyl]carbonyl}amino)-7-methoxy-N-methyl-N-(oxetan-3-yl)-3,4-dihydro-2H-chromene-2-carboxamide;

rac-1-(2,2-difluoro-1,3-benzodioxol-5-yl)-N-[(2R,4R)-7-methoxy-2-(morpholin-4-ylcarbonyl)-3,4-dihydro-2H-chromen-4-yl]cyclopropanecarboxamide;

rac-(2R,4R)-4-({[1-(2,2-difluoro-1,3-benzodioxol-5-yl)cyclopropyl]carbonyl}amino)-N-[2-hydroxy-1-(2-methoxyphenyl)ethyl]-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-[2-(3-hydroxyphenyl)ethyl]-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-(1,3-dihydroxypropan-2-yl)-7-methoxy-3,4-dihydro-2H-chromene-2-carboxamide;

rac-(2R,4R)-4-({[1-(2,2-difluoro-1,3-benzodioxol-5-yl)cyclopropyl]carbonyl}amino)-N-(2-hydroxy-2,3-dihydro-1H-inden-1-yl)-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-N-(2-hydroxyphenyl)-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-N-(2-hydroxy ethyl)-7-methoxy-N-propyl-3,4-dihydro-2H-chromene-2-carboxamide;

rac-(2R,4S)—N-benzyl-4-({[1-(2,2-difluoro-1,3-benzodioxol-5-yl)cyclopropyl]carbonyl}amino)-N-(2-hydroxy ethyl)-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-N-(2-hydroxy-2-phenylethyl)-7-methoxy-N-methyl-3,4-dihydro-2H-chromene-2-carboxamide;

rac-1-(2,2-difluoro-1,3-benzodioxol-5-yl)-N-{(2R,4S)-2-[(4-hydroxypiperidin-1-yl)carbonyl]-7-methoxy-3,4-dihydro-2H-chromen-4-yl}cyclopropanecarboxamide;

rac-1-(2,2-difluoro-1,3-benzodioxol-5-yl)-N-[(2R,4S)-2-[4-(2-hydroxy ethyl)piperazin-1-yl]carbonyl-7-methoxy-3,4-dihydro-2H-chromen-4-yl]cyclopropanecarboxamid;

rac-(2R,4S)-4-({[1-(2,2-difluoro-1,3-benzodioxol-5-yl)cyclopropyl]carbonyl}amino)-N-(2-hydroxy-2-methylpropyl)-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-N-(1-hydroxy-2-methylpropan-2-yl)-7-methoxy-3,4-dihydro-2H-chromene-2-carboxamid;

rac-(2R,4S)-4-({[1-(2,2-difluoro-1,3-benzodioxol-5-yl)cyclopropyl]carbonyl}amino)-N-(2-hydroxy-1-phenylethyl)-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-N-(1,1-dioxidotetrahydro-2H-thiopyran-4-yl)-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-7-methoxy-N-[3-(trifluoromethyl)oxetan-3-yl]-3,4-dihydro-2H-chromene-2-carboxamide;

rac-1-(2,2-difluoro-1,3-benzodioxol-5-yl)-N-{(2R,4S)-2-[(4,4-difluoropiperidin-1-yl)carbonyl]-7-methoxy-3,4-dihydro-2H-chromen-4-yl}cyclopropanecarboxamide;

rac-1-(2,2-difluoro-1,3-benzodioxol-5-yl)-N-[(2R,4S)-7-methoxy-2-(1,4-oxazepan-4-ylcarbonyl)-3,4-dihydro-2H-chromen-4-yl]cyclopropanecarboxamide;

rac-(2R,4S)-4-({[1-(2,2-difluoro-1,3-benzodioxol-5-yl)cyclopropyl]carbonyl}amino)-7-methoxy-N-methyl-N-(oxetan-3-yl)-3,4-dihydro-2H-chromene-2-carboxamide;

rac-1-(2,2-difluoro-1,3-benzodioxol-5-yl)-N-[(2R,4S)-7-methoxy-2-(morpholin-4-ylcarbonyl)-3,4-dihydro-2H-chromen-4-yl]cyclopropanecarboxamide;

rac-(2R,4S)-4-({[1-(2,2-difluoro-1,3-benzodioxol-5-yl)cyclopropyl]carbonyl}amino)-N-[2-hydroxy-1-(2-methoxyphenyl)ethyl]-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-N-[2-(3-hydroxyphenyl)ethyl]-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-N-(1,3-dihydroxypropan-2-yl)-7-methoxy-3,4-dihydro-2H-chromene-2-carboxamide;

rac-(2R,4S)-4-({[1-(2,2-difluoro-1,3-benzodioxol-5-yl)cyclopropyl]carbonyl}amino)-N-(2-hydroxy-2,3-dihydro-1H-inden-1-yl)-7-methoxy-3,4-dihydro-2H-chromene-2-carboxamide;

rac-1-{[(2R,4S)-4-({[1-(2,2-difluoro-1,3-benzodioxol-5-yl)cyclopropyl]carbonyl}amino)-7-methoxy-3,4-dihydro-2H-chromen-2-yl]carbonyl}pyrrolidine-3-carboxylic acid;

4-[(2R,4R)-4-({[1-(6-bromo-2,2-difluoro-1,3-benzodioxol-5-yl)cyclopropyl]carbonyl}amino)-7-(difluoromethoxy)-3,4-dihydro-2H-chromen-2-yl]benzoic acid;

methyl 4-((2R,4R)-4-(1-(6-bromo-2,2-difluorobenzo[d][1,3]dioxol-5-yl)cyclopropanecarboxamido)-7-methoxychroman-2-yl)benzoate; and 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]-N-(methylsulfonyl)benzamide.

51. A pharmaceutical composition comprising a therapeutically effective amount of a compound of formula (I) according to claim 1, or a pharmaceutically acceptable salt thereof, in combination with a pharmaceutically acceptable carrier.

52. A method for treating cystic fibrosis in a subject comprising administering a therapeutically effective amount of a compound of formula (I) according to claim 1 or a pharmaceutically acceptable salt thereof, to a subject in need thereof.

53. A pharmaceutical composition comprising a compound of claim 1 or a pharmaceutically acceptable salt thereof, and one or more additional therapeutic agents.

54. The pharmaceutical composition of claim 53 wherein the additional therapeutic agents are selected from the group consisting of CFTR modulators and CFTR amplifiers.

55. The pharmaceutical composition of claim 53 wherein the additional therapeutic agents are CFTR modulators.

56. A pharmaceutical composition comprising a compound of claim 1 or a pharmaceutically acceptable salt thereof, one potentiator, and one or more correctors.

57. A method for treating cystic fibrosis in a subject comprising administering a compound of claim 1 or a pharmaceutically acceptable salt thereof, and one or more additional therapeutic agents.

58. The method of claim 57 wherein the additional therapeutic agents are selected from the group consisting of CFTR modulators and CFTR amplifiers.

59. The method of claim 57 the wherein the additional therapeutic agents are CFTR modulators.

60. A method for treating cystic fibrosis in a subject comprising administering a compound of claim 1 or a pharmaceutically acceptable salt thereof, one potentiator, and one or more correctors.

61. The compound of claim 48, or a pharmaceutically acceptable salt thereof
wherein
$R^1$ is hydrogen, $C_1$-$C_3$ alkyl, or —$OR^{1A}$; wherein $R^{1A}$ is $C_1$-$C_3$ alkyl; and
$R^h$ is hydrogen.

62. 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid.

63. 3-[(2R,4R)-4-({[1-(2,2-difluoro-1,3-benzodioxol-5-yl)cyclopropyl]carbonyl}amino)-3,4-dihydro-2H-chromen-2-yl]benzoic acid.

64. 3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid.

65. 3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid.

66. rac-3-[(2R,4)-4-({[1-(2,2-difluoro-1,3-benzodioxol-5-yl)cyclopropyl]carbonyl}amino)-7-methoxy-3,4-dihydro-2H-pyrano[2,3-b]pyridin-2-yl]benzoic acid.

67. 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid.

68. 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid.

69. 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]-3-fluorobenzoic acid.

* * * * *

UNITED STATES PATENT AND TRADEMARK OFFICE
CERTIFICATE OF CORRECTION

PATENT NO. : 9,642,831 B2
APPLICATION NO. : 14/925649
DATED : May 9, 2017
INVENTOR(S) : Robert J. Altenbach et al.

It is certified that error appears in the above-identified patent and that said Letters Patent is hereby corrected as shown below:

In the Specification

Column 26, Line 37, detailed description: "–C(O)OR$^1$" to read as -- –C(O)OR$^{1B}$--

Column 45, Line 26, detailed description: "–OR" to read as -- –OR$^j$--

Column 56, Line 53, detailed description: "–SR$^A$" to read as -- –SR$^{ZA}$--

Column 57, Line 40, detailed description: "–OR" to read as -- –OR$^j$--

Column 80, Line 15, detailed description: "intracistemally" to read as --intracisternally--

Column 124, Line 7, Examples: "OC" to read as --°C--

Column 129, Line 4, Examples: "hydro-2H-chromen-4-yl]-1-(2,2-difluoro-3-benzodi-" to read as --hydro-2H-chromen-4-yl]-1-(2,2-difluoro-1,3-benzodi- --

Column 170, Line 16, Examples: "1 OF" to read as --100F--

Column 203, Line 66, Examples: "792" to read as --(792--

Column 203, Line 67, Examples: "mmol" to read as --mmol)--

Column 228, Line 6, Examples: "aminormethane" to read as --aminomethane--

In the Claims

Column 231, Line 1, Claim 1: "–N(R$^h$)C(O)R$^1$" to read as -- –N(R$^h$)C(O)R$^i$--

Signed and Sealed this
Second Day of October, 2018

Andrei Iancu
*Director of the United States Patent and Trademark Office*

CERTIFICATE OF CORRECTION (continued)

U.S. Pat. No. 9,642,831 B2

Column 232, Lines 10-24, Claim 2: " 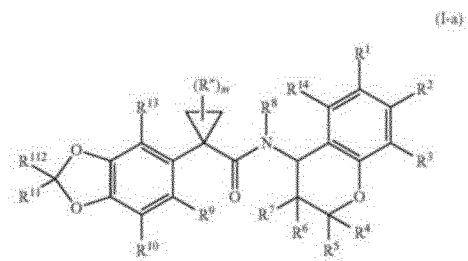 " to read as

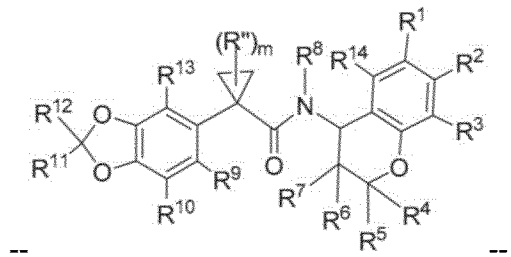

--   --

Column 235, Line 47, Claim 18: "–S(O)$_2$R$^h$" to read as -- –SR$^h$, –S(O)$_2$R$^h$--

Column 236, Line 11, Claim 18: "–S(O)$_2$R$^j$" to read as -- –SR$^j$, –S(O)$_2$R$^j$--

Column 236, Line 45, Claim 19: "wherein R$^1$, R$^2$, R$^4$" to read as --wherein R$^1$, R$^2$, R$^3$, R$^4$--

Column 238, Line 60, Claim 34: "with for 2" to read as --with 1 or 2--

Column 239, Line 64, Claim 38: "G$^{2A}$ is C$_6$" to read as --G$^{2A}$ is C$_3$-C$_6$--